US012805531B2

(12) United States Patent
Wu et al.

(10) Patent No.: US 12,805,531 B2
(45) Date of Patent: Nov. 24, 2026

(54) **FORMULATION OF A LYTIC BACTERIOPHAGE COCKTAIL FOR BIOCONTROL OF SHIGA TOXIN-PRODUCING *ESCHERICHIA COLI* STRAINS**

(71) Applicant: The United States of America, as Represented by the Secretary of Agriculture, Washington, DC (US)

(72) Inventors: Vivian C. Wu, Burlingame, CA (US); Yen-Te Liao, Concord, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 251 days.

(21) Appl. No.: 18/948,160

(22) Filed: Nov. 14, 2024

(65) Prior Publication Data

US 2025/0160335 A1 May 22, 2025

Related U.S. Application Data

(60) Provisional application No. 63/599,751, filed on Nov. 16, 2023.

(51) Int. Cl.
*C12N 7/00* (2006.01)
*A01N 63/40* (2020.01)
*A01P 1/00* (2006.01)

(52) U.S. Cl.
CPC ................ *A01N 63/40* (2020.01); *A01P 1/00* (2021.08); *C12N 7/00* (2013.01); *C12N 2795/00031* (2013.01)

(58) Field of Classification Search
None
See application file for complete search history.

(56) References Cited

FOREIGN PATENT DOCUMENTS

| | | |
|---|---|---|
| KR | 1020160005728 | 1/2016 |
| KR | 20220164757 | 12/2022 |
| WO | 2012/036580 | 3/2012 |

OTHER PUBLICATIONS

Callaway et al., Bacteriophage Isolated from Feedlot Cattle Can Reduce *Escherichia coli* O157:H7 Populations in Ruminant Gastrointestinal Tracts, journal, 2008, p. 183-191, vol. 5-2, Mary Ann Liebert, Inc.
Carter et al., Bacteriophage cocktail significantly reduces *Escherichia coli* O157:H7 contamination of lettuce and beef, but does not protect against recontamination, journal, 2012, p. 178-185, vol. 2:3, Landes Bioscience.
Liao et al., Discovery of Shiga Toxin-Producing *Escherichia coli* (STEC)-Specific Bacteriophages From Non-fecal Composts Using Genomic Characterization, journal, 2019, p. 1-13, vol. 10, Frontiers in Microbiology.
Liao et al., Characterization of polyvalent *Escherichia* phage Sa157lw for the biocontrol potential of *Salmonella typhimurium* and *Escherichia coli* O157:H7 on contaminated mung bean seeds, journal, Nov. 10, 2022, p. 1-17, Frontiers in Microbiology.

(Continued)

*Primary Examiner* — M Franco G Salvoza
(74) *Attorney, Agent, or Firm* — John Fado; Mark McNemar

(57) ABSTRACT

The present disclosure provides for a combination of bacteriophages from various environmental sources combined to produce a phage mixture targeting shiga-toxin-producing *Escherichia coli* strains. Techniques and methods of production and use of the phage combinations are also provided.

13 Claims, 6 Drawing Sheets

Specification includes a Sequence Listing.

(56) References Cited

OTHER PUBLICATIONS

Liu et al., Complete Genome Sequence of *Escherichia coli* Phage vB_EcoM Sa157lw, Isolated from Surface Water Collected in Salinas, California, journal, Aug. 22, 2019, vol. 8, Issue 34, p. 1-2, American Society for Microbiology.
Rodriguez-Rubio et al., Bacteriophages of Shiga Toxin-Producing *Escherichia coli* and Their Contribution to Pathogenicity, journal, Mar. 29, 2021, vol. 10, 404, p. 1-23, MDPI-Pathogens.
Sharma et al., Effectiveness of Bacteriophages in Reducing *Escherichia coli* O157:H7 on Fresh-Cut Cantaloupes and Lettuce, journal, Feb. 12, 2009, vol. 72, No. 7, p. 1481-1485, Journal of Food Protection.
Wang et al., Phage Cocktail Targeting STEC O157:H7 Has Comparable Efficacy and Superior Recovery Compared with Enrofloxacin in an Enteric Murine Model, journal, May 10, 2022, vol. 10, issue 3, p. 1-14, American Society for Microbiology.
International Search Report on PCT/US2024/056165 dated Nov. 15, 2024.
Callaway, T.R. et al., Bacteriophage Isolated from Feedlot Cattle Can Reduce *Escherichia coli* O157:H7 Populations in Ruminant Gastrointestinal Tracts, Foodborne Pathogens and Disease, 2008, pp. 183-191, vol. 5, No. 2.
Liao, Y-T et al., Discovery of Shiga Toxin-Producing *Escherichia coli* (STEC)-Specific Bacteriophages From Non-fecal Composts Using Genomic Characterization, Apr. 2, 2019, pp. 1-13, Front. Microbiol. 10:627.
Liao, Y-T et al., Characterization of polyvalent *Escherichia* phage Sa157lw for the biocontrol potential of *Salmonella typhimurium* and *Escherichia coli* O157:H7 on contaminated mung bean seeds, Nov. 10, 2022, pp. 1-17, Front. Microbiol. 13:1053583.
Liu, Fang et al., Complete Genome Sequence of *Escherichia coli* Phage vB_EcoM Sa157lw, Isolated from Surface Water Collected in Salinas, California, Aug. 22, 2019, pp. 1-2, vol. 8 Isssue 34.
Sharma, Manan et al., Effectiveness of Bacteriophages in Reducing *Escherichia coli* O157:H7 on Fresh-Cut Cantaloupes and Lettuce, 2009, pp. 1481-1485, Journal of Food Protection, vol. 72 No. 7.

FORMULATION OF A LYTIC BACTERIOPHAGE COCKTAIL FOR BIOCONTROL OF SHIGA TOXIN-PRODUCING *ESCHERICHIA COLI* STRAINS

CROSS-REFERENCE

The present application claims priority to U.S. Provisional Patent Application Ser. No. 63/599,751 filed Nov. 16, 2024, the content of which is expressly incorporated herein by reference.

SEQUENCE LISTING

The instant application contains a Sequence Listing XML required by 37 C.F.R. § 1.831 (a) which has been submitted in XML file format via the USPTO patent electronic filing system and is hereby incorporated by reference in its entirety. The XML file was created on Jan. 22, 2025 is named Sequence_Listing_B-002023.xml and has 434 KB bytes.

BACKGROUND OF THE INVENTION

Field of Invention

The present disclosure provides for a combination of bacteriophages from various environmental sources combined to produce a phage mixture targeting Shiga-toxin-producing *Escherichia coli* strains. Techniques and methods of production and use of the phage combinations are also provided.

Background

Shiga toxin-producing *E. coli* (STEC) strains—commensal to the gastrointestinal tract of ruminant animals, particularly cattle—have been linked to numerous foodborne outbreaks, causing approximately 265,000 illnesses, 3,600 hospitalizations, and 30 deaths every year in the United States (National Enteric Disease Surveillance: Shiga toxin-producing *E. coli* (STEC) Annual Report, 2017. Atlanta, Georgia: US Department of Health and Human Services, CDC). More than 30% of these outbreaks are associated with various produce—alfalfa sprouts, iceberg lettuce, and melon—contributing to over 350 identified cases in the United States between 2018 and 2021 (Glaize et al., Int'l J. Food Microbiol., (2021); 347:109196). Besides meat products, global epidemiologic data showed an estimated 147, 000 cases of produce-related foodborne outbreaks reported from 1988 to 2020 contributed to 214 hospitalization and 58 deaths, primarily from the infection of STEC 0157 serogroup (Miyahira & Antunes, Int'l J. Food Microbiol., (2021): 352:109266). In 2018, a massive foodborne outbreak involving 22 states in the United States was linked to consuming *E. coli* O157:H7-contaminated romaine lettuce, causing 46 hospitalizations and 10 cases of the hemolytic uremic syndrome (CDC, 2018. Multistate Outbreaks of *E. coli* O157:H7 Infections Linked to Romaine Lettuce (Final Update)).

The use of antimicrobial intervention is a common practice regulated by regulatory agencies to ensure food safety during production and upon consumers' consumption. Chemical-based antimicrobial treatment, such as chlorination, is commonly used in the produce industry because of its easy access, easy installation, and low cost. However, the major drawback is that frequent application results in the development of bacterial resistance, thus compromising the efficacy of these chemical antimicrobials. Additionally, chemical residuals may also negatively influence the produce quality (Fong et al., Front. Microbiol., (2017); 8:2193) and result in an environmental burden (Kraemer et al., Microorganisms, (2019); 7:180). Therefore, alternative interventional methods are critically needed to ensure microbiological safety in the produce industry with the minimum adverse impact (Mir & Kudva, Zonoses Pub. Health, (2019); 66:1-13).

Phages are bacteria-infecting viruses and are highly diverse and ubiquitous in the ecosystem where their bacterial hosts exist (O'Sullivan et al., Ann. Rev. Food Sci. Tech., (2019); 10:151-72). Phages bind specifically to the receptor proteins on the membrane of the target bacterial cells to initiate the infection (Milho et al., Scientific Rep., (2019); 9:18183; Pinto et al., Crit. Rev. Biotech., (2020); 40:1081-97). Due to the nature of the lytic cycle, phage infection always leads to the lysis of bacterial cells and the release of phage progenies for subsequent infection (Clokie et al., Bacteriophage, (2011); 1:31-45). Moreover, lytic phages can evolve with the constant changing of their bacterial hosts to combat the potential development of phage resistance. Consequently, we sought to examine a phage-based intervention technology to specifically address the challenge of STEC contamination using biological, genomic characterization, and in vitro antimicrobial tests to formulate a phage cocktail that can effectively control *E. coli* O157:H7 using environmentally isolated phages.

SUMMARY OF THE INVENTION

Provided herein are bacteriophage cocktails, wherein the cocktail comprises at least two isolated bacteriophages that target *Escherichia coli* selected from the group consisting of: (1) a bacteriophage having a genome sequence at least 95% identical to G1571w (PTA-127634)(SEQ ID NO:1); (2) a bacteriophage having a genome sequence at least 95% identical to Sa1571w (PTA-127635))(SEQ ID NO:2); and (3) a bacteriophage having a genome sequence at least 95% identical to Elw (PTA-127636)(SEQ ID NO:3). In a particular embodiment, the bacteriophage cocktail comprises a bacteriophage having a genome sequence at least 95% identical to G1571w (PTA-127634) and a bacteriophage having a genome sequence at least 95% identical to Elw (PTA-127636). In another particular embodiment, the bacteriophage cocktail comprises a bacteriophage having a genome sequence at least 95% identical to G1571w (PTA-127634)(SEQ ID NO:1), a bacteriophage having a genome sequence at least 95% identical to Sa1571w (PTA-127635) (SEQ ID NO:2), and a bacteriophage having a genome sequence at least 95% identical to Elw (PTA-127636)(SEQ ID NO:3). In a specific embodiment, the bacteriophage cocktail contains bacteriophage G1571w (PTA-127634), bacteriophage Sa1571w (PTA-127635); and bacteriophage Elw (PTA-127636).

A method of treating a surface, comprising administering any of the bacteriophage cocktails recited above to the surface. In some embodiments, the surface is a plant or plant part, such as a seed, pre-harvest crop or leafy vegetable (e.g., lettuce or spinach). In other embodiments, the surface is a food contact surface, such as food packaging or a food processing surface.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the claims. Features and advantages of the present invention are referred to in the following detailed description, and the accompanying drawings of which:

STATEMENT OF DEPOSIT

Figure 1:
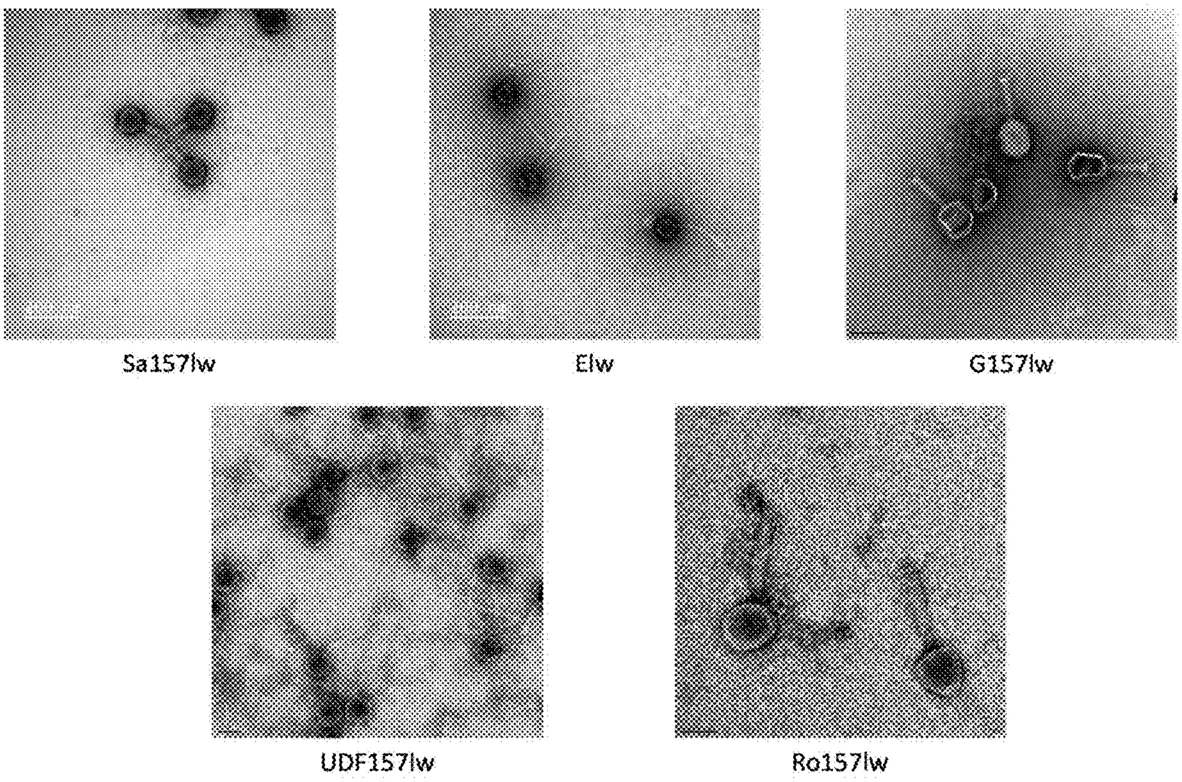
FIG. 1 provides transmission electron microscopic images for the lytic phages used in this study. Phages Sa1571w, G1571w, and Ro1571w show that the morphology belongs to the family Myoviridae (long and contractile tail). Phages Elw and UDF1571w belong to the family Siphoviridae (long and non-contractile tail).

Strains representative of the inventions disclosed herein were deposited on Sep. 13, 2023 under the terms of the Budapest Treaty with the American Type Culture Collection (ATCC). A representative bacteriophage G1571w (*Tequatrovirus* genus under the Straboviridae family) was deposited under ATCC Reference No. PTA-127634. A representative bacteriophage Sa1571w (*Kuttervirus* genus under the Ackermannviridae family) was deposited under ATCC Reference No. PTA-127635. A representative bacteriophage Elw (*Tequintavirus* genus under the Demerecviridae family) was deposited under ATCC Reference No. PTA-127636. The microorganism deposits were made under the provisions of the "Budapest Treaty on the International Recognition of the Deposit of Microorganisms for the Purposes of Patent Procedure". All restrictions on the availability to the public of these deposited microorganisms will be irrevocably removed upon issuance of a United States patent based on this application. For the purposes of this invention, any bacteriophage strains having the identifying characteristics of PTA-127634, PTA-127635, or PTA-127636, including subcultures and variants thereof which have the identifying characteristics and activity as described herein are included.

DETAILED DESCRIPTION OF THE INVENTION

Lytic phages are innovative antimicrobials that can target bacterial pathogens without killing background flora (Mohammad et al., Int'l J. Food Microbiol., (2019), 289:57-63). Most importantly, they do not contribute to the development of antibiotic resistance in the target bacteria, commonly seen from current chemical interventions (Moye et al., J. Food Safety, (2020), 40:e12763). These phages can combat antibiotic-resistant strains in the agricultural field (Kahn et al., Ann. New York Acad. Sci., (2019), 1441:31-9) and minimize any environmental burden on subsequent terrestrial surroundings (O'Sullivan, et al., supra). Furthermore, FDA has authorized several commercial phage products as Generally Recognized As Safe (GRAS) since 2006 to ensure safe application directly on ready-to-eat food or during food production (Vikram et al., J. Food Protection, (2020), 83:668-76). Therefore, phage-based technology sheds new light on developing a green and novel antimicrobial intervention measurement. It also helps provide the resolution of antibiotic resistance in the food industry.

The instant disclosure focuses on the formulation of phage cocktails, including the three-phage cocktail of G1571w+Sa1571w+Elw, from five different lytic phages isolated from agricultural-associated environments. During the formulation process, we used whole-genome sequencing technology to ensure the diversity of phages and the novelty compared to the reference phages published in the National Center for Biotechnology Information (NCBI). Additionally, sequencing technology is used to thoroughly screen the unwanted genes, such as toxin, lysogenic, and antibiotic-resistant genes, in the phage genomes that could be potential threats to human health and jeopardize the phage application.

As detailed herein, phage G1571w is included in each version of the cocktails, as it showed the most significant antimicrobial activity against *E. coli* O157:H7 as a single phage and the largest burst size among all the phages in the cocktail. Phage cocktails of the present disclosure show a wide host range capable of infecting other top 6 non-O157 STEC and provide additional mitigating effects against bacterial pathogens other than *E. coli* O157:H7. G1571w was isolated from the compost sample of food scraps and yard trimming, and phages Sa1571w and Elw were isolated from produce pre-harvest surface water and municipal sewage water samples, respectively. Geographical differences in the source of isolation ensure the natural diversity of the phages besides the genomic variety. Many studies showed that lytic phages were highly associated with the presence of their bacterial host (Liao et al., PLoS One, (2018), 13:e0190534; Wang et al., Can. J. Microbiol., (2015), 61:467-75). Therefore, the samples with high animal contaminations, such as animal feces and sewages, are usually favorable for isolating phages specific to foodborne pathogens, like *E. coli* O157:H7. However, two (G1571w and Sa1571w) of three phages in this phage cocktail were from the environmental samples with low animal contamination, making our phages, particularly G1571w, unique for developing a phage cocktail.

The instant disclosure provides in vitro antimicrobial activities of various phage combinations to determine whether combining different phages had facilitating, neutral or antagonistic effects compared to that of fewer phages combined. As a result, a cocktail comprising phages G1571w and Elw was an effective combination among all possible two-phage combinations in reducing single *E. coli* O157:H7, contributing to non-detectable bacterial level, with 7 log reduction (99.99999% reduction) at a 6-h time point. Furthermore, a three-phage cocktail, G1571w+Sa1571w+Elw, demonstrated stronger in vitro antimicrobial effects compared to the two-phage cocktail (G1571w+Elw) at 24-h treatment, with 1.1 log more reduction (92.3% reduction). Surprisingly, the three-phage cocktail was able to mitigate a single *E. coli* O157:H7 strain and a four-strain *E. coli* O157:H7 cocktail more than a commercial phage cocktail in vitro after 24-h treatment by 6 log (99.9999% reduction) and 3.4 log reduction (99.96% reduction), respectively.

Further disclosed herein are methods of treating various known contamination sources, such as agricultural irrigation water, commonly susceptible to external contamination and associated with various foodborne outbreaks (Lacombe et al., Front. Food Sci. Tech., (2022), 2:1068690), was used to determine the efficacy of our phage cocktail. The phage cocktail, G1571w+Sa1571w+Elw, formulated in this study continued to mitigate a four-strain *E. coli* O157:H7 spiked in agricultural well water throughout 24-h treatment, with a maximum 1.3 log reduction (95% reduction) at a 6-h time point. Moreover, the efficacy of the phage cocktail, G1571w+Sa1571w+Elw, was superior to a commercial phage cocktail product in controlling the pathogenic bacteria. Furthermore, a previous study showed that the single phage Sa1571w reduced *E. coli* O157:H7 on mung bean seeds by 1.1 log (92.3% reduction). Based on the current in vitro results, the phage cocktails of the instant disclosure provide surprisingly better antimicrobial efficacy than Sa1571w alone. Phage cocktails of the instant disclosure may have significant versatile application values with the potential GRAS approval for the application in animal feeds, directly on food, food-processing environments, and food packaging, in addition to the pre-harvest agricultural environment, such as in-farm application and irrigation treatment.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of genetics useful for selected aspects of the invention include: Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted. This invention teaches methods and describes tools for producing bacteriophage cocktails to target STEC.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g and all values within that range, whether specifically stated or not.

The term "consisting essentially of" excludes additional method (or process) steps or composition components that substantially interfere with the intended activity of the method (or process) or composition and can be readily determined by those skilled in the art (for example, from a consideration of this specification or practice of the invention disclosed herein).

The term "antimicrobial activity", and grammatical variations thereof, refers to the ability of a composition of the present invention to impede growth of a microorganism, or kill a microorganism, when present in an effective amount. "Antibacterial" refers specifically to the capability of a composition to impede growth of, or kill, bacteria when present in an effective amount.

The term "controlling microbial growth", as used herein, denotes any activity for completely inhibiting or at least reducing the growth of bacteria (such as *E. coli*) in a given environment. The term "inhibiting", as used herein, is to be understood as not only to include the prevention of further growth of but also to killing of any given bacteria. The term "reducing", as used herein, denotes any decrease in a bacteria's growth (or growth rate), for example, a decrease of at least 5%, 10%, 15%, 20%, 25%, 30%, 40%, 50%, 60%, 70%, 80%, 85%, 90% or 95% as compared to control conditions (i.e. in the absence of antimicrobial agents according to the present invention). Levels of reduction or inhibition of bacterial growth can be indicated by log reduction, for example 1 log reduction=90% reduction (e.g. bacterial counts dropped from 100 CFU to 10 CFU); 1.1 log reduction=92.3% reduction (e.g. bacterial Bacterial counts dropped from 13 CFU to 1 CFU); 1.3 log reduction=95% reduction (e.g. bacterial counts dropped from 20 CFU to 1 CFU); 2 log reduction=99% reduction (e.g. bacterial counts dropped from 100 CFU to 1 CFU); 3.4 log reduction=99.96% reduction (e.g. bacterial counts dropped from 2,500 CFU to 1 CFU); 6 log reduction=99.9999% reduction (e.g. bacterial counts dropped from 1,000,000 CFU to 1 CFU); 7 log reduction=99.99999% reduction (e.g. bacterial counts dropped from 10,000,000 CFU to 1 CFU).

The term "effective amount" of a bacteriophage mixture composition provided herein refers to the amount of the composition capable of performing the specified function for which an effective amount is expressed. The exact amount required can vary from composition to composition and from function to function, depending on recognized variables such as the compositions and processes involved. An effective amount can be delivered in one or more applications. Thus, it is not possible to specify an exact amount, however, an appropriate "effective amount" can be determined by the skilled artisan via routine experimentation.

The term "fresh produce" as used herein refers generally to farm-produced fruits and vegetable crops including, but not limited to fruit and vegetable crops such as e.g., lettuce, spinach, cilantro, cabbage, almonds, cucumbers, cantaloupes, etc.

A "phage cocktail" as used herein refers to a. composition comprising two or more bacteriophages combined according to the methods of the instant invention which can provide a control for at least one strain of *E.coli* when administered to an organic or inorganic surface.

The term "plant" includes whole plants, plant organs, progeny of whole plants or plant organs, embryos, somatic embryos, embryo-like structures, protocorms, protocorm-like bodies (PLBs), and suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seeds (including embryo, endosperm, and seed coat) and fruit (the mature ovary), plant tissue (e.g., vascular tissue, ground tissue, and the like) and cells (e.g., guard cells, egg cells, trichomes and the like).

The terms "G1571w" and "PTA-127634" refer to bacteriophage of the *Tequatrovirus* genus under the Straboviridae family having the biological and genetic characteristics of the virus deposited under ATCC Reference No. PTA-127634. The terms include genetically modified versions of this virus. A representative genome is available as GenBank accession #OK331996 and this sequence is incorporated in its entirety (SEQ ID NO: 1).

The terms "Sa1571w" and "PTA-127635" refer to bacteriophage of the *Kuttervirus* genus under the Ackermannviridae family having the biological and genetic characteristics of the virus deposited under ATCC Reference No. PTA-127635. The terms also include genetically modified versions of this virus. A representative genome is available as GenBank accession #OK322699 and this sequence is incorporated in its entirety (SEQ ID NO:2).

The terms "Elw" and "PTA-127636" refer to bacteriophage of the *Tequintavirus* genus under the Demerecviridae family having the biological and genetic characteristics of the virus deposited under ATCC Reference No. PTA-127636. The terms also include genetically modified versions of this virus. A representative genome is available as GenBank accession #OR621298 and this sequence is incorporated in its entirety (SEQ ID NO:3).

As disclosed herein, a plurality of individually isolated phage was obtained from diverse environmental sources. Members of the same bacteriophage species detailed herein (e g., PTA-127634, PTA-127635, and PTA-127636) have not been shown to reside together in nature, but can be collected from diverse environmental locations, including soil, water treatment plants, raw sewage, sea water, lakes, rivers, streams, standing cesspools, animal fecal matter, organic substrates, biofilms, or medical/hospital sources. The present disclosure includes phage mixtures produced by combining phage of the same species as reported herein, or phages with genomes having 95.0%, 95.1%, 95.2%, 95.3, 95.4%, 95.5%, 95.6%, 95.7%, 95.8%, 95.9%, 96.0%, 96.1%, 96.2%, 96.3%, 96.4%, 96.5%, 96.6, 96.7%, 96.8%, 96.9, 97.0%, 97.1%, 97.2% 97.3%, 97.4%, 97.5%, 97.6%, 97.7, 97.8% 97.9%, 98.0%, 98.1%, 98.2%, 98.3%, 98.4, 98.5%, 98.6%, 98.7%, 98.8%, 98.9%, 99.1%, 99.2%, 99.3% 99.4%, 99.5%, 99.6%, 99.7%, 99.8%, 99.9%, or 100% genomic identity to SEQ ID NO:1, SEQ ID NO:2, and/or SEQ ID NO:3.

Individual phage utilized in the instant disclosure can be purified by any purification technique known in the art, including, but not limited to cesium chloride gradient ultracentrifugation, removing cesium chloride, differentiation filtration, column chromatography and phase partition chromatography.

Any of these compositions described herein can be used to treat bacterial contamination in an environment, or on specific surfaces. Exemplary environments and surfaces that can be treated include, but are not limited to, meat processing facilities, fresh produce, unharvested crops (e.g., lettuce), sprayed or dipped leafy greens (such as mung bean sprouts and lettuce), irrigation water, ready-to-eat foods, seeds (such as mung bean seeds), controlled environment agriculture systems, biofilms, food-contact surfaces, and water troughs.

The embodiments illustratively disclosed herein suitably may be practiced in the absence of any element [e.g., method (or process) steps or composition components)] which is not specifically disclosed herein. Thus, the specification includes disclosure by silence. Written support for a negative limitation may also be found through the absence of the excluded element in the specification, known as disclosure by silence.

Having generally described this invention, the same will be better understood by reference to certain specific examples, which are included herein to further illustrate the invention and are not intended to limit the scope of the invention as defined by the claims.

EXAMPLES

Example 1

Isolation and characterization of candidate bacteriophages *Escherichia* phage "Ro1571w", "G1571w", "UDF1571w", "Sa1571w", and "Elw" were previously isolated with *E. coli* O157:H7 (RM18959, ATCC 43888, or ATCC 35150) from various environmental samples, such as non-fecal compost (Ro1571w and G1571w), bovine feces (UDF1571w), surface water in a produce-growing area (Sa1571w), and sewage water (Elw). Phage propagation was performed by mixing 50 μL phage lysate (~$10^9$ PFU/mL) with 45 mL of the log-phase bacterial host culture in tryptic soy broth (TSB; Becton Dickinson, Sparks, MD) and $CaCl_2$ at 10 mM for incubation at 37 °C for 20 hours. The propagated phages were filtered through a 0.22-μm filter membrane, following centrifugation at 8,000×g for 10 minutes before downstream analysis. A proprietary commercial phage, ECOSHIELD, was used to compare with our developed phage cocktails.

A collection of the top 6 non-O157 STEC—the serogroups O26, O45, O103, O111, O121, O145-*E. coli* O157:H7 and generic *E. coli* strains were obtained from the Produce Safety and Microbiology (PSM) Research Unit at the U.S. Department of Agriculture (USDA), Agricultural Research Service (ARS), Western Regional Research Center, Albany, CA, USA for this study. *E. coli* O157:H7 (ATCC 43888) was used for propagation and quantification of Elw, Sa1571w, and G1571w, *E. coli* O157:H7 (RM 18959) was used for Ro1571w, and *E. coli* O157:H7 (ATCC 35150) was used for UDF1571w. Fresh bacterial culture was prepared by inoculating 10 mL TSB with 1 μL loopful of each strain for overnight incubation at 37 °C before use.

The phage cocktail formulation started with the determination of phage varieties based on morphological and genomic characterizations. Additionally, the whole-genome sequencing data of individual phages was used to ensure no toxin genes or lysogenic genes were encoded in each phage genome for the safety of the application. Later, the bacterial host range and productive infection of individual phages against the top six non-O157 and 0157 serogroups of STEC were obtained as a preliminary antimicrobial criterium. The phages with a wide host range were promising for cocktail development; therefore, phage G1571w was selected as the core phage for phage cocktail development.

All selected phages were purified through a CsCl gradient and subsequently subjected to DNA extraction and DNA library preparation prior to sequencing as previously described (Liao et al., Fronts. Microbiol., (2022) 13:1053583). Later, the samples were loaded to a MiSeq Reagent Kit v2 (500-cycle) and sequenced on the MiSeq platform (Illumina, San Deigo, CA, USA). The raw 2×250-bp paired-end reads were subjected to quality control via FASTQC and Trimmomatic with the setting of Q30. De novo assembly was conducted on the resulting quality reads using Unicycler v0.5.0, followed by annotation via the Prokka pipeline Galaxy 1.13 (Seeman, T., Bioinformatics, (2014); 30:2068-69) with default settings. Subsequently, the annotation was manually curated with Universal Protein Resource (UniProt) database (Bairoch et al., Nucl. Acids Res., (2005); 33: D154-D159) using Geneious (v11.0.3, Biomatters, New Zealand). tRNAscan-SE (v2.0) server was used to confirm the predicted tRNAs in the phage genome (Lowe & Chan, Nucl. Acids Res., (2016); 44:W54-W57). The final annotated sequences were deposited in National Center for Biotechnology Information (NCBI) database. The presence of antibiotic-resistance genes and virulence genes in the phage genome was identified using the ResFinder 4.1 webserver (Florensa et al., Microbial Genomics, (2022); 8:000748) and VirulenceFinder (Malberg Tetzchner et al., J. Clin. Microbiol., (2020); 58:e01269-01220).

Purified phages were purified using a CsCl gradient and subsequently subjected to negative staining as previously described (Liao et al., 2022 I, supra). The specimens were then examined in a transmitted electron microscope (FEI Tecnai $G_2$).

The host range tests for the phages included in this study were conducted against non-pathogenic *E. coli, E. coli* O157:H7, top six non-0157 STEC, and various *Salmonella* strains using a spot test assay as previously described (Liao et al., Antibiotics, (2019), 8:74). Briefly, each bacterial culture with 100 μL was mixed with 50% molten TSA and then poured into a Petri dish containing 10-mL bottom TSA. After solidifying, 5 μL of each phage at approximately 7 log PFU/mL was spotted on the plate, followed by incubation at 37 °C. The phage-sensitive strains were subsequently tested with productive infection of each phage using the efficiency of plating (EOP) assay described in a previous study (Liao et al., J. Virology, (2011), 85:6567-78). Briefly, fresh cultures were prepared in TSB at 37 °C overnight and used for quantification of Sa1571w using double-layer plaque assay with diluted phage lysate with four successive dilutions (10-3 to 10-7). The plates were incubated at 37 °C for 18 h. The experiment was conducted in 3 replications. Generally, a high phage-producing efficiency had EOP of 0.5 or more; a medium-producing efficiency had EOP above 0.1 but below 0.5; a low-producing efficiency had EOP between 0.001 and 0.1; inefficient phage production was any value lower than 0.001.

Growth factors of the phages included in the phage cocktail were determined using *E. coli* O157:H7 (ATCC 43888) based on the previous method with subtle modification (Liao et al., Microbiol. Spectrum, (2022 II), 10:e02220-02221). Briefly, 0.2 mL of fresh overnight culture in TSB was sub-cultured in sterile 19.8 mL of TSB and incubated for 2 h at 37 °C to reach the log phase of bacterial growth. Later, a single phage was added to the log-phase bacterial solution (MOI of 0.01) with $CaCl_2$ at 10 mM and incubated at 37 °C for 10 min, allowing phage adsorption onto the bacterial membranes. The phage-bacterial mixture was centrifuged at 10,000 xg for 5 min at 4 °C to discard the supernatant. After washing, the bacterial pellet was resuspended with 20 mL of fresh TSB before further 10-fold dilution (0.3 mL of resuspension in 29.7 mL of TSB). The sample was then incubated at 37 °C for a specific period (varied by different phages). Meanwhile, the phage-infected bacterial cells were quantified before incubation (time 0) by mixing 50 μL of the 30-mL phage-bacterial mixture (no filtration) with 100 μL of fresh overnight bacterial culture for a double-layer plaque assay. Subsequently, a 1 mL phage-bacterial mixture was obtained from the selected time points and filtered using a 0.22-μm filter membrane. The phage titers at each time point were determined using the double-layer plaque assay. The experiment was conducted in three replications to estimate the latent period and burst size of the selected phages (G1571w & Elw).

A quick antimicrobial activity screening on various two-phage combinations from the first included phages G1571w, Sa1571w, UDF1571w, and Ro1571w was conducted using a spectrophotometer (Elw phage was isolated later to increase the morphological variety). Detailed information regarding the experiment and assay used in the formulation step is described below.

Results and Discussion

Figure 2:
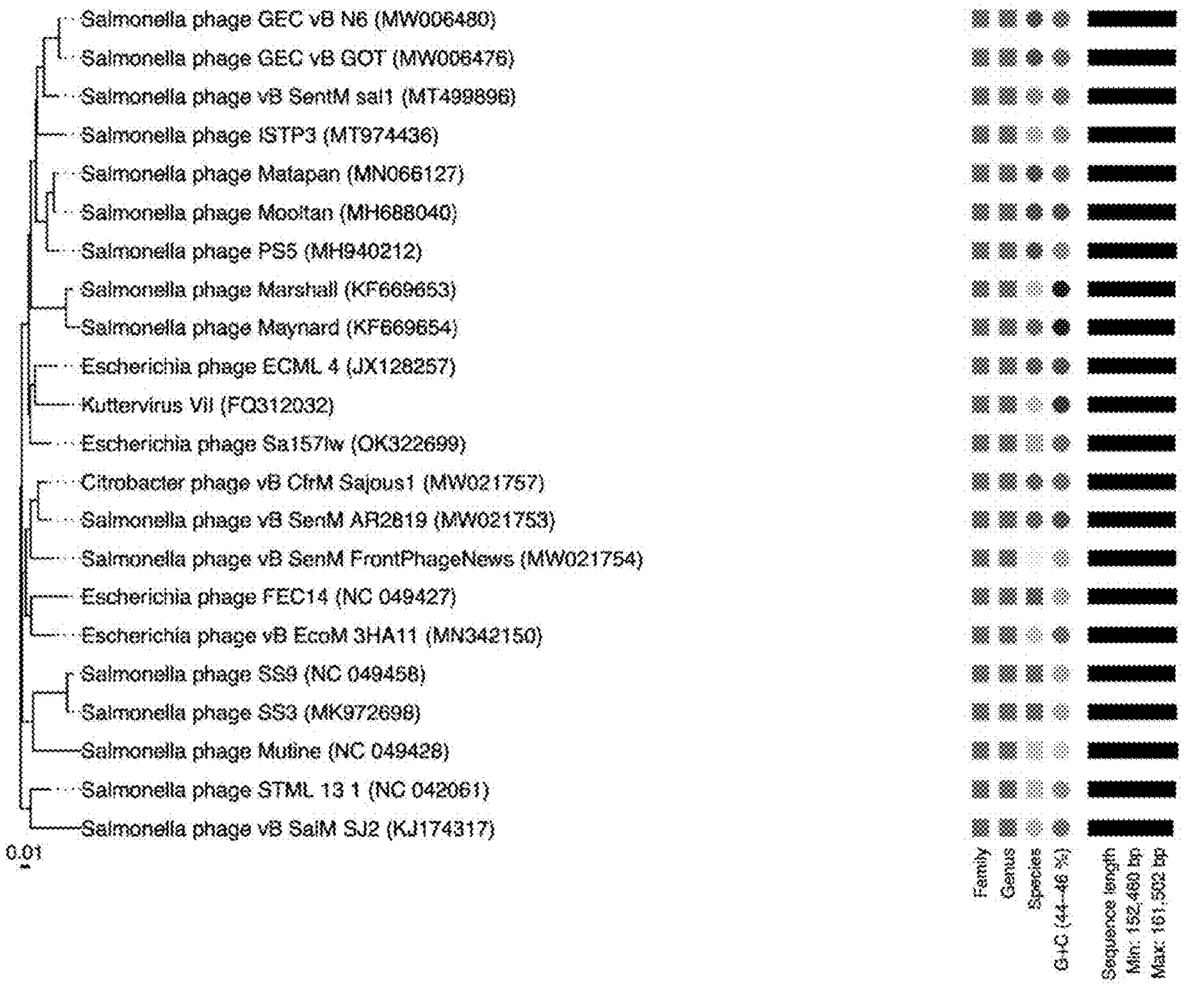
FIG. 2 provides a graphic representation of phylogenetic analysis of whole-genome sequences of Sa1571w and closely related reference phages belonging to the Ackermannviridae family at the nucleotide sequence level using VICTOR (formula d0). Annotations, including family, genus, and species cluster proposed by VICTOR, genomic G+C content, and sequence length, are given to the right-hand side of the tree.
Figure 3:
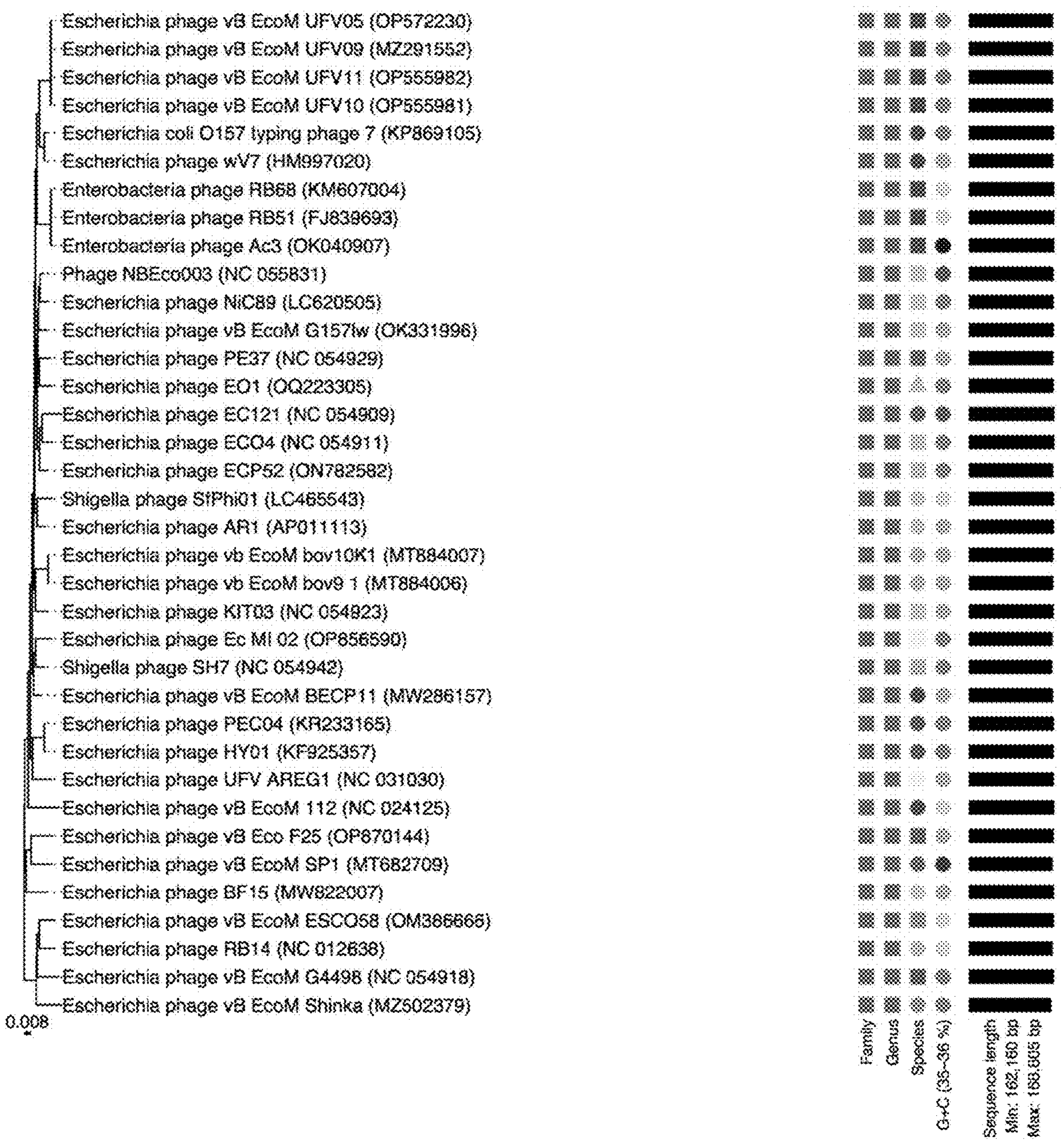
FIG. 3 provides a graphic representation of phylogenetic analysis of whole-genome sequences of G1571w and closely related reference phages belonging to the Straboviridae family at the nucleotide sequence level using VICTOR (formula d0). Annotations, including family, genus, and species cluster proposed by VICTOR, genomic G+C content, and sequence length, are given to the right-hand side of the tree.
Figure 4:
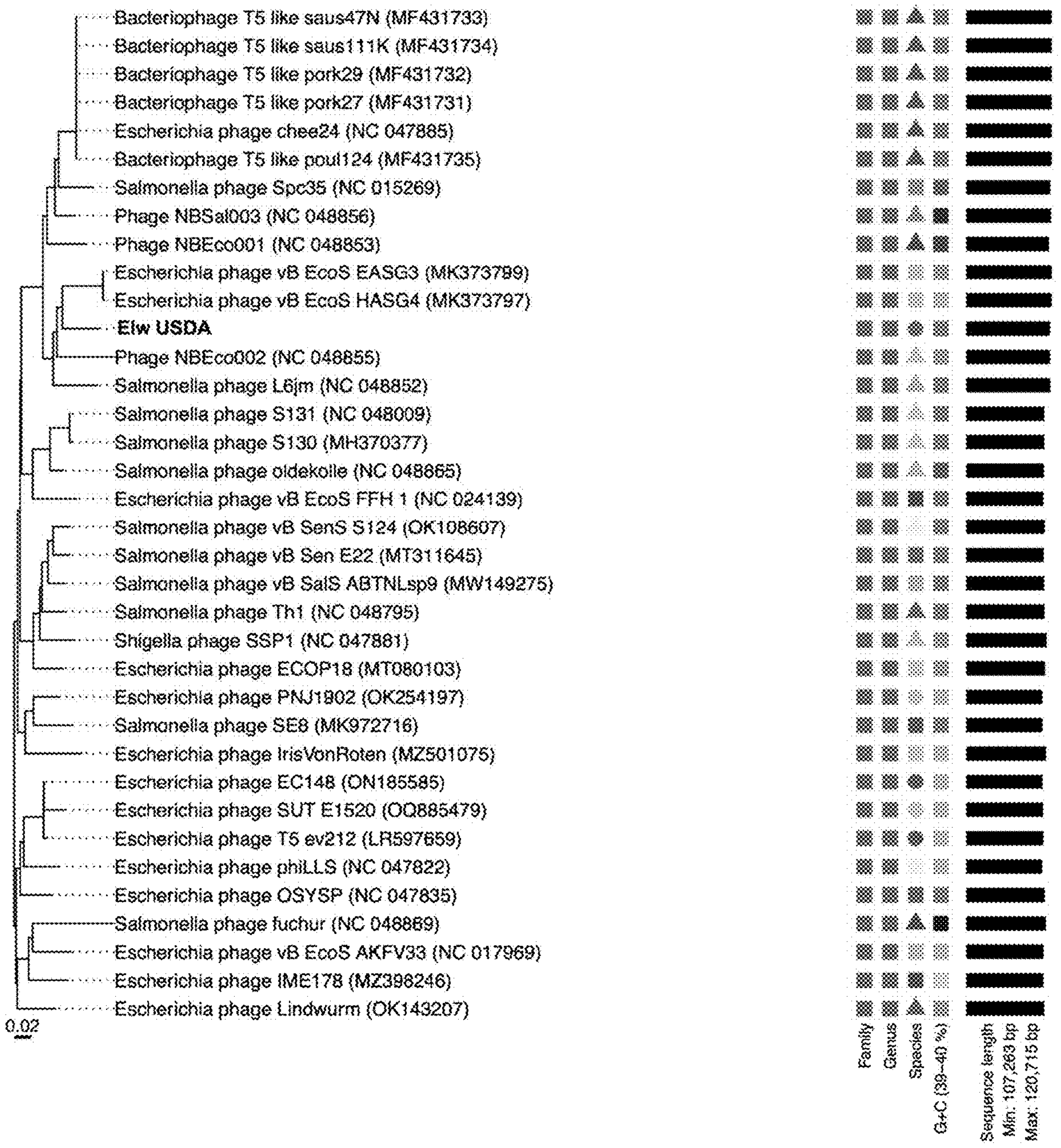
FIG. 4 provides a graphic representation of phylogenetic analysis of whole-genome sequences of Elw and closely related reference phages belonging to the Demerecviridae family at the nucleotide sequence level using VICTOR (formula d0). Annotations, including family, genus, and species cluster proposed by VICTOR, genomic G+C content, and sequence length, are given to the right-hand side of the tree.

Five lytic phages isolated from various environmental samples are in genetic variation (Table 1) and morphological differences (FIG. 1). Although all phages Ro1571w, Sa1571w, and G1571w have a long and contractile tail showing the Myoviridae morphology, their genomic taxonomies vary. The sequencing results show that G1571w and Sa1571w have larger genome sizes, classified into the *Tequatrovirus* genus under the Straboviridae family and the *Kuttervirus* genus under the Ackermannviridae family, respectively. Ro1571w belongs to the *Wifcevirus* genus, a new phage classification without an assigned family. UDF1571w is genomically classified in the *Rogunavirus* genus under the Drexlerviridae family and contains a long, non-contractile tail demonstrating the Siphoviridae morphology. Elw also has the Siphoviridae morphology and the taxonomy belonging to the *Tequintavirus* genus under the Demerecviridae family. The phylogenetic analyses show that phages Sa1571w, G1571w, and Elw are at their own leaf (FIG. 2, FIG. 3, FIG. 4), indicating the nucleotide sequence novelty of these three phages among the close-related reference phages.

TABLE 1

Genomic classification of lytic phages isolated from different environmental samples.

| Phage ID | Isolation sources | Genome size | Family | Genus |
|---|---|---|---|---|
| Elw | Sewage | 118,119 bp | Demerecviridae | *Tequintavirus* |
| Ro157lw | Non-fecal compost | 72,179 bp | not classified | *Wifcevirus* |
| UDF157lw | Bovine feces | 46,604 bp | Drexlerviridae | *Rogunavirus* |
| Sa157lw | Surface water | 155,887 bp | Ackermann-viridae | *Kuttervirus* |
| G157lw | Non-fecal compost | 167,170 bp | Straboviridae | *Tequatrovirus* |

Among all five phages, G1571w has a broader host range targeting different STEC serogroups, including 045, 0103, and 0145, than the other phages in addition to infecting *E. coli* O157:H7 strain (Table 2; H=host strain used for the phage isolation and R=the bacterial strain is resistant to the phage). For Table 2, the EOP was calculated by the ratio of phage titer on a test bacterium versus the primary bacterial host. High production efficiency is EOP≥0.5, medium production efficiency is 0.5>EOP≥0.1, low production efficiency is 0.1>EOP>0.001, and the inefficiency of phage production is EOP 0.001. H means the host strain used for the phage isolation, and R means the bacterial strain is resistant to the phage infection. Additionally, these phages express a variety of productive infections against different *E. coli* O157:H7 strains. The phenomenon is favorable as the development of a phage cocktail. Phage Sa1571w was a polyvalent phage able to infect various *Salmonella enterica* serovars: Heidelberg, Saintpaul, Agona, *Typhimurium*, and *Enteritidis* (Liao et al., 2022 I, supra). However, these phages show a wide infection capability against generic *E. coli* strain. Growth factors—the latent period and burst size—were examined on the three phages included in the cocktail. The results show that phages G1571w and Sa1571w have similar latent periods of 30 min, whereas Elw has around 40 min (Table 3). Additionally, G1571w has the largest burst size of approximately 1,220 PFU/CFU among all the phages.

TABLE 2

Host range and efficiency of plating (EOP*) for phages against various top 6 non-O157, *E. coli* O157:H7, and non-pathogenic *E. coli* strains.

| | Tested phages | | | | |
|---|---|---|---|---|---|
| Strain Ref. No. | Elw | Ro157lw | UDF157lw | Sa157lw | G157lw |
| STEC O26, O111, and O121 | R | R | R | R | R |
| *E. coli* O45:H16 | R | R | R | R | 0.1 |
| *E. coli* O103:H2 | R | R | R | R | 0.04 |
| *E. coli* O145:H28 (RM13514) | R | R | R | R | 0.14 |
| *E. coli* O157:H7 (RM18959) | 0.88 | H | 1.1 | 0.8 | 0.2 |
| *E. coli* O157:H7 (ATCC 35150) | 1.84 | 0.9 | H | 0.82 | 0.2 |
| *E. coli* O157:H7 (ATCC 43888) | H | 0.8 | <0.001 | H | H |
| Generic *E. coli* ATCC 13706 | 0.52 | <0.001 | 0.06 | R | 0.04 |

TABLE 3

One-step growth curve for phages on *E. coli* O157:H7 (ATCC 43888).

| | Bacterial | Growth factors | |
|---|---|---|---|
| Phage ID | strain | Latent period (min) | Burst size (PFU/CFU) |
| G157lw | ATCC 43888 | 30 | 1220 |
| Sa157lw | ATCC 43888 | 30 | 130 |
| Elw | ATCC 43888 | 40 | 55 |

Example 2

Development of Phage Combinations

A bacterial challenge assay was performed to measure the effects of phages Ro1571w, UDF1571w, and G1571w with different MOIs on the cocktail of two *E. coli* O157:H7 (RM 18959 and *E. coli* O157:H7 (RM 35150) based on bacterial optical density at a wavelength of 600 nm ($OD_{600}$) as previously described with minor change (Zhang et al., Microorganisms, (2021), 9:1527). In brief, fresh bacterial cultures of *E. coli* O157:H7 (ATCC 35150) and *E. coli* O157:H7 (RM18959) were prepared in TSB at 37 °C overnight and further diluted in TSB to $1\times10^6$ CFU/mL. An aliquot of 200 μL diluted bacterial solution containing both bacterial cultures per well was added to a 96-well plate. Later, 10 μL of individual phage with different titers was added to the wells to reach MOIs of 1, 10, and 100; the control group contained only bacterial solution without phage. The reading of $OD_{600}$ was measured using a spectrophotometer (Promega, Madison, WI, USA) at 25 °C every 30 min for 12 h. The experiment was conducted in 3 replications.

A culture of *E. coli* O157:H7 (RM9995) was used to evaluate the antimicrobial activity of an individual and different combinations of phages using the method as previously described with subtle modifications (Liao et al., 2022 II, supra). In brief, the bacterial culture was prepared in 10 ml TSB at 37 °C for 18 h, followed by dilution in LB broth (Invitrogen, Carlsbad, CA, USA) to reach the final concentration at approximately 4 log CFU/ml for the experiment. Single phages or multi-phage cocktails in SM buffer was added to 4-ml bacterial solution at an MOI of 1. For the control, SM buffer, with the same volume as the phage used in the treatment, was also added to 4-ml bacterial solution. Both control and treatment groups were incubated at 25 °C or 30 °C, and the bacterial counts were quantified at various time points (0, 3, 4, 6, 8 or 24 hours) during the incubation. Bacterial counts were quantified on Sorbitol MacConkey agar (SMAC; BD, Franklin Lakes, NJ) overlayered thin TSA (Thin Agar Layer Method, TAL) (Wu, V., Food Microbiol, (2008), 25:735-744).

Agricultural water from a produce-growing area was collected and used to evaluate the efficacy of a phage cocktail formulated in this study versus a commercial phage cocktail in reducing a four-strain *E. coli* O157:H7 cocktail (RM9995, RM18419, RM6416, and ATCC35150). The water sample was filtered through a 0.22-mm membrane before use. Each bacterial culture was prepared in 10 ml TSB at 37 °C overnight. An aliquot of 0.1 ml per bacterial strain was added to a sterile tube to prepare the bacterial cocktail used to inoculate 60-ml water sample at the final concentration of 5 log CFU/ml. The *E. coli* O157:H7-inoculated water was evenly dispensed into three conical tubes (20 ml per tube) and treated separately with a three-phage cocktail and the commercial phages at an MOI=50. The SM butter, with the same volume used for the phage cocktails, was added to a 20-ml bacterial cocktail as the control group. The control and treatment tubes were incubated at 25 °C for 24 h with shaking. Bacterial counts were evaluated for control and treatment groups by plating on duplicated SMAC TAL at 0, 4, 6, and 24 h. The plates were incubated at 24 °C overnight for bacterial quantification.

A quick screening assay was used to determine antimicrobial suppression regarding two-phage combinations of G1571w, Sa1571w, and Ro1571w against a cocktail of *E. coli* O157:H7. The results showed that the order of antimicrobial activities for the combination groups from high to low is G1571w+Sa1571w or G1571w+UDF1571w and G1571w+Ro1571w (results not shown). As a result, the combination with Ro1571w had the worst antimicrobial effect among all and thus was removed. Therefore, phage Ro1571w was excluded from the subsequent antimicrobial activity test in LB broth.

The remaining phages and phage Elw were subjected to in vitro antimicrobial activity tests on two-phage, three-phage, and four-phage combinations to determine "facilitating" (greater efficacy than the most effective constituent phages acting alone), "neutral" (no better or worse than the most effective constituent phages acting alone) or "antagonistic" (lower efficacy than the most effective constituent phages acting alone) effects among different phages used in the same cocktail. First, antimicrobial effects of individual phages of G1571w, Sa1571w, and UDF1571w were tested against *E. coli* O157:H7 (RM11781) at 30 °C for 3 h. The results showed that phage G1571w was the best among the three phages, resulting in more than 6 log bacterial reduction (99.9999% reduction) in 3 h (Table 4; *numbers represent the viable cell counts of bacteria ($\log_{10}$ CFU/ml)). Later, G1571w was used as a core phage in combination with Sa1571w or UDF1571w to test a two-phage cocktail against the same bacterial strain. The results showed that the phage combination of G1571w and Sa1571w had an enhanced antimicrobial effect in mitigating *E. coli* O157:H7 (RM11781) in comparison to phages G1571w and UDF1571w combined (Table 5; *numbers represent the viable cell counts of bacteria ($\log_{10}$ CFU/ml)). The other two-phage combination (G1571w and UDF1571w) had a similar bacterial reduction level compared to the single phage G1571w. Furthermore, phage Elw was tested in combination with G1571w to compare with the two-phage cocktail of G1571w and Sa1571w. The results showed that combining phage Elw greatly increased the antimicrobial activity of G1571w alone at 6 h and 24 h of the treatment at 25 °C (Table 6; *numbers represent the viable cell counts of bacteria ($\log_{10}$ CFU/ml); $^{\alpha}$O represents a non-detectable bacterial count). Additionally, the combination of G1571w and Elw had better antimicrobial activity than G1571w and Sa1571w combined in LB broth.

TABLE 4

In vitro antimicrobial activities of individual phages.

| | | Phage treatment | | |
|---|---|---|---|---|
| Time | Control | G157lw | Sa157lw | UDF157lw |
| 3 h | 8.7* | 2.4 | 3.9 | 4.0 |

TABLE 5

In vitro antimicrobial activities of two-phage combinations.

| | | Phage treatment | |
|---|---|---|---|
| Time | Control | G157lw + Sa157lw | G157lw + UDF157lw |
| 3 h | 8.8* | 2.2 | 2.3 |

TABLE 6

In vitro antimicrobial activities of two-phage combinations.

| | | Treatment groups | | |
|---|---|---|---|---|
| Time | Control | G157lw | G157lw + Elw | G157lw + Sa157lw |
| 0 h | 7.0* | 7.0 | 7.0 | 7.0 |
| 4 h | 7.5 | 1.3 | 0.5 | 0.7 |
| 6 h | 8.0 | 1.3 | $0.0^{\alpha}$ | 1.5 |
| 24 h | 8.6 | 6.5 | 1.7 | 5.4 |

Next, phage Elw was added to the combination of G1571w and Sa1571w against *E. coli* O157:H7 (ATCC 35150) at 25 °C for 6 h. The results showed that the three-phage cocktail combination containing Elw reduced more bacterial cells of *E. coli* O157:H7 at 4-h and 6-h time points than the two-phage cocktail (G1571w and Sa1571w), with 1.3 and 1.1 log reduction, respectively (Table 7, *numbers represent the viable cell counts of bacteria ($\log_{10}$ CFU/ml); $^{\alpha}$0 represents a non-detectable bacterial count). Subsequently, the phage cocktail of G1571w, Sa1571w, and Elw was combined with UDF1571w to combat *E. coli* O157:H7 for 24 h; however, no synergistic effect was observed (results not shown). Subsequently, a three-phage cocktail, containing G1571w, Sa1571w, and Elw, was used to compare with ECOSHIELD, the sole commercial phage product tested herein, to mitigate single *E. coli* O157:H7 strain (ATCC 35150) or a four-strain *E. coli* O157:H7 cocktail (ATCC 35150, RM6416, RM9995, and RM18419) at 25 °C for 24 h. The results showed that the three-phage cocktail in this study reduced single *E. coli* O157:H7 to the non-detectable level after 6 h to 24 h of the phage treatment (Table 8, *numbers represent the viable cell counts of bacteria ($\log_{10}$ CFU/ml); $_{\alpha}$0 represents a non-detectable bacterial count). For the commercial phage product, the bacterial growth rebounded starting from 6 h. For the antimicrobial effect against a four-bacteria cocktail, our phage cocktail was able to reduce the bacterial levels from 6.5 log CFU/ml to below 1 log CFU/ml up to 8 h (Table 9, *numbers represent the viable cell counts of bacteria ($\log_{10}$ CFU/ml)). Although bacteria grew back after 24 h of treatment, the bacterial levels mitigated by our three-phage cocktail were significantly lower than that caused by the commercial phage product by more than 3 log.

TABLE 7

In vitro antimicrobial activities of two-phage and three-phage combinations.

| Time | Control | Phage treatment G157lw + Sa157lw | G157lw + Sa157lw + Elw |
|---|---|---|---|
| 0 h | 6.4* | 6.4 | 6.4 |
| 4 h | 7.3 | 1.6 | 0.3 |
| 6 h | 8.1 | 1.1 | $0^a$ |

TABLE 8

In vitro antimicrobial activities of a three-phage combination and a commercial phage product (ECOSHIELD) against a single *E. coli* O157:H7 strain.

| | Phage treatment | | |
|---|---|---|---|
| Time | Control | G157lw + Sa157lw + Elw | ECOSHIELD |
| 0 h | 6.4* | 6.4 | 6.4 |
| 4 h | 6.6 | 2.2 | 1.7 |
| 6 h | 6.8 | $0^a$ | 1.9 |
| 24 h | 8.5 | $0^a$ | 6 |

TABLE 9

In vitro antimicrobial activities of a three-phage combination and a commercial phage product against a four-strain *E. coli* O157:H7 cocktail (ATCC 35150, RM18419, RM6416, and RM9995).

| | Phage treatment | | |
|---|---|---|---|
| Time | Control | G157lw + Sa157lw + Elw | Commercial phage |
| 0 h | 6.5* | 6.5 | 6.5 |
| 4 h | 7.0 | 3.1 | 2.8 |
| 6 h | 7.6 | 0.9 | 2.3 |
| 8 h | 8.1 | 0.9 | 2.5 |
| 24 h | 8.6 | 3.2 | 6.6 |

The efficacy of phage application was determined in treating agricultural well water inoculated with a four-strain *E. coli* O157:H7 cocktail. The results showed that using the MOI of 50, the 3-phage cocktail continued to mitigate the bacterial levels examined at 4 and 6 h time points at 25 °C, with a maximum reduction of 1.3 log compared to the control group. Although the *E. coli* O157:H7 bounced back at 24 h, the treatment with the 3-phage combination kept the bacterial level lower than the control group by 0.6 log and that treated with a commercial phage. Besides the antimicrobial activities, some nutrients might be present in the commercial phage product to facilitate bacterial growth in the water sample (Table 10, *numbers represent the viable cell counts of bacteria ($\log_{10}$ CFU/ml)).

TABLE 10

Phage application of the 3-phage cocktail and a commercial phage product against a four-strain *E. coli* O157:H7 cocktail (ATCC 35150, RM18419, RM6416, and RM9995) spiked in agricultural water at 25° C. for 24 h.

| Time | Control | G157lw + Sa157lw + Elw | Commercial phage |
|---|---|---|---|
| 0 h | 5.0* | 5.0 | 5.0 |
| 4 h | 5.0 | 4.0 | 5.0 |

TABLE 10-continued

Phage application of the 3-phage cocktail and a commercial phage product against a four-strain *E. coli* O157:H7 cocktail (ATCC 35150, RM18419, RM6416, and RM9995) spiked in agricultural water at 25° C. for 24 h.

| Time | Control | G157lw + Sa157lw + Elw | Commercial phage |
|---|---|---|---|
| 6 h | 5.1 | 3.8 | 4.4 |
| 24 h | 5.7 | 5.1 | 6.8 |

Experiments subjected to statistical analysis were conducted in three individual replications. The quantification of bacteria and phages was calculated as CFU/g and PFU/mL, respectively, with logarithmical conversion for statistical analysis.

Example 3

Antimicrobial Activity of Phage Cocktails Against Pathogenic *E. coli* Other than STEC The susceptibility of the tested strains, such as EPEC, ETEC, and EIEC, to phage cocktails, was determined using a spot test assay. Later, the susceptible strains with strong lysis were used to determine EOP. If the tested strains showed medium to high EOP with the 3-phage cocktail, further experiments would be used for an in vitro antimicrobial activity test.

The results showed that the 3-phage cocktail (G1571w+Sa1571w+Elw) did not infect EIEC or EPEC and rendered weak antimicrobial activity against two ETEC strains of the serogroups 025 and 0117, with low efficiency and inefficiency, respectively (Table 11; the EOP was calculated by the ratio of phage titer on a test bacterium versus the primary bacterial host. *E. coli* O157:H7 ATCC43888 was used as host strain for EOP. High production efficiency is EOP≥0.5, medium production efficiency is 0.5>EOP≥0.1, low production efficiency is 0.1>EOP>0.001, and the inefficiency of phage production is EOP≤0.001. R means the phage cocktail did not infect and lyze the bacterial strains). The results suggested that the 3-phage cocktail is specific to STEC strains and has little mitigating effects on the pathogenic *E. coli* other than STEC O157:H7.

TABLE 11

Susceptibility test and efficiency of plating (EOP) of the three-phage cocktail of G157lw + Sa157lw + Elw to the selected pathogenic *E. coli* strains other than STEC.

| Number | Pathotypes | Description | Spot test/EOP |
|---|---|---|---|
| 1 | EIEC | O21:NM | R |
| 2 | EIEC | O29:NM | R |
| 3 | EPEC | O55:H7 | R |
| 4 | EPEC | O119:NM | R |
| 5 | EPEC | O142:H6 | R |
| 6 | ETEC | O19 | R |
| 7 | ETEC | O117 | inefficiency |
| 8 | ETEC | O25 | low efficiency |
| 9 | ETEC | O159 | R |

Example 4

Application of Phage Cocktails on Mung Bean Seeds Contaminated with *E. coli* O157:H7

Mung beans were disinfected with 2% of NaClO for 15 min and then rinsed with sterile water five times to remove NaClO residue. The sterilized seeds were air-dried in a biosafety hood. Before the experiment, the sterilized mung beans were homogenized with 20 mL sterile 0.1% peptone water for 2 min and plated on Sorbitol MacConkey (SMAC) with a thin TSA overlay to check the beans were free of background flora.

Mung beans (100 g) were submerged in 140 mL bacterial solution containing a four-strain *E. coli* O157:H7 cocktail (RM9995, RM6416, RM18419, and ATCC35150) at approximately 5.5 log CFU/mL for 1 h at room temperature (~20 °C). After air drying under a biosafety hood, inoculated beans were stored in a sterile zip-loc bag at 4 °C overnight before the experiment. Later, three groups of ten grams of inoculated mung beans were measured and subjected to the control, a test 3-phage cocktail (G1571w+Sa1571w+Elw), and commercial phage treatments, respectively. For the phage cocktail treatment, mung beans were submerged in 50 mL phage solution with ~8 log PFU/mL for 1 h at room temperature (~20 °C). For the control, mung beans were mixed with 50 mL 0.1% peptone water under the same condition. After removing the phage solution and peptone water, the control and treated beans were dried on a separate sterile aluminum foil sheet under the hood for 2 h. Subsequently, the bacterial levels were quantified by plating on SMAC with thin TSA overlay plates.

Figure 6:
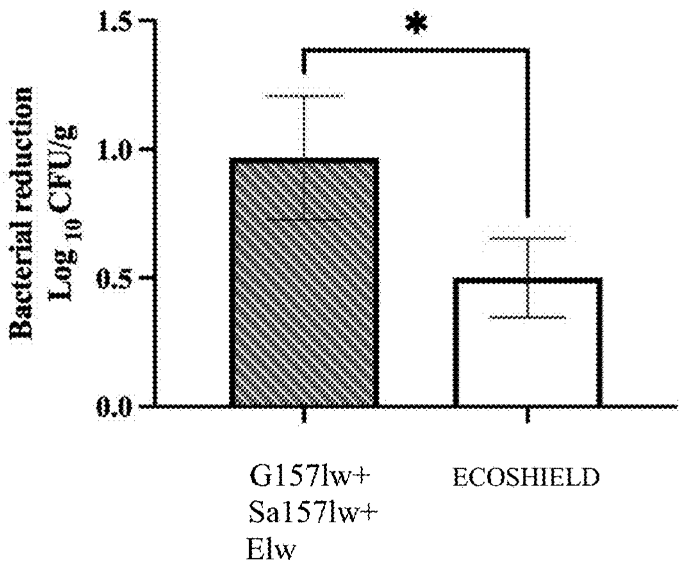
FIG. 6 provides a depiction of bacterial reduction of the mung beans spiked with a four-strain *E. coli* O157:H7 cocktail by the treatment of different phage cocktails (G1571w+Sa1571w+Elw vs. commercial phage cocktail) at 8 log PFU/mL for 1 hour at room temperature (~20 °C). The inoculation levels of the control group were ~3.5 log CFU/g. The asterisk indicates a significant difference at $P<0.05$ between the two treatments. The error bars show the SEM.

The results showed that the 3-phage cocktail (G1571w+Sa1571w+Elw) reduced the four-strain *E. coli* O157:H7 cocktail on the contaminated mung beans by 1 log after phage treatment for 1 hour (FIG. 6). Moreover, the 3-phage cocktail caused a significant reduction compared to the commercial phage product by 0.5 log. The findings reveal that this 3-phage cocktail is a promising and alternative antimicrobial agent in preventing *E. coli* O157:H7 contamination on seeds and other plant tissues.

Example 5

Antimicrobial Activity of Phage Cocktails Against *E. Coli* O157:H7 Biofilm.

*E. coli* O157:H7 (RM9995) culture was prepared in 10 mL TSB and incubated at 37 °C for 20 h. Later, an aliquot of 0.1 ml of the overnight culture was placed on each sterile stainless coupon (n=9), put and sealed in a sterile 12-well plate to grow the biofilm at 22 °C for 48 h without shaking. After incubation, the planktonic cells were removed from the stainless surface by washing with 1 mL 0.1% peptone water twice. Later, three coupons per group were individually subjected to 0.1% peptone water, a 3-phage cocktail (G1571w+Sa1571w+Elw), and ECOSHIELD (commercial phage product) for 1 h at 22 °C (room temperature). In brief, each coupon was submerged in 3 mL peptone water or phage solutions at ~8 log PFU/mL for 1 h. After treatment, each coupon was washed with peptone water, followed by biofilm cells being removed from the surface into 10 mL peptone water using ultrasonication before bacterial quantification on SMAC TAL plates.

Figure 5:
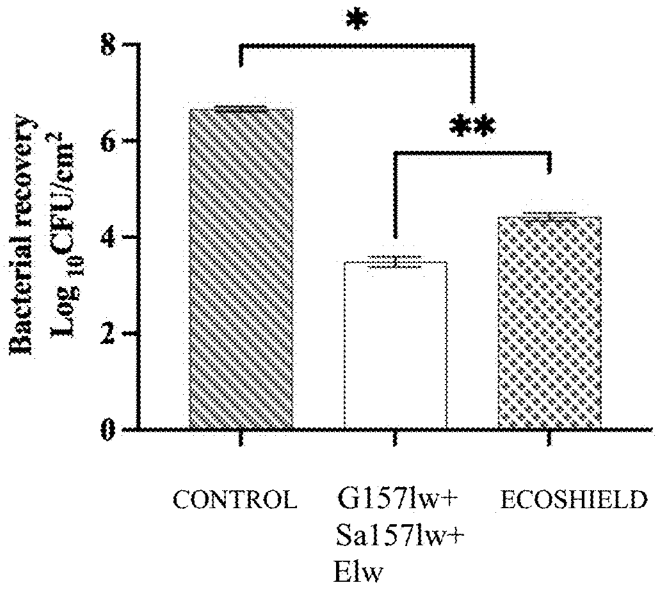
FIG. 5 provides a representation of the recovery of *E. coli* O157:H7 RM9799 cells from 48-h biofilm treated with different phage cocktails (G1571w+Sa1571w+Elw vs. commercial phage cocktail) at 8 log PFU/mL for 1 hour at 22 °C. Peptone water was used for the control group. The number of asterisks varies, indicating a significant difference at $P<0.05$. The error bars show the standard deviation of the mean (SEM).

The results showed that both phage cocktails with ~8 log PFU/mL significantly mitigated 48-h *E. coli* O157:H7 biofilm on the stainless surface (FIG. 5). Additionally, the 3-phage cocktail rendered much stronger anti-biofilm activity ($P<0.05$) in reducing the biofilm with 0.9 log more than commercial ECOSHIELD. The findings indicate that the 3-phage cocktail reported herein is superior to the commercial phage product used in this study as an anti-biofilm agent.

Example 6

Additional Phage Combination Testing In Vitro and in Agricultural Water

Additional phage cocktail experiments in bacterial culture and additional experiments in agricultural water were carried out substantially as described in Example 2 above, including bacterial culture preparation, single phage or multi-phage cocktails, agricultural water handling, incubation times and media utilized.

Additional Bacterial Culture Analysis

The results from these experiments showed that G157+Elw had the best antimicrobial activity within 6-h treatment at 25 °C (Table 12; *numbers represent the viable cell counts of bacteria ($\log_{10}$ CFU/ml)). However, Elw+Sa1571w had further reduced bacterial levels to 1.2 log CFU/ml, with the highest reduction among all treatment groups. We selected G157+Elw as the two-phage cocktail for the following experiment because this two-phage combination reached the maximum bacterial reduction faster than Elw+Sa1571w.

TABLE 12

In vitro antimicrobial activities of two-phage combinations with MOI of 0.1 against *E. coli* O157:H7 (ATCC35150) at 25° C. for 24 h.

| | Phage treatment | | | | |
|---|---|---|---|---|---|
| Time | Control | G157lw | G157lw + Elw | G157lw + Sa157lw | Elw + Sa157lw |
| 0 | 6.6* | 6.6 | 6.6 | 6.6 | 6.6 |
| 4 | 7.0 | 6.8 | 6.7 | 6.7 | 6.7 |
| 6 | 7.8 | 3.5 | 1.7 | 2.2 | 4.2 |
| 24 | 8.8 | 5.5 | 5.1 | 5.5 | 1.2 |

The results also showed that both two-phage and three-phage cocktails are better than the commercial phage product over a 24-h treatment period, even though the commercial product (ECOSHIELD) reduced the bacteria to the minimum levels (in 4 h) faster than both of our phage cocktails (in 6 h) (Table 13; *numbers represent the viable cell counts of bacteria ($\log_{10}$ CFU/ml)). Additionally, the three-phage cocktail (G1571w+Sa1571w+Elw) continued to reduce the bacterial population to the non-detectable levels at the 24-h timepoint; however, the bacteria grew back at 24 h from the treatment of the two-phage cocktail and the commercial phage cocktail.

TABLE 13

In vitro comparison of antimicrobial activities of various phage cocktails against *E. coli* O157:H7 (ATCC35150) at 25° C. for 24 h.

| | Phage treatment | | | |
|---|---|---|---|---|
| Time | Control | G157lw + Elw | G157lw + Sa157lw + Elw | ECOSHIELD |
| 0 | 6.4* | 6.4 | 6.4 | 6.4 |
| 4 | 7.0 | 6.7 | 5.9 | 1.8 |
| 6 | 7.6 | 0.6 | 0.5 | 2.0 |
| 24 | 8.4 | 3.2 | 0.0 | 5.5 |

Additional Agricultural Water Analysis

The results showed that both two-phage and three-phage cocktails are better than the tested commercial phage product (ECOSHIELD) upon application in reducing a four-strain *E. coli* O157:H7 cocktail (ATCC 35150, RM18419, RM6416, and RM9995) in agricultural water (Table 14; *numbers represent the viable cell counts of bacteria ($\log_{10}$ CFU/ml)). Additionally, the three-phage cocktail (G1571w+Sa1571w+Elw) continued to reduce the bacterial population over a 24-h treatment period, contributing to a 1.6 log reduction compared to the control. However, the bacterial levels were suppressed by the commercial phage product until the 6-h timepoint but grew back at 24 h.

TABLE 14

Effects of a two-phage cocktail, a 3-phage cocktail, and a commercial phage product with MOI of 50 against a four-strain *E. coli* O157:H7 cocktail spiked in agricultural water at 25° C. for 24 h.

| | | Phage treatment | | |
|---|---|---|---|---|
| Time | Control | G157lw + Elw | G157lw + Sa157lw + Elw | ECOSHIELD |
| 0 | 4.8* | 4.8 | 4.8 | 4.8 |
| 4 | 5.1 | 4.7 | 4.6 | 4.8 |

TABLE 14-continued

Effects of a two-phage cocktail, a 3-phage cocktail, and a commercial phage product with MOI of 50 against a four-strain *E. coli* O157:H7 cocktail spiked in agricultural water at 25° C. for 24 h.

| | | Phage treatment | | |
|---|---|---|---|---|
| Time | Control | G157lw + Elw | G157lw + Sa157lw + Elw | ECOSHIELD |
| 6 | 5.3 | 4.7 | 4.6 | 4.8 |
| 24 | 5.6 | 4.7 | 4.0 | 5.8 |

While the invention has been described with reference to details of the illustrated embodiments, these details are not intended to limit the scope of the invention as defined in the appended claims. The embodiment of the invention in which exclusive property or privilege is claimed is defined as follows:

What is claimed is:

1. A composition comprising a bacteriophage cocktail, wherein the cocktail comprises at least two isolated bacteriophages that target *Escherichia coli* selected from the group consisting of: (1) a bacteriophage having a genome sequence at least 95% identical to G1571w (PTA-127634) (SEQ ID NO:1); (2) a bacteriophage having a genome sequence at least 95% identical to Sa1571w (PTA-127635) (SEQ ID NO:2); and (3) a bacteriophage having a genome sequence at least 95% identical to Elw (PTA-127636)(SEQ ID NO:3).

2. The composition of claim 1, wherein the bacteriophage cocktail comprises a bacteriophage having a genome sequence at least 95% identical to G1571w (PTA-127634) and a bacteriophage having a genome sequence at least 95% identical to Elw (PTA-127636).

3. The composition of claim 1, wherein the bacteriophage cocktail comprises a bacteriophage having a genome sequence at least 95% identical to G1571w (PTA-127634) (SEQ ID NO:1), a bacteriophage having a genome sequence at least 95% identical to Sa1571w (PTA-127635)(SEQ ID NO:2), and (3) a bacteriophage having a genome sequence at least 95% identical to Elw (PTA-127636)(SEQ ID NO:3).

4. The composition of claim 1, wherein the bacteriophage cocktail comprises bacteriophage G1571w (PTA-127634), bacteriophage Sa1571w (PTA-127635); and bacteriophage Elw (PTA-127636).

5. A method of treating a surface, comprising administering the composition of claim 1 to said surface.

6. The method of claim 5, wherein the surface is a plant or plant part.

7. The method of claim 6, wherein plant part is a seed.

8. The method of claim 6, wherein the plant is a pre-harvest crop.

9. The method of claim 5, wherein the surface is a plant.

10. The method of claim 9, wherein the plant is a leafy vegetable and wherein the leafy vegetable is lettuce or spinach.

11. The method of claim 5, wherein the surface is a food contact surface.

12. The method of claim 11, wherein the food contact surface is a food packaging surface.

13. The method of claim 11, wherein the food contact surface is a food processing surface.

* * * * *

SEQUENCE LISTING

```
Sequence total quantity: 3
SEQ ID NO: 1             moltype = DNA  length = 118119
FEATURE                  Location/Qualifiers
source                   1..118119
                         mol_type = genomic DNA
                         note = Bacteriophage
                         organism = unidentified
SEQUENCE: 1
gtccactggc tggctagatg agaatgagtc tcattaccgc ccggtactta gcaggctaat  60
agtcacggca tgttatcatt acacaccgtg actatttcaa ctttaattat tacgcaactt  120
ttaatttctc aatatattgt tgcgggctgc aactatattc tgcgcgttct tcctcggtca  180
tactttccca acataattgc aggcggtcgg ctaggaactg ataatcatta tcatcctcaa  240
gagattcatc aataaaggtt tcacctatca atgtaacccc aatcgataga atatcgttaa  300
cggcttgcgc gtccagcgtt ttaaatccgt atgatgccgc cgctgatagc acgcctttat  360
gatcatcaat catcgtgaaa tcagcgttcg gatataattg tttaaataac tcaaagtaat  420
ggcttttata aatagcgtct ttgctgtggt atatctcgct aactttatca gcctcaaaat  480
atttgtgtag tgtatcgcgg gaaaatacac ggatattact atccccacgc cctcgcaatc  540
cttgtttgcg caaataataa taatccgact tgctcattag tcgagcggtg caaataatgt  600
ttaacgtgtt aacgtcattc atacattggc gcatatatgt aacaaggggc aatagtgtat  660
cttgcattat taaatcatgt ttgcaggctt catttttata cttatttaaa tctaaattgc  720
cctcgctatc aaagcaaggc gctacgcgat ggaaagaatt aatgatagtg ccgtccagat  780
cccaaatcat gacgcgggaa atatgcggga aattacgggt aatattcgtt ttaacttgat  840
tcattttgtt acgttctcca tttaagggat tagattaatt cagcattacc cgctatttat  900
aagcgggtaa taataaatta actattaaag accatacgcc aacgcatcag caataaaact  960
aatatcttca ccagatacac cggaacgaat gcccgcgcag gtatatacct ttgcgctggt  1020
caattgatca tcgaggcaag cggggcaagg cgcgacaact gcaaaggcta ggccggattt  1080
tacggcgtcg atgataatcg tttcttgttt cacagtgtca acataaacac cttttgcttt  1140
aatatggcta gttagtttac cttgcgtata ggcaaaggta gtaacctgca aagcgtcgtt  1200
aaagtccaat agctcatcaa taacgtgccc cgcctcgacg tggtaacgtt caccattaga  1260
ataaaccaga acaatggaag attgagcgcg atcgaatggg atattttgct ttttcatatt  1320
tataaaactc caattaattt aataaagggt atttaattta cttgataata atctgcattt  1380
gatacggcgt taattcacca tttacgggta aattattatc gcttagccac tcataaaaag  1440
cgtcatcatc gtcaaaaggg ataatatcat tatcacgata atcgaccgta ataatcccat  1500
ccgtattagt tttggcggct aggataggcc cgaagctgta aactttatcg gattccattt  1560
catccggtga aataaatgct ttttcgtcca gcgttttggg taatgtaact ttcattctaa  1620
tttagctcct ataatagcgg ctatatttca agccgctagg gtattaatta tttacgcaaa  1680
aaatttaccg ttcttaaaat cgatcaaagt acgctgacca tttgcatagg taattaaatg  1740
cgtttgtgtc cagcttgacg cgccaacgtt gtaacccatg tccagactac cagccacgcc  1800
agcggtatat accccgccgt aaatgctggc ggtatgagtg tgccccgtgt ttaatttgcc  1860
caatttctta aactgtttcg gattgccacg gctgccgttt atgccattgt gaccgtgtac  1920
gccgcattca atgcctgcaa ttttaaatga ttggtcagtc gttaggaaaa tggcgttaaa  1980
ctcgcaacct gcaaccttac gcagcgcata atctagcacg ttgaaagtat cgtctttttc  2040
tgcaatagct ccgtaaatcg cggcattcag gcggtgatat agttccgcgt tcgctgggtc  2100
gtctttaatg ttagcattac gatcatcaag ccaacgggat agcgccaaat cgtgattcga  2160
ttcaacaatg attgtttgcg agaaatcgcg ctccattgat tccagtacgc gccccgtatc  2220
gatgagatca tccagaactt tatcacgtcc ggcggcgtat tgttttgcta ggaatacacc  2280
cgaagcgcgg ttgtgatggt tgcgtgatgt aaaatcgtga acgtcatgga taaactgata  2340
ttttggttta agaatatcaa gcaagctatt ttcgccagcc catgacgcaa tggcacaatc  2400
atcatcaagt ttttcggcgt gtatgtcgcc atattgcaag cctaaaacat gccccgatgt  2460
ttcatagcat ccggcgggag tagcgcaaac attcagatca taaaacaccc cgctttcgtc  2520
cattgtttca agctggcgaa caaaaaactc accgtcttcg tcgaactcaa caatcagcgc  2580
accgaagtta tgcagtgctt ccgctttctg tcctgctttc tgctggatgt aatttttaag  2640
cgttgccgtg ccagttgaat acatgcggcg cactacttca ccttttaaag ctggcacgct  2700
ttcggcggtg attttagcgt gaccaattgc cagaccttcc agattaagcg cggttgcagt  2760
```

-continued

```
ttcagcgaat ccagaaagcg gataatctgc ggtgggcaaa acattaattt cagccatgaa  2820
agcaaaacgg cgattattca aaaacacgtt tttgctgcaa atatatttat cgaacgcgga  2880
atcatatttt attccatccg cgccctcgcc attttggaat ccgtttttat tataaatata  2940
cttgctaacc agcaaatcag cgccgatata tttagcaaat tgctccagtg aggctaaaaa  3000
gtttttatgc gggaacgtat tattctgaat cgatgtaata ataaagcgtt tgccttgttt  3060
tacttcccag ctttccaccg tgctagaaac aatccccgcc gcttctgggc gctcatcgtt  3120
tttaatggct tttgctactt tcgccgcttt cggtttcgct ggtttatttg cttccagcca  3180
atcacaaata gcggtggaat gttttggagt atcgtaaacc gcttttgata tatcgtcaca  3240
aacttccaat ttagtggcgc gcaggcgttt accgtagaaa ttaaagtcag cggccatttt  3300
caggataacg gtttgttttt ctgcggaaat aatcatagta ataaaactcc attaaaggga  3360
ttaaaaaacg tttgttattg gcaaatattg ccaaatataa cgcctattat ttgaggcgtt  3420
ataatttgca acattaattt aaaggcataa ggctagaact aacaccacaa acaacggcgg  3480
caataaaaca aatcagacct aaacgctttg ctaacttaga tttacgttta aaataatatg  3540
aatctaaatc attttgaaaa taagcgaata gtaatgaggc cgccataata aataagccta  3600
gaattaagga ttcagtaggg taaaagatca ttttaataac tccagtcaaa gggaaattat  3660
agtggggaat attccccact aattaaattt attcgcctgc ggcttgtttc acttcatcgg  3720
caacgcctaa cagttgcgcc acggcgtcca gcgtttccag ttttgcgctt tccagtgatg  3780
ccagatcgtc ggcgtctttg ataatgccgg aatcgatagc gtgttttgca ataacgcgca  3840
cataatgcgc tttgcggatt gagctaccgc cgccaacttt gcgcggctta tcgcttttct  3900
gatacgcttt tgcgctggtc aattttgagc gaacggacac gggggaggcc gcgccaactg  3960
cttttgcaat ctctttcagg ccgtcgctat ttgcgaaatc taaaccgttt tcattaatta  4020
actgctggta catggtaaca gctttttggg tgttttcttc attccatgca aattttgcgg  4080
atttttcggt tttaacgtta gccatgattg tagctcctat tagtttaatt taagggataa  4140
gattaacata atgttaatcg ttatatcccc cgaactacta gggggatata aagttaacac  4200
taaattataa aacagcttcc catttttcgt tacgctggac aacctttaca acgtcgccgg  4260
atttaacgcg aacgctaaaa acggttttgc cgttgttact ccgttccgtt tcagcgtata  4320
ccgcgtcgat tgtatcgaac ggcataagcg ccgcgccttt aatgcgttcg gcctttccgg  4380
ttaattcatc cgttttagta acgaaaggaa taaaaacgga ttgaccaact ttcggcgcgg  4440
taataacgtt ttgcataata taaactccta gttatttggg gattgttccg cattacctgc  4500
tagaaagtaa cagcaggtaa taagtaacaa tccgctcgcc aatataatca atttaaagaa  4560
ctccacgcag gccgctatat cccagttagg gggcggggca cattatggta agtgccgacc  4620
gtcaaatttt atcaagttat cgctcttatc gaactgggta catcttaaag cctatcggct  4680
agggtgtcaa acaatttttt gcagtttttt atgattttct tttaagtcaa tcataatatt  4740
acgccagatc atttccagac cttgctggcg gcctttcttg tactgcttaa atcgatattt  4800
taccgatctt tgcgctactg tcaacaaatt ttttgttttg ctgtccagtg ccttgctagg  4860
tttaccagtg atcaataaag tttgtttcat atcgtcgatt ccttataatg tataagttta  4920
ccgccgatag gctttaagat gtacccaatt tttaaagagc gcggcggtaa acttcccgcc  4980
gtgtagttcg tcattgccgc cctacgagat aaataatagg ggattcccga aaatggcgca  5040
accttatttt tgtaaagaaa tgtaaagaca aacgccaccg gacaccatgc ggcgaccggg  5100
gcgcggcgca ttaaaattaa aagaaacggg cgcgcgaata ccataaaacc cagcaggttg  5160
gcaagtaatt ttttcattta tatttgcctt gccctacttg acaaaactta aaaagctcgt  5220
ggtagcgata aacgagggta ggcaatgcaa tggcatggct aaaactttca tcgcgttcta  5280
gggcgtttta ggcgcattct agccttgttg ataacttatc cccaaaagca aaaatgaaat  5340
tttcctagtt atccacttga cttttatttt ccagtggata actacttatt ttatgaaata  5400
aattaattga cttttatttg ttagtatgca tcggaagaat agcagactaa taattactag  5460
aataataatc atgctggtgg attgtaacgg cctaaactat cagcagacta ttaatcacga  5520
aaaatctcgt tagctaacta actatttcat gatgtataat atacatataa attaatgaga  5580
aataataatt ataataaata ataactacag taaataataa ctataagaaa ctatcggcct  5640
aagtgagaac cactatcatt taagttatac acaaagttat ccacagcact ttttgacttt  5700
acacgatagg cggcgatata aggactttta cacagactta tccacaggtt attccactgt  5760
ataaatatac agggtaaaaa ggtagtgtta acaactgcaa tcaattttaa gcggcttaaa  5820
tcgcattcta acgagctaaa cgctgcgggg taatattaaa gtaaagcctt aatgcgtcac  5880
cctggtggct tcgccgtggt ttgctcttta ttgcaccgct gcgcggttag cataaaaata  5940
ggcgctaggc aaggaaaata aaaaggtaaa ataatatttg cctatgctag aaatttacct  6000
ttatcattca ctcaccgatt aacgagggag gccgaacaaa tgaggcttta taaacctgat  6060
aatgccaccg ttttaaaagg tgcattgcgc aacctgctgg atggtagcaa gtcaaccagc  6120
attaaacatt ttattaacaa gattgaaact attcatcaaa actttttga tgattatgac  6180
gcttatgata tggatagttt tctaccctta tatagacaag ggcaacgct agttttatat  6240
aatcgggatt gccatatctt tacaggcagg ggagcggggc cggataccga ttttattgtt  6300
gcgcagggta ataatattgt tgcgtatcat agcaattcag gccgtcaatc atttaatata  6360
aatagttttg agcttattgg acttgatctg ataaatggac tttctagcat tgagggattt  6420
ttagatgtta tctggaagta tttacccgct ggatggcata agccggataa cgacggatct  6480
caatataccg gtataatggc ttttgatggc gacggtaatt ttttgttacc acgggagcta  6540
tacccatata tttatgatgg ggatatagaa agcgctggtt tttctttctg gaaagatgaa  6600
gatcagatta ttgacagcgt agaaaaccat gctgtaaatt ctaacactca aagcgttaac  6660
actcaaacta ctgaaaacaa aggaaaaaac actatgacca agattgctaa catcgttgcc  6720
gctaataaat ccgccgttgt aaatgctgca aaactggaag cgggtaaaat tgcactgact  6780
caaattacga aagtagcggc taaaaaagca ccgtttatga ttaaaggtta tattgataca  6840
cctatcggtc gagtagtgat tgccaacctg ctgggcgtag cggttgacca gtacgccaca  6900
agtaaccaaa aggcgaaagc ggtggcaggt gcagctatgg aagcggctat gttagaaatg  6960
gtgcaaagtt ttaacatcgc tgagatgatt gatgaaatgg taaaaggtat tgatatttct  7020
acttttacca ctagcaccga aagcgagtaa taatattaag cggggattgt taccccgctt  7080
tactattccc ttgttaacta ataggaggct aataaatggc tgatgaaaaa tatggcttct  7140
cactgggaga agtgagcacg gcaaaacatg atatgatcat tttggtcgat tgtcatactg  7200
gctattgcgg ggaagggaac accgaggaat attttgttcc tgctggtacg gatctggacg  7260
ctttcgctca ggaaatggct attgataatg cttctcgttt tggtagcgat ggttacgaag  7320
acgaagaaac tggcgaatgg tatgaaaatg aaaacgtata tgcaagcctt tatcattatc  7380
aattaagtaa atccggcaca tatgtaaacg gcggcgatcc tattaattcc gtcatgagat  7440
taattattaa atatggcggc gtcgagatag ttggtaacaa agcggtaata tacgcaaatc  7500
```

-continued

```
gattaaaaca gcttgtttat attcctgata gtacccgatg ggatgaatat gctgttttgc  7560
atgacgaatt gaaacgatgt ttcaatattg aatccttaca agtagtctaa tgtaaagttt  7620
tgtaaaggtc gcctttttatg gtggcctttt ttgttataat gcctttacac cgtttgagga  7680
cggttgaaaa ttttcccaaa aattggaggc ttaaaatggt tgcttattct tctgctagtc  7740
atctgttcac cgctcaaggc tgggtatcta accgcgttat tattcacgaa atggtgcaag  7800
aatatggcat tgctaaaaca tacaatacca ttcaggcgct ttatgataat gatcaaatcg  7860
atcagcaaac ggcgggcttt ttgctggata ccctgaaagc agaacattgc accaaaaaac  7920
aagcggctaa aattgtttta atgtaattaa taacggggcg ttattttcgc cccactaact  7980
agggggaatg aaaatggtta tttttcgagc tattttagcg ggtatcttgg gcgctatttt  8040
atcgttgttt gcaatagctt tcggcgttca cgcggttatt attggcgcgg gtatcgctgc  8100
atttcttat ctgctgggct gcatgactag taaaggagaa taaaaatgat ccgcaatgtt  8160
tcccttgccc gttcgaaagg ctttaagctg gtggatgtta acacgttcga gcgtgaagat  8220
tgtaaaatcg aatatgtagc acgtaataag aatgcctttc gtgttacaga aaagaaattt  8280
gacaagcgcg gcaacgtgat cgctgaaacg gttaaacact ttgccacctt ttacgctgcg  8340
tttcgtgggg tgttataaaa tggttattta tgagggcaac cgctttgttg ctaattgccg  8400
ccctgcattg ctagcaaatt acttaaatca gctttcacca gcttataagg gcgttattaa  8460
tatttatgaa ggcaaggcgc attataaaat caatgcggtc gttgcccgtg aactagcgtt  8520
tcaatttttg acctttgcat cttgtgacgt tcaggtcatg ggtgaagcgt taattgcaga  8580
aaatgaagat gattttatta atatttttcg caagatatgc accgagcgcc tgataatgaa  8640
aggcgcttat attcaatcca ctgcggatag tattgaaaca gcgtttcgaa aggtggcgca  8700
atgagcaata aaattgttgt aaccaaaatc agtacaatgg ttgatgtttt ttacgtgccc  8760
gatacgccgg aaaaccggca agcggtcgag cgtggcgagt atgataaagt gatttatgat  8820
cacgatggtt attatcagca tttggtcgat tcctatgggg aagaggaaaa gatcacgcat  8880
caattaccgg aggatggttt atgaaacgat ggtttaatca ctggtataag cggtttttag  8940
tacgccgtcg caaatctaga catcaagatg agtggcggga gtgggcaaag cgtaacggtt  9000
gcccgctact ctgagaacga cggggattag ctccccgttt ttccatgcct ccagttaaat  9060
acccccttgt tttagtatcc ccaccaaaat taaacgcgtt agaatgcgat ctaggacgtt  9120
ttagcggtat attagaatta ttcactacat aggaatactg tatatttata cagtaggata  9180
agctgtggat aagtctgtta ataacgcctc aaaatggcta ggattctgtc aagtcaaatc  9240
gtgctgttaa taagtctgtg gataacttaa ataatagtgt ttctcacttc cattcttaaa  9300
tgcaaatcat tatcattcgc atttcacttt ctaaatgaga atcatttcac ttcttgaata  9360
gttctcattt cactttttaa atgcgaatta ttatcattct catttcgctt tttaaatgat  9420
tcttattatc attcgcattc aggcgcgcag ggcaattgcc ctgcgctttt gtgcaaatcc  9480
gacattgctc cacgggtgtt acgtgcgggc gtgtatgtgc gaatccgaca atttttggta  9540
gtgtgcaaat ccgacccgaa aaatttttat agtgtgcaaa tccgacaatg aattttccca  9600
aaaactccag caatccgatg ctgcgcatca atcctgtgga attagctaga atatgtgcaa  9660
atccgacatg ggttatttg tgcgaatccg acaagatttt tgtgactttg attggagggt  9720
gtgtgattgt atgggtttga ggagaagatg agagagcgag aaaaatttga gggaactgtg  9780
agaggggcgc aggattggtg cggagcacct gatttgcggg gattttgggg aagagttgag  9840
ataatttggg aagatttggg ataggtgcag ataaagtaaa attttattag caaaacgagg  9900
caaaatagct tgacaagtga aaatttctgt ggctctaaaa actcaggcaa tcatgggcct  9960
tcggcccgaa ataatgctgc tattttcagg agattatatg ttcctaaaaa cttaggcgtt  10020
tgtgcaaatc cgatcataaa tttctagaaa tgcagtgtgc aaatccgaca gtaatttctg  10080
gaaatgtgtt ttcaaaaaat gtcttctaga aataaccgcc ctccctataa ccgcctattg  10140
ctggagtttc taggaacaat gaaaaccgcc tgagttggct agagaaacag atttaaagtt  10200
taatgtaaac tctagagtta gtgctcaact attcctagaa actcaggagt ctagaagaaa  10260
gtgttgtgcc atcctagcag atgagcagca acaggtgtat catcttgaac acagatattg  10320
cctttaaata ttctcttgta aataaaaatta atagtttccc caatctcgtg agtctgctgc  10380
tctaggcgtt caagatctgt atgctaatcc cgtgagaact gctgcagaat acatcctatc  10440
gccggaggcg tcggtgtact cttcgagttg ggatagcaat aatcttgttg cctagagcta  10500
aaaacagaag ttgtttttaa tctatgagat tattataaca tgtttgggta tgagaatgca  10560
agaaattttt gctactattt attcctttcg tctgtatttg agaacgatgc ccttcgaaac  10620
catgaagagg aaagttgcta gataggaatg tgggctttta agcgcatcat aatctactgt  10680
cccgaaagaa ccttcgccga aaacttcaga gttctcaaat gtaggaagta aacgtgccaa  10740
tcctacagct cctataatct taaagaattg atcccagtca tttaacattg ctttatgtgc  10800
agactgtaag attaatggca tctctaggtt cttttcgaga catagatgaa cctgcgcaat  10860
cgtagaggca atccctagca acacttcatc ttttgtataa gggaatccag tatctttttct  10920
ttggagtcta ggaagatgat catattcaca acgtttaggt gggatgaact tttcctcggg  10980
atataattct aatgcaactc taacgtttcc ttctttaaat actggaagtt cctgatctgc  11040
aaagacatga tatgaatctg ccttgaaccc tacaatctta tcaccaacag aattgatgat  11100
ctttctcatt gcaatataag aaggggatag agttacgaat ttttcttctt tattatattt  11160
aacaattcca gcttctgtat aagctgcggg atgaaactca gaacagaatg ctactgcatg  11220
agcttcatca ggagttagtt cagaaacaca tttgccgtca gcattcttag ccagcttaat  11280
aatagtcttt aaattctcac taatactcat atcaagcctc ctgaactttg tctgccgggt  11340
agaaatcttc tagtgaattg tagtgagcgg taaagaattc aaaacttaag taatcagcag  11400
tattctggat gtaacgcagc tcattaataa aagactcttt gaagatcttg cgattaggtt  11460
tgagctttat aatttcttct accaaagtct ctaggatctt ttttgcgtct tcaacttggt  11520
atgcagctaa ggcttgagat tcatagatta cttcatctac tccattagta attaaagata  11580
cttctatgat tattccatcc tcttctggat ggactctatt tgcatccagc tcacgaatga  11640
taacacgagt ttgactagtt atttgacgat ttaacgcgat tgtgtaatgt aacatattat  11700
tctcctaatg tgcctccccc agtaaaaggt ctgaggaggc gtagacctat aaattaatta  11760
acgatcttta ttgatccttt ttactctcat taagagcagc ccccaacgcc tcaaggatag  11820
tatcatttat gctcccaggc ctaagattat taaagtgagt aacatagatg ggacttttaa  11880
aaccttcagc attcgcaggt gctacgcttc gcatatcaga ttcaaaagct tcttgagtat  11940
gtttcagctg tacagaaggc ccataatctt caccaactcg atatgaggaa ctattttcta  12000
tagtgccgcc gcatggaaca ttgtgcattt ccgacgttat tttagaatta aatgcgatac  12060
cacttttggt ccaggaacct ccaacagtca caggagtact aggacgattc acctcagtct  12120
tcacgagttt ataaccagca tctattaatg cgttaataag gttatcagct ggaatccgag  12180
ccttgccaaa gatcttacga gcttctttta atttatgctc aagatcttta caggctttaa  12240
```

```
tatcagtgta cgagtttata accagcatct attaatgcgt taataaggtt atcagctgga  12300
atccgagcct tgccaaagat cttacgagct tcttttaatt tatgctcaag atctttacag  12360
gctttaatat cagtgtgcgc aaaggttaat ttcatagatt tgaactgtac agtggcagtt  12420
aagtctttaa aatcataatc ccatgtattt aattcatggt ctggtactac ttgaacaggt  12480
tgttgtgcat ataaagtcat tacttattct ccaatttgtc taacagctta tgagctgcta  12540
ggttatattg tttaagttca cggttaagga tttggttctc acactttaac tctaaattct  12600
tattattaag aatattacag attagtagaa gtgctagtat aactagcagg gaacctacta  12660
gcattaaaag aaaaagagtt tccattattt aattcccatg taacgtttga gatacgtgat  12720
gaagtcttct gttgtatgtt ctacgctacc ctgaaccaca aacaacttta aagcctcacg  12780
ctgtaattta agagcagcta actcaccacg tatatcttcc gctagttctc tagctctgcg  12840
cataatagca aatgatacaa atgttacaat aaataacata actgctaaaa taattactat  12900
gatctccata ttaacatcca gctcttatcg tatatttggg catgttctac taattcattt  12960
atcgatatag aattatcgta gataccctct agtaaacgtt ttctgtcaaa tttatcaacc  13020
aaatactctg tgccatttat cgctacccta tacagctctg gaactaaagg gtgtttgttt  13080
ggtattggac gactacctaa gtctatctca ttatatcccc aagttgtttt aaatagtttg  13140
ttactaagtg ctgctagtgg atttgaccat acaatatagc tactcactac ttatctccat  13200
tcttagcttt gaaaacttat tataccaaac tatatgatta tcgtcaatta caaatttatg  13260
gtaacatgct ggtacggtat aagttccata atccgtgacg cgctgcacaa ccttgtgtgc  13320
acacagtcga caaccatgcc cttctaaatg agatctagca gtctgccagt aataaccatc  13380
atgatctgga caataaatct cgacttgctg ctgcattgtt ttataattta cacgctcata  13440
tccgaagaaa gccccgtgag ctgcaacggc tttcttgata aatataaggt ttagtgcttc  13500
ttgctggaag tcgggatgta gctgcttaat cttagttcta ttaatagaac catccgattt  13560
aatgaaccta tttattggaa agttgttagc ttcctcgatt aataattcat ttactttctc  13620
tctcatatta aatagtctca cagttaaggt agaaacattc gtaagcatct ccagtaaact  13680
ctttatcttg tagtaaacac ttagtttggt cttccggtac tccagcatct aataattgtt  13740
gtttacttgg cttttcagcg aatactttta caaaatactc accatcctga ttatactcat  13800
ttatatctct ggtaaggaca tatacttgca tttgaagttc cttgaaaaca taaaaggcca  13860
gaacaattaa gtcctggcct ctagaattag tgaagttgtt taccacttcg taacatagtg  13920
gccgtttcca taagacctag cgtagtatca cgcttattga tctgtttacc aagttcatcg  13980
gtacgtttac caatgtaaac gttaatagcc atattcatag ctgtagcgag atcttctttg  14040
gttatctctt catcgtctaa agctaattta gccaaagaat caaatgtgct agagagtcct  14100
ataagatcgg aggtttcttt ggccaaaata ggattaatat tatctactgt tacttctagc  14160
atggagttaa caatatcttc tccgtctact agaccagatt caatattact ctcccactcc  14220
ttcatctgct ccaataatgg atttttcttt tctgtcatgg tagaggtttc ctgtgtcagt  14280
tggtaagaag gatgattgag ctttaggcgg atgttgttta gcaatccagt taagaatcag  14340
tacacgacta ggaacaatat cagtgttgta ccagaaatca tggacccatt gacgagcatc  14400
ctcaaactta ccaaatttat atgctttctt aaataattca aacccaaaac aatctggtgt  14460
aaagtctact tcacgatatt gaactacttt agaaccagtt aggtcttgga tcgctgcatt  14520
aatttctgta tgcgagaatt ttgtttcgtg aaacttgtta aagaatcggt agttgaagcg  14580
tccgttcgtt tcgacaaata actggataaa gagatcgtta aattggttat caaaccagta  14640
attctgtagt tgttgtagtg ctgtcattta cgaactccgt taattgccac gatgatgcct  14700
tcgtacataa aaggaagtag cccagaagtg tagaagatat tttccgttat tcctagatgt  14760
cgaaaaagta tattaaataa tgctgttaga aatacaatct gaggcagtaa tacaaaatac  14820
tcagttacaa tctttggtgc ctgataaaca agacgtttta tcattgtttt taagtctcct  14880
tattactttg gcctgctcca caataataaa aactgcaagc actaatagtg ctattagccc  14940
cgcagtaatt ggtattaaat caatcatggg agacgccata cgtaattagc tgtctgtaga  15000
accttaggtg tgtcatcatg atacattact acagactttg gtgaataact atcagctagc  15060
tctttacgaa tcatcttaca ttcttcacca gtatcgatat ttttaactat cactttcata  15120
ttaagaggtg ttaatacaga aagcggtttc caagagtcct caatttcaat tcctaccttt  15180
ttctcgatta ccatgagaac ttctagtgta tcatctggaa tactaatatt attattcaca  15240
aactgtaata tctcatgtaa ggtatttaat tcattaaaat taagcttcat ctttaagaat  15300
atcctcaatc atatcacagg actgttgcaa ttcgtcagca atgcgcttaa catctgtttt  15360
tgttacttta cctattaaca tcaccagtaa catagaaagt ataataagtg gaactgggat  15420
aacaaacagt gctaccttaa caacattctt tggtgcccat gtatggtact tagtaactag  15480
aacccctacc acgattatat aaaatgctag aataaacatc atcatttttt aatctccgtg  15540
attatctgtg tacgcattac tttagcaggt aatttattat tcccaactat tgcttctata  15600
ttatttaatt tttcttttag aatatctgag cgtctctgtg ctagttcaat atcttgttct  15660
tgttctatta agcggcagtg aagtccacta ttagtagtaa gcatactctc tatatttttt  15720
cgcatgctta caataccaat aatcccgcca atcgctacta gtgtcataag cactagcaat  15780
ccaatgagaa tttcagttaa cattaaatgc ccctacattt ttcgttattt ggcgttactt  15840
tgcaaatctc tacgtttagc tcatgaagag ccttgtctac ttcagttaag cgtatgttaa  15900
gagaaaccat attatatatt agtattccta taaggaatga cagtattgaa attgatactc  15960
tttccattat ttcttacctt tcagttgctt aacttcacgc tcaaaagatg ctgcacgacg  16020
ttcggcagtc gcttgatgct ctttagcaaa acgtgcttcc tgttttgcaa ggttgaatgc  16080
catagcattc ttattcagag aatcatacat ctttttcatt gccggaatag acatcttcat  16140
gagctgaccc tcaaaaccct gcatgtcgag gagaattgcc agaacgttag ccatttcatt  16200
tttagtcatg ttttccatta gaacttcctc tctcattaat ttatgaactt attatacaga  16260
attttaaggc ttaaagcaac tgaatttttt aattacttac caatcattaa caacgccgga  16320
gaactcagaa gcaaaaactt tttcaaattt ctctgtaatt tcaggatgat ctttgcagat  16380
cagctcaatg catgcttctg gagtcattcc ttcatcttca ggatcaccat agtatttatc  16440
ccaaagatca tcggggatga tgtgctccgc caaatcttgg aaagagatta gctgataacg  16500
ttctgcttcc tcggggataa ggatttcaca aagatcttta tctatatcgc tacgataatc  16560
cgcaattaat agggcattgc aagcatgaca ctcccaaacc atcaagcgtt cagaaatagg  16620
attagactta tcctgaacgt aagactgaaa cagggttcgg aaagttgcct taacttgttc  16680
aaacttatct gctgctgcga aaactagagc tttatcaact ttgttcattt tgattccttc  16740
tcatcaattt ataaagtaat tatacagaaa cttaagcatt ttagcaaata aaacttttag  16800
ttaaaatgcc taatcctgtg ccaatagcaa tacaaatgat tataagtatt gctactgttt  16860
gtatgattcg tttaataata gcctcagcta tatacttaga catttatatc tccacgcaat  16920
acggcagcta catcttcccc tatttgtaat acttcgccgg tagtacaatt aactactcta  16980
```

-continued

```
tcatagctag taaacttacc agatacaata tcctccagtg ggattggagt tttactcatt  17040
tcaaatgaga cattaatata atgtggatca cgtagagaag tagtatgtac atgtccgtga  17100
atatttagtt tgccacgaag ttcattaggg tgcaaagggc agtgagatag ccaaaacttt  17160
ttgccgcctc cagtctgttt acctagagcc tggatatcgt cataaacttc cgctaaatcc  17220
ctgatgctca gtccttgacg ttccgcatca tgattaccca taataagttg attagggaca  17280
ttgtggataa ccgactttaa tttggttaga ccttcacgac ctactgcaat atctcctagc  17340
aaaataagtt ttgttcgttt accaatatgc ttagacaaag tatctagaat atactcatcg  17400
tgctctttca tgttcttaaa ccacggacgg aaacgtaacg ctccagggtg gtctagatgc  17460
aagtctgacc agaatttaac tttcattact cttttcctta ttctgtatta aactatcaac  17520
ccaagaggtt aacactttgg ttttaaactc ctcgggagtc tctccttcct taagatctac  17580
ctcattaagg taggtagtaa gccttgtttc tatctctatt tcagcaggag aattaaaaca  17640
aaaattgact gctattccag aatatattac tccggtgtct cctttgacga aagcattaac  17700
taatgccctc caacgaaggg catcaatacg cattgctcgt aattcttctt gtacttcttt  17760
cattctatca ttcattaaag gatcctctgt acaccgcagc tatcattttt gtctgtggta  17820
aatgtggtga ttttgccagt ttcatcgtta acctgcgcaa ccgtcaactg cccgttgaaa  17880
acaccgccag tatctaggta aacacggttc tggtataaaa tcgggtaagg tactccggta  17940
tgcccatgaa atacaaagtc tactccatta accggaggta cttctaccat gtatttctct  18000
ttaaaccctg cataacgctg gaaatgtgag tgttcttcac catttttagc taagtgaaaa  18060
cctatttctt ggattacatc tcgatcccat aagtatggct caacatggta tccaggatgg  18120
tcatgtgggt cttccttagc tgcttctact tgtgcaataa ggctatccca tactggggtt  18180
tctacttcgt taccacattc tttgtacgta aaaggtacac caccatgaac aacaccatac  18240
tttttaccac gatgcaatac agtcagaaat actggcattt tttcagccat gtcttcagca  18300
atatttttaa tggtatctgc atctagttca ttcatggccc acataccacc gttatacatc  18360
cagttagccc aatctcccac aatcataaat tggtcatgat taccacggac actgataaag  18420
cgtggattat acaggaattt ggctaaaact tgtaggttct gcgtgcctcg atcaattaaa  18480
tctcccacgc atacaacgca gtctttcttg ccattatagc cagctaattg tagtgcatct  18540
tctagtaaat cgttgcatcc atgaatatca ccaacaaaga ataagttaac atcatcaggt  18600
actactagtg ttttatgcac attaaattct tttttcataa ttattcccaa ataacagtta  18660
aaatagttgt gccatactca ttagataact ggagagtata accctcttta ttgagggctt  18720
ttatagcttc ataactaatt tcgtcacgat taagctgtac aaaggaacct ccaatctcta  18780
cagaagatac tatcctccgc ttaacccatc tatacgtttt ctttcggctc ttaaggagtg  18840
cagctctatt tattctagct aaacgttttg cttgttctgc taacatttaa tcctcctatc  18900
aatttatata agtattatac caaaattttt agctgaaagc aagtaaaata aaagcctgat  18960
ccgctaagat caggcttggt ttattaatcc tctggattat catccaggaa atttttaata  19020
gcttcgtgca tagtttcttt acgaagctga cgtccaatca aaatatgatt agcttctact  19080
cgaccattag gtaagcgatc cgctagaact actacaggaa cttggcgtac accaaatttc  19140
tgcattaatt ctgtattatc agtctcttta tggacttcca aattatagtc attgactact  19200
ttatcaaata ctggctcgaa aagtttacac gggttacaag tagaaccttt caatagatat  19260
actaatttac tcatagttat taatggcctc taagaagttt ttcatagttt ttacggttgc  19320
ggtgctcaga tcaagattta cacccaaaca ctcggttaat gcttcctgat agggagcctt  19380
taatctgcct tccgggactt ctaccttctt atattcttta tttttgacct ttttaatcat  19440
agtctctagt acaagaagtg gtaatttagc accttcaata tcagtaccca aaagttcagt  19500
taaaatttta ttaagatcaa gacgagttaa ctttttgcct ttagacatag gagcacctac  19560
ctttgtacca atagattttt ccgctttctt ttcgagcttt ttgtactcag gagagtcatg  19620
atcacggagt gcaatgttta gctcgtaatg tggtatacga aaatgttccg ccatttgagt  19680
atagaaacga tcagacataa tatatacctc tcttaactaa tttatgtata tattatataa  19740
taactagggc taaaagtcaa ctactttttt atcttaatct actgcatgta taaatctttt  19800
cctaactaga tacatagtta ttgggtaaat tgagtacata agtatcgggg agaaaagggt  19860
gaaatacgct gtaactcccc cagctaacat caaaggtatt aatgctagag taagggccat  19920
aagaatcatg ccgaatgaaa cagccaaagc tatggatata ggattctcta gttccatcca  19980
taaccaacaa tatttcgtat ctctatggca attgcattta caaacgccga atgaacccat  20040
aattatatac tctagtccgt gaataacctt tattaataag ctatttcggg tagttaatgc  20100
aatgatagta aagactatca ttaaaacgaa tactactaga cttattttcc agatacctag  20160
cagcatcata gtgaatagtt ctgcaaacat ggctttctcc tatcttcaaa aattattaaa  20220
gccccctttg cctaaaaagg cgggagtatt cccgcctaag ttattaatta aactagttcg  20280
acatgaccgc catcataggt accacgtttt atttcatcgt gatagtctcc cgaagcattc  20340
caatcagcac caaaacgaag cttaatgcct agttctttac cagcttgttc aaaagccttt  20400
ttaactgccc aaaatgcttc taagtcattc caatcaattt tgccattaat gtatggagca  20460
aaatcaagag catccccagt aatatgctta cttttactag gatcctttaa aaatgaagta  20520
ccattagcaa tattctgggc actttgtgct actgtacgaa taccttgtac gatcgtaaaa  20580
tcatatggag ataattctaa agctctacga gctacttttt gtagctctgg cttaacggta  20640
gctaattgtt tttcgctatt tttaccaaat ttaaaactca tattgatcta cctaaagatc  20700
tctgttgtgg ggaacagagc tttgttaaat actcgttaaa tttctcagaa tcggctgcat  20760
ctacaggatt atctttccaa gcaataccaa tatatccagc atagatattg tttagattga  20820
aatacggaca agtgtatatg taattaaaag taacgttctt aaacgcaggt atatttaacc  20880
ccatgtattt atttactttt acacttaaat ccgatgcgta gttaaagcct tccaagtgac  20940
gtctatatag ctcagacgtt ttatttaccg ctttatcggc caagtcagcc ctatctaatt  21000
gcgcattgct ttcccatgca ataatgttag aataatcatt aatggcatcg ggtttatact  21060
tgacgacaaa aacagcatcc gcacccgttt gagaaaagag taccatgctc ttttctctag  21120
ctacattagg aaagttatct atcctttgag tttgaacatc ctgtagaacc gcagacgtgg  21180
agaaagtctt taagaatgac atcacctcgc tagtattact aacaaataag aaaataatga  21240
cagcaactaa gatagttagc agacgtttaa gaagcgatgc tggatctttc gcttcttgga  21300
gcagtaccgt taataattgt aagaactttt ccaattgtaa cctcctctaa ccagtaccat  21360
tatactaatt ttggaggaaa atttcaatgg gtttttaaat gttacacttg gagcacaaaa  21420
ttatgtcgtt gtcaagaaga attttagata aaagaaaagc cagggtactt aaccctggct  21480
taaaattact tactcttcgt tgtgctcttc tgattgaggt aactgggctt tattatattg  21540
ctcagatcga tattttgcca agatttcaat acgcttacgg atttccttgc tatctagata  21600
gatatttttg ttgtctttta ccatctcgtc gatttcatct attgagaaga acggatagta  21660
gacatctagc atcatatctt ctacaaactt gttgtaagat tcataggctt tcttgatttc  21720
```

```
ttgacctttc tcacagaacc cgccagagaa cgtgtgtccc attagcgtag catgtggatg  21780
tactacccat ccatgacagg ataggaaaat tgtgcagtaa gcagaagcac taggaccaat  21840
caggtgtcct ataactgttc cacggcaatt agcaattaag ttagataact gtgcagcagt  21900
atcaacataa ccacccggac cattaatcat cagattaatt tcgtcgtcct catttgcctg  21960
cataagtacc attgataaat cacggtattc atccggcggg cctaattctt catcaaagaa  22020
gaaggtatac tcgttagatt ggcgaatgga gtgaaacaga ttagtctttt ctttttattt  22080
agccatagcg atccttgatt atccaactag tggttctagc tctaagtcac agaagttata  22140
aacttctagt ttaaggttat tgataccatc gaatttatta actaattcgt gagtaatata  22200
ttttgcagga ataccacttt cagatggatg atctgattta atagtgaact tctgctcagc  22260
gggtactaca tttactatca aagaatccat atctaaatgg tttgtttctc tgagtaactc  22320
tccttcattg gggaatctaa catctgttat tacggcgaca tctgggtcgt ctttagcgat  22380
ggattgctcc agaattatga gccaaatgcg ttcatgcacc agctgccttc ctagctctgt  22440
ccctacgagc tgtaacattt ttctcggaga aataaataaa ctataaagtc cgtcttcttt  22500
attctctgag ataagttgtt gaggattaag atatttttcc tcaaaaatag gccaaacgta  22560
cgagaagtct tcaaacttat cgataccgta cttaaaccac acatctctgg ctcgctccag  22620
ttgagattgt gtgaccgtaa accattggtc aatctctttt cccctgcgct ctcctaaaaa  22680
ctctggagtt acaccgagga ttacggatgc aagttcataa acgggcttag caaaactata  22740
acgacgggat aaacacgttg gatacgtgtc attacaccaa tcgataatta attttgcaac  22800
ggtatctttt cccgaaccag cttcaccatg taaaccgact aatactgaca ttaatctttc  22860
ctattgttaa ttggtggata gtaaactaag caacgttttt cttgtaaatc ttggcgatag  22920
aagcaaacca taccagtcag tcgtgaaatg taagagtaaa ctgcttcctc acattttgct  22980
tttgcattcc aatctttata cggtacaaca actactacgc catcttctcc atttgtagct  23040
aatttctttt caaacttaaa gtcaaagcta caaggttgaa gtcctttagg ccagtctaca  23100
tgagcttgct ttaactcatg agatggctct ggttttattt cttctgcaca gcctgtgatt  23160
gtgattgtgg ctgcgagcag tactccaagt ttccagttaa acacgctaat ctttcctcga  23220
actctttatt ctgcttttta gcaattaatg ttaccaatcc aggctttgca gcgataacat  23280
cttggcgact aagagcttta tctagctgct taatcttttt gtctagatct gcttgagata  23340
cattattcag tgtaaaatat tgattcatgc gtgtctcacg acgttcactc tcaactttta  23400
cattattcaa ggaagtttct agagaagaga tctttttagt agctaccgca agatcacccg  23460
ctaaagtctc cactttatct actaagtgat aagcaccgaa cccgatgcct attgctagac  23520
ctgctcccag gatacaccac ttaccgtgcc atattcctga aagaagtttt tgtatcaaat  23580
ccatgcgctg ctaacctgtc tttatctgat actttaatca tatcaggctc accagttcct  23640
agtacaccga agatatactg ttcgagaact tggtgtaaac ggtataagtt actttcaatt  23700
tcctgccacg gaataccgga ctgatggaaa cgaatgttag tctgaattac gaagttacga  23760
acatcatcgt tatcgttctt tttaatacct ttcacatatg caattggtac acgcagttcg  23820
gataagatac gttctgcttt aggttttgct tcagcgagca gatcacgcat tgtttcacga  23880
acatctccac gactcttatc cattaagtaa gagcgagcat gtaatcccat ctcttccatt  23940
ttatcaaaca tagtgtcgag attaaacgtt ttgaagctaa atgctggatg ccagcagtac  24000
agctcgtgta accagtaaac ttcacctgca acaaacagtg ggtttacaaa gtattcgaag  24060
tcgccacgga aagatagtga accatcccga aatacttggc gagtatgcac aatgttcttt  24120
tctgcatcat cagttacctt aaccagtagc tcttcagttt tacgctccca aacacgatcg  24180
gggtcgaaca aactgttctg caaatcatac acatcggcga acttagaaat aatcctcata  24240
tttaatcctc ttgcctcaat ctataaacat attatacaaa agtttgggca tctaagcaac  24300
taaaatttta ttataaaaat agcccagtcg caaaagtgcg tgctgggctt tgtcattatt  24360
tgcttttgct agtaagttga cttagtgtca atcttatgta atattagttt ctctagcttt  24420
gcgtagtacc cctgcatttc tccataactt aatatcgtct actgtttctt tataaggagc  24480
tatggtaaaa cctagtgggc cagcactaaa taaccctaag aatcctattg cacgcatata  24540
gaacaagcat tcttcgcctg tcatttcttc aactgctttt ctttgttttt cgttttcaaa  24600
ctcgtgctcc ttgttgtcta tacgaaggtg tttaatgaac cattcagcag aatattcatc  24660
taagtgtcta agtatagcta ctgcataccc agcgccaatt aaaaaccaag tggtaacaag  24720
aattagtatt atagtcatat aatctccagt taaggtcagc gaccaactca ccacttaccg  24780
cactaagggg cacgactccc ttatccgtaa cagttgcagg tgacgcaact cggtcctacg  24840
cgagttcttt aggtattctg catttcagct ttaaattttt tcatattacg agtctttcta  24900
taaaagaaaa acacagatgt tgggcctaga agaatatcca caataaatat catagatcta  24960
gcacatctga gtaatgtttt atcatcaaga ggaggcagat ctaacggtcg agttttatgt  25020
ataacgtata atattacatc tttattctta gaaatataca gatcatcaac caagctgtaa  25080
atagctacta tagatccaat gacgaaccaa agagcaaatg gagagataat catttcagat  25140
ccttttcatt aattagaata ttagtaaaca gtggaataac ccctagactc atagcaggtc  25200
caaacgtatt catagctacc cacagctgca tagtgatcat cccatcttta atctctggat  25260
ctttatattc ttcgatacgt tttttggcaa aggcaactac atctggatta tttttatttt  25320
cctgaatata gtcatgccaa aactgggtat tctcactacg taggaatgtt aaaacatcct  25380
tagttgctgg aatctgcacc gtgctgttga tgtttagctt tttcacgttc ttctctccta  25440
cgtttgcatt ctttcatcat atgagctgct acaacttcat ggtagtagtc attaatgtta  25500
ccttctggca agaaatgctt aatagtctct agctgacaaa taactcgatg aagatggtta  25560
tttggtagac acaattttat acctgcaaca aatccagaga agcctggaac actgaacatg  25620
ggttgggctt ccactctacc ttcagagttg atattaagat caattgagat acccattttc  25680
atgctataaa gctggcaata ttctccatta ccagatcttg accaaacagt gaaatcctca  25740
tcaatttgat cttggatttc tgtaattgca aatttaattc tagggtctaa attattcatc  25800
ttcaccttca aagtcgcaat cataacgaca agtaaaagaa ctggagctat tagtacgttg  25860
agtggttatt tcaccgcgtt tgctaatagt aacggctgga gtagagaagt ttttattagt  25920
atatatttct actttaccat tacgttcctt aacatcacga actttaccat actcggtaat  25980
aatgccgttc tgttggactt taacattacc atttttcata gaaactttgg tagatgccag  26040
agaaccgaaa ctaactgtgg agatcatcag tgcaataata aacttattca tcttcatcct  26100
ccccactaca atcacgacat acatcataat cgttgaaaga acgttcgtga gcttcacacc  26160
accaagaaca agaatcgcag agaaacattt cggttttctc tagtgcttga cctaaaagat  26220
catcagcttc ctcagcagta atcttcaatc cgcacacatc tgccacacgt tctttaatta  26280
aacgacctgc ttcgtgataa gacatacagg ttcccacaac atcatgttca agaacatgaa  26340
cagcacagtc tagacgagtt ttcatttcaa acctctctca tcaatttata aatatattat  26400
agcaagaaaa gagaggttta gcaaatgaat tatttcagaa tttagtcata gcaccaccat  26460
```

-continued

```
aatccacgct tacgcatgtc atgatcgcga ttataatcat aattttctgg atctttcatc 26520
acgcggtgga gttcttgacg attcccttga cgaaccattt tattagaatg ccacttaaca 26580
ttcttactaa tagaattcca gttataacca tcctttttct cattacgaat ggttgcttcc 26640
ttcatttcct gttctacatc atcccaggat ttagcataaa taacacgaat ccagtagcca 26700
ttttctttga tgaaagaata ttcttgagag aattgttctt tagacttcca ccactgatca 26760
ccagattgtt tacgataagt acggctcata ttacctccat taagtctttt aaattaacct 26820
aatgtggatg aattttgtta tacatatatt atgtaccttt atacagaaaa accccagact 26880
acttattcaa tagctggggt ttgttattaa ttacagatcg gggcgttcat cttcgaaaca 26940
gcctgagcta attccttctc cgaatcctac aaagccatca aattcatcat ttgagatgcc 27000
cataatcatt gcttccattt tcctaacctc cgaaattttc atgcctgctt tactattctt 27060
ataatatttg cgagggttcc cgcacatcca acaagaacag atgcaaggag tagtagtgat 27120
aatacctaac cgcttagggc tttcttcatg tgggaagact gtccaatact tcttgcggtt 27180
gttcttcaca cgttgccggt gatggcgtct taatgctcga tccacacatt tctcctaaaa 27240
cttgggagat aaacggagtt tgctcgacta ccttgcgtag ctgggagaaa tcgtatccaa 27300
accccattac atcgcctgag taaatgtacg actaataacg tcgttctgtt gttcacgagt 27360
cagtgcatta aatcgaacag cgtagccaga gacacggatg gtcaactgag gatatttttc 27420
aggatgtttc tgcgcatcca aaagctgatc acggcttaac acattgacat ttaggtgctg 27480
accaccttcg atttgagggg cgacttccac cttaacttca cggaaggctt cgggatcgaa 27540
ttgtggtgtg ataccttcta gatcttcaac tagaactttc tgtttaagtt caccattgtc 27600
ggagtatagc tgaataatct ggttttcatg aacaaggtta attacgccag acttaagatt 27660
ttgatatgct ttcattagat ctccctgatg ttagaatttg gctcagctct ttattgtcta 27720
tagtttacca cgatatacag aaactgtctt accagtttgg ttcataacgt atgctacttc 27780
atcttctttt aagaagattg cttgatctat tccagaaata gctatgcttt tatttctggg 27840
attaaaccct acgcttttac caacatgaat ctgctcacca ccatcagtgg acattatttt 27900
aactgttaac ataattgctc ctatatttag ctatctctag ctcttttaat ggtagttagt 27960
agtggatttg aaccactgta gtcgctccgt atgaaggagg tgcataacca ctctgccaac 28020
taactgttat gttttactag actaagtaag tattctttat actctttaga ccaattagct 28080
tttttaaact ttcctggacg catagtctta attcctagat ttggtactcc gggagggatt 28140
taaacccccg atctctcggt tatcagccga gtgctttaga tcgctaagct accgaagtat 28200
tagaatattt acatcataca ctgtctaagt aagaagtata atggaattta gcttctccag 28260
tcttatctac ttctacctca gttcgtggta cttgacgaac cacaccatga atcatcttat 28320
agcgaatgcc tttagctggt tcatgatctt ttgggaatac ttgtttaacc gttactactt 28380
tatatccttc acgcggtgtt aacactacta cttgatcacc ttctttgatt ttccaagaag 28440
atggaaattc ataggtatat ctttgaccac cagtttggaa tactacagaa agataacgtt 28500
tcatttggtt tccctctcat taatttatat agatagtata acaagaaata agagagaagg 28560
caaatgaatt tttaaatttg gtgctcccac caggaatcga acccggttca gatgcttaca 28620
aggcaactgc atcgccagca atgctttagg agcgatgatc ccgttatttc aacgggattt 28680
ctttttcaat aacaggagac ttatcagtca taactgtcat tgccatttgt tgtagaaatt 28740
caaaggtgaa ggctacacgt tcttcaccaa tctctacttc tacacgtttc ttttgtttat 28800
cgatcttgac ttttaggttg tcagccatct tcgggttctc gttgctgcgc tacttctagc 28860
cagtctggta gaagaaactt tgtacgaaat tcttcgtaag tttctttggg ataaaagcta 28920
aaacctcctt tctcatcatt caggataaca gaaccgtcag tttgttcgta tgctcggtat 28980
gtttccccaa taacaataac tcgtttatca gtacttttat tacgaaactc aaaaacgtgc 29040
ataatgttcc cttaaagttg gagcggctag agggaatcga accctactca gcgaggcttg 29100
gaaggcctgc gacacaaccc gtgtgcttaa ccgcttattg tttggcaggg gatattggat 29160
ttgaaccaat gatctcgact tcaaaggccg aagctttaga ccaggctaag ctaatcccca 29220
actgtttggc agaaggtagt aggttcgaac cactgatcgg ggtttcagag accccagcct 29280
taaccgactt ggctaacctt cttcttaata ctttttggat cttctaaacg tttgccttca 29340
tgatctactc gaataactcc gcacccttcg caaaccacaa ctacaccata accttctttg 29400
acctcagctt ctgtaatcaa accagaaaga tcaccagtat ctctgcccca catatcaatg 29460
gagcattgtt tgcagaaatc agccatattt tatttcctat ttaagttaat ttggggtggc 29520
tagtggaatt cgaatccaca taggcctgat tcacaatcag gatcattaac caattatgat 29580
atagccacaa ttgaaaactc gcagggttag cgaaaccttc ctcaattagc atgttctaga 29640
atactaatca agttatctcc tattgcacgc agctcaagac gagtacgaat tttcaattgt 29700
ggtggctctc agaaactctt ctactctagc cttagcagct tactcccgaa cgcatgtcgg 29760
ggaagtctta ctaagagctt cgaatagcac cgttacactt tgagccatag atgtatcaag 29820
aagcagaagg acttgaacct tcacgagata gaccatttat ctcagccgct ttatgaggta 29880
tgttgcaggg agtggatgtt ccctataaac cttttaggca gccccgtcta ccgattccag 29940
catacttcaa gaatttttat aaaccagcag aagcctcatt taaagcatca acaatagctt 30000
cacgttgggt cattccatac ccagtggaat ctaggtgtgg caaataagcc atccatccct 30060
tatctgtttc atgaaggcat gctttaaatt tttttttttt ttttttttacc gtccttcatt 30120
gttacagtaa ctgttttgct cataatgatt ccttatagtt aattggagga aggtaatgga 30180
gtcgaaccat caccgtatca ctacagcggg ctagttttca agactagttg cgtaccacta 30240
cgcccctacct tccatttgtt tggcggaaga ggagagattt gaactctcaa gccgttttac 30300
cagtcagcca ctttccaagc ggttttcgtc gccaattcga tttgctcttc caataataag 30360
atgatgcctc tatcacacca ggcagttacg cctcgctggg attcgaaccc attaaaacag 30420
ctcaaccgag atagtagatt taatttactc tgaccatcaa atttggtgcg tgacaaggga 30480
ttcgaaccct caaaacccga cttctaagga cggtatgtat gccaattcca tcaatcacgc 30540
gtatttggtg gacaaagagg gactcgaacc ctccctacca gattgcaaat ctggtgtgct 30600
cccgctgaca ctattcgccc aaatttatta atccagcatg tacttctcta tggcagttag 30660
agcataatag tacgcacttt ttaagttctg ctattactac ttctctgttt ctacgagaag 30720
ttctaaacct tgcaatggag tattcctttt cttctggatt agtatggtgg aaatctaagg 30780
cttgtttaca cctattatat ccacaaatac tacattctaa tacaggaaat acttctttaa 30840
ttaattcttc atgtccagct actcgttcag ctttttcaca tgctttacat gttggcttcc 30900
acttctttgt gccattagga gtaaatccat tcgaataaaa atattcggtt gttaacggat 30960
attcattccc acaggctcta catgtttttg tacacactgc gttaacccct gtaagtttac 31020
taaggctatt agctcggcgt aactacagca ccttcgcttc gagcggaagg aactgcgtca 31080
tctcgcaaac ccgatacact attcagttgc cgctgaatct agtggactaa tctagaactt 31140
ctcccgaatt gtagggatcg tgctttttgg cagccagtcc taggtcgagc taataccta 31200
```

```
gtgaactaaa ttgatggata ccagactaat tttgctacga cgtttatcct gaggatctct  31260
ttttcggtag ctctgctagt gtagacgtca tacacctggt atctaggcag ctattttcgc  31320
atcaatttat ataaatatta taacaagaaa ttaagcatta agcaagtaca tttttagcga  31380
tttcctgtag ttcctttaca tcacgaacgt aaaggtaatc agagcttcca gagtgcatac  31440
tttgcataac cacaccttca tctggtgcat tatccttcaa ggtaattcct agccagaact  31500
cggcaaaact aggtgttatc tcaccttgac ttgccttgaa tacatcatat tctgtaagtt  31560
cttgaccagt agataatccc aaatagacag aactaagatc aatctcttta tgagactcat  31620
aaaattccga tagatctttt tccatatccc agccatgctg caatgcgaac tccattgtca  31680
catgaccgaa ataaccttga atcttgtttg ataattgcat ttgcaattcc ttattttgag  31740
ttaattggta ctcggtgata gaatcgaact atcacaaccg ccgtgtaaag acggggttct  31800
cccattaaac taaccgagca atttggtaga tcgcctggga ttcgaaccca gaactgacgg  31860
attaaaggtc cgctactctt atccagttga gctagcgatc tattagtaac cattatatac  31920
ctctttaata gagtgaactt tcaagtaagg gtgattagta ttaaactctg ccattacttc  31980
atcccaattt ttaccataat gtgcaagtaa ggatcttgag gtattattac ctaaacgttt  32040
gtcacttact actaatcgaa atactttcat ttcgaaatcc tctattaaag tggaagcggg  32100
tgcaggaatc gaacctacct ctttctagct tatgagacta gcgatctcta ccagagatct  32160
aacccgcaat tgtttggtct ccgtgggagg atttgaaccc ccgaccctat cgccccaaac  32220
gaaacgctct ggccaaactg agctacacgg agaatattat ttcttcaacc acaacaaaga  32280
taagcccagc atactaaagc cgctaactaa tccgatacat ttttcttcta tagtaaaagt  32340
atctagatta aatgctgtta tagctattgg catacaccat aatgtcataa aaacttgagc  32400
tatcttgtgt ttcattttgc tttccttctc ttcactttat aaaatatatt atacagataa  32460
tatagcagaa tagcaaatga atttttaata aatttactta ttgtgtaggc cacctggagg  32520
ctaccaaccc cacggctgac aaagaagttt gcgagacctc tcttaaatgc cagaatagac  32580
ccgccgatct atcggaacct acataataag taaactttcg tttacttacg ccccgttaga  32640
gggactttag cgactagaac cggccggaaa cttcatcgcc ttgtttattc agaagtccgt  32700
tctctaggga gcagaaatct aaatttggtg gagtttggga gactacgtgt tactccctct  32760
gtccgaagta ggatagtgct taaccgttta gctgaacccc tttaaatatt tatacgtttt  32820
atctaacaac tcttgtttag agattatacc atcacgatat tcagtaataa aattatctat  32880
gttggagtcc tttgatacaa cgttatcaga tagctctgtg aatttatttg ctaaaagatc  32940
taattctttg taattcacaa aacctccaga atatgccatt ctagacagga ctcgaacctg  33000
ctatcacttg tgcggactta cgagaaccat tctttcactc gaatcgaacg agcttctgcc  33060
ctagccaagc tggtttcccc atcaaccacg ctagaatgtt tgattgtttt cagtgcaaga  33120
gtccgagtct tggacacgac cgcttcgcaa gtacataggc agcttatcat gagtcagcac  33180
ttccgaattg ctagctccgt gttctgcact gagattttgt taatttaata gtaaagtacg  33240
atctacttca ccattaattg ttcggcattc ctctggaatt gctggtgtag tcttatattc  33300
ccaccattca gaaccatcat attcaccacg ttctaaccaa gttccatcag taaaccatac  33360
gttaccataa agcaattgtc caccgaaacc agaatcatat ttaaagtcta gattatttag  33420
aaaatcttca atatcttttt ctgtataacc tacgggtaat acccaaactt ctttgtctcc  33480
ataataaccg aattctatct taatacactt aacttcagaa ttagtattct ttagggcaag  33540
taacaattct tctttagcat taatcatagc atatttctca tactaaatta atttggtaca  33600
cccactagga cttgaaccta gaaccctccg cttaagaggc ggtagctcta accattgagc  33660
tatgggtgta ttaaattact tttccagttc atcagctatg gctttgattt tttcaaagtt  33720
tacatcacta ataatgatac cttccagtga cagagatatt ctagcatttt tcatagcaga  33780
ttcttttatc tgctctattt cttctggagt aaactcccta cgttccatag ctaacctacc  33840
ttatttggcg cgaccgatgg gatttgaacc cacattccct cccgtgacag gagagtacca  33900
ttaccaagcc agccccggtc gcataattca tttactcagc tttgagcttt tcaatagctg  33960
cattaagttc tttaagaaac tcttttcgta cattaagacg attgagactt actagtatat  34020
cgtgtttaag ttcttcgatg tatttctttt caacttcaat attgttgata gtgctatcac  34080
gatgaacttc tagctgcgca attacattct tggacatgct tgtttcctca gttattaatg  34140
aaaatggtat ctgtggctga attcgatgtc agcaatgata gctggttggc taccggttta  34200
cttaactcta cacagaattt ggcggttcct gctggattcg aaccagcaaa cctcaactta  34260
acaagatgcc gctctaacca attagagcta aggaaccata taagtcagaa ctagagttaa  34320
tacgttctag atatttacta agatccctag aatttatact aaaccactca tgttctttta  34380
aatctttgaa atactggtga attagttttt cacctttttcg tttgtcaaac caaaacgacc  34440
aatgctctaa tttataatcc ctatatgggg aataggtctg atattgagct aatctctctt  34500
ttggattttg actcatacct attttatact gatttttcca tgcaggatta ctaatacagt  34560
atacaaaacc ttcagaaata ggaagtttat tttcctgctt aaactttata aaggaaagtg  34620
cggcaagttt tctcgaatac atagtattcg tattcttttt ggtattacca ttagttcctg  34680
aaagatttat atattcttcc ataaatcttt ggattagttc tgcggttata cagaaaggcc  34740
cattagtaac aacgcctttc tttaccaaac tatcaaaaac ttttgtatgc actacttctt  34800
tcctttagta aattggacga ccgcatgaga tttgaactca cataaaaagg atttgcaatc  34860
cttcgcctaa gcccttcagc caacggtcgg tttatcttgt tctgtcatgt tgcttctcca  34920
gttcaattta tgtaattatt atacagaact tttggaaact aagcaactac attttttaag  34980
aatttgatgc ctttcttttt cttcttatat ttccacgtta atggattctg tcgattatga  35040
acgcttgaga tctttgtctc gtcaaagttc ttcaatatca tgtaatcaca ggataattgt  35100
tctagtagaa tgtgatcacc gtcaaaagcg tatacataag gctgttgact aacacgataa  35160
tgatagactt tgttaattct acgtttcagc gacttatcag cgcagtaaat aaagaagttt  35220
tcaggatgca tcagcagctc cttcaatttg gtgcaccctg ttcgtatcga acgaacctct  35280
caagctcttc aggcaagcgc taatccatct cagctaaagg tgcaaatttt ggcaaaccta  35340
ctaggactcg aacctagacc gtacggtttt ggagaccgac atgctgtcca gtaacactct  35400
aggaatgcag aaattggcgt cctgtgcggg gatcgaaccc gcaaatccta ccttgaaagg  35460
gtagtgactt taccagtttg tctaacagga cttaaatttg gtgttggatg atggagtcga  35520
accacccgag acccttccga gtcggcagat ttacagtctg cttcgctacc tctacgatac  35580
taatccaaca tatttagaag tattcaaaaa ttctcattta aacactttta aatatgcttt  35640
caaattaggt aactattata ccaagtttta aggcactgag caagtcaaat tttaaagaac  35700
ttgctcagtg ctatattagt tagtcgaact taggagtgac agttaaggag aacggaagtt  35760
cgaaaacttc ttcaccctca ttactaacgg taactacacg acctttaagt tcagacatta  35820
aaatatcaat atcagctttt gcatctggag ccatgccagc ttcaatacat ttagctttaa  35880
cctccggtag aagatctacg ttatagagat agagccactc aatctcacct tcccagtctt  35940
```

-continued

```
cccaggattt gcagattgca ctttcaatac cagttgctac aacacgattt tgcattcgtt  36000
aactccttca tcaatttata caactattat atcagaaatt taaagcaaaa ggcaagtaca  36060
tttttaaaaa ttctgtttgg aggagctaaa ctccagattc ttcagctaag tctaggctaa  36120
taagagttat agccataatt gctgcaccgt gttctttttc tccggtgttt ttagcagagt  36180
ctataatagt cttaatctgt tcgtaatagc cttttacttc ttgttcaata cctgcctcgg  36240
ctatcatgcc tttagtcatg attcgttgca tagtaatttc acggttagcc atgatgtttc  36300
tccagcttca tttttaatag tttacaaatg aaatcaacgt cttcatctgt acctagatct  36360
ctatcttcaa gagttgcctt gaagttttta gtcaattcca tgaggataac ttctctagaa  36420
cgacgtgttg gcggaggtgg atgtctatac atcttatttc cttagtttgg taggggtggt  36480
gggattcgaa cccacaaaac ctgaatttta agtccagtac ctatgccaat tcgattacac  36540
ccccgtgtag tttagtcaat tacttttgag gcttcaaggt agtcgatata gtgtatgttt  36600
tctaccgtaa tcatataatc tgccacttta tccatagctt gggcttcaga ggtagctctg  36660
gctaacctat atcctttttt atattcatcc gggtattctc tatcttggat aaacacaaca  36720
taaactatat atagatccat ttgtgacctc tatttaattt ggtggctccc cgaggattcg  36780
aacctacgta ccttccggtt atgagccggg tgctcatacc atatgagctt gagaaccaga  36840
atttggcgga agaagcggga atcgaaccca caaggctata tttcaaaccg acagattagc  36900
aatctgctgc aataccgtta tgctattctt ccgaatttat aagatatatt atattagaaa  36960
tttagcttca tagcaagaaa atttttcaag ttttcggtag acatctcatc cacatctacg  37020
ggagaaacaa agccgtttaa ttttctagca aatttttcac ccgcaggatc attatctccg  37080
acagctacca atttaaaagg tagtaatttc agttgcttta ataacgcttt tcctggagaa  37140
gaacccaaca ttgctagggc tggataacca gcattatgta acgcaactgc cttaaataca  37200
gattcagcaa tcaatactac tttttcatct ccattgagag tttctagtcc ccatacacac  37260
tgggtagtag aataagtaaa gtatttagct tcaaaggggc acttaccatg accttttgga  37320
gcagaaggat tataagtttg atagcccctc aacatcccag agaagtcata caacgggact  37380
gttagccatc cttccggact taaccagcaa tgatatttat ctgtatcaaa tcctctagat  37440
aagaggtgct gtgttagctc atcaacattc atatttggtt cctctttcaa atttatagat  37500
atattataca gagaatttag cattcaagca atcaaatttt ttaacttttt agaggaaaat  37560
catagggcac ttaaggatag cagataagtg gtgaggacca aaatttgtga ccccactaaa  37620
aattcagggg caatttttaa agaccccttg acattttcgc tggggtagtg taaagtatat  37680
gttatggatg agtgatcaaa gagacacaca ttttctatat actaggaggt gtcaaaaatg  37740
acagaagaag tagctaagag tcctgagacc gtcgctagcg ttgcagcaga actgcaccgt  37800
cacgaggaat cagataagaa aaagtgggag aaggtcagag cctacgaaga aaaacatcgt  37860
gaacacgatg atgaagaaga tgatgatgaa cattgtcata aatatggaaa acataaaatg  37920
caagaaccag taaacgtatt tactagtggc ttccctggcc tactgggtgg ttacccagca  37980
aacgcaggtg ctttcggtgg tgaaggtatg ggactattcg gagctatcct aatcggtgct  38040
ctattaacag gcggattcgg tggtttcggt ggattcggtg gacgtggtgt agttggtgat  38100
ggtaccgcag ttgatgcagt acttcagaac caagataccg ctagtattct agcagctatt  38160
aacactactc gtacagaagc taaccagggt actggagctg ttttaagcgc agttaacaat  38220
gggtttagcc agacatccca aaaccagagc cgtgatactc agtctgtact aactacgatc  38280
tatggtacag gtgctaatct gtctaatcag atctgtcagg aaactcgcaa cgttattcag  38340
ggtcagttcg atctttctcg ccagattgat caatctttcg cagctaatca gatagctcgt  38400
gcacaagata agtttgattc tgcacagatc gctttccagc agactttaca aactaataac  38460
cagtttgccg ctgttcaggc tcagatgtgt gctaaccaga actctctgga acgtcagatc  38520
gctgaatgtt gctgtgaact tcagactgcg atcgctggtg taactactgc gcgtattcag  38580
gatgagttag atgcatgtcg cctacgtgaa gcaatcgctg cgggtaacgg tgctaacggt  38640
caggtaatta atcaaatcgc tgtaagtctt ggtgctatca ctcagactct ggctggtctg  38700
caggctaaac tgccggctta atattaaggg gaggagccca ttatgagtaa atatggtttt  38760
gtaaataacg gacttaatca aagtatgggc tcccagcagc ccattccggg tctggataac  38820
ccctacttac aacaattgca acagcgttta gcagaagcgc aacagatgca gcaacaactc  38880
cagcaaaacc ctggaagtgt gagtcctatg caaatgatgc agcaaatgag cgggcagtcg  38940
caaatgcctc aacaaatgca gcaacaggtg ccgcagcagc aagctcagca gcaaacccaa  39000
caaccgcagg tttctgcgga aggacaggca gtactagccc ttttcgaaga cttcgcaaag  39060
acagaggatg gtaagcagct tgtatcactt atgggtaagt ttaatagctt ctgccaaagc  39120
caggttgcaa aagctcaaaa tagtggtaat aactcctaag gaggaattat gtgttgcaga  39180
aaatctgttt cgtgctgccc aatgcctgta gcacgttgtt gctctccagc aatgtttacg  39240
caaataccgg cgttcaatcc gtttgccttt aagcctactc ttatcctgcc ccctagagta  39300
gattttcagt caagattggc ctcccgtatg ggtggttgct gtaataagag tatatggttc  39360
tgaagaacca aacaataaag cccctagtcg aaagacttag gggcttttct tttatcttaa  39420
atacagaaaa gccctgcgct ctccaggaaa cgcagggctt atttcagatg ttacatgcgg  39480
gtattactta ttacgcatat ccataatcat ttggccatca tagccagtgc caaccacagt  39540
ctgcggtaca ccaccttggt atttctgagc acgaatcatt tcaacttcca gttgcttcca  39600
gcgaatcatc tcaggagtaa tggtacgttg caacgcggcg ttagcttcag cttctttctt  39660
agctgcgtac agtttggcat ctgcgtcacg ctcattggca atagcttggt tattacgagc  39720
ttcgcgatct gcttctgctt gtttaacctt ctgctgtgct tcttgttcaa cacgagccag  39780
ttcagctttc gcagcattaa cttgctcttc acgaactttg gtattctgta cctgttccat  39840
gattaccggt ggcaaagtaa tatcctgaag gaatacctgc ttaactgtat aaccatatgg  39900
gcgtgcatac tcttcaactt cctgttgaat tgcagtttgc aattgagcct gaattttagc  39960
atcaaacaaa tcttgtgctt taggtacaga cttaccaaac tcacgaatag tagacagtaa  40020
tttttcagtt acatatttgt ctagcgcttg atcctgagta cctgcgttaa tacggttaat  40080
cggtgcctta gaaccatcaa actgcaacat aacagtcagg tcaacagtgg atttaaactt  40140
atcctgacta ggaacctgaa gtttatctaa ttttagagca atatctttag tactaaaagt  40200
atcgaaagaa gcaaaaggat ttacaatatg aaagccgggt agtactgggc tagggtcaac  40260
tttacccagg aaagtctggg ttttaacagt accgtcttga acaacggtat aagagttaaa  40320
ggctagaatc aagcctgcta aaccaactat agcaccaata ccccaacgtt taatagtacg  40380
aattactttc tgctcagaag tcagttcttt catattttta gtattaaaca tatatttcct  40440
ttgttttagt tacagttaat aaaattggcc gaggtgacag gattcgaacc tgcataaagg  40500
aatttagaag actcctgcct ctccattaga ctacaccccg tttaagtatt tttaagaact  40560
ctcgtaaaaa ctcttaaaaa tacagacgat accgggagag tcataagtct cactcattaa  40620
gtatttcaag acaaaataca gtaacgtcta ttattttcca gtttaagtca aggtgactta  40680
```

-continued

```
gtggttatgt cctgcggtat actgaggact cggttaggat tggggtcatg acttcccgcc  40740
ttttgctgct actcaacagg agttatcgcg aattacctgt gctattgtgc accattagtg  40800
acatctctca tgtcagcatt tcccactttg tggatagctt gaaaaactac tccgatatgg  40860
agaaagaact tcactatcct agaatacctt ctaaagttct tctttagcct ggacatagtt  40920
aaatcgtaat aaaactattc agcagactag ttggttagtc tggaaccaac taccgcgtgg  40980
tttaggcagt gcgcaactaa cctcggaagc ttttacgtta aaagcatcag ttatccagtt  41040
cttaccgacc gtaggattcg aacctacatc ttccaccagt tacggcttga taataccaat  41100
tatactagga cggcagtgtt actacataag tgatttccac accccactat ttataaatta  41160
gggaagagtt taggggagag gtttcagacg cctcatttta tacgttctag ccactaaccg  41220
ggattgccgc cccctgtgta ctagttttac aactaaccca ccgactctat tcaatgcgct  41280
ccggttggga ttctgcactc agcgtaatcg gctcgctgtt ccctaattta tgaatatatt  41340
atacagaatt tataagcatt tagcaaatga atttttagaa aaattcacta gcgatcaaag  41400
cagttgtttt accgtcataa cgtccaggaa attctgcctt aatagttttc attaatagag  41460
ctttggtaat acctggattt aatttaacca gttctgcaaa atactcacga atctgaactt  41520
cagttaactg ctccagagca tattcatgct ctagacctgc taacaagtcg agatattcag  41580
catctggagt atattcgata tttgcttttg cagcagaagt cattgtattc tcaattgctt  41640
tgaactgtga tttaacccag ttagtaaact ctagtctaga tacgcaatct ttatcaattc  41700
gttgtaagtc gcctaaaatc gtactaaggt gcttgactga cacagtatca ccgtgtttgc  41760
gagctttttc aattaattct cgcagcacac gaatcatatt cgtacccatt atttcatccc  41820
caatgcttgg ttaaaagatt gttctgtcat aactgctgag actttggcga aatcaaactt  41880
tttagggttc gtagtgattt cagcaacgtt agaagtttta acagttttcg tagtacgaat  41940
accacgagtg ttaacaccaa taattacaac tgatttcata tttcgcttcc tctcattaat  42000
ttatgaaagt attatacaga aatttaagta gttaagcaag taaattttta agttttagtg  42060
acaacaggtt tataaaacgt atgtccctta atcttagttg ttttcttaaa cttctttgtc  42120
cagtaaggtt tatctttacc actatggaag tatagtgctc catgtgtagg atcttgtggt  42180
aaatcaacgt agtatatcac tctagctaaa ttcttagcgg tttgccaagc ctcatcagtt  42240
ttatcaactt ttggtctctt agatacccaa gagaactggt tagactgata tactacttta  42300
cagtaggaat ctgggaattt accggagttt acacggtttt tagtaacata tgcaatcgcc  42360
gtcattccct ttatgccctc accacgactt tcgaaataga tatttttagc aatgcaatct  42420
atttcttttg catcgtgcga tgcctgacta ctaaagctga aggtaagggc agctactaaa  42480
agcaaagctg ccttcattct ttttactcct gccaatcata ttcaacacga ttgggatttt  42540
ctttataccc taagtcaagc aaatcattac gcatattttg cttagctact gggttcgagg  42600
ttactagtac cactttcttt ggtctctgtc caaattctaa gagtaaacga agaatttgat  42660
aaccttccat accatctaca gccaagtcat tatccatata aacgaaatgg cctgtggtat  42720
cagttttatt cagaaactct acagcggctt ctggggttcg aatgataatg tccattccgt  42780
gaagattgcg cacatcatca atcaaaatat gaaaagtcat aatagcctcg tttcatcaat  42840
ttaaaaatat attatacaca taatttagta aattagcaaa tacattttta aattgtgaaa  42900
ctagtaaacc gataaacagc ctagaggcgc cacaggccat atcttatgag ccatgtacct  42960
ttgatctagg gtttgaatca tcaacgaata ctttgcatct tttagcttta gaagtttaga  43020
agtttgagtt ctttaaactt ttcagctttc atacttaaat gttgatcttt gaagttgtgt  43080
cggtaatatc aacgacgctt tgtttttacg tgtcagatta aatgtctgat gtaataaaca  43140
taatctccaa tagattatac tttatagtat ggtcagcggt cttatttaac ctcgtatttc  43200
aaccgctgct gcgaggtaag atgcttgggc tttcgtctac cgatttacta gcttttaaat  43260
tattactcta cttcaatgaa ggtagaggcg ttagactcgg acagaacaaa gtcaacattt  43320
gttgcaaagt cctgatattc ctcgtcatgc tgcttaatca gcttctccag ttccagcgga  43380
tcaatcaaga atggagtatt cttgagttcc agcaggttga gctgcatttt aacctcatct  43440
tcggaagttt tcttatcgcg ggtagccatg ctatcctgca aacgctcata tttagtatca  43500
aactgtgctt tctgcgtatt aaacttaacc gtagcggcgt ggaactgctt acgcatgtta  43560
gccagcagtt gagctttaag ttccatagaa cgcttagctt caattgcttc cgcaacagtc  43620
atcttacgag aaccaatctc aactactgtt tccgcattgc tcttaatcag agcagctttg  43680
atacgatcac gctgggacat catatccagg agagattgga aatctgcctt aatacgagca  43740
gatagatcgt ctacttcgat tgcagcgcca actacaacct tatttttatc cttaccttca  43800
ccaacagcga tcagaagctg ttgttcagta gctttacgga ttttagcttc cagagatttg  43860
atagttgcca gagcgcgagt tttagagata cgagtagtca ttatttgctt ccttatatga  43920
agtttgagat ttgaatttgt ttaaatttgg tctattacag accaattgcc agcagagtgc  43980
gcagaacagt atcgttactg ttatcaattt taggattagc acgatttagc agatcaaaga  44040
ttttctggat acctgattga cgttcagcca tacgacggat acccagatta cgagtagctt  44100
tcttaccatt tttacgaaca tttttagata ctggcatatt tgttttcctt ttattgtttt  44160
ctcaaattta tgaatatatt atacagaatt ttggagccgg aagcaaatca aattttcatt  44220
ttttcgatca tagctgcaac acaatagctc tcaactaagg catcaaatgc tgggtcgtgc  44280
ttaaccggat agatcccata acgaatggtg tccatcttct ccattttagc ttttgcccag  44340
ctaatacctt cagcttctag atctttgtaa ctataaccag cttgcatcca gagattacga  44400
agagatcgaa cattgcccaa attccagaat ttccacggaa ctacctcttc attggttcca  44460
gcatggaacg tgtttgccga gtagatagtc atatcaaact ctgggccatt gccgtaatac  44520
aaagcatttt cgcctagagc caactccata atattttgag ccatagagaa ggcagcatag  44580
ttagagccaa gtttattagt gcaatgatgt ttaccatttt ggaaggcaat cagctttgga  44640
ttacgcccgt tcatagcttc cataatgtgg atagcagacg ggctattttt agcttgatcc  44700
atccagaatg ctagagtaga tgctgtaact ttggcaccag aattaagttg atcttgtaca  44760
tccaaagtaa caaatactag atcagggtct ttatcaattc catgcatagc cacaaaagcg  44820
aatgaaggca tcgcgatatg agtagtacca caatctcctg gagttcctag agattcaata  44880
tctagcatac caaatggttt tactttcata acttatcctt tattgtgtag aaaactatta  44940
aagagctgtc tctttaatag actcccactt cttggggtct ttaaaaccag gaagcatatc  45000
ctcactgaca tcccagttct cttccataga aaagtcaggc cattcattcc agctaccttc  45060
cagctcttca taacaggtat ccattatctc atgactagaa agtcgtgtat aatccctagc  45120
agacttatga gtgctagcac ggttaaaatc attctttgct acaaaattac gcatagtttc  45180
tccaaataag aggggctttc gccccctgat ttaaatcact tgcccagcag tttaaggata  45240
ttttccataa tagtttgggc agacttttca ctcttgttgg tttcagccaa ctttaaagcg  45300
agttcttcct gctgtttctg aatatccgca gcaatttttt gatcagcctc aatacgagct  45360
tgaagctcat cagtgatagt ggtaaaggaa gcaacgattt cagtaacgga gcgtggtttc  45420
```

```
ttagagaaca taaaaaatat ccttgattag ttagagaatt agtagattgt aggggcttct  45480
gcccctattt atctattact tcgctttacg cttgcgagct ggtttagcag atttacgagc  45540
agaatcaccc gtgaacttaa tgcctacacc gtaacacaga gcacgaacgt tatctttgct  45600
atactctaca ccgaagatat ttggcttaac agaaccaaac tgtccacgag catcacgcag  45660
tacatctgcc gttggtttgc gtttctggtt aactgatttc tcgtaatctt tcatggccat  45720
gccattacga gggaacaatt ctgctccagc attgaaactc agtgttactg gaacagattt  45780
gtgaccataa ccttgtacat aggtcacaag gcgggctaca gaacgagtag cgttcttagc  45840
cttcggcttt tgacgaatcg gggccggacg attcagtgcc tgtgcagctt gagcatcagt  45900
agggtgtttg cgcaggtggc gttccagacg agctttgcgg ttagcctcag tctgagggaa  45960
agttttaact gccggagctg cttgagtttt tgcgtttttc tgcttagcca ttatttgttt  46020
tcctttttgt ttatcaattt atgaagtata ttatacggta atttgaagcg tttagcaaat  46080
gaattttttaa tttattaact gtaagcttct tttaatttca gaccttacct gcatcaaaag  46140
aactcctaaa gtattgtccc cgatgcctcg gcaaacaccc caatatgtat ctccccaggt  46200
atttccttcg atcaaagttg catttttttgt tgctaacagt ttgtctctca aatcagggat  46260
tgcaaacttt aaccgtaaaa gctctagcat tacatcatct tttaccttat cccagtcaga  46320
gcgtagagtt aatttacgtc ctctacgttt ggcaactcct gcatttaggg agcgcagtac  46380
atgagctaca tcatcttttt ggtcagattt catagcctga aaagcatgtt ctacagtatc  46440
agcatgccat atttcattta gatattcgaa agtaattggt gataaataaa agttagataa  46500
gaaactataa gtacctttaa attcagtaat cttcattttt tacgccccgc atctttagcc  46560
tcctcggctg tatagatata ctgataagcc cctttggagt aggctggagc agtacacatt  46620
ttcttacgct caatctcttc ttgagctttt ctttcgcgtt cagctaattc ttcgtccaga  46680
taaactaaac gttgttctgg aggaggtgga agacgtgttt ctggctcacc aatattagcc  46740
tttcttattt gacgaggtga ttgtgcacgt tttctcaatg gtttaaatcc tagtgaattt  46800
gagttataaa tccgcataaa gccctcctca ctttcaatac gaatattata ctaaattaga  46860
gagctttaag caagagaatt tttaatttat ttattacatc tcagccattt cagcttcagt  46920
aataactgtg ttacacagtg catctacagc ttcattacca ctaataccag aatgtccttt  46980
aaccttaata aaggtaggat tagtattatg aaagttgata tactgctgtg ttaatttaaa  47040
tgcttcctgc caaagttcta gattaagagg aacttcacca tctgctttct tccagccttt  47100
cctttgccaa gaaaacatcc aactttccat accatttttg caataagcag aatcagtata  47160
gataacaatt ggtctattat cttttttaac tgaccaacgt agagcctcta caatagccgt  47220
gagttccatc tcattatttg tagttttagg actatatcca gatttagaac ctaaacgatc  47280
atcgttatca tcatagacaa taaatcccca agcacctgga cctgggttag acttacaagc  47340
accatctgtg taaatgtgga aaaccgacat tatttgctcc agtcaatttc aagccaaaaa  47400
ccttcacgct gctcatactt agcttctacg acatagccta gtttagtgag tcgttgcata  47460
acgctgtttc tggcgtttc tgaatattca gttaatccct gaatatggca gttaaattct  47520
ttttctttga ttgctttatc aatctctacg gcaataagtg actctagatt aagtacttcc  47580
tgtttaataa cagcaatagt attttgtttt gcttctaaag cagataaaag aatagacatt  47640
agttttcgcc ttctataatt accctagtcg ctggaggaat tggcggcata ggaggaatac  47700
atggttgacc tctctgtgca tcatttagta ctcttggcgg ttcaggtcta attgccttta  47760
attcctttc taggaattgt tctaacgccc gttctacaaa atgatcgaaa ggtaagtgat  47820
aatactgaga cagagctaag aacctacgtt cttgactttg tgttaaataa actttctttt  47880
taaatagtcc catagttgtc tccgatttat aaaatatatt atatctaaat ttcactcagt  47940
aagcaaatga aatttaaata taatagcccc gaagggctat ttgagttaag aagacatctt  48000
agctttaaga gctgggtgag gatcgtaccc ctctaaatgg aatgaccaag ctgcagtatt  48060
attctccagt aaatcgtaga gatctacaaa ttctggcatt actagagttg gtaaagaacg  48120
aggtttacgt tttacctgtt cttctacctg ttccatatgg tcattataga tatgagtatc  48180
accgccacta aagataaggt agcgaggttt taatccagtc agttttgcca ggatatgtgt  48240
taataaagca taactagcaa tattgaaagg taaaccgagg aaacaatcca cagagcgttg  48300
tgtccattta agatctaggt atccatcgtt acttacatag cactggaagc cgtagtgaca  48360
aggtggtaat gccattttat caagttcagc tacgttccac gcagaaacta gatgtctgcg  48420
gccatgagga ttattcttga gtccttcaat aagttctaga atctgatctc gcccaccaaa  48480
gttacgccac tgtttaccat ataccggtcc tagattaccc ttatcatacc ccatacttat  48540
agcttggtct tcataatttg gagtccagat ggtccactgt ccttcgtcac gaccaaatgt  48600
gaatacacgt agatcatgga gatttgtgga accagacaag aaccataaga gttctcctac  48660
tacggatttc caagctagac gtttagtggt tacagctggg aatccctcac gtagatcgaa  48720
tttagcgtaa gaatcaaaaa ttgaaactgt gcctgttcct gtacggtcat tacggggttc  48780
acctagtaaa attacatctg tcaaaatttt taagtattgt tgcattaata agtaaccaat  48840
tcctgtacaa atcgcaggct gttatcactg tttgcgccaa ctgcatagac taatcgagtg  48900
gattcatagt tataatccag tatcatacta tctaggtgtg tatctgcctc tagcttctgt  48960
tcgctaaaga ttgtagatac aaaagcgctt tcaatatgcc catgttggta catttctaga  49020
agaagattag ccccacctag aactactgtt tgttgatctt ttagaaaagt aggtaatgta  49080
tcacctatca ttgatatggg agtgtaaata tcatgtgtaa tatcgtctgg cagtggacga  49140
tcagcacgaa taaataggtc agaagctcca atcatacgtt ctctaacggc gtatggaaga  49200
gctaaataag tacccgcacc aatgataata ttatctggat tcaacacgtc cagttgagaa  49260
tagaaagcat ctagttcttc tttgaaggaa ccccatggaa gtttaccgcg gaggccgaac  49320
tccccattcg gcccaactgc atacattgct gtaatcataa gaaatctcca aattcattac  49380
ccagatcttt cagagtatca gtagaggtct cagttacctg acctacacgg taggctgcac  49440
caatctggat ttcttgcgga gcaggctgta gagaagtagt atccaaccag ttcatgatcc  49500
acggaatagg gtttttggtg attactggta agtgactagg ccattctaca ccaatgtgca  49560
taaatgcatt acgccccaca aagtacagat attcttctag aagttctgcg ttcaagccaa  49620
tcagactacg acctttgaaa atgaaatgac cccattcaat ttcagttttc agagttttca  49680
ggagctgtgc tggtgcttta gccactgctt catctaccag atctttatca aactgctgga  49740
acataatctg gatgattgct ttagacatct gggtgtgcag agcctcatct ttagcgatta  49800
attgcagatt tttagcaata ccttgcagaa tatcgttctc tgctaatgca aaggtacatg  49860
caaaggatgc gtaaaactgc attgcttcca gaccatagat agcaaagtaa gcgtctaata  49920
gtttagcctg agtttcacgt ttaacttcag ggaactccgt ttctggatat gtattgtcgc  49980
cacgatgatc gcgtactgcg atgaaatact gacctaactg gtacagttca tcgaatagtt  50040
caacagaatc agcgatgcgt gcgaatgctt cttggttttt ggttacagaa tcaataaatt  50100
ctgctgggtc agtcagcaca ttacgaataa tattgctata agcacgacta tgcaggtctt  50160
```

```
caaaatagct ccactgtttg agcatacctt ccaattctgg acgacttaca agtggcataa  50220
tagctgcttc aggggcacga ctgataaagg aatcagtttg agtctgccat gctaggttca  50280
ggagtgtaat ttcctgaatt tcccgtggga ggttaggcca ttgtttctta tctgcttcca  50340
gactgatttc agtttcagtc caaaattgag agcgttgcag aagtgccaga cgttctagtt  50400
ctggatgtgc tacacgtaca taatctgcga taccgagaga atctcccagg aaaaggtcag  50460
cattagtatg ctcccaattc aggtttagta aagtagtcat tgattttcct ctttctcact  50520
atttcaggaa tattatagca aatctggtag cgattagcaa gtaaaatttc aaagaaaaag  50580
gagacccgaa gatctcctta tttttattaa atagtacaac caccggatgc acaaccggct  50640
gcttcttctc cagcacctcc accatttgcg gtattgaagt tagcataata ccaagttttc  50700
cacccatact taacagcagt catgaaatca cgaactacta ctggaccagg aatgatttca  50760
ttctcaaact tggtgtagtc atagtacata ttcgtactga tagactgact gaagaatttc  50820
tgcatagttg ctacccattt gatccactcg atacgatcta catcataagc cagtttatag  50880
ctcattaacg tttcccaatc ggttgcaccc ggagcaattg caattacttt attcactgca  50940
ctacccttga tagatacaat cttacgaggc ggttcaatag agttagtaac acctaacaga  51000
acagaagaac tttctcccgg catctgagca gtcagaacag agttacgcat accgtatttc  51060
agaatatctg cacgcagaga ctcccaatcc atttctagac ctacggatac cagttcatca  51120
acagtttcct tgtacgtgtc tattaccaga attcctttag atggtttagt acgatcaaac  51180
cactcacatg caccctgttc tttagctagg cgtacagagg ctttatgcag gaagtaagac  51240
agtttttcag cctcacggtg aatccagtta cgggcttcaa taccttcata agccagacct  51300
tctgctgcca ttgcacctgc tgcgttcatc aggccaatac caacattacg acgtttctta  51360
gccgtatatt ccatagttgg gaacggataa tcctgaattt caataattgt atcaacgaat  51420
ttcagaagga tgtagcaagt tttttcccac tcagccagag attccatgcg ccccagtaca  51480
acaccaccta agttacacag agatacttca ccaatgtcct ccggcttcat ttgatcaagc  51540
tgctcttttg tcttatacag ctctgtaatg tgatggaatg ggcgtgtagg ctgagtaatc  51600
tcaacacaaa ggtttgtcat acggatcgga tcaaggaaat taccgtgacg attagattcc  51660
ccgatatgat gagcatacat acgtcctgtt tccattcgga tacgtagcca agtatctagg  51720
atttcttttg cagagacttt aggagctgca ggaactgttt ttccttcgtg gtcgatcttt  51780
gtaagagatg ccacacgttt ctccgctgcc acgtagattt cttcaaattt agcctcgtca  51840
tcactataaa acgcttcatg aacttctgga gcatagaagt atgacattag cgtaatatct  51900
tcatttttca gataacgttt taacaaaaga ttgttgaaac tcagagaata atccatctta  51960
tcgattttat tctcatctgt agcacgttgt tgcttaacct gcatcaattg aatgatttca  52020
gggtcgaagt acggataaga cactgtagca gaaccaccac gagtttgctg agtattggcc  52080
tttactgagc ggtcaatgtg tcgataatat ggcagttttc cggaatgcgg gaatgcccca  52140
tttcgcaccg gatcagcaat tgatcggctt tcaagatgat acccgattcc cgctctggct  52200
gcgaccattt tgaagacgat gtgctcggcg gtgtcgattg aatccaacgt gtcagtggaa  52260
tccacgaggc agcaactagc aaatccacgg tcactagagc gcagaccaac cagtggcggc  52320
gtaggaacgt tgattttgtg gagtgacatt gcgttgtaga ggtcgattgc atctagaatt  52380
gtccagttag gttgagatag catcgccatt gccataccca tgtaggcaaa ctgcggggtt  52440
tcataaattt caccagtggc tatattacga cgggaatatt tatcaaagaa ctgtttcagc  52500
ccaccactag taaaaagacg gtcacgatca tggtcgataa cctgattcag agcttcaaat  52560
tgctcatcgg taatccatgc actcatgtct tcccatgcac ctacgctaac catgtggtca  52620
tggaagaaac gtagagaagg tggttcgaaa gagtcataaa ggcgcttacg catttgcgca  52680
agacgtaatt cctttgctgg cacatcgtat gctgggttat ctttgataag actttcagca  52740
gctttaatta atgcgtccat cagagtgtcg gaatctacaa cccctttagg tagagttttt  52800
tgagcagcca tagtaatggc tgaccaactt acatcaactg ttttgcaacc atactccgcc  52860
caaccattga gtttttcagg agcaaagtct tctacagtac cgtcacgttt aattactttt  52920
tcaatgcgat ggctcatttg gctttccttt ttatatttat caggatttaa ggaatattct  52980
actttattat tggtcattag gcaaataaaa ttttctgata gaaaaggccc gggtattttc  53040
atacccaggc cctgtatatt accagtctag ctttttagct tattcaatta ctttagctct  53100
agccacttct tttaatagaa tatctatgga ggtgctcagc tcgttataat tgaatggttt  53160
atttggattt gaggttacaa ttttccacgc tagggttgtc ttaggacttt cttccccttc  53220
cttacgtgta atcatattgg cagcactcag tgaagtacga tgtattttag ttttacggct  53280
cagatgaacg acgtttccca tattacacct tccccatgtc tttaaagatg tcatagaatg  53340
ctttagactc aacagaacga acgttatcaa tcaattcaat cattgagaat ggggcatttt  53400
cgtatttctc atagacttcc ataaggagtg ctagacctga gtcaccttta atgtctttct  53460
gagctatatc tccgcagata attaaacggc agtcttgccc tacacgagtt agaagacaaa  53520
tcattgcctc aacggaaata ttctgagctt catcgacaat tacataggag ttgttgaaag  53580
ttctgccacg agcatgttcg acagccaaaa atttaatttt ctgacgttcg acatatccct  53640
tataggcgtg atcgccgatg gcccatttca taccatcagc tattggctct aaccaaggct  53700
ctagcttttc cgctagatca ccaggaagca taccaagaga cttacctaga ggttcattag  53760
gacgtacgag aatcacttgc tcaatatctg agtgaatgtc tacgagttcc tgagctgcaa  53820
gaacggacgg aataaaggtt ttaccagtac ctggctcacc gatacccaca gttactgtgt  53880
tgttcttgat catattgata tatgattttt gctcgcggtt tttacctact agggatttag  53940
caactgggtt agcgtaatca ttagaaaaat cagcctgaat tacgttattc tcatatttgt  54000
tgccacgctt tcttgaacca ttgcggttct ctcttttttg acgtgctttt cccataaata  54060
acactcctat agtgtacttc gctaacagag gatcaacaaa aagatcttgt ttatcaactt  54120
acaaatatat tataccaata tatacagtaa aaagcaacta caattttaaa taagcctatg  54180
atattgcatt taaataaaaa atttgcttgc ttttaacgtg agatgtgtga tactagataa  54240
tcattttata tcgcgtgcac gagtgcgtga ttatacaatt tttaatagaa attggcaaat  54300
aaaatttttt gactcagatc atgttgcaga actttatagt aaaatattgt tgacatccgc  54360
cctcgaatga gttataatag tagtcttagt tagagaagga gagtgtaatg aatcgtaatg  54420
aagaactaaa atataaagaa atgcaggcgt taattagaaa ctgcaaagag attatcgaag  54480
ggtcagcgga tgaagagctg ctgtttaata atgccaataa accctcagaa cgtttcccta  54540
cacagaggga tatgcttgca ggtgaattga gtaagtatct gattctagaa gaaatgccaa  54600
ttcagattcg aaatgctcat atgattgggg atattcattt ccatgatgct gattatgctg  54660
cattaggcat gactaattgt tgtctggtag ctctggaaga tatgttgaag aatggtatga  54720
aggttggtaa tgctgaaatt agcactccaa actctatcac tactgcagcg gctattactg  54780
ctcagattat cactcaagtt agctcccatc agtatggggg cacttccgtg gatcgccttg  54840
atgaagtatt agctccttat gttcgtaaat cctatgacaa aaatcatgcg tttgcaaaac  54900
```

-continued

```
gttggactaa ggatgaagcc aaagcatcag taatggctac ggagatgact gaaaaagaag  54960
tctatgacgc ttgtcagggt ttagaatatg aaatcaatac catgttcaac tctaatggtc  55020
agagtccatt tattaccttt ggttttggtc taggaacttc ttgggaagca cgtctagtac  55080
agaaagcaat attgaaagta cgcatggatg gtttaggtat caataaacgt acagctatct  55140
tcccgaaact ggtatttgta cttcgtgatg gcgtaaatat gaaaccaggg gatgttagtt  55200
atgacatcaa gaagttagct atgaaatgta ctgctgaacg tatgtatcca gattatatca  55260
gctatgacaa ggttgtagaa gttactggag actataaagt ttctatgggc tgccgttcat  55320
tcctagctgc tacagaagat ggtgaaactg ctggtcgtaa taacttaggt gttgtttctg  55380
taaacttgcc tagaattgct atcgaagctg aaggaaatat tgatctattc tttgatttgc  55440
ttgagctacg tgtggataca gcgttaaaag cattggagtg gagagttgat cgcttaaaat  55500
acatccaagc taaagctgca cccatcctct atatgtcagg agcctttggg ttacgcttgg  55560
agcctgatga atatgtattc gatcatttct ataaccgtgc ttctgtatct ctaggatata  55620
ttggttgcca tgaaatgcta cagttcatgt ttggcaaaga tgtagataca atgtccgaga  55680
cctgcatcaa gtttgttcag cgtgtgctgc agtacatgcg agatagagtc gatcagaaga  55740
aggaggagac taagttaggt tatagcctgt atgctacacc gtcggaatcc ctatgcgatc  55800
gtttttgtcg tctagaccgt gaatatttcc cggagcatga agatattctg tccaaaggat  55860
actacactaa ctctcaccac cttgatgtgg aacgtaaagt tgctcccaac gtgaaatttg  55920
attatgaatc taactttact ccgattgctt ctggtgggtg tatttcctat gtagaactac  55980
cggatatgaa acgattccca gatgcactag aatgggttat taattatgct gctagtaaag  56040
ttcattactt cggtattaat actccggtgg attcttgtgg taaatgtgga ttcttaggtg  56100
aaacagtagc atccgaagat gggtttaagt gccctatctg tggtaatcat gaccccgaaa  56160
ctcttgaagt aactcgtcga gtttgtgggt atcttggaaa tccaggtgct cgtccattta  56220
acccaggcaa acagcatgag gttatgggca gagtgaaaca tcaggatatt cgagctaaat  56280
aagctaatca gccgggttgc tagtcgacct ggcttttatt ttatttgctt tcagccaaaa  56340
atttatatat aatagattta taaatttgag aggagaaaga tatggaatta aagcactata  56400
tagttgaatc tacatgtggt agtttccatc tgggtgtaga tgatgttgct gaggctgtct  56460
ttgctgccac aggtgattac tcgcatatag agggtgttgg ataccctacc attattggcg  56520
attgggtggg aacaaatcta gatgtatcac cttataaccc atattgcttg tttgatgaag  56580
acagagatga agtaaaatgt aatcttgaat ttgtgtataa tagagtgtta aaagtatacc  56640
aacgtagccc caatgggtac gaagatatta cttggagtat taaacagtat cttaaagatg  56700
tgtactctag tttttctgac gaagacctag aaacagttgc agtggagttt aataatgact  56760
aagaatgtga aacaccttaa atatcgctta atttacaacg gacgtatgga aacagaagat  56820
ctggcccagt tagctattaa ttctaatgag gttacggtgc gtgcgctggc aattgaaaag  56880
ttgcgtgctt cttatgaaaa tcgtgttatg gaactagagg agaaacttta tggcattctc  56940
gaagccgatg ctaccagata agggtttaaa ctccgctttg gaaaacgcat taatgcagca  57000
ctgggaaact ggctataagg atggtgttga atcctgcgct actatgctag aagttattgc  57060
taatacctta atggagaaag gcaataaaga attagctgag ctattagaca gtattgggca  57120
aaacttcaga gaacaggtga aaaatgcgta gattaattat tattagcggt gcaggtttga  57180
gtgttgaaag tggtgtacga gcttttcgta ctgatactgc tagtggtaaa gcactgtggg  57240
atgattatga tctagaagaa gtatgtaata ttcatgcctt tcgtggtaat ttttatcata  57300
aaacccatat gttttacaac aagcgtcgtg aagagctaaa aactgttgaa cctaaccttg  57360
cgcatcttcg tattggtgag tggtataaac aatacccagg tcaagtagta aacttgacta  57420
ccaatgttga tgaccttatt gaacgtgctg gcgttccaca tagtgacatt ctgcacattc  57480
acggatattt aaaagaggtt gttgtagctg acagctacaa tagtagtaat aaacgaatta  57540
ttgatgttgg gtataactct attgacccag atgattataa atgggttaaa cctaatgtaa  57600
tcttctttgg tgagcatgct ccagcatata cagaaatgta caatgttttt gatggtatta  57660
ccagtcaaga tatgatcatt gtggttggtt gctctaacca agtaattaac ttctactggg  57720
aattatttcc tgttcttaat ttgactgctg ccaaattaat ggtagttaac tactatgata  57780
gtgccctagc gacagagccg ggctaccaag gtatgactcg tagtgagatg taccagctgg  57840
aagaacgcgg tatcccttac tggagtaaag gggctgtaga tgccttcagt gaccctgatt  57900
ttattgctcg tgtagaagct catctagagg gtagacctta tatgccgggg aaacaaatat  57960
gtccataatt aaatctgtgt atacacaccc tgatgatata tttgtatggg cggacggtag  58020
ttggtgttat cgctgtgagt tgtgggaaat ggactataaa tccgatgact atggtgttat  58080
atatgtggat acggttgagt atgatacgtt cttagaaagg aacaaaaatg gaaataagta  58140
atactccaat tatttttcta gacattgatg gggtgctcaa ttcgagcatc tcccaccatc  58200
atgcacctga tgatgaaaag attttctttg gaagtgactg ggttttcaaa ccacttctca  58260
aggcttttca ggactttatt cgtccttctc cgataatgat tgttggagta tcctcatggt  58320
tctctgtcag gaatgagatg gagaacgttc agattatgac cggattaggt cttatcgatc  58380
gttttcttgg tacaacggat tttaccgggg gtggattatc taggggtaat tctgttcttc  58440
gcttcgttga aaagcataag ctcaaacatt ggtgtgtgct ggatgatgcc ggtgctatga  58500
tgtatcagta tccaacggtt atagtcaatg gtagaacagg aataaatctt caggatttaa  58560
aagctgttag ctatatgcta gaatttagcc cagatcttga aatgtgtaaa tccttacaac  58620
aatttaaggt gtaaatatgt tcaataatgt attctctaaa gaagctaacc caattttggt  58680
taacttttgg cgtactctcc cggctagcct gtataatgag gctattaact ccttgaaaat  58740
atggtgtgag aataacgaaa tctcctttgc ttttaaagat gatattgatg aggccccctg  58800
tattggtcta gttgtgcagg tagaggaggg tcttgaagag attgtgggct ggaaagagtt  58860
agacgaaatg ggcttagttt ttgcgttaaa ttataagctg tttatgcctg ctaagcatcg  58920
cctagttgtt aactataaaa ctagtgaatc tcctggtttt caggttaatg aacgttatgg  58980
ttggtcttac tcaccggaag aagtaaatga tggtatccaa aaacttcgtc gttttggtta  59040
tcaaattccg ggtttaaccg cctaaggggg cataatggaa caagtatatt ggcgtcagat  59100
tgatcctagt ttggtgaagc gtgcggagaa gctgctacaa cgttggttgg tggtaagaca  59160
agtctccttc acttttccgg agcagcaaac ggatgatcca tgcattggcg ttttcctgtc  59220
tggatatgcc ggggaatggg aattggattg gaatgaattg tctgctatgg gcttgattgt  59280
tgccctaaac ttctctatat tccatccacg tggtttggcc atatgtcgtg tgcctgatga  59340
cggttgttcg ccccatcttt tacaggtgga agatgatatt tgggagtaca ctccagatat  59400
tctcgcagaa gctaaagaac aattaaatcg tgttgggatt tatgttccgg gcttaaatga  59460
tggatgattt ttattagcta aactctgatt accgagtcat tttggctcgg ttttatccgt  59520
acttaagacc aatgatagca ccatccggaa aattttactt gcatgatgcc caaaatcttg  59580
atataatatt tatattgaat tgagagacat tagtaaaaat tgattttgct aatttttctt  59640
```

-continued

```
gtttacaatc cgcgatacgg aacagttagg ctgccccatt aagggttgtt ttaactatta  59700
ctagtgttta tattgcatta gttaatcttc aattaagtga tctgtgtacc ctgaattcgg  59760
aaaggtaaat ccaaaccgtg catatttagc tcgttatata ggcagagttt tatatggggg  59820
tgcgaacgaa aagagcagcg aatggcggca cgtacagtag tcacctacca ataggatagt  59880
gaggacaaat agaatcggct tagcggccaa tgacctaggt tctattctgt atatgagcga  59940
agagagcaca gcactgagat atgataactt attcatattg cttgatgata attaatgttt  60000
acgtaaatag tagtaatagt tgttctattc tttctgaata gtcctaaaga aaagatttcg  60060
attaaccaac acaggagtat tgttgtgttt tctattctcc aaggtcacgc cggattttct  60120
cgtgatttag caacaggtat ttggcgagaa atcaaagcgg aagattatac ctttgccaag  60180
cgattctcga aaaagcatcc agaaggtaaa ccagcttcta tgcccttcaa atttgatgta  60240
atagaagagc atgacccgca aagccttgcc gaaatgttac cacttatgag acgtttaacg  60300
tctgaccctc atatcgttgc ggtacgaggt cgatgtcttg cacctaaaaa taacgtgcga  60360
cgtaagaaag gtaactttaa tgtatctaat cctagtaata ttattgctat ggacgtggat  60420
ggtatcctag ataccggtgg gtatgacaag tttaaccttg ttggtatggc ccgccacatt  60480
attaagatgt tgaatagtat tagtgaggac atgttccctc ttgatgcagg ctttatagct  60540
catgcatcgt cttcggctgg gcttaaacca ggtatccgaa tgcacttaat gctagaatct  60600
aacgtcaagg taactcaggg tcagttaaag ttcttattta catctatcaa cgatagtagt  60660
aagcaaaaat ttggttttga tattgccgac ttagcttatt attcatctgt ccagctccac  60720
tattttgccg accccttatt tagtgatggt attgttgatc cgtttaaagc ggagagtaag  60780
ccacgtctgg tgtatgttaa aggttcgaaa gtaaatttgc ccaataatct ggttgactat  60840
gaaacaacta gaggggagtt taaggaagag ttttattctt tacttgatca aattaaaggc  60900
aaaaagatcg cgtctgataa agtagaagaa accatcagcg aattggaaga agctgaggat  60960
ggggtgtacc tgcgtattat ccccaaacta taccatagag cattagagga tggtgttgat  61020
tttgcatggc tagaacgtga gattaaaccc gctttatctg aatatattgc aactaaagat  61080
aacagtcgta atattcaaga ttactttaat aacggtcgta agcaggctct caaagcgttt  61140
gttaataatt ctaaacgtga gattccatta aatctgaaag gtgttccgct caagaagtta  61200
gaagtggatt ctccaccaga agttccgtac ctgaagatta acattgtgcc tccaaaaggc  61260
catataacat ttgttaaggc aagtcttggt actggtaaaa ctacggcagt aactaaatgg  61320
ctggacgcag gtgttcttcc tggcaacttt ttagcagtta caaatactag agcactggta  61380
tcttcaaacg ctaagaaatt tagcgcagga caatatgata agtctgtaga tatgctcaac  61440
tttaaacgtg gagctattga tcgtatgtcc acaactattc actctttgca taagttcaaa  61500
agttttattg gtcaaataga taccattttt attgatgaat gtgatgctgt aatgaatgat  61560
ctattattcg cacctgttgt taagcaacgt cgcgaatgta ttcaagttct acgtgacatc  61620
ctcatgacag ctaaaactgt aattctatca gatggtgata ttagtgccga aactattgaa  61680
gcatatggtt ctctaattga ttttgataaa ccagtagcat tttataatca tcaccgtaag  61740
atgctgtcaa aagctcatgc ttatgagttc ccggatgagt ccagtatttg ggttgcactt  61800
cagacttctc tagagatggg tgagaaatct atcctagtat ctgattgtgg gccggatgaa  61860
ctgaatgaga agggcatggc gttgcgtcgt aatacgggtg cattagttaa ggaaatccac  61920
tcaaactcta cgtctgatgt agatattaga cgtattctgg attacacaac taatgagcta  61980
attgaccaac aaattgattg cttattatgt agtccatctg taacgagtgg tgttgacttt  62040
aactattttg ataacgtatt cgttatcact agaactagca accaagcgcc aaacatgcgt  62100
ttccaagcaa tcaggcgcga ccgtggtgct cagaatatct attattttat tgataaatcc  62160
actagtgggt tctccgcagg ttctgaacaa tataatattg atgaaggttg gctggagtta  62220
gcacagcaat tatacgcacg tcgcagagaa ctagaatcta ggaactatac tagtacttta  62280
cgttattact tgcttgatca gggtgcaact attgatattt tcagcgaaag ctggggaact  62340
attgaaggtg ctggtaaaga atacacagaa gagcgaatca aagctatcct acattcaact  62400
ccggattact gtgcaccacg tcatgcggat gcgtatgagg ctaaactact tcttgttcgc  62460
tattatcatc ttgagtctat taaagatgta acagttgagc atgttgaaca atatatcaaa  62520
gataaaccga atgatcgagc tgcattcttc cataagatgc acgagatgtt ctgggaagat  62580
attaagaagt gttcaaatgt gaccattaaa ccattcatag aggctctgaa aggtaagaag  62640
aaagacttct tccttaaaac aggtcagagt gctaacccaa aatatgctag aatgtatctt  62700
ggtatgatgg gtattggtaa ggatatgaac actgaaaata ttgtagactg gtacagaacc  62760
tattgtaaaa tcgagtgtat gccaatccca tataagttta tgactgatga ggagaaacat  62820
atgcatgatg aagcaatggc agagctaggt gctagaaatg acagtgaaga ataaaaaatg  62880
ggaaacaagg aagttcccag taaaagaacg taaagttcct gtttatgata cttcggaaaa  62940
gctatgtagg gtggtaccac gtagattagc tggtatccct aacatatccg agtggttact  63000
taaacaacgg aaaacaaacg tgtctcttcg catcggcttt gaattagata aagtctatgc  63060
tgaacttgct tctttgctca aggaatcgta aaaatttatt tgctttcagg aaaaattttc  63120
tgtataatag attcataaat ttgagagagg agtttaaata tggccggttc tcgcagaaag  63180
aaacatatcc atgaaatccc ggatgaagtc tttaaaaaag ttatagagca tctggagaac  63240
ggtggtacta agaaagcagc ttgtgagatg ctcggcgtat catccaatcc aactatggaa  63300
aggatgattg aagagtggca agaccgccag attcaagttg ccgaaatgaa gaaaaagaaa  63360
cgtggcacac tcattgaagg tattgagttg gccaacgtta ttgaacagta tttatctggt  63420
gattcttttg aagagattgc cgatcgtaat tatcgctctg tagcaatggt taaatctgtt  63480
ctggaacgct atggtgctct gcttcgtttg aacgatattg tagacccgtt gaatcctcct  63540
attattcctg atgatgctgt agcagaagaa tttgaagttg gtgagcttgt ttgggttcct  63600
ggataccagt gtatcggtga aatcaaaaaa gcaatggata atcctgttgg ttgctaccgt  63660
gtatggcttc tatcggaagg caaacaacag aacgttcatt atatgaatta tgagctggct  63720
tctgttaaac acctggaaaa gttaggagtt gatgtaaaat ctctggggta taaatggact  63780
cgggaagaag tcattacgtt gattaacgaa gctgttaagg ccgccttgaa acttgataaa  63840
gaaaaaggaa aacgccgtga gtagactaac tgatttactt aaagatgggg aagtaaaaac  63900
actatatcgt agaagctggg gtaacgataa taacggctta gtattactaa ctttagatgc  63960
tgactcggat gtagctactc agcatacctg ggtagccggt aactatccat atagcgaggt  64020
tgtttcatta acagtatgcg aagctattgc agacgattgg gaggttgcca gcatcgagga  64080
tatgctcgct gttggcctgg tggagtaact acttaaaaat ttcagttgct taatcctata  64140
attcttgata taatattctc atagtttgaa agaactattc tgtttaattc ttaattaagg  64200
aaatataaaa tatgactact ccaactcagt ggactgatga actgttcgaa aaaatgtctt  64260
ccgaatacgt tgctcgtatg gagcaattcc cagaggatga acgtcctggt gttagcatgg  64320
aaattgttag cgaaattgcc caggaaaatg gtgtaactcc gaacggtttt cgtatgaagc  64380
```

```
taactaaagc aggtttgtac atcaagaaag ctgctggctc tgcttctaaa tctagtgcat  64440
ctactggaga aaaagcttct ggtggttctc gcacttctaa agctaaagct catgccgacc  64500
ttcgttccgc attctctgat gctggcctag caccagattt tctggatgat gcaattattg  64560
acaaactgac cggtaaagcg gctgctcatc tggcagaagc aatccgagct atcactaagt  64620
aatttttaga taaatccacc aacaaaagga actatagcta tgactaaagc tgaaattatt  64680
gcacagtgcg aaaaatttgg tgagttttat cttcattacg agaaacttcg tcagaaagga  64740
accacgtacc ttcagggtac gatggaattt gatccagccc aagataaata tctggctgag  64800
cgtattaaac gtgaacgtat tcgtaaagcg aaagatgatg aaattcttgt cttctctcgt  64860
actaatgata gtttccgttt tattcctgtc gagaaagtcc gtcgtgtgac tagcctccaa  64920
tcagagttag atcgtgcttc tccagtaggc cgataagaaa ccaattagcc cctatatggg  64980
gctttttgtg tatttgggat atgtaaatga gcgaacaggt aaatcaaaac tatgaaggac  65040
acgttgatga ccagtccatc atactttggg agaaggaggg ggaacaagta agattaacag  65100
tatctgaatt tcgtgggaat ctatacatgg gtattcgtta ctggcttctt gatattaatg  65160
atgaatggtt tccaacgaaa tctggcttct cttttcctta caccctagaa acaacatcac  65220
agcttttcta tgcgtttaca cagattctta gcgaatctga ggttttacat gaagtacaga  65280
aacgagctga agaactcaaa gccaagaatg cctagttctt ggctttttct ttataaatgt  65340
atttgctttc aactcagttt tgttatataa tatttatata aattgataag aggatcaatt  65400
atgaaagtaa cacttccaaa aattcaagca aagttaaatc tagtatcgaa tgctagaaat  65460
aactatctag ataactttgg tggaatcaac gataaagcgt acaaagatgc gtggttgaaa  65520
gaagcacaag agttagccga tctcattgct cagtataata aagaactaca ggtagaaatg  65580
aatgactaat gtaaaagact ttattaaacg ttgccaagaa gcatattatc aaggtatgtc  65640
tttaatctct gatgaggagt atgattgcct ggtaaaacgc ttcccactag aagaagagat  65700
cggcgcctaag ggcgatattc cacatctgta tcgtatgtat tctttacaga aagtttatta  65760
taatcgtgga gataaacccc catttaaccc attaggtcag gtagaaactg acaagttaga  65820
tggttgtgcg atttctctac tatatattaa tggcgaattt gttcaagcac taactcgtgg  65880
taatggtatt ctagggaatg atgtcacaag caacgtaaga ttgctgaaca ttcctaaaaa  65940
gatttcccaa aaagtaccta ctcaaatcac tggtgaagtt ctaattacaa aagaagtaga  66000
aaataaacgt aactttgcct ctggtgctat taacctaaaa gatagtgatg ctttcgtaca  66060
acgtatcggg gaaggtggtt taatcttcgt tgcatacggt atccagtgtt ctgctgaatc  66120
tgtaggtatt acagaatcat atttaaaaga tatgctttgg ctagagaatg aagacttctt  66180
aacagttgtt aatgtgcgtt ccttctttag atggattccg acggacggta aagttgttcg  66240
tattaatgac aacaacaaat tcttccgaga aggctggact aataaattcc ctcgcggggc  66300
gttcgctatt aaagaggatg aagaaggaga gattacaact cttactaaag ttgaatggca  66360
ggtaggggct tctggtaaag taactccagt tggttatttc gaaccggtaa ttattgatga  66420
tgctacaatt gttaaagcga ctcttaataa cgttgattat attaactctc tcgatctaga  66480
gatcggttgc cagattcgag tgattcgtgc tggtggtgta atcccgtgca tagtagagcg  66540
agtatactat taatacataa ccctttgcta cccatctacc atataggaat tataaagtgg  66600
ttattgacat tttcgccgct taggtatata ctattatcat tcagttgagg gatagaaagt  66660
tatggcgagg gtaagcaaag ttagttaaaa ttgtagttgc taaatgctta aatacttgct  66720
ataatattta tataaattga taaggaagaa atttgatgaa aatcgaaatt ccaacacaat  66780
gtccctcttg tggttctaag ctagatcttg tcaacggaca attattctgt cgtaataagt  66840
ccaactgtcc agcgcaatca agcaagttaa ttgagaactt ctgttcaaaa atgaagttaa  66900
agggctttgg cccaaaaact attgagaagc tggagctgac gaagatttca gaactatttt  66960
acctaaccga agaagatttg gttagagccg tgggtagcaa ggttgccgct aagttaatta  67020
gcgaattaaa tactaaagtt cgcggagaca ttgactttgg ttcagttctc ggttctttag  67080
gaatccctct aattggagag gttgcagcaa agaaaattatc ccaaaattgc actagctttc  67140
acgatgtgaa ggctgacggc aaggctggag aaaattacaa agcctggcta aattccccac  67200
aaggcaagga tgttattaaa ctaccgtgga aattttcaac tggtattaag ggcactaaag  67260
ctgacgtcat cattacagat gaattagttg cccagccaaa tggaatcgcg gtatgtatta  67320
ccggatcttt gcaagatttt gcaaatcgaa cggatgcaac aaactattta gaaggtctag  67380
gatatacggt taagaaatcc gttaccaaag acgtcaaata cctaatctgt gaggatgaat  67440
caaaacgttc ttcctcatct tataagaaag ccgaaacgaa tgggatagaa atcctgtcga  67500
ttaaagaact attggagaaa aataataatg tctaaactga actggaacgt agaaggtgta  67560
accgagtctc tgaaagcaaa agccactgct ctgggtgttt ctgtaatctc tcaagaacag  67620
gtagctgcta tcgctgctga actggctgct gaaactggca aagatgttac tgctcgctct  67680
gttggctcta aactgcgtaa agaaggtttt gaagtacaga aagctaacga agtacagaaa  67740
tccccgtgga ctcctgagca ggaagctgaa ctggttgatt tcctgaacgc tcatgctggt  67800
cagtatacct atgctgaaat cgctgctgct gtagctggtg gtcagttcgg tgctaagcag  67860
gtacagggta agatcctgag tctggaaatg accgcttctg ttaaaccaac tgaaaaagct  67920
gctgctgttc gttcctttac tccggatgaa gaaactgatt ttgttaatca ggttgttgct  67980
ggtgctacta ttgaagctat cgctgctcac ttcggccgca atatcaagca gatccgtggt  68040
aaagctctga gcctgcttcg tgaaggtcgt attgctgcta tgccggtaca ggaaacttca  68100
agtgctaaaa ctcgtgaaga tctgttagaa ggtctggatc tggttaacat gactgttgct  68160
gagatcgctg agaaaaccgg taagtctgag cgtggtgtta aatctatgct gtctcgtcgt  68220
ggtctggttg ctaaggacta tgatggtgcc gctaagcgtg ctaaactgga tgcaaaagct  68280
gcggctgctg aataatctgg taaattaaac ctaaggggag ggggctatgc tccttcccct  68340
ttttgcattt agaaggcacg aaagcgtgca aaggagaatg accttgttta acgtgcaagc  68400
tgtagtgttg aagatgcttc tagcttccga acagaagcaa atagcattgg aaacattctc  68460
aaaactgcat aaagatcatt ttaatgacgc tttctcctca atttaccaag ccgtccagaa  68520
ttattataaa aaatataaca caatgccgtc cattgacgca cttatgcttg aagctaatag  68580
gaacgcccgc ctttctcaag ctctagtcgt cttagctaac actcaaattc cagaagtgag  68640
catggaacag gcacttgaag tcctagaagc cgaatataca caggatttat tcctgaagct  68700
tctagaaaca gacgtgcttc aagatttaac aatgctggat cagggagaaa ttctcaaccg  68760
agttgcctcc cttcacttaa aattagaaga gaaagtaacg aatactggaa aagtattcaa  68820
cgcagataac atgcgtattt tccagagaga agaagatacc aaactgaact taatcgctct  68880
tggtatttgt aatgagttcg acgctcaaat tggtttagct cgcacagaaa cgttactgct  68940
tggtggttgg cgtggtactg gtaaatccat tatctgttca aacatacagg ttcagcaata  69000
tttgaatgga gatattgctc catacttctc aattgagatg aaagaacacg aagtatttag  69060
acgtaatcta gccatgttag ctggtgtatc agcactagca atgcgtaata atactctaga  69120
```

-continued

```
aggtgcagct ctgttgagat tagccagaac tagagccaga atgtttaatg gtggtgaaga  69180
gctttttgat aacttcgtta aacagtacac gatggctaag atgagtgatt tctacgatat  69240
ggagagtaag ctaatagagg gatatgaact acatactcct atgattatcg tttatgaccc  69300
tgaactgtcc attacaacag ttgacgtaga attaaataaa ttagttgcta gatatggtga  69360
taaagttaca gtagctttac tggactatat taaccaaacc cgacttccag attctaaaac  69420
cattgatatg tatgactgga aagaacagat ggttgttagc tcgtctttca aatctatctg  69480
ccagaaacat aacgtggctg gtgtagctcc ttaccagatc gatcaagatg gtagaacacg  69540
tatgtcaaag gggattcttg attccgcaga catggctgct aatcttaatg ctgcaaaagc  69600
tgataatggt caaggtgcta ttatgtttga cttcgttaag actcgttctt ctgatagcgt  69660
gaagtttatg cctaagatga actgggaaac tctgcgaatg gataatacaa ctaacctagc  69720
aatggaagat atatctcaaa tggaagctga gttcgttatc cctattgaga aggataagcc  69780
ggctcaacct aaacgtgcta agaaagacaa aactgaaaat ttaacaggtg aacaggccag  69840
cgatatatga gtagaataac agaactactt gatctgaaag gcattgaata taaagacaca  69900
ggtggggaca tcctcatctg ttgtctcaat ccagatcatg acgataaaca cccaagtttg  69960
cgtattgatc ctgaaacagg tattatgcac tgcttgagtt gtggcttcgg taaaggtata  70020
ccgagcattt accattattt taatgagact cagtaccgac agtctccaag actatcacag  70080
gtacgtaaaa agatttcaga gattaggaat ggatcaacga atcttgcaat tcctgaatct  70140
gcttaccttt tcgaaggtga tttccgaggt ataagttcta agaccttgaa gaaatatttt  70200
gctttccaac accaagcaga ctgggaaggc agaattgtat tcccaatcac agatgctgtt  70260
ggacgcaata tcctattttt gggtcgttct ataaacagtt ctgcccctcc taaatactta  70320
gtaaaaccaa aacaagtttc accgccaatt tttcctgtac gatataatac tccagttctt  70380
attctagttg aaggcatctt tgatatgctg aacctagagg ataatggtat agactatgct  70440
tcttgctgct ttggtacaca tcagtttact tcggataaca ttgcagataa gttcagtcct  70500
tatattattg ctggggtaaa agttgttgtt atcttactag ataatgatgc ttctggtaat  70560
aaagctgcac aagcattggc taagctaatt cgtacaaaaa cgcgtttaac acctgtagtt  70620
gctaacttcc tcctgcctga aggcaaagat ccaggtgatt taaacaaaga tgaaattgat  70680
atgttagcaa aacgtattga aattttagtt gctgaatcgc ttaaagattt ggtataatat  70740
attggtaagt tagagaagaa acactgaagt tatacttact taccaagagg agattaaatt  70800
tgaaaatcgc agtagttgat aaagctctaa acaacactcg ttatgataaa catttccagc  70860
tatacggcga ggaagttgat gtattccata tgtgtaacga gaagttatct ggtcgtttgc  70920
ttaaaaagca cattactatt ggaacaccag aaaacccatt tgatccgaat gattatgatt  70980
ttgttatact agtaggtgct gaacctttcc tgtacttcgc aggtaagaaa ggcattggtg  71040
actatactgg taaacgtgta gagtataatg gatatgctaa ctggattgcg agtatcagcc  71100
cagcccagtt acactttaag cctgaaatga aaccagtctt tgatgcaaca gtagagaata  71160
tccacgatat tatcaatggt cgtgagaaga ttgcaaaagc tggtgattac cgtcctatta  71220
ctaaccctga cgaggcggaa gaatatatca agatggtgta taatatggtt atcggacctg  71280
tagcattcga ctccgaaacc tcagcactat actgtcgaga tggttatctg cttggcgttt  71340
ctatgtctca ccaagagtat cagggtgtat atatcgattc tgattgtctc acagaggttg  71400
cagtatatta tctccagaaa attctggata gtgaaaacca cactattgtt tttcacaact  71460
tgaagtttga tatgcacttt tataagtacc atctgggact tacttttgat aaagcacata  71520
aagaacgcag gctccatgat actatgttgc agcattatgt tctagatgag cgtcgtggta  71580
ctcatggctt gaaatctcta gcaatgaagt ataccgatat gggcgactat gactttgaac  71640
tagataagtt caaggatgat tactgcaaag cacataaaat caagaaagaa gatttcacat  71700
atgatttaat tccgtttgat attatgtggc cttacgctgc aaaagataca gatgctacca  71760
tacgtttgca caacttcttc ttaccaaaaa ttgagaagaa tgaaaaactt tgcagtctgt  71820
attatgatgt tctaatgcct ggttgtgtat ttctccagcg tgttgaggat cgtggtgtac  71880
ctatttctat tgatcgttta aaagaagctc agtaccagtt aactcataat ctgaataaag  71940
ctcgtgagaa gctgtatact tatccagaag tcgttcagct agagaaagat cagaacgaag  72000
cgtttaaccc aaactctgtt aagcagctac gtgttcttct gtttgattat gttggcttaa  72060
ccccaacagg taaattgacg gatactggag cagactctac agatgcagaa gctctgaacg  72120
aattgtctac gcagcatcca attgctaaga ctctactaga gattcgtaag ctgactaagc  72180
tgatctctac ttacgttgag aagattcttc tgagcattga tgctgatggt tgcattcgta  72240
ctggcttcca cgaacacatg actacttctg gtcgtctgag ttcttctggt aaactgaacc  72300
tgcaacagtt acctcgtgat gaatctatta tcaagggttg tgtggttgca ccacctggat  72360
accgtgtaat cgcatgggac ttaacaactg cggaagttta ttatgctgct gttctatctg  72420
gtgatagaaa tatgcaacag gtatttatca acatgagaaa tgaacctgat aaatacccctg  72480
acttccactc taacatcgca cacatggtat ttaagctcca atgcgaacct cgtgatgtta  72540
aaaagttatt cccagctctg cgtcaagcag ctaaagcaat cacctttggt attctgtatg  72600
gttctggccc agctaaagta gctcattctg ttaacgaagc tcttctggaa caggctgcta  72660
agacaggcga accgtttgta gagtgtactg ttgcagatgc taaagagtac attgaaactt  72720
acttcggtca gttcccgcag cttaagcgtt ggattgataa gtgccacgat cagatcaaga  72780
atcatggatt tatctatagt cactttggtc gtaaacgtcg tctgcataat atccactccg  72840
aagaccgtgg tgttcagggt gaagaaatcc gttctggatt taacgcaatc attcagtctg  72900
cttcttctga tagcctcctt ttaggtgcgg tagatgcaga taatgagatc atttctcttg  72960
gcctagaaca agagatgaag attgttatgc tggttcatga ctccgtagtt gctattgttc  73020
gtgaggattt gatcgaccaa tacaatgaaa tcctgattcg taatattcag aaagaccgtg  73080
gtatcagtat ccctggctgt ccgattggta ttgattctga ttctgaggct ggaggttctc  73140
gtgactactc ctgtggtaag atgaagaaac agcatccatc aatcgcttgt attgatgatg  73200
atgaatatac tcgttatgtc aagggtgtat tacttgatgc agagttcgag tataagaaac  73260
tagctgcaat ggataaagag catccagatc atagcaagta caaggatgat aagtttattg  73320
ctgtatgtaa agatctggat aacgtgaaaa ggattctcgg tgcttaattt caaattgccc  73380
gtctatgcgt tacgggcatt tgtatcaatt gagcaagaag gtgattattc cgtaattaca  73440
acaagatata ataaatatgt gctagataac aggaagttgc ctggcacgtt ttctcaacgt  73500
aggcttattc tatttgagaa acggaaagaa ttaccataca agctctatcc tattaggggt  73560
agaatatcaa tgttgtctca attagtgggg tcaaagcgta accaatttat agattctgat  73620
ggaaatctta ttaattggaa gaaaactacg ttctatgatg ttgtcacctc taaagttttg  73680
cattcagcta gaatttataa tggaaaatac caatgctatg tggctaaagt tccatatcca  73740
tttgtattat cctatgttcc agcttatata agctatattc tggtaaataa tagccctgtt  73800
atttatcaag tccatcaaga ggagcctgaa attcctagac ttagaataaa attatgaaag  73860
```

-continued

```
ttgttatatc taataaagcc tatttcaagc ccgatgatga actttgggat tattgtagta  73920
agcaaaccac ttatcacata gagacaatga ctagtaaata ccctattatg tacaagaata  73980
gtggtgttgt tgccaaagag attaagtgga ttcctattac gcgtctggac ttactagatg  74040
ctaaaggagt aaaatacgaa ttagtagata aacgcacatt agctccggta gctataccag  74100
aacctaagtt caagctgcgt gaagaagatc agcttccaat atatgaagaa tgtgacgata  74160
cctgtattat taatggtaaa cctggatttg gtaaaactat cctagccctt gcacttgcgt  74220
ataaatttgg ccagaaaact ttggtaatct gtacaaatac atctattcgt gagatgtggg  74280
cagcagaagt tcgtaaatgg tttgggtttg aaccaggcat aataggttct gggaaatata  74340
acattgatcc accaattgtg gtcagtaata ttcaaacagt gaataaacat gcgaataatc  74400
tttctaaagt attcggtact gttatagttg atgaagttca ccattgtgta gctacaactt  74460
tcactaactt cctagaaata tcctgtgctc gctataaaat tggactatcc ggcacattaa  74520
aacggaaaga cggtctacaa gttatgttca aagatttctt tggatataag atatttagtc  74580
cgccggttaa taatactgtt gcacctacaa tccataggta ctccgtacct gttgagttat  74640
caggaaacca aaacgtacca tgggcattac gtgctaacga tgtgtataat catcctgaat  74700
atcgagaaac tattataaac ctagcacatt tatatgtgaa tatggggcat aaagtactca  74760
ttgtaagtga tagaacagag ttaatccaaa cagtactaga agctcttgca cagcgtggtg  74820
ttacaacata tgaaattata ggggcaaccc acttggatga ccgattaaaa attcaagaag  74880
atatagcaaa aggtggtcct tgtgtacttg cagcagctca aagtatcttc tctgaaggta  74940
tttcccttaa tgagctatct tgtttaataa tgggaagcct cattaataat gaatctctca  75000
ttgaacagct tgcaggccgt gttcaacgta ttgtcgatgg taaactcgac cctattgttg  75060
tagatctaat tatgaaaggt ggtactgggc taagacaggc ttctgggcgt atggcagtat  75120
atcgtaataa cgggtggaaa actattacca tgactcctga gaaagcagtt caattagcta  75180
aaattgcatt tggcaatagc tcataaatga tgtataaatat atacataaat ttgagagaga  75240
aagtttcgga ttgataagaa agtccgaagc agaaaaataa aaattttagt tgctaaattc  75300
tctcgaaatc tagtataata tatacataaa ttcgaggaga aaacaaaaat taaattcttc  75360
gattatgaaa agctatactt actagctaga ggaaattccg acctaattat taagctattc  75420
aaaagaatgc ttacagagcc tgatgctcat caattattgg tcggttcctc attcattttg  75480
aatgaatcaa caatagttga taatccaaat aaattgtcta atagacaact ggcagaatat  75540
ctaggaattt taagtctacg aaattatgcc gaatacaagt ttacaaacga tcctagtttg  75600
gacatacaat atgttccagt atggatacca cgtttagtaa tcgacactaa cccactaatc  75660
gcaattaaca aatcgaaatt aatctttaaa gaggaaataa aatatggcta agtcttgggg  75720
cgaaactact ggcggttcta acgataaaat cgaattcctg aagttcaaca acggtatcac  75780
tcgtgttcgt atcgtttctg gtgttcttcc acgttatgtc tattggctga ctaataaaga  75840
gggtagcgta gctcctttcg aatgtcttcg tttcaaccgt gacaaagaga gctttgttcg  75900
tggtaaagcc gatccggttc atgagatggg cttctttgag aaagagctgg ataaagacgg  75960
taatcgtgtt ccgctgaaac cgaagaaaaa ctatatcgct tttgttattg accgttctga  76020
taacaagctg aaagtaatgg aagtcaaggc tactattctg aaaggcatcc agtctatcat  76080
gaagcagttg aacctggcaa ctccgtttga tattgatatt tctatcgaga aaaaaggtaa  76140
aggtttcgat actgagtatg atgtacagca gattgctgct atgcagttcc agattaagct  76200
gcaagatcct aacagtgcgg aatctaagca atatgctgcg gatgtagatc tgatcggtga  76260
agctatgtgt gatgaagatg gtgacatcat taagttcgaa aaagttcctt ctctggaaca  76320
aacctatccg gttcctacct atgaagagca gaaagaagca attcaagcct tcatggaagg  76380
tcgtgagaat aaagatgatg ccaaatctgg taacagcaat gctggttccc agaaaggtat  76440
tgaccaagaa gctgcaagcg atctggacga ctaataaata gaggggcttc ggcccctttc  76500
tttttaacca atgagaatat tatttagtgc tgatcatcat atcaaactag gacaagataa  76560
agttccaaag gaatggcaga agcgtcgctt cctgatgcta ggagaacggt taaatgatat  76620
attccataat cataactgtg atcttcatat tgctggtggt gatatacttg atgttgccga  76680
cccgtcgtca gaagaaatag aactgcttga acagttcatg tcaagacttg accatccagg  76740
caaaatcttt actggaaatc atgaaatgtt aactaaaacc atttcatgtc tatatcatta  76800
tgcgggggtt attaataaag taacgagtgg taagtgggaa gtaattacca aaccatatcg  76860
ttcccctgaa tttgatattg ttccatatga tgagatccat aaatccaaat ggaaaccatc  76920
tgaatcaaaa ctatgtttca cacatgttcg tggtgaaatc cctccacatg taaaaccaga  76980
aattgatcta actaagtaca actgttatga tactgtaatt gctggcgatt tacattctta  77040
tactaatagc cagactatcg gatctactag acttctctac ccaggatccc cattaactac  77100
atcgttccat agagaacgca caaaaggtac aaatggttgc tttatcattg ataccgacac  77160
attaaaagta gaatggattg aactaggtga tttaccacaa ctgattcgta aaacaatcgg  77220
agctggtgaa gagatggaac ctagtgatta tgatcgtgta gtctatgaag ttactggtga  77280
cgttgttcaa ttaaagtcta tcaaagactc tgatttatta gataagaaga ttaatcatcg  77340
agtcactaaa gacgctaagt taaatcttgt tgatcttgat atgttaggtg aacttgaact  77400
ttacttccgt gaagtcgaga agctatctca aggcgacatt gatagaatct tggctagagc  77460
tgcgaaatat gtcaaagatt acaattaaga cactaaaatt tagtaacgtt atgtcttatg  77520
gtaaggacat cgtaattcat ttcgataaga atccagttac tcaactaatt ggtggcaatg  77580
gactagggaa atccaccatc gctacggtta ttgaagaact attttataat aagaactcac  77640
gcggcattaa gaaggatgct ctgttctctt ggtcttctcc gaagaaagag tatgatatgc  77700
acgcttactt ctcgaaagat gaagatgagt acgaactgca taaagtagtt aagtcaactg  77760
ctaaagtaac ccttattaag aatggagaag atattagtgg acacacggca acccaaacat  77820
acaagatgat tgaagaaatt atgggtggtg acttccaaac attcaccaaa ctgatttatc  77880
aatcggtggg ttccaatcta gattttctaa aagcaacgga tgcaacacgt aaggcttttc  77940
tggttaactt gttcaatcaa gaacagtata aagaaatgtc agaaactatt aaggctgacc  78000
gtaaagaaat agcaaatacc ttaaataatt tgcagggcca gatggctgta attacgaaaa  78060
tccttaatgg gaaaaataat ctaggtactt tgcaggaacc tgtagaagta ccggagtttg  78120
atgaagagcc attagcacaa gaacttactg aatcgaaaat taaggcggca ttagccaagt  78180
ctcaagaggc taatattact aaattgcgta atttggacaa agctgtacaa gttgctgaac  78240
aatctttcga gcctttcaaa aatttacccg cgcccactga ccaaaatgaa gagatctcaa  78300
gtgttacgcg tgacctaacg attgtgacct cacgtgcggg cgaagttaag aaacgttatc  78360
agaagttcaa gcaagaggct tcaaatactg aatgtcctac ctgtggtact catctggata  78420
caactgctgc gcaaaaagca atggatatgg ctagaataga atatgaccct ctgttcaaag  78480
agaagcaatc tcttgaagct aagctagaac agttgaagaa agaacaactt gagtacgttg  78540
catatactag agcaaaggat gctttggata aggcagtagc agctagagac gaattcaaaa  78600
```

```
attcaatgag tgatacttct tttgaagaac tcaatgtgca aaacctacag gtgcaaatcc  78660
gacaattaga acaggaaata gctgatggcc gttctaaggt tgcaattgcc aaagagcata  78720
atgcaaatgt tgaattagcc aatgcaaaat ataaagcgaa actagaacag attgagaaag  78780
ctgaggcaga aatgtctgag attacttcta aactggatga ggtatcagaa gctgttgctg  78840
atctcgatat tctgatcgct gcattaaaga atctagtagg atataaacta gagcatagtg  78900
tgaaagtatt tgaagagctt atcaataaat atctttccat tatgactggc ggtaagttcg  78960
cacttggatt tgaacttgat gaaacaaaat tacaagtagt aattttcaat gatggaaacc  79020
gtaccagtat ggagaactgc tctactggtc agcaaagtcg aatcaaccta gcaaccctgt  79080
tagctattcg aatgctacta acatctatta gtaaagttaa tattaatctt ctattccttg  79140
atgaagtaat tagctttatt gatactaaag gacttgacac tcttgttgaa ctattaaatg  79200
aggaagaaag tctaaactct atcattgttt ctcatgggca tacgcatcct ttagctcata  79260
agattactgt caaaaaagat gcagaaggat tttcctactt agaataaaac atggctgtag  79320
atagtagaga gaagggtaaa cgtggagaat atcaagtaag agatatttta cgcgaacgta  79380
caggtcttga gtgggaacgt gttccaggct ctggtgcttt tggccagagc catggactga  79440
agggcgacat ctaccttcca ccacaaagcg gacacattag taaatactgc ttcgaggtta  79500
agtggtataa agatgataat atatcaagta atttatttaa tgttggtgaa tccactctag  79560
agaagtggtg gcagcagtgc tcacgtgaag gtgagcagat gaactccaag cctgcattaa  79620
tattcaaaaa agacagagga cagtggttaa tagctttgga tagctcagac ccgatggttg  79680
acaacttaat gagtcgtacc catatggtgt taaataagaa agacatggaa atcgtaattg  79740
gtttatttga gccgtggcta catcatgcat ctgttgagga cttaattaaa taatgagtaa  79800
atcctgggga aaatttattg aagaagagga agctgaaatg gcttcccgtc gtaacctaat  79860
gattgtcgat ggaactaact taggctttcg cttcaaacat aataatagta aaaaaccatt  79920
tgcctcaagt tatgtttcca ctattcaatc tcttgcaaaa tcttattctg ctagaactac  79980
aatagtttta ggagataagg ggaagtctgt attccgctta gaacatctcc ccgagtataa  80040
agggaaccga gatgagaaat actcgcagcg tacggaagag gagaaagcgc tagatgagca  80100
gttcttcgag tatttgagag atgctttcga attatgtgaa actacattcc caactttcac  80160
cattcgtggt gtagaagcag atgatatggc ggcttatatt gttaaactca ttgggcatct  80220
atatgatcat gtttggttaa tctctacaga cggtgactgg gatactttac taacagataa  80280
agtttctcgc ttctctttca caacacgtcg tgaatatcat cttcgtgata tgtatgagca  80340
tcataatgtt gacgatgtag agcagttcat ctctctaaag gcaattatgg gtgatttagg  80400
ggataatatc cgaggtgttg aaggtattgg ggcaaaacgc ggatataata ttattcgtga  80460
atttggtaac gttctggata ttattgatca gcttccactg cctggaaaac agaaatatat  80520
acagaattta aatgcttcgg aagaattgct ttatcgaaac ctaattctgg ttgatttacc  80580
tacctactgt gtggatgcta ttgctgctgt aggtcaagac gtattagata agtttacaaa  80640
agatattttg gagattgcag aacaatgatt aaaattaaat taactcatcc agattgtatg  80700
cctaagatcg gttccgaaga tgccgcaggt atggatctgc gagcattctt tggtactaac  80760
cctgctgcag atttacgtgc tattgcacca ggcaaatcct taatgattga caccggtgtc  80820
gcggtggaaa ttccgcgagg ctggttcggt ttggtagttc cacgtagttc tttaggtaaa  80880
cgccatctga tgattgcaaa taccgcaggg gtgatcgact cagactatcg tgggactatt  80940
aagatgaacc tgttcaacta cggttctgaa attcaaactc tggagaattt tgaaagactt  81000
tgtcagctag tagtagtacc acactactca actcataatt ttgaaatcgt tgacgaatta  81060
ggggagactg atcgtgggga aggcggattt ggaagttcgg gaagcaaata attttactga  81120
tcctaatatg atcggtgttg atactagtat gtcaacttat cagattaaaa ctgctgaacc  81180
agaaacgttg gtgctaaaaa cagataaaga aggtaatgtt actttctggg accctgaagg  81240
ttttgtagag ctttgtacta atacggataa tgagcagtta aaattactac taactattta  81300
taatcttggt gttatagaag gttgtagaag caagtaatag aaaaaccccg gtggacaaaa  81360
tccaccgggg tttctttgta ctatgtatat gtactatgag ttatctggct taataagctc  81420
gctaacaagt ttcttcagtt cggttaattc ttgctcaagt ttgttaactt tatcagcttg  81480
ataacgaaat gcgcaagcta gatctgccat aatgacgttg ttatcaagcg ctaatgtgtc  81540
atccgctttg tcaacaacaa tttgacgatc tacatactct tcaccctcat cgttaacacc  81600
tataacatct gcaaagatgt ccccgccagg aattaatttt acatattccg gatctatttt  81660
tagcaggtct tgggctatta agccgaaccg ctgaatgtcg ctgccgttgt atttaaacat  81720
tgttggcagc cactgcataa ctcggtcata gctttctttt ccgtccgtat agatgatatc  81780
atgttttaag tctctgtcag aggaagcagc cttttgaaaa acgtagttac cagtggagga  81840
ccatgttgtt atatcatttg acgctggttg aaactggaag ttgcagaaaa actcaccatc  81900
gccacgaagc cttaacgagc aaaaaggcca attattatta ccttgtgcaa taagacccca  81960
tgttgcgcga agtggatatc caccagtgga ttgtgtaccc catgaaaggc caggtgccca  82020
tccaccatca ttgttaggaa taatctcgcc ccaaacaaga gcattacccc aatagttagg  82080
atcatcccat cccatttgtt tggttttgcc agtgtattga gcagaatgcg ttctgccgtc  82140
agggtaaaac ttgtgcatat aggactgtat ccctgcttga tacaactcta ttccaaaaga  82200
ttcaacgtgt gtgtcgcctc ttctgattaa accagcgata gcgtaatcgt cataccagtt  82260
gtaacgactt acaccagtcc atgtgtttat tggtggattc atgattgaaa atagttgtga  82320
cgcattgcgt tcattcccat ctgcataaat accagcccca ggagctaagg aaatactttt  82380
cgctcctgaa aaagtaccat tttcattaaa ctgataatac tgtgatgccc cattatgaaa  82440
tacgcctatt gtatgctttc ctacgcctac ttgagtctca aaataagact gagaagaacc  82500
aatatcttcg ccttgtgtat tctttaattt tgaatgatat atacctgcat ttgcagtagt  82560
tgcattttcc gtttcgtttt caacattaag acttaggaac tttggtgcat gtttctcacc  82620
aagccctata ttatttctga taccattcgc atccttagca cctgtaccac caaattgaat  82680
acctagtggt atccattgat tggttgtagc atcataaacg ccccaatgat ccccctcatc  82740
tggaatggtt agatacttgt ttttatttgg agaatataaa actgtttccc cagaattctg  82800
aaacagccta tcaactccta aattatatct agcaccttca ggagtatctg ctcctgtacc  82860
accagccgca gttgataatg gaagagtttc ccatgatatt ccgtcacctt ttgtatctct  82920
ctgaagtaca ataagaccat catctctaat aacaaatcta tataatctat tatgtgagta  82980
tagaaaagta tgaaccccat cttgtacaag tgagtctata aggagtgtct gacgagaagc  83040
attgatattt gacagatctg agagattatt ttcttttagt aacgatttac taatgatacc  83100
ttcagctttt ccagcagcca cttctgcgcg tccggcatct gtaaatgcac tttgtgcgct  83160
accagcagca ttgccagctt gttgtcctgc ttcgatagcg ctattacttg cttgtgcagc  83220
tgaagcagca gcagcatctt ttagcactgt agtttctgtt actgcgctat ctttaatact  83280
ctgtgtatct atttttaatt gctcaacatc agattttaaa gccgttgttt cacttatagt  83340
```

-continued

```
gctgtcttta attagttgag tatctgtttt taattgctca acatctgatt ttaagccttg  83400
aatagtagtt actgattggc tagctgaggc tgcggaatgg gctgcattag tctcactagt  83460
ttttgcatta gtctcactag ttttagcatt tgtttcacta gttttagcat ttgtttccga  83520
ggtttttgca gcagatgctg atgcgccggc ttgtgcagag aatatctccg cctcatctct  83580
ataaccttta gaatccgaag cagaagcagc agcattagtt tcactagatt ttgccttatc  83640
ttcactagct tttgctgcaa tagcagaagc agcagcatta gtttcactag attttgcctt  83700
atcttcacta gcttttgcat tagtctcact agtttttgca ttagtctcac tagttttagc  83760
atttgtttca ctagcctttg ccttatcttc actagttttt gcgttagttt ctgatacttt  83820
agctgctgcg gctgattctg cagatctatc agctgatgca gcagattgag tagcagatgt  83880
agcggactga gcggcagagg cttcagaagc tccagcagaa atagcagctt cctgttcaga  83940
gttcttagcg ttaagctccg aggttttagc cgctatctca gaatcttttg cagcagcagc  84000
agacttagct gctgcctcaa tagaagatac taattcactt gcagtaatag agctaataga  84060
attacctaga gttactgtat atctaggaaa cttactagca gtagctttag tatcatcaat  84120
atttaatatt tgttgtacaa taattttagt agttactgcc attatttagt taccccatca  84180
ctgataaata ctttaccctc cattatacga aaggagctaa ttgcagatcc tataacatct  84240
ctagtcataa ttatatcata gtatcctgcg aatcgctgac gagggttata tttatctcta  84300
tctttagatg ctttagcccc tatattttcc acagattcta ctggcaaact tatagctaca  84360
gccccttgag cagcatcaat aattttagta gtaaaagatg ccaatatctc cgcattctca  84420
tctagactat tttttacagt acctcttaga gaatatccag ttaagttaac tggggtatct  84480
gtagacgggt aagtactatc atcaacgtct aaaaactgca tcattaaacc atatggtaca  84540
ttttcgtcta ttactaagtc tataactcta ttttcagtac tcattattta ccttatatga  84600
atatacccgt tttgcaggtc tatcttcatt ctgtaatagg cttccggatt atcagataat  84660
gcagcgtttc tatcataaat aacgttaaca ccgatctgag ataagaaggc attatttgct  84720
acaatcttac tggcagttac cgtaccgtta actatcatat caccatgcag taccattgct  84780
ggattaatcc aaccggaacc attccattga cgagtaaacg cagattgcgg agcattacta  84840
ttaaactcag tcaatacgtc atatctaact ggtgggctac caaagttatt ctggaagaag  84900
gtattagctt gcccatcatc ccaaccacca agacctggaa tacctaagga atacatgcca  84960
ggacctcttt gcccatctgc accgatagta ccttcagtac cactccattg aactacatca  85020
gaccagctag tacccgcaag tagcttatta gttactggat caagcgtgcc tgtagtcaca  85080
tagatatttt gagtcatatc tgtgcgatta ggtggggttt tagaccaacc aggaggtgga  85140
taatcttgtt ctagtggttt tgctggaagt gcagttgcta gcttataaac aaatactgtt  85200
tgcttgccct gtatacctgt ttggatatct acatcgccat ttggtgttcc aattactaca  85260
ccactagaaa tacgcagagt agtaccatca taacgaatcc attgtgtagc gttaccaatg  85320
tctaatttag ctttggcaga ggtattatcc atacccatcc aaataccaga gttattatca  85380
ccccaagatt taccttgagt gtaaattgct gggttatcct taccagataa gttggtcatt  85440
ataaaattcg cagcgttaat atctctagta attactttac catcaacgtt aacaacacgg  85500
tttataggat caaaagaaat aggtgctttt ccctcttcat ctagcagacc aatgttaata  85560
gccccagtag ctgcgtcgat taagaatgtc tgtctccata tttctccatc tttcatgctg  85620
cccttaataa aggcatagtt aacatcaata cccgtctcat tgacaaagct gttgtctaga  85680
ggggtatctt catttaatat aaatgttaca ggagctgatt ctgttatatc ttgtttattt  85740
ggtccccagg caattgacga aaccttaaag gtatgttcaa ctttccacgg gaatgatata  85800
atcgttgcag ctctagcagc accaacgttt atcttttgag ctttagtcca gccagtctta  85860
gcgtattctt cagaatttat ataagtaacc aagaactcac gaacattagc accagctccg  85920
cgttcccaat cccactcaat tctaacatca tagcgttctt taccatcagc aattcgtgca  85980
gctttaaaaa caatattgat aggtgcagta ggaggaacaa aattataagc tactgttaaa  86040
atattaggga attcatagta cccagaggaa tcaactgtaa caccatcagg catagttact  86100
tgaccggata ttctgatctt ataatctccg ataggaactc caccaaattt aatagtagaa  86160
cctaaagccc ccatgtaata cttagtccaa ggactgtctt cagtagctgt actttttaac  86220
tcaatagtac aatagctcgc ttcaccagtt gtttctacga caactatcgg tgcacctacc  86280
ccaacatcca caggttctga ttcagatctt gctgcaacaa ttgttggctt ctcttttgtc  86340
ttaaagttgg tttcattaga tagattgata ccaattttag cctctagtaa ttcagaatct  86400
ataatagaat cataaaaagc cccttgaatc tcgtaagagg ttgaaggggt tagattatta  86460
atcattacga aaaaagtatc tataccggta taatcacgtc tatctatact ttctcccctc  86520
tttaaccaaa aagatctacc aataacatca tagtcagtat atatagagtg ctggacatac  86580
gccattgtat atccagtcat tatactattt aagaccattt tggctggtgc attattcgaa  86640
atcattaaat ggatgcccac tccacagact gttctccatc atctccttct gctctaatac  86700
gaaaatatag ttttctattg attcctagag catcactatt atgaagagca aaatctgcct  86760
tattatacat taataaatag tcataagtat actgattttc aatacgtaca cttcttagca  86820
ttctattctg ggaatcatag atttccagag tatagaatat actttctatt atatcttctt  86880
cgggtatcct atcccaagct agttttacat ctgggcctac aaattcagtt acatccccag  86940
aagccgtatt agttacccta aaattagata ctacgcttag gtttttagca gagttaagtt  87000
ctatagataa tgttactgga gagcttcttc taccgtttat atccacagcc cttatttcaa  87060
atattgctaa acctgcgggc tctccaatta tctcttgtat catgcgttca ttgggatttg  87120
tttctagttg ctgcacaata taaggttcag catgaccgga atgcacgata gagtaataaa  87180
ctacgttatt agttaagctt ggaagccaag ataactcacc attttttcct atagaaccaa  87240
ctaaaccacc tggtgtcggg gtatatttaa aatctctagg aggaagaacg ttgttactaa  87300
tatctggtat atcattacca ctattatcta cttgatcaga gttgataaat acatcttccc  87360
catattcctg tagagtaaca tttatctttc cttctctaga gttttctact tcatctacta  87420
aaaagtactt cttatcccat ccgtaacggt cgtatgtaaa tgcaatagca tcgttaggct  87480
caataccaat gaattgatat ggtaaagaaa atgagagggt tctagaatac ctagatttct  87540
taagttctct gtctgcaaaa cttctagcag tatagtagtt agttatattt gcaaaagata  87600
attgtaattt tttgtctaaa tttttatctt gttctttata tttagagttg taaaaggtaa  87660
tagagttagt tttccagcta agagctgggt ctacgatgga tgcttgaact gagttgaatt  87720
tatttctacc agtagtatct gatagctcta aatcaccata agtatccaga aaattaatct  87780
ctaatggagt attagaatat ttttctacag taatcctata ttgaccagat aagttgttaa  87840
tagccccacc gtaggactct agcaaacctt gcacgttttt aaatactgat tcagacgtat  87900
ctagaatagt attcatttgt actatttgtc tattttctgc taatggatca gtccacccaa  87960
catatctcca gtatggctgc caggatactt ggtaagattc atctataata tctaaaatag  88020
ctgcttcctg tattaattgc tgaaggggga actgatcaat ggtaatatta gcgccatatc  88080
```

-continued

```
tatcagaggt taagtaatca agtgtttgcc aaataccatt taaactagta ctattagcag  88140
ttactctacc atcagaatga tagactttta cttttttacc ttgaatttca gcactaactt  88200
caggaatctc agtcctattt tcattaatag tgaaacgcac cactgcgtat gcagtatcta  88260
gtagtttata cctagcatcc cagtactccg gtccattgcc attcatattc tgaaggtaga  88320
acccacgttc tttagctata tctactagta cttcagaagc cgtttggtca ggttttccat  88380
gatacgtcca aatccttata tcaccattac catcattata cttatattcc tgaccatgca  88440
cagaaggact actagaagat attcctgatg ctattctttg catggtgtct ccggctactt  88500
ttttaacacc gaaacaggtt ctagcagagc tatcattaga gtccatacaa atcatagggt  88560
tatccccaaa ggaaaagtca agaaaaccgt ctatctctcc ttcagcaaaa gcatatacta  88620
cgtaaactat attaggattg tgtaattccg tatccgcaaa aataggtatt ccaggtattt  88680
tctgtacacc ataaactact ggtagatact tagcagcaag gttaaagtct atatctactt  88740
ctttagtaac agtctcgtaa tactttttaa gactataact tctagatagt ccaaatagct  88800
ttttcttaga ctttagcttg tatctttctt cctgtacctg atactttgct agaatagaga  88860
tacttttatt ggcatgaaag aaaccgtagt cttcttggta ctcaagtctt ttagccccgt  88920
tagatggaag taattgtcct gctacaactt caagccctct atgagaagca tcatcagtaa  88980
atctaccatt aaccctatca aaatcataga attggttaga acaattccaa gtaattgtgg  89040
aggttccaac tcccgaagtg ctaatattat ccttaatacc cccaccagta attctacctc  89100
taaagtataa taaaggccca tttgtgtctg ggtctacagg taaaatagaa ccatcttctg  89160
taataattgc ttggtgaatt gatactaatc tatctaaaaa agacacacca ttctgcacta  89220
atttcagtac ttcatcatgc gctgtacctg taatagtaaa agataggctg ccaatagata  89280
aatctctatt ttgtttatgt gtgctaatag acttaacttt accggcctgg tacaaaatac  89340
cattatatag tacatctcta aaatagtcag ttaagtaaat aaaagcagta ctagtaccag  89400
tagagccggg taattctaga gaaattagac tagcagtttt tattctgcta ttattttta  89460
agtagtttct agcactatct aatatttttt tcatagactt tcccgtaaat ttaatgagat  89520
gttggagtat gttccgttat tatttagtgt agatccaaaa gcatcaccat tcatgagttt  89580
tgttctaaat agtattccat taaatactgg cttctccgct ccagtagtag ttataaataa  89640
atcagggtat aagtttatag accatgtatt acctgatttg ttaaatgatg ttattttata  89700
tacttttggg tggttagaca gcttaaatag atcccccggt tttggagtac ctgtaagaag  89760
tcctttttgta tccatagtta tattagaacc cttctgtcca gcaggtatat ttactagact  89820
agtattacct ctaactctaa aagcttcgta ttggggtaat ataacatcta tataaccacc  89880
agtccttttg tattctagaa taaaagcatc tagaacacta tattcatctg gaaataattc  89940
tggataagaa atatttatac cccagtattg agcagatacc ttaacttcgt taactttacc  90000
atttggtaac tcatcacgaa ttactgggtc attatcaatc aggttaacac tttcgaatcc  90060
taagcctgaa agttctggat tcgtgtatgg gtctggtaat ctcatagtta atttctcctc  90120
tttaataaca atattataat agtattagaa aattttatca agaaattttt atttttccat  90180
aaagaaaagg aggactcaaa gtcctcctcc agttttaaga atttcctaat gttttcagac  90240
tagcaccgtt ctcattcaga gctaattcta ctgcgtctct tagagcacca ctattactag  90300
aagcaaactc tctaaaactt gcagcatcca tagcactaat attcaagatg ataggtcttc  90360
ctgaagttga gttagatgag gtttttagct catcattagg cgtagctttc ataggaacca  90420
taggggtaac tacttctgta ccatgctcac ccatttgata gctaacccca gggtacatat  90480
taccaccctc agcacgagga acgaaagagt tagcaccgcc tatgccttta tcaccacgga  90540
tataagataa ttcaccagca ttagcagaca tagacacatc tatattcttc tgacgctctc  90600
ctaaggttag gtaactagtt gtatccgctc cagaatcagc aatacttgac ataccagatg  90660
cagaagatgc ttgtgctaat gccaatgcac ccgctaaacc tgccgcaacc attagtggaa  90720
tagagaacgg atatggaaca gcggtggctg cctgcattac agctactgca gtttggatga  90780
taatctgctt cttagctgcg tcttgttgaa tcttcagctt ttcagcttcc aacttcttca  90840
acttagcttt agatgcttct gatttaccat cacgtttctg ctctgctgca atagcctgat  90900
caattgcact aacctgctgg ttggtactat actgtatcat agaagatacg gtttgcatac  90960
cagaagcaat cagggaagta gtatctaaag acccctggga gaactggatc atggcattag  91020
ttagattacc catactttga gccacagcgg ttgcttcaga gtttagctca gataatttag  91080
agattgcctg gtcataagaa gccattctat tttgcatatc agcaaaatct ttatcttctc  91140
cagatagtcc agttgtagga gtatatacag cacctacaga agatccaaca gaagcttgca  91200
tctccgcatt tctctgtgcc cttaaacctg ctagttgtgc cctagtttca gctatctttt  91260
tattatactc cgcttgtgcc gcagcattac ctaatgtttt ctgcttaag tcttcatata  91320
attttagctg ttcctgtaag cgctccgcat ttcccattaa tggtttagta gtaaattgtc  91380
tttgctgttc ttcctctcta ccagcagcca ttgaagcaat ctgatcttgg cggaatttcc  91440
agatttcacg ttcaatttgg gcttgagcac gtctagactg ttccgcctcc ttctgtttat  91500
cagcttgttt tgtataccat tcgtacttct ctttttcaat ggtcaattca agatttaact  91560
gtgctagacg atactgagta tctgtcatag tacggttatt taagagagct atctcacgat  91620
ctacacccag gattttatct gtataatcct taaccttctt ctgggcctcc ataccctgat  91680
tggtaagttt aagtttctcc agctgaattt tttcaatttc tttctcaaca gctttatttc  91740
cctggtttgt ttgaagaaca cggcgtaaag cagcttcttg ctcttctaac tgttggagtt  91800
ctaaacgcct accggcttcc tgtgcttttt ctttatcctt agtttggtta tatacatcag  91860
ctatcttctg ttgaactgct aactgatttt tagtttcatt accagttagt ttaacatact  91920
cagatagagc ctgagatgca gttttcattt cagacagggt gttataaccc agattaaggt  91980
ttttaacata ttcatcagca ctcttaccag tacctagaga tagagattct atgtttttta  92040
tagcatctgc taaagtagca ctagttttag cagcagtatc tgtattctga gcaacgttct  92100
gtatgtcatt agctaagtca ctagccgttt tcttagtctg attgtacgct ttctgctgct  92160
cagttagtcc ttttaataca gtagagttaa aatcgtatac agcatcagga tcagtagtat  92220
ctctctgtag attaatttgc ttctgaaact ctggactagc ctttgcagca gcggccccag  92280
cagcttgata cgctgatttc caagcattga gattctctgt agaatcctct acttccttac  92340
caagtctagt tacttgtaga cccatagctg cagtttctgc tacaaattgc ttattggcct  92400
ccgaagcacc tgctgctgca agaccaacag gaataccttc accaacttga cgtatagcta  92460
attttgtata gaaatctgct tgttccattc gtttatcgaa ctcagatttt agcttattac  92520
gcttatcaag agattcctta tacatatcta gagctttatt ataccctctct tcagaagcgg  92580
ctaaacttaa agcaacagca ccaacgttgg taggatctat ctgtctatta gtttttttctt  92640
gagctctagc tgcttcagca gatacagaag cctgagaagt ataaaatact gtgttgatag  92700
catcaattac gggccctaag tatttagcag cagcctgctg aatctttctc agtgcggcat  92760
cagcattagc ggcaaattgc tcccacggag tagcacgtaa aacttcatct aagtagccaa  92820
```

```
aacgtttagt agactctgct ataacagcat tagcatacgc ctgctgtttc tggaaagtag  92880
taaggctgtt aatattatat gttatacctg tgtttgcagc atttaactgc ttaacgtaat  92940
cagcataagc atcattaaga cgaatagtaa caccaagttc atccagaagt tcgatttctt  93000
gtttagatac acccttaatt acacggttaa gtgcatcagt catatcaacg ccaagaacag  93060
cagcagcacg acgagctact aaaccaaatt tattaagttg ttcggcgtca aatccataag  93120
cggacgctga ggatgcttgc ctcatagctt cttcaaaaga gattgcatag ccagctgcct  93180
cttgtagtga tctagcaagg gactgaacag gagtacctgt ctgagtacct actataacac  93240
caaatttttc tagacgattt agctgatcac ctagtttaag ttgttcaaat gctgattgca  93300
aaacgaagat gttggaagca agagctgcgt acataatagg tagactacca ccgatcttag  93360
ccattgccgc aaaatcacga gttgcaccac gtgctgaacc agaagtatta ccaatagctc  93420
tagaagctct accagcggca ccagcagtat cattaaaacc cctagctgtg ccacctaatg  93480
ctctattagt atcatataat ctatcctgga ctttttctgt tgcagctgca acatcattac  93540
ccattgtttt aacagatcta gaaactccat cgaatccaat ttctagttta tctgttactt  93600
caataagctg gatagccagg tagtctagct tatcaccaat accatcaatg gatttagtga  93660
taccagccat accccctacta gcttgcattt tagtaagact tttcgctgct ctatctgctg  93720
ccctctcaat ggaataaaga gttctgggca ttttacctaa ctgctcattt gtcagttcgg  93780
aagcagcagc agcattttcc aacgcatcag atacgttttc aatagacttt gcagtacgag  93840
ttgccccctt ctgtttaacg tctattagta attctcgtat tagcttatca gtcatgtttt  93900
atttttccca ataaaaaagg ctctgggcaa atcacccaga gccaagcctc atcgtggaac  93960
gcccattgga ggaaactttt accgtgcacg agatctagca tgtggcttaa cgttaggaat  94020
ccttccgttt tgcggtttat gcttctcagc acgtttacgt gcagcatcta cagctttagc  94080
atcaaatata ttgataatgt gtagaacaaa ttctttctct ataggatcag taatcccata  94140
aatatcaaat aaaacaccta gagcagcctt atctttacct ataaagatag gaaagtcacc  94200
tggtatgaag cagtcaatta gactgttata aatattcata ctagtagcta caataggtgg  94260
aaagtcttca agttcaacag gcatggcctt aggatcaggc tctataccca ttgattcaca  94320
aagtattaaa tattgttgtt tagtcatttt agatgctgag cttttaatac acttatctgc  94380
aaaatcagca atagcatcta ggagttcttt acgcttttgg gctacgaaaa gtgtctaagt  94440
ggaacactgt ctggttgatc caagaatcaa acgcagcaga gttctgcatg agcattacag  94500
cattatcgcg gctaaaagga acttcagtag caggatcagc atctgtttca atcagcatca  94560
gtttttcaac gtcacctaca gtcaaaccgg tccaaccttt aatagctgcg tcaacgaagg  94620
cttcaatgaa cttatcatca tcctgtacct gaatcaaagt accattaacc cattcatcgc  94680
gtttagcaga agaaataaca cgtttagagg tagcacgaga catatagtta agttctaatt  94740
taaagttcgg catacctggg taggaaagag taatagtacg agtatcaaga gtaatatctt  94800
ttaaattaat catttttaat ttctccaaag aaatctattc tcactgggtc tgaagaagca  94860
gtaggtataa tatcccactc aactctatac acatctgaga aatctaggcg ttttgtaata  94920
cgtgctgaag gaaaatctat agaaatatta ttatttctta tatttaaagg tacatctgtc  94980
tccggttcga tattgtaaac catatctcct gcaaaacgtt ttaagtaata tagagaaatg  95040
gttgccgaag cattcatttc atttacataa gctcttttat tattataaat tttatttata  95100
tcaaaaacac tcttatcctc tctccaggag cactgctgtt ggaaagataa agaggcagaa  95160
ataagaccgg gtaagatgct gccattagta gaagctatta ctgggctgta agacattact  95220
tcaccctgta taatagaagc tgcttctcta taggtagata cttctgagaa tttcccagac  95280
tcaataccaa cattaagaat tggtatgttc ttatctaaag aaaaatctac cgtagataca  95340
taacagtttt caaaatatgc acagttatta tctttattta ctatatagat attgaacata  95400
ataggttcaa tattactact atatagtggg agtaagaaag tattaccttt tctatcaaaa  95460
cctaaccatt caaagaagtt agcctctgta agagtattac tgaaatttat tgctagagag  95520
atagaagagg gggtttgagc atttataata gagtctgcat agttagttct acgatgaaca  95580
gtcctacgaa gagtcttgaa ttcctcgtat gaagtctgta tatcatagtt tgatagggca  95640
tcaaaatgaa atgccctacc atcatactca actataactt ttgactctcg cattagagag  95700
tagtacattt atttaaccac cagcactaac tgtgatagtt ttagtacctt ctacaccaga  95760
accatcttta gctacagcct tcacagtaac tgcaccagtt ttagaggcat cagctgttaa  95820
taacccagat tctgcatcaa ttgtagctgc gttaccacta gaaatagacc aagttacagc  95880
cttattagta gcttctgaag gtgttacctc aacagacatc tgtaaagtat tactatttgt  95940
tacagaaaca gcctcacctg ccgacttaac tgtaatggat ttaacgggaa ctggaggagt  96000
tttagcacca tcccccgtag caatcagatt agccacagta gtttttgtat acttgttaga  96060
aaatccaaga taaccttcgt caccagtatc caaatcagta ggaatagctt taaactctac  96120
tgaagtacca agtacatcat cagtctcaat agtagggata ttaacgtgcg cctgtttagc  96180
aactaacaca gctgccggac gttcctcgtc atattctcca cccaaaataa gtgcgatttc  96240
aaaacggtta actaccttaa gggttttaat cagatctttg tacagttcca tagaaccaag  96300
agacttatca ttaaggtaag ctgtcaaaga acccgttaac tcaaacgcac ccgtaaatga  96360
gccgattgga atatttacac gtgacataat attcggggtt aggtacgtga tgttgttatt  96420
aatggtaaaa gtaccaccag taataggaat atcatatgcc ttatcagaat ccatatcctt  96480
aatttttagg atagttaact tgttcttaat gtaagaactc tgaatagtca tataagtttc  96540
atcatcaatg cctaatgcat cagggtcaaa tggttggcta tctaacggaa tgagctgatt  96600
accgttacca gaccaagtta cacgaccaat atcttcaata tcaacgttaa cttctgcctg  96660
gttgatctgg caagagtcaa tgtaactcca cgcattgtca gttagaatgt aaatatgcag  96720
catagccagt tcgtgatatg cgttatcttt gaagttaacc atgaagttag tagcattatt  96780
atgtgctcca gtatctccat caaggttaat agctttacca ctagaaagtg catgccataa  96840
catatagtca ggaacaattt gtttgctagt agttttatcc atgtatggca ggatataggt  96900
ggagaagctc cactcagctg cattcaagga atcgttaaaa cgtttagaac cacgagtagg  96960
acgcggacca gcttcgttaa cagtaatatc tgttgagtta ctgtcctgac cccaagaaat  97020
atcatcctga actagaatct cttgcgtgtt ggtcttatcg tgaccagtct taaccgtaga  97080
cacgaagatt cgagtattac gtaatagttg taaagacatt taattatttt ctcctaatct  97140
gtaacttatc tgcgaagtga cctacgtgga ggctgatacc tcactgttac atttatttct  97200
gctaaaccat atggggccag tagaccctca tctgtactaa ctgatgtaat gctcatatca  97260
gtcgcctcac atgggaaggt cgatccatta ggtttactaa cagtatattc taaatttcca  97320
cctgtgtcaa taacggtttt tatatccgct acgagttttt caagttgctc ttgaatgtct  97380
gttttctctt tatcatacac caggatagga agttctaaaa acatccactg ttgacctgag  97440
ggaagatact gcccagtttc agttccgata tgaactgcaa cataaggaaa ctctcgtatc  97500
tcctcaaact tataagtttg acgtgagacg tttccataca agttattaaa atattcatct  97560
```

```
ggttgagagc catccatttg tttggctatt cgatcaacca gagcttgtgc tatacttgtt  97620
ctgtgatcca tttattaggt tccttgatta accttaattt tgtatctgga gtgaattaag  97680
tctcttgcag ctttagctat cgcctctcca attagtcttt gagggtttct agcacctggg  97740
tagggtcgta gtgacaatct tcgatatgta gatactgcag gattaaatac tgaatatgga  97800
cgtaccatat aattatatgt aacgtttaat tccggagcac ctttgctagt tccagcatct  97860
ctaagcataa catctttaac ttttagagag tttgcaaaac gacctgttct aaatttaagt  97920
ggagctcctg ctttttcat atcctttatt aagtattctt tagcaaccaa ctccagaata  97980
accttcatat tactatttga tacaaaacga ccagaagcac ctgttactgc accagaatat  98040
ccatcttcta cgtctctagg atccccaaag tttacttgaa ctctaccagt agaacgtttt  98100
ttacctacag cagatttttt accagcggtt gcttgtatta aattctctag agcacctaaa  98160
tctcctgtta gatctaagct agaagaaact gcttttagaa tagaagcggt cctaacatta  98220
aggagatctt gggatacagg ttttgagaat ttaaaagata cctgagcaac agtaccatct  98280
ctagtaggat ctttcagtcc tgtttcaaca gaatatacaa cagtattctt attgttctcg  98340
gaacgcccaa cattatctag ctgctcctta ataatttgtg tagctaaatc agaaagagac  98400
attatactct cctgtaaact tcaataatag tacgaatatg ctctggaata ccagacttag  98460
tattattaaa agtaactgtt tctccgccaa ttgttttagc ttgacggtaa tcctgtttat  98520
gccaatgatc tactagcata catgctgcaa gtttgagatc ctcaggtatt ggattaaatc  98580
caccttgtgt gtattctaca tccatataac cttctggggg attaaattta agaagtataa  98640
ccccatcaga atacaactta tattgttctg gatctatctc cttgtcgtta atagtcattt  98700
tggttactga agtagccgag ggagaactta agaagtattt tttacgagta ggttttgtat  98760
tgattaactg gtctaccgca tcagcatcat ccatacctaa aaggctagta atcagcgcat  98820
tggcagcagt aatcatcatc tctactccag attctagttc aggtcgtttt aacccaccat  98880
ataatctata gtcttcagct gtgattattt gcatttattt ttcccaataa aaaaggagag  98940
ccgaagctct ccttatcggc tgaaaagcct gtattaagat gcagcgtaag caccagatac  99000
aacgccattt gcaaagtaac gttgcaggtt aacacgctga gtaacgtagt atgcgtcacg  99060
ctgtttacca gcttggcgct cacgttcaac agtaacagca cgctggcgtg gcattacgaa  99120
gttatcttta taaacaataa ctgcgaactc tgcggaagta gctttagctg ggaagtactc  99180
agaaactaca accggcagac cataaatacg accaacctga ccctgcagtt taacagcatc  99240
attaccaact tgggcaacat cctgccattc ttcatcttcc agcagatcat agtaagcatc  99300
catagataca atcagtacca gtttgctcag tttcagacca tgacggccca gtttacgacg  99360
caatttagag atagttttag cagttaccag tacggaacca tcagctttag cttcagtaat  99420
aactttagca ctatcttcac tagcaagagt cagcagacct ttcggtttac cggaaccatc  99480
accagtcatg aaggcttctt caatagaaac agcgtgtgct tcgatcagac gcttacgaag  99540
cagtggcagc agggagaaga ttgcatcttc ttcagtttca tcagtaatga aggacttagc  99600
agccagtttg taagtactga agtggatttc tttaagagca cctttaactt catcaccagt  99660
agttgcatca gtaccataag tagaagcagc aacccaagta gctttaccag catccggttc  99720
aaccagcata gtaagaatct tactggacat cggcagttct tcgaacagtg cgccaactac  99780
aagctctttc tgcaggtcac ggataatacg ctgagagaaa atagtttcat agctttcact  99840
agaaacttct acagaagaag actgattcac tgctttcagg tgtttttgac cgtgttcggt  99900
ctcgaatacg ccctttcca ttacataaga taacagaacc agtttttcaa cttcatcttc  99960
aaagttttcc tgagtaccgt atagtgcttt agcaacacta tcaccaacga aggaacgacc  100020
ttcacgagct gtcagcagag atttaatttc atcctgaaga ccaacaatag tttcctgttg  100080
tttttctaca gtttgtgcaa acagttctgc gctcttctta gatttctcat ccagagactt  100140
aaccagatcc agagcctctt ccagacgctt acgatcttcg ccaactgctt tagaaaccag  100200
gtcattcata cgagccagtt ctttttcttc ctgctcttta cgcatacgtt cagcttcctg  100260
agctttctga gcagcggtca gaccttccag agatttagcc agatcaccca gaccaagttc  100320
ttctttcagc ttattaatat caatagtcat ttttaaataa ttctccgtta ttctttaacg  100380
tagcctaaag ctatcgcaag tttttctagt tcagaaagat tacgttcttg agctgggaca  100440
gctttagaac ttattgcagt aaaagattta cgccattcag tataatcatg accattcatg  100500
ctcttagcga gattgaacgt tgagtcctga ttacaaggta cagaaactac cgaaacttcg  100560
tatagttcta aatctttaat aataaatata tcagtagctt catcccactc tgcatctagg  100620
cagcggaatc cgatactaaa agttttcagt acaccgtttt taattagtga aaagatagcc  100680
gggtcagaac tttcatagat ctcgcattcg atttcgagac ccatttcagt agggttaaga  100740
tcaatacact taccgattgg acgacgatga tcgtgtccga aaagaataat cgggtttttc  100800
atatagttag taagtgcatt agatgtttc cacgcagaag ccggaattac atcaccagcg  100860
cgatctttac taattgtatt agcgaatcca cggattttta caacgccctc tttggattcg  100920
ctatcaatag atttaatata agcatctaaa tgaacgggtg ctgattttaa cttgttatag  100980
tcaatagcag cttgtgtcat ttattagcct ccaggaacag taggattaac tgtcacagca  101040
catgcagtag aatccttact tacttgctta ctatctgtta cagttacttt ataagagccg  101100
gcatcctctg ctgctgctgt aggcttagta taggtagctc ctgaagcttc cggaatagga  101160
gaaccatctt tagtccatgc ataagtatat ggactagtac caccagttgc agtaacagaa  101220
agtgttaatg ctgctccctc ttcaactgac atgctcgcag ttaaatcttt agaaagagtt  101280
aatggtggag ccggtggagc aggaggaact gctttaccat aagcctctac aaatttcttc  101340
catactttac ggttagtatg cgcagatgaa agccctagtt ctctacgcag aaaagcatag  101400
ctaggaacat atttatgcgc agcaaccgta gcaaagaaga tatgagattc tggtagtttt  101460
tcaccaaaaa tggtctttag accattataa tcaatcattc tttatctccc tcggtggaac  101520
cttgaggtct accaccttct tgaccagata cacctgttgc agaaccagca acgttagcag  101580
gaatacgaat cctatccatc tgctcatcat ctaaaggttc aaggttcagc tctaaacgag  101640
cttcgttacc agtcataata ccattattaa ccaatgaggt taaatgttta gcctcagctt  101700
ctttatctgg tgttaatgca gctacctcct tagtattagg agtaatctta taaccaaaaa  101760
agaaagtaag agaactagtc agtttgttca gcataggaat gatagtcata taatagaaca  101820
attcgatgtt tggtcgaata ttcgcgttat taccaccatc aagcagtact tgcggaactc  101880
caaaggctag acaaatagat ttattaaatc cttcgatgtc ttccttaaag tctagatctt  101940
taaaagagga tatttgggag tacggtttag ctttcatacc accatctaga atcaggacag  102000
aagactgacc agtactagga ttataatcga gttgtaattc ttcttgttta cgctcacgca  102060
atttcttgtt caggatttca tccgtttcaa gaataagacc aatcacggtt ccgttatcga  102120
ggaatttctc tttaaagtta agcatcttag aacgcttctc aagagaatca ataacagtag  102180
caacacgaga ttgtccagaa atttgagaat ttgtgccaca cacgtaactg ttatccttta  102240
taaagataat ctcatctacg cgatagtcta tctgattatt aaatataaat tttttgataa  102300
```

```
acttattggc atctgcctcg acctgcataa gagcagccgg gacgtggtaa agcgatgtgc  102360
catcccaata gatgtatgca caaccttcaa aaagtaggtc agtgactaca agtctacgga  102420
atgtgcttat atccatgaat ggattaggtc gtacatttaa gagagtgtct agagtctttg  102480
ttttgacgcc attagcgtac gtaacaatat tatatttatc tccgacagta taagaacact  102540
ccgccgcact atctataacc atattagcag ttctattgag aatctcaatt ttactgtagg  102600
cttgtccagt ggtaaaaggc ttacggttag tgcgatgact aactggttcc atgtctctta  102660
taatacgttg acccggattt agcttttcag taatccagct tttaaaaccc attataagaa  102720
ccttgcgaat cctgatttg tttcagtctt gacttgtgtc ttttcttgag gattctgtaa  102780
tttgtctttc tgcttttgaa cccacacttt ttgcttatta gcagaaaata aaggaggttc  102840
ttttgtgtaa accttatgta ataattggtg atggtgtaca cagagggtaa cagtgtcttc  102900
tactagctca tgcctatatc gatcatagaa tgccgtccta tttgaaagga ctgtttcttc  102960
gtcagtgaaa tccaattgga gttctttagc aaatttttta actagtagag acaccgtatg  103020
gtaatgatga agctctaatt cttcagcaca accgcagata gcacattgag agtctttttt  103080
atattgactt tttattccgt ctctcataag ggatatagca tcgcgtttat attttatatt  103140
gcttgccata gtgttctcct caactgtatg aatatagtat acataatcgt atcgaatttg  103200
taaaggggat tttaaaatac aggaatggga taccaactga gtagtatccc atcctatact  103260
tatttattta ccacgggaaa tagaataaat tccatagcgg agcgcatcac aaaggtgaga  103320
gttagcatca tgacgtggtt tttcacgtga taatttctct tcaccttctt ggaagtccca  103380
cttgtaattc tgcaatgcat gaattaagga ggaacatgag gcatttacaa taatcttgcc  103440
ctgttggaac agtgcttgca ggcatgctag gccatctagg acagattttt tagctggagc  103500
tgaggcaatt tcatgctcat aagctaagtc ctggcggaac tgagctgctg cagagtcaac  103560
aaaaatacga tcaactttat aacgatctat acagtgctga atataagcag catgctgagc  103620
tgtagttttc tccgcctgct ggtactcttc taatacatag taagtatccg tatcgtaatg  103680
atatttaata gtaagaactg ctgtaggatc acgataacca acgtcaatac caagcaacgt  103740
ttcgaatgct tcatcatctt taaagaagtg acgcatacct ttgagatctt taacatgatc  103800
gatagcatta aaggtatcaa atatctgtcc ttcgaataca gagaagtcag cttcgtattc  103860
ttggcggaag tagtttttac taaccgtacg gcgtgcctcc tcaatgtcat tcaaatcagc  103920
acgtgggtta tcacgatatg taccatgaat agacacccag ttaggtaacg tatcatcgaa  103980
tccgtaggcg taaaactctt taaaccagtt acctccgcga ggggtggaaa taaatagagc  104040
cttagaatta ggcttatcta gggtaggacg cagctgaacc ctgaaggcat caccacccac  104100
atcggaaatt gccgcctcgt caaagatgat aaaatcatat gaacgtccaa ccgcggagtc  104160
agcctgagcc gcggaagcta gtttaaatag agaaccatta gctaactcaa tctctttatc  104220
tttagcgttt tcacgttcgg tttgtaggcc gtacttctta ataagaccac gaatctgaga  104280
ccatccgata ttagctagtg aatagttagg ggcaactact agtaccttca cattaggttc  104340
cagcaatttt aggaacccaa gtgtatacgc tataaaagat ttacctacac ggcgtgatac  104400
acatgccgtt acaaaacgat gtctagggtc ttctagggca ttgataattg ctatttgagg  104460
gccattaggt gtgataccct cttgtgctag tattccggaa acgggtaaac gaaagaaacg  104520
cttatctatt ccgaaatcaa taacatctac tgtattaaca tagggtcttg atacttccat  104580
tacttcttac ctccagtagc tagggaagta attaaatcca tgtagttttg atccccggct  104640
ccagcaataa tgttattctg gatattagtc tgattagcag gagctcggac ggcagcttta  104700
gctttttcta actccaccat catcttcatt tcttccatct tcattttgtg tgctttccag  104760
agaatatcca taatatcctg gtcagaaccc atgccagttt cttctagttc ctccagctta  104820
cgcttaataa cttcatccag aacaccaaat aaacgatccc tattacggaa accactctcc  104880
ataaaaatat catttaagta gttcttaacc tcactacgat tcataaatatc tcggaaagca  104940
atttcggaca ttccaagact acgtgcggca gaaggcacat cgctgccgca ctgtaaataa  105000
gcttcaatta catccatccc ttcaggggac ataagatctg gtactaatac atcatttgcc  105060
atatttcctc ctttaggtaa ggcgttgaat tataagttta atatttggta agcatgcttt  105120
catgccaatt atattgctca tagaggattc taaccaaata gagatattat tatttccatc  105180
atttctcata tagtatgtta gagtatagta acccgtttga cctacggatc ctggcaaccc  105240
agatacccag tacggagttg gagtataccc agcagcctgt aatttacaag catttactac  105300
agtaccttta atagtaaaaa atggtacata ttctcctgca ggtagggaca atatttggtg  105360
aagtttttta tcaatagtat tgccacccat tctaaaccta ctatcgccat attcagcgcc  105420
tttagatagc atttccgtag gattaaagca gccaatacct cctgcagaca accatgtgtc  105480
atctaggaac tccatagtac atacaattgc accatttcta ctactattaa gatctagtcc  105540
cacggtacca acatgcacgg aaccattacc ctgaaatact atgttaccag atagtacagt  105600
acttccgcta ccacctagaa gtcttaaagg tagaagattt tcactccaaa cgtccccata  105660
attactccct atttttggag gattactaga aacataccaa gatgctgaag gtaaaaagtt  105720
ataaatacta actacattag tatttaaacc accaacgtta ccacccttaa tacttggtgc  105780
gttattgctt tctgtggttg gtagtccaaa tgttgctatg ccagagatcc cagtagaggg  105840
gccacccata ctcaagttac acccaacatc acgaaaatca gctctgctcc ctacattaaa  105900
gtttttctca acaaagttga taaacttcca agatgtatta ttaacgttaa tacctttaat  105960
aataaattca gtggggctta attttatatc attacctgta aataatccag catcaatact  106020
ataacctgaa ccattataca ctaagttagt aacataccag gtaattttag atggataaat  106080
accgaggtgc tcactatata tacctatggg cccattagca gcatcattcg gatcacccat  106140
actttcccaa tacgcatagt tagtgggatc agcacgtgcg aaacctacag agtacttagg  106200
agccgaggga ttgctaggat tagacataaa gttaagagcc cctgaactcg acgccccatg  106260
tacagctcca gcagtggtgt agttgggccc ttccatacca taaagaactc tattacaaga  106320
cctaccacga acatatatgg cgttaaatcc aaagtttcta gctccgggat gcctaacgta  106380
gtcgctaggg atagttagag ttcctgaatc cggcactaca tatcctgaac catcccaggc  106440
agacttataa agagcggcac cccctaaata cattgcacta gatgcaaacc ctctacgccc  106500
actaaaggcg ccaaacatat gctgacatcc agtaccgtct cttaatttct gggggatcgt  106560
accgctagta ccactattaa aatagcctac atcaagagat agatcagcac tagctgttat  106620
ttgtgttttt aaaccacctt gagacatgac ctgcggattt ataattccat acgctttagc  106680
tcctaccccc atagacatgc cagatagcat atgtctagag ccatctgaga actcaatctc  106740
tgtcagcaca accctattag gatcattatt atgtaactgg gtaattctgc taggcatatc  106800
agaccagtag taatctccag caccttgatc tagcctcaac cctgtggagt gagtttctgt  106860
tatgataaca tggggcatat ctgaatggaa tatggtctga gagtcaggat taatatgttg  106920
attagtatct ccgccactac ccctgcgtag agagagtata gatttgttat ttagcttgcc  106980
agcgaaaaaa ctcataagtt ctccaaaaat ttaattgctt atgttgctat aattctgtat  107040
```

aatagtatta taaattaaac agaggagaat gtaaatgaaa aaattatttt tagctatggc 107100
agtggtactt ctttcggctt gctctacttt tgggcctaaa gatattaaat gtgaggccta 107160
ctatgtacaa gatcatgtga aatataaggc taatgttttt gatagaaaag gggatatgtt 107220
cctggtggca ccaatcatgg cctatggatc tttctgggct ccagtaagct actttaccga 107280
ggggaataca tgtgaaggag ttttctgagg agaatccctc ccataaaccc atgccactta 107340
gggtggatcc taggtcaaaa ctagttcaca atgcaattga ggtcattcag aacaccatat 107400
aagataaaat gttatgactt gtgcaattgc tagaatattc caaataccac atttacggga 107460
gtatgaaaga catgtcaaac ggcaacaaaa gaaagaacag acgtggagaa gtgtacgata 107520
gctggattaa tagctttggg ttcggaacta ttctattctt tattttcgta ggtttttggt 107580
tagcagctat ggcggggtgg atctaatgga ctgggtaatt attgcactac tggggattgt 107640
gattattggg caatgtatct tagataatca cttagctaga atcgaaacct tactatcgga 107700
gaaacgtaaa tgatggaagt ggcaattaca ctaatggtaa tattagtctg ggcagttttc 107760
attatttatt acaccgtgta cgttcgccta aaaacgctag aagctcaagt gaagcaacag 107820
caatttgcta tagaaaaact atcagaattg caacgttgtg atagtacccg tattctgcaa 107880
attgggaggg aattagatgt ttagtattgt aattgctttt attatcggga tactcgcggg 107940
ggttttcggg acaactgcgg caatcaacaa gcatcgtaaa tatattgcgg gagtgacgcg 108000
ggagattgcg gaaagggagc ggaagtttga cgagaaacgt gcggagtttg agcgagaatg 108060
gtcggatgga tctcgggcgt cgcggaagag atttcgtgag tttagacctg aacatctgtt 108120
tgatgaccct tctatgcgct aatttgactt ttgccaaatt tcataagatt acacatggag 108180
gtgtgtccac tggctggcta gatgagaatg agtctcatta ccgcccggta cttagcaggc 108240
taatagtcac ggcatgttat cattacacac cgtgactatt tcaactttaa ttattacgca 108300
acttttaatt tctcaatata ttgttgcggg ctgcaactat attctgcgcg ttcttcctcg 108360
gtcatacttt cccaacataa ttgcaggcgg tcggctagga actgataatc attatcatcc 108420
tcaagagatt catcaataaa ggtttcacct atcaatgtaa ccccaatcga tagaatatcg 108480
ttaacggctt gcgcgtccag cgttttaaat ccgtatgatg ccgccgctga tagcacgcct 108540
ttatgatcat caatcatcgt gaaatcagcg ttcggatata attgtttaaa taactcaaag 108600
taatggcttt tataaatagc gtctttgctg tggtatatct cgctaacttt atcagcctca 108660
aaatatttgt gtagtgtatc gcgggaaaat acacggatat tactatcccc acgccctcgc 108720
aatccttgtt tgcgcaaata ataataatcc gacttgctca ttagtcgagc ggtgcaaata 108780
atgtttaacg tgttaacgtc attcatacat tggcgcatat atgtaacaag gggcaatagt 108840
gtatcttgca ttattaaatc atgtttgcag gcttcatttt tatacttatt taaatctaaa 108900
ttgccctcgc tatcaaagca aggcgctacg cgatggaaag aattaatgat agtgccgtcc 108960
agatcccaaa tcatgacgcg ggaaatatgc gggaaattac gggtaatatt cgttttaact 109020
tgattcattt tgttacgttc tccatttaag ggattagatt aattcagcat tacccgctat 109080
ttataagcgg gtaataataa attaactatt aaagaccata cgccaacgca tcagcaataa 109140
aactaatatc ttcaccagat acaccggaac gaatgcccgc gcaggtatat acctttgcgc 109200
tggtcaattg atcatcgagg caagcggggc aaggcgcgac aactgcaaag gctaggccgg 109260
attttacggc gtcgatgata atcgtttctt gtttcacagt gtcaacataa acaccttttg 109320
ctttaatatg gctagttagt ttaccttgcg tataggcaaa ggtagtaacc tgcaaagcgt 109380
cgttaaagtc caatagctca tcaataacgt gccccgcctc gacgtggtaa cgttcaccat 109440
tagaataaac cagaacaatg gaagattgag cgcgatcgaa tgggatattt tgctttttca 109500
tatttataaa actccaatta atttaataaa gggtatttaa tttacttgat aataatctgc 109560
atttgatacg gcgttaattc accatttacg ggtaaattat tatcgcttag ccactcataa 109620
aaagcgtcat catcgtcaaa agggataata tcattatcac gataatcgac cgtaataatc 109680
ccatccgtat tagttttggc ggctaggata ggcccgaagc tgtaaacttt atcggattcc 109740
atttcatccg gtgaaataaa tgctttttcg tccagcgttt tgggtaatgt aactttcatt 109800
ctaatttagc tcctataata gcggctatat ttcaagccgc tagggtatta attatttacg 109860
caaaaaattt accgttctta aaatcgatca aagtacgctg accatttgca taggtaatta 109920
aatgcgtttg tgtccagctt gacgcgccaa cgttgtaacc catgtccaga ctaccagcca 109980
cgccagcggt atataccccg ccgtaaatgc tggcggtatg agtgtgcccc gtgtttaatt 110040
tgcccaattt cttaaactgt ttcggattgc cacggctgcc gtttatgcca ttgtgaccgt 110100
gtacgccgca ttcaatgcct gcaattttaa atgattggtc agtcgttagg aaaatggcgt 110160
taaactcgca acctgcaacc ttacgcagcg cataatctag cacgttgaaa gtatcgtctt 110220
tttctgcaat agctccgtaa atcgcggcat tcaggcggtg atatagttcc gcgttcgctg 110280
ggtcgtcttt aatgttagca ttacgatcat caagccaacg ggatagcgcc aaatcgtgat 110340
tcgattcaac aatgattgtt tgcgagaaat cgcgctccat tgattccagt acgcgccccg 110400
tatcgatgag atcatccaga actttatcac gtccggcggc gtattgtttt gctaggaata 110460
cacccgaagc gcggttgtga tggttgcgtg atgtaaaatc gtgaacgtca tggataaact 110520
gatattttgg tttaagaata tcaagcaagc tattttcgcc agcccatgac gcaatggcac 110580
aatcatcatc aagtttttcg gcgtgtatgt cgccatattg caagcctaaa acatgccccg 110640
atgtttcata gcatccggcg ggagtagcgc aaacattcag atcataaaac accccgcttt 110700
cgtccattgt ttcaagctgg cgaacaaaaa actcaccgtc ttcgtcgaac tcaacaatca 110760
gcgcaccgaa gttatgcagt gcttccgctt tctgtcctgc tttctgctgg atgtaatttt 110820
taagcgttgc cgtgccagtt gaatacatgc ggcgcactac ttcacctttt aaagctggca 110880
cgctttcggc ggtgatttta gcgtgaccaa ttgccagacc ttccagatta agcgcggttg 110940
cagtttcagc gaatccagaa agcggataat ctgcggtggg caaaacatta atttcagcca 111000
tgaaagcaaa acggcgatta ttcaaaaaca cgtttttgct gcaaatatat ttatcgaacg 111060
cggaatcata ttttattcca tccgcgccct cgccattttg gaatccgttt ttattataaa 111120
tatacttgct aaccagcaaa tcagcgccga tatatttagc aaattgctcc agtgaggcta 111180
aaaagttttt atgcgggaac gtattattct gaatcgatgt aataataaag cgtttgcctt 111240
gttttacttc ccagctttcc accgtgctag aaacaatccc cgccgcttct gggcgctcat 111300
cgtttttaat ggcttttgct actttcgccg ctttcggttt cgctggttta tttgcttcca 111360
gccaatcaca aatagcggtg gaatgttttg gagtatcgta aaccgctttt gatatatcgt 111420
cacaaacttc caatttagtg gcgcgcaggc gtttaccgta gaaattaaag tcagcggcca 111480
ttttcaggat aacggtttgt ttttctgcgg aaataatcat agtaataaaa ctccattaaa 111540
gggattaaaa aacgtttgtt attggcaaat attgccaaat ataacgccta ttatttgagg 111600
cgttataatt tgcaacatta atttaaaggc ataaggctag aactaacacc acaaacaacg 111660
gcggcaataa aacaaatcag acctaaacgc tttgctaact tagatttacg tttaaaataa 111720
tatgaatcta aatcattttg aaaataagcg aatagtaatg aggccgccat aataaataag 111780

-continued

```
cctagaatta aggattcagt agggtaaaag atcattttaa taactccagt caaagggaaa  111840
ttatagtggg gaatattccc cactaattaa atttattcgc ctgcggcttg tttcacttca  111900
tcggcaacgc ctaacagttg cgccacggcg tccagcgttt ccagttttgc gctttccagt  111960
gatgccagat cgtcggcgtc tttgataatg ccggaatcga tagcgtgttt tgcaataacg  112020
cgcacataat gcgctttgcg gattgagcta ccgccgccaa ctttgcgcgg cttatcgctt  112080
ttctgatacg cttttgcgct ggtcaatttt gagcgaacgg acacggggga ggccgcgcca  112140
actgcttttg caatctcttt caggccgtcg ctatttgcga aatctaaacc gttttcatta  112200
attaactgct ggtacatggt aacagctttt tgggtgtttt cttcattcca tgcaaatttt  112260
gcggattttt cggttttaac gttagccatg attgtagctc ctattagttt aatttaaggg  112320
ataagattaa cataatgtta atcgttatat cccccgaact actaggggga tataaagtta  112380
acactaaatt ataaaacagc ttcccatttt tcgttacgct ggacaacctt tacaacgtcg  112440
ccggatttaa cgcgaacgct aaaaacggtt ttgccgttgt tactccgttc cgtttcagcg  112500
tataccgcgt cgattgtatc gaacggcata agcgccgcgc ctttaatgcg ttcggccttt  112560
ccggttaatt catccgtttt agtaacgaaa ggaataaaaa cggattgacc aactttcggc  112620
gcggtaataa cgttttgcat aatataaact cctagttatt tggggattgt tccgcattac  112680
ctgctagaaa gtaacagcag gtaataagta acaatccgct cgccaatata atcaatttaa  112740
agaactccac gcaggccgct atatcccagt tagggggcgg ggcacattat ggtaagtgcc  112800
gaccgtcaaa ttttatcaag ttatcgctct tatcgaactg ggtacatctt aaagcctatc  112860
ggctagggtg tcaaacaatt ttttgcagtt ttttatgatt ttcttttaag tcaatcataa  112920
tattacgcca gatcatttcc agaccttgct ggcggccttt cttgtactgc ttaaatcgat  112980
attttaccga tctttgcgct actgtcaaca aatttttgt tttgctgtcc agtgccttgc  113040
taggtttacc agtgatcaat aaagtttgtt tcatatcgtc gattccttat aatgtataag  113100
tttaccgccg ataggcttta agatgtaccc aatttttaaa gagcgcggcg gtaaacttcc  113160
cgccgtgtag ttcgtcattg ccgccctacg agataaataa taggggattc ccgaaaatgg  113220
cgcaacctta tttttgtaaa gaaatgtaaa gacaaacgcc accggacacc atgcggcgac  113280
cggggcgcgg cgcattaaaa ttaaaagaaa cgggcgcgcg aataccataa aacccagcag  113340
gttggcaagt aattttttca tttatatttg ccttgcccta cttgacaaaa cttaaaaagc  113400
tcgtggtagc gataaacgag ggtaggcaat gcaatggcat ggctaaaact ttcatcgcgt  113460
tctagggcgt tttaggcgca ttctagcctt gttgataact tatccccaaa agcaaaaatg  113520
aaattttcct agttatccac ttgactttta ttttccagtg gataactact tattttatga  113580
aataaattaa ttgactttta tttgttagta tgcatcggaa gaatagcaga ctaataatta  113640
ctagaataat aatcatgctg gtggattgta acggcctaaa ctatcagcag actattaatc  113700
acgaaaaatc tcgttagcta actaactatt tcatgatgta taatatacat ataaattaat  113760
gagaaataat aattataata aataataact acagtaaata ataactataa gaaactatcg  113820
gcctaagtga gaaccactat catttaagtt atacacaaag ttatccacag cactttttga  113880
ctttacacga taggcggcga tataaggact tttacacaga cttatccaca ggttattcca  113940
ctgtataaat atacagggta aaaaggtagt gttaacaact gcaatcaatt ttaagcggct  114000
taaatcgcat tctaacgagc taaacgctgc ggggtaatat taaagtaaag ccttaatgcg  114060
tcaccctggt ggcttcgccg tggtttgctc tttattgcac cgctgcgcgg ttagcataaa  114120
aataggcgct aggcaaggaa aataaaaagg taaaataata tttgcctatg ctagaaattt  114180
acctttatca ttcactcacc gattaacgag ggaggccgaa caaatgaggc tttataaacc  114240
tgataatgcc accgttttaa aaggtgcatt gcgcaacctg ctggatggta gcaagtcaac  114300
cagcattaaa cattttatta acaagattga aactattcat caaaactttt ttgatgatta  114360
tgacgcttat gatatggata gtttctacc cttatataga caaggggcaa cgctagtttt  114420
atataatcgg gattgccata tctttacagg caggggagcg gggccggata ccgattttat  114480
tgttgcgcag ggtaataata ttgttgcgta tcatagcaat tcaggccgtc aatcatttaa  114540
tataaatagt tttgagctta ttggacttga tctgataaat ggactttcta gcattgaggg  114600
atttttagat gttatctgga agtatttacc cgctggatgg cataagccgg ataacgacgg  114660
atctcaatat accggtataa tggcttttga tggcgacggt aattttttgt taccacggga  114720
gctataccca tatatttatg atggggatat agaaagcgct ggtttttctt tctggaaaga  114780
tgaagatcag attattgaca gcgtagaaaa ccatgctgta aattctaaca ctcaaagcgt  114840
taacactcaa actactgaaa acaaaggaaa aaacactatg accaagattg ctaacatcgt  114900
tgccgctaat aaatccgccg ttgtaaatgc tgcaaaactg gaagcgggta aaattgcact  114960
gactcaaatt acgaaagtag cggctaaaaa agcaccgttt atgattaaag gttatattga  115020
tacacctatc ggtcgagtag tgattgccaa cctgctgggc gtagcggttg accagtacgc  115080
cacaagtaac caaaaggcga aagcggtggc aggtgcagct atggaagcgg ctatgttaga  115140
aatggtgcaa agttttaaca tcgctgagat gattgatgaa atggtaaaag gtattgatat  115200
ttctactttt accactagca ccgaaagcga gtaataatat taagcgggga ttgttacccc  115260
gctttactat tcccttgtta actaatagga ggctaataaa tggctgatga aaaatatggc  115320
ttctcactgg gagaagtgag cacggcaaaa catgatatga tcattttggt cgattgtcat  115380
actggctatt gcggggaagg gaacaccgag gaatatttg ttcctgctgg tacggatctg  115440
gacgctttcg ctcaggaaat ggctattgat aatgcttctc gttttggtag cgatggttac  115500
gaagacgaag aaactggcga atggtatgaa aatgaaaacg tatatgcaag cctttatcat  115560
tatcaattaa gtaaatccgg cacatatgta aacggcggcg atcctattaa ttccgtcatg  115620
agattaatta ttaaatatgg cggcgtcgag atagttggta acaaagcggt aatatacgca  115680
aatcgattaa aacagcttgt ttatattcct gatagtaccc gatgggatga atatgctgtt  115740
ttgcatgacg aattgaaacg atgtttcaat attgaatcct tacaagtagt ctaatgtaaa  115800
gttttgtaaa ggtcgccttt tatggtggcc ttttttgtta taatgccttt acaccgtttg  115860
aggacggttg aaaattttcc caaaaattgg aggcttaaaa tggttgctta ttcttctgct  115920
agtcatctgt tcaccgctca aggctgggta tctaaccgcg ttattattca cgaaatggtg  115980
caagaatatg gcattgctaa aacatacaat accattcagg cgctttatga taatgatcaa  116040
atcgatcagc aaacggcggg ctttttgctg gataccctga aagcagaaca ttgcaccaaa  116100
aaacaagcgg ctaaaattgt tttaatgtaa ttaataacgg ggcgttattt tcgccccact  116160
aactaggggg aatgaaaatg gttatttttc gagctatttt agcgggtatc ttgggcgcta  116220
ttttatcgtt gtttgcaata gctttcggcg ttcacgcggt tattattggc gcgggtatcg  116280
ctgcattttc ttatctgctg ggctgcatga ctagtaaagg agaataaaaa tgatccgcaa  116340
tgtttccctt gcccgttcga aaggctttaa gctggtggat gttaacacgt tcgagcgtga  116400
agattgtaaa atcgaatatg tagcacgtaa taagaatgcc tttcgtgtta cagaaaagaa  116460
atttgacaag cgcggcaacg tgatcgctga aacggttaaa cactttgcca ccttttacgc  116520
```

```
tgcgtttcgt ggggtgttat aaaatggtta tttatgaggg caaccgcttt gttgctaatt  116580
gccgccctgc attgctagca aattacttaa atcagctttc accagcttat aagggcgtta  116640
ttaatattta tgaaggcaag gcgcattata aaatcaatgc ggtcgttgcc cgtgaactag  116700
cgtttcaatt tttgaccttt gcatcttgtg acgttcaggt catgggtgaa gcgttaattg  116760
cagaaaatga agatgatttt attaatattt ttcgcaagat atgcaccgag cgcctgataa  116820
tgaaaggcgc ttatattcaa tccactgcgg atagtattga aacagcgttt cgaaaggtgg  116880
cgcaatgagc aataaaattg ttgtaaccaa aatcagtaca atggttgatg ttttttacgt  116940
gcccgatacg ccggaaaacc ggcaagcggt cgagcgtggc gagtatgata aagtgattta  117000
tgatcacgat ggttattatc agcatttggt cgattcctat ggggaagagg aaaagatcac  117060
gcatcaatta ccggaggatg gtttatgaaa cgatggttta atcactggta taagcggttt  117120
ttagtacgcc gtcgcaaatc tagacatcaa gatgagtggc gggagtgggc aaagcgtaac  117180
ggttgccccgc tactctgaga acgacgggga ttagctcccc gtttttccat gcctccagtt  117240
aaataccccc ttgttttagt atccccacca aaattaaacg cgttagaatg cgatctagga  117300
cgttttagcg gtatattaga attattcact acataggaat actgtatatt tatacagtag  117360
gataagctgt ggataagtct gttaataacg cctcaaaatg gctaggattc tgtcaagtca  117420
aatcgtgctg ttaataagtc tgtggataac ttaaataata gtgtttctca cttccattct  117480
taaatgcaaa tcattatcat tcgcatttca ctttctaaat gagaatcatt tcacttcttg  117540
aatagttctc atttcacttt ttaaatgcga attattatca ttctcatttc gctttttaaa  117600
tgattcttat tatcattcgc attcaggcgc gcagggcaat tgccctgcgc ttttgtgcaa  117660
atccgacatt gctccacggg tgttacgtgc gggcgtgtat gtgcgaatcc gacaattttt  117720
ggtagtgtgc aaatccgacc cgaaaaattt ttatagtgtg caaatccgac aatgaatttt  117780
cccaaaaact ccagcaatcc gatgctgcgc atcaatcctg tggaattagc tagaatatgt  117840
gcaaatccga catgggttta tttgtgcgaa tccgacaaga tttttgtgac tttgattgga  117900
gggtgtgtga ttgtatgggt ttgaggagaa gatgagagag cgagaaaaat ttgagggaac  117960
tgtgagaggg gcgcaggatt ggtgcggagc acctgatttg cggggatttt ggggaagagt  118020
tgagataatt tgggaagatt tgggatagt gcagataaag taaaatttta ttagcaaaac  118080
gaggcaaaat agcttgacaa gtgaaaattt ctgtggctc                        118119

SEQ ID NO: 2           moltype = DNA  length = 167170
FEATURE                Location/Qualifiers
source                 1..167170
                       mol_type = genomic DNA
                       note = Bacteriophage
                       organism = unidentified
SEQUENCE: 2
atgaccaaag atatgacgtt agaagaggca aaggctaaag caaatgaagc tttggatttg  60
cttcttaaaa ttggcagtaa aatgatggaa gaaaatgaga aatatatcca ggaaaacaaa  120
attcctgatg gtccattagt aggcaaaagg aaatcacatg attgaagtag caaaattata  180
ttcaatagaa tttatgtcca aagaaggtaa atcagtaaat acacttgata aaaagtgctc  240
attaattatt cctttagcag aaaatccgga tattttaatt aaagatataa aagaaagaaa  300
atatccagaa aatgttattc taattataaa gcatactgaa gatattttgc agaatactga  360
ttcaccgttt tcttcttctg aagctttaac tattaaaggc tataaaagag ctcatgaata  420
tggtcttttt gacatgtttg aagacgataa agttaaatta gcgagtcaac cttctaaaag  480
taaaacattc attattgaag atattaaaga tataaatgca tttgttaaga tggtctgggc  540
tcattttgat gttggactac gctggagaat gtccgaagaa gaaagaaaga ttattgaagc  600
taatcgtcaa tttggttttt atcgctagga attagtatgg atttatttga gatgttagaa  660
gataatcatt ctatgaatat ccagaatgat tctagtgatt ataagaaaga gtaccgtata  720
gtattacaga attatggaat tgaagcccca gatgctcttc tagaagaact agcttcatac  780
catcttgacc ctccgccttg ggctccctgg gcaaaataat tcaaaaagtt gtttactttc  840
ctttctaacg atgatatgat agcttctgaa gtatacggag gctatcatga ttattaatcc  900
tgcagatgtt gaacagttat ctataaaagc tgaaagcgtt gattttcaat atgatatgta  960
taaaaaggtc tgtgaaaaat ttactgattt tgagcagtct gttctttggc aatgtatgga  1020
agcaaaaaag aatgaagctc ttcacagaca gttgaataaa atcattaaaa agcatttaac  1080
taaatcgcct tatcaattat atcgtggtat atcaaaatcg acaaaagaac ttattaaaga  1140
tttgcaagtt ggagaagtgt tttcaacgaa cagggtagat tcatttacta ctagtttgca  1200
tacagcgtgt tctttttctt atgctgaata tttcactgaa atagtacttc gcttaaaaac  1260
tgataaagct tttaattatt ctgaccatat cagcgatatt atactttctt ctcctaatac  1320
tgagtttaag tacacgtatg aagatactga tgggttagat tcagaaagaa ctgataactt  1380
aatgatgatt gtacatgaac aagaatggat gattccaatt ggaaagtata gaataacttc  1440
tatttcaaaa gaaaaattac acgattcatt tggaacattt aaagtttatg atattgaggt  1500
agttgaatga aatactcagt aatgcaacta aaagatttta aaataaaatc aatggatgca  1560
tcggtgcgtg cttctattcg tgaagaatta ctttctgaag ggtttaattt atctgaaatt  1620
gaacttttaa ttcattgtat taccaacaaa ccagatgacc atacttggtt aaatgaaata  1680
atcaaatctc gtttggaacc aaacgataaa cctctttgga gaggtgttcc agtcgagact  1740
aagcaagtgt taaatcaagg aattgatatt attacatttg ataaagtagt atcagcttca  1800
tatgataaaa atatagctct acattttgct tccggtttag agtataacac acaggttatt  1860
tttgaattca aagctcctat ggtattcaat ttccaggagt atgctataaa agctctacgc  1920
tgtaaagaat acaatccaaa ctttaagttt ccggatagcc atcgttatcg taatatggaa  1980
ttagtttcag atgaacaaga agtaatgata ccagctggaa gtgtatttag aattgcagat  2040
agatatgagt ataaaaagta ttcaacatac actatctata ctcttgattt tgaaggattt  2100
aatctataat ggaaggactt agattcatta taccacgaaa gttttaaagc attttacata  2160
aagttgttta caagctgaag taaaaatgat atagtataag taagttaacc gtccgtgaga  2220
aaaatatgaa actgtctaat aaccaaattc gtaaaattaa acgtcgttta gagcatactc  2280
aggcatctgc aaaaagacgt tctaaagatt ttaacttaga cttcaattac attaagaaca  2340
ttttagatca aaaagtttgt gcctattcag gagaaccttt tgataatcgt attgaaggag  2400
agaaattatc attagaacgt tttgataata acattggata cattaaaggg aatgttattg  2460
cagtaaagaa aaagtataat acatttcgtt ctgattatac tttagaagag ttgattgaaa  2520
agcgtgattt atttgctttg cgaattggtc gttcatctgc gaaaaaagtt cataaactaa  2580
atttagatga aaagaaatgg gctaaaatca aaaagactta taatcaaatt aaagctatac  2640
```

-continued

```
agaaaaaacg tgaaaatcga attgaacaca tttctcagct ttctaaatca aaacagacct  2700
ctgatattaa gctaagaatt atagcactta aagctcgtat tgatggttct cgcatagcag  2760
aaggcgctga agttgttaaa ttgaacgttc ttcttaaagg ctcggattgg aaaattgtga  2820
aaaagttgtc agaagcagaa atgcaatatg atatgtgtga taaaattatt caaggtgtag  2880
agcggtatca aaacttgtct tttattgata aacttaaact gaaaagagga tacccgctaa  2940
attgttcaat ttttaaactt atccgaggat aatatggttt atgtatatgc gatagtttac  3000
cgagacaaag acggatttac ggcgccagtt ccacttgatg aacatcgtcc tgctgtgttt  3060
tttgaaagag agattgctga tagagttttt actactctca aagaccaata taaactagct  3120
ttaggtatgg gaattccaag actagttgag actccacgca agttttggtt taataaaata  3180
gaagttaaac atgttaagcc tgatgtagat acacaaagat tatatcaacg aattctagat  3240
actgggcgta ttgttagtat tccaattgca gggactttac gatgacattt gatgatttga  3300
ccgaaggcca gaaaaatgcc tttaacatcg ttatgagggc tattaaagaa aagaaacatc  3360
atgtaactat taatggacct gctggtactg gtaagactac tcttactaag ttcatcattg  3420
aagctttaat atctacgggt gaaactggta ttattttagc agctcctact catgcagcta  3480
aaaagattct ttcaaaactg tcggggaaag aagcgagtac tattcacagt attcttaaaa  3540
ttaacccagt tacgtatgaa gaaaacgttc tttttgaaca gaaggaagta ccagatttag  3600
ctaaatgcag ggtattaatc tgcgacgaag tgtcaatgta tgatagaaag ctatttaaaa  3660
ttctgctttc aactattcca ccctggtgta ctataattgg aataggtgat aataagcaaa  3720
ttagacctgt tgacccagga gaaaatactg cttatatcag tccattcttt acgcacaaag  3780
atttttatca gtgtgaactc actgaagtta agcgcagtaa tgctcctatt attgatgtag  3840
ctactgatgt tcgcaacggt aagtggattt atgataaagt tgttgacggg catggagtac  3900
gtggatttac tggtgatacc gctttacgcg attttatggt aaattatttt tcaatcgtca  3960
aatctctaga tgatttgttt gaaaatcgcg taatggcatt tacgaataaa tctgttgaca  4020
agttaaatag cattattcgt aaaaagattt ttgaaactga taaagatttt attgtcggtg  4080
aaattattgt aatgcaggaa ccattaatta aaacatataa aattgatgga aagcctgtgt  4140
cagaaattat ttttaataac ggacaattag ttcgtattat agaagcagag tatacatcaa  4200
cgtttgttaa agctcgtggt gttcctggag aatacttaat tcgtcattgg gatttaacag  4260
tagaaactta cggcgatgat gaatattatc gtgaaaagat taaaataatt tcatctgatg  4320
aagagctata taagtttaac ctgtttttag gtaaaacggc agaaacttat aaaaattgga  4380
ataaaggcgg aaaagctccg tggagtgatt tttgggatgc taaatcacag tttagtaaag  4440
tgaaagcgct tcctgcatca acattccata aagctcaggg tatgtctgta gaccgtgctt  4500
tcatttatac gccttgtatt cattatgcag atgctgaact agctcaacaa cttctttatg  4560
ttggtgtcac ccgcggtcgt tatgatgtgt tttatgtgtg aggatatatg attaacatca  4620
attcaaaata tttaaatcgt ctaatagatg gtataaggaa gcatactaat aagcaagata  4680
atctcgatgt tatggtaaca ggagctgagc tccttcataa gctttatctt ataagtgata  4740
ctatattagc aattaaacga attgaaaaac aatcatatca cagtaataca gatacggtaa  4800
ttacactaga tgaaagtgtc tgtaaattac taattaaatt tgaggaagct attcgtggaa  4860
ataactaaag atcagtttta tcttcttcag gataaagtta gcgaaattta tgaaattgct  4920
catggtaaaa atcgtgaaac tgtaaaaatt gaatctagta agttgatgct tcaattagaa  4980
gaaattgaac gagatttaat tgcgttagaa ttcttttgtg gcgaagtgaa aactgttaca  5040
atcagtgatt atgttttagg tgaaattagc catctttata aggcggttat taatgattga  5100
attaagtttg catcagttta aatctcttat gacaaatgtt aaagctgtca ttgaagaaaa  5160
tccgggtcct gaaaatatta ctattcgcga aaaagcttca aagatagtat acagtcttga  5220
agagatacaa aaagacattg aatctattgc aaaatttatt gatgagccta ttaataaagt  5280
ttatattcaa gactatactg taggtcaaat tcgcgattta gcaaggaaaa tttaatgttt  5340
gattttatta tagattttga aacaatggga agcggcgaaa aggcagctgt tattgattta  5400
gctgtaattg cttttgaccc taatccagaa gtcgttgaaa cattcgatga attagtttca  5460
cgtggcatta aaatcaaatt tgatttaaaa agccaaaaag gacatcgtct tttactaaa   5520
agcactatcg aatggtggaa gaatcaatcc cctgaagctc gaaaaaatat tgcaccgtca  5580
gatgaagatg taagcactat tgatggtatt gcaaaattca atgattacat caatgcgcat  5640
aatatcgatc cttggaaatc tcagggttgg tgccgtggaa tgtcgtttga ttttccaatt  5700
ttagtcgatc tcattcgtga tattcaacgt cttaatggcg tttccgagaa tgagcttgat  5760
acatttaagt tagaaccgtg taaattctgg aatcagcgtg atattcgtac cagaattgaa  5820
gcacttctac ttgttcgtga tatgaccact tgtcctcttc caaagggaac tttagatgga  5880
ttcgttgcac atgattctat tcatgactgt gcgaaagaca tcctgatgat gaagtatgct  5940
ttgcggtatg ctatgggtct tgaagacgct ccatcagagg aagaatgcga tcctctatct  6000
cttccaacaa aacgataaaa agttgtttac ttcctcggtt agttgtggta ttataacacc  6060
atagctactg aggataataa aatgaaaatt tatcgtgttg aatcatcgtt tagtattctt  6120
gattatgaag atgctataac aatacgtcga aatctttgtg ttcaaataac gccgtacagg  6180
agtataatag attcatggag cgaagagtgg ctattacacg taggttatga cagacctaat  6240
tttatgcatc atagcgataa taataaaaga attcctttac cacacgaaga taaactatta  6300
gttaaaaatg ctaatatcgt aattaatact aagttcaaga aagattatgt tggagtagaa  6360
tatcatattc ccggatggtt tatagctctt tatcattttg cttttgctag cgaatatgat  6420
atgatgagat ggttcacacg agaagagcgt gaagaattat cttcgaaagg attttatctt  6480
gctgtatacg aagtaccaga tgaccaagtt attattggtg ggcatcaagt aatgttccgt  6540
aaatcccatg ctgaacttgt agattttatt gaaatgagat aattatgaaa tttaattata  6600
atcctgaata catacccaaat ccggtagcta aactgattga ttttgatgtt gtaagcactt  6660
atgtatgccc tgttaaacca ctggaaatta aggaacctac tatgactacc gctattgaaa  6720
tcggcaaaac ctacaaacta gttgaaactg aaattaaaac aactgaacta aatttgggtt  6780
ataaagcatt gactagtgtt tttggtgaag gtgagtttgt ggttaaaagc ttttcaaaaa  6840
gtaactggta tgataaaaat aaagcttacg tgattcgagc acatcgctta gataatgatg  6900
aagtaattaa aactatagtc tttgaagcag agttcatcct ctttcaagaa tgcgatccta  6960
ctgacctttt aactcgtgcg gtagctatca agactccatt tatttcggtc tgtggttggg  7020
taacagacca atggattgaa gatggtgttg aacttctgaa cgttgttcat gcaggtgatt  7080
ttagcgtagt acctcgtagt gcagtggtag ctattttgaa ttaatagttt acaaactctt  7140
gggaccagag tataatggtc ctgtggagta taaaatcttt ttaacaagtg agagataact  7200
atgattatta atattggtga aattgctcgt gtatctgata aatcccgttc taaagcagca  7260
ggaaaattgg tcgaaattgt aagcattcag cttaaacacg gcgttaaaga tgaagattct  7320
gaagtaaaag tgcgtatcat tcctaaagat ggaaagtcta aacctcagtt tggctatgtt  7380
```

-continued

```
cgtgcgaaat ttcttgaatc tgcgtttttg aaagctgttc ctgctaaagg aattgaaacg  7440
attgatactt cgcatgtagg tgtatacttt aagtggaaac tcggtcaggc tattaagttc  7500
gttgctcctt atgaattcga atttactgaa gatgaggaag gggttgttca aaaacaccgt  7560
actcgtgcta tgtgcgcata cattaccgat cagtgggtag aagacggtgt taagctgtac  7620
aacgcggtat ttttaggaac atacaaagtc attcctgaaa gctggattaa acactatagc  7680
aaagctcgct gtgcataaag tttaaatttt ttcataaaac tatatacatc agtagttgat  7740
tatggtacta tatcaatatc aactactgat acagaaaata acttggagaa taaaatggaa  7800
aacttaatta tcatcgagca atctttcaac gattatggta tggcttacgg ttatcgtgca  7860
ataatggaag attctcgtgg atgtgttatc gatattgctg aatgtaaaga tttactgcag  7920
cttttgaaga ttgttcgcaa aaattgggat tgtgaaaaca ttaaagctcg tgttgtaacg  7980
gaagaagaaa ctgtttttca tgatgtaaaa ttcgctaaag gtgctgctac tcttctgaaa  8040
cgcatcgctc cactgttcaa ttaatgagga aattgtaatg aaacgtaaaa ttgttcagaa  8100
ttgcactaat gacgaatttg aagatgtatt atttgatcca aatcttgtag tagttcaaaa  8160
ggaacatact aataagttta ctcacttgac ttcggtttat gtgtacgaaa aagttggtga  8220
taaacaacca atttatggtg tgtttcgcga aattactgaa gatggtacaa cttattggaa  8280
ggaaacttat taatggctat taaatttgaa gttaataaat ggtatcaatt taaaaataaa  8340
caagctcaag aagattttat caaggaccat actgaaaacg gaatttatgc acgacgtctt  8400
ggtatggaac cttttagagt tacagatatt gactatcttg gtcgtcctac taaacttgtg  8460
acatctagtg gaaaattggc gttatcttct ggtaaagata ttttggatga agattttatc  8520
tggctttcaa cgagtgaagc tgtgttcttt gatgaagtgg aaaatccata ccaggcagct  8580
gaagagcaag agcaggaaga gaaagagcaa gaacaaatag aagatttcac agaattcccg  8640
gtcatgaaag ttactattga aaataatgaa caggcatggt ctttgtatca gatgttgaaa  8700
gcacacttta aggaatatt atgccaatgt atgattataa atgccaatcc gaagattgcg  8760
ggcatgaata tgaaaaaatt aaaaagattt ctgaacgaga aaatgatgtt tgccctaaat  8820
gtcatcgttt gtctactcgt cggccttctg ctcctaagca tgtgaatggc ggtttttacg  8880
atttacttaa agggtgatta tgtttaaaat cggtaagaaa tatcgtgttc gcgaaggtga  8940
agaaaagaaa tatctacttt ctgctagtaa taggaatggt tctattaatg ccgtaatatc  9000
tacaagcgaa tttatcgttg aagatatgaa aggtcataat gttacaatga ttagtacagc  9060
aactagcaga aatgctggaa aaattcttca cagtctgcgg agtgaagttc taatttatga  9120
tgaagaattt gacttcttcg aagaagttcc tgaagatttt gattttgaat gcactatcac  9180
tatgaaatct ggcgaccctc tttcttttac agttaaagat gaaagaagcc gtttgagaat  9240
tattagtctc cttcaagcca ttaaatttaa gtgaaaacta tgaaatatat taatcgttct  9300
attgcagcat tagtattagc agtatcttta gtaggatgta ctgatgctga taatgcaact  9360
aaaattttat catcgagtgg ttttacgaat attgaaatca ctggatataa ttggttcggt  9420
tgctctgaaa atgatttcca acatactgga tttcgtgcta ttggacctac tgggcagaaa  9480
gtagaaggaa cagtatgttc tgggttgttc tttaaggatt caactattcg ttttaaataa  9540
aaggccttcg ggcctttagc tttatgattg ccggagtata atattcccga aaccaaacga  9600
ggataagtga tgattaagaa tgaaattaaa attctgagcg atattgaaca tatcaaaaag  9660
cgtagcggca tgtatattgg ctcttctgct aatgaaatgc atgagcgctt tctgtttggt  9720
aaatgggaaa gtgttcagta tgtacctggt cttgttaagc ttattgatga aattatcgat  9780
aactcagtag atgaaggtat tcgtactaag tttaaattcg cgaataaaat taatgttacc  9840
attaaaaata atcaggtaac agttgaagat aacggtcgcg gtattccaca agcgatggtt  9900
aaaacaccta ccggtgaaga aattcctggt ccagttgctg cttggactat tccaaaagcg  9960
ggtggtaact tggtgatga taaagaacgt gtcaccggtg gtatgaatgg tgttggttct  10020
agtttgacaa acattttttc tgtgatgttt gtcggtgaaa ctggcgatgg tcaaaataat  10080
attgtagttc gttgttcaaa tggcatggaa aataaatcat gggaagatat tcctggaaaa  10140
tggaaaggaa ctcgtgttac tttcattcct gattttatgt catttgaaac taatgagctg  10200
tcccaagttt atcttgacat tacactagat cgtctccaga cacttgctgt tgtttatcct  10260
gatattcaat ttaccttaa tggtaaaaag gttcagggca attttaagaa atatgcacga  10320
cagtatgatg aacatgctat cgttcaagaa caagaaaatt gttctattgc ggttggtcgt  10380
tcacctgatg gttttcgcca attaacttac gtgaataaca ttcacactaa gaatggtggc  10440
catcacattg actgtgtcat ggatgatatt tgtgaagacc ttattccaca aatcaaacgt  10500
aaattcaaaa ttgatgtaac taaagcacgc gttaaagaat gtttgactat cgttatgttt  10560
gttcgtgata tgaaaaacat gcgatttgat tctcaaacta aagagcgttt gacttctcca  10620
tttggcgaaa ttcgtagtca tattcagctt gatgctaaaa agatttcacg cgctattcta  10680
aataatgaag caattctaat gccgattatt gaagctgcgt tggctcgtaa attggcggca  10740
gaaaaagcag cagaaactaa agcagctaaa aaggcttcta aagctaaggt tcataaacat  10800
atcaaagcga atctttgtgg taaagatgct gacactactc ttttcttgac tgagggtgat  10860
tcggctatcg gatatcttat tgatgttcgt gataaagaac ttcatggtgg ttatccattg  10920
cgcggtaaag ttctcaacag ttggggtatg tcatatgctg atatgcttaa aaacaaagaa  10980
ctatttgata tttgcgcaat cactggatta gttcttggtg aaaaagctga aaacttgaat  11040
tatcataata ttgctattat gactgatgct gaccatgatg gtctaggaag catttatcct  11100
tctctgctcg gatttttttag taattggcca gaattgtttg agcaaggacg aattcgcttt  11160
gtcaaaactc ctgtaatcat cgctcaggtc ggtaaaaaac aagaatggtt ttatacagtc  11220
gctgaatatg agagtgctaa agatgctcta cctaaacata gcatccgtta tattaaggga  11280
cttggctctt tggaaaaatc tgaatatcgt gagatgattc aaaatccagt atatgatgtt  11340
gttaaacttc ctgagaattg gaaagagctt tttgaaatgc tcatgggaga taatgctgat  11400
cttcgtaaag aatggatgag ccagtagttt actttaccac aaggatgtgg tataattaat  11460
tgggcaaatg aggatattga aatgaaatca tatagagtaa atttagaact ttttgataaa  11520
gcagttcatc gagaatatag aatcattcaa cgctttttcg atatgggaga agccgaagaa  11580
tttaaaaacc gctttaaaga tattagagat aaaattcaat ccgacaccgc aactaaagac  11640
gaactactag aagttgctga agttattaag cgtaatatga attaatgagg aaattatgat  11700
tatcaccact gaaaaagaaa caattcttgg taatggttct aaatcaaaag catttagcat  11760
cacagcatct cctaaagtat ttaaaattct gtcgtctgat ttgtatacaa acaagattcg  11820
cgcagtagtc cgtgaattga ttaccaacat gattgatgcc catgctctca atggaaatcc  11880
tgaaaaattt atcattcaag ttcctggacg tttagatcca cgatttgttt gccgagattt  11940
tggtccgggt atgagtgatt ttgatattca gggtgatgat aattctcctg gtttgtataa  12000
ttcatacttc agttcatcta aggctgaatc taacgatttc attggcggat ttggtttagg  12060
ttctaaatct ccgtttagtt atactgatac gtttagtatt acttcgtatc ataaaggtga  12120
```

```
aattcgtggt tatgtagctt acatggatgg tgatggccca cagattaaac ctacattcgt  12180
aaaagaaatg ggtccagatg ataaaactgg tattgaaatc gtagttccag ttgaagaaaa  12240
agactttaga aactttgctt atgaagtttc ttatatcatg cgaccgttca aagatttggc  12300
tattattaat ggtcttgacc gcgaaattga ttattttccg gattttgatg attattacgg  12360
tgtaaatcca gaaagatact ggcctgatcg tggtggatta tatgctatct atggcggtat  12420
tgtttatcct atcgatggtg ttattagaga ccgtaactgg ctaagcattc gcaatgaagt  12480
gaattacatt aagtttccaa tgggttcact tgatattgct ccatcacgtg aagctctttc  12540
attggatgat cgtactcgta aaaatattat tgaacgagtt aaagagctta gtgagaaagc  12600
atttaatgaa gatgtaaaac gatttaaaga atctacatct ccccgtcaca catatcgtga  12660
attgatgaag atggggtatt ctgctcgaga ttatatgatt agtaattcag tcaaattcac  12720
gactaaaaat ctgtcatata aaaagatgca gagcatgttt gaacctgaca gtaagttatg  12780
taatgcaggc gtggtgtatg aagtaaatct tgaccctcga ctgaaacgca ttaagcaaag  12840
tcatgaaact tcagccgttg catcaagtta tcgtctgttt ggtattaata caacaaaaat  12900
taatatcgtt attgataata ttaaaaatcg tgttaatatt gtccgtggat tagcacatgc  12960
gctagatgat agtgaattta ataacacttt gaatattcat cacaatgagc gtcttctgtt  13020
tattaatccg gaagtagaat cgcagattga tttactacct gatattatgg caatgtttga  13080
aagtgatgaa gttaacattc attatctgtc agaaattgaa actttagtta aaagctatat  13140
tccaaaggta gttaaaagta aagctcctcg tcctaaagct gctacagcat ttaaatttga  13200
aattaaagat gggcgatggg aaaaagagga actatttaca cttacgtcag aagcagatga  13260
aattactggt tatgtagcgt atatgcatcg ttctgatatt ttctctatgg atggtactac  13320
atcactttgt catccatcta tgaatatttt gattcgtatg gctaatctta ttggcattaa  13380
tgaattttat gttattcgtc cgcttttaca gaaaaaggta aaagaactcg gtcagtgcca  13440
atgtattttt gaagctttac gtgatttata tgtagatgct tttgatgatg tagattatga  13500
taagtatgta ggttattcaa gttcagctca acgatatatt gataaaatta tcaagtatcc  13560
tgaactagat tttatgatga agtacttcag tacagatgaa gtttctgaag aatatacacg  13620
acttggtaat atggttagtt cattacgcgg tgtgtatttc aatggtggaa aagataccat  13680
cggtcatgat atctggacag taactaatct ctttgatgaa ttatcacgta atgcttcaaa  13740
aaatagtgat aaaatggttg ctgagtttac caagaaattc cgtattgttt ccgacttcat  13800
cggttatcgc aactctttaa gtgatgatga agtttcccaa atcgctaaaa ctatgaaggc  13860
ccttgcggcc taataaggaa aattatgtac aatattaaat gcctgaccaa aaacgaacaa  13920
gctgaaattg ttaaattgta ttcaagcggt aattacaccc aacaggaatt ggctgattgg  13980
caaggtgtat cggttgacac aattcgtcgt gttttgaaaa atgctgaaga agctaaacgc  14040
tctaaagtta ctattagcgg tgatattaca attaaagtta atagcgatgc agttattgct  14100
ccagttgcta aatctgacat tatttggaat gcatctaaaa aattcatttc aattactgtt  14160
gatggtgtaa cttataacgc aactcctaat actcattcaa acttccagga aattcttaat  14220
ctgcttgtag cagataagtt ggaagaagcg gcacaaaaaa ttaatgttcg tcgcgctgtt  14280
gaaaaatata tttccggcga tgttcgaatt gaaggcggaa gcttgttcta tcaaaatatc  14340
gaattacggt ctggtttagt tgatcgtatt ctcgattcga tggaaaaagg tgaaaacttt  14400
gaattttatt ttccgttctt ggaaaatctg ctggaaaacc caagccagaa agcggtatct  14460
cgactctttg atttcttggt agcaaacgat attgaaatta cagaagatgg ttacttctat  14520
gcttggaaag tagttcgtga caactacttt gactgtcact caaacacctt tgataacagt  14580
cctggtaaag tagttaaaat gccgcgtact cgtgtgaatg acgatgatac acaaacttgt  14640
tctcgtggtc tgcatgtgtg ttctaaatct tatattcgtc actttggcag ttcaaccagc  14700
cgagttgtaa aagttaaagt acatccacgt gatgtagtat caattccgat tgattacaac  14760
gatgctaaaa tgcgtacctg ccaatacgaa gtagttgaag acgttactga acaatttaaa  14820
taagggcttc ggcccttatc atattaagga aaattatgtt aggttatcaa gcacgagtaa  14880
aagaagaata cgatcaatta atgctcaaaa ttaatgcact gagcaaattt ttagaaagca  14940
caaagtttct aacggttagt gcagttgagc aagaactgct gctttcacag ttcatctcaa  15000
tgaaatctta tgctgagtgt ctagagaaaa gaattgcaca attcaaataa aataagggct  15060
tcggcccttt tgttttaagg tgaattatga tttattgtat gaatatcggt gattccgaca  15120
taaaagaaat ttctttacat ggtaatcatc acgctaatat tgtgtactgt aataaatttg  15180
agtttggaca cgaaaaactt gggtttcttt actgtaatga tgttatagtc atggataaaa  15240
aggagctcga tgagcttgac ctcgagtctt tagatgaaaa tgaccgaatt tattatggca  15300
ctcttaaagt atataacgcc tatctcagcg gtaaaaagga aagtctaaat gcagaaaacg  15360
aatccgggtt tacagagact atttcagatt ccgacattta ccctatcgaa cagtgacttg  15420
actagtgaaa tgaaggtcaa aattgctgat acagcaagat actctttaaa acaaaacccg  15480
aaccaggata aagcagaagt tattgaaaga tgccgtatcg cggtgtacgc agagtttttt  15540
gtggcagatt ggctaagcgg atatgtcaat aaaggccaag aaaatgtcga tgatccgtac  15600
acgtatgcat gggatgtttt agcgcatcca aaatattgcg ggcttcgtgt agaagtcaaa  15660
acacatcaaa ctgactcgcg ttggatttcg gtaacaacgg gatgcagcgg agagtatcca  15720
tatggttctg gaataaattt agggcccatt ctaaatcatc aagtcgctga ctgtataatt  15780
atattcaaca ctaaagaaat tcatccaggt gtcatccagt acactccgaa gttcatcggt  15840
gacagagaag accttcgtaa ggttgtaaga aaaagcaact acaacggatg gtatctttcc  15900
atttaaaaat tttcacaaaa cggtttacat accacaagga ctgtggtaat atacaactat  15960
caactgatac ggatttggag aataaaatgt ttactacagc tgaattaaaa cgagcaaaag  16020
ctaagaaagg gcaaggaaaa tataaagctg aattagttaa agaacttcag tttgctgagg  16080
ctgaattgaa ttcaatgatt attcaaaatg ctccagaaac tgaaattgct cttaaacgta  16140
ttgcgaataa gtgtcttcgt gatgcaatcg tcgatctttt agcggattat tgagtaaaat  16200
gaaaatcgtt gagattgaac tatgagttca ttatggtggt gttttgtttg gttaattagt  16260
attccattaa tttgtttaac atttactttt gtgatgaggt tattatgaaa atttttaatt  16320
ctgtacttat tgcttgcgcg tggtgggttg cacaggtttc agcggtagta gttggtattc  16380
acatttatta cgaatatttt taaaaaagtt gtttacaaga ctgttcctct gtggtactat  16440
acaactatca actacggagg aacacaaaat gaaaaagatt gttaaagcta tatggaatgt  16500
agttataata ctaatagttt tgagtatatt cccaatcgtt ttaatgattg atatgttaaa  16560
cgcttatttt ggatttatgt gaggaaaata tgaagcgtaa acgcggtgct tttacattta  16620
ttgaatggtt tttcgataat atttttccgg ctttatttat ttttatgctg attttcgcct  16680
taggttcagt tgtagttgga atctatttga tggcagtagt cggaatggat atttatcaaa  16740
atggtttaaa atccgtagtt gaaacaattt ggaatggtgt aaaatgatga atttgttgag  16800
cggttggttt tatattctta tgttttacat tggtgcaaat tttccatatt ggatgggatg  16860
```

```
gtcaacaact gcatttggat tttatactcc ttgaggtgaa ttatgaaaag ttttaaagat  16920
gtaaaagttg gtgaaatttt ctgtttagat aacggtgatc agttaattcg tatttcacct  16980
cttaagagca ctagcgagaa accgacagtt aacgctactt tagcaaataa cagtaatgaa  17040
cgtttctgta ttgaaaatga tactgaaact tataccgtag aagagttttg ggaattgagc  17100
gtcgactgcg acgattaatt taatggccgt gtgtattcat gcggccttgg agtagaaaat  17160
aatttagagg aaattaatat gaaatatatg actgttactg atctgaatga tgcaggtgct  17220
actgttattg gtacaatcaa gggcggtgag tggtttttgg gaactccgca taaagatatt  17280
ttatctaaac ctggatttta ctttttagta agtaaattag atggtcgtcc atttagtaat  17340
ccatgtgtgt cagcacgatt ttatgtaggt aatcagcgtt ctaagcaagg attcagtgca  17400
gttctaagtc atattcgtca acgtcggtct cagcttgcac gtactattgc aaataacaat  17460
gttccataca cagtgtttta tctgcctgct tctaagatga aacctctgac gacgggattt  17520
ggaaaaggac agttagcttt agcgtttact cgtaatcatc attctgagca tcaaacactc  17580
gaagaaatga accgtatgtt ggctgataac tttaaattcg ttttgcaggc atattaatga  17640
gtaatttcca taacgaacat gtgatgcagt tctatcgtaa taattttaaa actaaaggcg  17700
tcttcggacg ccagtgagga aaatatgaaa tttgtttatg gtatagcctt tttctgctgg  17760
tcctttttat tcgccggaac agtaataact ggagaaactt cagtattttt acaagcaaca  17820
gctcaaggcg tattagcaat tttatcattg ttttggctat taaatgaaaa tgattaagaa  17880
aatcttgggc tattcattag cccttgctac tttattagta gcactatatt atggagtaat  17940
gttcggatta attcaagtcg tgcttttcat ttctgatgtt attatggcac tacattcact  18000
agtatggtaa atttatgcaa ctgaataatc gcgatttaaa aagtatcatt gataatgaag  18060
cattggctta tgctatgtac acggttgaaa atcgtgccat tccaaatatg attgacggat  18120
ttaagccagt tcaacgattt gttattgctc gagctcttga tttggcacga ggaaataaag  18180
ataagtttca caaactcgct tctattgcag gtggtgtagc ggaccttgga tatcatcatg  18240
gtgaaaactc tgcgcaagac gcaggtgctt tgatggctaa cacttggaat aataattttc  18300
ctctgttaga tggtcaagga aactttggtt ctcgtaccgt ccaaaaagca gcagcaagtc  18360
gttatatttt tgctcgtgta agtaaaaatt tctataacgt atataaagat actgaatatg  18420
ctccggtaca tcaagataaa gaacacattc cgcctgcttt ctatttgcct attattccta  18480
ctgttcttct taatggtgtt tccggtattg caactggtta tgcaacttac attcttcctc  18540
atagtgtttc ttctgttaag aaagctgtat tacaagctct tcaaggaaag aaagtaacta  18600
aaccgaaggt agaattccca gaatttcgtg gtgaagtcgt tgagattgat ggccaatatg  18660
aaattcgtgg aacatataag tttacttcac gaactcaaat gcatatcact gagattccgt  18720
ataagtatga tcgtgaaact tatgtgagta aaatcttaga cccacttgaa gataaaggct  18780
tcattacatg ggatgatgct tgtggtgagc atggttttgg attcaaagtt aaattccgta  18840
aagaatattc tttgagcgat aacgaagaag aacgccatgc aaaaattatg aaagacttcg  18900
ggttgattga gcgtcgttct cagaatatta cggttattaa tgagaaagga aaactacaag  18960
tttacgataa cgtagttgat ttaattaaag actttgttga agttcgtaaa acttatgtcc  19020
aaaaacgaat tgataacaaa atcaaagaaa ctgagtcagc ttttcgttta gcctttgcca  19080
aggcacattt cattaagaaa gtaatttcag gtgaaatcgt tgtgcagggt aaaactcgca  19140
aagaactgac cgaagaactt tcgaaaatcg atatgtattc ttcttatgtt gataaactag  19200
ttggaatgaa tatttttcat atgacttccg acgaagcaaa gaaacttgct gaagaagcta  19260
aagctaagaa agaagaaaac gaatattgga aaactactaa tgtagttacc gaatacacta  19320
aagatttaga ggaaatcaaa tgagtccatt catagtattt acaagcgctg cattagtatc  19380
cggtagcatt ttactggcgg gtttaggtgt tgttccagcc gtagcaggag gtcttcttgc  19440
gttcggcatt caacgtgtta tcatgccagt tatcacagtc atgcagtaat ttttagggag  19500
agccgaggct ctcccttttt tatttcaaaa attttttttca caaaacggtt tacaaccaaa  19560
gcatactgtg gtactataca actatcaact actgatacag aattacggag attagaaaat  19620
gtctaaagta atttacatca tcaaagcttc taacgatgtt ctgaatgaaa aaactgctgc  19680
gattttaatt actattgcta agaaagattt cattacagct gcagaagttc gtgaggtgca  19740
tccagattta ggtaacgcag tagttaatag taatattggg gtgttgatta aaaaaggcct  19800
ggtggagaaa tcaggtgatg gattaatcat tactggtgaa gctcaggata ttatttcaaa  19860
tgcagcaact ttatacgcac aggaaaatgc tccggaacta ctgaaaaaac gagcaactcg  19920
taaagctcgt gagattactt ctgatatgga agaagataaa gacctcatgt taaaactttt  19980
agatgaaaat ggatttgttc ttaaaaaggt cgaaacttat cgtagtaact atctcgctat  20040
tttagaaaaa cgcactcacg gaattcgtaa ttttgaaatt aacaacaatg gaaatatgcg  20100
aatttttgga tacaaaatga tggaacatca tattcagaaa tttactgata tcggaatgtc  20160
atgtaaaatc gctaaaaacg gtaatgtgta tcttgacatt aaacgctcgg aagaaaacat  20220
tgaagcagta atcactgtag catctgaact gtgaggaata aataatgaac aagttagaaa  20280
ttatcaatga acttcgtcgt tgtgcagaac ctactcaaga gggttgggat atttggtacc  20340
atggagctta tcttggaact attgtaaaga ttaagactgg taaatacatg attattcgtg  20400
aaagtaaaga tgctccagta ggtattcgca ataatttcat ggcagcgata agttccttta  20460
cagatgcagc ttacgaaatt taccttgccg attataaaga attccaggaa tctcaaccag  20520
ttattcgctc aattggtgtt aacaaagctc aacagaaaac tttgtggcaa cgtattaaag  20580
gatggtttaa atgaacccat ttatcaatcg tttaaaaatg ctgaatgttc ctttatctcg  20640
tgaaactcca gaaagtcttg ctgaaaaatt taaagcgcat ggttataaat gcacagaaga  20700
agatattcta aaagaagttc ctgaaatatg ttggcagact gcatattggg atgaaaacca  20760
aaagtatcaa cgacgaattg tctgcgcggc caaccgtttt aaattaaaag atggacgaac  20820
tcttattatt ccaggtgctc gtcattattc taaagatatg gccgaagttt tagatgtagt  20880
taaacctcaa ttagttactc aacaagtttg tgatgatgac caagggttta ttgaccaata  20940
tagtaattat tggacacgtg aagaagcaat gattattgca acttacgctg gacaagtacg  21000
tattgaacgg ggtggtagtg aaaaagaact ttactctgag gacctttact aatgaatatt  21060
aaaaagtttc aaatcgatgg aattatgaat caaattcagg cactggaata tgccaataaa  21120
atgatgtcaa ctaattgggg aatttatgcg aatgagccag catttaaatt ttgtgatatg  21180
gaatttacca aaaagcttgt aggaaaagat tatgtatgcc catttagttc tccggtaaat  21240
ggaatgctaa aacctgcttt acgcgatctt tatattgcga tgaacgaaga aatgataaaa  21300
gaattaaaac gtcaactgaa ggtgattcaa tttggccagg gaaattaatt caaaatctga  21360
ttattttaat tctctcaatg ataaagataa aaatctaata aggcatttta ttgttgagat  21420
gggatatact gatacacgtg atttaagaga acatatattt gaatgtggtg tagctaaaaa  21480
gttttcattc acatgcaaat gtttaagaga ggtaattcag cactatgaac aatttagtcg  21540
caaaacataa ttttaataaa gcttctgttc ataaggataa gaagaaagtg tttaaagaat  21600
```

```
ctaatcgcaa acagaaacat aaggggaagg tctatgatta ttgattctca gtctgtggtt  21660
caatacacaa tcaaaattga tattctagaa aagctatata agtttctacc aaatttatac  21720
cactcaattg ttaatgaatt agttgaagaa ctacatctcg agaataatga tttcttgatt  21780
ggaacttata aagacctctc aaaagcagga tatttttacg taattccagc tccaggaaaa  21840
agtattgatg atgtattaaa aactataatg atttatgtcc atgattatga aattgaagat  21900
tatttcgaat gagtcataat cttgaaaaag taatcgagca taatgtagct caggaacgtg  21960
agtcgttcaa ggaattcgta gaaaaaattt ttcaagaaaa taacacagac cagtttacaa  22020
atcaaacgtc tgatgatatt ataacaaagt caactaattg agtggtatag ttaatgaata  22080
aaaatattga tacagttcgt gaaattatta ctgttgcgtc tattttgatt aaattttcca  22140
gagaagatat tgttgaaaat cgtgctaatt ttattgcatt tctgaatgag attggagtaa  22200
cgcatgaagg tagaaaatta aatcagaatt cattccgtaa aattgtttct gaattaactc  22260
aagaagataa gaaaaccctc atcgacgaat tcaacgaggg ttttgagggt gtatatcgat  22320
atctagagat gtatacgaac aaataattat ttagcccttc ctaatattct ggccgcctga  22380
gaacatattg attcaaggcg gtcattactt atatgatcat ttctatacca gtacatggtt  22440
atcgttccag catagatatt atccaaatta aaatatggac aactgtacat gtagtttatt  22500
tcgggagtag gctttttagt tggtaaaaaa gcaaattttg agttggaata ataatgacgt  22560
ccatttaaat gaactgcata ttcatccata gttttatcaa caggatatcc tccaagtgat  22620
ttttcactta ttgttgaagg taattttcct tcatatgcta taatatcgac aaaatagttt  22680
aagtttttag ggcggaaaga atacaccgca ctaaagtctg cctcagatga tatgtgaact  22740
atctggagtt gttccagggc gacagattca aagcgtgcat ttctttcctt ttcaataatt  22800
tcactgtatg tttcatactt tgattgctta tagtactcaa agaaactatc tcccctatac  22860
caaacaatcg ccatcataaa caaaagaatt acgacagcta cccgggaagc aagaactttc  22920
ccggtagcgt tatctttgaa caagcgatct agaacaccaa atagaatatc agagggcgaa  22980
aatgatattc taggtgctgc catagaccct ccttttaagg atatttattc aaaaattata  23040
ctcttgaacc gtatacggct ccaacgtttt gccatgttgg agccgatcct gctacagcag  23100
caccaggatt tgtcggaggt gttgaataac cattacctgg attagcatat tgacctggtt  23160
gaccaacttc acctccaccg ccagcccaat attggccagt attaccacca gcaccaggtg  23220
ctgttaagct agcatttcca ccaggccatc gagcaccatt atttccgcct aaaccaaatg  23280
gacgaccacc gccgcctcca catacatatt ttcctgccca gttattggct tgcgaatatc  23340
caccgccacc gccaccgcct ccagcaatag ctccccccatt attaattcgt aggcgtccac  23400
ctatatcatt ttggatacat acaccaccgt cagacgctcc aatcgctcca gcagcccaac  23460
cattcccgcc gcgaccatac atcgttacgc cgtgtatatt caattgaaca tattcattcg  23520
gtgtatctcc gtacatgaag aataaaggaa cgtctctaga atatgatact aaatctccag  23580
tgatattaaa cactataggt gcactacctg cctcaaaaca tctatctcgg aaccattgac  23640
cattgaagtt atggtccgct ccaagtgtgt gaattacttc aacagatcga cctatcatat  23700
tactcatcca gaacggaatg cccattctta atcgttgggc cgcgccaccc atccaatttt  23760
gtcctgtatt aattactgca gacgatccta cccacggtcc tgctactgcc atataaacct  23820
ccaaggggcc gaagcccctc attttatttt aacaatgatt taactaattt tttaagctct  23880
tcaatctctg acttaagttc tgcaatttct gcagtatgct cattgattgc agctgtattt  23940
aaaccaatta caccgttata gttcaaacga agtaaagctt cgccatcagg gtcaccttca  24000
actaattcag gcaaaatagc ttgaacttct tgagctatca aaccggcgtt aggttcccat  24060
ttctgattgc cttcttcatc taggcctcgc ttctgcatat aagtgtaacc gttaattttt  24120
gaaagtgttt gtgaagcatt ttcaaattta acaaggtctt ttttaacacg aatatcagaa  24180
cggacataaa catcgcggac atatgtggaa taactgtcat tcgcctggac aagatggccg  24240
tgagaaataa ttgctttgcc aacttctgtc caaaaagctc catttgaatc ccaaaggcca  24300
ggatgagaat gataagatga agaccacgaa gcaatatgcg ctccatttgc aaccatattg  24360
attcggccgt caccaccatg aactaatcca gtatcattat caccaataac aagacacggg  24420
ccggtccata cagggtcacc accgccagct gataatcttg ctccagcttg aaccatatta  24480
ggagcataca gaactccatt gtggtgaaat tcatagatag cttgtgggtc agaaccattt  24540
tcctggttac caacacggat aatagcctga gcccattggt tagtagtgcg tcgcatacca  24600
aaatcaacac ccgatatgta tccttcatta gtaataccag attttccttt gataatcggg  24660
taataactat cattaccgac attgccaaaa tctacaaata ttggcgcttc ttgtcgccat  24720
tggtttcccc aatcaccagc ttggtgcgca acccattgtg taccgtttat atgaaggcgg  24780
tctctattaa aattaaatgt tccttgacct tgaggagaaa gcgatatttc gccgttattt  24840
gttatgtata caccgccttg tgtaatgtaa ctataaaaac ctagaccatt gtcgccgccg  24900
cctttgccta tataccagtt acctgtacca cctacatcac tacggatatg tgatgaagca  24960
ccttcgcccg cagttaaaat gagagcatca ttgcctgccg ataaagtcaa tttaccagtc  25020
atcgtgtcgc cttctttaga aacacgagta gctattgcat cgcgaatatt tgtggtttct  25080
cccgcagaag taaacgattt ccaaatatct gagaaaatat taccattacg agcaatagta  25140
gcttcaccgc cgccaacttg aacgttatcg gggaaattaa ctgtaccatc agcattaaat  25200
cttgatgtat ggccttgtga accatcttct ttcaaatgat gtaaaacaaa tgtaccagaa  25260
ttaatttcag tacctaaaga ccaaacggct ttaccgttta aaaacttctg tttaacaata  25320
ggataatatt tgcttacagc agcatcatcg atttcttgga aaataggagc agcttgtgaa  25380
tactgaatat cataaccacc ggcaccagcc ccatgaccag caaatttaat ataaccattt  25440
gcagcgaacg tattataact tgactgtaaa tctggaatag taactttacc ggaatttaaa  25500
gctacgctga gaggacgtaa aggcccaata tcaccggttt ctccttcgcc aaatgctgta  25560
ggaataatat gaagactttc ttctgagcgt ctaaaaataa ctccgtaatc attgttccaa  25620
atacgaagac cattaacagc atttgtagtg atttcgccaa tggtatgaac tgctcggtca  25680
acccaaatat cctttttcgc aataatattt tcattaattg tttgttgacc atttaacacg  25740
gcttcaaccg tattatcttt attacgttga atataatgca tccatccaat accatcagaa  25800
atttccatga catttttacg ggtgccttca cttggattag taaaagtatt tccccaaaca  25860
gctatataca tgttatcaac ggagctttga cccatggtat agcctttaaa cattaaagtt  25920
gaattattat ttctaccatc gatattaaca gaaccaccaa taacgtcaat attgcctgga  25980
gtaactaaca aaccgccatg agtattaata tttgtagtgc ccttgccgcg gaaataatga  26040
tgatagttac cgccttgata atatcctaaa agagtctgac catccccaaa cgcgttatta  26100
tcatggtatg tcactacagt agcaagagca taattttcag ttggaggagt agttaaatcg  26160
gttccgttag tagaatatcc agctataaat tttcttaggc tagttgtttc gcttggacta  26220
aataaaaacg tttttgtgcc attgttaaca ctgaaataat atccgtcttg atgccattta  26280
aatccagtat cattatctcc taaagcgata ctagacggtc ctaatattga gtaatcctta  26340
```

-continued

```
ggtccgggtg ttaaaccgat ggaaattgag tgacttgatt taattccgcc gctccaagta  26400
aatgaccaaa gataagcgtc taatccatct ccactatacc atgttattcc atcattatct  26460
ttaacttcat ggaaaatacc agaaccaact gcattacgca taacacgaag atgattaata  26520
gcagtagtgc tttcagataa tggaacatta tctgccatcg aatagatgtc ataatcatct  26580
ttaacttttt tattggtgat aactttattg gtataaatta ccggagttga tacagatttc  26640
cacccaaaaa cttctggtga agaaaacaaa ccatttccat taaaaacgaa agtgcttttct  26700
gaaccagctt tgtaatcttg aactctgatg ttaactacct gtgtagttaa accgtcatta  26760
gcaggagaaa aaataatacc gcgttcacgg tcagctgaat catgaaaacg aacgtgtgcc  26820
gttcctgaac tttttgtaat aagttctccg ccttcagtca taatctgccc agcagcaata  26880
atatcacgag ttactcgagc aataccggtt aaattaaaat taccagtctg ggtgaatgta  26940
ccgtttaaag tataatcgcc agtttggtta taattgcctt tatgaataac attcccgtca  27000
atactaccgc ctttagcaaa acctaaatca ataatatttc cctggtcatc tttagtaaaa  27060
agtacacggt cttttaagtt tatagccaat tcaccttcgg ctaatactga agcagctgga  27120
cgttgacctg ccgttttgct tcttttaaat tgtatttgtt ttaaagtagc cataagtcct  27180
cttaataata gccgaaatct tgaacagaat ccttaattac gatttggtca aatcgcggaa  27240
catgcgaggg ttgagatgca ggattctgtg aaaaaaggtt tggcgcagtt aaatttccta  27300
tcatagtgtc tccagagcgt aatactctag agtttgcatt tgttgtaaca atatttattg  27360
ctccatcaac ataatctttt ctcgtaaggt cataattatt tactggtgat aacgaagttg  27420
cgcgtatttg tgatgcttca attacaccct ttgagctaat atctccgttt cgtgtgttaa  27480
ttactacagt tctacctgct gccccttgtg atgatttaaa gccgatacca taccatgaaa  27540
caatatccat atttgtagta tcatatgtag cattatcacc aggaccggca aaaataccgt  27600
tgtcacctga cccagcacca ggaacagtca ttcctttatt aaaaattact ttatttaaat  27660
atgtaccacc attagcttta gaaacgaaat cgttatcagc agcttgtggt ttattatatt  27720
ctgaatatat tttaaatgat ttatagagta catcgtcacc ggctggattc aatggaaaat  27780
ttccttgatg ccaaatgaca gagcctccag ttgttgaacc tacttttaaa tcagccattg  27840
tatgcccctt tattttaata gtatttataa agaaaaaggg aacccgaagg ctccctcaat  27900
ttaaacttct ctaaattcct gtccaaacac tttaccagtt ttagacgatg cttgcgtagg  27960
aagtaccatt atatccggag gtgaagcaga ttcacagata taattaactc gaataccatt  28020
gacgccaaac tcagcaggtt ttgaaatgcc accatttctt gacacttcag aaaagcttaa  28080
atttctcata ccgccttgac ccgcttgtgc agttctctgt gcatatatcg taaatccaac  28140
tgcattttct ggaacaacta catagtcttc ctttaattcc caagacccag cctgtccagt  28200
aaactcagct tgtgtcgagg aaatatatcc attcgacgca ttataaaaac gaattgaaat  28260
attagtagtt cccaacgcta ataaatcagc gtcagcatat agttgtgctt taagataaag  28320
aacatctcca ggaattaaat tatagtcaga aagtttactt attgcagatg ctgtaggtag  28380
acgtgcaatt tcgttattag ttccaccaac agctgacata aattgctcaa cgctttcata  28440
tgttctttta ggaaatcctg tcgctccaac atcttctaaa ctatcaaata ctacatctaa  28500
tatagtttga tagtcatctg tgctttttct gttactcagt ttaacatgct ctagtgcgat  28560
agctctttta gaagaagtgt aaaaggcagc atatgatacg tcaaatcttg acaataaaga  28620
atcagatgga aaagcagatg ttcctgccgt tcttaaccaa gatactactt caggaggaaa  28680
attaaccttt ccgctagtta atatagcaac aagtctattg cttgaaaaag aattcatgaa  28740
actaacaaag gcagcagatg ttgtatcatt tgaagtagaa aaaacatatg acttactatc  28800
aaccaatgct cctgtagaag ggtcaaaaac tcttaaatga agacctgcac taaatgtttg  28860
acttcctaca ggattatctt gaaatttaac gtatggtcct gcggtagaaa gcgggcaaga  28920
acccgctata cttattttat atcttactga attgctttcc gataaaaatg gcgtttggac  28980
atatccttgt ccaaactctg ccataaattt ttccataata cctcttattc aacccattca  29040
aatttaacag ttttattcac tgggtcagga ataatgcgaa cattaccaat tcgtaagaaa  29100
tcacgaatag taagattacc cattgtagca ttatcagatg gtaaagcacc aatatcagat  29160
ggttgaggag gattacctcc atcaaatacc tgaacaaaac ttgaccaaga atttttggtt  29220
ttctgccatg tacgtgtcca gcgagtggta cgcgcttctg gcgttgttgg ataagtaatc  29280
caatcttggt aaagcgaatc aagtgtgtta ccaaactgag tcagtgtacc aggagattta  29340
acttcttcgc cacgttctaa atatggaaga ccagtcactt cattagtttt ttcaaccatt  29400
ttaaaataac ctgggaactg gttataagta gctgaatcgt taatatcaat tgaccagaat  29460
cctacagtat cagatgttgg cgcacgtgta tataagtcag atgttttagt accttgagaa  29520
cgaattctcg agttaacagt taaaccacca gaatttatag tagcaccttt ggcgatgatt  29580
aagctttcac caatcgttac ttgaccagat gcattattaa tagctaatgg gcgtaatccg  29640
ttaaatccac cagtctgatc acccgatgca gtaagcataa aattcgttac tgatccatca  29700
ttgcgaacaa tgaaaccata atttccgtta atagcacgga aagcatttgc gcttcgagaa  29760
ataatttcac cagctgcagt gactgaatta ccaaatgttg ctacgccatt tgcattcaat  29820
gttcctgaag cattaacatt tatcggtgtt actgtaccgt tgatattaaa tgttatattt  29880
ccggctttat tgcgctgaga ataaaaatga ctagatgttt catcactaac ttcaaatacg  29940
gtagaacgtg ttgtatctaa ttccccacta aattgatttc cccacactct aacagtcatc  30000
gtttgggctg ggtttgttcc agtttgaggt cctttctcaa aaatcaatcg agttgctgtt  30060
ccagtattag aaatagttaa tgtactattt gctgaaactg atccaccgaa cgtagcagta  30120
ctagatgata caagaggggc actcagattc gtttgttgag ttaaggttag tgaaccatta  30180
accgtctgcg caatatccct acgaatgaac tgagatgaat ctagaccatc caataaatta  30240
ctatctgcag cttttgcttt taatggcaaa taatttgcta atacacggtt taattcgtat  30300
ggtgatactg catagctatt tttctcgtat agctctaagt cctgggtaga accggctgta  30360
tcattaccaa cgaatgtaat tgaaccagat gaagttttaa caaagcctct tactgcagta  30420
gtagctgccc aagtaggttc actctgcaca atccatttta aattttttgg agatacagca  30480
gtatttgccg atgttccagc aacagtttcg gtttgtgttg caactttaat aacaccttct  30540
tgtgcttcag tagatttagt acctaaaagc tttttaggag ttattaaaac attatctaat  30600
tttccagcag cagcttcaac ttgtgtagcc acacgaagtg taccacgttg tgtctcattt  30660
gcttcaagaa tattaagggt ataatggtcc cagagagttc ctgattcaac taatccagat  30720
agagcaacaa cagaagtacg atcagtacta ttaaatctag ttttaatttt taatggtgta  30780
gagatacgag tatcgtcgac gcctgcgtcg aattcaactt gtgtagcaat ttcagctata  30840
ccacttaaac tttcagttgc tctacggtca tttaaagttt taggagtgac tgcacgagta  30900
taatcagttc ctgtattaac ttcactttgc gtagcaattt caattaaacc aattcttcca  30960
tcagttgatg tctttttatg taacgtttct ggcgttacaa cagcatttgc ccatccttcc  31020
tgactttgtc cagcaattac ttcactttca actgctaaaa ttactgcacc ttgttgcgtt  31080
```

```
ggagtagctt tatactgatc caaggcttta ggtgaaacaa ctaagttatt agtgttttta  31140
ttataaacat ttgtaccatt taattcacgg ctagaagccg gagtagcacc tgcagtagat  31200
acaaaagtta caataccaga taatgattca gaaccttgac gagcttgaag ctttttagga  31260
gtaatgatgg ttgtatcatc tgttcctgtg tttgtttctt gctgcgtagc aatttcagcg  31320
acacccctac gagtttctgt agcagttctt tcattcaact ttttaggagt gatgataaga  31380
tcatctgcaa aagagaatgt ggtatcctgg tttacttgcg cagttgttgc tattcttgca  31440
atacctctac gagtttctgt agcagtacga ttagctaacg tttctggagt aattgccagt  31500
tctttttgtg gagaattttc tagatcagca ttagcttgag cctgtgtagc taaagcaatt  31560
acgcctaatc ttgctctagt agaattattt aaagagtcta ctctttctac agttggaacg  31620
ttttgctgta caacccaata ttttccatcg gaatcttcga tataagcaag ctgtaaaact  31680
ggaacataat tggtttcgcc attaaaaact aattcttgaa cagtcaccca tttagtttca  31740
ggtgggtatt ctgaacgttt tggaaattgc agcaattgaa ctgaagaagc aattttatct  31800
tcaccggcag ctttgatttt aactgtttgt ccttttctca tataattcat ggaaatctta  31860
acagtatcac cgatagaaat atcagttgga agctgaagtt caattgtttg ggttgttcca  31920
ttattcgcgc caaataccat gacttcttca tttggacgaa tattagaatt agtcgttata  31980
atgcgtaaac gtgctttact atccccgtca aacaatctcc acaatttctc attatcatca  32040
aacattaaga aaccatcaat agatgtacgg ccttcaatgg aatgagttcc aacttcttgt  32100
actgaagttg tttcatcata cgtggtaaca attgtgtgat aaagtggatt taatttatct  32160
aaatcaacaa aattaataat atcgccatga ttagcaaatc ttggaagttt aacattaatt  32220
ggtgcagcag aagtaaatct acgtacgata aaatcgtttg attgcgcttg ataaagactt  32280
gccggtgtta caactgccgc ttctctgcta taatcagcaa catacatttg ccacagacga  32340
ttactaaaaa ttaaaactat ctgtgatttt ggatgagtca ttagtactga gcgtacttgt  32400
tgacctctaa agtttacaat gctttgtacc ggagctgtaa ttaaaacctg gttaactcca  32460
ggttttcctc caatatcttg gagaacgata gtatcaccat caattggaga agatggcaaa  32520
gtaaatgtaa tgtcattacc cgctgcggtg ttaactgaaa tcgattcgcc tgattttaat  32580
tgataaggtc ctgacgaaac agttgtccag tttgcatcag tgcgtaacgc tctccatcgt  32640
acgctattaa aagctcctgc tggttttgga atatcattta tagcagccca aaaacggtta  32700
tcataaatga ttacaaaatc ttttaaatat ccacgagttg gatcatattg ttgaactgtg  32760
ttttcttgaa ttaagtaatc aacgtttaca ccgtcagttc ctacggtacg atcagctaaa  32820
gctacgttga ttattttatc accacctgcg tccagaccgt cttctgctct gaactttctt  32880
ttaatctcgg ccattctccc gggctcctat tgtgttttca ataataagta tttatacttg  32940
tttactttaa gatttggatg gtatataata gaaatctcac taattgaacg aggttcatat  33000
ggatttagaa atgatgttgg atgaagatta caaagaagga atttgcttta ttgactttag  33060
tcaaattgcg ctttcaactg ctttagtaaa cttcccagat aaagaaaaaa ttaatttatc  33120
aatggttcgt catttgatat tgaactcaat taagtttaat gtcaaaaaag caaaaactct  33180
tggatacact aaaattgtac tgtgtattga taatgcgaaa tctggatact ggcgtcgtga  33240
tttcgcgtat tattataaga aaaaccgtgg aaaagcacga gaagaatcta cttgggactg  33300
ggaaggttat tttgaatcca gtcataaagt tatagatgaa ttgaaagctt atatgccata  33360
cattgttatg gatatcgata agtatgaagc agatgaccat attgctgttc ttgttaaaaa  33420
gttctcttta gaaggacaca agattttaat catttcatct gatggtgact ttactcaact  33480
tcacaaatat ccaaatgtta agcaatggtc accgatgcac aagaaatggg ttaaaattaa  33540
aagcggttct gctgaaattg actgtatgac taaaatcctt aaaggcgata aaaaggataa  33600
cgttgcttca gttaaagtac gatctgactt ttggtttacc aaagttgaag gtgaacgaac  33660
tccttcaatg aaaacttcaa tcgttgaagc tattgctaat gaccgtgaac aagctaaggt  33720
gcttctcaca gaatctgaat ataatcgtta taaagaaaat ttagttctaa ttgattttga  33780
ttatattcct gataatattg cttcaaacat tgtgaattac tataattcat ataaattacc  33840
accgcgtggc aaaatttatt catattttgt aaaagcgggt ctttctaaat taactaatag  33900
cattaatgaa ttttgaggtg aataatggct aaaaaagaaa tggttgaatt tgatgaagct  33960
atccatggcg aagacttggc taaatttatt aaagaagcat ctgatcataa actgaaaatt  34020
tccggttata atgaactgat taaagatatt cgaattcgtg ccaaagatga acttggcgtt  34080
gatggtaaga tgtttaatcg tctattagct ttgtatcata aagataaccg tgatgtgttt  34140
gaagctgaaa ctgaagaggt agttgaactt tatgacacag ttttctctaa atgatattcg  34200
tccggtcgat gagaccggtc tttcagaaaa agaactttca attaagaaag aaaaggatga  34260
aatagcaaag cttcttgatc gtcaagaaaa tggatttatt attgaaaaaa tggtagaaga  34320
gtttggaatg agttatcttg aagctacaac agcattctta gaagaaaatt ctattcctga  34380
aactcaattt gctaaattta ttccttcggg tataattgaa aaaattcaat cagaagctat  34440
tgacgaaaat cttttacgcc cttctgttgt tagatgtgaa aaaacgaata cgttagactt  34500
tctgctatga ttaaactccg catgcctgct ggtggtgaaa gatatattga tggtaaatca  34560
gtttataaat tatacttaat gataaaacaa catatgaatg gaaaatatga tgttattaag  34620
tacaattggt gcatgcgggt gtctgatgcc gcttatcaaa aacgaagaga taagtatttt  34680
tttcagaagt tatcagaaaa atataaatta aaggaacttg ctttaatctt tataagtaat  34740
ttggttgcta accaagatgc ttggattggt gacatctctg acgctgatgc acttgtgttt  34800
tatcgtgaat atatcggacg cttaaagcaa attaaattta agtttgaaga agatattcgc  34860
aatatttact attttagtaa aaaagttgaa gtttctgctt ttaaagaaat ctttgagtat  34920
aatccaaaag ttcaatcaag ttatattttt aaacttctgc aatcgaacat aatttcgttt  34980
gagacgttta tcttgcttga ttcatttta aatataattg ataaacatga tgaacagact  35040
gataatttag tctggaataa ttattctata aagttaaagg cttatagaaa aattttaaat  35100
attgattcac agaaagctaa aagtgttttc attgaaactg tgaaatcttg taagtattga  35160
tatgaatata gtatattggt ttacatttga agaccgtgtc aaaaataaga ctccaccata  35220
ctactatatc ggtagtaaat taaattgctc atttgagaac ggaataatat atgactcttc  35280
cggaaaggaa tactggagct catgtaaaca aaaaagattt ttgaatgcgc taatgcttca  35340
aaaaccgagc gttaaaataa ttcaaattga tgatgacttg gatgttattg aagcagaacg  35400
aaaataccaa cttgaagtaa atgccagaga taatccagac tattttaatc tggtatatgc  35460
tggtggtgga tttggtgtga gtggtgaaac tcatccagcc aaagacccgg aagttagaga  35520
gcatatgaga ttggctaatt atatgaaccg tgacgatttt agaccttgga aaacatcacg  35580
agctaatata gagtcttgga aattatctca tattgcttat gagaattatg tgttattatt  35640
atcctctaat ctgtacggta aaactcctgg atggcgaaga gttaaaggta atataaatat  35700
aactgataca actgctaaat cgatggtaaa gtatttcaac tcaggttgga tacctctcga  35760
agacccagag tattgcaaat tatgccagct atgaggtaaa gtgtcatagc accaactgtt  35820
```

```
aattaaatta agttaaaaag gaaataaaat gtttaaacgt aaatctactg ctgaacttgc  35880
tgcacaaatg gctaaactga atggcaataa aggtttttct tctgaagata aaggcgagtg  35940
gaaactgaaa ctcgataatg cgggtaacgg tcaagcagta attcgttttc ttccgtctaa  36000
aaatgatgaa caagcaccat ttgcaattct tgtaaatcat ggtttcaaga aaaatggcaa  36060
atggtatatt gaaacgtgtt catctaccca cggtgattac gattcttgcc cagtatgtca  36120
atacatcagt aaaaatgatc tgtacaacac tgacaataaa gagtacggtc ttgttaaacg  36180
taaaacttct tactgggcta acattcttgt agtaaaagac ccagctgctc cagaaaatga  36240
aggtaaagta tttaaatacc gtttcggtaa gaaaatctgg gataaaatca atgcaatgat  36300
tgcggttgat gttgaaatgg gtgaaactcc ggttgatgta acttgtccgt gggaaggtgc  36360
taactttgta ctgaaagtta aacaagtttc tggttttagt aactacgacg aatctaaatt  36420
cctgaatcaa tctgcgattc caaacattga cgatgaatct ttccagaaag aactgttcga  36480
acaaatggtt gacctttctg aaatgacttc taaagacaaa ttcaaatcgt ttgaagaact  36540
gagcactaag ttcagtcaag ttatgggaac tgctgtgatg ggtggtgccg ctgcaactgc  36600
tgctaagaaa gctgataaag ttgctgatga tttggatgca ttcaatgttg atgacttcaa  36660
tacaaaaact gaagatgatt ttatgagctc aagctctggc agttcatcta gtgctgatga  36720
cacggacctg gatgaccttt tgaatgacct ttaatagatt ataattacta attaattggg  36780
gaccctagag gtccccttt ttatttcaaa aattttttca caaaactgtt tacatccctg  36840
ttcttctatg gtactataca actatcggca atactgctga tgatcaaaga ggaaaataat  36900
atggctaaag ttgatattga catcgttgat tttgaatata ttgaagagat tattcgtaat  36960
cgttatcctg aacttagtat cacaagtatt catgatgatc ccaattattg caatttttct  37020
attgtcattg aaggtcctct tgaagacctt acccgcttta tggctaatga atattgcgat  37080
ggcatggatt ctgaagacgc agaattttac atgggactga ttgaacaata attatcaagg  37140
ggctatttga tagccccgtt aaaatgagga aatcaaagtg gaagttggaa aaacttatat  37200
cattaaccct ttatttaaaa atgactttgc taacgagtgc cgttgcaatg taatgatgct  37260
aaatttaata gagaagcacg gacctagttt tgttgtagat gaaatggaaa gtgatgattg  37320
tgctggtgac tgtgtggtac gtgtaactat ggaagacggc actgaataca tggcgggtgg  37380
cccacttgag acgtatttg agatttactc tgaagaattc aaatacttta ctgaggtaga  37440
tttagtaaag cctcaatctg ctaatgaagg tatagtttct ggcgtaacaa aaattcactg  37500
cattgttgat gaaaacaatg tagatgaaat cattgaactt ttgcgaaaaa cttttaaggc  37560
ctaatatgac taaagatgat ttcctggatg cggtagaaaa agctagtgag aaatttgaag  37620
tgatgggtgt acgggtccat aaagacagaa attacggact cgatattcaa acgtattcgt  37680
tatggcttgt gggtgaacac agtcttgtaa ccagtttagt tatgggtgtc gatacctatc  37740
ctctattggt taagttcaga agtatggaaa aggctactaa agaaatgatt aagcttggta  37800
agtggctcga taaaattcaa aaataattgt ttacaacagg gtagtagtgt gatactatta  37860
ccctatcaac ttgaggagaa taaaatgaga ttacaacgcc agagcatcaa agattcagaa  37920
gttagaggta aatggtattt taatatcatc ggtaaagatt ctgaactcat tgaaaaagct  37980
gaacatcttt tacgtgatat gggatgggaa gatgaatgcg atggatgtcc tctttatgaa  38040
gacggagaaa gcgcaggatt ctggatttac cattctgacg ttgatcagtt taaagctgat  38100
tggaaaattg tgaaaaagtc tatttgagga aaataatatg tccgacattc atgtaaccgg  38160
aattacccaa gtaagaattc gttgccaact taaaactgca cccgggatgg cttatattaa  38220
tttatcacat gacctagatt ctcgcgaaag tctgttaact ggtgtaatta cgttttacac  38280
tggaatcggc ggaaacgaat ttactgtagg cgagattgtt ggtcataaat taaaagttca  38340
gaagaacgtg ttagaacttt ttaatgacct ttatgatgat agcgatgaag tttttgatga  38400
aatcgcacaa gcagttaaca aaggaatggt aactttagtt aaaatgatta actctatcgg  38460
atatgctcct gaccctttc gatgggagat aatataattt ttgtatttga gtttatgaat  38520
gatgaattct attatacaat gctttaaaaa ttgcatagtc ttgatttaaa tgaatttgag  38580
gaaaatataa tgcttactga atacacttgc tttgctaaag atgatgcaca tcctgaactg  38640
attcttgaag ttaaggttaa tacgcttgaa caaaaaattg attggagcct ttacatctat  38700
cctaaaaata ttattgatgg tccacagaaa tatacgctta atgacaagtg cattagtggt  38760
atcattggat atggtacaag tgaaagcaag tattcattag aagatattcg caattctcgt  38820
tgtgcggtat catattttga tacagatata attaaacatc tttataaatt ggttcttgat  38880
attcgcaaag attttactgc catcaaaaag gcaactaagg aattaaaatg attaaattag  38940
tatttgctta tgctccaact aaaacagtcg aaggctttaa tgaattagca ttcggtttag  38000
gtgatgggtt accatgggga cgagttaaaa aggacctcca gaattttaaa gctcgtaccg  39060
aaggaacaat tatgattatg ggtgctaaaa cgttccagtc attatctaca ttacttcccg  39120
gtcgtagcca tattgtggtg tgtgacctta cgcgtgatta tcctgtaact aaagacggcg  39180
atttagcaca tttctatatt acatgggaac agtacataac ttacatttct ggcggcgaaa  39240
ttcaagtgtc aagccctaat gcaccattcg agactatgct tgatcagaat tccaaagtaa  39300
gtgtaattgg aggacccgct ctactatatg ctgcgttacc ttatgcagat gaagtagttg  39360
tttctcgcat cgttaaaagg catcgtgtta attcaacggt tcaattggat gcaagttttc  39420
ttgatgatat aagcaagcgt gaaatggttg aaacgcattg gtataaaata gatgaagtaa  39480
caacccttac ggaatcagta tataaatgaa ataacgcgtg gctgaaaata tgaattttaa  39540
ttattatcct attctattag aaaaagatga gaaacagcca aagtggcagg gtcctcagtt  39600
tattaaaggt gtctatcaat tagtagttcc taaagacaag atttatagta gctgtttcac  39660
tgaatccgct tgtagtattt ttggtaatag ttctccgtat tggaattttg acataaagct  39720
ggatagaaat atcgatattt ggttgaaagc tatggatatt ggtaatatta cgtttgatga  39780
gaataattat catattattg gtcgcttttc caaacgcggt aaagaattat atttcacacc  39840
tgaaattgag agaaaatttg atgctaaacc gtattgatta tttagcttca taaaatgtat  39900
tataatttat ataaggtact aaatgaaaca ataccaagat ttaattaaag acatttttga  39960
aaatggctat gaaaccgatg accgaacagg cacaggaaca attgctttgt tcggtactaa  40020
attacgctgg gatttaacta aaggttttcc tgcggtaaca actaagaagc tcgcttggaa  40080
agcttgcatt gctgagctac tttggttttt atcaggaagc acaaatgtca atgatttgcg  40140
attaattcaa catgattcat taattcaagg caaaaacagtc tgggatgaaa attacgaaaa  40200
tcaagcaaaa gatttaggat accatagcgg tgaacttggt ccaatttatg gaaaacagtg  40260
gcgtgatttt ggcggtgtag atcaaattat agaagttatt gatcgtatta aaaaactgcc  40320
aaatgatagg cgtcaaattg tttctgcgtg gaatccagct gaacttaaat atatgacatt  40380
accgccttgt catatgttct atcagtttaa tgtgcgtaat ggctatttgg atttgcagtg  40440
gtatcaacga tcagtagatg tttttctcgg ccttccattt aatattgcat catatgctgc  40500
gttagttcat attgtagcta agatgtgtaa tcttactcca ggagatttga tattttctgg  40560
```

-continued

```
tggtaatact catatctata tgaatcatgt agaacaatgc aaagaaattt tgcgtcgtga  40620
acctaaagag ctttgtgaac tggtaatagg cggattgcct tataaattcc gttatctttc  40680
tactaaagaa caattggaat atgttcttaa actcaggcct aaagatttcg ttctcaaaga  40740
ttatcagtcc cacggtgtct tgaaaggaaa aatggcggta taattttaat ttaattgcga  40800
ggatatatga ttttacgatt taaagatact tctggtgtag ttctttttac acttcctaat  40860
ccaagtgagt tagaagttcc aggaccaaat cagcctatta tcatttatgg caaaaaaatat  40920
tatactcata aaatgactcg tgagtatttt gataataaaa tttccacagt taaaacttct  40980
tctgactgtt actacgatat tactgtttta acggaagaac aatatgaaca cttacaaccg  41040
cgcaggccgt atatgccgag tagtgaataa atataaatcc gactttgatg ttaatattca  41100
ccgtggtaca ttttggggaa attacgtcgg taaagatgct ggcagccggg aggctgccat  41160
tgaattattc aaaaaagatt ttatacgtcg aattaaatcc ggagaaataa ctaaagcaca  41220
tttagagcct ttacgtggaa tgaggctagg atgcacatgt aaaccaaagc cgtgtcatgg  41280
tgatataata gctcatatag ttaaccgatt gtttaaagac gattttcaag ttgaggactt  41340
atgcaattaa ttaatgttat caaaagtagt ggtgtttctc agagctttga cccacaaaaa  41400
attattaaag ttttatcttg ggcagctgaa ggaacatcag tagatcctta tgaattatat  41460
gaaaatatta aatcttatct ccgtgatgga atgacaactg atgatattca gactattgtc  41520
attaaggccg ctgcgaattc tatttcggtt gaagagcctg attatcaata tgtagctgca  41580
cgctgtttaa tgtttgctct tcgtaagcat gtttatgggc agtatgaacc acgttcattt  41640
attgaccata tttcttactg tgtaaatgaa ggtaaatacg accctgaatt gttgtcaaaa  41700
tattctgcag aagaaattac atttttagaa tcaaaaatta agcacgagcg ggatatggaa  41760
tttacttatt ccggggcgat gcaattaaaa gaaaaatatc tagttaaaga taaaaccact  41820
ggtcaaattt atgaaactcc acagtttgca tttatgacta ttggaatggc attgcatcaa  41880
gatgaacctg ttgatagatt aaaacacgtt atccgttttt atgaagcagt atctactcga  41940
cagatttcat tgccaactcc tattatggct ggttgccgta ctccaacccg gcagtttagt  42000
tcatgcgttg ttattgaggc aggtgattca ttaaagtcta tcaataaggc ttccgcttca  42060
attgttgaat atatctctaa acgcgctgga attggtatta acgttggtat gattcgtgct  42120
gaaggttcta agattggcat gggtgaagta cgccatactg gtgttattcc tttttggaaa  42180
cattttcaga ctgctgttaa atcatgctca cagggtggaa ttcgtggcgg cgctgctact  42240
gcttattatc ctatttggca tttggaagtt gaaaatcttc ttgttttgaa aaataacaaa  42300
ggcgtagaag aaaaccgcat tcgtcatatg gattatggtg ttcaactgaa tgatttgatg  42360
atggaacgtt ttggaaagaa cgattacatt actttgttca gtccccatga aatgggcgga  42420
gagctttatt attcttattt taaagaccaa gaccgtttcc gtgaattgta tgaagccgca  42480
gaaaaagacc ctaatattcg taaaaagcgt attaaagctc gtgaactatt tgaattgctc  42540
atgactgaac gctcaggaac agcaaggatt tatgtacagt tcattgataa tacgaataac  42600
tatactccgt ttattcgtga aaaggcacct attcgtcaga gtaacttgtg ctgtgaaatt  42660
gctattccaa caaatgatgt gaatagtcct gatgctgaaa ttggattgtg tactctctct  42720
gcattcgtac tggataattt tgactggcaa gaccaagata aaattaatga attggcagaa  42780
gtccaggttc gtgctcttga taatcttttg gattaccaag gatatccagt tcctgaagca  42840
gaaaaagcta aaaagcgtcg taacctcggt gtaggtgtta ctaactatgc agcttggttg  42900
gcaagtaact ttgcttctta tgaagatgct aacgatttaa cacatgaact atttgagaga  42960
ttacagtatg gactcattaa agcatccatt aaactcgcca aagaaaaagg accttgtgaa  43020
tattattcag acactcgttg gtctcgaggc gaattaccta tcgactggta caataaaaag  43080
attgaccaaa tcgcagctcc aaaatacgtt tgtgactggt cgtcgctgcg ggaagacctt  43140
aagctctttg gcatccgtaa tagcacacta tcagcactta tgccatgtga gtcatcttcc  43200
caagtttcta acagtacaaa cggtatcgag cctccacgtg gaccagtctc tgttaaagaa  43260
tcaaaagagg gctcctttaa tcaagtcgtg cccaatattg agcataacat agacctttat  43320
gattatacat ggaaattagc taagaaaggt aataaacctt atcttacgca ggtagctatt  43380
atgctgaaat gggtttgtca atcagcttcg gcgaatacat actatgaccc ccaaatcttc  43440
cctaaaggca aggttccaat gtcaataatg attgatgacc ttttgtattt ctggtatttt  43500
ggcggaaaaa atttctatta tcataatacc cgtgacggtt ctggtactga tgattatgaa  43560
atagaaactc caaaagctga agattgttca tcctgtaaat tatgatataa tttgactcac  43620
ggacgagtca ccaactatta actaagcgga aaatttatga gcacagtttt taatacaaat  43680
ccagttgatg ttttaaaaga acctatgttt tttggttcag gtcttggtat tgcgcgttat  43740
gatattcaac gtcataaagt ttttgaagat ttaaccgaaa agcagttgtc atttttctgg  43800
cgtcctgaag aagtaaactt aatgatggat gctgcacagt ttaataagct tcctcaatat  43860
cagcagaata tttttactaa taatctgaag tatcaatcac ttctggatag cattcagggt  43920
cgtgcaccgt ctgctgtact tatgtcattg atttcagacc caagccttga tacatgggtt  43980
gctacatgga cttttagtga aactattcac agtcgttcat acactcatat tatgcgaaat  44040
ctttatactg atccgtcaaa ggtatttgat gagattgtat tagataaagc tatcatgaaa  44100
cgtgctgaat ctattggtcg ttattatgat gatgttattg agaaaactcg tgaatgggaa  44160
aacgcaaaag aaatttttag gtgtttttca gagaatgaat atgatttgga cgcatattca  44220
aatagcctta tgcatgtaga agaatgcaaa tacgaactaa tgcgttctct ttacctttgt  44280
ctgcatgtaa tcaacgcatt ggaagctatt cgtttttatg tatcctttgc atgtactttc  44340
aacttccata agaacatgga aatcatggaa ggtaatgcga agattatgaa atttattgca  44400
cgtgatgagc agcttcatct taaaggtaca caatatatta ttcgtcaact tcaatctggt  44460
actgatggcg atgaatgggt taaaattgcc aaagagtgtg aacaagaagc agttgatatt  44520
ttcatggaag ttaaccgcca agaaaaagat tgggcagttc atttatttaa agatggcgat  44580
gttcctggat taaatacaaa tagcatgtgg agctttattg attacttaac tgtatctcgt  44640
atgaaacagt gtggtcttcc atgcccgatt accgatgctc cggttaaaca tccatatcct  44700
tggattcgtg aatacttaa ttctgataat gttcaatccg cgccgcaaga agtagaactg  44760
tcatcttatc ttgttgcaca gattgataat gatgttgatg ataaagttat gatgagtttt  44820
aaaaaatact tttaaggagt gggccgcaag gcccatttta ttatgaaaga aattgcaaca  44880
gaatattcat ttattaaata tactgagtta gaattagacg acaacggaag tataaaacaa  44940
ctatctattc caaataagta taacgtaatt tatgctattg ctataaatga tgagcttgtt  45000
tatattggaa aactaaaaa tttacgtaaa agaataaatt attatagaac tgctattaat  45060
cgtaaagaca aaacgtctga ttctactaaa tctgcattaa ttcatgctgc gctaaaggaa  45120
ggaagcaaag ttgaatttta cgcccgccaa tgttttaatc tttctatgac aaatgagtta  45180
ggtacaatga caatcgcgac gattgaccta gaggagccgc tattcattaa actgtttaac  45240
ccgccttgga atattcaaca caagaaaaaa tgatgcttcc acatggagtg tggtactata  45300
```

```
ttcaaaacac aaaagaggat acacaatgca agaacttttt aacaatttaa tggaactatg  45360
taaggattca cagcgtaagt ttttttactc ggatgatgta agtgcatctg gaagaactta  45420
cagaattttc tcatataatt atgcatctta ttctgattgg ttacttccag acgcattgga  45480
atgtcgtgga atcatgtttg aaatggatgg agaaaaacca gtaagaattg cttctcgtcc  45540
tatggaaaag tttttttaact taaatgaaaa tccattcacg atgaatatcg atttaaatga  45600
tgttgattac attctgacaa aggaagatgg gtctttggta tcaacttatt tagatggtga  45660
tgaaattctg ttcaaatcaa agggttcaat caaatccgaa caggctttaa tggctaatgg  45720
tattttgatg aatattaatc accatcggtt gcgtgataga cttaaagaat tagctgaaga  45780
tggatttact gctaacttcg aattcgtcgc tccaactaat agaatcgttc ttgcttatca  45840
agagatgaaa atcattttat tgaatattcg tgaaaatgaa acaggcgaat acatttcata  45900
tgatgatatt tataaagatg ctgctcttcg tccatatcta gttgaacgat acgaaatcga  45960
tagccctaaa tgggtagaag aagctaaaaa tgcggaaaac atcgaaggct atgttgctgt  46020
gatgaaagat ggttctcatt ttaaaattaa gtctgactgg tatgtgtctc ttcatagcac  46080
aaaaagttca ttagataatc cagaaaaatt gtttaagact attattgatg gtgcatcaga  46140
tgatcttaaa gcaatgtatg ctgacgatga atattcatac agaaaaattg aagcatttga  46200
aacgacttat ctgaagtact tagaccgagc tctgttttta gttcttgact gtcataataa  46260
gcattgtggt aaggatagaa agacttatgc gatggaagcg caaggtgttg ctaaaggtgc  46320
tggaatggat cacctgttcg gtatcattat gagcctatat caggggtacg atagtcaaga  46380
aaaggtcatg tgcgaaatcg aacagaattt tttgaaaaat tataaaaaat ttatcccaga  46440
aggatactaa gctgtttaca agtccctcgt gttgtgttat agtagtctta ctgacataac  46500
atgaggactt tatgatggat ttgcagctta ttactactga aatggtcgtt gaagcatacg  46560
gtgatactac agatgggatt tctgtattca aaggaaatcg tcgagttgga tatatcaccg  46620
atcttaagaa agatttagct aagcaagtca agtggaaaac gaccattaaa gaatatcgaa  46680
atcgtcgtct tgagcaagcc cgtgatatgc ttcctgatgc ggttgaggag atgaaagtct  46740
ttttagaaaa tcaactcgct aagtatgatt gtgaagtgtt tattaatcag actcaaccta  46800
atgttcatat caatagctgc aaatgctata tcatcgttaa tcctttgaca ggaaagcatc  46860
gtcttggaat tagtaatcca aatcgtagcg catcggatat ggcagaagat gttgcggcgt  46920
gctttaaaat ttctaaatct ccggctgaac atcatatttt aattaacggt ctttctcaag  46980
acgatattat agaggttatt aaaactttat gcatgtaagt aattttacag ctggattgct  47040
attacttgta atagcatttg gcggaacatc tattatttta aaaaataagg tagaaagatt  47100
agaaacgtct gttgtagaaa ttacaaaaac ggccaatgaa aacgccttag cattaaataa  47160
tttgcgaatt cagtataatt atattgatgc gatgaataat aaaaatcgtg aggcgattgc  47220
tgctattgag cgtgaaaatg aaaaactgcg caaagatgca aagaaggcgg atgtggtggc  47280
tcgtaagcca ggattggttg aaaaacaaat caacaactcc ttcaacaagt tcgcagaaga  47340
catccaggac ctttctaaat gattaaatta tctgcagtaa tattatctat tggtcttcta  47400
gttggttgtt cgacaaagcc tctagaagta aagaaagaaa cagttcatcc taattggcct  47460
gtgcaaataa agtcatatga cgaagctaaa ctatcttggc aagttaaagt tattgatggt  47520
aaagcttggg taggtatgcc atttgaagat tctcaggaat ttcgtatttg gcttaatgat  47580
gtaaaacgat atgtacatga ccagaaaact atgatatgtt attatcgtca agagctaaaa  47640
gaggataaat gtaaatgatt tcatggtatc aatttgaaca tctaaaagga ttaatttatg  47700
aatccgagat ggctgcaatg atttatggac gacagattca acgattagaa tctttacctc  47760
caactaatga tgttttatta gctcaatcac gcgctaatct caaaaatgaa tatcaaaata  47820
agtggggtaa agcatctaaa gacctgcatg attatattca atcattggtt gagaaaaata  47880
aatgaaaact ctgttagaac gttatattga atgctcagac cgttacattg acgtatgccg  47940
tgaaaatgta tcaagcatta gcgaagacat tgaacatgct aaagctttag atgatgctgg  48000
taaagccctg cgaaaagaag cgaaagctcg tgggcttgat atgtatcagc ttaaaaatca  48060
catgataaaa tttatttcat ccaatgttca gagtaaatca gcgaatcaat caacagctga  48120
attgtacaaa ggacggcgtg agcataatat tcgtattctt gaagttttct taggaattaa  48180
atgatgaaaa agattatttt gactattggc tgtcctggtt ctggtaagag tacttgggct  48240
cgtgaattta ttgctaaaaa tcctggattt tataatatta atcgtgatga ttatcgtcaa  48300
tccatcatgg gtcatgaaga acgtgacgag tacaagtata ccaaaaagaa agaaggcatc  48360
gtaacttaca tgcagcatga tgttgctaac atgattctat gccaagacgt aacgaagggt  48420
gtaattgttt cagatactaa tctaaatcct gaacgacgta aggtctggga agagtttgcc  48480
aaagagcttg ggcatcaaat tgaatataaa gtgtttgatg ttccttggac tgaattggtt  48540
aaacgtaact caaaacgtgg aactaaagca gtaccaattg atgttttacg ttcaatgtat  48600
aaaagcatgc gggaatatct cggacttccg gtatataaag ggactcctgg taaaccaaaa  48660
gcagttattt ttgatgttga tggcacatta gcaaaaatga atggtcgtgg tccttatgac  48720
cttgaaaaat gtgataccga tattattaat ccaatggtcg ttgaactagc taagatgtac  48780
gataagcaag gatattacat cgtagtcgtt tcgggccgtg aaagtggaac cgaagaagac  48840
ccaacaaaat attatcgtat gacccgtaaa tgggttgagg acattgctgg tgttccatta  48900
gttatgcaat gtcaacgcga acaaggcgat acccgtaaag atgatgtagt taaagaagaa  48960
attttctgga aacacatcgc accacatttt gatgtgaaat tagctattga tgaccgaact  49020
caagtagttg aaatgtggcg ccgcattggt gttgaatgct ggcaagttgc ctcaggagat  49080
ttttaatggc tttgcatcat gaaatttggg ctattattat tgtaaatagt ggtttagtcg  49140
gtactagtaa tgggcaattt tgtgtattca ctagtgaaat cagagcttgg gaggaatgcc  49200
ttaaattaag agaaaagaat cctgatgttg aactaacagt aaagaaaact aaactgcctt  49260
taccgtggaa aacttatgaa taatatagaa aaaatttatc atctttgtga taaaattgaa  49320
aaagaaaaga aatacctgtt ttgtttatgg cctattgtta atggaagagt aggtttagat  49380
gttcttgatt atgaaacaga agacaaagta gatggttcaa cttttgataa tgcgttggat  49440
gttattgatt ggctcgaaga aaattatgtg aggtaaatat gtttccgact tattctaaaa  49500
ttgtagaagt agtgtttagt caaattatcg ctaataatat gtttgaaaag cttgataacg  49560
cagccgagct tcgaattcat gctcaagtga ctcatgtatt gaacactttg cttccagacc  49620
aggtggattc tgttgccatc acgttgtatc caggttccgc gcatatcatt gtcgtattcg  49680
gtcttgatgc tgagttagtt atcaaaggcg atattcgttt tgaatcgcag acagcagaat  49740
tcaaagcaat ttaatagttt actttacggt agagttgtga tattatagct ctaccaaaca  49800
aatgaggaaa acaaaatgct gctaagtgaa aaaccgatta ctgttaaaga attccaagaa  49860
aaagttaagc tatttgcaca ggaattggta aataaggttt ctgaacgatt tcctgaaaca  49920
tcggttcgtg ttattactga aactcctcgt tcagtattag taattgtgaa tccaggtgat  49980
ggcgatcaaa tatcgcatct taaattagat tttgatggat tagttgaagc acaaagggtg  50040
```

```
tatggcgtac tatgatgaat ttaactgata taattgataa ttgtcttgaa aatgatactg  50100
gcgatcatag agcgcttgac tctgaaacag cacagttcat tagaataact ttaatgaatg  50160
acactctagt aaatagtatt catccttccg tatatgatgc tattattgtg acgaagtatc  50220
cagttgagct tcacaaaaag atggttggcg caatttttat tgataagaaa aaccgcttta  50280
aagatgggca gaatataatt agttctgtta ttaaaagtat aactaaactt cgtcacgaaa  50340
tttatcgtgt tgaaactgct aaatctgctt atctggtgat tatgaaatga aagcgagtac  50400
agtacttcaa attgcatatt tagtatcgca ggaatcaaaa tgttgctcct ggaaggtagg  50460
agcagtaatt gaaaagaatg gacgtattat ttctaccgga tataatggtt cacctgctgg  50520
tggtgtgaac tgttgtgatt atgctgctga gcaaggttgg ttgctgaata agcctaaaca  50580
tactatcatt caaggccata agcctgaatg cgtatcattt ggttcaactg atcgttttgt  50640
cttggcaaaa gaacaccgga gcgctcactc tgaatggtcg tctaaaaatg aaattcatgc  50700
tgaactaaat gcaattttgt ttgctgcacg aaatggttct tctattgaag gtgctactat  50760
gtatgtaaca ctttctcctt gtccagattg tgcaaaagcg atagctcaat ctggtattaa  50820
aaaactggtt tattgcgaaa catacgataa aaataaacct ggctgggatg atattctgcg  50880
aaatgcaggt gttgaagtgt ttaatgttcc taagaaaaac ttgaataagt taaactggga  50940
aaatatcaac gaattctgtg gtgaataatg aaatttcgtt tggtaaagct cacagcaatt  51000
agttcttatt ctaatgagaa catctcattt gctgtagagt ataagaaata ttttttctct  51060
aaatggaagc agtattataa aactgattgg actagtatag atagaccata tagttggaaa  51120
tctgatttag aaaaatgcca aaaattgctt tccactctta aagaacgtgg aacaactcat  51180
attaaaactg tgataggtaa ataaatgaaa ctgacgactg aacaaaaagt agcaattcgt  51240
gaaattttga aaactaaact gtccatgggt gtttcaaacg tagtttttga aaagtctgat  51300
ggtactattc gtactatgaa aggtactcgt gacgcagact ttatgccaac catgcaaact  51360
ggtaaattga ctgaatcgac tcggaaagaa tctactgaca tgattccagt atttgatgtt  51420
gaacttggtg catggcgagg tttttctatt gacaaattga tttctgttaa tggtatgaaa  51480
gttgagcatt tactccaatt tattggtaaa taaatgcttt aagaattatt tgttattatt  51540
aattcatctg ttaacaaaaa ggaaaaacga tgtctgaagt acaacagcta ccaattcgtg  51600
ctgtcggtga atatgttatt ttagtttctg aacctgcaca agccggtgat gaagaagtta  51660
cagaatcagg acttattatc ggtaaacgtg ttcaaggtga agttcctgaa ctatgtgtag  51720
ttcactctgt cggtcctgat gttcctgaag gtttctgcga agttggtgat ttgacttctc  51780
ttccagttgg tcaaattcga aatgttccgc atccttttgt agctctgggt cttaagcagc  51840
caaaagaaat taaacaaaaa ttcgttacct gtcactataa agctattccg tgtctttata  51900
agtgatataa ataataatat gaattgggtg tcggaataat aagttaaccg aacaattcta  51960
tgtggtagtc tacaactgag agatctgtcg aaagaagatg aaattcagaa gaacgtgact  52020
accgagtttt aatctctaac gagaattttt aaatgattaa acaattacaa cacgctcttg  52080
aactgcaacg aaacgcatgg aataatggtc acgaaaacta tggcgcatct attgatgttg  52140
aagccgaagc tcttgaaatc ctgcgttatt tcaaacatct gaatcctgct caaactgcat  52200
tagctgctga gcttcaggaa aaagatgaac ttaagtatgc taagcctctg gcttctgctg  52260
cacgaaaagc agttcgtcac tttgtggtaa cactgaagta atttattgga gattcactac  52320
cttagtgtga gctaaaatcg aggagccgtc gaactgtctg attaatgatt tgcgaatcat  52380
tatagtttta agaccccggc agttttacgg tgtacctctt gaatgttact atcatgcgtc  52440
agaaaagtgt tatctgtgta agtcttggtg gtatgttgac gaggtttatg gttatcctgt  52500
cggtaaatat acaaaaccta tgttccccct tgagggcttg cgcaggcaat gccaataagt  52560
cctgcatttt catttaaaag agaatttata atggcaaaac aagttaaagc aaagaaagca  52620
gttgaaaaga aagctggtga ttctaaacgc gctggttaca agcgtgggtc gaactctcgt  52680
atcaatcaaa ctgttgagaa gatcatgcgc cgagcacgtg cggttcttcg agatgatgct  52740
tctcgttttg gtaagcagaa agcataagtt gaggactcct tcgggagtcc tttttttattt  52800
tccaaagatt gcacaaagtt gtttacagta tggttccttt gtgatagtat tatcttacac  52860
aaacaaagga gaataaaatg aaaacgatta atctgaacgc tgcagttaag actaaatgct  52920
tcaatggtaa atatgatgaa actatgtggt tcttaatggc agttgaaggt gatattattg  52980
aagtagaaac aacagaaggt atgggaacag atttcacctt tacaattcaa gttcataatt  53040
tctttactgg ttggatttat gaattgaata cagtaatcgt tggaaaaatt gaacaaaatg  53100
aattaggcga atggtattat gttacagctc gccaacgtgt caaacgtttg attgagaaga  53160
tgaaaaaagt tggtaaactt gacatgaagc actggaaagt agtaaaataa ttgtttactt  53220
tggtacagga tatgatatta tatacctgta ccgcaattaa acatctcgga gaataaaaat  53280
gaactacatc aactttgaac gtaaatatgt ttctaatagt attgcaggtt ctattgatac  53340
tatctgcctt tggaaacatc aaaatggatc agtatgcgaa attgaacagt atatgactcc  53400
taactatgtt tatatgcgat ttgaaaatgg catcacggtt tcaatcacaa tggaaggttc  53460
caactttaaa atcgctttgg atgatgattt tcgtcaacgc gatttaggga ctcatccttg  53520
ctggaatggt gataatcgca agcttttggt taaaacttgg attcgtcata ttctgagtaa  53580
cagagctaaa cctgagcatc ttgaagcaat ctttgatgta gttcttaacg aatttgatat  53640
ttaaaataaa atgaggggct tcggcccctt actgaggaaa atattatgtt tatgactact  53700
tattttgata cccgcaaaaa tttttgtgaa gtggtttttt ctaaggcgcc taaagacctt  53760
cctgctcatt tgcaacctac tagtgaatcg attaaaaatt atgttgatgt ggtttgtcct  53820
ttagaattcc gtacagtaaa tgggcgtgat actttagcta tcgctaaact taatcgtgaa  53880
attgacattg acccctcaat tgcgtgtgaa attaatattt ctgatattgg cggcggtaat  53940
gttaaatcac acggctttca gatgaggttc tgatgaaatt ctttttaggt caaactgttg  54000
aattaaaggg agttggtata cctggattaa tttctaaggt tctacctcca tttaaatgga  54060
gcggtgttca aataaaagag gcttatattg tttcctgggt agatggaaat gaagaccttc  54120
gtatgggtga tgaattatct cctatttacg gattaaagga attagtatga atataattaa  54180
taagattttt ggaattcagt acattaaggt tacgtataaa gtaacagata aaaatccata  54240
tactgacgag catgaagaac cgcaagtcga gtctattata ctagaaaagg gtagtgactg  54300
gccagttgag tttcgtcttc cttgctatgg tcattgggct gatgttgaaa ttataagtat  54360
tgaaaatgtc tgagttagag attagaagca attttaaatg gccatcatgc gcattaagta  54420
atttcgccca atggcctttc atcatggatg gtattcaatt tggaggtctc gaaggattcc  54480
tccaaggatg caaggtgaaa aatgttgagc aacaaagacg tatatttggg ttatccgggc  54540
ttgccgccca acaagctgga aggtcttatg caagagccca ggaccgtggg accctcttct  54600
ggattggagt tccgttttca agatactccc cggcgtggaa agagttgtac acaaatgcat  54660
attttgaagc agcgattcaa aacaagggct ttcgtgatgc attactagcc tcgaaaggaa  54720
aagttttgaa gcacagcatg gctagtggtc taacaaaaga tgatacaata ctaaccgaag  54780
```

```
ctgaatttat tgatgtgtta aacctattaa gagactctct atgaagccta ctattttgac  54840
tgatattgac ggggtgtgtt taagctggca atcgggcctt ccttattttg cccaaaaata  54900
taatcttccg ttggaacata ttttaaaaat gattcaggac gaaaaattta tttctcctgg  54960
taagctcttt aattgcgatg aagaacttgg tgttaaatta atcgaaaagt ataatcgttc  55020
agatttttatt cgttatttgt ctccatataa agatgctcta tgtgtaatta acaaattaaa  55080
agaagattat aattttgtag ctgttacagc attgggtgat tctattgacg ctctgctgaa  55140
tcgtcaattt aatttgaatg ctctttttcc tggtgccttc tcagaagtat tgatgtgtgg  55200
tcatgattct tcaaaagaag agttgttcaa aaaggcaaaa gagaaatata acgtaatttg  55260
ttatattgac gatctcgctc accactgcga tcacgcgagt gaaatattaa atgttcctgt  55320
ttattggatg gctcgaggag agcgtgacaa tattccaaaa actgcgcagc gagtttatac  55380
atggaatgat gtagagaata agctttttcc atcgaaggaa aataaagaaa gttttgatag  55440
tgaaaaagct ataaaagatg taattgaaaa gatgattaaa aacgattctt ttcgttggaa  55500
tactacctgg agaactcctg gattaaatcc ataccatcca tattatacac atccatatca  55560
tgtgcatcca tttcatacat ggaactatat taaacctggt ggcatagagt atttgtataa  55620
tagacctact agtggtgata atattttaca aggagcattc taatgtttgt tgttcatact  55680
atttatgaaa atgaaggtaa tactacacgt gattacggtc acgtaaatca attttttaga  55740
tgcaatccag aattccgagc tcaaaaagac gaacgaattt ttaaaaaatg tgtagagcaa  55800
ggtttcattt acgtcaagca ctggatgcaa ggaaataaag ttagaaccac gtaccacagg  55860
tctttgactg agcttaatga tgaattgatt tataatagag ctgtaaacca aactctaaag  55920
gatgaacaat gattcttaaa attctgaatg aaatagcatc tattggttca actaagcaaa  55980
agcaagcaat tcttgaaaag aataaagata atgaattgct caaacgagta tatcgtctga  56040
cttattctcg tgggttacag tattatatca agaaatggcc taaacctggt attgctaccc  56100
agagttttgg aatgttgact cttaccgata tgcttgactt cattgaattc acattagcta  56160
ctcggaaatt gactggaaat gcggcaattg aggaattaac tggatatatt actgacggta  56220
aaaaagatga tgttgaagtt ttgcgtcggg tgatgatgcg agaccttgaa tgcggtgcat  56280
cagtatctat tgcaaacaaa gtttggccag gtttaattcc tgaacaacct caaatgctgg  56340
caagttctta tgatgaaaaa ggcattaata agaatatcaa atttccagcc tttgcccaat  56400
taaaagctga tggagctcgg tgctttgctg aagtcagagg tgatgaatta gatgatgttc  56460
gtcttttatc acgagctggt aatgaatatc taggattaga tcttctcaag gaagagttaa  56520
tcaaaatgac tgcagaagct cgccagattc atccagaagg tgtgttaatt gatggcgaat  56580
tggtatacca tgagcaagtt gaaaaggagc cagaaggcct agattttctt tttgatgctt  56640
atcctgaaat tagtaaagct aaagaattcg ccgaagtagc tgaatcacgt actacttcta  56700
atggaatcgc taataaatct ttaaagggaa ctatttcaga aaaagaagct caatgcatga  56760
agtttcaggt ctgggattat gttccgttgg tagaaatata cggtcttccg gcgtttcgtt  56820
taaaatatga tgtacgtttt tctaaactag aacaaatgac atcaggctat gataaagtaa  56880
ttttaattga aaaccagata gtaaataacc tagatgaagc taaggtaatt tataaaaagt  56940
atattgacca aggtcttgaa ggtattattc ttaaaaatat cgatggatta tgggaaaatg  57000
ctcgttcaaa aaatctttat aaatttaaag aagtaattga tgttgattta aaaattgtag  57060
gaatttatcc tcaccgtaaa gaccctacta aagcaggtgg tttcattctt gaatcagagt  57120
gtggaaaaat taaagtaaat gctggttcag gcttaaaaga taaagccggc gtaaaatcac  57180
atgaacttga ccgtactcgc attatggaaa accaaaatta ttatattgga aaaattctag  57240
agtgcgaatg caacggctgg gtaaaattag atggacgtac tgattacgtt aagctatttc  57300
ttccaattgc aattcgttta cgtgaagata aaactaaagc taatacgttc gaagatgtat  57360
ttggcgattt tcatgaggta actggtttat gaaagcttac ttagaaacaa ttgtcgtggc  57420
tcaaaaagaa ggtggagatg tttccactgc ggtatcgcag gttattcttg aattcccaga  57480
taaactagca tatgatgaat tcacggaaag atttgatcca tatgaaaaag gtccaaagtt  57540
tgaagtatat cgtactcttt tagctctcta ttaattaaag gccttcgggc ctttaatttt  57600
ataaatagaa taaacactag agaggataac atggaactta ttacagaatt atttgacgaa  57660
gatactactc ttccgattac aaacttaaat ccaaagaaga aaataccaca aatttttttca  57720
gttcatgttg atgatgcaat tgaacaacca ggctttcgtt tatgtaccta tacatctgga  57780
ggtgatacta atcgcgattt aaagatgggc gataaaatga tgcatattgt tcccttttaca  57840
ttaactgcta aaggttcaat tgctaaatta aaaggtcttg gtccaagccc aattaattat  57900
atcaattcag tttttactgt tgcaatgcaa acgatgcgtc aatataaaat tgatgcctgc  57960
atgcttcgta ttcttaagtc taaaaccgcc ggtcaagctc gacaaattca acttattgct  58020
gatagactta tccgtagtcg ttcaggtggc agatacgtcc ttcttaagga actctgggat  58080
tacgataaaa agtatgcata tattcttata catcgcaaaa atgtatcact agaagacatt  58140
ccaggagttc cggaaattag tacagagctc tttactaaag ttgaatcgaa ggtcggtgat  58200
gtttatatca ataaagatac tggagctcaa gtaaccaaaa atgaggcaat tgctgcatct  58260
attgcacaag aaaatgataa acgttctgac caagctgtaa tcgttaaagt taaaatttcc  58320
cgtagagcaa ttgcgcaaag tcaatcattg gaatcttcta gatttgaaag tgaattattc  58380
cagaaatatg aatctaccgc agctaatttc aataaacctg ctactgcacc tttaattccc  58440
gaagcagaag aaatgaagct tggaattaat tcattagctt ctaaaacaaa ggcagcaaaa  58500
attattgctg aaggaacggc agatgaactt cactatgatt ataaattctt tccaatgagt  58560
caagtcggtg aagtttcaga aaaaattaaa gaagtaattt ttaatgcaat taaaaatgaa  58620
ccaactactt caataaaatg tttagagaaa tacgcagcag ctgtaaatca attctttgaa  58680
gattataaag ataaatggct tgctaatcat aataaaaatc gtaaaggaca atcagatgaa  58740
gtctgggaag aaataactaa aaattcctgg aacgcagcaa aaactaaatt cctcaaacga  58800
atgatttaca gtttttctgg aattggtgct ggtccaatga ttgatattac tattgcacgc  58860
gatggttcta aatatactcc atcacaaaag cgtggcatta gagaatattg cggttcagga  58920
tatactgaca tcaataatct tcttttaggt cgttacaatc cagaacgata cgatgtaatg  58980
agtgaaaaag aaattgaatc tgctataaat aacttagatt cagcttttga aaatggtgac  59040
cgtataccag aaggcattac agtttatcgt gctcaaagta tgactgctcc tatatatgaa  59100
gcgttagtta aaaataaagt gttctacttc agaaattttg tatctacttc tttaactcct  59160
atcatttttg gacgttttgg aatcacacat gctggtattg gtcttttaga accagaagct  59220
cgcaatgaat taacagttga taaaaatgaa gaaggaataa ctattaatcc aaacgaaata  59280
agagcgtata aagaaaatcc tgaatatgtt aaagttcaaa taggatgggc aattgatgga  59340
gctcataaag ttaatgttgt atatccagga agtctcggaa tagcaacaga agctgaagtt  59400
attctaccac gcggattgat ggtcaaggtt aataaaatag ctgatgcttc taataatgac  59460
ggaacaacat ctaataatac aaaactcatt caagctgaag ttatgaccac agaagagctc  59520
```

```
accgaatcgg taatctatga cggagaccat ttaatggaaa ctggtgaatt ggttgcaatg  59580
acaggtgata ttgaaataga agacagagtt gactttgcat catttgtttc atcaaatatt  59640
aaacagaaag tagaatcatc tcttggaatt attgcgtctt gcatagatat tacaaacatg  59700
ccttacaagt tcgttcaagg ataaatcatg gaacttatta cagaattatt tgacggcgct  59760
tcggcgccgg ttgttaactt aaatcctaag cataaaatac ctcaaatttt tgctattcaa  59820
gccggtgaag aaagcgtgct tcctggattt agattttgta catacacctc tggcggtgat  59880
acaaataaaa acgttaagcc aggcgataaa atgatgcata tcgtaatgat aggtgttaat  59940
gagaaactat cattagttaa gcttaaaaac ttgggtggaa atccaattgg cgtcattaat  60000
gctgtttttg atactgctct tcaaacaatg aagcagtata aaattgatgc atgcctattc  60060
cgcgtactaa aaagtaaaac aaatggcgca gctcgtcaaa tgcaagttat tgctgaccgt  60120
ttagtacgta ctaaaggagc aggtcgatat gttcttttaa aggaaatctg ggattatgat  60180
aaaaagtacg catatattat ggtttaccgt aaaaatgcca atttagaaga cattccaggt  60240
gtacctccta tttcaaccga gttattcaca aaagttgaat caaaggttgg tgatgtttat  60300
gtagacgtta aaacaggtaa tgctgttcct aaagctgttg ctgttgctgc ttctattgct  60360
ttagaaaatg ataagcgcac ggatcaagct gttattcaga aaactaaaat tagtcgtcga  60420
ttagcagcac aagctcaata ttctactgtt gatgcttcac ttcagggtga tagcttcgct  60480
gctaagaaat atcaagagtt tgaatctaaa gttccggtat ataaagcaga aggaccaatg  60540
aactctggcg ttattcagat tggttcaaac tttagcaaag gagctatcgg tggtatgaga  60600
agtgcttctc gttttaaatc tagtgattat gaactcgaaa gcttccgaaa tcatattgca  60660
ttggctcatg cacgtttacg tgatccatct atcaagttac agagcgatat aacatatcaa  60720
ggttctcaag aatatttaaa gaataaagaa ttctttgatt ataaaactga taaaatttta  60780
agcgatcttg ctgatattaa tatttctaat agctttgatg ttattaagaa aattatcaat  60840
gatttagtta aaggttctaa agctacacca gatgaaaaga cagctattat tcaatttgtc  60900
atgaatagca tttataaatt aattgatgaa tccgctgctc aggcgtatga atatgcaagc  60960
actgaagtaa ctccaaaagg attgactcag gctgaatctg atgtaattga agattattgt  61020
gcagattcgt atgttgaaat gaactcattc cttttaggta aacctgattc tacacgtgaa  61080
gaatacatgg agcgcgctat taagcacatc gagactatgg attctgcgtt tgctaaaggt  61140
tcagttcttc ctccaggaac tacactttac cgtggacaag aagttacttt taaaactttg  61200
cgtcataaca ttgaaaataa aatgttctat ttcaagaact tcgtatctac atcacttaaa  61260
ccaaatatct ttggtgagta tggtaaaaat tatatggcct tagatgattc cggagcagta  61320
ttttctggtg aaggagaagg ttccgttgat gcagaagatt tgatgcatat gggtagtcat  61380
tctacatatg ctaatgaaga tgctgaaact agcgtgggta tggtaattaa aggagctgaa  61440
cgagttaaag ttatcgttcc gggtcattta tcaggatttc catcagaagc tgaagttatt  61500
ctaccacgtg gaattttact gaagattaat aaagtaagta cttactttat gaaagaaact  61560
gcttataaca agtatctaat cgaaggtaca atcgttcctc cttctgaaca attagaagaa  61620
tcagtatatg atggtgacta tctaatggaa actggtgaag ttcgtccaat ggctggattt  61680
aatcaattcc ttgtagaaga atcaaaagaa gaggaaaacg aagtttctca aatcttagct  61740
tctttggtta acattaacgg aatgtctaaa aagttcaaaa tgtagtttac aagtccctcg  61800
tgttgtgtta tagtagtctt actgacataa catgaggaac acaaaatgaa atcttctttg  61860
cgcttttttag gtcaagaact tgtagttgaa ggcgttattc ctgctgataa tgcttttaat  61920
gaagcagttt acgatgaatt tatcaaaatt tttggaacag ataaaaagtt cggaattttt  61980
ccttctgaaa atttttcaaa gccagaacag actgaaagta tttttcaggg tgtagtaaca  62040
ggtaaatttg agtcagaagc tccggtaaaa attgaagttt atattgaaga aacctctgtt  62100
gcttcagttg ctgcttttat ttcattccgt aaataaaaat atggggacct ttcggtcccc  62160
attgttatat tgctcctaat attttacttt gcgaattgac aattcctgtc atagtattaa  62220
tatttgaaat gcttcctgca gttcccccta atctactaag tcgtgaaagc gaattagata  62280
gtccagtaac acctccacta tttccgagaa cgctttgaat accatttata gtagcagatt  62340
caagccattc aagggcagct tgtctatcaa ctgctccagc ctgcatgact ctataagcga  62400
aagtaacatc aaatgtagtt atttggttat ctccatcata tgataactca ggagcactca  62460
cagatattgg aatacagcca gtgaacatca ccgcagtatg tggtaatcca ttgcgagaat  62520
gaagattgac ctgaatatct gcctcgacat cttgcggtaa agcacgcaat ccagttactg  62580
ggtcttgaac agcgttaacc cagtcttgca ttgcacgata gttacaagct tctgaatcca  62640
ttctaaatga aataaccaaa gggtctaatt ctcttccagt tatacgaata ttaggagaat  62700
tatagttcca gtcagttcca taggataatc tattctctgg catttttaca gaatatatca  62760
tcaatccaga tgagttatat gccatgttaa agaagtcaat taaatatgta ccaactgtaa  62820
atgagcctaa taaactttga actgtacgtt gactcatggc accaataaga tatttactaa  62880
cccctgattt tcttatcagt ttttgtgtgc cagcggtaat tagcgtggta attccctgat  62940
taatatcgcc ttgagttaat cccaaccaat ctgaatttag acccaagtta ttataagcaa  63000
agttactaat tgagcttatt aacgatgagc ttttagttga tggagttgta gcaaaaacac  63060
agctgaacat attattacgt tggaagtctg cgtttattgc ttgattatta aattcctcta  63120
aagaatacat tagaaagtcc ccgtatataa agaagcacgg tttaacgtaa taatctctct  63180
catagtaatc tcgagtgtaa aagaacttgg aaggttagga gcaatagcta atccattaaa  63240
gttaccattt ggtgttttat caaatctaat actctgtatt tggcatggac cgaatacttc  63300
agtctttcca tcaaatttag aagttgcacc aaagtttttc accatccaaa ttgtcgggtt  63360
tgaaactaca agaacgttcg ttaaactcga tgtcattttt tcaaataacg tcttgttttt  63420
aatcgcgtct tctggcgtta atggttcaat aaatgtagaa cgataccact catctaaata  63480
tcctttttatt tcagcagcat attgagattt accagtttca ccgtaagaaa aatagttaaa  63540
atactgatag atattaataa tagccattaa atcttctgtt gagcgcggag tcaaatccca  63600
ggtgaacact tttgttctat tttcagcacc gccatacata cttctagctg ttgtatagat  63660
ctgttcatta ttatcagcca ttattccttg tgttatactt tcaagcgcac caaatactgc  63720
agttgaagcc atattactta gcacaccagt agcagtacct ccgccttttg taataagact  63780
atcttgaaca tcattaaatc tatgtgatga cgtatcgacg tcagatttag atctaggtaa  63840
aagaatattt gcaacaggaa ctttacttat tgttcctgaa ttattatctg atattagtcc  63900
atttgatagt tttgatactg tattactgat agtgtttctg gctgtacgta aaatactcga  63960
agatgaagaa gagtagttag atctcatcgt tctaagactt ccagaatccc tagatgacat  64020
attgtatgca gtaaataata atccattctt atatagatct gttacctgga agtcccctgt  64080
agtgtcatta ccactagcac gcccagttgg aaactgggct gtgtatgttt tagttcctac  64140
ttctgattta gtactctgtc cggctgaaat tgtttcaccg gacttttttaa ttaaatcagc  64200
agttatttct ttaacaattg ccatattatt ccttaattaa ctcccgtcgc accaaataca  64260
```

```
ccaggagcag ttgtgcttgt gacaggtgtc atattatgaa cgacagtatt tttcttaata  64320
acattattag tattattgat tgaaggagat gcttgttgaa caggagcttg ttgtgctttg  64380
ttcttttcaa tcacctggac ctgttttgct tctggtgatt tagcagaagt ttcaggtttt  64440
gcttcaggtt gatttttctt gagctcttga taagtggcat caattttagc aaatctagaa  64500
gcaagttctt ttttaactgc tggtgaatta tttaaatccg gatcattcat tcgtttttta  64560
aggtcttcat gagcagcttc aattgattta actgtcgagt ctttgctcat atcagctgaa  64620
tcagcgtatt tttcaaaacg aatcatcgca gcacgagctt cattagcttt cattaaagca  64680
tattttcttt cttccggtga aagttgtttt aatttttctt cttctgctgc acgttcttcg  64740
tcagtagtca atgcttcttt attatctaca ccacgaatcc agttagatgc acgagttttc  64800
cagttcgcaa ttttgtctaa tccttttgct attgggccaa gatcatcatt cattcgttta  64860
tcttgataat ttgctacttt ttcttggtct tctttattaa gagatgctcc agtagaattt  64920
tggaaatttt ctaatgctct tccttctact tcatcagcag tatccttcat gccaggaatg  64980
actcgaagaa ttgctgcaga taatttagcc atacctaatt gaataagctc tcctaaatta  65040
taaagaacac ttccaagccc ttcaacaata gctactgtca atccgcccca atctccagct  65100
tcccaaagtt gtttaatttt atcaatagaa tcaaagatgc tctgtaataa aggaccccat  65160
gttccggttt cgctagagaa tttagtaaaa tcagtgctaa ataaatccca tgcttttgaa  65220
aatttatctg accagtattt aaaatgaacc atcagcaggt ctattccaat aacaacagcc  65280
attatcaatg caaccatttt agcagcttca atagcagcac tgacggtata cttaaatagc  65340
atgctagata ttttatcagt aattgaaata gatttcttaa atccgaaatc aactgtcttt  65400
gttaatttat ctaaagcttg agataatttt aagttaaatg cgtctctttt ttgcttctct  65460
tctggagact cttgttttgg ttcaattggc tgaggagtag ggaaaaaatc agcatcagga  65520
tcattattaa ctgcttcagg agccggtaat aaaggaccca cagattcagc tgtatcatcc  65580
tcgacgactt taacaggaat agcattttcg actactgcta aactcgttcc agtttgctga  65640
attccagctg tctgaatttt ttgttccagt aaacttgtta atttatctaa tttgcttccg  65700
agcgattcac cgatttcttt attaatattg tttccaattt caacagtttc agcaattaac  65760
tcagaaccgg cagtagtatc acttactgcg ctttcaacgt tatcaattgc tccaactatt  65820
tcatttgatt tttcttcaac agtctgagct attaattcag aagcagcttg agcatcatct  65880
aattttgtag aaatgtcatt aagaccagat aaagtattag aagcggattt agccgcgtcc  65940
tgtgttggtt tattatctga aataactttt ctacgcatcg tttgcatttc ttgtggcttt  66000
ttcattcaaa taatccaata atattgccaa ttccggttat tggaccatta gggccaggaa  66060
ttgctaaagt tgtagaaata tcattttgccc attttaaaac aaatgctggc atctcaagaa  66120
aattaatttc tttaacttca tcattgacct taagcaagca tttggataac atatcgctta  66180
cagttaaaaa ttgttcaaat tttccaggag gtctaaaata aaatgtattt ccttggtatt  66240
gaaattccaa tctttgacat acataaacgt cattaatatc ataagtataa ccatctattt  66300
ctttacgaga tttaatcttt ccattaaatt ctagcaaatg aatagaaacg aaatcaactt  66360
ctgccggtga taaatttgga caaatagaat caataagaag ctttaaattt tcatcaggac  66420
ctttaacatc ttttaaaatg ttataatgtt taagacccat cttaggaata gaaacttctt  66480
tattacttat cggaagaact actttcttca gtggtagtat cagttttaaa ttcattttta  66540
accttaactg ggtcaattgt ttccagtttc gttgcattag tgaacatata aagatgagtt  66600
acggaattat tatttgataa ttcgtgaata acttcatcga cgtaaaattc tgttttaaat  66660
tggtttttac tatcattaaa aataatttta acgccaggag tcaagttaaa attaccgaca  66720
gtagaacatt tagcgtaacc atcatactgc gccatagtct gaagacgaat agcttcttca  66780
tatccatttc tataagtcat ttcagaataa gcacctgacc ttgacactac aatagagttt  66840
tcaccctttc ctgtagtaat cattggtaat gaagaatcta aaaatgaatg agcatagata  66900
gtagcatttt tcattggatc acgtttatgc gggtttgatt tagtcaacca aacaaaatca  66960
tatgctaatg gatatttcaa ttcttggacg aattgaccta ttaaagttgg ctcacctaca  67020
atcattggat atggttcttg atttatcatc atatcatagt ccatcatgtt aactcccatg  67080
atgtcttgcc atacaaatac gaacttatcg cttcctaccg ctagagcaac ttctcttaca  67140
tatgacaaat agttttcaaa tgtgctagtc catggaatat caggaacata agcatttata  67200
gcatttattg ctggagttaa taatgtgcgg tcttgataaa tgacaccaag catttccttt  67260
atagattccc cggcatcagg gaaaaatggt ctaccaaatt taagattttc tatagaatga  67320
atagttccca attcaatagc aatgatgtta tcgccttttg aatctactga cacggaaaaa  67380
tgcttgcatc cataaattcg tgttttaaca ttattaatat cgtttgcatt agctacagaa  67440
atctgaatta tttcatttcc atccattttt gtatgaatgt ttttagaatc ataaaattgt  67500
agcattcctt catttcgacc ataaagagag tcacgcatag ttaatgtggt aatagtagca  67560
gctaattcaa caaatctatt attactccaa gcgtcataac tctcaaataa tttaacgctg  67620
agatttggat atccggggcg ttgcaacata ctcattattg tttatccttc tcaatcagtt  67680
ttaatacgaa tccgcgctcg gcaggaatca ttttcattat tgaatttaag ctataattac  67740
tttttacaag cgtgtgatta atttgataaa aagtaaatat ctcatctgga ttaactaata  67800
gcttaaacac atctactata tcagtgtatt ttttaatgta cttatcacaa cacgacatgt  67860
gcaatgttaa attaatagga ttcattgcat cgagaatttt ttctaatgtt tctatctcga  67920
tggcgtcaac aagttctatt tgacttgatt cactaatttc cttccaatca taccacattt  67980
catctacttg aacagaatga atattttcag taatcatctt tgctttattt tcataaaact  68040
cagaaggaaa atttaattta attttaacat tagctacatc aaaaataggt tcctttaatt  68100
ctttttgata tatttcaaat ggaactgtct tttctttttt acattttgga catatgaatg  68160
tgactggtac tttagtttta cctattgaac ctacaaatac ctgcaaaaat ataaatggtt  68220
gccaagtctt tggatagtct ccaaaataat cagcaattaa atcagcaatt acttcttttt  68280
gttcttgtaa tgaccgatgt tctatatcgt ttcgaactaa caaaaaatct cgataatctt  68340
ctaccgtaaa tggtttaaaa cgatgaacac catcaggtaa tttacaacga ataatgtttg  68400
ccatagatgc tccttttatt ctatttataa atatgataaa taaaggagct aaatatgtat  68460
gaatacaaat ttgacgtgag agttggttct aaaataatca actgtcgtgc atttactctt  68520
aaagaatatc tagaacttat tactgccaaa aataatggtt ccgtagaagt aattattaaa  68580
aagctaatca aagactgcac aaatgcaaaa gatttaaacc gccaagaatc agaactatta  68640
ctgattcatt tatgggcgca ttctcttgga gaagttaatc acgaaaactc ctggaagtgc  68700
acctgtggaa ctgaaatacc aacccatata aatctattac atacacaaat agatgcacca  68760
gaagacctct ggtatacact gggtgacatt aaaattaaat tccattaccc taaaattttt  68820
gatgataaaa atatagccca catgatagta tcatgtatag aaacgattca tgctaacggt  68880
gaaagcattc cagttgaaga cttaaatgaa aaagaattgg aagatttata ttctatcatc  68940
acagagtcag atattgtagc tataaaagat atgcttttaa agcctactgt ttatttggct  69000
```

gttccaatta aatgtccaga gtgtggaaaa acccacgctc atgtaataag aggactcaaa 69060
gaattctttg agctattgta atggcaaata ttaataagct ttattctgat attgacccag 69120
agatgaaaat ggattggaac aaagacgttt caagatcact tggattaagg tcaattaaaa 69180
atagtctttt aggaattatt acaacaagaa aaggttcaag accgtttgac cctgaatttg 69240
gatgcgattt atctgaccaa ctttttgaga atatgactcc tcttactgct gacacggttg 69300
agcgtaatat cgaaagcgca gtaagaaact atgagccacg tattgataaa ttagcagtta 69360
atgtaatacc ggtttatgat gattatactt tgatagtaga aatacgcttt tcagtcatcg 69420
ataaccctga tgatattgag cagataaaac tacaactggc ttccagtaat agagtataat 69480
gcttcacgta taaacgtggt ataatgaatc taagtccatc caataacaat tgaatagaga 69540
acaatatgag attagaagat cttcaagaag aattgaagaa agatgtgttt atagattcga 69600
ctaaattaca gtatgaagca gctaataatg tgatgttata tagtaaatgg cttaataagc 69660
attcaagtat taaaaaggaa atgcttagaa ttgaagcaca gaaaaaagtt gctcttaaag 69720
ctaaattaga ctactactcg ggacgaggag atggtgatga atttagtatg gatcgttacg 69780
agaaatcaga aatgaaaaca gttctatcag ctgataagga tgttttaaag gttgatactt 69840
cattacaata ttggggaatt ttattggatt tctgtagcgg agctcttgat gctattaaat 69900
cacgtggatt tgctattaag catattcaag acatgcgggc atttgaggct ggaaaataat 69960
gagatataac attgatgatg cttttaatta tgaagaagaa tttgaaactg agattcaatt 70020
cttaatgaaa aagcataatc ttaagcgtca ggatattcgt atcctggccg accacccgtg 70080
tggtgaagat gtcctttata ttaaaggaaa atttgccgga tatcttgatg aatattttta 70140
ttctaaagat ataggcattg atatgcatat gagagatatg gggtaaatat gataaattat 70200
aaagaagtat ttagactttt agcagaaatg gaagcatgtt taaagcgtgt acaagaaatg 70260
cgctttaaga tggggttata aatagatata taattcagag gagacaatca tgtcagataa 70320
gatttgtgtt gtctgtaaaa ctccaatcga ttctgcattg gttgttgaaa cagacaaagg 70380
tcctgtacat cctgggcctt gctataatta cattaaagaa ctaccagttt cagaaagttc 70440
ggaagaacaa ttaaatgaaa cacaactttt gctatagtgt gacctttagt ctatagtttt 70500
ggcccttcct tttttggttg ggcctttttt aatttaaaag ctttcttcta cttcatcatc 70560
gtctgaatct tctaattcag ctctttttcc tgccaaagca tctctgactg agatgtcatc 70620
agtatctttt aattcagttt ctttaactct tttcttataa taagcttcaa gttcttctaa 70680
accttctatc gtttggcaag aggcaatttt acccataaat tcatcaatag aagcttcata 70740
aagaaattgt ttaaattcta gtaacatctt tttctccaaa gggccgaagc ccttataaat 70800
taactgtttt cattacgtaa ttaaattttt catctgcgta gcgctgaata cgatcaatgc 70860
cgtgttttaa aagatagttc aaatgaacat atttcttttt cgtattagca gattttggct 70920
taacaccaca atcatctatg aggtcccaga ctgttgctat tgtcttagaa ccatgcttac 70980
gtaatacacg accgattgtt tgtaatacaa tgatttttga tttaacaccg tgcgctaaaa 71040
caacgtgatg cagattttta actgaaatac cagtagaaaa tacaccataa ctagctacta 71100
taattattcc tttgccattt tcagctaagg ttttcattat attgcgggtt tcggtatcaa 71160
cttcccctga tacgtaataa actttatcat attcattttt aattaaatcg aaaatagctt 71220
taccatgtga tacatgttta aacatgacaa aagcgttttc atctttttgt gcaagcttaa 71280
tagctaattt agcgatccat ttatttcttt tactgagccc agtaataatt tttatttctt 71340
cttggtaagt ttttcccttt aatttagtag tgaactcatc gggatagcga agaaaaatac 71400
tattaatttt taactcagtt acttgtccat cttccattaa tttagaggtc gttactggct 71460
taaatatttc accgaacatt ccaacatact gcatgatatt ggctttgcca tcacgtaatg 71520
aaccagatag accaaatttg aacatgcagt tatttaaacc tgatatgata gatgaaatac 71580
tttttcctgt agcaagatgg cattcatcat tcatcatcat tccaaactgt gagaaccatt 71640
cttttggttg ttttactaca gtttgccatg taccaacaac gactggtgca tcatttttat 71700
atttatcatc ttttgatgct ccgccaccaa ttttctttat cattgcatga ctgaataaac 71760
gatagtcaac gaagtcatca gccatctgag ttgttagagc agttgttgga acaatgataa 71820
gaattttacc ttcgtaattt tccaaataat atcgcgcaag caaagcttga attaacgatt 71880
taccagcaga tgttggaaga ttaagaattc tacgacgatt aactaatcct tcgaacactg 71940
catctttttg ataccagtgt ggttcaattc ttttatttcc tgaatagatt tctaatttag 72000
aaagccattc atcaaaatct tttcttgata attcttcttt ttcgttaatt tgtgggtcaa 72060
tccaggcttt atagccaaag ttatcacaga actttttaat ttgcccgact aagccgaatg 72120
gaagaagtcg attataatct aaaagacgga ttcgtccatc ccagttgcca tatctgaagc 72180
gagggttaaa tctatatcca tcggcctcaa acgaaaagaa atctcttaat tcgtggaacg 72240
tgctctcttc acaatcgatg cgtacatgac tgaagtcgtg aaaatgtact ttaatatcca 72300
taattatgcc ttactaaatt tgcctttaga atctcttttc atgagacgac ctttaataaa 72360
tccgtcggga ataataccgt ctggttgtat taatttattt attgcgccat tattgaccca 72420
aaaagttcct gtggtagtcg gtttgacttt acatcctttt ctggactttc tattaggatg 72480
aaccatccct tttacaaatc cttctggaac aagttctcca ggtttaataa aaatattttt 72540
agttccatta gtgtaacaag ttttacctaa taccgtgcct ggtgagtttt caaatctttt 72600
agcggaagat tctttcatct ttgttataac ctctgtagtc ataacaattc caccaattcc 72660
accaggtttc atattataat aatttttgct ttttattagt tcaggagtta taatttcttc 72720
ttcatacatg tacgcttctt cggaagtttt aaactctttt agtattgttc tagagaaatt 72780
gttttcacca tatttcttta tagcctgctg aattgcctta ccggaaccaa ggtaaccatc 72840
attcaagtca tcagtagagt gttttcctat atacttttta ccatttatta gatttgttgt 72900
ttcatataca aagtggtaca tactattttc cgagtaataa atatatctat atttatactg 72960
aggaaatatt atgatagata aagattatat tgcagagctg aaggctcttg atgataataa 73020
agaagctaaa gctaaattag ctgaatatgc tgaacagttt ggtataaagg tcaaaaagaa 73080
taaatctttt gataatatcg ttgttgatat tgaagaagct ctccagaagc tcgctagtga 73140
acctatgcca gagactgatg ggttatctat taaagactta attgatgctg ctgatgctgc 73200
agagggatta aaatatgacg atgaagaagt caatccagaa gcagcacttc tgattgattc 73260
tccagttaaa tctgatatta aaattgaagt ggtagaaacg gataaaattc ctgaaaatac 73320
tgatgttttg attgaagata ctccttttgt tgaagaaaaa ttcgaacaag ctgtagctga 73380
gattattgaa tctgaaaaac ctgtattcgc tcttccagaa aactttagtc caaatcttca 73440
attattagga aaaaatccag gtttctgcac tgttccatgg tggatttatc aatggatcgc 73500
tgaaactcct gattggaaat ctcatccaac tagttttgaa cacgcgtcag cacaccaaac 73560
tttgtttagc ttaatttatt acattaatcg cgacggatca gttttaattc gtgaaacacg 73620
caattcttct ttcgtaacat taaaataagg ataacatatg gcttttacag ttgatataac 73680
tcctaaaaca cctgctggag ttatagatca gacccagcag tttactgcta cgcccagtgg 73740

-continued

```
tcaaactgga gatggaccta ttacctatgc ttggactgtt gacgatgcac cacaggaaga  73800
aacgtctgca acttttgatt atacgttaaa aggacctgcc ggtcaaaaga ctattaaggt  73860
agttgcaaca aaccaagttg cagatagtag tcctgaaaca gctcaagcat caactactat  73920
aacggttaaa aataaaactc agacaactac attggcagta actcccaata gtcccgctgc  73980
tggagtaatc ggaacagctg ttaaatttac tgctgcctta gcttctcaac ctgatggagc  74040
gtctgctaca tataaatggt atgtagatga ttctcaagtt ggtggagaaa ctaactctac  74100
atttagctat actccaacta caagtggagt aaaaagaatt aaatgcgtag cccaagtaac  74160
tgcagaaaat tacaatgaaa aggaagttac ttctaatgaa gtatcattaa cagttaataa  74220
gaagacaatg aatccacagg ttacattgac tcctccttct attaacgttc agcaagatgc  74280
ttcagctaca tttaccgcga atgtcactgg tgctccagaa gaagcgcaaa ttgaatattc  74340
atggaagaaa gattcttctc ctgcagaagg gtcaactaat gtatataccg ttgatacctc  74400
atctattgga agtcaaacta ttgaagttac tgcaactgtt actgcaactg attatgatag  74460
caaaactatt acagcagaag gtcaagttca ggtaactgat aaagttgctc cggaaccaga  74520
aggtgaattg ccttatgttc atcctcttcc acaccgtact tcagcttaca tctggtgcgg  74580
ttggtgggtt atggatgaaa tccaaaaaat gacagaagaa ggtaaagatt ggaaaactga  74640
tgatccagat agtaagtact acttgcatcg ttatacgctt cagaagatga tgaaagatta  74700
tccagaagtt gatgttcaag aatcacgtaa tggatacatc atccataaaa ctgctttaga  74760
aactggtatc atctatactt atccataatc gaaaggggct tcggcccctt ttttcatttt  74820
gaaagcacac aaaacacaat cagaaaatga tgtatataat ggcaccaact cgataacatg  74880
agattgatta tgagaactga agttgtggtg tttacgcttc atgagtctgg aaagtcattc  74940
attgaaattg ctcgtgaatt aaacttacag gcgaaagaag tggctgtatt atgggctcga  75000
gctatgactg caaagaataa atttgagact cgagaaaaag ttgtctatag aaaaagacac  75060
attaataaaa aggtgaaaaa tggaacagta tgatctttat gaaaatgaat cttttgctaa  75120
tcaattacgt gaaaaagcat taaaaagtaa acagtttaag ctagagtgtt ttattaaaga  75180
tttttcagaa cttgctaata aagcagctga acaaggtaaa acatatttta gttattattg  75240
tactgctcgt gataaattga ttactgaaga aattggtgat tggctgagaa aagaaggatt  75300
taattttaaa gtcaatagtg atcagcgtga tggtgattgg ttagaaatta cattttgagg  75360
attaattatg tttaaaaagt atagcagtct tgaaaatcat tacaactcta aatttattga  75420
aaaactttat agcttgggat tgactggcgg cgaatgggta gctcgtgaaa agattcacgg  75480
cacaaatttc tcattgatta ttgagcgtga taaagtaact tgcgctaaac gtactggacc  75540
gattcttcct gctgaagatt tctttgggta tgaaattatt ctaaagaatt acgctgattc  75600
cattaaagca gtacaagata ttatggaaac ttcagctgtt gtatcttatc aagtctttgg  75660
cgaattcgct ggacctggca ttcagaagaa tgttgattat ggtgataaag atttttatgt  75720
atttgacatt attgtcacta cagaaagtgg tgatgtgact tatgtcgatg attatatgat  75780
ggaatcattc tgtaatacat ttaaatttaa aatggctcca cttttaggtc gcggtaaatt  75840
tgaagagctt attaaattgc caaatgattt agattctgtc gtccaagatt ataattttac  75900
agtagaccat gctggattag ttgatgcaaa taaatgcgtt tggaatgccg aagcaaaagg  75960
cgaagtattt actgctgaag gatatgtatt gaaaccttgt tatccttctt ggctgcctaa  76020
tcgcaatcgt gtggccatca aatgcaagaa ctctaaattt agtgaaaaga aaaagtctga  76080
taagcctatt aaagttaaag ttgaattgtc agaagctgat aataaattgg ttggaatttt  76140
agcttgttat gttacattga accgagtaaa taacgttatt tccaaaattg gcgaaattag  76200
tccaaaagat tttggaaagg tgatgggatt aactgttcaa gatattttgg aagaaacttc  76260
tcgtgaaggt attactctaa cccaagcgga taatccttct ttggttaaaa aggaattagt  76320
taaaatggta caagatgtac ttcgtccggc ttggattgag ttggtgagct aaataaaaag  76380
ggacctttcg gtccctttgt tttattcatc aatgataatt tttggtagct taacacctaa  76440
taaaacggac aaatctgaac gacccgccat tttatccatg tctccaccat caattactct  76500
tgcttctttt tcatcttttg ctacggtgta aggatttgca gataaagcat atctaactaa  76560
taaaccgata gacggttgta agctttctgg atcaaccaca actttaaatg cacctacatg  76620
ttcagggtca tctaagtcga gaccttctgt atacggagca tagaaaattg atccaacaat  76680
ttctttttca ccgatatttt ctactacgcc aacgattaca taatctaatg ggctgttagt  76740
atcgcaataa agcggtaaac cattagctaa gaacccatag gcattttgtg aaagatactt  76800
gtcatcttct ggtttatgtt ttaaccaacc agatgcagca agaatcgcag cggcacgagc  76860
agaagcaaca cagaacgttg ctgtataagt tgattctttt tggatatgcg aaaccatttc  76920
gcataccatt cggtataatg aacgaccagc ttcaggtgca gatgcataac tcaaatcaat  76980
gaatccagta tcagtaattc ctgtaacttt ataacgtttt gatactgtaa tcaaagactg  77040
cagaatatct ttattgattt catctgccat ttcagttgca agcaaatctt ctaagaaatt  77100
aggagcatcg aatccattgg cttctaaatc ttgtgctaat tcaaccgtga taccagtttt  77160
aagtttacga gatttaactg cggtttgcca tttattaatc tggaatctag catccgcaat  77220
ttcactatca gagctttcaa atttgcttgt tgacgctgcg tcagaaaata gacgaacctt  77280
taaaagaaca attgcaatct gaagagctaa ttctaaatca ctttcttcaa tatcagcaaa  77340
tggtgtatct tctaatactt tataaacgat attattatat ttgaataaat cgcctttatt  77400
gagagttaat ttagactctt ctgttaattc tgtgattttt tctcggtcta catatccagc  77460
ttcgccagca taagtagcac cagttttaaa tgtaaattcg ttgtctgggt taaggtattt  77520
gataccataa aaagcagcaa caggttgatt agttctttgc gttgctacaa tgtcagaata  77580
tattaattta gtggtagcgc gagtcaaagc aacgagattt gggcgaccga ttgagttgct  77640
attcgttgtg gttgattcgc gcagaagttc gttgatttta gccattgcgc tttcctttca  77700
gtttatatga tttatttata ccataaaaac aactaaaggg acccgaaggt cccttaaatc  77760
gtcaaagatt agataccttt aacatataca cggcggaagt aagcgttctt accaaggctg  77820
ttcaggatag aaggcatacc actctgaatg cgagaagccg gagcctgagc agcggattct  77880
gcaaatgggt tgataccgat accgtaacga gttttgaacc ccattaccgg ttggaagttc  77940
ttcggatcag aaccacgcag tggagtcaga gctacatatg gagcgtagta aataccagca  78000
tccatttcgt tcggaccttt ataacctaca gtgaaataat cctgtttagc atactggtcg  78060
atatatacac ggtatttacc acccagaaca ccagcaaata ctgacttggt agtatcagtg  78120
ttaaagccgg tagccagacc ttgtgcagca taagaaatgc cggtatcaac tgaagccaga  78180
acgttaacta cgttacggga agcgataatg aagttacctt caccacgacc ggtttgacga  78240
gcaatttcaa ctgcttcttt gtcaatctgg aacaacagag ctttaaagga ttcacccgcc  78300
cagcgagcac cacgaatatc gattgggtcc tggaagtcaa atacaccagc tttagaaccc  78360
ggagtcaggg tcataccaga tttaccaacc tgagctgagt agttaatcca atcaacaact  78420
tcacggttga tttccaacat gatttcggta gccagaatac cagacagttc agcatcagca  78480
```

```
tccataccat gaacagcgcg gaggtcttgt gctaattcaa tagagtaagc agctttcagc  78540
tgacgagatt tagcttcgat aacttgctta tcgatacgga agcccatttc attccatggg  78600
ttatcggtag aaccgttaaa accttcctgg agttcagcga tagaagtagc cataccttca  78660
gcgatttcta ccagtacacc tgcttccatt tgtttcttaa tttcagcatc taatttagct  78720
gcgtcagatg cgcctgaatc aatttgttta gcttctgtag cttgcagata cacagtacca  78780
gtgtcctgga agaagtgggt gtaaatagtt ccaacttcaa gagtatcact tgctttcaaa  78840
gcagcgaatt tcttagcagc accctgacca gagaacattg catctggacc atacattggg  78900
tggaatgctt ctttagcgcc ggaagcgatt gggtctttac catataccgc acgaagtgcg  78960
aatacctgac cagtcgggct gttcatcggc tgaacaccgc aaatatcgaa agcaatcagg  79020
ttaggaatag cacgacgtac catacccata acagctgggc caatctgagt tactgcgcca  79080
gaagtctgac ctgcagcgat gttggtagca ttgtaaccgt ggtcaccacc gatttcagct  79140
tctgttaaga aagaaccgaa tgcctgagca atttttcgt ctttatattc cggagctgtc  79200
tggaaatctt tttcctggtt ttcaaagatt ttagcgataa tcgcttgttt gctattagca  79260
atttccggta aaccttcacc ttccagtaat ggcttccatt tgttcaaaag ttcagcttta  79320
gttttgatag tcatttgtgt taacctttaa aattagaaac gagatgcgac tttcgcatat  79380
acacttacaa tatcttctgc accttgcgca gatttatctt ctacagcttc agtgacgaaa  79440
ttcagtccgg ctgcttcagt atcaggagta tttatactct cagtaatagt gctttcatct  79500
ttattagatt tcttcaccat ttctacgatg gcactcaatt tgcttgagaa tgcatctgaa  79560
taatcaatac cttcgaccag agcagagact ttttcttttt gagactcagt cagatcttta  79620
gtactttcgc tcaatgccac ttcacgctgc acataattga tatatgcgtc acgcttattg  79680
agttcttcga acagacgagc tgattcttct ttgtgttctt gcagttcttc ttccatttca  79740
gctacaacat caactgattc ttctggaaca acaacgttgt gttcaacgaa gagctctttc  79800
aatccaccaa gcatggattc aaacagttcg gctttgatgc ctttatctac tgctaattta  79860
ttttcagtga gccattcttt tgcaagatgg tcaaggaatt tagaagcttg ctcagcgatt  79920
ttcttctcag ctttttcttc tgcttcttct ttattttttt ctacttcttc ttctgctttt  79980
tcagcaattt tagcgatatg agattcagct aatttaacgg cgtgctgctt gacggtagct  80040
tcgaatacag tgccgaaagt ttcttttgct tccggagaaa tattaactga ttcgaaaata  80100
ctatcaagag caacggaagc atcaattttc tgcgcttcgg caatcagttg ttctttaagc  80160
attttgtagt cctgttgttt agataataat atttataacg ctttttttcat ggcctctgcg  80220
agagccatat aggcgtcatc ggcacttgta tcggcttccg ccgtctgtga ttcggtaatt  80280
tccttaggag ttacccatgc atctggagca cttggacccc atactgcatc aacacctaca  80340
gttaatttga atccttcgtt tacgatacga taacctttat ttgtgtcagt caatgaacct  80400
aatccacgag aagaaactcc tggaatccat ccggcacgaa tattagctgc taatttatct  80460
ccaggaccat ggtcaccttc aataacacga gctcgtccgt atacgtcatt tcctttccac  80520
cacatatctt ctataatgat agcggcttgc atcgggtcaa cattagcgcg tggaggatga  80580
tttaattctc cgagagcttg tttagttaaa acttgctcat taatatagtc ttttaccgct  80640
ttttctaata tgcgttttgg ataaagacgt ttatttctat tgacgacttc cgcttgcata  80700
aatattcctt cgatgtataa accaggtttt aaacctaagt cttttccatc atgagattca  80760
agcattggta cgccatcaat aatttcgcca ggttgacccc aagtttcaat tagtaattgg  80820
ggttcattca ttagcttaat cctaatgctt tacggcgttt aagagctttt ttacgcttac  80880
gctgagcacg agattgacct gctggattgg caatcttcgt tttggtagct ttacgagcaa  80940
tttgtctacg ttttgcttta gacaacccgg tagtttgaaa tgcattacgt tcgcgggttt  81000
tgcgatcttt agtgcgagta atttcaccac gggcagaaac atgtttaacg atgaattcat  81060
ttaacggcat attttcatta atagaagcta atgcaaccgc taaatcagtt tcatcatcaa  81120
gcatattctc gataatttta tttatatcgt ctttatttaa agcagaagac aactcgtcaa  81180
agcgaccctg tgcttcagga ataagtgctt cgacattctc gagaactaat tcatgagttt  81240
cagggattag aatcattatt catcatcctc gtcttcgtca gagtctttgt ctttttttgtc  81300
gtctttatca tcgctatctt cgtcatcatc ttcatcttca tcttcaggtt cttcaccctc  81360
gattaagaaa ttacgagcga tagtgatttt ttcttctttg attaaatcag tcgttcttgc  81420
agccatggct tcagcaaaga atttacgagc ggctacgagg tcgtttgatt taatagcttc  81480
aattaaacct tccattaaaa atcctcttgt tcttggtcgg ggtcttggaa acgagcctct  81540
ttagactctt cttcaatttg cttggcttct tgttctattt cttcatcagt catctgcaaa  81600
atatctttca tagcagttct gtgagaaata tatttaccaa taaatggttc tgccatggtt  81660
agcatattaa ttcttcgttc caaaatttct gcttctttga gctcagcaaa gtagctatcc  81720
cgatgaaatt ctatcttaat attatttatt tcatcattcc actcatcttc tgtgattata  81780
cctttaagca aaagatttgt tttaagcgga tctaggaaaa cttcttcaaa cttatgctgc  81840
agctcacgaa taaatttagc aaacgttaat tcatcacgtg taatgctagt tccggaatca  81900
aacatcacac cgccttgttg gtcttgcgga atgcgtgaaa gaggaacacg taatgccata  81960
taaagagctt gtctaaacca acgaacatct tccatattac cggtattatc agcaccagga  82020
agagtatcaa cttctgtcac agcttacca tcacggcgct gcaaccaata gtcttcggtc  82080
atagacatat tatgttgttg atttttttatt ttacctgttg atgcatcata tactactcgg  82140
tttttcatcg tgttcataac atgttgcata tgctcagcag ctttacgagc aggcatatta  82200
cctgtgtcta cataccacac acgacggtca ggagcacgag taatgcgata aatgactaca  82260
gcatcttcta ataattttaa ttggttagca ggtttaacag cacgatgtaa atacccgatg  82320
atatttttac cacaacaatc gactaatcca gaatgggcat aaacaacagc agctttagga  82380
atttttattt ttgtgccagc ttcatacatt ctaccatcac atgcatatga ctcatgggca  82440
gtatcatata taaaatattc tttgtaacct ttaactattt ttgtgccagc ttcagtttct  82500
gttataattt cacgaacata ctggacttga cgagggtcta atctacgtaa ttcctttatg  82560
ccttcttttg gacgttttgg atcaatgatt ttatggaaga aaattcttga atcgacatac  82620
caacgtctaa aatgatcaga accttttcgt tgaaacgata gatgatttaa tacatcacta  82680
aattcatcta acatcatatt tttaattttt gggctaaatt tagatttatc caaatttaac  82740
gctacgactt cagtatcatc ttcatagacg atagcatctg aaacgatttc tgaaactgca  82800
ttatctactt catagttatt catgagatta cgatatgtat caataagctc acgagtagtt  82860
ttcattcctg gttcatatga accaaaaatt gtttggaatg cagcattata aggagaagca  82920
gcttcattcg agcttacttc aaattctctt gctccatcat caagctttgg ggctgtaatg  82980
gaaacaagat cttcttttc ttggtcttta aaatttcgtt cgtccatttt agcccatgga  83040
gcaaacaaac ttaatacatt aaatttcatt gtattctcca aatgggaatt atagttatat  83100
ttataatgga cttctctgct ttaagcagga tggggatttc tccccattca ttttattccc  83160
aataatcgag agcaagagtt acttcaaagg tttgaatttc attgtttgaa tcccaatcta  83220
```

```
attgaagttc acccacgtta gtaggccaca gacctttaat ttcaatttct tttgttactg  83280
ttttagcgtc acgagcatat tgacgaacga tagcgctctt tttatactct gcaggttttc  83340
caccagtaat ttcgtttcct tgccccgcag caatgctttg ccaatcaacg aacttctggc  83400
gagcatcatg tgcctcatcg ttcattactg taacagtcca gtcatcgaat gtacgatcac  83460
ctgctacgtt aattttacgg ttcataaatc cgactggaat tttttctaca ataccagctg  83520
gtaaagcagt ggctttacat tggaacgtaa aattttgtcc aagataagaa atttctactt  83580
ggaataagtt aggtcgagca aaatcaccag attcaaacgc tcgtgttaca tcatctacaa  83640
acatattagc ctctgtagta tttatatccc tatgtttaac ctagggcata tagaattaaa  83700
gaattaagga tatagtgtat ttatatggcc tgccgaaaca ggcctttaga atgcaccgta  83760
ttaaccagca agaccagtta actcatcgaa atctgcacca gtagcagtcg caacgaagtt  83820
aagctggata taatttatac tgcgcgccgg ttggatgtag aatgttgcaa caaactcatt  83880
tctatcaatt actgacggag tgttatttgt tgtatcgcaa actacacgat attcataaat  83940
tccgccaaga gctttaattc cttgcaagta ctgagcagtt tctgtacgga atgaagaacg  84000
agtaaacgcg ttgtttaatt cgaacaaacg atattttgaa ctacgtccga tattcgtttt  84060
caacatatta aacagacgac gaacgttaat acgatcaaat ggagaaggaa cagaagtagc  84120
tgttttatca ccatacaata cgtaaccatc accaccagta ccagttactg ggttgatagc  84180
ttcttgatat aagcggtcac gttgtgcctg gcgagtttca atagcaagtt taataacgtt  84240
aagaatctgg ccacgattat aaccagctgg tgacatccaa gtctgagata cgttatcagt  84300
tcttgcgcat aaaccagcaa tatcagctgc taatggaacc caacgattca catcattata  84360
tttgtcatac tgatatttgt agttaccatc aattgctgcg taggttgaac taatattaaa  84420
gttattatca gtatatgaac ctgcggcagt tctccaattg actaagttat caacagcacg  84480
ggttacagga attccaacta cagtttcacg cggtggtgag cacaatacta agcaatcctg  84540
gcgagcatca ccaattgaaa cgacgtgttt ttggacagta gatgctgttt ctaaagattc  84600
accagcacaa gaacccgcaa taaacagttg aacgtcaaca gattcacggt cagcaaagaa  84660
gtcccaagct tccatcaaat ctcctgctgt tacttcagca tttgatgata atccaccaga  84720
cagagttaaa attccagaga agccttctgg ccagttttgt gcagttgcaa aaatatattc  84780
tgagccgcct tttgcgaaaa agtcatcgat atagatgtta ctatcgtaaa tatctttttc  84840
gccacgctta gttgaaagaa caacgctttg aacaatagca tcatttcgac gaactataat  84900
agcgtactgt gagtcagtct gcggcccata tccaaatact gccttggcag tagatgcacg  84960
agtaccacca cctggataaa ttggcagtaa tgcagaagcg cctttcgcat agtcagcttt  85020
agatacgatt tcaatttcaa ttttatcgcc taattcgcct ggatagagag ctactactcc  85080
tggaattcca tatttttcaa gatttgcctg aaaatcaact gctgtcatag cagtttcagc  85140
gctctcgatt tcagctaata aaataccgga atcagtaata atttttccaa gagttattac  85200
tgcagctaaa ccggaagaag atgaagaaat ttctgcagtc cagttagaac ctaatgttgg  85260
gtattcgcca acttctttag ctttagcaat aatttttgca gtaggaatat taattttctt  85320
aatttttcca tctgcgtcta cttcggtaat tttaccttca gtttcaatat catctgaaac  85380
atatttgacc gtgattttat ctccaactgc atagttacta cctggggtag aaattgtgta  85440
ttcaatatta ccagcaatcg gagatgagtt tttagcggta tctctatcaa cagcacgaac  85500
tactcgtaag tcatttccgt actgcaagaa attcatcgca gacataaaat agtcagcagt  85560
ttcagcggtt ggttgaccaa aagtattaac taaatctact tcatttgtaa cctgtttaat  85620
ctgaaaagca ggaccccact ggaatttacc ggccaaagct gctgtaccag tagagttatt  85680
aaccacggtg ctttgaaccg tagtttcttt gagctcaatg cccggagata ataaagtcat  85740
ttttaatcct ctttaatatg ctttaatata tttataccat tgacatacca tgagatactg  85800
gaacatactc agcagaatga accgaatcaa caaatataac tggagcgtat tcatcaccca  85860
tatcttggag ttcttttgaa aacacttcag atgctaatcg catgtcatct ttgtcagcat  85920
aatcaataaa ttttgattgt gttgataacc atccaaaaat tactaaagac attactaaat  85980
cgtcgtgata accttcttca gccgcccaag acacgccttt ttcactaaac gttctaaact  86040
cttgaatagt tgcacggtga tgaataataa gcttatcttt ttcaataagg tcttttaatg  86100
tagagcatcc gactgctttc gttcgtttag tttgcttcat tcctaaatca gtatatgaat  86160
cgcaaataac gccttcgtat tctaaatcca tataaagcga tttagcaact gacacaccag  86220
tactatttaa ttcaatataa actgggcatt cattatattc tactaaataa cgcataacga  86280
tgtcaggtag aattaaatga gaaatagtgt ttgagtgtaa aacaccaact tgttcccaca  86340
catcatcggt aacatcaata atatgtaaag cgtggtaatc ttgcccacga ccttctgagc  86400
agtctagagt tgcaatatat tttctatctg gttcagggct tttaaatcga tgaaaaccgt  86460
gatcatctgg agttacttca atgaaatcca taacagctaa tttcattcct gaaattaatg  86520
taccagaagt cccttcaaat gctgcggtgt gttcttgacg aaattgagct aaagtagaac  86580
cattaatggt ttgtatgctc cattgccatc catcgtcaaa aatatcttca tcgttataaa  86640
gacgttcttt aactgaattc caaatagcag tatatggttc aaatccagat ttaccttcaa  86700
cggctgcagt ccaaatatca taaaaatgat ttaatccatt aggagtcgta gtaataataa  86760
ttttagaacg acgaccagat gaaattactg gctgaatagc aagccaggaa tcatggaagt  86820
ttggaataaa tgcacattcg tcaatgtaaa tcattgcgaa cgagttacca cgaactgcgt  86880
caggagagga agcataggct ccgattgagg aaccattatc aagttcaata gaccctttat  86940
tccattcaac aattcctggc tgtaaaaagt caggaagcag ttcaattgct tgcttagtac  87000
ggtctaaaac ttccgcagac attgagcctt tgtgcgcaag aatacctaca gctttatcct  87060
tgttaaaaca tacaaagtgt gcaaggaaaa tagctactac agttgtttta ccgagctggc  87120
gcgatagatt acaaacagtc atacgtttag atgacattat tttgagcata tcacgctgat  87180
agtcacgtaa ttgaaccttt atgacaccat agtcgatatg agtaatggcg cagtatgttt  87240
ctgcaaaata aacaatatcg tctcggcatt ttttccattc ctcaaccatt tcacgagtcc  87300
attgtgtttt aatattagct cgttttaagt taggaagacc catataccga gatcttttat  87360
tattcttatc tttataagtt tgaaataatt caggcttatc agaattattt gggattttta  87420
ctattttgtg taaacgaaga taatcgctga atttttcagg ataccatttt ccatcccact  87480
gagattttat ccaatgaatt ccgtcttcat cttttctttc cgctaaactt gggtgtttta  87540
ttaaaatttt tccagcttca tttaacggat ggaaatcatt taatgcatta atcggttgtt  87600
ccatttatca ccttctcacg agcttcttga gcctcgtaag catcaccaat ttcgtccatt  87660
aattctgttg gtgaacccat gaatactgtc gcgttctgaa tattcatttg acctgtagga  87720
acagcgcctt tggtgccaac ctgctcagat gtaatatctt tcatatcttt atgaagcttc  87780
agtatttctc tgttcgtcgt agtcatttgc cccataagag ttgcaaatac ttccatgtga  87840
cgaggagaat cagcattctt tgctgtctca agaaaaatct tggccgcgtc cattagcatt  87900
tgttgttgaa aatgcatatt tcgacgaact actccataat catcttctaa atctggagta  87960
```

-continued

```
cggttttgtg gattactttt aacttctact aattgcagag gttcatatac tttaatttcc  88020
tccccgtcaa ttccggggag gtcagaaata tctaaaagtt tgtttatatc aagaccttcc  88080
ataataacct ctatgttctt gggccaggag gttctggcgg tgttggtcta tttacattgt  88140
tagtgaaagt ttgttttact gttccatccc agtcttctgg gtcaatatct cgaggaacaa  88200
cttcattatc aacagattca aaaacgcctt cgccatcagg caaatctctg gtattagcat  88260
gaaaatctgt ataagtagta cgaattaatc cttctgcatc atctactgga ggatacatcc  88320
atccatttac ttcaaatgtt aatgaccatt caattctacg acgagataaa ttgtccccat  88380
ctatagcttc gtctatagca gcagacatca gtacaatttt aatatccctt ttaaatggaa  88440
tatcatttcc aaactgctcg tacatagttg tattaaaatg aggttgaaaa tatggaagaa  88500
tctgttcaac tatttgaaac atatcatctt cgtagcgagt aaagatactc aattcataaa  88560
tcattttaat aggagatgga ttatactgcg atactacaga agttgtacct ttttgcagta  88620
aattctgatt taaaatgttt gttttaaatg gagcgttata gctaaaatca actaaatgca  88680
aatttatacg aggtagaata gtttcaactt tagctacatc ttcttgtgaa tttattgatg  88740
tccatttatt caatttcatc ataaagtgtt cctttgatgc atacgtaata ggaacacgta  88800
taaacttatc accagattct aactgacgct tgatttggat atttgaaaac aaatcgccca  88860
tcaaggtagc atatcgtcta aaagacgaat tataaaaata accaaacatg atttctccta  88920
atctgggctt taattagttt ataatattta ttaatccatg aaatcattat caaatgggct  88980
agattcgaaa gattttcctc tgttattgac aacaacataa ggttcaacat attctttagc  89040
ttcagaatta atttgatcta cttcagcata ttgatcaata ttaatatcat gaataccgtt  89100
aagattgcga acaggattta gttctaattc actaaattct ggaatgttaa ttccttcgtt  89160
tttctgtaga actggattaa tttcttctcc agaataaatg aatttacctg ctgtaatttt  89220
acgaatagcg ttttggccta attgataaaa tgggtcatat ggttcaaccc agttgatttc  89280
aaataagctg ttatccatag gaaaatatat caaatcacct tccttgggtt cttttccatt  89340
tacttgatgt ttaaacaggt ttggattaat ggacaaagtt acttcatcct gtacttgcat  89400
accaaagtta ccaaagaacg atttagctcc ttcatatcct tcaaatgaat ttaaatatgc  89460
agcaaatttc catgctttag taaatttatt ttttaggtct tcgccgaata ccaaatcagg  89520
ggaaacatac tctcttggaa cataatagca ttctacacct cgcatttgaa tgctttcagc  89580
tactaataca tcagctagta tttggctgtt ttgatagtgg ttaaaattta cataaggatt  89640
tagtatttct gtttcattgg tctgagaata acctgtgcgg ttttccaatt tagcaaaaag  89700
atttttatca taagtagcca tattaaccta caaaaattcc aaatggaggg tcaagtaagt  89760
ataattcttc gcgcagtgct tctttttcta aacgagcttc ttctattaaa cgttgaccat  89820
caattgtaac gccgccggga agcatcattc cttggtgacg tgctaaaatt tggccattta  89880
gttctttagc taaagctgtt gcatagtctt tcacccaacg attattataa gcaccttgct  89940
taacatctgg atcttgacca acaacacggc ctactaaatt gcggtctgga ttattatatc  90000
gttcagataa tgaccagcta tcttgtggac cgactgttcc atatcctact gtatttccaa  90060
ccattttgtt tgtatcaatg tatgatttag tccagctttc tacgataatc aaatcatatt  90120
tttggaagtt tcccatgact ttgagttgtt catttgctga attaaaccaa aagtctggaa  90180
taggcgaaag catatcttgc atcattccca tgtaactagt aagctgggta aaatatccta  90240
aatcagctcc aaaggcattt ggtccataaa atctattaca agaagttccc atgccaccat  90300
taataccagc cattcctaaa agaaagtcag taaaccatgg atatgtagcg tttccgtcca  90360
ttgacgttat tgatccaata ttcgtgcgca aaatgcgagt tactgcaaat acgttagaac  90420
ctcttaaatc aaatactcca gtcttatact tttcttcatc gtctcctaca taaaatacgt  90480
gaaaaccttt gttaagtcca tcaaaatggt attcaccgta taattctagg gcacgctgga  90540
tacaatcata aatttgatcg ggtgttaact caacattaat aattggagcc cctaaacgtc  90600
ttagaatgac atctttgagt tcctttggat tctgagaatt atatcctgac atttaaaatc  90660
ctttagggcc ttgcggcccc atgttatgct ggtgataaaa aggtagaaag caatacccat  90720
tcgccgtctt tacgaacgta agcttgacca tcttttggag cttcaggaat ataaccagct  90780
tcttgtaaag tctggacatc cctctgcaat gaggacacat tacctttaat actacgaatc  90840
tcttgattaa ttgaagaaat gttagtctca ttagctttta ttgaattagt caatccgcgt  90900
tcttcgacag ttgaaccatt cggatttgtt ccatttacta atttatttag tgttacaact  90960
tgccctttaa ttccggaatt gttattacca atttcaacct gtaagttttg aacatcattg  91020
ttaagtctat taacagaggt ttcaacagtt gaaactctat ttaaaagaga ccccggagga  91080
gaaggttgac ctccgctaga atcagttcca actatctgat ttagccatga aacgttagct  91140
cttaaaccgg acgaggtgtt ttcacctaca attccattta aagattcaat agaagtggta  91200
ttatctttaa tttgaccttt aatactagaa ggaatatcat ctgaaccaat cgatgtttca  91260
ataacagtta atcgctgttt aacgccgcca cttttattta gttcatcatt taaagctgaa  91320
atttcttgac tgttgacatt gacatctgtg attattgaag tatttcctgg atatccaata  91380
gaagttttga tagatttaat ttcggaacta agattaatct gtgattgatc taaattatgc  91440
acacgtgaat atatgctttc actaaatgaa gatggtcttt gtccaagttc ttgtctaaga  91500
tttccgactt caattgtcag tgaacctaca tcagattcaa taaatttttc ttccaaatca  91560
cttagacgta ttccttggga agttatagca tctgtattat taatgatacg gtgcttcatc  91620
cccgtgctgc tatttcctac aacaggaaga ccattaatat cttgcccagc atattgtcct  91680
aattcccttt taatccataa caaatcattt ctaatcgttc tataaactga atttgcttgc  91740
gaattaaatg gaccaatatc agaaagaata ttatcaaccg tagtatttgt accatttaat  91800
atatcagtgt gttcattcgt aagcgtcttt aaatttgata tgtcattttt attaacgcta  91860
atctgtgata gtgcttcgat atctccagat acatccaaaa tgccttgaat tgttttaata  91920
tcttcctgtg atgtttcaac gacagtttta agaattccta tattttcatc aagaacctca  91980
acatttttaa atacggacac aattggtcta ttcattgatc catcgtttcc atacttagta  92040
ctagctccta gtatttcttc accattttta atccatgaaa tacgttcctg accttcgcca  92100
ggaacgctat caacaaaagg taaatctttt aattcaatca tttgtaatcc ttagtaatga  92160
attttaataa tatagtttaa tgatatattc catggtctag tttcataacc aattaatcct  92220
tcacgattaa gtgtaccaag ggcatctctc ggtccaccta attcaaatcc atcattagtg  92280
aagtatgaag cattatccca gtcggcatat tttctagttc caagatatcc ttgataaacg  92340
gacgcgccaa atggagcttc atgtctttgg tattctcccc aaccgccagc atgtttatgg  92400
tatgacatct gttgtgcttg aacaccgcca acatgcattc cgtcacatcc tacaccaagt  92460
ctatccttcc cgtaaccatc ttgccctcgt tgatttaaaa tatgaccacc agtaccagct  92520
cctctgacga aaagacctcg catatcagga atgccaggat tattccaatc gccaccaaat  92580
ctcgttccaa ctgtgtttct ataatcagga tattgatctc ctgacacagt tccaccatgg  92640
cacataatcc aaccaggagg agctgaatct ccagcaaaca tcataatagt tccaactgga  92700
```

```
acccttttcgg acgcatatct ttcagtggca acaggttgat cgccattttt ccacattccg  92760
ccgcgtgacc aaattccatt tgctgttaaa tgatctaaat ttaaagaacc attaatagtt  92820
tgtccaccgc gagtattaat tacatctgcg ttccatgcta atgctccaga gctatcacct  92880
tcaggggcaa taccggcttg cgtcgttaat tttactaccc cacgcataga accggtagct  92940
cctcgaccat ttaatgtttc acctgttaca gcaacatctc ccaaattact gttaatttcc  93000
gattgcgttc ctaaacgtat aacaccctta tattcttgtg ttgcaacaga attcataaag  93060
gtatacggag aaattgcata tccttcgcgg agagttcctt gacgagtttg agcgacagtt  93120
gataactgaa ctacgcctct aacagattct gatgctgtgt cttctgaagg agctatttgc  93180
gaaattaatt ttattgcaag tttttgtgtt tttagcggag tcattgccgt agtatcatct  93240
acaccagcta aagctgcagg tgtagatgat attttaataa ccccgtttga tgactcagac  93300
gaatatctat tttggaacac atcgtcagta tggtatttca gtttttgcgg cgttattgat  93360
gaattattat ctgagccttc taatgtttct tcatttgttg aatagcgcgt taaaccatac  93420
ttagtttcag tagcatttgg atacaataat cttgttgcta atgtagctgg tgtaacgatt  93480
ttagaattat tagttccatc taaaacctct tgctctgacg caatcattgc tattccttta  93540
acttccatag ttgcatcagg aataccattt acgccgatgt tacttatttt tgataatgca  93600
gactgcactg tcgtgacagt gtcaggaaaa ttcgatccta caggatcgaa tttaacgtat  93660
tttgattcat ttgatacgtg ctgatatgta ttgttactca tgctattctc tcaaaataat  93720
aaaataccgt aggttgtgtg tgactatcta gcgtgacagt ttgcgcacct aataattgcc  93780
aagttccgta tccaggttta gaaggagaaa ttatttcttg tttgaaagta attcctttat  93840
cagagtattg ttctaagata tgttcttggt tatctaaata cttaacttgt attttatttc  93900
ctatggtagg atggtcttca aatgaatcaa ttgcaataaa ttttgcaacc atttcctgta  93960
gagctgttct aacggcactg gtaaattcga ttgaagtcat tccattagta gctttaactg  94020
gaataccaaa catgttaaca ataactgtgt cacctggttt ggctgaagta tcattgacag  94080
ttccttcaaa tgaccagtag tctgtttgtt gcactccagt aggagatacg ccacttatat  94140
taactaatac agctccaacc tgttgctctg ccatatttct aacatcattg atagcagatt  94200
ctacatttgg gtcataaaaa ccttttgcta tttgtgaaat tgttacagca cctactggct  94260
gattattcat aaccgaaata tcatttttct tagttctaaa accaagaaaa tctgctaagc  94320
gggaaataac tcccgcttta ttattaagta aactcattat gcaatcctta tccaacggta  94380
tacagtaata gacggttgaa tattactaat attagcagga ggagtatgtg aagagtttgt  94440
tgttgcgtag tcttcacgat attttgtata tataggacca gtttcgtctg ggtcatattg  94500
acatcctcca ataataactg atccattttc gtcttcaatt aaaactcttt catcggtttt  94560
agtcgcagga agatttgcgt tttcaagcgt tactgatgtt gtaccaactg ttccaccggc  94620
ggtatgtgaa ggatttccgc tagaatctaa atcattattg tttaatgcaa agtttggatc  94680
tgtgacatca tcattccatc ctactaaaac ctgcccttta ccaaataatt tccatgaacc  94740
aaatcccata taagtcaccg gattatttgg gtttatagca ttttcataaa ttgaaccaac  94800
aggataaatg ctgtcgaaaa tagatgatat tgaattatac gttctagtat aagaatcaac  94860
tttttcaaca tttggccaac cgattttatc aaaatctgtt aaggctacat caccagtaac  94920
ttcagtagat gatcctttac taacataacg gtcatcagtt aattcaataa tgtcatcttt  94980
ttctaaaaga gttcctaaat cattattgaa ccatgttata acgattatat cgccagattc  95040
aaattttcta tcaaataaaa gactgacagg ttttccatct tcatattcta tagaataatc  95100
tgtattcgat tctttccatt caccaccaag agatatacat cctgcttgcg tatctgaatt  95160
agcaccttca cacaaaaaca gaggatatcc ggctgttcca gcttgttgtt gtaaaattcc  95220
attaaaacga acttcaagag aattaggatt aataggttct ccaggaatta atccaaatgc  95280
agagaatgga attgatttca ttgttgataa atcagtaacg taaatacttc cttctaaaga  95340
agtttttgac gttaattttg aatctaatac ttttatttgg cgtcttgtat atgaacttct  95400
ccattgtgat acaccatcca taaatgtttc aatttgaaca gtgtcaccaa tattacaagg  95460
ctgtcttaac ctaatattaa atccatcaag aggaatcaat tctccttcat tttccccagg  95520
agagccaaag tcactgtttt cactaaatac atcgccgtaa tataattcat taccgcggtg  95580
ttttactcgg atgttattaa cattatagct agttccacgg aaaacatcta aaaagtctgt  95640
ttgtccttga acttcgacta aaaattcttt acgtgctaca ttactaatat ctgaactaat  95700
aattttgtca atttgtttgt ttttgacata ttcccaacgt cctggagcac aataaactaa  95760
ctctaaatcg ctaaattgaa cattaatttc aactgatgac gatgatcctt taatagtatc  95820
accagaagcg gctactagag taactggatt aacattccat gttgcaaata cgtccctagc  95880
tttaattact ttattataat cattaactgt tcctttagga agttgtagag ttactcttcc  95940
agatgaagtg ttaatggcat atgattttcc ccattctgct gctaatgttt gtcctgatga  96000
agcattataa gttttccagg caccagctga atatggaaca tcaccgtcac caagctcgta  96060
ataaagctca tcaaagtttt catttatttt tataccacct ttacgcaggt agtcaccggt  96120
accatcatct acaacattac cgatattaat attttgtttc attattgagc caccccgatt  96180
ttctgcgtag cgataacttt aactgctgct ctcataccga cagttgaaga acttatagtc  96240
gccgttacat aattttcttt aatactaaat gcaatattag cgatttcgtc ttcttcggtt  96300
tcattcccaa ctcgcatgac agcatattca gaagaaatga cctctgaatt aacaatatcc  96360
acaagaatat ttatttctgc tgttttaatt tttcttccat ctgctgactg gcatgtaact  96420
aacaatttag ccatgttata ttcagtgcga tgaaacaatg gaatgtcaac tgatccagat  96480
gtagaaatat tccacgtacc ttcaactggt gattcctttt gaccaaacat gctttcaata  96540
gaataattcc aaaccgacgt agaattatca gatgaaatac agcgtaaagt aactttacta  96600
tatggagtag ttactaccaa attacctgaa acacctttaa ttgaatcaat agcctgaatc  96660
gttaaaggat tagtaactga tattgatcca ttagaattaa tgaattcaac acaatcgcca  96720
agttctcctc tttcaatgat aactttaaca cctacagtag aggtatcaat atcatgtcta  96780
gtgccaactt ttactggagt tgcatactca gcaatagagt gtttttgata atatccagta  96840
gcatggataa tttgaccatc agctccggtg ccatttgcta ctgccatttt acgctgatcg  96900
ccaaacgcat tataaattgc gttaaaatca ctattaattt tattaccacc gtcgaataag  96960
atatcaccag tagaagcgtt accaatttcg ccggtatcaa tcaatttctt tggttcttga  97020
atgaacatag cggtttcctt atgagtttat agtatttata aagaaaaagg gagcccatgg  97080
gctcccttaa tttaaaatgt aaacagaata ttgatttctt ctgtttgatc cattgccata  97140
ataataggtg gcctattttc catataaatc atttcacccg aatgcctcat taaatcttct  97200
gggtcataat aatccttttc agctttaacg tttgggtcat ttggatgagc tttagcttca  97260
agaggattcg taattattga tatttgtcta aatcctttat ttcccggcaa tgcagcttca  97320
ggaaaataaa ctgaatctaa atatgcttta aaacggatag tatttgcctt aacacggtaa  97380
attaatccaa aatcatcttg ttgccaagtg agattatctt cataccccca tctagtcggg  97440
```

```
tcttctttta attcctcagg ccaaggaacc acgatatatt cattcgtgca tctatttata  97500
gatacatcag gcggaatctc aaaaagatat tcccacacat acccgtctcc gggttcaatt  97560
gttccttcag catctcctcg gccttcaggc ggagtcattg acctaacaga aggtgtccat  97620
tttccaccta atttgaggca ttcatcctta tcagttaaag atgttattga acacattcca  97680
gtatcaggaa catctaaaca acgatatact aaccagcctg cgcctgattc agtagcattg  97740
taaggagctg agttacacac tacaatatcg ttaattctaa atgtgtatgg atccggatat  97800
ctagtatctc cccaatctcg acgaggaata acagcatcaa gcattgatgg aagaaccttt  97860
actgttccca tcatatgcgt ccacatgtca gttacgccta atacagaatc agttggataa  97920
ggtggggcaa agcccacctc attttcattt gatgaccacg gttctgatct tccaaatgtg  97980
ataaagatag tgtttttatc cggaccactt ccaattgaat tataaaaatt caacattttt  98040
tctgttctaa attttgaagt aactatcgca cgatagataa cacttgaatc attcatctat  98100
tttaacctgt gttggatttt cagggtctct tggatttcct atattatctt ttagacgttt  98160
attaactaaa tctctaaatt gcgcaaatgt tgttccagat gcatcaaata aaggactcat  98220
taatttacgt cgttcagacg gcaattgacc ttgaaatatt gaattattat tttcagcatt  98280
atagtcatca ggaagaggat attctacacc agccattggg ccaggctcat aaattgcttc  98340
gcctgttact gaatcatgct caatttcacc ggttggagtt aatttagcta ctctatcagc  98400
atattcagta ggcaatccag aatcccattt atagtttttg tatttattaa ttatagtctc  98460
tgtgtgttta agagttaaac caacattaat aaacatcgtt aaaagggtaa ttgctataaa  98520
tccaaatcct actggatgaa caaaacgaat aacgtcagat ttccaacggg aagaaggtaa  98580
attggattta attttcatta catagtatga tctacttcta ttaatatagt ctatattgtt  98640
ttgaagcaaa tcctttcctt taaccccacg aataatttcg ccttcaaaac cagggagtct  98700
ttctgcttta acttcttgac cagcaattaa tcgtcctaaa agattatgaa tagttacggt  98760
ccattgcaat ttaccattag aatagcttct ttctatataa gtaacattac atcttcctgt  98820
tgccgtataa atcgtttgtc ctactaaatc ttcagtcaaa gaatcagatt gaacgattat  98880
gtcatattca gtaccggccc cagattcaat ttcaatttca acttcttcat tataaagaac  98940
tttaaaaaga aacttgtatg atgcttcaat tcctttagta gaataaaaat catagctacg  99000
tgattcaaag aatctcgcaa cagcatcacg tttatcagca tttaaataaa tgtttctttt  99060
atatatctct gaccacaaat attcccacgc atgctcttct cgtggatatt ggttacgaat  99120
taaatttcgt aaattgttat actgagttcc atatccgtca gaaagatatt gaatatatgc  99180
ttcacaaaat gcctcaaaat tagaatcttg taacaagtaa gaatcaggca tcattgtgcc  99240
aatcaatggt cttaaatcag ggtcagctaa tccacgttct tcttctggtg accaaggagt  99300
ttcgcgctct tggttttgta aaaatgcttt taaaaatact tcagttggct tccaaataat  99360
ttctactgta tctctcacac gatagttaaa atcataataa gaaattattt cgccagaaga  99420
tttgtagaaa agcattcctg atgcgtattt tttaaatccg gtgaatttaa catttggcat  99480
tactatcgtg caatcaccat catcccagta ttcatgaact aatctatctg gtgatgtttc  99540
tggaatattt tctataactt tagtgtattt taaatcagca taaactacta cagctctatc  99600
agagttgttt atccaacatc gtgtgttaga ttttttagac cagttaaaga acggttctgc  99660
gtagtatttc attggttgag gagtaaaagt ctcccaatca gatttttcat ccgctataaa  99720
tgccatcata tgataatgct tatcagctaa ccattcacga ggaaattcat atttaacagc  99780
accgattaac tgatatttca ccacagtttc agggtcatta acaatgttat cacttaaaaa  99840
tttaaaatta ctcgaagata gagaaactaa tttaccgtca gttgacatat tcgcatatcc  99900
gggttgaata cgtcttcttt cttcttcggt attaccgaaa actcttttcc acgttttcgt  99960
atcatggttt aaaacatata ttcctttatc agcagaatca attatttttg atgttctagg  100020
attggcattt aatgtttcaa cttcaccaat aataagagca aaaactttat caccaacaga  100080
atccatttta tagcatactg ctttaggatt tccggttata gtcatggtat caggttcaaa  100140
aagtctttcc gaatatgttg gagataatgg atcagaatct ataggtgcat tactcgtttt  100200
tatgtatcta actttgtctc tggcgacaac gtaaatgtaa tcatcggtgc aagtaatagc  100260
ttctgcaatg cggtatacat tcgctggtaa agtcgcataa gtggcaaaaa tttctacatc  100320
aaatcctaaa tgtaattggt cgccaagttt agcgaatgtt atatcctgtg aactgaatct  100380
gacatcatca gctgaccatc taacatcagt agatttgcgg ccatagaaaa tcttgtcgta  100440
tcctagaacg tatgtagtgt tcgcagattg gtaatatact gtcttagata aaggatatcc  100500
tacacggtca ttgaagagct ttacagcttt ccaggtttgt cctttatcat tagatacttt  100560
aaccacgggt tgataacgct caaaaagata tagaatccct tctgattcca tcaaataaac  100620
tcggttaata tccttacata cttgctgaat ggaaccttgt atttcatgat actcattttc  100680
accaataata aaattactga ttgatgaaac atcaacatat gatgggctga attggaacga  100740
ttcattcatc aatgcagcca ttatagtgtc attattaaaa ttgacataat tagaattgtt  100800
aagagtaaac ttttcctgaa tgaatttatt ggctaattgc atttcaatca tgttttgaaa  100860
tgtgtaagca ttcgtagcaa aagtttcaaa ctcttcagta taaatccaat cagactgctc  100920
aaaatcctgc gcagctgtag ctactctaat aatgtacgat gttaatggat tagcattatc  100980
aaaaaagaag ctgttatttg cagtatatcc taagttaatc catctgtatt gattgctcgg  101040
gagattttct cccgagtttg tttttgtctc agcgatttct acaaaatagt agaaattagc  101100
accaacgtca tcccagcgta cttgcacctg atttgcggat aacttggaaa ttctgagact  101160
agtgactgaa ggtgctttta ctgtcattgt gatataggct ccaaatcgat agttaagtat  101220
tgtggacgta aatcatttcc aaatacaatc agtgaaccat cgcgcgtgaa aataacatcg  101280
tctattggat cagaatatag ctcaatagtc tgaacctcaa atttatcgga tgttaaatta  101340
atttagcga tattccaata aatcatgtca gctggataat ttatttcacc gataacatag  101400
tatttgtcac gtccatcgga acttgctaat ttattaaaat cattgcctgt atatggctga  101460
atgttttcat tttctgtaac atcgccagaa gcaaatggac caataataac tttgccaatt  101520
cctttagaat ctcggtctgt tgatactata tgaacgtcat ataatacatc ttcttctaaa  101580
ccagtatcag gatttacaac ctttcgtcca gaattaaatg aaaacgtatt agattccata  101640
gaacgatctt ttatttgatt attgtattta atacccgctt caggcgtttt atagaagttt  101700
tgtacttcac gaaccatttg aatagtcgct gatgaaccaa tgacagaatg atctgcatca  101760
tctacatatg tcaacatctt agatttagcg aaagatgagt taaaaatttc tacatcttct  101820
gtataatagc gatcaatttt atcaattatt tgaccttcaa gccattgctc ggattcttgc  101880
agttttattta aagcatatgt gacttttaaa ttagtcttaa taaaaagata attaggagaa  101940
ataattgatg gcgtaatagg agctaaatta tagtctttga gataattttt aatatcttca  102000
cgctgtacgg tagttaaata cagacctgat ttaggtttgg cagcaatgaa tgcataccca  102060
ggtttagtag aatcagtgaa agtttgaaca gcttgaataa tagaaccaaa tctttctgag  102120
acaaatgtat cataatctgt cgcagttaca catcgctgct gagtttcacg cttaatagta  102180
```

```
cccaattcac gaatacgttc aatatcttct ggatcaccac caccatcagc accaacaaaa  102240
tctgggtcat cgtttggatt ttcattaata ttgatgacag ttatatttgt taatgtatct  102300
gcatatgaaa atccgactgc gccattcgca tctgcaccgt tagtactgat gtactcaata  102360
acaatcgtag agttctgggt aggtttaaga cctccgatat aattagcggt caaagctcct  102420
tcagaagcat taacagaaat ttcaccttcg ccaaaataga attcagtgtt tccatcaata  102480
gtttcacgca tgtagtaaat tgttgatgta gaaccagcat ggaccattga ctttcttgtc  102540
cagttaatcc attccgctcc atcaacatat aatttaacct ggtttctatc aatattttta  102600
tcataaatga taataggtgt taatttatca taaatgattt cagttcttac tatacgtccc  102660
tgggccaatt tcaatcgtgg aaaatattgg ttatttttat cacgaatagc aataacatct  102720
tcggtagata caaagttata aggattaaca gaagtatcct ttgcatatgc taaaaagcga  102780
gttccgcgag gaatagtaat gtaattccta ttcaatgcgt cggtgcatgt taacataatt  102840
tcggtctgcg cagcggattt tgaagtaggt aaatatccgt tatcttgtgc agcttgaaca  102900
actgaacttc gtaagttagc agtacgcata aagctttcat acacagcagc attaccaaac  102960
tgctgaatgt acagcgtatt ataagccaaa aggtcgcaca gaacgtttaa tcttgagcct  103020
tcaaaatcat aatccaaaaa ttcattttgg ccattaagcc attcaatgag gttttgtttt  103080
atttcagcaa acgtaccccc gacgaatatc tcgggaatag catttgctgt tcttgttaat  103140
tgataattta caggggtatt tgccatttta aatcctattt aatgaatact ttagatgatg  103200
cctgagccac agtatcaccg catgatattg gatcagccat ttgaacagct ttctttccag  103260
tgacatatac cttagaagtt ctgggttgtg tcactccgcc atgtgtttca tatggctttt  103320
taatttctgt atgttctgta attggatcgc ctgctactag aacagcaatt cctccagtga  103380
atactttact ttgtgtagca ttcacaactg ttggaggcca cgcttcatga ccagcagtaa  103440
cacatttatc ataacttaat cctgacatta ttgcctctca tacacgtagc ttctcagttt  103500
attagcccaa cgactccaat ttccaactat agttttagta taatttttaa cgagagtttt  103560
tcttattgga gcaggaggat ccgttggttc agtagtatca gaagatgacc tagaattact  103620
gccagaaccc ccagattcac tttgttcttg gtagtcatat attaatgtta cttcgtaagt  103680
gaatgtcttc tggaggtttt gaggagcttt ccatagatat aactgagtat tagaatcagt  103740
tgggaggtct tcccatgaag cagcagtttt aaattcatcg cctaaacgat atttcaacgc  103800
gtcatctcca aatccaaaca cagattcata tgttccatat aagcgatttt cttctactaa  103860
aaccccagga gtttcttcgt aactagttat atttatagat actaacgttt cacctgtttc  103920
taattgagcg gtaaaggtga cgtcgataga agaaccttcc atggattctc ctaaatcagc  103980
gctcattgga agtatattag ccaatgtcaa tcctcgatcc atcaattgtg tattgaccgg  104040
atgaaataga actcatagat gccatttttt ctgtccaatc accaccaacg tcccaatcaa  104100
ctgtcccagc aactttccaa gaaagatttc catttactgt attagtctga tttccttcaa  104160
ctaaagtggt agcatctcct ttaactgtaa tgtcagcatt accttcaact acaatagtaa  104220
cattaccttt aactaggata gttccattac cttcaaccgt cttagtttca tcgccacgta  104280
caaatattgt attgcttcca tctatttggt gaagacgatt atccatgttg taataaattt  104340
ctgatccacc gacgttagtc tttttatcgc cggctaccaa aaaattacca tcagcgttgg  104400
ttatatcata caaattatca acagtttttc ttgttcttct ccctgacggt gatacttctt  104460
cataagttcc agttggatga actaatctat atcgttcttg cccaggggta tcatcaaatt  104520
cctgaatatg tccactttca gtttccattg tatgcacata cggatattcg cctttatatg  104580
aagaaactgg ttctttgaat aaaattcttg agtcatttgg aataggaggg tcagctggat  104640
cagaagactt cgccacagta gcagccattg ccgacaaaga cctagctggt gttttaactt  104700
caataccata tgattccaaa tttccggtaa gaataatcat ggtaacacgg gatgcacggc  104760
cttttgtttg ttgataccac aacgaatcac gaccagcttt atatgctttt tcccaatctc  104820
ctgctaacat agcagttaac attgtgttaa atttagctac accgccaaca cccatctgaa  104880
atgccatatt ttctaatgcc atttgacgag aacggttgac agcttgccag actggtccta  104940
ctttagaatg tgatttaatg tcacgttgca tatcagctaa atcacgttca aataaagtta  105000
ccgcttcttc cattgtaata gaacctggat ttccagtaat ttcacgacca acttgttttg  105060
ataaaacttt attaatttga gccatatcac gaactggctg tttcatgata agatgaccaa  105120
taccaattgt cggatatcct tcagtatccc aataaacttt tagtcttaat ccttcatcac  105180
ggcgaagcat ttcagccatt gacatatttg gattatcatc agttggaatc tctgatagtg  105240
gtctatcatc gggatttatt gcggtgtcta agttactatc ttggataacg ttagaagacg  105300
aatcatatcc tacttctccg ccttggttta gtacgttagt atcatttcct aaacgtctag  105360
gatattgtcc agttggatca gaaaatcctt caagtctatt cggtttttcg cgaactattc  105420
caccatacgt gccaagaaca attccgttgg ttttccattt gtctaaaaaa tgaccataaa  105480
ctctagttcc ttctaccggt ccagtaacgg agcctccaat tccagacatt gctgcagaag  105540
ttataggttg aataactgac atccatggta atttttcagt tggaataccc attacatcac  105600
cttgtgctct ttgaggtgga tgcagaccaa caacacgaac acgaacacga cctaatttta  105660
atgggtccat tctatcttca acaacaccaa caaaccaatt aaggttatta cttatcattt  105720
ccataagatt tctccattat acgtataagg tcgttcataa atgaattaat gtctgatttt  105780
gctattattt ttatttgacg aagtttttca ttttcaagaa cagcagcttc atacgtatta  105840
acagcagcaa gcgctccttc atattgagga tattttttag ctttatcgcc tttatcatac  105900
caaacatatg gattatcatc gtatgatatt aaattgtaaa atttttcacc gttctcattc  105960
acatgatata ctatttggtc tccacctacg tttttgtatt tttgtataga tgcttgataa  106020
gcagcttctt gcgaagtaat ccatccataa tatggatcat aattatcatt acacatcaat  106080
aaaacccaat acaactgtgg atttccatat atagtatttg ctaattcttc cgggcgtggt  106140
gaacctttga tataataagt acgtaagcgg tatcccgcaa gagcgcgttt aaaatagtct  106200
ttatagtttc taaaaatatc tgtcatagga atagtcggcg cgtttttatt caccgttttg  106260
gccgcatatt caatcggatc aaaaaatgta aagagcatgg gccctcctgt ttataaatat  106320
attatctatt tataaggaga atccaatggc atattctgga aaatgggttc ctaaaaatat  106380
atcaaaatat agaggtgacc ctaaaaaaat tacgtataga tcaaattggg aaaaattctt  106440
ttttgaatgg ttagataaaa atccagaaat tattgcatgg ggtagtgaaa cagcagtaat  106500
tccttatttt tgtaatgcag aagggaaaaa acgtagatac ttcatggata tttggatgaa  106560
agattcttct ggacaagaat tttttattga aataaaacct aaaaaagaaa cacaaccacc  106620
agttaaacca gcacatctaa caactgcagc gaagaaaaga tttatgaatg aaatttatac  106680
ctggtctgtg aacactgaca aatggaaagc agcacaatct ttagctgaaa agcgtggaat  106740
aaaatttaga attctaacag aagatggatt acgagctctt ggctttaagg gggcataatg  106800
gctatttttc aaataattaa tgaaagcact ccccaagttc caaaggttaa gcaatcatta  106860
aacgaaaaga aatggattca gataggtctt gaatataaaa aggccaaagc aaaaggaatg  106920
```

```
acaggaaagc aatttgctga agaaagagga atcaaatact ctacgtttac ttcggcaatg  106980
tcaaaatatg cttcaggaat taaaacagct gaaaagattc aaaagcttga atcaaaacca  107040
atgaataagc tcaataagca agaaagacaa ctgcttatga taaattcatt cagacaaaca  107100
ttgcgtgata aaattcgtaa tgaaggcgca gcaattaata ataaaaccag aaaatggttt  107160
gctgaaacta ttaagcaagt aaaaggacat aaagttgttc gcccgcagcc gggacgaata  107220
tatgcttttg cttatgatgc taaacacaag gaaactcttc cttactggga taaatttcct  107280
ttgataattt accttggttt aggtaagcat aatttaatgt acggattaaa cttgcactat  107340
attccaccta aagctcgtca gcaatttcta gaagagcttt taaagcaata tgcaaataca  107400
cctactatta ctaataaaac gaaattaaaa attgattgga gtcaagtgaa aggatttagg  107460
ggtgcagacc aaatgattaa ggcatatata cccggtaata ttatgggtag ccttgttgaa  107520
atcgccccga aagactgggc gaacgttgtg ttgatgccac ttcagcagtt cgtttcaaaa  107580
ggaaaacgtt tctctgcaaa caaagtctgg tcaaatatct aattctatta tcttccattc  107640
ttttctgttg tttgttctaa atggaattga atggaaggga cttagaccca ttataccacc  107700
aacagttata aagcattatg aggaatatat gtcgcaagct ctgcaacaaa tttttaacca  107760
agcaaataca actaactttg tagtatcaat accacatagt aatactacat ctgcttttac  107820
tttaaatgct cagtcagttc ctattccagg aattagaata cctgttactg ataccgtgac  107880
tgggccgttt ggactgggcc gagcacaacg tccaggtgtt acatttgagt atgatccact  107940
cattgtgaga tttatagttg atgaagaact taagtcatgg ataggaatgt atgaatggat  108000
gctaggaact agcaactatc ttacaggtga aaatactgcc caaaaaacag gtcctgagta  108060
cattacgctt tacatcttag ataatagcaa aactgaaatc gtgatgtcaa taaattttta  108120
taagccttgg gtttctgacc tatctgaagt agaatttagc tatacggaag attcagaccc  108180
ggctttagta tgtactgcaa cgattcctta cacctatttt caagtagaaa aagatggaaa  108240
aattatagca gaagtttaat gcttcagttt tgtgtgttat aatcttaatt aaatttgagg  108300
agaaacacat gaaactaatc tttttaagcg gtgtaaagcg tagtggaaaa gatactactg  108360
ctgattttat catgagcaat tattctgcag ttaaatacca acttgctggt cctattaagg  108420
atgcattggc ttatgcatgg ggagtatttg cagcaaacac tggctatcct tgcttaactc  108480
gtaaagagtt tgaaggaatt gactatgatc gtgagactaa tttaaatctg actaaattag  108540
aagtaattac gattatggaa caagcatttt gctatcttaa tggtaaaagc ccaattaagg  108600
gtgtgtttgt ttttgatgac gaaggacaag aatcagttaa ttccgtagca tttaacaaga  108660
ttattgacgt tataaataat attgaagatc aatggtcagt ccgtcgtctg atgcaagccc  108720
taggtacgga tttgattgtt aataacttcg accgcatgta ctgggtaaaa ttatttgctt  108780
tagattatct tgataaattt aactcaggtt atgattatta tatcgttcct gatactcgtc  108840
aagatcatga aatggatgcg gctagggcga tgggtgctac ggtaattcat gtagttcgtc  108900
ctggtcaaaa atccaatgat acacatatta cagaagctgg attgccaatt cgtgatggcg  108960
atttagtaat tacaaacgat ggttctcttg aagaactttt ttctaaaatt aaaaatacac  109020
taaaggtact ataatgtctg aacaaactat tgaacaaaaa ctgtctgctg aaatcgtaac  109080
tctgaaatct cgtattcttg atacgcagga ccaagcggct cgtctgatgg aagaatccaa  109140
aattctgcaa ggaactttgg ctgaaattgc tcgtgcagta ggtatcactg gagatactat  109200
taaggttgaa gaaatcgttg aagctgtcaa gaatcttact gctgaatctg cagatgaagc  109260
aaaagatgaa gaataatgga atttaaagac ttttcaacgg gtctttatgt agcagctaag  109320
ttttcagaat taacacttga tgcgctggaa gaacttcagc gctctttacg tgttcctaat  109380
ccagttccta gagaaaaaat tcattcgact atatgttatt caagagtaaa tgttccgtat  109440
gttccatcaa gcggaagttt tgaagtagct tcttctggac atttagaagt atggaaaaca  109500
caagatggat ctactcttgt acttgtacta gattctgaat atctgcgctg tcgacacatg  109560
tatgcgcggg cgctaggtgc tacacatgat tttgacgatt acacaccgca tataacattg  109620
tcttataatg ttgggccctt atcatttagc ggtgatgtac aaattccggt cgtattagat  109680
cgtgaataca aagaacctct taagcttgat tgggcagacg atttaaaata atttcacaaa  109740
gttgtttaca cgatgatgga gaagtgatat tatctccatc aacacattta ttaatttagg  109800
aaaataaaat gaaaacttat caagaattca cttcaacgac taacgcttct actttgactg  109860
aagcgaccct tacttctgaa gttattaaag caaacaaagg acgtgaaggt aaaccgatga  109920
ttagcctggt tgatggcgaa gaagtcaaag gtactgttta cctgggtgat ggatggtccg  109980
ctaagaaaga tggtgctaca atcgttatct cccctgctga agaaactgct ttgtttaaag  110040
ccaagcatat ttcagtagct cagcttaaaa ttattgctaa aaatcttttg taataaattt  110100
ttcgcaaagt tgtttacaca gggttttagt agtgatacta ttaccctatc aactactgag  110160
gagaataaaa tgaaacgttg tgaattaatt cgaaatgttg ctatcgcaat ttctgcttcc  110220
gcttttagtt tttcaatgtt tgttggattt atatgcggat tattaactac agcagaaaat  110280
gtattttcac ttgtagtagc atttttaatt ggtttaattg ctatcgttat ggataaaatt  110340
tctaaaggtg agtaaaatgt ataaagtata tgcagattat caggctaatc catctgaaaa  110400
gccagattgc caaattggat gggctcatga taccttgctt gaagcagtag atgctgctca  110460
aaaattagga tatagttatg tagatattgt tcaacctggt ggaacagtta ttactcttga  110520
agagttcaat aacattaaac caaacttttt actttttgca ggtgataatt attatcctcg  110580
cggtggatat gctgatttaa tcgcgaaagc cgctaccgaa gatgaactcc gtgacattat  110640
caaagaaaat gagaacaaac caatgtatgg ttctaatcgc tttgattggt ggcaaattgt  110700
aaatgcccac actcatacta ttgttgatga agggtaaata atgattcttt atgcaaaagt  110760
atcatccatt gaaaatggat ataaatatga tcaagaagca gctaaagcct tgattgatga  110820
ttatggtatt ttaacatgtt ttgaagttga aaaagtttac attgaccgtt catcttctca  110880
agttaaatta gtgaaggaag accataaatt taatacagta aattttgatt tctttattga  110940
aacagaaaaa ggtcctcttg aatatgatat tttcaagaat cctttgggtc ttgagtgcat  111000
cgtaaatatg tattatcata aatggtaaat atgctttaag aattatttgt tattattaac  111060
tcataccgca ctgattaata ccctctatca tcaagggctc ttgcttgaga gcctttgtta  111120
ataattggga attagccaag ttggtaaggc actggatttt gattccagga tgcaaaggtt  111180
cgagtccttt attcccagcg cgagaatggt caaattggta aaggcacagc acttaaaatg  111240
ctgcggaatg atttccttgt gggttcgagt cccacttctc gcaccaaatt tgcggatatc  111300
gtataatggt attacctcag acttccaatc tgatgatgtg agttcgattc tcattatccg  111360
ctccaattta atttactccg tgtagctcag tttggtagag cgcctgattt gggatcagga  111420
ggtccaaggt tcaaatcctt gtatggagac tggaggcgtg gcagagtggt ttaatgcacc  111480
ggtcttgaaa accggcagtc gctccggcga ctcataggtt caaatcctat cgcctccgcc  111540
agttttgctg atttagctca gtaggtagag caactcactt gtaatgagaa ggtcggcggt  111600
tcgattccgt caatcagcac caaggccctg tagctggaag gttcaagcaa gcgactcata  111660
```

```
atcgccagat ggtggttcaa ttccacccag ggccaccaaa ttatgaatta ggggagttat  111720
cccgtagagg tagcggtgtg gactgtaaat ccattgtcat tgcgactcgg gtggttcgac  111780
tccatcactc cccaccaatt tggatgtgta gctcaatggc agagcgatcg cctgttaagc  111840
gattggttat aggttcgaat cctatcacgt ccgccaaatt tgtgacagtt gtcacattaa  111900
tatctacttg acgcgattat cggggttgaa ctgatcactc ttctcttaat ttcgtgtgaa  111960
gacatcttga ttgttggagt aggtattaat gtggccgtag ttcagttggt agaactcgag  112020
attgtgattc tcgtagtcat gggttcgact cccatcggtc accccaatta cggggcatag  112080
ctcagaagga agagcaagga ccttctaagt cctaggtcgt aggttcgatc cctactgcct  112140
cgaccaatta agtgaggaaa atatgaaagg taatgtttat ttagtagttc atgatttaac  112200
attttacttc aatgaatatg aaaaacatat ctcatttcgt gaaattaatt tactttatca  112260
acacgcggat tatatttata ttcaaaacga atttggtcat tggcaatttc tcaaaaatcg  112320
ttcatttggc ttagatggtt acgaatactt tgaacgtaaa gaccttttag ataaaattcc  112380
gttatctaca caatatcaaa atcacaagtc tttatataaa tgccgtccaa ttcgaaatgc  112440
tgaatctgcg tatgaagcaa ttgatttatg gcgtaaacgt cgtgaacaga ttgatgcttt  112500
aaaagaatat taagaaaccg ggtcgctacc ggtaagtcgt cggactgatg ttccctgagt  112560
aaggaattgt gttaataaat ctttatgatt tgttgatgcc ctcttacatc acagctgaaa  112620
cggcgcaccg aattatcgat tcgaggaaat atctttgccg taagccgagt agcgtttttg  112680
acggaacgtt cggatatggt cgagatatgg ccttttaaaa atattgagta gcgtcaactg  112740
cttgataacc gggttcgaat cccggcgttt cgtacaaaca cttgccttag caggtggaac  112800
cccgacaagg ttgccgcaag gcttagcccc agccgaaagg ttggggcttt ttagtataaa  112860
taagtatatt aaatctacaa attaaaacag gaaataagat gaaatcatat actcaatttt  112920
taaatgaagc ggtgttaaat gaagcatcta gcaccgaaat tcaagctgtc gcaaaagcag  112980
ccattgcagc gggtaaatat tcttacaaag atgcttctga tgaatcacga ttccagttcg  113040
cacgcgacat gaaagcggaa ggatttacgg gaaatgcagt tagtatggcc tggaaaagtt  113100
tagttgctac tggcgctgct tttgcaaagg cttcgggtaa acctgctcct aaagcagatc  113160
ctaaagtcgc acaagagaaa aatattgtta aaggaattat ctccaaatat gaagctatcc  113220
ttaaagagct tttagtaatc aaaactgaag gccaaaaact agctcgtgct tatagtttca  113280
aagataaccc acatgctcac tctcttgagt atgttgaaga catccaaaaa attattaaag  113340
accgcatttg gtctgctaaa caaatcaaat aacattctta gccctagccg aaaggttggg  113400
gctttttggt atctaggcct ttccaggcct ctctagacat catttagttt ctacccttta  113460
taatatatta tcctatcctt tgatttcccc tccctgccct agaattcccc aaaacttttt  113520
aaaaattttt tcacaaaact gtttacatcc ttgtccttcc atggtactat acaactatca  113580
actactgata cagaaaacaa cttggagaat gaaatggata attacggtga actgttcaac  113640
ttctttatga aatgtgtttc agaagatttc ggtcgtacgg tgaatgatat taaagttatc  113700
ggtcctgatc atccgatgtt tgaaacctat gcagtaatgg gtaatgaaga tggtcagtgg  113760
tatactgtaa aggttgtgat taacatgttc actgctgaag gttatgttaa actgtcttct  113820
aaagtttacc atgataacga cgaaatcgca gaagaatatt tcaataatat gaaataagtt  113880
tacataggct catgattgag atattatgag cctataattt gaggaaaact gttatgtctc  113940
tttataccga actgaatgaa acttccgaaa aatcttttga tggtatctta tcaataatgc  114000
aaaagcaggt attagaagag cttagtgaag ccgcaagcaa tgggtacaaa gcttgtcgag  114060
ttcaaagccc acatcgccgc atgtatgaac gccctcttat taattggcta gaaagcgaag  114120
gtcttacggt taagatttgc cctgctaaat ttgatgttcc acgtattctt aatatttact  114180
gggataaacc ggttgagaaa agtgacactt gggttgttaa tgtaaaaaca tgcgataatg  114240
gatgctcact tgaggtgtct gctgtaatta aaggcaccca tggtgaaaaa tcgtggggtt  114300
ggcctggtaa agataaagaa atcgtgttaa gtgtaaaagc tactagtatt agtactccta  114360
tagctaaaag cattatcact gccgctgttg aagaagctga acgaatttgt aaaattaaaa  114420
atagtttaca tctcttaagt agcatgatat aattcttctg cagattttaa tttctaatca  114480
acctaaggaa atactatgaa cacactgaag aaaattgttg agtttattcg cactaaactt  114540
ggttctgcta tggctaaaaa tctatctgtt gaagagcagt atactgccgc agcagcaaaa  114600
ttgcttgata aaattaaaga tctaaaaact gcttctgtta aatctattaa tgaagaaaag  114660
cgtattcgtg aacttattgt cgaaaagaat aagcaggccg aatcaaaaga gcgtgaaatt  114720
cgcaagctcc tttctgaagg tcaagatgta acaatgcatg ctaaactcgg tttactatat  114780
cgtcgaacag ctgagcagtt gactactaaa gctgatggtt atgctgaaat gcgaattgaa  114840
atcgccaaga aagtagttga gttagatgat gctcgccaag aacttgcagt taaattggaa  114900
tatatccgtg aaactcgcgc cgcgaatgcc cttggaatta gtactgctga tgatgtagtt  114960
gaaattgcag cactgactaa ggttgatatt gaagatactc ttgctcgagt tgaaaccttt  115020
aatggtaata tttctggggt tgaaactacc tctgccgatg ttcaggaata tattaattct  115080
ctgaaataat gataaggggc ttcggcccct attacttgga gtaagtagga atgaaaatgc  115140
aaagtgattt caattcaatg tttgaagagt tccaaagaca ggttgatgtt ccagaccaat  115200
tattaaatgc tcttaaacgt atggcagaag gacgtaatta ttattggggt tcttcatatg  115260
aaactgttga aaatctttct ggaagatttt ctagaggtaa aaagtcttta atacgtcctg  115320
gaatacttat taacagtatt gaatcaattc atttattaac atgcgatttt gacgttgaat  115380
ttactgattt tgtttctcct gaatggacgg tctgttattt aaacgacgat tatgattatc  115440
ttggcgttta tagtttaagt gatgcatggt ttaaacgtaa tttacaaaag tcaaatttat  115500
tctatattga tactactgta aaatttcagg gcaagaaata tttctttact cttatagttg  115560
actctgaaac aaaatatgaa aataaacgta ttcttagtaa aaagaatatc ttaactattg  115620
tcgatgatct ttttgataaa ttcgtagaaa atcccaattt tgaaagcgat ttattattag  115680
aaaaatttgt taaggaatgt agagaatatg tcaaaaccat cactatacct tccaagtaaa  115740
ccgttgaagt atgaattaaa gcgtcagata atttctactg atgtgttaat aggtcctgtg  115800
gtagttgtat catttgtgat tctggtgatt gctggaatgg ttatagacgt tatgactgat  115860
attgaatctg gtgcaatatt tggagcaaca ctaattcttc cgttggtagt tccgctttta  115920
ttagtaccta taaattggat aggatattgg tatcaaggaa gacactatcg taaacgtgta  115980
cgtgattgga aagctcagtg taaaaagatt aaaaaggaac atcagcttaa acttgctgcg  116040
catgaatttg atgaaattat gaaatttgtt aaggaatcac gatgcaaaag ccaaaactaa  116100
ataaagtcaa atattctctt cctgagtcat ttttaatttt tactgtagcg ttggctgcat  116160
ctcttgcggg tagtcttttt ggattgttaa ttgactgtct tattttaaac atccgtagta  116220
acgtcagcgg tataatagat ataatagaag tttggagtga acttcattat actatagcga  116280
tttcattatt ttcattcttt ggtacaatgt tatattttca ttatgataat tttaaaataa  116340
attggcaaag aaaaaaagat tacaaaatac aattaaagga atataatagc tacatgtctt  116400
```

```
atattgaaaa agaatcaatg gaagagtttg tgagtgattg taggaaaatt aaatgatttt  116460
aaaaactcgc tggtatgatt tagatgatgg ggatgatggc atttcagttg atagagttga  116520
ctggaatggt tgttccgaag atatgaaaaa tttgttgatt agggagttta gaatgggata  116580
tcaagcagct aagccatcta ttataacaga tgataaattc gtgtgtattc ataatggtcg  116640
cgctaagtta acgaacgctg attggttcac agataaaatt atgattctgt ggtatattat  116700
tagtcttcct gtgacatcat tcgtatttta ctttttttata aaaaatccaa tggacagaat  116760
aggagattgg attcttttaa ccatacttgt taatattttt actgcagcaa tattatctgg  116820
gatatggtgc gtgttcattg aaatgccatg gcggctacgc agacagcaaa agatttttga  116880
tgaaaagaaa tacactcaaa atttaaataa ctttatcact gaatgcagga aattaaaatg  116940
aaaacattat cagctggtat tatctttatg acagaagata aagatttatt tatgggtcgg  117000
gttactggtt ctcgtaagcc tggaatgatg gcacatcgct gggatattcc aaaggggcgt  117060
gtagaaagtt ctgatttaag cgcattagat gcagcacgaa gagaatgctt agaagagacc  117120
ggttttagca attataatcc agaccttcta gaagacctag gtgtatttaa atattctagt  117180
aataaagacc tacagttatt ttattatacg attccagtag agcatgagat gtttagaaat  117240
tgccattgcg agtcttattt tgaaaataaa gatggtgtta tgattccaga gatggatgct  117300
tttgctctta ttcctcgtac tcagtggcaa tatgtgatgg gtccttcact ttaccgaata  117360
atgaacaacc tcttttaatt ttataaatac cttctataaa tacttaggag gtattatgaa  117420
tatatttgaa atgttacgta tagatgaagg tcttagactt aaaatctata aagacacaga  117480
agactattac actattggca ttggtcattt gcttactaaa agtccatcat taagtgttgc  117540
taaatctgaa ttagataaag ctattgggcg taattgcaat ggtgtaatta caaaagatga  117600
ggctgaaaaa ctctttaatc aggatgttga tgctgctgtt cgtggaattt tgagaaatgc  117660
taaattaaaa ccagtttatg attctcttga tgctgttcgt cgctgtgcat tgattaatat  117720
ggttttccaa atgggagaaa ccggtgtggc aggatttact aattctttac gtatgcttca  117780
acaaaaacgc tgggatgaag cagcagttaa cttagctaaa agtagatggt ataatcaaac  117840
acctaaccgc gcaaaacgag tcattgctac gtttagaact ggcacttggg acgcgtataa  117900
aaatctataa agttgtttac tttctcctag aattgtgata gtatattcac agttgcttga  117960
agagacaaat tactaattaa aatatttaaa ggaaacccat gaaaacatat caagaattta  118020
tcactgaagc agctattaat tctcaaatta ttgctgaatc ttttactgat cttttgaaat  118080
ttaaaaaagg tcaaaaaatt actgctgtat tggatgatgg tacagaagtt gagatggatg  118140
tacagggata taattatgca gtagatggaa aattgtataa taaatctcat gctaaatttg  118200
attcatttga cgactttgtt aatgcagttg aagatgaaaa aactcgtcga tccattgcaa  118260
ctggtgatgc taaggttctt atggcacatg gtcatgaacg cattcgcgct aaacagaata  118320
aaatgggtga agataatttt gcattagttg gttatcaatc tggtaaacaa acctatggtt  118380
atcagcgtac tgctaccatg tataataaaa atggtaaaat tgcctttgtg aatagtaaag  118440
gttctattca gtacgttaaa tcgttcaaat aatatgggaa caacctggac ctcatgattc  118500
tatgagggat tcccgccaac ctgtaataag gtcgagtcca ggtgcggtaa tgggtaaata  118560
cagaaatgga caattcatgc gccatggaat ggcccaaact tagagagaag aaatgagaac  118620
atttttaact ggtccttatc tatccctgat gaatgctttt acacaccatt ctgatgctag  118680
agtagaagaa atttgtaaaa acgaatatat cccgccattt gaagaattac ttaaacagta  118740
ctgcacactt cgactagacg gtggacgtca atctggtaaa tcaattgctg tgactaactt  118800
tgctgctaat tggctgtatg atggcggaac agttattgtt ctttctaata cttcagctta  118860
cgctaaaatt tctgcaaata acattaaaaa ggaattttcg cgttattcta atgatgatat  118920
acgttttcgt ttatttactg attctgtgcg cagttttatt ggtaataaag gaagcaagtt  118980
cagaggttta tcgctttcgc gaattttgta tataattgat gagcctgtca aatctcctga  119040
tatggataag atttatagtg tccatattga cactgtacac tactgctgta atagtaaatg  119100
ttgcattggt ggtattactc gtcctcaatt ttttgtgatt ggaatgcaat gatgacagac  119160
actcagcttt tcgaatatct ttatttttcg ccaaaaacta ttaaaaataa attggtgaat  119220
cattttgaaa ttttggcaaa aaataacatt ttaagcgaat tttatcctaa gcaatacaaa  119280
ttacaaaaag gcgtattcaa aggatgcaga gttttatgta ctgctcctaa tgcacggcta  119340
atgaataaaa ttccatattt taccatggaa tttattgatg ggccttttaa aggactaatc  119400
acacagagtt taatggcata tgattctgag ccatttttaa ttaaagaaca atcttggata  119460
aatttatttt ctaattgagg tttatatgaa agcatatcaa attcttgaag gcacacataa  119520
aggtactatt tattttgaag atggtattca agcacgaatt attgtctcca aaacctttaa  119580
agaggactct tttgtagacc cagaaatttt ctacggtttg catgcccgtg aaattgaaat  119640
tgagcaacag cctacagtta aaattgaagg tggtcaacac ctgaacgtta acgttctgcg  119700
tcgcgaaact ctggaagatg cagttaagca tccggaaaaa tatccgcagc tgaccatccg  119760
tgtatccggt tatgcagttc gctttaactc tctgactccg gaacagcagc gcgacgttat  119820
cgctcgtacc tttaccgaga gtttgtaatg gcaaagataa ttattgaagg ttctaaagat  119880
gtgctaaatg ctttcgcaga atggtttagt aattcaggcg aacagcaatt taatgaagcg  119940
tggaacatgg gtgatattaa tggaatttat cctacgacag aaatttctgt tcaaggatat  120000
ggcattcatg aacctattcg tttagttgaa tatgatttat gtactggtga ggaagtcaaa  120060
tatgattgaa gacattaaag gttataagcc gcatactgaa gagaaaatcg gtaaagtgaa  120120
tgctattaaa gacgctgaag ttcgtttagg acttatcttt gacgctttat acgatgaatt  120180
ctgggaagca ctagataatt gtgaagatga tgaactcgcg aagaattatg ctgaaagcct  120240
cgatcagtta actattgcta aaacgaaact caaagaagcc agtatgtggg cttgtcgtgc  120300
agtgttcaaa ccagaggaaa aatactaatg gcgcaattaa gtgcagggtt tggttatgag  120360
tattatactg cacctcgtcg tgtatctgcc gcttctaaga aaattcaaag tcttgatgac  120420
ttccaggaag tagtccgtaa agcttttcag gactatgcac gttatcttaa agaagattca  120480
caggactgtc tcgaagaaga tgaaattgct tactatgagc agcgtcttga acagcttaaa  120540
aacttacatg aggttcgtgc agaagtttca aagtctatga ataaattgat tagatttaaa  120600
gaataactgt ttacttttcc tcttgactgt ggtataattt ttctatcagt taagaggaga  120660
ataacatgac tatcaataca gaagtttta tccgtcgaaa taagcttcgt cgtcactttg  120720
agtcggagtt tcgtcaaatt aacaatgaga ttcgtgaggc atcaaaagca gcaggggtct  120780
catcgtttca tctaaaatat tctcagcatc ttcttgatcg tgcaattcaa cgggagattg  120840
atgagacata tgtttttgaa ttattccata aaataaaaga tcatgtttta gaagttaatg  120900
aattcctgag tatgcctccg cgtcctgaca ttgacgagga ttttattgat ggggttgaat  120960
atcgtcctgg acgtttagaa atcacagatg gaaatctttg gcttggattt acagtttgta  121020
agcctaatga gaagttcaaa aacccgtcac ttcaatgcag gatggcaatt atcaacagtc  121080
gtcgtttacc aggaaaggct tctaaagcag taattaaaac tcaatgaggt aaacatgaga  121140
```

```
aaagcactac tcgctggtct attggccatt tcaatgatgg cacatagctc cgagcatact  121200
ttcagtaatg tccaactcga taacatgcgt tacgcgtatc aattcgggga acaattttct  121260
aaggatggaa aatataaaac acacaaaaat atccacaaga gcggattagg tcatataatg  121320
gctgctattt tatggcaaga aagctctggc ggagttaatt taaaatctaa accaaagcat  121380
cacgcctatg gaatgttcca aaattatttg cctactatgc gagcaagagt taaggaactt  121440
ggttataata tgaccgatgc tgaaataaaa agaatgttga ataaacggtc caattcagct  121500
tcctgggcgt acattgaact ttcttattgg ttaaatatac ataagggcga tataagaaaa  121560
gcaatatcct cttataattc gggatggaat gttaaagcag gttctaaata tgcttctgaa  121620
gtcctagaaa aggctaatta ccttaaaaat aataaacttt tggaaatagt aaatgactaa  121680
aattttggtt ttatgtatag gattaatttc attttctgcg ttagcagata catcatatac  121740
tgaaattaga gagtatgtaa accgtactgc agcggattat tgcgggaaaa ataaagcatg  121800
ccaagctgaa tttgcgcaga aattaatata tgcatataaa gacggagaaa gagataaatc  121860
aagcagatac aaaaatgata cattgttaaa acgatatgct aaaaagtgga ataccttaga  121920
atgttcagtt gcggaggaga aagataaagc cgcttgtcat tcaatggttg accgtttggt  121980
agattcttat aatcgaggat tgagtactag atgattgtaa aatatatcaa gggcgatatt  122040
gtcgccctat ttcttcaagg taatattatt gcgcacgggt gcaattgttt tcatactatg  122100
ggttcaggtg tagcgggtca attagcaaga gcctatccca aaattttaga aatagataaa  122160
accactactg agtacggttc tcgtgataaa ttaggcgata tgtctattat ttttaaacat  122220
aaacctaatg gttttggcat atgttataac ttgtatacgc aatacgaacc aggtcctaat  122280
cttgattatg gtgctttagt aaactgcatg atagaattaa atctacaggc agaaaccctt  122340
ttgtttaaac cagtaattta cattccacgc ataggttgtg gtattgctgg cggcgattgg  122400
gataaggttt ctaaattaat cgacatgttt actcctgata ttgatttaat agtggtggat  122460
tatgaaagta cattacccac atccgtttga tcctaaaaac aaagtggaaa ttattcgtca  122520
atgggaacgc atttgccgta ctaaatgtcc aattaatagt ccacatgatg tagataaaga  122580
ctacattgga acattcgttg aatatacctt tattgataag aaaggtcgta aacaacatgt  122640
agaagaatat tgcttaaagg ttacatggtt atgagccaaa ctagtattct taaaaatgcc  122700
cactgtgaaa agtgtaagtg gcctgttgtt tttgctttat gtaatgatga aatggcttgt  122760
gatttcgatt attggtgcta ttgttctaat aaaggatgca tcaatcataa aggtgaagga  122820
ttttattcgg gattttatcc ttatcctgat ttcgttaaag aaggtaaacc aaaatgaatg  122880
atgatttaaa atatcaatta ttacgtgaac ttgatgtttt gattgaactt tctgcacaaa  122940
aaggatttat aattggatcg ggtcaaaaag accccaacgg tcattcaatc gtagcggtta  123000
tgaatcagaa acgagtcatt ttaaaacttt tggggattga catactgtga gcctaagcaa  123060
agaacaaaaa gataaattgt ttgagcttat ccatgaactt ctagatgagc atgcagaagc  123120
aaacaccttt tatgatgaat acggcccgct atctcccgaa cagcaggaag aatttgctga  123180
tcggtttgat aagaaagaaa atgaattaat agcttatgtg aatacgcttt aagaaggtga  123240
tatggcgagt ttaattttta cttatgcagc aatgaatgct ggaaaatctg cttctctttt  123300
gactgctgca cataattata aagaacgtgg aatgagtgta ttagttctta agcctgctat  123360
tgatactcgc gattctgtct gtgaagttgt ttctcgcatt ggaattaaac aggaagcgaa  123420
tattattaca gatgatatgg atattttcga gttctataaa tgggctgaag cacaaaaaga  123480
tattcattgc gtatttgtag atgaagctca gtttttaaaa actgaacagg tgcaccaatt  123540
aagccgaatt gttgatacat ataatgttcc tgttatggct tatggattaa ggactgattt  123600
cgctggaaaa ttgtttgaag gttctaaaga actttttagcg attgcagata aacttattga  123660
actaaaggca gtttgtcatt gcggcaaaaa agcgattatg acagctcgat taatggaaga  123720
tggaacacca gttaaagaag gtaatcaaat ctgtattggt gatgaaattt atgtttcttt  123780
gtgcagaaaa cattggaatg aattaactaa aaagcttggt tagtgcaaaa gttataaata  123840
ggtttatcta actaaagggg tatatatgct acaattaact gaaaagcaac ttcgcaatct  123900
tactgtgctt caattagatg aaattcgtag ggaagttgga aatatcattt cagctttgcg  123960
tcgagaagta tcactcaacc aatctccggc agactatact agattgcgaa attttgaaaa  124020
ataccttgat aaagttaagg ccgtgcatcg gcataaagta aatacaggac aaaaatgata  124080
ggaggccttt atggccttaa aagcaacggc actatttgcc atgctaggat tgtcatttgt  124140
tttatctcca tcgattgaag cgaatgtcga tcctcatttt gataaattta tggaatctgg  124200
tattaggcac gtttatatgc tttttgaaaa taaaagcgta gaatcgtctg aacaattcta  124260
tagttttatg agaacgacct ataaaaatga cccgtgctct tctgattttg aatgtataga  124320
acgaggcgcg gagatggcac aatcatacgc tagaattatg aacattaaat tggagactga  124380
atgaaattca gcgacttttc acaaagtgga aaaccttcaa aggcagatga atacttaggt  124440
ttattaatgg ctgcacaagc ttattttcat tctgcacatt ttgaaactaa aagttatgct  124500
agacacaaag catacgattt tattttctcc gagttgccag atttgattga taaatttggt  124560
gagcaatatt tggggtattc tggtagaaaa tacacacctt caattccaga tgccagtaaa  124620
cttcctaccg acacaattaa aatgattgat cacatactag accaatctaa cagcatttat  124680
aaagaaatgc ctccagccat tcaaagcacg atagatgata ttactggaat gttttaccag  124740
agcaaatatc ttctttccct cgaataacat tagtctcctt cgggagactt tttcatttta  124800
ccagtttact ttcaatttga gctgtgatac tatacaacca tcggataaag aggagaacat  124860
catgaaaatt gaagcactca atcaagaagg aaatatctac gtcatcatta atggtgattt  124920
tttcgtcgac atggatgaag ttactagtga agaacttgta gaacttctta agaaacgtta  124980
tgatatgtgt gatgaagctg caactcatat ggcgtgtgca atattctctc tttcatatgt  125040
ggtggaataa tgactagaat tgaacaagca gataaaatta aagaattggt agctttaatt  125100
cgcaaagcag atgaggaact tagtgacttt gcttggtttt cggcaggcat tgcaaataaa  125160
ggtattgaaa aatttgaagc taaagttgat aatgctgtag aagctttaga tatgtttctt  125220
gatgaaatta tcgatcataa tacgagagtt taagtatgct aacacgtgaa cagtttgaaa  125280
aaattattaa attagcacgt gatgttgaaa tagattcata tcaattagca gttgagcact  125340
gtgaaggata ctcatacgat ggtatagaag cagctaaaaa ggatttggat aaatccaaag  125400
ctaagttagt tcaatatctt gaaatgatta ggtggaataa tgaaaactga aaagcagatg  125460
tttttaatga agctaattga agaatatgct aatgcagttt ctgactatga gtattctgct  125520
agggaaagag gtacagcttt cgcaaaggaa gaaatgaaaa tcatggttga tgctcacaca  125580
aagcttcaga attttattga aaacgtcatt taatggttta caagttggca aggttatgat  125640
atagtaatct tgtcaactgc caaggagaag agaatgaaag ttttgtttgt tgtgtatgtg  125700
atgattcaat ataattatcc aatgtttact tataatctgg tgaacaacat tattgatatt  125760
attcaaagga gtatgtaatt gtgggtgagt cgaagagaat caatatgaaa cgattagtat  125820
tagaagttag tccgcttttt ggtgaattag ctatagaaaa agtaaataat atgtatcgtt  125880
```

```
tgacacaaga agacgatatg ctatatttta cgcctagtga aatcattcat ttaacccaaa  125940
ttgaatatcc ttatactgat aaaatagtaa gcatcaatga tgagcacaaa attcattttt  126000
attcttcatg cccaggattt aatattaaaa gtgagtcaat gtgtttatca gttatccatt  126060
gggatagttt tatagataag attaaatatt tttattattc taatgaaaga aaacatagtt  126120
taaaatggct caaaaattgc aatgctatta ttactaacgc ttgcaatcag aatgatgaaa  126180
ctgttttaaa cgtatcaaaa tgctatgaag atggtgatgt cttaactatt cgtcaaattg  126240
atgattttcg atcgtatatt gtcacattta ccaaagacga agctattgcg ctaaagactt  126300
atctcgattc tgtcattcca actatgattt caaagtgagg aaatatgttt atttcaagtg  126360
gaagtggttt aattcgtgtt gaatttaaaa atgacatctt ccttattcaa ggagatgata  126420
ttattaaaat gagttatgat gaaattaaga aaatttgtaa tgctcttgaa agtcatggaa  126480
aagtgaacgc tgttattgat attggtgatt tatgggtgac actttatgaa gtatccgaag  126540
gatttaatat tgaagatgaa aacaacatct tagctattga taaaagaagc gatttgtttg  126600
atgtgttaaa agtttatgaa cagtcaaacg gtggaagaaa agctgtattg atttatcaaa  126660
aaccacattc atgtggaact gcttcaatca tttcagatat tgaagatgaa actgatactt  126720
atatgtgtgt tttaaaagct ggtggtgacc gtcatccgga ttttatttct attcgtcaaa  126780
acaatggaga aatttcatta tcaaaatcag aagctgaagc tatgattaag tatttaacaa  126840
ctgttacacc ttcaatgaaa ggataattat gattattaat gaaaactctt ggcactataa  126900
attattcaaa ctgtttaacg acgaatggaa acgacctaag acactgtgtg catacttttg  126960
gtctattgtt atccctacat ttttcgtttc ttttttcgga tgtactatac tcgcaggtct  127020
aactattatc tgtgcagaaa tcatacagaa atggcttatt tttggtagtt tatggactct  127080
tattccatca gcatttatac ttgccatttt gcttatttta cttattattg gttcatttgt  127140
tattcctgca caactgcatg aaaaatataa agattataaa tggaaaaagg attatgcttt  127200
acatgtagaa aatattgata gggcgtataa aggtttacct cctattcaac ccaagaaatc  127260
tattatcgtt gaatttttaa aagctcgtaa agctaaagta tgtcctgtta ttgaatataa  127320
ggctgaatga tgaaaacagt aatgaaaagc tattttggta gtcatcttta tggaacttct  127380
accccagaat ctgatgtaga ttttaaagaa atctttgttc ctcctgctcg cgatattctt  127440
atcggaaatg tcaaagagca catgagtaaa aacactaaca acacatcatc taaaaacact  127500
aaagatgata ttgaccatga actatacagt cttaaatatt tctttaaatt agcagcagat  127560
ggtgaaactg tagcgttgga tatgcttcac actccacctg aactagtggt taaatctgat  127620
ttgcctgatg tgtggaagtt tattcaagac aaccgttctc gtttttatac gactaacatg  127680
aaatcatatt taggatatgt ccgcaagcaa gcttctaaat acggtgtcaa gggttctcgt  127740
ttggctgcat tacgtgatgt attgaaagta gttaatcaaa tccctgagca atgggttgat  127800
taccaagaag atggttctat taagcagcgt cgtactaaag ttgaagatat taagcatcgt  127860
cttccagaaa acgaattctg tgaatgggtg ttccataatc atgagaaaac aggcccacaa  127920
acgttctaca ctgtgttggg tcgtaaatat cagacaactc tttctcttat tgagcttaag  127980
cagtcactga acaaattaga tgctgaatac ggtgaacgtg ctcgtaaggc cgaagccaac  128040
gaaggcattg actggaaagc tctgagccat gcttgtcgtg gtggacttca actattggaa  128100
atttacaaaa ctggtgactt ggtttatcca ctccaagatg ctccatttat tctcgacgtg  128160
aagttgggta agcatccatt taaaacagtt caagagtttt tggaagatgt ggtcgatcaa  128220
gtagaagcag catctattga agcttctaag aacggtatgc agcaaaaagt agacatgggt  128280
ttctgggatg acttccttga gaaggtctat cttgaaaacc atcgaagtta ttataaatga  128340
tagggagcct tcgggctccc tttttttattt caaaaatttt tcacaaaacg gtttacaagc  128400
ataaagcttt atggtactat acaactatca actgatacgg atttggagaa taaaatgaaa  128460
actgtaacta tcaataaggg tatctacttc ggtaaagaaa tctctggaac ttttgagctc  128520
ttaggcgaat ggttcccgga taatgctccg gtagatgcac aaggagatgg taaagttttt  128580
gttgaaattg acggtaaacg tcgcggtgtt tgggtttaca aatcagacat ttcatatgat  128640
ggtgtaaaag ttgaagaagt taaagaatcg tatgaagata tgaaaacccg cattaataaa  128700
agatttaatg ttatgggaat gatgacgaat ggtattatta acggaaacat tcgttcatta  128760
attatttctg gtgcggcggg tattggtaaa acgtattctt tagataaagc tttaaataaa  128820
gcaaatgata ttggatacat tgaatataaa agcattaatg gtaaaatctc tggtattggt  128880
ctttatgaac agctttggaa taatcgtgaa gagaattctg tccttttgat tgatgatgtg  128940
gatgttttct ctgatatgga cattcttaat cttctgaaag ctgctctgga cactggagag  129000
acccgtaaag tctgctggag cactgcatct tcttacttag aagaaaaagg aattgagcgt  129060
gagtttgaat ttaaaggaac gattgttttt atcacaaacg ttgacattga ccgcgaatta  129120
gaccgtggta ctaaacttgc tccacattta caagcattag tgtcccgctc agtttatttg  129180
gatttgggtg ttcacactaa tgaagaaatt atggtcaggg ttgaagatgt tattctttca  129240
actgacatga tgcaaaagcg cggtctttct gatgaagaaa cttataaagc attatcatgg  129300
atgaaagtca atgttaatcg tttacgcaat gtttcactgc gtactgctct ttatcttgct  129360
gactttatta tgaccgacaa aaacggttgg gaagaaatcg ctgaaacggt attattaaaa  129420
tgaaaaaata ttttactatc tataaaactg aaatattaaa tttaaagaca ggtattaaga  129480
aatactatta tggtcgacat ataactaata acatcaatga ttcgtatgtt ggtagtggaa  129540
attatataga acgtgtaaaa gtgtcaaatg accacatatt atcaaaaacg gttttagaag  129600
tttttgataa ttatgataaa atggtacaag ctgaaatatt atatatcatg gcaggtaaat  129660
tgaaatatgg aaaaactgtg ttaacctgtc atacgggggt gaaggaggaa aggttgcaga  129720
tgaaactagg ataaaatgca aaaagcattc tataaattta tggaaaaatc ctaatcatat  129780
acagcatatg aagaaaaaga tgaaagaggt cacatccacg ccggaagcta aattaaacac  129840
ttcaataaaa acttcgcaac gatataagga cccagttttt gttagaaaag ttagtaatat  129900
tattaaaaag aaactaaaca atcctgcagt aaaagaaaag catattaatg gaattaaagc  129960
tgcaaagcgt tctcatttaa ctatatggca gtatgaagat gaattattcg agctttggaa  130020
agaaactaaa tatggatgga gaaaatttac aaaggaagct ataaaacacg gatatccaaa  130080
tgaaccgtat cgtagtatgg tatcaacttt tcagaaaaga catttagaag aatcctaaga  130140
caaaaaggca gttcagaaat agattatatg gactgccatc aaaaagatga ctagaattaa  130200
actggtaaat ggaggtaatg atgttatact caaaggctcg tgaaatttac gaaactaaaa  130260
ttaaagaagc agtatttcag ttcgcaacaa caatgcgatg gacaaatgat tgggagtatt  130320
caaaaaatca taagaagcct ttggtgacaa gaaaggctca tatgttagtg ttaatagacc  130380
gtgagcagat taaagcccga gaagccctcc agaatcataa aaaggctgcc tttgaatggt  130440
ttatggataa cactgctcct gagactaaga aagcagtgag cgcttggttc agtggaaaaa  130500
attgtgaaag aagtttcttt tagttgttta caagaccgtt cctctgtggt actatacaac  130560
tatcaactac ggaggaacag aaaatgaacg ctaaagatat tttcaacctg gtaaattata  130620
```

```
acgatggtaa atttaaatct gaagctcaaa gcaagttctt taatgatgtc tcaatcggtg  130680
gtgaaatcac tgttgatgga ggacaaattt acaaatcccg ttggaattgg atcgttatta  130740
tcgatgagat tggtattgta gaaatttaca agaatacgaa taaaaatcgt acattacact  130800
ggtctcgtga tactaacgaa cagtacaaaa aggataaagc atctaaatta tctcgtgtaa  130860
ctcaagaaga tattgagttc atcaagaaag atattttgat gtatgataac ttaattgctg  130920
aagagcaagc tgttattgat aaatttgacg agattaaagc ttctcgtgaa attcctgatt  130980
ttatgaaaga atcagtaaat gaacgataca ctctcatttc agagcgtatt gaaacttaca  131040
aaaagcaaag agctgaacgc cagaatactc ttcggaagtt tgaagaacgg ttaaagacgg  131100
tactcgcata accgctttat accaaggatg gtataatggt tctaagccct tttaattgag  131160
attattatga aacagttgat aattaaaaga ttgaatttat tgatatgttg tttatgtata  131220
gtaattgcat atggttatta tgctattaat gattatatgc attataaaga ttatgatgtt  131280
actgtagtta ataccattac aggaactcaa ggaaaggggt ctaatttatc gtttattgcc  131340
gtatatgaac tcaaagacgg ttatagattt agtgaatata tttccccaga gatgtattct  131400
tcaatagaaa aaggtgataa tattactgta agtttacgtc ctttcgacgt aaaacagaca  131460
ttgtttgata atatcgtttg gttctttgga atggtattag ttcaatctgt atgcggtgct  131520
tatatagtct tttccatcat attctgcgta tttagtaaaa ttgaaaattg agtgaggaaa  131580
atatgtcagt agtaattaat aatgtcaatg cagtaattaa atctttagtt aataaaaaat  131640
tgaatgaatg gactgtactt cgtcgtggag agccagataa attttttcat agatttaacc  131700
caactttgga tttgaatgtt attgacagag atgttcatgc tgaaatttta gataaattta  131760
aagttgatat tggatttgga ttagaaaaac atttacagcg aacaaacggg tctggaatgg  131820
gtttatctaa tcgcattatg aaagccctta ataaaattgg agcattgtct cgtattaatg  131880
caagtgaaat tcttcgcaat tataataaag gatatgacct ttatggtcga ctaatgccaa  131940
aattatcatt cgatcaaatg attgaggatt tgtgggaaaa tcaacgacga ttattagcat  132000
taggcgctcg attagctaaa ggtctagata aacaaatgat ttttaagacc aataatacag  132060
aagaccttaa atgctttaaa tttagcactc gtggagatga ttattacgtc agagctcgct  132120
ctactgatta tgtcaatatg ggtcatcatc tctgtttagc ttttgaagtt ttaaaagaat  132180
ctggaacatt agaatattca tctggtgcaa aatgtccaat tggttcaagt tgtattttaa  132240
tttatcgccc ggatgaatcc agttcaacta aattgcctac aaaacctgta ccagttcgta  132300
gtaacgaaaa acattctgag caaattgatt attttaataa gcaaattgaa gagctgaata  132360
tttctattca acaatatgac gatgaaatct ttagactatc tggattgagt agtaaagcta  132420
aatctgagcg tgaaaagtta attaaaattg ttgatttact taaatcttaa ggaacactat  132480
gaaaactcgt tctcaaattg aagatatggt tcgtaatgcc agctatactc gtgatgttat  132540
gacattttttg tgccaaaata atttagaccc tgatagagtt aatagttcca ttcactttaa  132600
gtatatgaat agcagtgaat ggttacgtca ttttagtaaa gcgggatata ttacacaaat  132660
gactgctcgt gagcagctca ccgatttctg taaaactatt gattataaaa atcctctatt  132720
tgttcaaggt gttggtcaga gtaaggttga tttatcatct ggatttttca atcccaatca  132780
ttatcgtatt gaatggagat ttattgctct attccgtaaa cagttaaagc aaattttgtc  132840
gacagctagt cgattaaaag gttctgacat taacttaaag aacctgaaat ttgatggtta  132900
tactcttcag atggaagtaa gaccattaaa agaaaaataat agaactgcac gaattagctt  132960
taaacctaat acaaaaaatt ctctttcaat ttgtgaatgc cttaaatcac agttgacaga  133020
agcatttaag tatatggatg ttgttgccgc tgttcagtct aagattttac ctcgttttga  133080
acgatttaag ttagatacaa catcatatga acttgatatg atcgtttcat ttaaatacga  133140
ttttttgaga aaggacgaag tcccgcaaga gaaaaagcag gaagtacaag ataacttaaa  133200
tttatccaat tacttatcaa acgatcctaa attttggatg tatagttcag gtaataatga  133260
tgcatggaaa ttcaataaag tgaattttct tcctgttgaa aatccgagtc ttaaacctgt  133320
tgaaaaatgg cacgcggatg cgattgagaa gtctatcaag gcagtagatg atgaactcgt  133380
taaagcgacc aatgaagtgc tagaagctga aaaggcgtta gaacaagctc agtcaagggt  133440
tcaaaatctg acaaagcaac gttctaaact gaacaatgca ttaaatgcac tgaactagtt  133500
tactttgcca caaggatgtg gtataatgtt cttactttct actgaggaga ttaatatgac  133560
tcgtaacgaa tatatcaaat cattcaatag ggttattgat gataaagtta aacccatgtc  133620
tagtcagaat gctgttcttt ctattatcaa tcaatggctc agcagtattg atgcaagtat  133680
tgtttcttcc agtaaattta ttcatgaagt tcgtgaaatt tctagccgtg tagataaaga  133740
tgatattaag ataatcttta aagggtctcg tcttctttca tatttagtta atcgggatat  133800
tcttggtaat tttgggaaag aaattaaacg aactaaaggt gtaataggat acaattggtt  133860
cggtgatgtt aattcttctt atcatcttaa tatcaaagaa gaccctaaga atatttttac  133920
tcgtcgttgg attagtaatt tcagactttt taaaggacaa attctaaaat cagcttctaa  133980
attatgttat ggcgattatc gtcaaattca tcctttggct tctgatatga ttatcgtaaa  134040
agaatatgag cttgataaaa ataaagtagc tatttttgtg aattatgaat tttttacacc  134100
agaagctaac caaaagaata ttaataaatt tttctcaatt gctagcacta taactcatca  134160
attagagacg gctttggatt gtatggaaac tgtaaaaagt attcatacat atcctttcaa  134220
aaatattggt ggttgggaag gatataaaat tgtaattagt cttcgtgaag tgaaatgtgc  134280
ttattcacta actgataaag aaatttacca acaaaaatgc gaagaaattg tgaatactcc  134340
taaagaagaa actacccttg aggaactaat ggataatctt gacgattcac ttgaaccggt  134400
agaaattcgt ccagaagttg ttgcactaga aaaagcttat aaagaagttc tagaaatttc  134460
taataaagcg cagaaagaat atgagaaggc taaaaagatt tgggaagaat ctgttaatcg  134520
cttggatcgt cttgaacaag ctttacagtt aattaagtaa tttaaagcca aggatggctc  134580
ggagtataaa tcattaacaa gtgagaagaa catgaaaact cgtaaacatt atattgatta  134640
ttttgacagt cttattacta aacatcgtaa ttatcagatc ggacacagag cagtaatcaa  134700
taatattctt cgtgatttcc ttcaatatgt tggccaggaa aatcatatct gtaaagatac  134760
tcaaaacgct tattctcatt cgttaggcaa tttgcttgaa tggtttaaac gttctcgtat  134820
gttatcttct actatagctc gtgataacat taaaaacttt atgaagccga gcttcattaa  134880
atctgagaca tctataaccg atttggttca atttactatt gttaacgatg ttaaaaagac  134940
ccatttggct gattggttat ctaccattcc tgaaactaaa tttgctgata aatttgcttg  135000
tcaattcaat acccaagtga atatgctttt taagcatgct cgcaaactgt ttaccgcggg  135060
cgatgatcgt acaaatacag ttcatgttaa ggactgggtt attgctgatg aagtaacaca  135120
caagccaggt ggttcatcag tattaattaa tatccaggtt ccttattatt actcacgtaa  135180
tctcggcacc atgacagcta aagaaattaa taagcacaac aaaactattc gttcgttgtc  135240
ttataaactc cgcatgatgt taaaaattat ggacgtagtg gaaatgtatg acgaaaccga  135300
agataatggt tcaatgttat acagttcacg cattctaatt aaactgaaga accctaatac  135360
```

```
atataagaca gttgtaaaag agcctaaagt agaaaaggtt gataatctgg gtgaagaacg  135420
tgaatatctc aatgcccgtt tgactgaagt tgaaaaacaa attgaagagc atactaaagt  135480
tcttaaggct ttaaccgcca aagcaaatgg tttacgtaat gctattgagg tattgaaatg  135540
aaaaagcgtt tattagaaga cattgcagct tcaagtaatt ctagtctaat taaaattatt  135600
atggctggtg aggaagatga tatggaaatg cgtggaaaga ttcacggctg cgatgattta  135660
gattttaaac ctccagcatg ggatgctatt atggctatgg ttgaacgtcg cgaaagggct  135720
tctaaaaacg ttcctaattg ccctgaatgc ggtactgaac aagttcaatt gattaactgg  135780
cgtaaaccag agcttgaata taaatgccgt caatgtaaac ataaattcag taagcatgct  135840
ccggaaatgg ttaaattgcc tgactctact gagttcttta aagaacttgt gagtgttcaa  135900
ccaatgccta ataatatttt ggattaaaaa tgaccaagcg taaagaatat atggaggctg  135960
ctgaaaaggc agtccgtgaa ttagcaatag cttattataa tgaacatggt aaatttcctg  136020
atagatacag cgtgcttaaa tctgctgtaa ctcgttcata caaaaatatg ctatcagaag  136080
taagtgatat tatatacaaa cataaagaac aaacgggcca aagtcttgat tacgacgaga  136140
cttttaaaca agtactagga attaaggaat aatatgttta aagtatatgg ttatgatagc  136200
aacattcata aatgtgtgta ttgcgataat gcaaaacgtc ttttgaccgt gaagaaacag  136260
ccgtttgaat ttattaacat tatgccggaa aaaggtgttt ttgatgatga gaaaatcgct  136320
gagcttctga ctaaactagg tcgtgatact caaattggat tgacaatgcc gcaggtattc  136380
gctccagatg gaagtcatat tggtggattt gaccaattgc gggaatactt taaatgatgc  136440
tcgaaggaac cgattatatc catgactacc gcggaagcgc ggtatatgta ggtgatgagg  136500
ttgcagttta ttatgggtat ggaactttga tgacagccaa ggttattcaa attaaaaata  136560
atcgtgctaa actcgaagtt tattattcta atggtgaaaa gtctatttct aagtggaaat  136620
acggcgattg catggtcaaa ctggggtaaa tatgatttac gatattaatg tatcacgagc  136680
tccgtcaatg gttactattc cagccgaaga actagatcgt cttcagaaaa ttgaagaact  136740
tctttgggaa attgaatgtg acctgccatc aggactagaa tcctggattg atgatgaaga  136800
acttaataaa ttgcgaaatt aattggtgaa aaatgactat tgaaaataaa ttagatgttg  136860
atgcagttct gagcgaaatc attgaagacc atgatgcatt ttcggaaaac tatgatttcg  136920
atttttccga ttatcttaaa cctgtcgaaa tagaagactg ggtgcaagat ggtaaatgtc  136980
aatatcgtca gtgtgtttac tttagtccaa aacataatgt acatgtagcg gtaaatgaat  137040
ctcggtcagg ttcttatcat tctgactggt attatgcagt tccgactgtt gaactagtcg  137100
agccccgtga acgtgtagta actcagatag tacgagaatg gattacgcta taaaaccttg  137160
gtgggcggct agatgggaaa ctgtagagcc agagccggaa gaaccggttt acactgatga  137220
agaaacagta tataatgaac caacgataaa tgacttaatt gatatggaga tgggacatga  137280
ttacagtaga taagtggttt agaattaatc gtgctgatgc agggctgtgt aattactggc  137340
cggaacttag tgcaggtact gtctttaaag ttcgtgaact tgcaaaagaa tgtgaagatg  137400
atatagagcc tgatactgga attattgaaa ttgaactttc tgatggaaag attattaaca  137460
tctacgataa gccaattacg tattggtgct tgtggaatac tgaatcagtc gaaaatggcg  137520
aaattgaaga agttgtagag cgaactaatc aagttgttca gaagcctaaa gctgattttc  137580
aaggtgaacg tatttcatac gcattagcta aattagctgc acaagaaaat aacgatggct  137640
atgaaggaaa tttgatgcaa gctgccgcag aatatattga atggcttgaa acccaaattt  137700
ctttttctga ccaaaagatt cggcaatata agcgattgaa tcaaatgttt tacaatactt  137760
gaaaataata aataccctta tctatttaag gtaagggttt tattatgtta ttgactggca  137820
aattatataa agaagaaaaa cagaaatttt atgatgcaca aaatggtaaa tgtttaattt  137880
gccaacgaga actaaatcct gatgttcaag ctaatcatct tgatcatgac catgaattaa  137940
atggaccgaa agcaggaaag gtgcgtggat tgctttgtaa tctctgcaat gccgcagaag  138000
gtcaaatgaa acataaattt aatcgttctg gcttaaaggg gcaaggtgtt gattatcttg  138060
aatggttaga aaatttactt acttatttaa aatccgatta cacccaaaat aatattcacc  138120
ctaactttgt tggagataaa tcaaaggaat ttctcgtttt aggaaaagag gaaatgatgg  138180
ctgagatgct tcaaagagga tttgaatata atgaatctga cactaaaaca caattaatag  138240
cttcatttaa gaagcagctt agaaagagtt taaaatgaca attgaaaaag aaattgaagg  138300
attgattcat aaaactaata aagacctttt aaacgagaat gctaataaag attctcgtgt  138360
ttttccaact caacgggacc ttatggctgg tattgtgtct aaacacattg ccaaaaatat  138420
ggtcccgtct tttattatga aagcgcatga aagcggaatt atccatttcc acgatattga  138480
ttattcccct gctcttccat ttactaattg ttgtttagta gatttaaaag gaatgcttga  138540
gaacggattt aagcttggta atgcacagat tgaaactcct aaatcaattg gagttgctac  138600
tgcaattatg gcacaaatta ctgcacaggt tgcttcccat caatacggcg gaacgacttt  138660
tgctaatgta gataaagtac tttctcctta tgttaaacgc acctatgcaa aacatattga  138720
ggatgcagaa aaatggcaaa tcgctgatgc gttgaattat gctcaatcta aaacagaaaa  138780
agatgtatac gatgcattcc aagcttatga atatgaagta aatactctct ttagttcaaa  138840
cggacaaacg ccttttgtaa caattacatt tggtacagga actgactgga ctgaacgaat  138900
gattcagaaa gcaattctga aaaatcgtat taaaggtctt ggtcgtgatg ggataactcc  138960
tattttccct aaacttgtta tgttcgttga agaaggtgtt aatctttata aagacgatcc  139020
gaactatgat attaaacagc ttgctctaga gtgcgcaagc aaaaggatgt atcctgatat  139080
tatttcagct aagaacaata aagctatcac tggttcatct attcctgttt ctccaatggg  139140
ttgccgcagt ttcttgagtg tatggaaaga ttcgactggc aatgaaattc ttgatggacg  139200
taataatctc ggtgttgtaa cactgaatct tcctcgtatc gcattagatt cttatattgg  139260
aacacagttc aatgaacaga aatttgttga attattcaat gaacgaatgg atttatgttt  139320
tgaagcattg atgtgtagaa ttagttcctt aaaaggagtt aaagcgactg ttgctcctat  139380
tctttaccaa gaaggtgcat tcggggttcg tcttaaacct gatgacgata taattgagtt  139440
atttaaaaac ggcagaagtt cagtgtcttt aggatacatt ggtattcatg aattgaatat  139500
tcttgtcggt cgtgatattg gacaagaaat tttaactaaa atgaatgctc gtcttaagca  139560
gtggactgaa agaaccggat ttgcttttag tttatattcg actcctgctg aaaacctttg  139620
ttatcgcttc tgtaaactcg ataccgaaaa atatggaagt gtaaaggatg ttaccgataa  139680
aggctggtac actaacagtt tccatgtttc agtagaagaa aatattactc cgtttgaaaa  139740
gatttctcgc gaagcgccgt atcatttcat tgcgacaggc ggtcacattt cttatgttga  139800
acttccagat atgaaaaaca atttaaaggg tcttgaggct gtctgggatt atgctgcaca  139860
acatttagat tattttggtg ttaatatgcc ggtagataaa tgttttacat gcggaagtac  139920
ccatgaaatg actcctactg aaaacggatt tgtttgttct atctgtggag aaactgatcc  139980
taaaaagatg aacacaataa gaagaacatg tggttatttg ggaaatccga acgaacgtgg  140040
atttaatctc ggtaaaaata aagaaatcat gcatagggtt aaacaccaat gaattatgat  140100
```

```
agattttatc cttgcgattt tgtgaatggc cctggttgca gggtcgttct tttcgttaca  140160
ggttgtttgc ataaatgtga agggtgttat aataaatcaa catggaatgc tagaaatggt  140220
attccattca ctggtgaaac actagaacaa ttaattgaat gtttgaataa tgattatata  140280
gaaggattaa ctataactgg gggtgaccct ctttatcctg ataacagaga cgtgattcac  140340
tctgtggttc aaactattaa aaatctttat cccaataaaa gcatttggtt gtggacagga  140400
tataagtttg aagatattaa acaactagaa atgcttaaat atgttgatgt tattattgat  140460
gggaagtatg agaaaaatct tccgactaaa aagctgtggc gaggatcaga taatcagcga  140520
ctttggtcaa ataccgatgg ggtgtggaca catgattaaa ttgaattaca ttatggatac  140580
tataaatgat atgatttttc attttggtcc agaattttat tcgcaatata gtttagtgct  140640
tatcaatgct tggttaatca attaagggta aaatatgtat aaatttcgta aaggtttagc  140700
tgattttctt acaactgtaa cgttctttct gtttatggca gttggagcta ttttccttat  140760
tccttttatt gttgtatttt tcgtgattag tttaatttct ccagaaaagg gcttatcttc  140820
tagtgagttc aatgagcgtc tggataaaat tactaacaag ctgaatgctg ttcttgataa  140880
aaaggcttaa ttatgattag ttttgagcgg tatgtagtag agagttggaa ggggtttgat  140940
atgtttggta atgactatta tttttacgaa tgtagtctaa atcctagttt ttgggctgga  141000
cgtgaacgag atctcgaaga aattaatgct cgtgccgaat tgttaggtga actgcctacg  141060
gtttatttta cctttgatgc atctggattt gttatccagg tttattttcc tgaagaaaac  141120
tctggtgagg attctgttaa tcctccttat tgggcttacc aaggaattat ttctcgtgga  141180
acaaaactcg aacttaaaga ataagattga agtctatgga attccagatg aagtaggtcg  141240
ttgtcctgga tgtcaatcag ttacaaaact tctaaaggag ctcaatgctc cttttacttt  141300
ctataaagtt cttactaata atggtaagat tgagtacgat cgcccattga ttgtatctct  141360
tgctaaacgc gctggattca catctcttaa tattcggtat cctgtcattt tcattaatga  141420
ttctagacaa aagaacatta aacacttcaa agaaactctc atttcacttg gatatgatag  141480
agatatcata gaagactaag acgggccctc tgggcctttc tttcttacat tctgtatatt  141540
accattctaa gctatcgttc ccttcttatc attccctaaa ataattttca caaagttgtt  141600
tacaacaagt tcaaaccgtg gtattattaa catatgaatt acctttgagg aattgatatg  141660
attgataaag agattaaaat tgaccagtac tatcgtgtta acggacatat cgttattgtt  141720
acagcagtcg atgatttaga tgttcattat actttgctta aatggaacaa acgtttgatt  141780
tgtgatcgtg ctgtatttag ttcagttgct aaggaaatta aactccatgg gtaaaacgta  141840
tcgtcgtaaa gacttaaaag tgcgtgatta tgactatttc ggaaagcgta aagctcctga  141900
tggtgtaagt cataaagata tggttgaaaa catttttcgc tcagataaat ggcgtagaat  141960
gaaaggtatt gattcagaag ttaaagatga gctaaatcgc caattacgtg gtgaagtaag  142020
aaagttgaaa aaatcagttt acattgacga tgattttgat tataatactt ctcaacgagt  142080
tgctaaacgt aaatcaaacg agtgttatcg ttatagctga ggaaaatatg aatatcaaac  142140
gaatgctttt taagcagggg ttatacactt taaatgttac tccaaaaggc gatacaacta  142200
ggtggtcagt aaatgactgg attaaattta ttgatgaaaa tggtaattgg gaaatttaaa  142260
tgaatcctga atctaaatta tcgcagcgaa ttgccgaagc tcgtcgtcag ttctttgaaa  142320
atatgatagc acaaggtatt gatgacgaag tttttctaaa ctggttttgg aatcacaaat  142380
attcaagttg ctcaggagca atattaatat cagccgcaat gatgtacgaa ggctggaagg  142440
gtgccaaaaa gtttagctaa gggcttcggc ccttttttgga taataaaatt ttaatgcaat  142500
tgaggataat gtatgactat tcaaattaaa aacgccatca attcttacgc atatgataaa  142560
gtagtttctt tgctagaaaa aggcgatatt gtaactcctc aaattttgga taaatgggaa  142620
aaagagcttc atcaaacgat gaaacagaat gatcagaaga ttggacgcaa tactgtccgt  142680
gaattattgg ttcaatatat cttgtcagaa tttgatgtta aagcttttgg tgtagaatct  142740
aaagcttatc aaaagcatga aatttccgat aaaactattc gtcgcatgaa aaatcaacgc  142800
aagaaaaaat ttgcagacct gaaaattact aaggtataat tatgaacgaa gctcttatta  142860
acgatttacg tcttgctgga tatgaagtaa atacaaatgg cattggttta actcaaattg  142920
aaggaaacgg attcatcctt gagtatgaat ttagccaatg gtggttatat gccaattatg  142980
gcgaattgat tgaatatgtt gaccaatttg attcactaga tgcagctctt ggagcggcta  143040
agctgatgaa tgtatgaaat ttattaatat ttctattact attgaaaatt atggcatttt  143100
ctatgttgat caatacatga aaatttcatt tttcccaaat aagactggtg ttggatattg  143160
ggaaagccat gtttctgaat taaatgaaag cgaatatgct agtacacatg aaaagttttt  143220
agacttttta tatcatgctg atctaactag tcattatata gatattcatg aatttaaaaa  143280
gatgatggag aaagtgttcc aagcatactg tttacttaga taactgatat cctctatgct  143340
ttaagataga tcttcaaata ttatgatata atagatctat gaattgagct aagaggtgaa  143400
aatgtcagaa actaagccta aatataatta cgtaaacaat aaagagcttt tacaagctat  143460
tattgattgg aaaacagaat tagcaaataa taaagaccca aataaagtag ttcgtcagaa  143520
tgatactatc ggattagcca ttatgcttat tgcagaaggc ttatctaaac gtttcaactt  143580
ttcaggatac acccagtctt ggaaacaaga aatgattgca gatggtatag aagcttctat  143640
taaggggctt cacaattttg atgaaacgaa atataaaaac ccacatgcat atataactca  143700
agcttgtttt aatgcattcg tccagcgtat taaaaaagaa cgtaaggaag ttgcaaagaa  143760
atatagttac ttcgttcaca atgtctatga cagccgtgac gacgatatgg ttgcgttagt  143820
agatgaaact tttattcaag acatctacga taaaatgacg cattacgaag aatcaaccta  143880
tagaacaccg ggggctgaaa agaaaagtgt tgtagacgat tctcctagtt tggatttttt  143940
atatgaggct aacgattaac ctctccggat tcttggaaga aatacctgaa gttgaagcta  144000
ttccctattt acttaaaatg tatctcaggg aagttttagc tcttgacatt gatattgatc  144060
cagaaaatcc gtatgatacc gcttttaaat ctaatggtgt agaattaaac tatcggtatc  144120
atttaacaga tgatgatttt tattttatat tagagaaata atatgactga taaacccgaa  144180
attaatgatg aagtggaaaa gcttatttct tctattgaag aaaagaaccg tcttgaagca  144240
gaaagaaaag caaataagtt attgtctaaa aacaaacgcg aactgaatcg tctttataag  144300
catgctcaga tcgcagctga aaacaataat tttgctcaat acgaatatgc tatcaagaaa  144360
agtcgggata ttctaaaaca gccatataac gatgaactca tcagtattct ttggaagact  144420
actagatcgc agattgagga tatgattgat gcttacacac gtaaaattca agcgtcttaa  144480
aattaatgca ggatttactg aatctttgaa tggtcatctt tgcgtgaaaa tttctgaaaa  144540
agaataccac gatagttcaa ttaaagaagt taatcctcct attgtaagag cagaccctaa  144600
tatgaaagtg tgggttgatt cctatcaagt caaaaaaatgg tggcagctgt gaaagatgaa  144660
cgcccagact tgtgaaatag attataataa aattcgttcc tctaaagtag aaatgatgag  144720
acgctttaaa gaatctcatg ataaagctaa agcagaagga actataacat ataagcgtat  144780
aaaatttaga agctctaatg agcctctgta tggtgtatta tgcggatagg agcttcggct  144840
```

```
cctatattgc tttataaatt tttggtaaaa taaaccaaaa caatgaggat attaaatgaa  144900
agtatgcatt tttatggctc gaggtcttga aggttgtggc gtaactaaat tttctcttga  144960
gcaacgtgat tggtttatta aaaatggtca tgaagtaact ttggtttatg ctaaagataa  145020
atcatttact cgtaattgcg cgcatgatta taagtcattt tcaattccgg ttttattggc  145080
aaaagaatac gataaaacac ttaagctggt aaatgattgt gatattctaa ttatcaattc  145140
agttcctgct acttcagtcg aagaagacac tattaataac tataaaaaaa ttattgataa  145200
cattaaacct tctgttcgtg ttgtagttta tcaacatgac cattcttctc tttctttgcg  145260
ccgaaatttg ggattagaag aaactgttcg tcgagctgat gttattttta gccattctga  145320
taatggtgat tttaataaag ttttgatgaa agaatggtat ccagaaaccg tttctctgtt  145380
tgatgatatt gaagaagcac cgaccgtata caactttcag cctcctatgg atattgcgaa  145440
ggttcgatca acctactgga aagatgtttc tgaaattaac atgaatatca accgttggat  145500
tggtcgcacg actacatgga aaggttttta tcagatgttt gattttcatg aaaaacatct  145560
taaacctgca ggactaagta ctattatgga aggtctggaa cgttctccag cgttcattcc  145620
tattaaagaa aaaggaattc catacgagta ttatcgtctt catcaagtag accaaattaa  145680
aattgctcct aatttgccaa cgcaaattct tgaccgttat gtaaatagcg aaatgcttga  145740
acgtatgagt aaatccggtt ttggttatca gttgagtaag ttggataaaa aatatctaca  145800
acgttcttta gaatatactc atctcgagct tggtgcatgt ggaacaattc cggtattttg  145860
gaaatctact ggcgaaaatt taaaattccg tgttgataat actccgttaa tttctcatga  145920
tagcggtatc gtttggtttg atgaaaatga catggaatca acatttgaac gtattaaaga  145980
actgtcatct gaccgagctc tttatgaccg cgaacgcgaa aaagcttatg aatttttgta  146040
tcagcatcaa gattcaaact tctgctttaa agaacagttt gacattatta caaaataaag  146100
ggcttcggcc ctttagcttt atacggagtt tgatataatg atatttcttg gatatgtgat  146160
actttttctt gcattttatc tattcactag agcatgttgt gttgggttct ttagcacacc  146220
agatgggttt atttcaataa ttttattttg catttcaatg acggttcttg atatatgaaa  146280
aaatatataa cttatttaac aatatatagt ggagataaac ttcctccttt ttatattgga  146340
tctacgtctt tagataggca tttagctgga tatcatggtt cagttttatc taaaaagtat  146400
aagaaaattt ataataaaga gctttcagat aatcctcact tatttgattc atgcatttta  146460
gctgaatttg atacgcgtga agaagctatt aaatgcgagt tatattatca acgattgcat  146520
gatgcagtta aaaatccatt attctttaat atgtcatatg ctgctccaaa aggttcattt  146580
ggaagagata ataaaggaca aaatcatcca ttatatggtt ctcataattg taaaggaaat  146640
atacattcac atgatccatt aacaggaaaa tctgcctttt tgccttatat tccagaaggt  146700
tatgtaaaag gaaggtcaaa taaatttaaa gcttcatcac ataataaagg taaaaaatgg  146760
tataataacg gagttaagca aatgttatgt catgaacctc ctggtcctga atggacaaaa  146820
ggaaaaatta aagaactggt ttcaaaagca gctaaattag gatggaaaag acaccatgaa  146880
aatactaaac ttgggtgatt ggcatttagg cgttaaagct gatgatgagt ggattcgcgg  146940
tattcaaatt gatggaatta agcaagcgat agaatattct aagaaaaatg gaattactgt  147000
atggattcaa tacggtgata tttttgatgt gcgaaaagcg atcacgcata aaactatgga  147060
gtttgcccgt gaaatagttc aaatgcttga tggtgctgga atcacattac atactattgt  147120
aggaaatcac gatcttcact acaaaaaatgt aatgcatcca aatgcctcta ctgagctttt  147180
ggctaaatat cctaatgtta aagtatatga taagcctact acagtagatt ttgacggatg  147240
tttgattgat ttaattcctt ggatgtgtga agaaaatact ggtgaaattc ttgaacacat  147300
caaaacttca tctgcttctt tttgtgttgg tcactgggag ctgaatggat tttattttta  147360
taaaggaatg aaatctcatg gtcttgaacc tgatttcctt aagacttata aagaggtgtg  147420
gtctggtcac ttccatacta tctctgaggc tgctaacgtc agatatattg ggacaccatg  147480
gacactaact gcaggtgacg agaatgaccc tcgtgggttc tggatgtttg atacagaaac  147540
agaacgaatg gaatttattc caaacaacac tacctggcat cgtagaattc attatccatt  147600
taaaggaaaa attgactata aagattttac aaatctatca gtacgtgtta tagtaactga  147660
ggtagacaaa aatctgacga agttcgaatc tgaactagaa aaagttgtgc attcattacg  147720
agttgtgtca aaaattgata actctgtcga gtcagatgac agtgaagaag ttgaagttca  147780
atctcttcag acgttaatgg aagaatacat taatgcaatt ccagacatca ctgattctga  147840
ccgtgaagca cttattcaat atgcgaatca gctatatgta gaggcaacac aatgactttt  147900
gatgaattta aaaatgttat gatgagtcag cattttgaat gcgaagtaaa agatgatatt  147960
gggcataaag aaattattga atattggttt gaaccgttag aggttgaaga taattgtatt  148020
aaaaaggtta cggtatgcac tgattgggcc gtatctttta acttcaacat tttagataat  148080
gatacaccta aatcattaca agatatggct gtatcttgta ttaaggatgc atactgtgaa  148140
gttttcgaca tttgacatta atgatgaatt catagcaaat attgattata ccgaagaaga  148200
ttctagatat gttggaataa tttatatcac atcaaaagta gcacaaggtg ttgtttgcat  148260
ggctgaattt gatgaatact ttttagatta tgatgatatg atagaatggt ctaaaagata  148320
cattaaaagg aatcttttgt gaagaatttt aaactaaacc gagttaggta tcaaaatata  148380
atgtcagtag gtggaaatcc tattgacatt caattagata gggttcaaaa aactcttatt  148440
actggccgaa atggcggtgg taagtctact atgttagaag ccatcacatt tgggcttttt  148500
ggcaagccat ttcgtgatgt aaagaaaggt caattaataa acagcacaaa taagaaagaa  148560
cttttagttg aactgtggat ggaatatgat gagaaaaagt attatatcaa aagaggacaa  148620
aaaccaaacg ttttcgaaat caccgttaac ggtacacgtc ttaatgaatc tgccagcagt  148680
aaagatttcc aagcagaatt tgaacagctt atcggaatgt catatgccag tttcaagcag  148740
attgttgtcc ttggtacagc aggtatacc cctttcatgg gtttgtcgac ccctgcgcga  148800
agaaagcttg tggaagacct gcttgaggta ggaacattag ctgaaatgga taagcttaat  148860
aaagcactaa tacgtgaatt aaattcacaa aaccaagtgc ttgatgttaa aaaagatagt  148920
attatccaac aaattaaaat atataatgat aacgttgaac gccagaaaaa attaacgggt  148980
gacaacctta ctcgtcttca aaatatgtat gatgatttgg caaaagaagc tagaacgcta  149040
aaatcggaaa tagaagaagc taatgaaaga ttagttaata ttgttttaga tgaagacccg  149100
actgatgcat ttaataaaat cggtcaagaa gcagttttaa ttaaatcaaa aattgactcg  149160
tataataaag tcattaatat gtatcacgaa ggtggattat gcccaacctg cttgtcacaa  149220
ttaagttcag gtgataaagt tgtttctaaa attaaagata aagtttctga atgtacgcat  149280
tcgtttgaac agctttcaac acatcgtgat aatttaaaag ttcttgttga tgaataccga  149340
gataatatta aaacccagca gtcgttggca aatgatattc gcaataaaaa gcaatctctg  149400
atcgcagcag tagataaagc taaaaaggtt aaagcggcta tagaaaaagc atcttctgag  149460
tttattgacc atgctgatga aatagcactg cttcaagaag aacttgataa aattgttaag  149520
acaaaaacta atttagtaat ggaaaaatac caccgaggaa ttttgactga tatgctcaaa  149580
```

-continued

```
gattctggta ttaaaggtgc tattattaaa aagtacattc cattatttaa taagcagatt  149640
aaccattatc ttaaaaataat ggaagcggat tatgtgttta cattagatga agaatttaat  149700
gagacaatta aatcacgtgg tcgtgaagat tttagttatg cttcattcag tcaaggtgaa  149760
aaagcgcgaa ttgatattgc tcttttattt acttggcgtg atattgctga aaaagtttca  149820
ggcgttaaaa taaacacact aattcttgat gaagtttttg attcagcgac cgacgttgaa  149880
ggtgtaaaag ctatttcaac tattttagat agtttaaaaa atactaatgt ttttgttatt  149940
tcgcatagag accatgaccc gcaagcatac ggtcagcatc ttcaaatgaa gaaagttggt  150000
cgatttactg taatggttta atttataaga gattatgctt taatttatta gagtataatc  150060
tctatggagg aaaaacatgg aatattcaac tggacagcat ctattaacta ttcctgaaat  150120
aaaacgatat attctgagaa ataattttc taatgaagag catatagtta ctgaatctat  150180
gcttaggaat gcatttaaag cagaatatac aaaaataatg tccaatagaa atgaagcttg  150240
gactgttact gattattatg actaaaggtg tattatgact aaaattactg tgaattatac  150300
tgttgatgta aaagatattc agccaaaaca cgtgcgttct gactcaaatc cgcaaaacca  150360
aaataaaatt cgtcgcgcat gggttttgtc tctttctgat aacgcaatgg aagttattca  150420
gaacaaaatt aaatctgcac ctgctcgtca tgcatattat gaagctatcg atcgtgaagt  150480
aagtaataaa tggattgaac taatgcgcaa acatacgaca gaatctctaa atgctggtgc  150540
taaatttatt atgacttcat gcggtgaacg ccttgaagat gattattgcg gtaatgcaga  150600
tgaacgtcta attgttgctg ctcaaattgt tgcggaaaca attgctgctg attttaatcg  150660
ttaattgctt tattaaatta gttataaaat taaatctcat ttgaattgaa ggaaattaca  150720
tgaaactgtc taaagatact actgctctgc ttaaaaattt cgctactatt aactctggta  150780
ttatgcttaa atccggtcaa tttattatga ctcgtgcagt taatggtaca acttatgcgg  150840
aagcaaatat ttctgacact attgattttg atgtagcaat ttacgatttg aatggttttc  150900
tcggtattct gtctttagtt aatgatgatg cagaaatttc ccagtcagaa gatggaaata  150960
ttaaaattgc tgatgcccgt tcaacaattt tttggccagc agccgatccg agtacagtag  151020
ttgctcctaa taaaccaatt ccattcccag tagcatctgt tgttactgaa attaaagctg  151080
aagaccttca acagctgttg cgtgtatctc gtggtctgca gattgataca attgctatca  151140
cggtaaaaga aggtaaaatc gtaattaacg gttttaataa agtagaagat tctgctctga  151200
cccgtgttaa atattctttg actcttggtg attatgatgg tgaaaataca tttaatttca  151260
ttatcaatat ggcaaatatg aaaatgcaac caggaaatta taaacttctg ctctgggcaa  151320
aaggtaaaca aggtgctgct aaatttgaag gtgaacacgc gaattatgta gtagctcttg  151380
aagctgattc tacccacgat ttttaataga gggcttcggc cctttataat ttacactaaa  151440
acttgaatga ggaaattatg attaccgtaa atgaaaaaga acacattctt gaacagaaat  151500
atcgtccatc tactatcgat gaatgtattc ttcccgcctt tgataaagaa acctttaaat  151560
ctattacaag taaaggtaag attccacata ttattcttca ttctccttct ccaggaacag  151620
gtaaaacaac tgtagcaaaa gcattgtgtc atgatgtaaa tgctgatatg atgtttgtga  151680
atggatcaga ttgtaaaatt gatttcgttc gcggtccttt gactaatttt gccagcgccg  151740
cttcatttga cggtcgtcaa aaagtaatcg ttattgatga atttgaccgt tcaggattag  151800
cagagtctca gcgacatctt cgttccttta tggaagctta tagttcgaac tgtagtatta  151860
ttattactgc taacaatatt gatggtatta ttaaaccgct tcagtcacgc tgccgagtta  151920
tcacattcgg tcaaccgacc gatgaagata aaattgaaat gatgaagcag atgattcgtc  151980
gattgactga aatctgtaag catgaaggaa ttgctatagc tgatatgaaa gttgtagcag  152040
ctttggttaa aaagaatttt cctgattttc gtaaaactat tggcgagctc gatagttatt  152100
catctaaagg tgttttggat gctggtattt tatcactggt tactaacgat cgtggtgcta  152160
ttgatgatgt tcttgagtct ctcaaaaata aagatgttaa acaactcaga gctttagcac  152220
caaaatatgc agccgattat tcgtggttcg tgggtaaact tgccgaagaa atctattcac  152280
gtgtaactcc acagagtatt attcgtatgt acgaaattgt cggcgaaaat aatcagtatc  152340
atggtattgc agctaatact gaattgcatc tagtttatct tttcattcag ttagcatgtg  152400
aaatgcagtg gaagtgatat gagcttattt gaagatgata ttcaattaaa cgagcatcaa  152460
gttgcttggt attcaaaaga ttggacagct gtccaatccg ctgctgattc ttttaaagaa  152520
aaagctgaaa atgaattttt tgaaataatt ggagctatta ataataaaac taaatgctct  152580
attgctcaaa aagattattc aaaattcatg gttgaaaatg cattatcaca atttccagag  152640
tgcatgccag ctgtatatgc tatgaattta attggatcag gcttaagcga tgaagctcat  152700
tttaattatc taatggctgc agttcctcgt ggtaaaagat atggtaaatg ggcaaaacta  152760
gttgaagatt ccaccgaagt attgattatt aagttacttg ctaagcggta tcaagttaac  152820
acaaatgatg caattaacta taaatcaatt cttactaaaa atggaaaact tcctttagta  152880
ttaaaagaac taaaaggttt agtcacggat gattttttga aagaagtgac taagaacgta  152940
aaagaacaga aacaactcaa aaaactagca ttggaatggt aaaatgattg aaattactct  153000
taaaaaacct gaagattttc tgaaagtaaa agaaactttg actcgtatgg gaattgctaa  153060
taataaagat aaagttctgt atcagtcctg tcatattctt cagaaaaaag gactatacta  153120
tatcgttcat tttaaagaaa tgcttcgtat ggatggtcgc caagttgaaa tgacagaaga  153180
agatgaagtt cgtcgtgatt cgattgcatg gctgttagaa gattggggac taattgaaat  153240
cgttcctgga caaagaactt ttatgaaaga tttaactaat aacttccgag ttatttcttt  153300
taaacaaaag cacgaatgga aactcgttcc taaatatacg attggtaatt aagcaagggg  153360
cttcggcccc ttatttggag tataatatat caagagccta ataactcggg ctataaacta  153420
aggaatatct atgaaagaat tttatatctc tatcgaaaca gtcggaaata acattgttga  153480
acgttatatt gatgaaaacg gaaaggaacg tactcgtgaa gtagaatatc ttccaactat  153540
gtttaggcat tgtaaggaag agtcaaagta caaagacatc tatggtaaaa actgcgctcc  153600
tcaaaaattt ccatcaatga aagatgctcg agattggatg aaacgaatgg aagacatcgg  153660
tctcgaagct ctcggtatga acgattttaa actcgcttat atcagtgata catacggttc  153720
agaaattgtt tatgaccgaa aatttgttcg tgtagctaac tgtgacattg aggttactgg  153780
tgataaattt cctgacccaa tgaaagcaga atatgaaatt gatgctatca ctcattacga  153840
ttcaattgat gatcgttttt atgttttcga ccttttgaat tcaatgtatg gttcagtatc  153900
aaaatgggat gcaaagttag ctgctaagct tgactgtgaa ggtggtgatg aagttcctca  153960
agaaattctt gaccgagtaa tttatatgcc attcgataat gagcgtgata tgctcatgga  154020
atatatcaat ctctgggaac agaaacgacc tgccattttt actggttgga atattgaggg  154080
atttgacgtt ccgtatatca tgaatcgcgt taaaatggtt ctcggtgaac gtagtatgaa  154140
acgcttctct ccaatcggtc gagtaaaatc taaacttatc caaaatatgt acggtagcaa  154200
agaaatttat tctattgatg gcgtatctat tcttgattat ttagatttgt ataagaaatt  154260
cgcatttact aatttgccgt cattctcttt ggaatcagtt gctcagcatg aaaccaaaaa  154320
```

-continued

```
aggtaaatta ccatacgacg gtcctattaa taaacttcgt gagactaatc atcaacgata  154380
cattagttat aacatcattg acgtagaatc agttcaagca attgataaaa ttcgcgggtt  154440
tatcgatcta gttttaagta tgtcttatta cgctaaaatg ccttttctg gtgtaatgag  154500
tcctattaaa acttgggatg ctattatttt taactcattg aaaggtgaac ataaggttat  154560
tcctcaacaa ggttcgcacg ttaaacaaag ttttccgggt gcatttgtat ttgaacctaa  154620
accaattgct cgtcgatata ttatgagttt tgacttgacg tctctatatc ctagcattat  154680
tcgtcaggtt aacattagtc ctgagactat tcgtggacaa tttaaagttc atccaattca  154740
tgaatatatc gcaggaacag ctcctaaacc gagtgatgaa tattcttgtt ctccgaatgg  154800
atggatgtat gataagcatc aagaaggtat cattccaaag gaaatcgcta aagtattttt  154860
ccagcgtaaa gactggaaaa agaaaatgtt cgctgaagaa atgaatgccg aagctattaa  154920
aaagattatt atgaaaggcg cagggtcttg ttcaactaaa ccggaagttg aacgatatgt  154980
taagttcagt gatgatttct taaatgaact atcgaattat actgaatctg ttctcaatag  155040
tttgattgaa gaatgtgaaa aagcggctac acttgctaat acaaatcagc tgaaccgtaa  155100
aattcttatt aacagccttt acggtgctct tggtaatatt catttccgtt actatgattt  155160
gcgaaatgct actgctatca caatttttgg tcaagttggt attcagtgga ttgctcgtaa  155220
aattaatgag tatctgaata aagtgtgcgg aactaatggt gaagatttca tcgcagcagg  155280
tgatactgat tcggtatatg tttgtgtaga taaagttatt gaaaaagttg gtcttgaccg  155340
attcaaagag cagaacgatt tagttgaatt catgaatcag ttcggtaaga aaaagatgga  155400
acctatgatt gatgttgcat atcgtgagtt atgtgattat atgaataacc gcgagcatct  155460
gatgcatatg gaccgtgaag ctatttcttg ccctccactt ggttcaaagg gcgttggtgg  155520
attttggaaa gcgaaaaagc gttatgctct gaacgtttat gatatggaag ataagcgatt  155580
tgctgaaccg catctaaaaa tcatgggtat ggaaactcag caaagttcaa cgcctaaagc  155640
ggttcaagaa gctcttgaag aaagtattcg tcgtattctt caagaaggcg aagagtctgt  155700
tcaagaatat tataagaact ttgagaaaga atatcgtcaa cttgactata aagttattgc  155760
tgaagtaaaa actgcgaacg atatagcgaa atatgatgat aaaggttggc caggatttaa  155820
atgtccattc catattcgtg gtgtgttaac ttatcgtcga gctgttagtg gtctgggtgt  155880
agctccaatt ttggatggaa ataaagtaat ggttcttcca ttgcgtgaag gaaaccccatt  155940
tggtgacaaa tgcattgctt ggccgtcggg cacagaactt ccaaaagaaa ttcgttctga  156000
cgtactgtct tggattgact actcaacttt gttccaaaaa tcgtttgtta aaccgcttgc  156060
gggtatgtgt gaatcggctg gtatggacta tgaggaaaaa gcttcgttag acttcctgtt  156120
tggctgatag aataaatcta gggacctccg ggtccctttt tcatacaagt aatataaatc  156180
tatacttatg aaaaacagat gattctggac atttagaatt ccctaaaaaa ttttcacaaa  156240
actgtttaca agactgttcc tctgcggtac tatacaacta tcaactactg atacagattt  156300
ggagaataaa atgaaaattg ttatgggatg cttagcagtt tgtttagttg cattagcagc  156360
agttccattt gttagtgttg aaaatgatac tcaacctatg attgaatcta gcaccgttat  156420
tcacactaat ggtaaaatat cagttaaaat tgatgataat cttcatgtga atacaaatgg  156480
atctttaggt gtacaaatag gtaatacctg cataagcact actggagtaa ttactacttg  156540
catttgagga aattattatg aaaatcgcta ttttggttat tgcattaggt cttactggtt  156600
gtgtagctca aggaccggta gtaaatcagt ctgatgtagg aaaaattgta aattgttcaa  156660
gtaaatttta taatcctaat gtcaagtgtt ataaagaagc tccaaagcaa acagtagaac  156720
aaatgcaggc gaattttgac gaagctattc gtccagatga atctgctcaa gcatatcgta  156780
attcggatgt aattacacgc gaagaaaaaa ttgaaaacta ctgcgccgag ctttgggcta  156840
attgggctaa taattaccaa tggcgtaccg gtaaaaatgc tccgatggag tatgtagtga  156900
attcttataa ttcatgcgta aaaaatttaa ctaagtgagg aaaacatgga aactttagta  156960
gcaggttcaa tttttatggt tttagtttca ggtgtgttgg ctattattat atacatgctt  157020
ccatggttca tcgccttgat gcgtgggtca aaatcgacag taggaatctt tttcacgtct  157080
ttactgttta actggtcaat tattggttgg tttattacat ttatttggtc aattgcgggt  157140
gaaactaaaa agtctgcaca gccaaatcag gtaattatca tcagagagaa ggaatgaaaa  157200
gcaaaattat agcagtgttg cttttaatct tgatgattat aataagtata tactatagtg  157260
taacggttcc tcttatgatt ccaactatta ttttaggttg gagcttatta ctgttacaag  157320
ttaaatatga atgtatcaat tgaggtttaa atgattagtg actctatgac agttgaagaa  157380
atccgtcttc atttggggct tgcattaaaa gaaaaagatt tcgtagttga taaaactggt  157440
gttaaaacta ttgaaattat tggcgcatca tttgtagcag atgaaccgtt tatttttggc  157500
gctcttaatg atgaatacat tcagcgtgaa cttgaatggt ataaatctaa gagcttgttc  157560
gttaaagata ttccaggtga aacaccgaag atttggcaac aagtagcatc ttctaaaggc  157620
gaaattaact cgaattatgg ttgggctatt tggtcagaag ataactatgc ccagtatgat  157680
atgtgtttag ctgaacttgg tcaaaatcct gattctcgac gtggtatcat gatttatact  157740
cgtccatcca tgcaatttga ctataataaa gatggtatgt cagatttcat gtgtactaat  157800
acagtacagt acctgattcg tgataagaaa gtaaatgcag tagtaagcat gcgctcaaat  157860
gacgtggtct tcggattccg taatgattat gcatggcaaa aatacgtatt agataaatta  157920
gtatctgatt tgaatgccgg cgattcaact cgtcagtata aagcaggttc tattatatgg  157980
aatgtcggaa gtcttcatgt atattctcgt catttttact tggttgatca ttggtggaat  158040
actggcgaaa ctcatattgt gaaaaaagac tataaaggtg tgtggaaatg attcaattcg  158100
taattccaag ttatcagcgt gtcggggcag tttctgccct tgatatgttt ccgactgatt  158160
atgaaccgca tattgtagtg cgtgaacatg aagaaaaagc ttattatgat gcctatgggt  158220
ctagagctaa aattataact attcctgatg atgtaaacgg aattgccggt actcgtaaag  158280
caattactga tatgtatgca ggtcaacgaa tctggatgat tgacgatgat actactattc  158340
gtatgagttc aatgcgaaaa agagatgacc gtcgttgtgt agataaagtc aatcaattaa  158400
cccgtgaaca gttctatgaa ttgattcaat acgtcgaaga tgccatggat tgcgggtatt  158460
atcacggtca tgctcgtcta cctattttta aaattacttc atcttggggt aattatcgtg  158520
aaaattcata tggattcacg aatacatggt atgaccttgg aaaacttacg acagaacaaa  158580
ttgggtatgg aaaaattgat ttgtgcgaag atatgtatgc atttctcaat ttaattaatc  158640
aaggttatcc gcatttggcc ttgttcaaat atctggttgt atctggaaaa gcacaagctc  158700
ctggcgggtg tagttcaatt cgtagtaatt ctaaacataa tagagcgctt gagcaaatca  158760
atagagagtt tccagagcaa gctcgttgga aacttctaa tattgaaaaa cgaaaatcgt  158820
tgggtgaaga agacgagcca ttaaaggttc ttcgcatgtg tgtttcgcgt aaagaaaaat  158880
cagaagcatt tcataagttt aatgctattc atccaatagc agttgattaa tgcctaaatt  158940
tattgtgtta taattactct atctttaacc agtgaggaaa atataatgat gcctatggaa  159000
aaaatgaatg tctattgcag atttaaaatc ccgtttgatt aaagcttcca cttctaaaat  159060
```

```
gactgctgaa ctgactacat ctaaattctt taatgaaaag gatgtaattc gtacaaaaat  159120
cccaatgctt aatattgcta tttctggtgc gattgatggc ggtatgcagt ctggtttaac  159180
tatttttgca ggtccttcta aacactttaa atcaaatatg tctttgacta tggttgcggc  159240
atatttgaac aaatatcctg acgcggtttg tctattctat gatagtgaat ttggtattac  159300
tccagcttat ttgcgatcca tgggagttga cccggaacga gtaattcata cgccgattca  159360
gtcagttgaa cagctgaaaa ttgatatggt gaaccagctt gaagctattg agcgcggtga  159420
aaaggttatt gtattcatcg actcaatcgg taatatggct tctaagaaag aaacggaaga  159480
tgccttaaat gaaaaatctg tggcagatat gactcgtgct aaatcactga agtcattatt  159540
ccgtatcgtt actccttact ttagcattaa aaatattcca tgtgttgcgg ttaaccatac  159600
aattgaaaca attgaaatgt ttagtaaaac cgtgatgaca ggtggtacag gcgtaatgta  159660
ttcggctgat acagtattca ttatcggtaa gcgtcagatt aaagatggtt ctgatcttca  159720
ggggtatcaa tttgttctaa atgtagaaaa atctcgtacc gttaaagaaa aaagtaaatt  159780
ctttattgat gttaaatttg acggtggtat tgatccttat tctggattgc tagatatggc  159840
tcttgaatta ggatttgtag taaaacctaa gaatggttgg tatgctcgtg aatttcttga  159900
tgaagaaacc ggtgagatga ttcgcgaaga aaaatcttgg cgtgcaaaag ataccaactg  159960
cactacattc tggggtcctt tatttaagca tcaaccattc cgagatgcta ttaagcgtgc  160020
ttatcagtta ggtgctattg atagtaatga aattgttgaa gctgaagttg atgaattgat  160080
taactcaaaa gttgaaaaat ttaaatctcc agaaagtaaa agtaaatcag ctgctgattt  160140
agaaactgac ctcgagcagt taagtgatat ggaagaattt aatgaataaa gatgatttag  160200
atttagatct agaaattatc gatgaatccc cctcttcgga gggggaagaa gaaagaaaag  160260
aacgtctttt taatgagtct cttaagataa ttaaatctgc tatggaaaat gttatccagg  160320
agattgtcat taaactagaa gatggttcta cacacattgt gtatgtgaca aaattagatt  160380
gggttgatgg aaaagtcgta atggactttg ctgttcttga ccaagaaaga aaagctgagt  160440
tagctcctca tgtagaaaaa tgtattacaa tgcaactaca agatgcattt aataaaaggt  160500
caaagaaaaa atttaaattc ttttaaggag taagtgtggt agaaattatt ctttctcatc  160560
tcatatttga tcaagcttat ttttcaaaag tttggccata tatggattca gaatattttg  160620
aaagtggtcc agctaaaaat acattcaaat taattaaatc tcatgtcaat gagtatcata  160680
gcgttccatc tattaatgcg ttaaatgttg cattagaaaa tagttcattt actgaaacag  160740
aatattctgg tgtaaaaaca cttatttcaa aactagctga ttctccagaa gaccacagtt  160800
ggttaataaa agaaacagaa aaatatgttc agcaaagggc gatgtttaat gctacgtcta  160860
aaataatcga aattcaaact aatgctgagc ttcctccgga aaaacgaaat aagaaaatgc  160920
cagatgtagg tgctattcct gacatcatgc gccgagcatt atcaatttca tttgatagct  160980
acgttggtca tgattggatg gatgactacg aagcacgttg gctatcttat atgaataaag  161040
ctcgtaaggt tccatttaaa ctcagaattc tgaacaaaat tactaaaggc ggagctgaga  161100
ctggaacact gaacgtttta atggctggcg ttaacgttgg taagtcatta ggattgtgtt  161160
cattggcagc agattatttg cagctcggac ataatgttct ttacatctcc atggaaatgg  161220
cagaagaagt ctgtgctaag cgtattgatg ctaatatgct tgatgtttct cttgatgaca  161280
ttgatgatgg gcatatttct tacgctgagt ataaaggaaa aatggaaaaa tggcgtgaga  161340
aatctaccct tggtcgttta atcgttaagc aatatcctac tggtggagca gacgctaaca  161400
cattcaggtc tctcttgaat gaattgaagc tcaaaaagaa ttttgttcca acaatcatta  161460
ttgtcgacta tctgggtatt tgtaaatctt gtcgcatccg agtttattca gaaaatagtt  161520
acacaactgt taaagctatc gcagaggaat tgcgtgctct ggctgttgaa accgaaactg  161580
ttctttggac tgcagcacag gtcggtaaac aagcttggga ctcttccgat gttaacatga  161640
gtgatatcgc agaatctgct ggtcttccag caacagctga ttttatgctt gcggtcattg  161700
aaaccgagga gctagcagct gctgaacaac aactcattaa gcaaatcaaa tcacgatatg  161760
gcgataagaa taagtggaat aagtttttga tgggtgttca aaagggaaat cagaaatggg  161820
tagaaattga acaagattct actccaactg aagtgagtga agtagcaggt tcacaacaga  161880
ttcaggctga acagaatcgc tatcaaagaa atgaatccac tcgagctcag ttagatgctt  161940
tggcaaatga attaaaattt tagtttacaa actgacaaga ctatggtata gtagtcttgt  162000
tggttaaatg aggagattgt tatggaattg gtaaaggtag tttttatggg gtggtttaag  162060
aatgaaagca tgtttactaa agaaatcaca atgatgaaag atgacgttca atgggctact  162120
actcaatatg ctgaagttaa taaagcatta gttaaagctt tcattgatga caagaaagtg  162180
tgcgaagtgg attgccgagg ataatatgca tattgtttta tttaaaccta ctccgtataa  162240
cgtcaggaaa aatactcaat tcaaagcact tattgcggat acgtgggaat tggtgttaga  162300
tattccggca gaagaaagcc ctccatttgg tcgagtggaa tttattaagt ttgctgtacg  162360
tcctacgaaa cggcagattc gtcaatgcaa aagatacttt cgtaagatcg ttaagctaga  162420
gaaacagttt gtaacatgtg attatgcaga agttttaaaa tagctgttta cttttgttgg  162480
aaattgagat actatataaa cataaactac tgaggagatt atcatgaaaa aatttatttt  162540
tgctacaatt tttactttgg cttcttgtgc tgctcagcct gctatggcag gatatgataa  162600
agacttgtgt gaatggtcta tgactgcaga tcagactgaa gttgaaactc aaattgaagc  162660
ggatattatg aatattgttg agcgcgatcg tcctaaaatg aaagctgaag tgcaaaaaca  162720
acttaagtct ggtggtgtaa tgcagtataa ttatgttctg tattgcgata aaaactttaa  162780
taacaaaaat atcgtaaccg aaatcacagg tgaataatat gatttattat atgcacaaaa  162840
atccaccgtt taaatacggt aaatttcctg atgcacaatg ttataatata acgcctgatg  162900
aaaataaccg tggatatctt attgacacaa tttttgtaat tgttaaagat aacgaaatcg  162960
ttgcctgggc agattttaaa ggtacaacac atgatgttaa tccggtgcct ttcacatatt  163020
acaatataat ggatttggca tatgattata attggtttaa tcatgacgcg ttggctcata  163080
ttgaaggtgt aggatttgac atctcttatt ctagctactc attgtgtcct atgagtcggg  163140
ctcataaaga acctgaatat ttttcattta ggaaacgtgt aaactttaaa cgcaacacag  163200
agtatgtcgg tggaatattt gttaaagata atcgaattac tcgcattatt tatcctttgg  163260
gctgtggtca aaaagatatt gatgttgatt tagactttac tgaaaacatc attaatcata  163320
ttgcttctgt gtattttgat attgatcaca aaattgtaat atgtggatat gaattaccat  163380
cagaaaaaca gtctaaagta aatgtttcta ttgatgacca aatttttaat gcttttatga  163440
atagaggtta atatgaaaac atataaagaa tttattaaag aagatatggt agctggagat  163500
tcaggtggta atcctgaaaa tatctctact ggaacaacgt caggcgctgt agtaaataaa  163560
ggtcctgaac agattcctaa aaagaagaaa gaggaatcta aagaaaaaga agagtaaaaa  163620
tgtcatcaat accttggatt gataatgagt ttgcgtatcg tgcattagct catttaccta  163680
aattcacaca agtaaataat agttcaactt ttaaattgcg gtttagatgc cctgtttgtg  163740
gagattcaaa aaccgatcag aataaagctc gtggatggta ttatggtgat aataatgaag  163800
```

```
gaaatattca ttgttataac tgtaactatc atgcaccaat cggaatatat ttaaaggagt  163860
ttgaacccga tttatatcgt gagtatatct ttgaaataag aaaagaaaaa ggtaaaagtc  163920
gtccagtaga aaaacctaaa gaacttccta aacaacctga gaagaaaata attaaatctc  163980
ttccgtcgtg tgttagatta gataaactgg cggaagacca tccaattata aaatatgtaa  164040
aagctcgttg tattccaaag gataaatgga aatatctttg gtttacaacc gaatggccta  164100
aattagttaa tagcatagca ccgggaacat acaaaaagga aatttctgag cctcgtcttg  164160
ttattccaat ttataatgct aatggaaaag ctgagtcttt tcaaggacgt gcattaaaga  164220
aagatgctcc tcaaaaatat atcaccatta aagcttatcc tgaggcaaca aaaatatatg  164280
gagtcgaacg agttaaagat ggcgatgtat atgttctaga aggacctata gattcacttt  164340
ttattgaaaa tggtatagct attacgggtg gtcaattaga cctagaagtt gttccattta  164400
aagataggcg tgtgtgggtc ttagataatg aacctcgtca tcctgacact attaagcgaa  164460
tgactaaatt agttgatgca ggagaaaggg ttatgtttg ggataaatct ccctggaaat  164520
caaaagatgt taatgatatg attagaaagg aaggtgcaac ccctgaacaa attatggaat  164580
atatgaaaaa taatattgcc caggggttga tggctaaaat gcggctatct aaatatgcta  164640
agatttaaat taacccaact aaagcaaatg ctaaatctac aaatgtatca agagtaacta  164700
ctggaatatt aataccatgc gcaattgcaa caggtgatag aataaagttc cagagtaaaa  164760
ttcctaccat agcagaaata gtaaaagcta tacgtttttt attacctttt atggcattaa  164820
caagtgccat taatttttgt accatatgtc ctccttattg ctttatatat ttattgtata  164880
attaatctac taatccatga attgaaagga aaaataacat gccacatttc aacgaatgta  164940
gtcaactgat cgaaggcgct gataaagctc aaaatgaata ttgggatatt ctcggtgatg  165000
aaaaagaccc gctgcaggta atgcttgaca tgcagaaatc tctgcaaatt cgtttagcta  165060
aagataaacc tgaatataat cgtcatcctg atgacttggc tactgccggt gaagttgttg  165120
attggttgcg taatcagaaa gattatattg acgatgaatt ccgtgaactt ctgacttctc  165180
ttggtggtat gagtaatggt gaaaaagacg catctgctgt atggaaacct tggaagtcgc  165240
agcatggtga acgtcgtgaa actctgatta ctgatttgtc tccacaagac caactggaaa  165300
ttaaatttga aatgattgat attctccatt tcgttctgaa tatgttccaa ggtcttggtc  165360
ttacagcaga agaaatcttt aaactttatt atctgaaaaa tgccgagaac tttgctcgtc  165420
aggaccgagg ttattaatgt ctcgtttaaa taaacgtcaa ctcaaaaagt tgaataagaa  165480
aagggcgaag gcccttactg ctttattacg taatgaaata actaaagaaa tagaccaaga  165540
gattattgaa caactctgga aagccgctaa attgtaagtt ataaatacac ctgtaattaa  165600
acaataaagg agtttattat gggtggtttc gttaacatca agacctttac tcatccagca  165660
ggtgaaggca aagaagttaa aggtatggaa gtttctgttc cgtttgaaat ctattctaac  165720
gagcatcgta ttgcagattc tcattatcag acctttcctt ctgaaaaggc ggcatattct  165780
actgtagttt ctgatgcagc tgactggaaa actaagaatg ctgcgatgtt tacgccccaca  165840
gaaataggtg gttaataatt caaggactcc ttcgggagtc cttttttcat ttaaatagtt  165900
tactttccaa aatgagtatg gtataataga attatcttat agaggagagc actatgttaa  165960
atcgttggat taaaccaaat gaagatttag atattatcat ttcacggcat gtaatgaaga  166020
aatatgaact gtagccatgg tccacagaag ttgttgtgca ttcatttatg atgtacgcag  166080
atggttctgt cgaatttaat gcagagattc gatatgatta tgacgataag caagtcgaat  166140
tcaaaagagg ctttttgtaa tgtttatctt taattggttt aaaaatttct ttacggattt  166200
tttctctacg actcctggag aaggtgtagt tcctatttca aatgactacc ttcctttaac  166260
tgtagttgag tatgtttata tgggagatgg aacagtagaa gcagttacta tgacttatga  166320
agaagcccaa gaatattata aaaatccttg gcgctggtca gtacctacta catcatctaa  166380
cgtacagaat acacagtcta gttctgattc atatgatact aatgttcctg ttcatgtatg  166440
gacgggcgat tcatgtggaa gttcttgtga ttctagttgt tcatctacat cttgtgattg  166500
aggaaaatta tggaagcgat tttgtttgaa atgtatatta gcagtaatag catgtcgttt  166560
gctaaagatg ttccaattac tgtagcagta atgattgata agggttattg tgacccaatg  166620
tatctcgtaa aaaaattcgt ttcaatgcca gttccagaag atgctgaaat aaaacttaaa  166680
aagattggta ttattgaaac tgtacaaaat attccattta gagcaattga agcatttact  166740
aaatcagaat acattaatgt taacacagaa aaatataatg atgaaccttt atctttttat  166800
tcatatgatt cagcatatag ttgggaaata gataaaggaa ataagtttat aattgtggac  166860
gaagatgctt tatcatattt tattacttct ttatggaata atttaaatcc aaatttgcta  166920
aaaattcatg aatttgacgg tgtccatact attgttttag gtaaaataaa tgaaagctct  166980
caagaagatt cttgaatggt tcaatagacc aaactcaatg tatattgatg atggttgggt  167040
tgaacaagca aataaagaaa tgcagaacga gtcagaagaa tggatgaaat caatgattag  167100
tgctgagaaa gaaaagaaat tagaacgctc aagcgcttaa attgatgaga gacatctatg  167160
gtgataaatc                                                         167170
```

```
SEQ ID NO: 3            moltype = DNA  length = 155887
FEATURE                 Location/Qualifiers
source                  1..155887
                        mol_type = genomic DNA
                        note = Bacteriophage
                        organism = unidentified
SEQUENCE: 3
aagcgcaagc ccgtgctgaa gaagttcgcc gtcgtatgct gggcacaacc gttgctgaag  60
caatcgccga cgttgaaaat ccgaaggatg atcaggcttt agcgaacgcg aaggcggttc  120
tggccaagaa atcttctgaa atgcgtcctg cgtcttctac tgaagaacgc aagcgtcgtc  180
ataacaaacg tgaagaaatg gttgaagccg ctcgtgcttc taactatggt ccaatcctgg  240
cggcggttga agcaggggtt actcctgaag tatatttgag ttatgtgaac cctgatatgc  300
gctggttcca gttccctgtc actgaattgg cagacgaagc caatccgcat gcccgcacta  360
acacctatgt tgatctggca cctatcgttt ccggcggctg ggtttcagt ctgtatgtga  420
atggtaagtc attcaccaag cgtcagaaaa tcaaagaaac tgacgctgaa tctctggtaa  480
aggctatcaa cgaatggcta cctcaggcgt tagccgaagc gaaagctgct gcgtaattta  540
actcagaagc attcaataga tgaaggggct gctataatag cagctccttt tgtttattgg  600
agcacaccat gtcgtattcg ctcaaagggt tgttgaagcg ccccgtacat ctgtttgtaa  660
aaccacctgc tgtcgaaggg gaatatccgg cacgaggaga gttgtattac gttaaaggct  720
ccaacggtag cggcaagtcc actgtccctt cctatctggc ggagaatgat cctcaggcgt  780
atgtcgtgac ctacaatggc aagatcatgc tcacagtttg cccttcctat aacattatct  840
```

```
gtattggtaa atatgacaag tctaagtcta aaggtgttga ttccctgaaa gataccgagc  900
agatgttgtt cgccttgtcc attgctgatc agccggaata tctgaaatat gacgtgttgt  960
ttgaaggaat catcccttca actttgctca gctcatggat tccccgcctg acgcgcccac  1020
cgcgcgaatt agtcgtgctc ttcatggaca ccccgcttga aacctgtgtt tcccgtgtga  1080
aatcacgcaa cggcggcgca gacttcaatg aaagcctggt tgtcgaaaag tgggagagag  1140
ttcatgacca ccgccaacgg cataaaggct tgttccctac cgttcccgca ggtatgatga  1200
agtccaatgg cctgactata gagcaggctg tttttgcgtt tctcaatcgt gattttggga  1260
gtattgattg atggaaattt ttgctttaaa caataatgat atgctgaaga aggctgtgtt  1320
ggccatccgt gaacacggca ttgagtcaga tcctggcaac gcagagatta acactgacgg  1380
cactcgtttc attgatggtg taacaattac agtatcagat ccacgtgacc gttggctttc  1440
cgttgaaggc cgcaactcgt cggcaattgc tgccatcggt gagacattct gggtgttgtc  1500
cggacgtaat gatatccgtt tcctttcgaa agtcttaccc cgcgccgcca acttctctga  1560
tgacggtgta acctggcgag gcgcgtatgg cccacgtctg tacaataatg gccagttgga  1620
tagtgtcatc agccgtctgc gtaataatcc caacacccgt caggcgtatc tcaccatcta  1680
tgatccggcg ctggactcag atgaaggttt ggccacccat agtgaaactg gagaagccaa  1740
gaccaaggac atgatctgta atcttgctct attgttcagt ataacagaag ggcgattgaa  1800
tatcactgtc attaaccgca gccaagatgt cttgtggggc atgagttcaa tcaatttcat  1860
tgaattctct atcctgcaag aagttctggc gaaagtgctg aatgtcgaag ttgggtatta  1920
caaactgttt tctaacaatc ttcattatta caacaatgaa gttagtcgga aacaactcgg  1980
gggtatcact aagaagacca aaacttcttc tgggatgtac aattctttgc tggaattctc  2040
ttcagaaaaa gtgaagtccc aaaaagatat ttgtaatcta ttcctcggcg tgttacaaca  2100
ctgtgacatc ggcagtgatt ttggtaaaat cagagaacat ctgaaaggat atcaagcaga  2160
cacgggattg atgatggata tgtcatattg cctgtggtgt cgcctcaatg ataccaaaat  2220
tgacaaacgc cgtatcgctg atgacggtct tcgtactgca ttactgcatt cccctgttga  2280
tcagaaattt atgtgggggt atggcgaatg atgtaccaga accttgaatt cttcacgggg  2340
cgcaagcgct ccggcaagga cttctgtttg gagtccctga tcaggtttca tcatattcag  2400
ggtgataagg atattcgtcg tctgtctttc tcagatgaac tgcgacgtgt cgccaatttc  2460
atctacccat ggctaccagc ggaggtggag gatgctgtga aggacgttcc attcgtacac  2520
cctgataacc ccaagggctt aaccccacgg cagatctggc ttcatctggg cagcgatacg  2580
ggcttgcgtt atgtacaacc agacctgttc ctgtcattct ttaaacgata tcaacttcct  2640
ttggtggagc agaacccaca cgttcattat atcgtgagtg atttgcgtac ccctcaggaa  2700
tatgaatggg cgctgagcac taaatgtccc atcacccgca tttcaaaggc ggatcgcggt  2760
ggtatcatag aggatgacat tgaggctttc attgataaga tggaagttga ttatgaattt  2820
gtcaatccgt ttgaaggttg gcaaccgttc gtcaaatttt atagggatcg gaaatgatca  2880
cagcagagca tattaaaagt ctgctcgaac ttcaaaaggc caccaacgtg gcctattttg  2940
gggaagagtg gaagaatgta tggagtcaga acgccgtcgt caactccata tatcgtgagt  3000
gggcagagtt tcttgacgaa acgaccgccg actggaaggt ctatggtaac gatatcggct  3060
tcgaccgcac gaaggcggtc tatgaactgg tggacgtggt tcacttcatg ctgtgtttca  3120
tcctcgtcga tcgcaccaaa ggagagatcg aggaagaatt agaggaaatg tctaaggata  3180
gttatgccat gtctatcgtt aacggcatag ttgcccacgg cggggtgacc taccgctttg  3240
gacagttcat gggcgatcct tgcgttcgtt ccctgatgta tttcctgagc gcgtcttgct  3300
cttacgtggg gctggacgcc gaaacttaca tgctggcaca caaacgcaaa aatgatcgca  3360
atcggctgcg tgctgctggc ggtgcgaact acgataagtc cgcagaaacc cctctgaccc  3420
tggagttcta atgtttacag ttgtcgtatc atattatgcg gaacatgccc cgcgcatggc  3480
agagaacttc gctgagttta ttaaaccagg cggtcatgtc gttattgcga ccaatttcaa  3540
gaaagagcca gatggtgcgg ctactgtaac acaacatatt acaaccaaag agccggaaac  3600
actttttaaa cgcattgaag attttgcttt tggcggggaa gaaattccag agtcattaca  3660
gcatatctat tttgaagatg cgatatatta tgttcatgct ataccaaaag atgttacaac  3720
cgaacaacta atgtatgttt tgaatattgc gttaaatttg tcatgtgtca atagggcaca  3780
gcataatcgt ctgcgcaata tgtatttaac agaacgcggg ggttccggaa tcagtgatga  3840
aaaactcccg tcggtaatgg caattcaaga agcaattaac atattgtcca agaaagtctt  3900
gggcaccgat ttattaatca cgatcaacaa gcaagaggaa acgaaatggc cgattcattg  3960
atggctcgca tgctcaagac agcaaagaaa ttggatccga atgccgaagt gctgtctaaa  4020
accgatgcgc tgaagcctga tattatttgt agcacgggta ttcctatcct gaatttggcc  4080
tggtctggtc gtattgatgg tgggctgata tctggtatta agcagttggt gggtgattct  4140
cgtacattca aaaccatgtt tggtctggta gatgtcaagg cttacatgga caagtttccc  4200
gacgcaattt gtatcttcgc ggattcggaa ggcggcgcga atgaaaacta ttggacgtcc  4260
atgggtatag acatggatcg tgttttatat ctgccgatcg aaaacgttga aaagacgaag  4320
atcaagctga ctcaacttct gaatgatgcc caaaaaggcg ataaaatcat cgtctttatt  4380
gactcaatca gccagttgcc gtctaccaaa gaagtggatg acgccatcgc gggtaaagat  4440
acacaagata tgacccgcgc tcgtgctctc aatagttttt ggcgtgtcat cactccgttg  4500
gtcactgaaa agaaattcgt tttggtgtgg atcaactctt attatgatga aatcgggaac  4560
cagtatgccg aaccaaatat caaaggcggt aagcaaggtt tcctatcatc taaccaattg  4620
tggttcatca cccgttccca agttaaggaa gacaaagatc ttctgggttg gcaattcact  4680
gttaacatca tgaaaggccg ctttgttcgt gaaaaagcca agttccctgt gacggtattg  4740
tatgaaggcg gtattgaccg ttggtctggc atgttggaaa ttgcacgcat gctgggatat  4800
gttgatctgg tgagcggttc ctggtatcag cgtacagcca aaggcgggtt tgatccagag  4860
aaagagaaga aatatcgcaa gtcagagctg gggatgact tctggtatcc actgctggaa  4920
aacccagatt ttgttgacga tgtaaacaat atgttcggta tctctcagag ttcggttatg  4980
cctgcagata tgctggagcg tctcgatcat gtcatcaaaa caaccgagta atattgcagg  5040
gggaggagac tcccccgtta attacaaaat catcgaccct ggttctgatc agttagctat  5100
tatcgaaata acggaaggca agttccgcgg tgttcaattt cgtataggaa aagtgggtgt  5160
ccatgtagac aatggagaac ctcggttatc ctttacgacg gatatattga agaagccatg  5220
gcgtttgtta tttgttaatt tgaaagaaaa tgacttgttc actgtggtgt ctggggatat  5280
cttagttgat ctgatacagc aaaatgctca ggattacaac aaaattttgg tggggtgagt  5340
ctggagtcct atgttaacac agcagtctct taaagaaata ctacattata atgaagacac  5400
tggttggttt acatggttgg tggaccgtgg tggtactgct aaagccggaa ctcgagcggg  5460
ttctttgaaa cctgacggat acagggcaat aagaatcgga gataagaaat atttagaaca  5520
tagattagca tttctctaca aaactggttc ttggccgaag aaattagttg atcacaaaaa  5580
```

```
ccggataagg gacgacaatc gttggttgaa cttgagagaa tccaataaaa gtcagaatgc  5640
ggtcaacaca gatttgtaca gccataatac cacaggtgcg agaggcgtgt ttcgatacaa  5700
gggtaggtgg tgcgtgcaaa tcagagttga cgggaaatat agatcgttcg ggtattacaa  5760
tgaattcgaa gaagcaaagg aaatggcaga caaggtctac aaagatttgt tcggagaatt  5820
ttatcaaggc tagtgattgt cctctgtcaa accaaataat ttaggaacac aatatgttac  5880
tcgaatctgt cgtgctttcc caattaatct acaatgaaga atatcaaaga aagatccagc  5940
cgtatttgaa agccgattat ttcgataacg aaggcgagaa gattatattt ggtcttatag  6000
accattacac ttgcgaatat aatgctcgtc cttcggttga agcgctgtct attatgctgg  6060
aaaagacttc gctcaacgaa cacgtatttg atcaggccat ttctgctctt gaaaatatta  6120
atgacaatac ttttcatcag gactggttag taaaagaaac agaaagttgg gcgcgtcaga  6180
aagctgttca taacgcaatt agacaagccg ttaacatata cggcgatgag aaacgcaaag  6240
atgagatgaa caacatccct actttgctgc aagaagccct ggcgattcag tttgattcat  6300
atctcggtca catctattgg gaaatggctg agcaacaata cgaccacatg aactctaatg  6360
aagcgaagat ccctttcgcc gtagagatat tcaacaaagc aactcgtggt ggtgttggca  6420
agaagacatt gaacatcgtt acaggcgcaa tcaacgcagg taagacaaca actctgattg  6480
atttggctgc tggttatgct gagcaggggt tgaatgtgtt cgtattcacc ctcgaagtgg  6540
ccgagaacgt ctggcgacac cgccttgatg cccgtatgat gcgcagggac ttcgagtcct  6600
tagagaagct ctcacggcac gagtatattg ccaccataca aaaactgaga acccgtcaag  6660
acggttccat gaagggtgat attgttatca aggaatatcc ttcgggcgcg gggcatacag  6720
gtttgtatcg tcgcgatatt cttgattatg cgactgcaac aggaattacg cctgatgtta  6780
tcatcattga ctacctgggg gaatctgcgt cttctcgcct tcccgctcac ttgatgcaaa  6840
acaccaacgt gtattataca tccgtggcgc gggaattccg tgctcttggg tttgagtttg  6900
attgccctgt ttggacaggc atgcagttta accgtgaaaa gcaatcagca actgatggtg  6960
atatcagtga cttggcagac gctatcggta tcccgaaggt cgctgacttt atcatggcat  7020
tttatgcccc agacgaactg gcggctgtta agaaagccag agcatcaatc ttgaaaaatc  7080
gttatgccaa caagcagaaa ctcaaatctt tcttgttcgg tatggaccaa gataaacaga  7140
tattgttcga cttggactgg aatgaagtca aacgagacct gactgatgaa gaagcccgtt  7200
atgttgaaaa cgtgcatatc aagcatgact tgaataaaac gggggactca aatgatgtta  7260
aaaaagccga gaccgtcaat agttggaatt tcggttaact tcaataatgg tggtcatagg  7320
gtataatctc tatgatctga atattaaccc aggagcacat catgtcggat gttgcattta  7380
tagctgacct gattcaggcg gcacaacagg tgtgccagtc tggacaaacc agtctcagtc  7440
tctctacaga gcagacattg gaattttaca agaatcgacg gcattggggt aaggctgtta  7500
agatacattg cgaaccagga gaattggttc agctcgatct tccatctttc ccgttgccag  7560
tgcagaccaa tactcaggaa tattataaag ttgaaggtgt cgacattatt cctaagtttg  7620
gtttccacag tatcgtttat ttcttcctgc gccgtttggg gaccagtatt ggcccactcg  7680
gttctcgtca ttaatgagga tatgttatgt cagttgaaca aatcgggttt taccaacttc  7740
cttctgatcc caagctgcgt caaaagatga tgcagacatt ggaaaattgc cgcgccgccc  7800
agatccgtat caagtctgaa cagacatttg ttaccgaagc tctggccgaa ttggcaaaag  7860
aaacaggcat caaagccgtt gatctgcgca aagtcgttac tgaccgcgct ggcggaacat  7920
acaccaagac catcgagacc agcgccaaat accaagatct ctatgagtct ctgtatccta  7980
atgcagcgcc tgatcgcgca gccgatcctc agccataaat cccccagaaa gcccaacaaa  8040
ttgttgggct ttttatttga aacctttact tcaataaaac atacggctat catttaacct  8100
actttgaaaa gtttcactat atcatgagag gcaaatatga aagccaagac cttcagtatt  8160
cctatcgaca acattggtcg tgtcaaggaa cgtctggcca aacttgaaag aacggccaag  8220
cgcctgaatc tcgagttccc tcttgtcgaa tacagcgaac catacaaaac ccagcatcgc  8280
gattctatca ctggtgaaaa attctatcgg tggtggcagg attgtacact cactggtgaa  8340
ggcatcgacc gccctgtttc ctacggcggg tggagcatta ttggacaatt caatcaccaa  8400
tatccaaaag tcatcttgaa taaattagca gatgacatcc accctaattt cattcaaaga  8460
ttcgaagccg aaaacgtgtc ttggtgtgag cattgtaata aatctgtgcg tcgtcataac  8520
acatatgttg ttcgtaacga acaatccggc gctcaaatgt tggtcggcag tagctgtatg  8580
caccattacg ttcctcatca gaaatcgctt gatgccgtga tgtcttatta tatgtcgata  8640
catgaaatgt tctcacctga tgaagatgac cctgaaggca tctatcgagt gaacgaacct  8700
gattacgttg acactgaagg ttatttgcgg aattgctttc aggttctgct atctggtatg  8760
agtatgaaga gcgatgattt tggtcgagtt cttggtcata tttctagcgg gactcgtccg  8820
gagaaaggtt ctgacattga gatattctat aacaaggcag ttaaagcccg tgaagatgct  8880
caatcagaga tgtaccatat gatgcttttc atcgccgcgt tgtctgagaa caatgatttc  8940
aacgttcgtc tgaaacgtat gtgtgaacct ggatatcacc tcgttaagga ctccacgaca  9000
gttcgttggg gagcagcaaa gtattatgat tatatccaca ccccccgcca aatgcgttct  9060
gtatcaaatt gggtgggggg agtcggtgaa atgttagaag tgcaagtcaa attcgaagca  9120
aggattttcc tgtattcatc tgattatggt gacacgtatc tgtatacttt caaaaccaaa  9180
gaaggcaata ccattacatg gaagacttct tatatggaaa ccgaattcct ggaaggtgat  9240
atgatcattc gtggtcgcgt caaagaattg accgaattca aagatgttaa acaaactcag  9300
gtaacaaggg caaaactgag gaaattatga ttcttttaca atttgttttg aaagcatttg  9360
cattcggtct tatcgcatgc ggagtgatca cagctatgct gttaatcata gccctgatca  9420
tcccctttaa gaggaagaaa tgaatgaagc gcgaaattaa ggatgtgtat gatcctggat  9480
cttgttgccc aggacacgac aaatatcctt cagaaaaata taaaaatcgt cgttctgtag  9540
ctaaacgttc cgaggggata aagaaagaac atcgtcacgc tcgccgtgtt aagcgccttg  9600
cgttgaaaat cgatatattc tattcacctc aggaggattt ttaatggaat gttcatgtgg  9660
agggcaaggc acaagtgcat acttgccatt taacaccgtc aaggaagccg aagacgctgg  9720
atatgccgtg gacaaggctc cctgtgtaat tgccattaag gattgtccgt gctgtaagag  9780
gcactctcag aacgtttggt atgccccaga agcaaagggc aaaattaatt tattgaatat  9840
gatgaggaag taatatgacc acactcgtag aaacattatt cccaggatgc acccttgggc  9900
gcggcggtag cgaagccaac gggctggcaa ttgacaccga accacagaac tgcgttgtta  9960
tcgacaaatt ccatgacaat cactatcctc tgagccatcg tcgtgatcat tatctggttt  10020
ctgtgggcga aacattggtc tctcttcgta tttgtgaagc aatgcctggt tatggttatg  10080
acgcatttgc atatatccat agcgtttcca atggggaaat ggagaaagaa accctgactg  10140
aacaattcaa aggatggaaa gaatctttca cttctgtcaa ggaaagaagt tagaataatt  10200
ctattgaagt ctctggggtt ataataacaa gacgaataac cctggagaca catgatgctt  10260
cctctcttag aaataatcca aaatcttcgt gataccaaag gcactaatgc taagaaagcc  10320
```

```
gtgttgaccg aagcgttcag gaccaatccg gaactggttg atttccttca atacgtttat  10380
gatccaatgc gttcttatta tcgcacccaa ttcaatctga atgcattccc tcgcatgctt  10440
tcgcgcggcg ttgtcggtag ctgggatcag gtttatgacg ttcttgatat gatgtcagaa  10500
cgtcgtattg gcgggatgaa ggccgaccaa gaactggcaa aagccgcaac gaatattcac  10560
cctgattatc acaccctcat ccagatcatt ctcgaccgag acattaaagc ggggattgct  10620
gagaaaggta tcaacgcagc attcaacgca gctggaggca caggtcgcct gattaacatc  10680
ctcccatatc atcgttatga caacatgacg attgatttgt tgaagacgat ggacttcaag  10740
cgcggcgtat tcagtcagct gaagtctgac gggatgttcg ccaacatcat ttgtcgctat  10800
ggaaaagatc cagagattcg ttctcgctct ggttctttga ttgcgggtgg ttccgttgat  10860
aacctatcat tggttttcaa agatatcatc tatgacgctg ggattgggga aagcgttttt  10920
catggtgaac tccttgttat cgatctgaag acgaatacag tccttcccag agctatcggt  10980
aacggtaaac ttaacagcgt catccagact ggtgaacctc tggaagatcg ttatcgagtg  11040
atttatcgtg tatgggatgt tgttccatac gacaaatggt tcaacgcaga gcgggttgac  11100
accccgtatg aacgacgctt cgatattatc cagcagctgt ttgatgaaga cgacgggttg  11160
gttcaggttc aggagacccg tgttgttcac tcgtttgaag aggcggttga tcatttcaag  11220
gacgcgctgg cccgtggtga agaaggaacg atctgcaaat cggctgatat gccatgggaa  11280
gacggcacgt cctctgaagg tctgaaattg aagatggaag tggaatgcga ccttgaaatt  11340
gtgggattta acgaagggga taagaaaggc aaacatgcca agacttttgg ttctctgtta  11400
tgtaagactt ccgacggcct attagtcgtt ggcgtctctg ggatctcaga tgagctgaga  11460
ctccggatgt gggaaaacca gggcgactac attggcatga tagctgcggt gctctctaac  11520
ggtgtccagg ataaaacaga tgacgccatg aagtccttgt tcctcccgcg acttgtcgaa  11580
gtgcgcacag acaagaaagt tgccaacacg ctggctgagg tctatgctat ccagaaagcg  11640
tacattgaaa acattctggt gttgctggag gccgcgtgag caaagaaacc agcacggaac  11700
tgaaatggcg tgaccttgct cttcagttcg acggtcatcg tatgcagtca atatgcttct  11760
tgaaacaaat cttgagcaca ttgcccgaaa ccgagtttgt ggaagcgcgt gaattcctga  11820
aagcaggtcc attgcctgga gaggaagtat tgcgccagcg cctggttgat atgatgaaca  11880
aggagcctga caatgggtga gtacatgagt ttctggtggg cgaagttcct tgttgaactt  11940
caaatatccg gcgcggtgtt tttgttactg ttcttgatag ccatgatacc cgttacacgg  12000
aaagcgatca agcaatggcg ttgcaagcac cccacctatc gtgagaacta cgcatgccaa  12060
gccatctgca cacattgcgg gaaggatatg ggcttcgtcg gtattattcg caaaatgaag  12120
aatcacaaag aggtgtggtg atgaaccaga tgtgtgagag ggtgaaagaa ttcatccacc  12180
ggaaccccaa ttgctcctac gcgcagatcg ctgaaggtgc caatatcccc atgagtatgg  12240
tcagtggttg ccttcgcatt ttgatacgcg atggtcatgt tgtgaagtat aaccataaag  12300
atgctcaggg taaaacccta tctaattcgt atgatgttgt gggttagaat tgaattaagg  12360
gggcgtaacc cccctttcaa taaatctatg gcagtataat tccaacaaat catcacaacg  12420
gtattgttat gaaacttgtt gacaaacaac caagaaagaa taatgactca ttacatctct  12480
taaccattat gcgggagttg ggagtttctg aattgcaaat gatgaagttg atgaattgct  12540
ctgacgttgt ctataattgg acaaacggtt atcgtcttat cccaaaatca ttccgtcgtt  12600
ttattttggc attggtgttt attcatcgcc aaggaaaaac agaagagttt caacgtttcg  12660
ttaaatcaga ggagagatca cgtggttggt aaaaatccgc cgtcatatgt aaaaatcggg  12720
atcgctttcc ggaacgcaat gcttttcatt aaagagaaag gcttgatgtc ggagttcaat  12780
cagttctgtt ctgaacgtca cagattacag aaacagaaaa gcagggagaa acgccatgat  12840
aactgagtgg gagaaaatgc aatatgaacg tgcatttaac gtttattgca tatatatggc  12900
gatcaagttg catttcacca ccaaagattt tgattatggt ctgtatgggc cgatgaacaa  12960
ttacaagttt gaaacattct attctaaaca gggcgtggca aagcaatttg ctaaacttgc  13020
tcgtcggttt gaatcttccc agggtgaagt ggtggaaaat tatatcatcg ccaactttgt  13080
taaatcaccc aaaacatggg tgacaacatt actcacccgt caggctcaag aaaattataa  13140
tgaatatcgc cgcctgtacg ataacttttc atataatttt cttgaccatt ttgaacgtta  13200
tatgattccg gaaataaaag aaagaggtgt gaactttatc cagtacatca aaggaaatgg  13260
gaatggtcac ccaccgttac tgacagacat tatcatcaaa cgttatccga tttggttttt  13320
ggttggattg aataaagtgg tgggatttat tcatttatat gatacaatac tcaaggaaga  13380
tatttattgg aattctgagt cgttcttatt gaaaaagact aattctgtgg ttccggatga  13440
aaatacagaa tacacgaaag gaaaactccg tgagctaatc cttgcccacg gaatttgatt  13500
accaatccca aagaatacga cctgcgtcag tacggttgga cggctccagt tgtgaactgt  13560
tgaagttgtt tgtcgtactg actttcttcg agttatcaac attttgttgt acaggcatta  13620
ccacactggc tggcgggttg gcgtaggaag atttaacttc ctcaatgttg ttagccgctc  13680
tcccctgaac cggatatgcc ccacccagag tacctccccc gatcccagca tatgcatctt  13740
tcaattgaga agtgcgatct gttacgttca cagcatccga agaaacccca gaaggcattg  13800
gagtcagcgt gctgatatct gcattaggtt gtgctggcga ttgactgttc ggtggtacag  13860
aggcattctc aggagcctta tcgtcttggc ttatcagcat agactgtctt gcttccgcca  13920
tcttattcct ggccgcttca ccacccaacg catcggggat aatactgaca aacttatcca  13980
cgatatcaaa catcgcattg gtgatagcat tcaacatgtt gaagaaaggt ttcttcacat  14040
tttcagcaaa tcctttcttc atgtcttcaa cgactttgtt tgcagccgcc atgccgtcat  14100
ctaacaggcc agttattcca cccgttaccc aatcaaccaa ttttatcaat tggccttgca  14160
agttatctgc aagtttacca ggtatttcgg tcagtgatgt gctcttccca atacccgcaa  14220
acaaatcgtt ggtgacccaa tcaacaatcg agttcaacca acgcacgggc gcttcggtca  14280
ttttcagcac ttgttcacgg aacgcctttc caaacccagc attgttccat ccgaatattt  14340
cagcaaccca atcagcgaga tccccgaaac taccgaccag ctctgttatc cctgcctgaa  14400
cccgatcaac gatcgatact tgcgctttac caaggatttc tttagcatta aagaaccctt  14460
taccgaattc aaatacagat gttattaacg ccagaggtcc aactcgaagc atcttggttg  14520
ctgctttcag gggcgcaagc aacccgccga tcccagcacc aaaccccatg aataatttaa  14580
tgaagccacc aacaagtttt aatggggaca tcaggagttt taacgcgccc agtccaagga  14640
gtgcccccag cgccgcgcct aacccagaag attgaccatc ttgtttaggc tcagacggag  14700
ggatagaacc agcctctgga ttgttcttgt tttctttacc ttcttcacca cgacggaatt  14760
tctcttcttc tctatatttt tgatcacttt catagatacg tgtcagagta tcattaagat  14820
cttcgttcat gtatcccaat ttgtcatcaa tgctgtcgag gcgggtaaca gtttcgttac  14880
tggcatcttt attgaaatct agcgtgtcct tatgcgtttg aagcattatg tcagtcaggt  14940
ttacgatctc ccctccgacc aacgccagct tatcctttaa tccatcaagg cgttcaagac  15000
tatcttcgtt ggccgcgccc aattgatctg atatcatgtc aagatattca actgacatgt  15060
```

```
cgtcaaccgg accattcgct gcttcaccaa atttttcgat cttggtggcg atacgcatca  15120
gttcttcatt gccatccttt gttagactga cggtgtcttt catccaagtg ctgtaatccc  15180
ttgtgaaaat gggactgacg cggacgaacc caccaacaat atcattcacc gatgggaatt  15240
taattggcgg tactttctgc tcctgattag acgcctgtcg tgtcttcaga gattgcagtt  15300
gtttgttgac atcggcgagc tgtttattcg tctcggattg ggcgcgcaat tgcttgcgct  15360
ccatcatttc ttttttgatt ttatccaaaa ccttgacgat gtcttgctgc cctggtgtcg  15420
gttgattgtt atctgccatt tgtcacctct cagaccttct gggcttgtcc tttctctatt  15480
ggcgtcggag ttggtgtaga agccacagtt tgaccagtct gaggtggtaa gaccttctgg  15540
atcatactat ctttggcaat ctcggcgacg cattgataat catttgtcag gcgtgaaatc  15600
ttgtggcgta tctttgtgac gatataatgg cctgttgata acttacttaa ctcggcaatg  15660
ttttcattag atttcgggcg gttcgacaaa tcttcaatat aataaacctg cccaacattc  15720
aggcggttat cccccacgac cagcaaacgc ataaccgttg acgcaaggct gaattctata  15780
acgcggcgag cataatctat ttgttcagca ccatcgggtt gcgcttcaat gtacctaaca  15840
ttctcacgat caaactgatc agaaaataat gggaatggat caaggtgagc agtgctgtca  15900
aaccattctg aataaatgcg ttgggtcgct gtcgtggatt ttgtactaaa gtcatacacg  15960
cgctcgttca ctgccaagat atcccgataa ttcgccatgt actgatcacg cgccagtttc  16020
ttttcagcct tgatgatcgt ccgcataaaa cgttcggagt tgaagttgtt gtcttgcatc  16080
aacggggcat cttgaggatc acggaagaat ttcttttccg cgcttgcctc ttgtttctct  16140
tcagcagtca tggactgatt gccctggttg aacaatgtcg tcatgctctt gaagtgatag  16200
cctgtgaagt cttcatagaa aacaaatggc ataaacaatt cgtcgtatgc gcggctggcc  16260
atataatcga tggaacgaag tacaggccaa agaggagttg cgaatcgttc ttgcacacca  16320
tacgacggat ctatgtcttc aaatttggtt cgagaattta actgctcaaa aatcttggcc  16380
gccatttctg aataagaacc gctcagaccg atagacttac gcagcatgct gtcacggtac  16440
gcatctgttg tcaccaagtg cagccaaaat gctttttttag atgatgaatt ggattcatcc  16500
gcaactctgc ccacccgact cacgcgcaat gagagagtag tgtaatcaga agccgctggt  16560
gatttgaatg acaccactac ttcttcaccg ccaagtatcg gcattgtgtc caatatatcc  16620
caaccttctt ttatcaagat attggctgtc agtgaaggag aagcattacc ttccaaacca  16680
agatcttggt agacgttgaa ttcttgaaat aaagaagaca ggtcatatgg tcttggcgta  16740
ccaccttctg gagtatgtgg taggatcgcc atatacttca aatcaaatgt ggtggacggt  16800
gttaaaatac cgtcttgaga ttctttattt tcgatcattt ggtcagctcc tgttccagct  16860
gattaacaaa ggaagaaaca taatctggat cgagcacttg gatgttacgt ttggcttcgt  16920
ttttgtttat tgcatcatcg tgatatgtaa tgcccgtcag cccgtaattc gcgatgattg  16980
tcgcgtcgtc catagcgcca aggccatatg ccaaacggat agcgcgggga tctgtttcat  17040
tcccaaattc gtcaacgtag tattttacgt cccacatccc atcgagtcca taacgagcag  17100
ttagctcttc aatgattctg cgttctggtt ttggccagtc ttctgtgata tccatgatac  17160
cattgataag acatggtatc cagaacaact cgaaggaacc atagacccgt tccgcaaaag  17220
accttggggt ttccccatcg aaaacagtat aaggcaggag aagcccttct atgtcccgaa  17280
ttttcttaac aaccataacc cgtcgtgtca agttttgcaa caggacttgg tcattttctt  17340
tgacaccaat tagttgatgc catacgagtg gaaatttctc aaaatatttc atggcatctt  17400
cccccttagaa gctgtcgcct tcggtatcaa agcggccttt gtgcaacggt tccagttcga  17460
taaatgtcat atcaatctgg gttgacacga tgctgtcatc tttgtggaca gcatatgaag  17520
aatccggcgt ctcgttgaca aacatgtttg acaaaacaca agtcgatatt cgatgtaacc  17580
atttattgcg ttccccctgc accatgaacg tgatatcaaa cgtggatgga tgaagataga  17640
atgcgctgga attcttgttg tatttgtatt ctggatacat atgcatcttg aacagacgaa  17700
tgatttccct caccattttc gcctcttttt gcgatcttgg agtgaatttg aatgtgaacg  17760
ggatttctcg gttgcgcacc ccttggaaaa tcatttccac atacgggttg gtcatcgtac  17820
ctgtaaacaa ttctaatgta tcatgagcat taattgtcgg caagaaagga attgcttccg  17880
aagcagattg gatggccttt gtcgccgcaa atctccccat ttctttccca acattcaaag  17940
catccccaag tttgaattga ctcatatctt gggcggcgcg tgataagaat tgggcaccca  18000
tacctgctaa tcccaactcg gagccgttcc agccaacgcc atagttggtt gtaatagatt  18060
caggcataca caacactatg gactcgttag agcggacatg acgtgcccaa gcatatttgc  18120
tgatagaacc tgatttagaa ccataaacca caggagtttt tcccagtggg ttttgaatag  18180
ggttctcaac ggtttgagtc gttgtgtcgc cgtatgacga tcctgatatg cggttaatat  18240
tgaataaaac ataatgaccg agggtttac ccccgttat atccaacgga tagaccaatt  18300
gcttctgaga cttggccaag ccttttgtgt tcagaacttt gatcttatcg atggtcgact  18360
tgaaattcgc catggtctga agcccttaat tagaatagag taatgacact atttaggact  18420
agaatatggc tatgtatttg caggggaagt atgttcccgt aaatcccaag aaatataaag  18480
gcgatgtgaa caaaatagtt tttcgttcat cactagaact tgtcgccttc aaattctgtg  18540
atatgaatcc tgctattgtt tattggtcat ccgaagaaac cgtaatccca tatatctctc  18600
cagttgatgg tcgcgcccac cgctatttta tggatttgaa agtatggact cgtcgacaag  18660
actctgaaga gttacagata acccttattg aaataaaacc caaagaccaa attaaagaac  18720
cccgaaaaac aaaaacgatg aaggaatcaa cgttcaataa ttcgatgcgt acatggctgg  18780
tgaaccaagc gaagtggacc gccaccaaag agcattgtgc taaagttggt tggaaattca  18840
ttatttggac ggaagagcat ttggtaccag gagaagatcc tgaagttaaa aaacaatttg  18900
cgctacgttc taagaaaaag cgcgaggtcg aaatggaaga tcgacgccgc gctcaaagaa  18960
ttaatgcgtt gaaagagcag atgaaaaagg aaacttccaa caaacaaacg acaaaacctg  19020
aagatgacgg tttgttgtta ccctgatttc cttggatgtc caggggcaaa acaagtttgt  19080
ttgtccctgc atatcaccca tccttccgaa cgggcttgtc tagcacaatc agcccaagtt  19140
tcaccagcat aagacttcat accgcatctt gggtggtgct cttgccaagc ccaatcacaa  19200
gatttgcatt ccacgcattc acaatacaaa tctaatgtgt atcctgcggt aatcatttaa  19260
tccaccaggc gttcgtaaat tttttgacgg aactcattcc cttttgcaca acctgtggcc  19320
agcaaacgag taccgcctgt cccgatgaca ctgatcgttg aaaatcttaa aatacggcct  19380
gtgatggact gatccacttt gatggtctca acttttccca ggcgaagttc atcagcatca  19440
cggcggataa accctcgttt tacgataacc cgtttgttgg tgactgcgaa ttctgtggtc  19500
atcacattca agatagttgg gatcaggaat aacaaactga aaccaaatgt tggaataatc  19560
gttaaagcga cgagaacata aatccagaat ccactccacc aagtcggacg agtgaatgca  19620
accacatatt cattttcgct cagcatacgg tcgacgtaac gcattttaat tccttacttt  19680
gtcaggatta gataagattt gttcgtatcc gacttctcct tgatagtcga aaacatgctg  19740
aagaatcgcc atatcgtcta ccatccgata aacttcaatt ccagcgttca tcaatttttt  19800
```

-continued

```
gattccatcc ataatacgat atggctcacg ataatatact ttatcgattt taccgctatc  19860
tattatcttt tgagtgcaat cagggcaagg actatgtgtc acaaacataa ccaaccctgt  19920
gaaatcatct gcattttcgg ggatacgcat tagagcattt tcctccgcat gaacgacaca  19980
cgggtttgta acaatttgcc cgtgttgttc catctcacaa acattcggca tgccaggagg  20040
cgttccgttc catcctatag ccacaggctg atcagtttca gggtttacaa taacacaacc  20100
gacttgcaga cgccgagcat aactggttac accatatgct gcagctgatc gcatatgagc  20160
aaacatcata cgtggtttga tagccattat tcacctctca gaagacgagc gaagcgttca  20220
acaatgcgat tgcgcggctt ctcgggaacg atgtcttcta ccgtaatggt cagtgtgtag  20280
tttgtagaaa aatcgcaatc ggactttgtg atgattttcc gttcaccagg cagcggatac  20340
atcgttaaag ccctatcgac ggaatctaga gaagaaccga ccaagtccac caccctttgg  20400
tgcccgaacg ataatggacc tacgacatcc ttttcaaaaa tttcaatcac gtcggtgact  20460
aacacaccca atgcaagtct tagtccaagg ttctgatttt tatcccctag tgtgtacaca  20520
aactgccgac gccacaactc tttccggtct tcagaacgga cgagagaata attcaaatgg  20580
tattgtttca tttcaccaac accttttcaa gtaaaaagat catgtcatcc tggtcggcgc  20640
ggccaaagat ctgaccgagg gataccatgg aatgaacctc tttgacaatc aggtctttgc  20700
ctgttacacc gctgttgtcc aattcgagaa ttgtagacat gcgctcaacc atatgaggtg  20760
gatgattgat ataacgttga agatactttt cacgcaacgc aattttttcg ataagatctg  20820
acatttctgc attctcttct gaatacagac gttctttaga tttcagttct tcgaggcgtt  20880
cgtgcatttc ttttaatgaa atcatgttta tctctcccaa taaattaagg ggaagtatac  20940
cttccccttt cttcaataac ctaaaatatt attcagtgca cgctttaccg aggtctgtaa  21000
gtctatagaa tgttacttca gacttcggcc aatgtttata ttcttcagag ttgtcatgaa  21060
ccattgtaaa cgcaggttcg atcagacctt tagataataa tgattgccct gaacgtgtat  21120
cccacggatc accttttaca gaacgaaacc caccagcaat cggaggggta tggaatgtcc  21180
atactgtctt gccctttttca ttcgtccaag acttcggatt gaaataccaa tgacaaaggc  21240
gtctggcttc accctttttca aaatttaaca ttcctaaaag gacgcagagt tgatgtcctg  21300
tgatgcgtgg cttttttcata agatccccaa gtcagtaagg taacgataaa acaagattat  21360
agacagaaat ccaattaaca tccaagacga caggataggc ttgcaattta gcgtagtctt  21420
tccattgggt atgttgggac ttccagtaat aacaaccgaa tccgttttag ctctcagcgt  21480
catgacagaa cccatgagaa tgattgggcg cacataatgt ccttcattat tgcgctttac  21540
gatacatggt gaagaaaatc gcaggaacgg atcaccgctt ttataaccga ataactcgac  21600
cttttgtatt tcttcgggta ctttctgacc aggaaagaat attttcataa tacaattcct  21660
aaatttgtgt ataacaactc agccagggtt acaggacgct tgaattgttc ccaactgcag  21720
ttcaggtatt cgcgctcttc gcggatattt tcgtgaagat gaccatggat attatacgcc  21780
caacggtcta attgataagg aacatgtgtt gtcaacacac ggccaacagg cgtgtcacgt  21840
tcgtacatag cgccgaagga gctaatccag ccgtccatat acaaagacaa cagcatctta  21900
aagctgtcat ggttgccttg tgccaccctg atgataaagt tcggacgcca gtcatcggga  21960
acggggcgtc gcttaaactc atcaatgttt cgcttggcac cctcccgcat caggcgaatg  22020
aacccttcag ccccgatgaa gcatatatca ccagccagtt caagaacgtc ccgagacttc  22080
aacccctgaa agatactgtc aatgaccgca gcgtcatggg cttcctgtgt atcaaatcca  22140
cgcggtttaa agaccttctt atgcccaaga tgagtgtcac caaggtgctt tacaattccc  22200
gccattatgg tttcctcagc cattctaaaa ttggtacgtt cacaaaccct ttgtgccagc  22260
ggtgaggttt atggcctctg ttgtgatcca gtaagcacgt gtcaggagga acactgaagt  22320
gaatgccttc aatgtcataa taattcccat caatcagggt gtatacatga ccttcaatct  22380
ggctataatg gatctctgct tggggatata cgtgcttcag aaccagagca acctgatagc  22440
actttccgtt cttcccaaca tactcgacat cgacctgttg tgggaacacg tctttgataa  22500
gatttatcaa tctcgtgata tcatttacaa caaccgaaca tttcatctct atgataactc  22560
atggcgatgt cgaacacagg cagggcaatt acagtctttt ctcaaaattg gcatttcaca  22620
ccacgtcatc aaaccatgta ttggagacat gtggtgataa aaccatgatt ttttgagact  22680
aatcaaagga tataaaattt caattggcct ttccccgtct cttgtcatca tattgtatcc  22740
ttcgatgacc ttattgaaag ctgggatcca gtggatcgcg tcgtccccgt tgacatatgc  22800
caatatgtat gtgggaggca aactccggcc tttaaattgt gtgtttaata accatatcgg  22860
ggattgtgct agacacgcac gaaacccgcc gtccggcacg tgaatgctac taatcggttc  22920
ttggtgatga gtccaacgat gcataagaag cggagcattc ttgttgatcc aattataaat  22980
tttatttcgc gcccaatttt cgcgtttaga tttaaattta ttattttcga ggtggcaata  23040
cacagtatga actgaatatc ctttcgataa caaccaaatc aacatgtatg tgctatccac  23100
cccaccagac cagaacaacg tcacttcttg attattctcc ggcaatggag catccccttg  23160
aagaacacgg tatacaaaat cacaatcaga tattgagaca acaatttcca ttaaaatatt  23220
cctcttaaag aatcatttat cctgcgcaat tcgttttcca cttttatctt catattttta  23280
tcgtcgttca cgaaaatcat tttatctaaa tcttcgccat taatctttgt ataaaaataa  23340
atgtcatgct caaagaaaat agtttttcca acagaacgca tggcaaagaa cgttgcgata  23400
gttcttggta aaggtttgaa tttaatggca ttgaaacgca aagcctgata gagaggtttt  23460
aatgttccta agcgaataca atgctggata atttcttgct ctttcatttg ttgtgcgcca  23520
taaagatatg atggtgcaat gataatacat tatacaaata gaaaagcccc tttcggggct  23580
tatttgtctt cagattcata caaacgccaa ttgccgatgc taaaccattc ccctacatta  23640
tttgaatatc tggttgttcg gactcctccg acttcatacg cccatttgaa gaatttccat  23700
ttggacgata aagaaggaca ttcgcttccg gatttcagag aacacgctgt gagccaacgc  23760
gtaatactga gagcctgaaa aatcggatgg ataaatgaag aatacaatat ccaaagcgtt  23820
atgacaacaa aaataatggt cgtgatcacc ccgacaattt gaaagaacat ttaagaacct  23880
ccaaaatatt gaacacagac tatgaagaaa accatgattg taaacaacca tgaaaacaag  23940
gaaagattca tccttccacc ttcagtccca tcaggtcttc catggttttc tgaatgcgta  24000
gccaatcaag cgccgcatca taacgaggat catgatagac catacccttcc agttcccacg  24060
ccttgatacc agcatatcga tcctgctgcc caacaccctt cagccagctt acgatgtcaa  24120
atgtgtggtg ataatcccaa ggttcgttgg aatcttgctt acacgtcacc tcaatgatgt  24180
gctgagcctt gcggaggtca aacagattcc tatcacacca gtcaaccgag cgcgggtcga  24240
tcccaaggcg atggcatccc ttgcgaattt catcggccaa ttcgaaaata gaaatatcct  24300
tgtcggtcgg atatagactg atagctcggg cggcgtcgca cgggttgcgt ttacctgtac  24360
ccagccacca ttccacagta ccctggtctt tcacacggcc aagttcaatc tgttctttga  24420
cattcagttt gataaatgtc gtgcgctctt caacaagctg ctgaagagta taacgctttg  24480
tcaggtcggc gatagtctgt gcccaagaca acatgacagc atcatcccaa cgaccgagag  24540
```

```
tttcgctatc agcgacggcc aagaaattag atttatacat cagtttcccc tgctttctct  24600
aaaaggagtt tcaaaggata tgtcccacaa gcggtggcat actcgacttt gaaatatgaa  24660
ttatcgttca tggcgaaatt tcgatgtggg aaatattccc cgtcatccaa cccgcctaat  24720
cccccgccga cgcgatattg tttcaactca acttcgccgc cataacggag ttgggcatat  24780
agtccgatag gagcgcgaac gtaatgctcc agccataccc aatttccatc gtgtaaacgt  24840
gtagggataa atgcaaaacg caccttggga tgaagaacgg ctttggcgag catctcttct  24900
gttatttcac gcttcatcca ataccttcct cttcgatgat atcttcttca ctagagacga  24960
cagagattcc gtagtctacc atctgggaaa gttcttgtaa atcttgttca aacccgtcac  25020
cctttcggat ataaaagacg ggtacgacac gacgcctggt atcttcgaag atagtctccg  25080
cgattttatt aatctggctc actacatgaa acagtttcaa tccaccgatg ccacagccga  25140
tggcgggtaa accgacatag actgtttcgt cggtttttgc ctcaatgata tcgtgaactt  25200
gttcaaacat aatctgaact gaactgataa tggaaggcat gcgtgcgtta ggaccagggt  25260
agaactgagt atacaaattg aatccccaga caccagtgtc atgatcaaac gcataggaca  25320
tgttccccaa acgttgttcc ggaccacgtt catctaattg gtcggcgcgg taaatctctg  25380
ggaaattcaa tcgaacgtga ttggcgatac ccgcgcccat tacagaccaa caatttgcgc  25440
cgtgagcaaa ggcattgata agattgaaac tcgtggcggc ttttaataaa tcgccatttg  25500
tgataatata agtggtcatg cgtaacgtct ccattgtata atttcgttgt cgacacagct  25560
aacctgaatg atacacatat tctggcgatg gtcggtgagt gtaataataa aactgtctgg  25620
ttgtgacatg acacgattaa cagatatccc gcgcgacatc aaacgaaagc aaatttcttg  25680
atacaaacgt tgcatatatc ctgaaacaga agccgattca tatgcgcgtt caaattcgta  25740
taattcgttc atttattcag accattaata gcattttcag agatgtattc gacgaattga  25800
ttgtcagccg ccatttttaa aagttcaaac aattcagttc caactgtact cccaaacatt  25860
ccttccaata cgccttggac atcttcatct atttcttcga tgatgagtcc ataagatttc  25920
aggcgtcgcg aaatagcacg gaactgggca atatctccaa tttcatttgc catggtatta  25980
tctcaatatg gggttaggcg gcaattatac cgccattttc ttcaatagag gtcttcggaa  26040
aagagttcac ggaaaggagt gttcttcaaa cgaacttgat tggtttgtcc agcttcacgg  26100
gctacaatag ccgcctcttc cctagacatc cattgcccat agttatcgat aaacccttgt  26160
tcacgcgtgc gggtgttttc gataacacct gcttccttca atcgtttcag ttgcgcattc  26220
attaatttgt cgtggtgacg ggcgcttaca acgatgacat caccatatct gttggcagcg  26280
gccactacgc ggcggtcaaa tttagttggg tctggtatat cccgagcata tagggcgata  26340
tgggtgtcgt caacatcccc tttgacttca gaatataact ggcccccatt aggagatcca  26400
gtgggtaaag aacgaaaata accgagtaat ttcataatct agtctatcca tatttcaggt  26460
tcggggatat caaccatctc cattgacata ttacgcctcc acttcttcat caggaaaata  26520
agggcgtaaa tccccaatta atttagggaa gagggcaaac ccgaacagat taaaagaacg  26580
catggtccca accataccaa catcatccaa ttcggtaacg tcagaaaggg cacacaacgg  26640
tatccacacg tcttcttgtc cttcgtaatt tacgaaggca acttcctctt tgatgaatcg  26700
aggacacaga atatcaaaca gccaatagac gtatgccagt aatgagagac tgcggaaata  26760
tacaaacatg gtgaacccct cacaggtttg gagggaattc accctccaga tttataggct  26820
taatgccttt tcaagatcat ctaaatcatc attgtagaga tcaatgtctt gtttgttatt  26880
taattcttct ctttgttctt ccagattctt tatctgattc aacaatcgtt cacgtgcgtc  26940
taacgtgatt gatgataaag acatcttgaa taattcatca agatcaccat caaaatccgg  27000
ataatccgtt tgaaacaacg ctttcagttc tgtaatgctg cgacgcatat ccgtaaccac  27060
agcccaactg atgaataatg cacggttgtt caggcgatga attttatcag tcatctcctt  27120
taacaggtat tgacgacggt cttcataacg gatcaaacga tagttgaaga aggaaagcag  27180
catctccttc cacccagaat aacgtcggat gacaccatct tcatcccatg ccgtccagac  27240
gggtttgttc gcagagtaca gtttgaacat ctgctcgatt tgtgcatcat ccagcttaga  27300
caattcacca cgtttgaaca cgacagtaat gtcccagccg tcttcggtcg tgtcattggc  27360
gtattcagtg agcaaacccg ccttatacaa cggcaacaga actttggtct catacgattt  27420
agcgaaccaa ccaattggga cctcggtgat gtgaagggtt gtagcattga tgcgtttgaa  27480
gatgccgcga ctgtatgctc ttccttcctc agtatagcct gtctctcctt tatatccatt  27540
ccagtacggt tttaagtccg tagggtcttc gccacggaga agtgctctca gagcgccgag  27600
gactgattta acgcaatggc atggggtgtc cgttgagtac ccagatccga taccattaat  27660
tccgttcacc aagaacatgg gaataacagg caaaaagaac tttggttcca attgttcttc  27720
acccaagtag ttgtaatcca aaatcccctc atcttcctta cggaatattt tacggataac  27780
atcggataca gaaacagaga tgtaacgagc agacgatgca tcacgtccca tgatagaacc  27840
aaattgacca tcacggtcaa agtatggaat attgttcgta ccaggaaacg cctgagccat  27900
gttaacaatc gtattgccca tgttctcacc accggacttg tagttggtac gagcggcggc  27960
gaacataccc aggcgatcaa caatctcttc cttgccatat tccaatgcag tgaaaagaat  28020
tttgcgctga cttggtttca aactgtcaat caactgaggt atttgacgga tgctgttgaa  28080
cacagaaaat gccttgtgat cattattgac ataatccgtg acattgatac tttgagcgac  28140
catcttattc tccctctgtt tcaaacaaac aaacatcact aaaccaggtt ttgcggtaat  28200
cggcggcctc atcaccgaag ccgttcttca gtgattcttt gtagttgtca tccaacgtga  28260
ccgtcgtagt atacgcatcc agattgttta gaatacgttt gaagtcttca gtactgttac  28320
cgccaagacc tttcagatat ttcttcttcg taatcttctt ggcgtcaggg gtttttaaaa  28380
attcttcata ttccgtattg ctcataaact catacatcgt tttaccacac caaatacgca  28440
tgtatggtgt gcgcaggagt ttcagcctac cctgacggac gtactccggc caatatgtgc  28500
aatacagagt aatcaacaaa ccacggatgt gaatgccatc atcgtccgca tcggtggcta  28560
caacagtctg tggatagcgg gtgatatcaa tcggctgacc tgggactgcg cctccatgaa  28620
tcgtgcaaag attcttgaac tcctcattat tcattacctt tgatcgcgga ttgtttaaac  28680
aattgataaa tttaccacgc aaagggaata atccgatctt tttagtatca cgggcgttca  28740
ggataggatt ggacgcgctg tcaccttcag tcaataacag agagcacccg ctgcgatcac  28800
cacgggcggt cgccggataa tacttctcta tctcacgata atcccgtttg ctaatatcct  28860
tcttggcctt ttcaaattca gcatcatctt ggtcgttacg caaggcggct aattctttac  28920
tcaggccagc tgtgacaaac tccagagcct tccggattag tttatcgctg ggcttgtagg  28980
tcgtaccaaa ctggctaaca ggagtcgtca tgcgctcctt ggtctggcta tcaaaacgag  29040
ggttgttgat atcagccgag atgaaaagca tcatatggtt tttaatcata gaaggcttca  29100
gatcagtctt aaactttttc accaattgtg ggcgaatcgc attcacgatc tggtcagcaa  29160
cgtaatccac atgaggacca ccgatatggg tggcaatgct gttcacatat gatgcatgaa  29220
taaacgtccc ctgcgaagga gcaacagcga cagaccactc ctctgtttca tcaacagaag  29280
```

-continued

```
aaccttggca aaagtaatcc acaaaatggc caaatcggtc gatacggatt tgtttcccgt  29340
tcagaatgac tttcaggcgc gggttacaag cagccacttc aaatgctcgg cgatagatca  29400
tcaacaagtt attttgatca agacctttga cacccagacg cgcataatca ggtatccatg  29460
cgatagacgt cccaggggca ttcaaattac tgatcaccgg attagaacgt ttgctcaaat  29520
tgtcttcaaa tgtttgagtg taagacttct tcccgtcatt tgtcgtgaca cggaaccatt  29580
ttgaaaatac gttgaccagt gaagcccctt caccgttctg accacctgat tttttgttat  29640
tgtattcttc atcgtcgtcg ttgaagttgc tacccgcata gagggagcca aataacattt  29700
cagggagcca ttcctttgtc tccccgtgtt taacaaccgg aataccccca ttgtcagcca  29760
cgatgatctg accattcata ggagaaacgg taatggtgat ttctgtgagg cttttacctt  29820
ctggcgtttt gctatgatct acagagttgg tgataatttc atcaaactgt ttaatcaatg  29880
caggagaata ttcaaaatta tccttgaata taacttgatc ttttattgga tcatatatcc  29940
aagttgttcc aacggctgaa cggatactgc ccagatgacg ctctgggcga agaaggatat  30000
gctctatgtg agtgagcttt ttgtattttc gttcaatatc aatcatatta gacatcggcc  30060
tatcccgtca atggtaaaca caagattatg tatggggtcg gcttatagac caaatttacc  30120
gcgccatttc tgtactttgt gttcaatggc atgctcaact ttgactatgg tgctttttag  30180
attatggttg tgatcacaag ccagtttggc agtgtgtcgg atgacaccat ttaccaaatc  30240
ggccagatta tcatctgttc tttgtggttg gttgagtaat ctggtaatgc gacctttgta  30300
gtggttgatc atcgctagtt gctcgtccaa actatcaacc ccaccacaga accaataatc  30360
ttctaaggtg tgttgtgtga ggtcacttgt acagttggcc cgagacagag agaacacgat  30420
cgaatcaaat atctcgtctt tgttcataga gccgtattgt tgaatatgct gatattcaca  30480
aacatacaac aagtccagtg ctgaaataat aacgtctgcc acttcaccat tcagaggttc  30540
tgaagcagaa atttcatata acacgtcaga caattcgcaa gtttcttcaa caagtttaca  30600
gaacacaaat acagatgggc gattcggttc tttctggctg agttcataag atgtttctaa  30660
gatgcgacga ataaatttca tttcaaatat ccttctaagc gaaagcggtt aatatgatgg  30720
attataaaat ccatagaaga ttgaaaacta tatttcccct gatgctcata tgcatgaata  30780
aggggaagtc ggctgtgagc caattggaat cgcagtcttg gtggcataga caacaacttg  30840
gctgatgtcg ccgcaataat acgagaacgc aatatggggg aatctgaatc aacgagaggg  30900
atttgtattt tacccaaatc caatccatac ttcttggctt cataaccact cagatgccga  30960
agagcatcat cgcgatattt tatccagtac caataaccct cgatagaatc gaagtgcccg  31020
tccagggttt caatcggatg atgggtaaaa tgcgatagga attttcccag atcagtccgg  31080
ctttggctgt atatgttgta atgattgaca ccctcagtta taggcgtcat cgctttcttt  31140
gaaacattca gtaatataag catgatatag agtctcaaat caaaattgct gtgtgtaatc  31200
aggtcaaatc tttttatatg ctttcagggt acagataata gagacgccgc caaatagaac  31260
gagcaatatg aatcgttcca tcctaaaatc aggaagggaa agcagtccca caaggctgtc  31320
taaagcaatc atgaacgtta ctccagtcag catgcccaac ttaaaggagt tggaacctct  31380
tttgcaacgt agcataaatc acctccgatt caaatgggga gtttcctccc catacaaatt  31440
atctagccca gaaacactac taaagtcaaa tttgtaaagc agctgcgatt atcttttaac  31500
atttgatggg cagcggaaag gcgcttagca tcatgcagag tatctgaaaa cacgatgata  31560
ttggccttgt cgattttggt tcccataaaa ttggccatgg tcgacgtttt ctcttttcga  31620
tcaaattttt catactgctc ccctgtggtt acatttttcg attgagtgaa aaacgtatca  31680
cgttcacgag cagtgtgaaa tacaccgaat acgtcgattt cattttcaat ttggaatttt  31740
tcagaaagga gtttctttaa cgccgcagtg tgaccagtct ggcgaagcat tcgatagtag  31800
agcatactcc cactgtctgc gggatcaagg tcgtgacgaa tccggcgatc tttttgaatt  31860
tcatacgcat ctagaaccaa ttgttgtagc atttcaatat gcgcattaag ggatacttct  31920
acttttcgtt taactaaaga tttcattgtt ggagcctcga atttacgttc cgctcatggg  31980
gaacataaaa attataccct tagacacaac aatgaaaaag aggccgaagc ctctttaatc  32040
gtcatatttg cctgtcctga aattccattt cctggccttg gataggtcaa gatctttgaa  32100
tatattaccg aagatctttt taaaccctga ctcttcttca agatctttcg gtctcttgac  32160
aggttcttga accataccgc cttcgggttt ccccacatca gcggtagtgg tggccggagc  32220
cgaagagtct tctaggtaat cctggaagct cttcatagat tacaccacag ccagttcaca  32280
acgggcggaa gttacagaat ggccgtccgc gtcttctaca acacaccagt actcaccctc  32340
agaagcagcg gtgacagcgt ggttgaccag agacgcagtc gctgctgttg ggttaacacc  32400
agcatcaatc accacacctt cgccgccagg ggtgtcagag aaataccaca cataagagta  32460
cggcgcggtg ccgccagcag caacgatagt gaatgtcgca tcagcgccgt cggccacgtc  32520
ctgagaagca gccagatcgg ttgtcaacga caacagtcct gcgatggtaa tgacggtaga  32580
atcggtgtga tttccttcta cagtaacacc ataaactgta acagaaccag actgaagcag  32640
tttgaattta ccaccgccga tatggatcgc cttcgtcagg tcgccagaat accagttcac  32700
tccttgatat gttgcgttca caggagcaac agtggccagc aattcaacga tttggcctat  32760
ttccccgctg gccgtagccg gagtaatggt cagacctgtg gtaagaacag cagtcggatc  32820
atggatttca taagaaacct ggaaacctac tggcttggtc ggatcaactt tggtgacacc  32880
gtccgcttgc agattacttt tggtcagcaa cgcatcaaga cctttacatt cggtcaggat  32940
ctcatcagga tcttgattta ggctggtttt ttgccaaccc tttgcaacac ccgtcacgac  33000
atgattgcgt tcggtttccg gtttgttgcg gacaacttcc ggcgcgacta atactgtgat  33060
tgttggcatg gtttcctcca ctcatccaaa tcgttgttca gagccatcat cagctcgtta  33120
tctggttcgt atgaaccgga acataaatca tctctccaaa ctcctaacgt caacagcgct  33180
gcctttagac gaggatgttg gttcttatcc gttttcaaca ccagcattcg acacacagct  33240
tcagtttcga aagtattgaa aagaataatc aattgattga taagcacacg aggacttttc  33300
cctggcacaa atctcttcaa tgattgatta attagcgaaa ttcgctgaat gtctaccatc  33360
aaatcatccc gtgagacacc agcagtgata tagtgtctca gggcatattc catcaaattg  33420
ctttcgtcaa cgatagccat attgaattat aatcagcagt tatacactgg gattatttaa  33480
tctggagttt ttcagtcaat tgagaaataa tttcattccg gtcggtagaa acaatcccca  33540
aaggttcggc caatgtttta agatcattga tgtcgagcaa aagaaggact tcaaccgtaa  33600
tatctgtcga taccacagtg cctggtttca taggcttacc gaacttgtct agcccatatc  33660
gacgtaaagt acccgccagc cccgtaagtt ccgcgagaag ctctttcgtg ccgtctttgt  33720
attcacagac ccaaccgtag tcaccagcat aaacaatgcc gccgtcgcca ccctgaggga  33780
tgttatccac cacacgctga agataacttg gaagtttgtt ttcttcctgg gcggtgattt  33840
cctgggacgt ttgggtattt tcaattttct ttggtgtctt cgccatgatc agttctccta  33900
tagactgtaa tgtatttacc acagcaattg cagcaataaa cgtgcatgga atatccgtcg  33960
tcattgaaat cacacccacc acaacgacag aacaatttca caaactggtc accactgact  34020
```

-continued

```
tctcttggag gaaaattctt aaacgagtat tctctgagtt caccctcaaa ttggaatgaa  34080
tcaacaagga actttgtttt tcggcgcagt gatccaaatg cctgttgctc atacacgaag  34140
taaacatctc tggtttccat attaacctca aagaaaagga ggccgaagcc ccctctttta  34200
tgtcagttcg cggttacttg tacagaccgt caacgtcaat agatttatgt tggcggttgt  34260
attccgtggt gtagtcatcc aacacgagat attcacagca gcggatttta ctagaaccgt  34320
aatcatcagt gatagacacg atgtctttcg ggttcagctt acaacgcaca acccgctggc  34380
ccaggctacc gaaacattgt ttcagatacg ccagagaaca aacgtgaaga ccataggagc  34440
acaggtcttt gttgttatcg ttcacgaatg agcgagccat ccggacgata gtgccaggtg  34500
cgttactgac tttacctgtg cgcttatcca tataatttcc gcgaacggat ttgtatagaa  34560
taatgtcgcc gtcttcatga atctcaatgt ctgagtatgc catgaattca tagatccgac  34620
cagactgaac cagcgcggcg ctcgggtttt ggaacatctt gtcaaggaaa cggcccaagc  34680
gttccaagtt cggataatcg ccttttaatg ccaaagccaa aatgcgtttg gcaacggaag  34740
ttccggtgat atcatagcca ccccagcgaa cacggttgtc tgaaagatca accatgcctg  34800
tagtgaattg tttgatggct tcacgcggtt tcatcagagt gtaagctgtt ttgacgtcac  34860
gatttttaat cgcttcaaca atacggtcat acgcctggtg gctcgttgtg atcgtttccg  34920
gtttaccatc gaccacaatc acgatacttt ccggcaaaat catgatctgg tgttcgttca  34980
ggaacacaga cagttctttt tcattaaatg aattctgagt ttgcttgtcg cctgtttctt  35040
caacaactgc aaccgtcttg accacgaata atacggatga caatgccaga cgaagtgtac  35100
ggcctaaaat tgcatcaaag taacccacgc gccgacgggc atcaagggaa ccgcgcatcg  35160
gatatgtttc accgtcatgc tgtacgctga ttttcacacc atcattgact ttaaccacgc  35220
catcaaccaa tgcagtagcc agttctgcta acggcgaaat attttcttca ttgaagcggc  35280
ttgaccgagt ttctaacggt ttcagttctt cgcttctgaa aagtttggcc tgaatagcag  35340
cagagctatc ataacgcata cagataaaca ctgtttggtt ttccaggaaa cggccaacat  35400
accattcttc gccttcagaa tcgacagaca ccgaaccttc cagaacttca taggtgtcgg  35460
ggattttgcc ttcttcagtc aattctttaa ttggcgaaat cacgaccacg ttattagatt  35520
ctttgatgat acgaaccatc agggcacggg caattgtttt ggcactgaca ccataaactg  35580
atgccagaga agaattgctt tcacctttgc tgctcttggt ttgtatttct tgaatctgtt  35640
cagtggtcag agacttaatc gaagccggat ccactcccag ttctttatcc gacacgcgtt  35700
gtatcattga gcgcggtacg cccaattcac tggctattga actttgactt ctgttctcat  35760
tcaacagctt gagaatacgt ttttctatag cattcatctt gtagttctca ctatggggta  35820
atggggctat tatgccccga gaatacgttt tgaaatagcc ttcacaaatc tagtggcatc  35880
ttcaatcgca ttatgcgccg ttggctgata ttttgacatc atgaatttca ccaaacgatg  35940
acattcaact cggtatcggt ttttggcctt ttgcttttga gatatagtgc tagtgacctt  36000
tatctcatca aatccttcag cagttaattt ttcattcaat aaatcaacaa cttgagttaa  36060
ctggttacag gcgcggaaaa atctcgtagt tgagaaaggc atttctatac gataatgtaa  36120
ttcctcaaca gccttgcgga aataaccgta ccccgatcca gacgggtttc gtttggccag  36180
catacgaaca accttccatt cttcttcagt gatttgttgt ttcgcataac cgatgattgc  36240
ttttgccctg tgttgatgat gagcatagcc atccgtaact tctccatggg aatcaatcaa  36300
cagcttggca ccataatcaa tgcgatgaga catgatgttt atgcccttgc gaagtttcag  36360
gagtttctta gattcaagcg cctgaaattc atctttataa tgctcaagca acatatcaaa  36420
cactgcgtca atggggatga atacttctgg gaatttcttc atcatcggaa cagatttacg  36480
acgcgcaaga acgattgttg gatgcgctcc cagcaaatca aacatgtttt cgtttccatt  36540
ctcgccgaac ttcgttcttt ccatcgcttc acgcaaatgt ccagccgtgg attgtcgtaa  36600
ggtattacca tgaattttat ggataccttc tcggccagat acttcgatat atacgatctt  36660
tttgcctgaa tcaataatat ctgaaacggt ttttccatcc aattcataaa cgctgtcgaa  36720
gttaaatgaa ttgtaatgga aactaaacat cccaggatct ttttcaacgg tcgggcgaac  36780
atattccatt tcatgcatga aataaacttc atccggattg aataaatcgc caaaaacctc  36840
gatcagttta tcggcaaaga ccaggtagtc cggtgttgtt tcttgtacac cgatccatga  36900
ttcaaaataa gacttcaatt cctcatggtt ggtgaatgat tctttatgtg ccgccagctg  36960
attccgatta ctgaaataat tttcattcgg cttgacgacg ataacgacat tgaagttatt  37020
gcgtgctgtt tgtatcttca ggtttcgagc acgattcgag ttatcaataa taacagcaat  37080
ttttgattta gatttcaacc aatttccgac agagttcaca taaatgctgt cgtgtactac  37140
accgtcgtcg tgtacttcaa tttcgtaagg actaccaata gaccggaaag gtgcatccac  37200
agagtaatcg cgcacgacgt ccggcgctcc gatataacgg aacgtgcctt tgtagaaacg  37260
gttatctgca ggaaattctc gctccactaa tttacggaaa ccactaccga acatatcggt  37320
caattgagcc ttcttcatat aaagcataag aggacccata gattcggcct ggcgaagttc  37380
atacatcttc gcctgcataa tattgtcagc cacatatttg aacactcggt tcaggctttc  37440
acgggtgaac tcgtcatatg acaagtcttc acgtgatgga ggaacattca attctccaag  37500
ttcaaagaat gtataggaac tcgggaattt ctccagcacc gaacgtattt cagaatccaa  37560
ttgctcaaga tctatcggat aagaaacccc gcccataacg gcatagtggg tattatcaga  37620
atcagacttc ggctgaatat acgtgttgcc cacacggttt tcaaaattga tgtcctgcca  37680
gcggaaagaa taactggcat tttcaacctt cgggcgcatt gatgggcgca taactcgacc  37740
cagacggacc agttcttgtt caaatgcggt aaatcgctga ttctttacag gcactttaac  37800
agtcagacca ttgaactcat cagtgtcttc tggtttcgga tcacgggtat ccaaatcctt  37860
ggtgatcagg tccacagtag gaatcctgtc cgcattcaga tacataagaa agcgatacag  37920
tttaccttca taacgacttt ctacagtaaa tgagtccgac actgcaaatg ggatttaga  37980
acccagcccg aacgcgccga tctgcccgtc gtcgtcctct ttggtgctgt ggaagagtgt  38040
ggtgtacaaa ccaggtccac ggatgatctc gccatcctca gcgcggaata ccaacacccc  38100
attgtaataa ccaggcgtcc caataacagc agtgctgtca gggatttcat cttccttcac  38160
aacaatgttg ccttcgacaa gcacttcatc ttcccgcgct gcgataggtt ccccgataat  38220
catttctaac ggaaggccaa tcccataatc cttgatttcc aaccatggtt ccataacatc  38280
aggtaaatgg accacaacgg gcgtcccttt gggagcaaga tgcttgctgt atctttgggg  38340
cataggggta agaggggcat aatgggacgg caaccaacgc tgttggcgat cacgcatatt  38400
atgcgagtct ataccgttac ataacgtctc acgcaaagat gcggcctctt tatatttgta  38460
gagacttgaa aataatgttt caaataattt atccgtcatc ttgacattaa atgtctgtcc  38520
gacgatagtg gaagaagagc gcacgaaatg ctcagacttg cgcattttca tagtatagaa  38580
ttcctattca gtttcaaagg gaacacatta ttggggtatg ggtatgatac tagcggggga  38640
ctcaatagaa aaagcctcca aaaggaggct taatcaggtt taactctggt ctacatttac  38700
aacggcagcg ttaaagttga atgtcggatg ggtagcgcct ggctctaacg tttcttccag  38760
```

```
ataacctgcg atattccgca ccacggtttt aggctcagaa cgtgaaggct tcgttgctcc  38820
aagttcaatg atactggaag taacttgttc gacttgggtg tgagccacaa caaaatggta  38880
acgactacca aacgccgcca cttcaacttc tgtaatttcc aaaccactca attcagagct  38940
gctcaactgc ttcacattca gttgtgaacg aaggtgttcc acaatgttgc tgtaaacata  39000
ttgtggcgtg atcagctgtt caatagaact catgacatat cctcatttct ttgggggtta  39060
ttgttactta accggacgac ctctgctcga aggaaaagga tttcatcggc cattatcttt  39120
ccctcttcaa acatcacatg gcaacgtgat aatctgggtt cgccttcaga taatgcgtga  39180
agacgatatt cagggatgac atcatttacg gcgtttcttt ttgttctttc catgcgtctt  39240
ggcctttttta tgacgactaa cggaaggacg ggcatgccca ggctccccag gggtacaacc  39300
ttgggcataa cgttggtcat cccagaggcg tcctttgtaa gacatatctt cagccatcgc  39360
ggacaaggcg agggttgcta cagccgcagc agataatggt ttagacatct gtttctcctt  39420
ttgctgcata tgccagtgct tttacaatca tcacggccaa tccgattggg tcgcacgtac  39480
cttcgaattc ttgttctaaa atctcacgta tttcatcaga agattgtact tcggagcagt  39540
tcttgctctg tcgacgttgt tcttgctcaa cgaggtcttt gaacagaagg tctttgaaag  39600
aatactcatc gaagtttcc agatactgct ggatacttgg ttgtttcgca tccatcgttc  39660
tacgcagatt gctgatagtt gaactcgcct gttcgcggtg tttgttcata acggaaaagt  39720
tcacgggttt cccccaagcg ttcgtcactg tgttggaaca cacttgtccg aagagatctt  39780
ggaaggcgtc atccagatga atcagcgcgg cggccagttc atcataagtt ggtttttgag  39840
cagtcatttt cgtttattcc tatttttaga tttcttggct tgacgtttat gctgagcggc  39900
tccatacaag cgcggaggct tttgataacg ctgtgaggca attatatccc tgtagtcggc  39960
ttcggcttca cagcaagaaa catccgttct tcgtaattgc gcgaccgctt gtgacaccag  40020
cattttacgt tcgctttcta ccaggtcatc acaaattatc atgcgctcgc ctggttcaca  40080
acgacgtttg ggaatgtcgt caacactgat gcattccacc tcaacgcctt tcaatttttc  40140
ttgaaggatg atggccatag tacgagcgcc cacccctcct ccaataattg caatctttct  40200
tggcttgtca gacatattac attccataaa aagaggatag agcaataata ccctatcccc  40260
ctttattgaa gaacgattag tctttggatt ctactttatc accgcgcaga tcctggacgg  40320
gtttgccatc cggcgacatg atgtagatgg tgttaattgt ctcaaaccaa gacaattcat  40380
caactccttc agtgtatgga gttaccggaa ctgaagtttt gatatgatca ccaacgttat  40440
ttggggcacc atcagacttc agcactggct ccaggaaggc gaaacggcca tttggataaa  40500
tcaccccgcc tttgaacatg cgaatcttct tacgaggatt attcgcctca ccaaggcaca  40560
ccaccagatg atggatcatc tcaggacggg taagcaacgt gtcgtcacgg atgatcccct  40620
gtttgatagc ggagatcacc acttcatcca acaaagcctg ttgctgttcc agagtcaaag  40680
attcagtaag tttcacgctc atggtctaac ctttgaaatt aattgggttc tgaaccccag  40740
agtcaaacgc ggcctgggta cgggtatcgc tcaccacctg acaggtcttg tcaagatcga  40800
tgcgagggta tccaaagatg ccagcaatga cagatccagg gaactggccg agtttggttt  40860
catagatagc acacgcgtcc aatttctttg tctggctgat acggaattca tcacgtcctg  40920
aactgatgac cacctgaatt tctttgtaca ggcttgaatc aaactggatg ttctgttcct  40980
ggatccattg cataaccgcc tttgaaccat cagcaccata acgaccctgg aaagtatctt  41040
tgatcacttc tttcagaccg tctttgtaca ggccaggtat ctgagccgtc tcttgtactt  41100
tgtttgtata gttgctcaga tggttttcag aatctttatt gaacttttg acttgctgtt  41160
caatacgatt gaaatcattg aaataactga cgaaactacc aacaccgatt acaacaaaag  41220
ccagaatcgc caaaccgatg atccaaccaa ttgaaatacc tttacgctgc gacatcttta  41280
cttcctcttg ttaaaacaaa cgtttgtaag tgcgaccatt gtactgcata tggcctaata  41340
tgaaaattgc ggtaaacgga acacaaccta ataaaacgac gataatcact tcccatgtct  41400
tgaggtcacg ccatttcaga tactccattt ccttcatttc aacgcggtta tagcctttgc  41460
tgatattgac tgcaacttct tggaatactg atatccccat gggtttgcca gtcaatgaaa  41520
gaccgtttcg ggaatggagt tccatgttat tcatcccatc agcaaatgac gtggatttac  41580
cccaattgat tttcatatcc ttcgatatgt cagtaaccac aatgacatcg ttctttttac  41640
caccggacca tgcatatagc agcccctgaa aatattccac aggctggcca gaagtcacta  41700
cccacacgat attgacctga cgtgatgccc ccaatgtttt caaagtgttg ttcagataat  41760
cattccaata atcaacggga atatccatcc ctgacatatt cagaacacga gtcacccgat  41820
aataatcata caccccttgga tatgacggga tatggtcttt gaacttctca gcgaattgtt  41880
ggtcagattt ggagaataaa gaatccttgt tccccagaac atagttcata tatgcatgtt  41940
cacgagctgc aggttctccg attttaactt gcgcccaacg cggaggctct gtagtaccct  42000
gacgatcaat acggtcaatg ctcagatcac cgacggttgt taatacgtcc caatcaacgt  42060
cataagagtg ctcatagcac gtgctgcaat gacgcgtttg tgtacaagat cggttatttc  42120
ctgaaccaga gcaagaagtt gtgtaatagc acatacattc ataagaatga ctacagctta  42180
ccttgtttcg ttgcttatcg gtaacgtatc cattcaaaat ttcaacatct cccgaactac  42240
ccagggaaaa tgcagcgtat gctcccgcct ggataagaca ggataataca accactatcg  42300
cagtagcaat tagcgtttct tttggttcat gggttttgcg atggtaaacc acgaacaata  42360
tggctaaaat aatagggacc acaaacagaa ggtaaatcat aacacaccat ccacgagttg  42420
ttccttcgtc ataccaagaa gttgattttt atgacctgat tcagctccat ttttcaacaa  42480
cagatcccaa cgttcttcat gatactgtgg agtcattgca tcgtcaaaag aaacatggtg  42540
gcgatgcata attgttgcaa cggtatgaag aacgattgct gtcgctcttt ttaaagcacg  42600
tgtatcagtg atatggtctt catattcaat acccatcaaa tcgagttctt tccgaatata  42660
tgcaatagac aaatcacctt cagaatgcaa tttaacaata gtcgctttct taggatgtaa  42720
cacgccgtct gtttctttca tgaacagatc gtacaaatat tgtttgtatt cggggcgcat  42780
catctcgtaa tccctccggc acagataata ttcagttcac cgcgacggaa accgccttgc  42840
ccctcgccat gtagtagacc aaacgcactc ttgccggaat ttttgttgcc gttcagtata  42900
ttccaaagag catcagcatc gcctaactca gtcatctggt attttgttgg atttttatga  42960
tcttcttcca gaatcaccga taccatagat tcaatatcga gggagtccat atcttcaatt  43020
cgttgcattg ccatgatgta tttccttgta aaagaaaggg gaacgggcta ataataaccc  43080
attcccccttt attgaagaac gcaatcgcag tcagattact ttttcttcag ctcttccagc  43140
ttggcttcaa tttggtccag aatctcttta cctttctgga cgatggcttc accgtcttgc  43200
gcgtgtttac gaaaaaccag agcgccagca atgaaaccaa caaccacgcc tgggagcgca  43260
tacaccaaca gatcttgtaa catgatttat atcctcactt ttataagcaa ggatatttat  43320
atcatcgttt caacaaagac atgaggttta cactggtcga cttcggattg tcctctatct  43380
tccggacggg cattttcaga ttagtgtaaa cctcagatgg ttcccaacgc gtaccctgct  43440
gcaggtgcca tatatgtaga ggaacacctg tctcaaagaa cacaggcatc ttccacttct  43500
```

```
ggacgccagg aacgtgccct gcaggagctt tttcgcataa cagggtatct ggtagccaga  43560
gggaacgggc ttcccataat gccttacagg agtactcagg ccagatgcgt tccatgtagt  43620
cgatctcatc ccaagtacgc tcggcatccc acccgatgta acgagtgttt ttcagacgga  43680
agaatttctt aagccaacaa gcaccggaag tctcaaagtt caaacgattg atgaacgtga  43740
tgtgaccaaa ctcggcgaca caatctttga atgcctgttc aagatcagcc tcaaggatgt  43800
cgcattcttc atcggtgata ggacagccgt tgatcttttt ctttccgtgc ttggtcaccc  43860
agtcgtcacg gtttgacaag aatgccgcgc cgttgcggtt ggactcacta ccatcacggt  43920
cacgcaacat gaacccaggg acgtcgatct gatacatgtt gccgaatacc atgttcaggg  43980
cttccaggaa gttccaggcg ctcaggcgac cgaagtattt ccaccccata gccgtgtccc  44040
atagcttaac gaattgatca ctttgcagtt tagtctccaa caacggacgg aaagcatcca  44100
tctgagtacg accagccagc caatcaatgt aggactgaac acacgggatc atcttcgatt  44160
tgcgatagcg gcaatcagta tcgaatcgca tacgctcgaa gttcaggtta taccaatcac  44220
agaatcgctt gaactcttgt ggtgactgag gcggtacagg aaactcacta taaatcgtcc  44280
atgggccaat cccattataa caacagcccc aaaggaacgc catccagatc ttgcgctcga  44340
tcttctcaag ctgcgtaatg ccttcagtga cttcaatcgc ataatccatc agacgaactt  44400
gttggttgtg ttcttccgta tacgacagcg cctccaccca tgctttgagc agatacatcc  44460
gattctctgg cttacgataa tcgattgaca aatcaattgg gtacttccat tcagccggag  44520
gcgtataacc tgtcggcatt ttagatagat gcgtcatcct tcacctcggc ttcgagttgg  44580
atatcttcag ggtttaaaac gggctggccc aaagaccaaa ttggaaggaa ccgacggtca  44640
ttggatacta cccagatttg cttggcggtt ttcgtttttt cagaaatata atgctgggca  44700
ttaacctgag tccgtgccag cccaatttgc cgccatgcac cgaaatcttt agaagatgga  44760
ttggtgttca gctggaattg gggaatgatt ttattctgtt ccggataata tcggacagcg  44820
ttaatcatat tggcatcgcc acgatagtca acagcaatag caatggcatt gcgtggaata  44880
agaattttca ttttaattcc ttttgaaact ttcaattatg ttgtaaacga acggcgttaa  44940
taaagcaaca ccgcccgaat aatataacgc gtaaacattc aatatttcgg ttgagtctaa  45000
ttcaacgatg cccaaatatt tcataacacc gacaagcata gctgaaaagc acatcaccag  45060
accgacgaac acaaaatatt tagacatctt tttcattatc tacaccttac gcattagccc  45120
cagaagggac acggatgagg tctttggttc ttccttggcg acggccttgt ttttagtttt  45180
ggatgccttc tgcggcttct caggcactct gtgagccaaa ggatcctgac cgccgacttc  45240
acgcgtcatc ggattggttt cgcaatagcc gtagaagtct ttcgacatca gattgttagc  45300
gcggcaaact gtgccaagct gatgatagat agcattaccc accacccaca acggggcgtc  45360
gaacggcaac atagccaatt cgctatcatt cccagtcttg aattcttggg tgttcgtaac  45420
cgtttggtgg tacaaaacgt cttgcccact gtaatcatcc acggcaacat tccagcccag  45480
cgccagcatt tcagatttcg acttctcgaa ctccttggag taagattcgt tgcgcgacca  45540
gccggaatcc cccgcttctt taccagagcg tccacggatg cgggcatcgt actgatagcg  45600
atcaggatac gcaaagtaca gcagcgccaa agaatcaatc ggatagttct tgaacatcca  45660
ttcaggacgc cacttgtccg acagcatcag gggttcgccc tcacacacca gggtatatcc  45720
ctgagccagc caacccttga tgaggtcgcg agcaatatcc ccagagcctg tggcagcatg  45780
aatggcgtcc atagaggtcc aagacgccag gccggattta ttggacactg tgtattggcc  45840
gacgaagatt aacttcagct cttcaaattt caggccgaag gggcgcgtct tatccccaac  45900
agtgtacgac aattcagtcg gcttcagctt agtgcggagc cactcgatga actgtacgac  45960
acgagtgcct ttacccgtgc cgctggttcc tttgattaca atgatctttg ccattatgca  46020
gcatcctcaa tgcgccaact cactccaccc aaccaaggtg cccaaaacac ggcaacttgc  46080
ggatgaccat tctcaacaaa cttcacttta tactggtcat caaagttata gaaaatttcg  46140
tcgtcatcag gtgccatacc gttttcaatc agaactcgtt ttaattccaa cgctgcgcca  46200
acggaagttg gtggattctg attacggatg aagttgttta catggataat gataccatcc  46260
atatcactgt caccggaacg cttgtcaggg ctttctacaa ctttattttg ttcttgcacg  46320
atgtgctcct atcggacata ttgataatga gaaaccaggc gattcaccac ttcatcgagg  46380
ttacgattta agaagtcaaa gtggttttgg ccttctacat gcttaatata aagcatatcc  46440
tcgcaattcg aaagatccag tttttcataa ttgccctgag ggacgaagat gacgaagatg  46500
ttattcaggg cacacggctc aacatacttc ggattgtcgt cgatcaggac atcgccagca  46560
agcagatgct tttcatccgt gctcacgaac ccattaatca acgattcaaa gtgatggtat  46620
atgaactgac gcttgctgcg ttcgtgttcc ggttcgcatt ttgtaactgc caccatttcc  46680
acttgctcaa acttctgaag gagagcggcc tttaaattcg taaggaattc aacagcccct  46740
ggcagtggtg acattctgga atacagatca ggcatacgcc accaatccat cggatcacgt  46800
cctgttggcg aatccatcca ctgaccagca acgaatacac ggcgcgttaa ccaggccgga  46860
tgcgcgcgtt cacgcatgag gatcgccaga tcaccagcgt gtgacatata acactctttg  46920
gtgattggtt gaaattcaga tgggtagtcg tgacatccca tattttccgc agcggcttta  46980
gaattagaaa tattgaacca ttcaacccac ggcgataggg aatcaaccag agtcaaatcc  47040
acatccacca gaacgcgata taacccgcca attttagaac atgcgtcata cagaccaacg  47100
tgattattca tcagatttct ccacattgtc ataaccagtt gcggtgcatt gctcttcggt  47160
gcaatcggca tacagaacca cagaagattc cttcacgtaa gtggtgcagt gataggtttc  47220
atcttcctgg atggaatcat cataattgca aacagtttgc aacggaccag gagtcgtgtt  47280
gtccaaagct gcatgtgcct tgatggtgtc ttccatctta ttcaccgctt gctgattggt  47340
gaacgtcggc gcatcgaggt caacagtaga cgcaacgtcc agaagggtag agcatgcagt  47400
ggtagagaaa gccagagcac acaccagaag aatcttattg agtttcataa caatacctgt  47460
tgtcaaaggg ataacagggg gaattatatc cccctttgtt ttattgaatc aacctttctt  47520
gcccatcatg gacaacagat taactcgacg tttgtgagac caaccaacca cgtctagaat  47580
agattgaatc ggctctatga aggtcttttc aaacgtggtg tgataatcta cccacttatc  47640
cagcccccaac tccggaggga ggaagtcagg gaaggctatg cggtcgttcc ccacagggtt  47700
cccaggtttc aggttaatga ttttaacctt atcgccagat tctatcggcg ggagaccgag  47760
gtcttcatgc ttgtctatca gcttgttgta cataatacaa gccttggcag caaagtgtgt  47820
gccactgata taatttccgt tgccgtctaa ccacttctca atatcactaa cgccagaggc  47880
ttgagcaata tcatccacgg ttaattccat atattccttc ttataacccg cgatcaattc  47940
ctgaacttca gcctccgtcc ccagaagaac tttctcatag catttaacca gacgctcacg  48000
acaccattcc ggcgttgtag atttacgcgc ttccagacct ttgaatttga tctttggctt  48060
ctcatacttg atgccttcgc tatcgtatac cgccatgcaa tacatcttct tggctcgcca  48120
tacagcagac gatgcgatga cctcacgttc ccagaccatg cgctgctcaa acccgttcat  48180
ggtattacat aacaactgcg cccattcgct ggtttttggc tggtaattct ctttgatcca  48240
```

-continued

```
ttggtcaatg ttatcaacga gtttgtgatg gtccttttct tcaggccaca attgcttgac  48300
caggcgttca atgcaaatgt agttggagtc agtatcaccc gcgataacaa aatcctgacc  48360
agtagtgccg caaagtttgt tcagataatc atcggtgtgg cgtttgttcc atttgttgat  48420
cagctggccg gaagtggtga ttgcttcagc gatgttgatg ttgaagtatt ctttaaacca  48480
gacgttggag attgcgccat aacctgcgtt catcaagatc ttcagacctt gttgtaacgt  48540
gtcttgagca acccccagat cttcccattt atgcatgact tcagtcaggt gatcaagatc  48600
gatatgcttg tgttcttcat accattcagg atcgtagaaa cgagacttca tggcagactc  48660
aaggtggaaa tcacctttag acatttcctt acaccaacca gcccattgct catacttcag  48720
gccagttgct ttctctcctt tacggtcagc gtatatgcct cgcataattt cggaaaggaa  48780
ggacatcttc tcattactga agaactgaac gttcggggta aacgaaacgt tatatcggcg  48840
tagtgtttca aaatggaatt cgcccagcgc gaccaattca tcaacaactt gtatgcgttc  48900
atcaatagca cgctgcaact tgtcgtgaag atttttgaga tgacgacgtt tattcatcgg  48960
cgttgtcata tcattcatcg ctttggtcaa ttcctcacac atggcctcaa taatatcacg  49020
gcgtgtgtgc ttatcagaaa cgatagtctc tggaccaagg ttgtattgct gtatgatgtg  49080
gggatacagg gagtttaagt cctcagagaa gacccagaaa tatatccctg gtgcaacctc  49140
catgacatat gcgccttcaa aatctgttgg cccatcatag acgcgctgga ttttcgggac  49200
aatccccttc tcataaagac gataatagca catcgccagc cacggtgcta cagtgccgag  49260
accgtcttca tagttggatt tagtgcgata agccaataca aacatcagct gtatcaaacg  49320
cagtttttgt tctaagcgcc acaccagctt gacgtctttg ataccatatc gcgtatgctt  49380
gcaataatca ttgaaataaa ggtcatacaa tgatttgctt tcactataat ccaacttctt  49440
ctcaccgagt tcacaataag cgatccagtc cagtgagtat ttttcgcggg tggtgtaagt  49500
gtgtttcttg tacacttgca tgtagtccat cattggacaa cccacaaact gataagacgt  49560
gacgtcgcct ttacggtctt tgatgaaacg tttcttcagt ttaccccaag gactgagacg  49620
ctgggcttcg gattcaccaa gaacctgcgt aattcgttca accaaatagg ggctatcgaa  49680
cgtttcaatg ttccaccccg tccaaccgtc aaattgacgc tgcgaccagt agttaaggaa  49740
tgaacgcagc agatcctgct cggtgacgaa ctccatatac tcaacctgaa gcccaccgat  49800
ttcaggatcg ttctcatcat acctgaactt cgcgcgatcc ttggaacacg gcatgcccca  49860
gacatagaat ttattggtat tcatatcttg gagctgtatc agcgtaatag ggaacgccgc  49920
attcatgttc tgtgtgattt taccgttact gtcaattata gggaattggt cagtcacgtt  49980
gttggaaata aaggaaccag ggaaatgctc ccgaacgaag tcatggttgg ccagtacttg  50040
cttatggaaa cgacgaaccc gcgcctcgct gcctttaaac gtgtgagatt cgatcgttgc  50100
gtgtgggaat ggacctttag tcatttctcc gtcacgccaa ccagccgaga acacttcgat  50160
atccacgttg gcgatgtgga tatttgaata atcaggtgtg atcatcccag gaaaactatg  50220
ggcgatgaat tgatatgcat aatccgtttg tccatacacc gcagcgcctt cgacctcctt  50280
gtactcctca agatagttgt cagcgtcgcg cattgatgca aactttttag acaccaacgg  50340
ttcgttgagg aggccaatct tttcaacttt ggaataatca gctgtgggta aatacaaggt  50400
gggttcgaat ttcttacgca acatgcggcg attgccgttg tcgtctgcga tacgaatcag  50460
aaggtcgtta ccctgtcggg caacgttcgt atagaaaaca gtcattgttt gtctccggtt  50520
aaccgtgccg tcagcacgtc cccgtaattt aaccgaggaa cgttcaatga ccaaggagtt  50580
taaaatggca atccccttg tgagcatgat tccaggggcg ctaaagcaac tctggaatct  50640
tgggactgat ttggtgcaat ataagcggga aattgttcag gctaaacacg atgttaaact  50700
ggaggcaata aagtcttctt cagaatggga actttctaag attaccgaag tcggcggatc  50760
ttggaaagat gaattctgga caatcgtttt ggctgttccc gctatccttg ttatgatcgc  50820
tccggttgtg gaacttctaa tgttccccac cgagtatcat aaaggggatt tcatcaaagc  50880
agtaattgat ggtatgcaag cccttgaaac agcgcctgat tggtatactg cttcgctatt  50940
gacagcaatt agtgcatcat tcggtatcaa ggggtacaac cattacaaaa gcaatagccg  51000
gaaggcgcaa gctgtggatg ctctcaaaca gtttggggtc aaagtggtta acaaagatcc  51060
cactgttgtt actcagtcgg gttctcccga tcttgagtct gctcccccag ctgggtctac  51120
tgcgacctct ggtgcgtggc ctgatctgaa gaaataagtt caaggggagg aaactcccct  51180
ttcttttggt gttagggaat gaaagtggta aacaagagat tgctcgtcac ccaaggcggg  51240
gcgacgatag tacgtggacg gatatatgaa caaaccaagc tgggtgatca taagactcgt  51300
ctgacggtta aagcccccga cggcggttgg ccaacaaagg tgattgtccc agacggcctc  51360
atagaacgag ggacggcgac gtataaggga gcagagttca aaatttatta aaatatttat  51420
tgaataaagt ttacttcttc aataactggc gtatacttct aattgtagta cgaacaaaca  51480
acaatctgaa gagaaggaaa tacatcatgg caatcgaaat tatcgctcaa tcaaaatcag  51540
gcaagactgt aatgtacggc actgaagaag gccgctgcat catcaactac ggcactatca  51600
ctggcgagtc tccagagaaa ggtggccgct atctggttga gtacggttca cgcctgctaa  51660
tggtaagcaa agtcgatggt cgtgaaatca tgattcctcg taaagaatac tttgactcac  51720
gctctgccgc gatgactttc ttcctcttcc agaaacgcca cgaactcttc gttgaagcga  51780
aagacgcagg tctggacgac gcgacggctg agctgattgc cgaaggtaaa atgactctcg  51840
aagctgctct gggagacatg gattgcgaag ccgaagcaca ttatattgaa tattccgcat  51900
atcagaacga atgtgaagat gatccggaag acgacggatt cgaccctgac ctccacggcg  51960
gtgaagacga taacacccct tccttagaag ttctgatggc tggcggccag gccgcgtggg  52020
aatggcagaa cgagaagaac gcctggctgg attcccgtat ctaattgact gaagcccctt  52080
cgggggctta ctttgaactg aaggactata tcatgatttt aatcttatgg tttgtattca  52140
catttctggc catggccgac atcggcaagt atcacgttct cccaagcgac ctgaccgtcc  52200
tgctatacgg catagtttcg tttgtgctgg gttccttgcg cgcccatatg aggactatat  52260
catgagcacc ccaaaaactc ctgtccgtat cgctgttgag cctctgctgg ttgatgctga  52320
gaatgctgct gagcagtacg cgaacaaaat catcaagaac ataatggacg atctagcatc  52380
caacggctgg gacgttgaga agtgcgctcc gtggccatct tcggttggcg tcaagtttgg  52440
tgatccagat taccaacgaa tgaaatcaaa acacgcactc taccgttctt tgacccaggc  52500
agtgaatcct tcttacacac ctgggaagcc ggatattgtc aaagctgatc ctgagcgcca  52560
tgctctgttt gtcaaggaag cacgtcgaaa cgctgcgatg caatatgagt ctttcatttg  52620
taaactggaa aacaaaattg gtggtcatag cgcggctgta ctgaacggtt cccatgtatg  52680
gggttattca atcctgaccg tgactacacc agaggggatc gagcgctgga agactcagac  52740
gattatcaat atgtccaagt tgggcaaact ttttaaccaa tatccaacga ggaaggtgaa  52800
atgatgaaaa acttcgcaca agaattacag actacgattg atcaggctca gatttgggaa  52860
gccatgggga tagttgaaaa agccgtcgat atctttgttt gcaaaatgaa gaagcaactc  52920
gtttcccaag caaaacgcgg agttgaaatt gatgacatgg tgtacgctgt tggtggccat  52980
```

-continued

```
aggtttgacg aaatattaac agcattccaa caggcacata agtctcaaaa atacccaaca  53040
gacaggcaag tcgaaaagtt caaaacattg ttggtggcga gtcttctgaa ggaaggtttg  53100
aagttcgaat tacacaagga tgaaaggaca gatgtcgtaa caatgagatt cacagtatac  53160
acaaacgata tctaaaataa aggggcttaa tgcccctttg tttatttccc atcccaaaag  53220
tcgtcttcat cgtctacttc atcaaacgca gaatccaatt cttcgtcaga gtactctgga  53280
aggcgaccat tctgtttcag atattcaatc tcgtcatctt ccaattgaag atccgttgct  53340
ataaacagtg ctccggtctc ttcatcatgt tcaatgctat aagacgtata ttcagaaccc  53400
tgaactgtaa tgatgataga tgtcggatct tctggatcca cgtgagcttc aaacgggata  53460
ccgtcaattg gggcgtcttc taagaacgtt gcaagggcta cggcagcgcg gacaacatcc  53520
gtgccctgta ccgatgcata aatttcttct gcacccgttt ccccgcgctc aaagaattca  53580
atcgtagttc cgtcttgaac accagtccag ataggcatat ctgctgggga atcagattca  53640
aataatttcg aaattggcat ggcaatgtcc tcttgaataa aacgctttgg actatttagg  53700
cttctctggt cgccaaccct ggcttaaaca ccaccatttc ctcaacgtta ttggcactca  53760
tagaggctat agaatcgaac cctttgttga caagttcttt cacattatca tgtatcttac  53820
caggctttat ccccaactct cgcattttat tttcccacac cgaaacattg ttggaatcta  53880
ttacaagagt cttcttggcc ttgacacgaa atgccatgac aataggttca ccagattgac  53940
gatagcgcac ggcattttct gcgtagatct gtgcctttcc ggatcccctg tcaggtaaaa  54000
cccagcaccc atcgtaccag agtcagtctg gccaaatttt tcaaaatcaa atatatcgaa  54060
ttcaacatta gacccatgat acaaaacgat attcgtaaaa tcaggtagcg ttgattcgcg  54120
ataaaattct agaaaggttt tcatagatac cccacactgg tcgtatgggg tatttaggat  54180
ggattagctg gggacaaact cattcacagg gacatgttcg gggattgata attcaggaca  54240
agcagctttc atcgcttcca gatatggctt gctccccacg atccaaaaca atgagttctc  54300
attaagcaat tctggtttgt gttcctgtat ccatgtcatg accttacctt cataacgagg  54360
atgcaactca atatcccccc actggtaatc catgaggtcg ttgtaacgaa cccaattagt  54420
ggtatgaaga tcccaatggt gtacctcaaa gcgaggaagc acgatatccg gctcgttctt  54480
tggcctgata ccacttagga ggccagccaa cgaaacgctc ttagaggcat gcggaagatc  54540
cttcttacca tacacatagt ctgggttgtc gtgatagcga cgagtgaaat cagttatgtg  54600
agggaggttt gcttgcttac cgataatgcg caaacgactt tcaatgaaat ctaatcggtt  54660
aggtccaatc ccgatcagat agacattctt cagatttggt ttcggatgca tcgccaaacc  54720
tgtcaggata ctggtgcacg aattacaaga accagcagga atgatcagat cagtgatatg  54780
gtctgggata ttggcaacct gctcaccacc cagcatatgg aatccagcaa tgcgttctgg  54840
tgaatgaacg gtatgatcca atgtaatgcc atattccaga taatacgcct ttggatttaa  54900
ttgttcaatg agtttcttac agcgcggctg aatggtgcta ttgtaaccag atccaacaaa  54960
gttaaattca ctaccaaacc atgctgacat tgaaaccata tcatggttca tgcatgtggt  55020
tggtttagtg gcacccagca cagtggttgt cttgccgccg aaatgccgtg agactgccgt  55080
cgcccatagg gactgcggac taccaacgac agtaccatgg ataagatctg gggatcctcc  55140
cgctttaaga tgctccatca tgagccagat ggcctgacgg agtttgctgc cattgatccc  55200
ctgcttgccg ttctcatagt gggacagggg cgcaaagtaa tcttcacgct tgaaccaaac  55260
cttctgatcg gtttctggat tggcgacgag ttcacacggg gtgtgcttgt agaggtagtc  55320
ttcccagtgc accagattgc ggtcgaggga gagagtggtg aatatagact tgctgtggtg  55380
ctgggagatt acaccattgg gtaatggctg cacagaacag agttcttcac aaatttttctt  55440
tgtgtcgatc gcctgaggta tgccagcggc tgacatctct tctttcaagg cggcggcagt  55500
ccattcttct aaagtatcgc gatcgatacc gtcgggaaag ataaaggggc tggcggtttc  55560
ttcgactgcc tgtttggtgt gatctataag tttctgaagt ttgtcgttca ttctatttct  55620
cctgtaggca ttggcttatc atagcgtatc tacaggagta tagaaaagga gaatctcggc  55680
ttacttcttg aacagacgaa ggaacttcat catgttatcc atgaaagtcg gcttcttgac  55740
cttttgtttt accggagcgc cctgatcatt cagaacacga ctggccggag gagtaggcgg  55800
tgtcgggatt gaactgtcat gtttaacaac cggagcacca ctggccagag gagttggctt  55860
caaagattta attgcctgat ccaaatagga attgtccacg acactcacgt cttcaccgac  55920
cgtaacgcat ggtttgatta gaacggattt cttagattgc tcatattgat gagcaatatc  55980
catatatttc ttgcgctctg cgtagaaatc aacattcttt actttacggc ggcgagcagt  56040
agaactctct tcaccataga aatcataacc atttttgaat aaccaattca cggcttgctc  56100
aaatgtattg aacaccatat acagaccgcg tcgaccattt accatgtcgt cttcgctgga  56160
ataaccaatg aataccgctt gccctttctt gttgatatca aaaggagtac acacaccagt  56220
ttcttcaagt gatcgcggag aaagatgccc gtcccgatag atatatgccg gatacaagaa  56280
ctcattcaga gtacgtttgt tccctttgta tgtgtacagg cgagcaaatg gaggcaggtc  56340
acaaacgata tcgttgtaat cccaaatcgt aacattacgc atgttgtttc ctcaaatcaa  56400
tgaaggggtt tataaacggt taaattttaa acccctcttc ctcattgaac aaatcaaata  56460
ctagtcatat agagtgggac aacctgctca gcgataaaca cgacctcggt aatggtaaaa  56520
tcaccaccat aagagtacag tttcatttgc gccccgttgg tcgccaggtt cccatccttg  56580
tcaacactga agaacgtaat gaaagacaaa gtgtccggcg gcggtacgct agcatcacga  56640
cttcttgata actggttccc cacagaaccc acaaaatcta atatcatggt tctattagaa  56700
gtagacccag accatgatcc gacaatatta accttcacag gaagaataga atcataggga  56760
aacgcatgaa atttgtgatc tgataattta aagaacggag ccaaaccagt aggagaagaa  56820
gggtttggtg tcttcccatc caactcagtt aacaaatcta ttccagttgc cccagaagtt  56880
agcagttgtg acaatccaga aaatctgact tctgttttaa tgcggtgggt ctgaagcata  56940
ttccccaaat agggagatgt caaaatagcc atatctcccc cttaagaaac gataaccgtc  57000
gcatcagaat taattgcctt aacccatccc accgtcggcg gggttaaaac gaccatattt  57060
ccttgatata tgatatgcgc gttgttaccc gttggagcgc tggggctatc acacagatac  57120
acagaaccgt gagtcacttg aagagttttc aaagatgtgc cgtctgagac ttgcgtccat  57180
gtacttgcgt ttggtgtgat cttagcagtt gccataatag acctccttta caagtcagat  57240
ctatttatta cagacaaaaa gaagcccgat cgtcctgatc gggctatgtt aaaccatcgt  57300
ggggatggaa agactactca cagcaatttc tgataatggg cgttgggaga gtgcgtcggg  57360
aatcgaaccc gaaatcgtca ggacgctgaa agctatttgc atttcacttg catatcctgc  57420
gactttctta acttccttaa ccccagattg ttatgaagtc agcatgcaca ccttcttcat  57480
cttcaggaag tcacactcat tattctgatt gcttcaactg gattcgaacc agtgacctca  57540
ggcaccttgt tctctcgaaa ctttcctgcg ctctaccact cgagctatga agcaatttgg  57600
cggaaggtga aggattcgaa ccttcggggg ctaaaagccc cactcgatta gcagtcgagt  57660
cccttaaacc tctcgggcaa ccttccaatt tggagcggga gaacaggatt cgaacctgtc  57720
```

```
cagtgatcgt cgccgatgat cagtcggcta ctggccaacc cctatggctc ccgcgaaatt  57780
tggacgggct tcacacccga ttgagcattt gatctgccgt agcccaactc cccgcgcttc  57840
acagcgccga ttggttaact ggcgaccagt gccttctggt tcgatctcct ggaactttac  57900
aggcttcgcg cccgaccatt tctggaagtt ggggcatcgt ttccgatgtg gagtcacccc  57960
attttataca cagctggctg caacgcttac tgtgtttggt ctaccgctac gtgctgggcc  58020
acgctcgagg acatcggcca tccttcctca gctaatccac gcagcggcag atttgtatca  58080
gagtgtccgg tgtagctttc cgtgaggtgc gcactactgt agcctctaca ctctgaaatt  58140
gtttgaagta ggtctcactc ccctgggtat ctgtatcctg cagccttaca ttggcagcta  58200
tcgcgcgatt cgcacttccg aaggcgcttc gagatactct acttcaattt ggcgacgatg  58260
gcaggacttg aacctgcgac atacgattta acagaccgcc gttctaccga ctgaactaca  58320
tcgtcattat ccgtgcttgt ttgcttcaat tgcccttaat tgggcatcag cgtcagcttt  58380
ggtgtcatgt gtcccaagaa ccttcgtctt ggtgtggtca aggacaaccc acttgtcgcc  58440
tcgcttttca acaaactcaa caatctcttt gttgtcagta gagaggccat cccactcagc  58500
aagaaactca ccgaacgttt tcatcatact caccaatcgt ttattgaaca actggtttat  58560
ttaggtgctc ccgaggcggt attttaatcc cgcgatccca tctcgcctgt cgtagaccgg  58620
agcatgctga cagtccaaca tatttggtga ccctggctgg acttgaacca gcgaccaatc  58680
gattatgagt cgactgctct aaccactgag ctacggggcc aaaattggcg gggtctgagg  58740
cttttcacct cacctgctgg attggcctcc agctgttctc tctggggact cgctgtccgg  58800
acagctatcc cttaaactat cgccccttaa ttcatattgc tgtgggtaat accaaagcgg  58860
aggtttggaa tctctcgccc tatagcgacc tttaaaccgt ttgatcagtc cgatccaaag  58920
gactacccac agcaatatga atttgttgtg tccaatcaag gactgtcaac cttttatccc  58980
gtttgtgcat gatcagttca tgcaggcctc tttgtgcgcc tcacagcaac gcgcttctgt  59040
aggtcattga cttgcaccgt agtctcacca caggcgttta tttttccagg gctttccact  59100
tacaagtctt aaccagatcg ggatacgggc ttgtaagatc agattggaca caactttgat  59160
ggctctagga ctaaagatcc cgcgtcaccc atagacttgg tttataaaat ctagagccat  59220
caaagttgca accaatgtcg caactcgcac ttcagcgtct tcgtctcgct tcagcacttg  59280
tcctctacgc tcggaccaaa cgaggctggc cgacagaaac atgacaccac tcatcactag  59340
agcgaggatg tggttgatag ccacgatgtt acatctctgt cgcagagtga tcacacttgt  59400
caggatgatc actgttttgc gaacttgaaa atactgcgcc tgtctcgggt ttccccttag  59460
ttcggcctct cattgttcgt ctagtcaggg agctaccctt gatgaccagc ttattttgag  59520
atcttcgcca gcacccacta gtgtctagaa tatgtaggtg tcgaggtctg caaggcattg  59580
ccctatttca tacaacgctc tctcaagtac gcaaatcgaa gttctctggg cttaacaggt  59640
tcgacccaac atgttgtata tcgcctaact tgctcatggg acggacacat ctgtgtacag  59700
accttgaggg ttaaaagata tacccaaaga acttcgattt gcgttgtggg ggcaaacccc  59760
cacacggcta cttctttgac agggattgct agccctgggg attccactgt ttaaggcttt  59820
atcccataac gcctgaggcg cgttttaact tattgagctt gcataactgc aaactgatgc  59880
gctgtgagac acatctttga gggcactcag tgtacaacag gctccgatat ttcatagggc  59940
attactgcct cggatttaag ttgcctttct cctgaaactc catgcagtct cgcgtctgac  60000
gcggaatgcc ctcaaagatg tggagccgtt ttagggagtc gaacccaaat gcttggccag  60060
cgctgacctt acatcccatc tgacttaggc aacccacctc tgcttactca ggagcttatc  60120
ccctttggac agtcagatat aacggctttg ggattggagg aaggactcga accttctcat  60180
gtacgctcct gatttctcag aagtagcctg ctcccatcga cctattaagt acacgctccg  60240
ctcattgttc ggcgggagct tattaatcac accctcccgc ctattgttag tgcgccgaat  60300
tttgttatga ggaatcggaa gacctcactg gtgtatggct attaagctac tgccaggaac  60360
gtgttatcat tagcgattat ttttgtggtc agtttctaaa aacccgcaaa gtcacgcaca  60420
acgaaaacga aaacctgttt gagtcctaaa cctacctgtc ttggtctcac atcgctatga  60480
gtggccagga ctcaaacagc ttgccgttca gtgagttaac tatactttgt aacccgttat  60540
tgataaaacc ttttattttt gttgacgagg gtgtggaatc gaaccacact tctgagcgct  60600
gccccgtgtc accaatgcac cacctcacca tcgatttgcc ggaacttacg catccggcct  60660
cgcctgttgg tgatccttcg aatccgggaa gattagtagg aactatgaat caagttaatt  60720
cgaccaacag gaatcctcgt gttgcccttt gacgcaacat tatgaaccct ctatgaagac  60780
tcataatgtt gtcggcgtga tggagattag cgccccccgac ctccccttat atgttggtgt  60840
cgacttgcca acggggtgct ctcattcttc tgagctaatc acgctacaac agggagtttc  60900
gttctccgac ggtcaagtgc gtccactgac accagcgagg tggatgtgac gcctctattc  60960
acacaagccc cagagactag gggttcactg ttttcggttt caagcctact cacactgtgc  61020
tgtttccctc atgtttgata ctttactgca agccagccaa tttgaaaaat cctctcccct  61080
ttgaattaca ctgcccacag cagtgcggac gaaccttcat tcaaaaccgg atgcgccgaa  61140
atgggcgact gtgtaccgga ctgatcaggt cgacccagga gagagcaggt aatcccgatc  61200
aggaggatga ggagtaacat catgtaaaac atagtgttcc ctcccttcca tgcaactaac  61260
tttaccgcat ttatttattg aataaagcgt tattttatca attctaactt cacaacgcgg  61320
cgcagaagat aaacatattc accagacgct tcatgcgaca tataatgtgt agaaggggtg  61380
gaatggttgt tctgggtttc ttttaaccca acgcgttcag cccaaccatt aatggagttc  61440
ccgtaaaacc cgataatcgc gccgaaataa atgcgctggc tttctggttc taaaatatag  61500
ttgacagtga agcagatgtc agaacgaata gattctaatt ttataccaac ccgaccttca  61560
gagaattcgt tgcgaacata caaatgacga aaacgatcgc gccgcgcttg tgatgactct  61620
tccaattctt ggcgaagtga ggatgttgca tcgatattaa atgaaaatgt cgggttttgt  61680
agatcggtac gggctaactc taatgctgat tcaacaacac ggcggtaatt aatatttttg  61740
ccagtcagac gtttcacttc ttctgtaatt gttccgaaag gaatttttgt agcacgttcc  61800
ccttcgtatt ttgctaacaa aggaatgatg tgtttcatta ttgctgtatt aatgtgcatt  61860
tcctgagcct cgtcaaatta attaaatgtc cccactatta tattgggaat atgtttattg  61920
aatataaccc caagaaaggc caataaaata atgacagcga ttattaatag gtaaaaacta  61980
cttttctaca acatcaagaa actgtatctt aacgcggtgc ccttcgagtt gtgagtgtta  62040
acgaacaacg agaagcagcc tccatggctg cggaatggga ctgcctgtca aggcggtgtt  62100
acgagcgagg gcgtcagccc cctcgcgagt atattcgaat aaattaacgc gcgagagcgt  62160
tttgattccc tttggctaaa tatcttcaac accatattca aactcaggtg atggagatta  62220
tcatggccac gcaaacagtt ccttcactcg acgtcagagc ctttgagtac attatcaaac  62280
agcgaatgaa agctgatccc acctttaaag attatgactt tgaaggttct ggtcttagtg  62340
ctattattcg tttgttggca tctgatgcga acgccatagc ctttatgcag aacatgctta  62400
atggtgaagg ccatttaaaa acagcaaatc aacgttctaa tgttggtttg tctgctgctt  62460
```

```
ttctttctta tacccccgac aactatcggg cggcatacat gtatgccaac atcaaagtaa 62520
cgccgtatga cgccagtaca gctcctaatg agatcattat ggaccgccgt gtgatgttcg 62580
ttggggcgaa ggatgggagt tcctacaact ttactgttga aaaacccgtg tccgccacgt 62640
tgacaacaga cggttattac atgttcaaca acgtgaaact gattcagggt aactggttgt 62700
acaagacata tgatgttgaa ggaagcgcga tttcgactta tacgatacct tcggaaaatg 62760
ttgatatcaa tcatctggtc gtacaggtac aggaatcaga gtcctctgat gtttcaacga 62820
cataccagag atacaacagt ccgttcgacc tgaatcaata tgcatatctc tattttgtgg 62880
aattagggat agatggcctg tatgtgtttg agttcggaga tggttatctg tctcgccgag 62940
tagaagatgg caacgttatt ttcctccagt atttagaaac ttctggtgct gaaggtaatg 63000
acatcactag tttatcttcc gcatcttcga taggcgggtt taaccaggtt gatatagaat 63060
tggtttccga acgcagtgcg ggtgggggag atccggaatc tattgaagat acgaagcgtc 63120
tggcaccttt ggcttatcag gctgatggcg ctgccgttac ggaaaccgat tacggtgttt 63180
taactgaacg cttgttttct aacgttgccc gtgctaaatc atatgggggt gatacgcttt 63240
cccctccgga ttctggttac gtttatatcg ctgtgatacc atctgttggg gagactcttt 63300
cagacgcaga gaaggctgat atcgttgccg cgttggacaa atacaacgtt gggtccatca 63360
cccccaaagt ggtagattct gagatcacat atatccaagt caccacgact atattttggg 63420
atccgacttc gacagtttat gttgaagaac agatgaaagt cgtagttggc aacagtattg 63480
tcaaatgggg cgaaaacaat ctcggtggat ttgatcagtt gttcgacaaa gagatattgc 63540
aggaagcaat tacgaaaatg gaacgttcca ttaactcaaa tatcacgtct gtcggttata 63600
aacgtcattt caaacccgat tatggtgtgt tggatagctt tactttcagt tatgggagaa 63660
gcattaaacc tggttctgtg aaaataacag ggtttaaacc gcttccggcc gaagttgatt 63720
tcacatatta tatgcgcgat gacaatggcg atttgaacat gtataaagtg aacaacaacg 63780
acaccactaa agaatttttg gttcaaaaga ctggtgttgt ggattacgcc aacggcgtcg 63840
tagatcttca gcagattacg gtttcaaact ataatactga aggagtaacg atcgttgtgc 63900
taccagatgg cctgaatcag aatatacagg cttcacaaaa ccaggtattc aaaatcggtg 63960
atgtggttgt tacgccagag gtgcgctatg tccaaagatc ttaataatgg tcacaatggg 64020
gttaagtatg aaaccccgtt gttttaccaa aacgattttc ctctgttcat cgagttcatg 64080
gacacgttct ttaattggct gtatcggcag cagggcttca ctcaagaaga aattttggca 64140
tatctggcag acacttcgag ttggatgaat cctgagagtg aagattcacc tgttaaacaa 64200
ctcatagatt taaaggccga caaaacgcca ggttctgaag ccaaagatta tttgtcagat 64260
aaattttttgg tcagaacatt tgagaacatg atggctcttg atgccgagat gctgctagac 64320
gctgatggaa ggccgttgct ttctattgaa gacaagaaca agcagataga cgactggtat 64380
aatgattttg ggtttcaacg aactgtcgat aaatcatttc aagaatttgg acattttatt 64440
ccagtcggtt cggattcttt attgacggcc acgggcgata cgttctctgt ttatattgaa 64500
ggaactaaac gaagaactct ggatcatccg cgttggctga aattgttgaa acacatctat 64560
aaaatacgtg gaacaaagaa agcgattgaa ttgttctttt ggatatattt cggttgtcca 64620
gtcagcgtct attttacgaa agaagacata ggcggactgg acggaaattt tgaatgtgac 64680
ggcacgacag ggatgcgtga tgattactat tatgatgaat acacttatgt tataggagtc 64740
ccaggcgacg tatctgattt tgaaggtgtg tttgagcgcg tcttccgtca gcatttccat 64800
cctgctggat ttactgtatt cctagaaagc acaaggagct aaaaatggcc gatttcctga 64860
gtcaatatac aggtcagcag atagatcaga tattgggttc tgttgacgac aaagtaagta 64920
aaaacgacgt cattgatgat tttgaagtca gtgacccatt gtttccgcct tctgctcgcc 64980
tgacttatga gttgaaaagg tctgtggata cgattaatga taccctgacc aacaaagtta 65040
taagaacgga tagtggcgaa cagacaatca acggtaagaa gacatttaat gcgctgttgg 65100
ttactaacgg gggaatccaa gtccccactg ggaaatctgt ttcaatcgcg gacgaaccaa 65160
ccaactcaac agacggtgtc aacctgagta tgttgaggaa acatggtgtc agtgaagaca 65220
ccgcgccaga tgggtctggt ttggctgggg aattattgac ttccggatat tacaaattca 65280
aactggattt taacagattg gctgcgtata cggaattaac tctcccaaca tcagttcccg 65340
tgcaaacaga ttctggagtt cgcacatggt caatgactgc attttttaat gcgttatttg 65400
ccgacaaccg ttttaacggt tatgtaacga cgaccacgta tgatgccgac atgttgagtc 65460
tggagtctca gcttaacaat atcaacacga cgttgaacgg caaagtcaac acgtcaactt 65520
acaacacaaa aatggcttcg ttggatttga gtatatccaa cattaacaca tctttgagca 65580
acaaggttga ggtcagcaca tataatacga agatgacttc cttggacggc agtatcagtt 65640
ctcttacgac tggtaaggtc gatgtatcaa cgtataatgc caaaatggcc acaattgata 65700
acagtttggg gaacgctgtt tatcgcacca aaacaaactt gtcatcactg acggtatcgg 65760
cttctggaac aacagctctg ccagactttg atttggtgaa actttgccag atattggtaa 65820
cagcacaatg gggtacagga gatgtcgtag acacatatcg agtcaccata actcgagatg 65880
ggacgattaa gtctgagctg ctgatccaga aaagtacgag cggaactgtg acgtttacgg 65940
gttctgtagt tggtgggaaa ctgaggattt ctgttgtcaa tgccaatacg acaacacctt 66000
gctcagtcga ttattctatt acagcatctt tctaaaacta aataccccta gatgacatga 66060
atacatttag gggtattaca aatggccaac aaaccaacac agcctctttt ccctttgggt 66120
ttagaaactt cggagtcttc gaacataaaa ggcttcaaca actccggcac catagagcat 66180
tcccctggtg caatattgac gttccctgaa gatactgatg ttgcgggtct cccatcttct 66240
gtgcgttaca atcctgatag tgatgaattc gaaggttatt acgaaaatgg cgggtggttg 66300
tctttgggtg gtggcggaat acgctgggaa acgctcccat acgctccctc cagcaatctg 66360
ttagaagggc gcggctatct cattaataac tccactggga cttctacggt ggttcttcct 66420
tcccctacgc gcgttggtga ctcggttaca atttgtgatg cctatggtaa attcgcgacg 66480
tatccattga ccgtatctcc agcgggaaat aacctgtacg gctccaccga agatatgacg 66540
atatccaccg ataacgtgtc ggcgactttc acttggtctg gtgctgagca gggttgggtt 66600
gttacatctg gtgttggcct cggtcaaggt cgtgtgtaca gtcgagagat tttcactcaa 66660
attttagcat ctgatacaaa tgaagtgact ctcaacatcc ctccgacaat tgtggacgtg 66720
tacactgatg ggaaacgcct tacagaatcc aaatattctt taaatggaaa cgtaatcact 66780
ttcgaccctt ctttacctgc tggcactgaa ttgcaggtaa tagaatatac tccgattcag 66840
ttaggtactg gcggcggggg ttcgggcgct tctgcaatca cctggattta caatggcgga 66900
tccgctatcg gcggcgaaac cgaaataacg ctagacatcg ttgtagatga tgttccggct 66960
attgatataa acgggtctcg tcagtacaaa aatcttggat tcacgttcga cccattgacg 67020
agtaaaatca ctctgacgca agaactggaa ccagaagatg aagttgttgt ggttataaat 67080
gggacaccaa acatttataa ccagatcgat cgttctttac aggaagttgc tcgcgcctac 67140
aattttacaa atgctcaagt tattttgagc aacgattata cttctgcact ggataataaa 67200
```

```
gtcgttattt atgatacgac atcccaacgt tcttggggga ttccatctgg aattccagca  67260
ggttctacag tggtttccgt caatggggat caactgaaat acaaaaatgg atcaactgaa  67320
accactgtta cattggtgag cgtaccaggt agtgcagaga agttgaagaa cgatctggcg  67380
tcgaactctg gcgcgggcat gttgaaaact tctagaggtg ataccgtaga agaagaattg  67440
acttttatta atcagaatat ggtcgttcaa atttcagatt tcgcgagcct tagaacttta  67500
gtgccagcca cagcgggcat ccgagtcaaa ttgaaaggtt attattctgg ttctgaaatc  67560
ggtggcggag aattcatttc cgtcgctggt gatgctgttg atgatgctgg gatgattgct  67620
cgagtgtcaa gcagctttta ttggaagaga attatcgaca aacatattac tcctggtatg  67680
tatggcatca aagggaatct tccagaagat ccggcagtga aactgaacgc tatgtttacg  67740
gctgcggctg cggctaacgc ttatgtctta ctgaacgatg ttgatactct ggtctgtaaa  67800
agccctgtcg tgatcccagc acattcatta gtgtacggca acaaacggac catattgaaa  67860
cgtgatgcat cgttgtcata tgctaatgat ttcttgacaa ttatgaatga ttcatatgtc  67920
aaggggatct atgttgatgg tagccgttta gattctcaga ctcctctaga agcagttttg  67980
gtgcgcatcg ctgggaatgt gactatccat aagagcgaga tccgaaacaa tgctggctat  68040
ggcgttgttg gtaacgcagt ccctggcatt cgtatcacca agaacatttt ttccaacttc  68100
gccaaaggtt gtgtggctat gtttggcgac ggaacggcga cgagtgatga tctgcaaatt  68160
aatgataaca gattctttaa cctgggcgcg ggaaccattt atgttggcgg ttactcaaac  68220
ttccttgtcg acaaaaacgt cggaagaggc acttacgtgg gttctccagg aaaccgtctg  68280
tatgttgtga ccaataccaa cggactatc  acccaaagcg ctgggccaga ttttggggcg  68340
ctgaaaacgg gtatgttctt tgtattgcct ggtggttctg aacatatgat aactgctgtc  68400
aacagcctta caagtgtgac agtaacccca ccaccgccgt cgaacgccac agttcgtgca  68460
atcgcaggga caggggatct tctgggcatc caatcatgct cctacggcac catcagccgt  68520
aacaacctga ccgattgtgt gacttacgga actggtggag gcacgatgga ggggagcact  68580
ctgggttgca attatgtcac ttgggaagac aacttcatcc gcaacacagg taagaacgga  68640
atcaacgtcg ggcaatcagg tgctggggtc gccacgtgtt ctatcctgag gaacactctg  68700
atacaggttg gtaacggcgg tcagggtgtt ggcccagcgt atcttctgcc ttggttcgat  68760
acggtaggta tcgctctgta tcagggaaac ccaggttata tggcgaatat ggacgtcagt  68820
gataacaacg tctctacatg gtctggcgat ctgaatgacg gcgctgcttg gtttggtatg  68880
agcggttgta cggaagccac tgtgacttgt acaggcaaca aatcttctgg ttattccgac  68940
ggctatgttc gtggagatat attagaagtc acgttgacag gttatggtac aggggcggct  69000
gcgacttcat tcgttagtga tggtgagtct atacagataa ccgttcaaac aggtacttca  69060
ccaacagctt ctccttattt ttcagtgcgg aaggcgatcc gcacccgcca tcaaccgatg  69120
ataacggcgc agatcgtcac cacaactggg aacatgtctc attgttgggg tatgcaatct  69180
agtacagcag gaaactggat ggtgggtcag aatacaactc cttcaggggt cacgacgtat  69240
tacgcaaaag ggtaatattg aatgcctaaa taccccatat tggacatcct ttatggggta  69300
ttatcatgat ttctcaattc aatcagccac acggctccac ttcaatattt gttaacaaac  69360
aatctatcgc tcgaaatttc ggtgtcaaag aagacgaagt cgtttatttc actgctggta  69420
ttgatctcag tggatttaaa gtaatttatg atgagtctac ccaacgggct tattctcttc  69480
cttcgggtat tgtttcagga acgactgcga taagtctgaa cgaacaagcc atcctcactc  69540
attccgctgg ctctgttgac cttgggggaat tagcagtaag ccgcgaagaa tatgtgactt  69600
tacctggttc ttttaatttc ggccatacca ttaatgtgaa aaatgaactt cttgttcacg  69660
atgataaaaa atatcgatgg gatggttcac ttcctaaaac tgtcgatgct ggctcaacac  69720
ctgaaacatc tggtggcgtt ggtattggta catggctgag tgttggtgac gcagcattta  69780
gacaggaagc caacaaaaaa ttcaaatatt cagtaaagtt atctgattat tctacattac  69840
aggatgcagc gacagcagcc gtagatggat tgcttattga tgttgactac acttttactg  69900
cagatgagag tgtagatttt agcggtaaag ttttaatcat tgaatgcaag ggaaaattca  69960
ttggcgatgg tatgttggtt tggaatggtt tgggtgcggg ttcagtaatt aagaaaccgc  70020
acatgcatac taaaactacg ccgtatactg tttaccgatt cgatgcaaac ggtaattggg  70080
ttacagaccc aacacaagtt ctggcatctg ttcagcagcg tttggatgtt ggatataagc  70140
caaatattaa cgatttagat atttgggacg accttcctga taatgtaaaa aatcaggttg  70200
ctggtgctac tttgcgaata atgagcggcg ataatatcat cgtagagaac ccagaagcta  70260
catttggtgg ttatctattt actttatgta ataggattct tgttaagaat ccacgcaatt  70320
ttattgcttt ggaatcgggc attacatttg agaaccatca tacaactgca tggggtactg  70380
gcaactgggt tgttgggggt gagattaaat atggctctgg ttccgctgta ctgttcattc  70440
gcaatgatgg tggtacagac catgatggtg gagtaaggga tttaatatcc tatcgcgttg  70500
gagaatctgg tgttaaaacc tatcaaaatg aaataggtgg tcgttcagcc aggaactacc  70560
gtttagtgtt cgacaatata actacaatcc agtgttacta tgatggtatt gatgttaatg  70620
ctgacacagg gtcgccaact gaacgtgtgg atgactactc actcgcagag tatccatggt  70680
tccacctacc tactcaacat atcatccgta atattattac tcgtgattgt atggggattg  70740
gtgcttggtg ggatggtcag aaaaatatta ttgataatgt tgttacttat gaggcccata  70800
aggaaggcgt cttcgatagg ggtactaaca atgatattac taacattact gtagtaggtg  70860
cgaataagga tttaactaac ctaaatcaga ttacctgtga gggaggtagt agacttcgtg  70920
gtattaacat ccatgcatat actacacaag gttacgctat atacgctccg tcttcagaag  70980
taagtaatgt ttcctgtgct ggttccggta ctaagaaatt actatgtacc tatataagcg  71040
atattcaggg aggtaatatc aatgttcagc atagtgccaa ccaaatgaca cttgcaatgc  71100
aacctgctat gggtggtact acaaacccat ctttgcttat gacggcagat tgccaggttg  71160
ctacaccagg gggtgaggca agtattgtca agctttcggc aattcaggag ggtgtacgtg  71220
taggtgagtt tcagcttaac cgcttaggct ttaagcatat gagtatacct gctgcccctt  71280
tacaattacc agagagcgct ctggaacata attcatctat aggattcttc ttcggaagtg  71340
acggagcatt gaggttgctt gctaaaaaac cagatggaag ttatgtaaca tacacacttt  71400
aatttatctt gagcaaaaac cccgctttgg cggggttctt attatacctt tgttcataaa  71460
ttttattagt tcagactaaa taccccatat tggcaaatcc ttatggggta ttttcaaatg  71520
accagaaatg tagaagaatt attcggcggc gtaatcacag ctccccacca gattcctttc  71580
acgtataaat caaatgtcgg tggagaaact ttcatttctc tacctttcta tcctgtcgct  71640
ggtgttgtca caattaacgg cggggtgcaa gttccgttag acaacttcga aatagacggg  71700
aatacgttaa acctcgggcg cgcattgtct aaagatgacg tggtttattg cctgttcgac  71760
aaaatccttt caccagaaga tacttctaaa ggtattcgaa tatacaaatt tcaagccgtg  71820
ggtggagaaa ctgaattcac gcctgacttt acttcttatg gtgtccagtc tctttatatc  71880
ggtggtgagt acaaaactcc tgatatagaa tattcataca acagtacgac tgggaaagtt  71940
```

```
tccttacaaa ctgcgctgac tgcaggggtg tgggttgttg cggagatgtc tgttaaacaa  72000
ccgaatatca gtccggcgtt cgatcgcagt atccaagaaa ttgcccgttc ggctaacgta  72060
aaagactctg aagtcattgt cagcactgat accatatctt tactcgacga caagaaagtt  72120
gtttatgatt cagcggcgca gattatttat ggtttaccaa ctatccctga tggttcagtg  72180
atttcttctg ttagtaatgg gcaacttact tataatccag gtaatgttgt agtggatttg  72240
ttgcctttag aagattcatt tattaatgtg ataaacactc tggggcgcaa tgatggtgcc  72300
aagtatatcg gagaatgcca ttctgttgct gatctcagga atactgaacc cactatggat  72360
ggacaacgca ttattcttaa gcaacacact gcgggtactc ttcttggtgg aggggtattc  72420
cgtgcgttaa ttgatggtac aggaaagact gatgataacg gcactgtgat caaaactgtt  72480
ggaggcgcag cctggttacg tgttaatgct gatagagtta acccattcat gtttggtgct  72540
ttgggcggtt ctaatgatga tactattcca gtacaatctt gtgtggacag tggtaaggcc  72600
acacaattaa ctggtgtaca ttacgttagc aatatccggt taaaatataa tacgtcgtct  72660
atttatgggt ctggattaca ttactccagg ttgcatcagt tgccttctgc tactgggaat  72720
tgtattacca taaaagatac atgctccctt attgtattag actcctttgg ggtatatggc  72780
acaggtgcac aacaaggcac atcatttact gcgggtacaa caggtatcta tatagaaact  72840
ccttcaggtc tctcagctga ttatccgttc cacactaccg cagacccaag acgcgacttg  72900
tgtatttcta aggtccatat agcaggtttt gatgaatatg ggttaaatat tgatagtggt  72960
aactttagtg ttactacaga ttctctttta gtcaaccaca tcaatcaggt gggcgtccgt  73020
tgtgctacta ctgattggac ttggacaaat atccaggtta atacctgcgg taaacaatgt  73080
ctggttcttg atggttgtgg taatggtcgt attattggtg gtaaattcat ttgggctaac  73140
tggcaacctt atggtacagt aggacagttc ccaggcatta ctattaataa tagccagaat  73200
atggttatta atggtattga ggtacaagat tgtggcggga atggcattga gattagcgat  73260
tcatattcaa tttccatgaa cggattgaac accaatcgta acggcatcaa cgctaacaac  73320
actttctaca acatcgtatt taacaaaagt gatgcagtta tcaacggatt cgtaggactc  73380
aattatgccg cgaatagtgg ttcaggtgct aactctagtg cgggcaattt tcagttcctg  73440
tctaatgatt gcagcgtcac cattaatggt gtggttgaga ctggttatat gggcattaac  73500
tttattggtg ataacaatat tatcaacccc acaaattccg acctgagcat taacggattg  73560
gttaattatt ccaagactgg tttgcaaacc atgaacgaga cccctacatt tgatggtgtt  73620
agcactacac ctgtttatgt aagtgtccca tcttctgtag ggcaagtaaa tggtctgaga  73680
ctatcacaag ccaacaaaga taaattactg tactcaagaa cagcaggtcc agaaggtatt  73740
accatggctg ctgttgtagt acctaccata tctggagctg aagtatttaa cttcatggcc  73800
attggttcag ggtttagtga tacatccaac agtcttcatc ttcaattagt tatagacgct  73860
tccggaaaac aaacaattgc tttgctattg gggggcgatg gtacaaccca aattttatct  73920
ggggatttac ctaacgacct taaactacaa agtggtgtgc catatcatat agctattggt  73980
gctaaacctg gatatttctg gtggagtatt cttaatattc agacgggtaa gagaatcaga  74040
cggtcattcc gaggcgctta tttagctgta ccatttaatt ctatattcgg attaacttct  74100
tcattaacat tcttctcgga tagcaatgct ggtggggatg cctgttctgg tgtaggtgct  74160
aaagtgtatg ttggtatgtt ctcttctgag aatgattatg tagcttcacg gtactacaac  74220
ctgattaatc ctgtagaccc taataagtta attagttacc gtatattgga ttcttctatt  74280
taaaaatata cccctcttcg gagggtattt actagagaaa aacaggagat tcttattatg  74340
aatccgcaat ttgctcaacc gaaaggttct acttcaaaag aaacgaacaa agatagcatt  74400
gcccgtaaat ttgggtgtaa aaagtcggaa gtcgtttatg ccaaagcagg acagtccttg  74460
tctggttata aagtgatcta tgataaggtg tctcaacgtg cctattctct tccttctaac  74520
attgatgctg taacggtcac cagtttagtt gacggcatcc ttacgcactc tggaggcacc  74580
gtagatttaa atgaattggc aatgacacgc cgcgagttta ttactttgca aggagacttt  74640
gtttccggtg ttaccgtcaa tgctaagcat gaagtgatcg catacggaaa tagccgattc  74700
cgttgggacg gggatctgcc gaaagttgtt ccccctaatt cagaacctgt cataccagat  74760
tgggttaacg ttgatgccaa cccagcactg tctgaattag cgaaatctgt tggctcgtct  74820
ctggtgggat ataaaccaac ggggacaacc actacgactg gtacggtcaa aggaaaattg  74880
gatagtttta ttgattttgc aaatgactat tgcggtggcc caattacagg acaacctgat  74940
ctcacttctc aattacaaca agcaattatt gatgctttta attctggtat tgccgacatt  75000
aagattgttg gggattttta tatatctggc atgatattat ggtatccagg tgttcgattg  75060
attggtggac gttatgactc tacattgata cgcgtttcca atactttccc agtgggtggg  75120
acaatgtttc gttcttaccg tcctccactg tgggcggcgg gttgtcatgg tctatctctt  75180
gaaaatgtgt atttggtagg ccgcgccgcc aaggacgttt atggcataga tatcaatgat  75240
gcatcttatt ttaatcttga aggtgtgcgt ctggatctgt ttgataaagc aatttctttt  75300
aatagatgga ttgatgaaac tcgtgtagac acgagcggta caattaccta tcccaacgcg  75360
catagtgccg aaatgggtgg ccaatcatat tttggtacaa taactcgttg ctacgcaggc  75420
aattgcgtca cgtgcgttga ttttaatggt gtggtaaacc gttgtacatt tattagcaac  75480
acatggacaa ctagtgatct ggcatataat ttcagcaacc cgcgtggagt ttatgaaact  75540
aacacattca tcacttgtaa tattgaaggt gtgaagagtg catttgaatg gttcttttct  75600
ataaattcac catatcacaa tgtgtggatt aatacgagca tcgataacgg gaacccagat  75660
atcacgagtt tagcgaaaga tggtggtcga cagacattta ttggtttagc gattttccct  75720
tatggaaacc catcgttggt taattggtat ggaattaacc ccaatggtca tcggagtact  75780
gtcttgggta ctgatcttgg ggaaaattta ccagaagatc agttaaaaac tcaggttcgg  75840
gaagaattac acactttaac aggtattgcc aacaagcaat gggctggaca acaagtaact  75900
gagacaattc ccgccaatgg ttacaaagca ttgaatatta gcgtgccagg attaaaaggt  75960
aactcagcag ttattgcttc attatctgcc atatatcatg gtattacagt tgatgccgcc  76020
agcaacaaca ctggtacagt ttcagtaata ataagcaatt acacaggttc tccaattgat  76080
gtaaatgctt acctgagtgt cacaggcata gccaaaagtt tcttgtgatc aaacaacccc  76140
gcttcggcgg ggtttttatt tctatctgtc tgttggctgt atactaaata tctctataaa  76200
tggcactcga tggagcatca aaatgcaatc tacaaatcta aaccgtcgcc cgtattggga  76260
cgactggaat cctggaaaac ggttttcacg gattcttttt cgcccgatgc ctattaaggt  76320
tcagacacgt gaactgaacc agatgcagac tattctacaa gaccagattg aaaagctggg  76380
aaaccatctg ttcaaagatg gatctatggt tattcctggc ggtctgacga ttactaacgc  76440
cgctgtgtct atgaaattca ccctggctgg tggcactgag ttcactgatc tggaagggat  76500
tactgaactt tatgttctgg gaaaagacaa taacgccaaa gcgcgtgtgc tatctcttga  76560
acgtgatctg tctgctccgg atacgatgtt ggccatcctt gaaatgacag aagtgggtaa  76620
tgcagatggc ttccacgtca acgacaatct gtatttccaa acttatgacg tcaatgacaa  76680
```

```
cttcattcgt attggttatg gtatcgcagc tgcggtgact ggttctatcg tcgctcgtat  76740
gacgaagggc gtttacttca ttcgtgggat gttccttgat gttgatgacg cgactctcat  76800
cgtcgataaa acttcaaaca cttcttccca tcgcgtcggg tttaaagtca ccgaaaccat  76860
cgtgactgaa tctgaagacg aatcccttta ttcaaacgct cagggaacga ttaactccaa  76920
agccccaggc gctcatcgtc ttcgaataga tctggtctta tctcgatttg attatgatgc  76980
tgtggttgaa gactttgttg aactggccaa agttcgtgat ggtaaaatcc agtctatggt  77040
gactcagtcc acctataata ttctggaaga cacgttggct caacggacgt atgaaaccaa  77100
cggcgattac aacgtttcaa cgcatcagat cgacatccgc gaacacctga aagtcaataa  77160
caatggtggt gtattcaatg ctgctgatgg cggcgacgaa agtaaattcg tgtctgtaat  77220
gaaaccaggt atttcctatg ttcgcggtcg tcgtatcgaa aacgtcgggg aagagttggt  77280
gatcgttgac aaggcacggg ataccgatgt cctgaataac acgcctgtcg cagttgctac  77340
agggaattat ctggtcacca agaactccaa aggtgttcca gtaatatctc gcacagtgcg  77400
atacaagtta ttgaacgcat ctggcgctgc tcaagccacg gcgttgtgta tatccgctga  77460
acgcaattca actgaattcc gtctgtacat gcgtgatttg gttgtgactg gggacgcgtc  77520
cactatcacc aaagtgtctt atgaagaaag tgggatcacc atgttctctg ccgaactgga  77580
atccaaccag tttaaccaga gttctatggt agacctgatc ttctctcttc cggtcttcgg  77640
tgttaaaaca ttagcgccaa caggttccgt ggatatcaac tacacagtcc tcagaactta  77700
taaggtgacg ctagacagca gcggttctgg ttctatttca gccccgctgg gatatagttt  77760
ctctcctgaa ttttcgttgt attcttctgc gaaatccgat ggttcagaag cgcaatttga  77820
tatctctggc tctttgtcac tgactggttc tccggtgggt tcggctttgc agatttccct  77880
gggtagcggt aatgctaacc agtcaatcaa tttgctggca ctgatgatcc gcactacggc  77940
cacgatcaaa acgaagacga taactgaaac cacagagtct gtgactttta cttcccaaac  78000
cagtagacct ctggcaaatc acgacggctg gaaattggta tctgtcaaaa atgatactgg  78060
cgcggacgtg acttcgagct tcaccctcga cggtggtcaa cgcgatgcgg gatattacaa  78120
ggctaatctg ttatccaccg ccggagccat ttcagggacg tatacggtgg tgtatcaata  78180
cttcgcgcat agttcggggg atttcttctc agcggattcg tatacttcaa tggattacaa  78240
agatatcccg aattatacat cctccacatc aggggcggtg tatggtttgg ccgatagcct  78300
tgatttccgt ccgaaaatta ccaacgggac atccgacact gatatggttc gcccgaatac  78360
ggctgtcatc ctggacacag agtattattt gcctcgtatc gacgcgattt atctggcaga  78420
taatggcgtg tttggtgtag cccgtggcat cagttccaac aacctggcgt ccccagcaat  78480
acctgcaaac tccatgcgtt tgtatgaact gttgattccc ccatacacgc cgaatatcga  78540
tgatatacaa attcgcacca tcgataaccg tcgttatacg atgcgtgata tcggtaaact  78600
ggaaacgcgt atttccaacg ttgaatacta cacctctctg tcgcagctgg aatcttcggc  78660
gatgacacaa caggtatttg atccaatcac gggtaatccg cgattcaaaa acggtatcgc  78720
cgccgatcca ttcaaagact tccgtcttat tgatgatctg tctgaagatt ggatgggatc  78780
tatcgatacg gaaaatggac gtttgcgtcc gtttgttcaa cagaacgccg ttgacatgac  78840
tccagtaggc tggaacaaag tgatggatgg tatggtggtt tgtaactaca cgcctgaaat  78900
ctccgtaaac caagaatacg cgacgacgac gatcaacgtt aacccgtatg ctgtattcaa  78960
ctgggaaggt ttcttgaaga ttaacccgac cacggattac tggtttgaaa actactatgt  79020
cgcccccgcgt gttatcaatg aaacgatcaa cactcgtggt actgtacaag aaggttcggt  79080
gtacgggacg tggcgtactg tttctgtttc tgatcgtgtt tgggagccgc atggcgctgg  79140
tggtgtgtgg tggggatacc gctatcgcac gactgtttct gcccgtgatg tcaccacata  79200
cacatacacg gacaaaacaa ccacgaccat gactggcgaa cagattgtgg aaacgcaggt  79260
tatcccatac atgcgcgaaa ttgatatttc tttcgacgct tctgggttgc gacctttcac  79320
tcgcatgtat gcattcttct caggtcgtga tgtgaatctg tattgcaagc cgaatggcgg  79380
taattttggt gacccaatca ccactgatgc caatggcgca gtcaaaggcg tgttccgcgt  79440
tcctcagaac gatacgatca agttcaacac aggtgacaac gtgttccgct taacggatag  79500
ccctgttgac agtaaatctg cagatgatac gctgaccaat gctgaaattg ttcacaagtc  79560
tttcggtaag aaacaaggga ttcaaaagac ctttgtcaac actcgagttc tgggttatac  79620
cgcaagcacc agcaccgaaa ccagcacttc tgaagttgtg gtcgatcaat ggcgtgatcc  79680
aattgcccaa tcgtttatgg tggcaactaa gatcggtggt gaatatatcg aaggcgtgga  79740
agtattcttc tccaccaagt cacgtgatgt tccgatcacc ctggaaattc gcgagatgga  79800
gaatggatta ccgtcccata ccgtcataac tcgtaaaact ttgaacccgt ctgaagtgac  79860
gatctctaca gactcttccg gcggaacgaa gttcaccttc gattatccgg tgtacttgca  79920
agcatcgact gagtttgcta ttgttttgtt ggcgaatact caggattaca acgcgtatat  79980
cgcggaaatg ggcaagaaaa accttttgtc caacgaatat atcgccaagc agccgtatac  80040
aggggtgttc ttcacttctt caaacggttc aacatggtct cccaaccaga tggcagatat  80100
gaagttccgt gtttatcgtt gtaactttgc tgctggacag aacgttgtaa catttgatcc  80160
gaaacttgga ccgaaacaac gtccgctggg attgaacact ctcaactgtg tgagcgggtc  80220
ttctgtcgtg accgtgtttg cgcctggtca tggtttggtt gctgggaaca atgttactct  80280
gtctgaattg acaggtggct gtggatttac tcctgaacaa cttaacaaaa catttaccgt  80340
gacagatgcg agctatactt cattcaagat cgatgtcggt tcagcggcag acagcaacgg  80400
gcaaatcggc ggggataatg cttcattctt gggcaattat ctggttgaca tgttctatgc  80460
cagtgtcacc aattcagctc tggaaggttc aattctgaaa ttggaatatc gctatcgcga  80520
tgctacttcc aattctatgt ctgattgggc tgaatttgaa actgacactg acgtggcgtt  80580
gccgactgaa gggatctatc gtcaggttgg ggatttccag atccgagcca ccatgacgcg  80640
cagtgaaaac aacgtgtaca ccgctccaat gattgatggc gatgacctga gcgtaatctt  80700
caactcatac ggcgtggatc catttgaaga tgtcttcaaa tatgtgacaa aagacatcgg  80760
atttgataac ccatgttcga ctgtgaagtt gttctttggt gcaatgctcc catctcagtc  80820
ttctatgaag gtgcaggtga aacttcttag agcaggtcag gagatggata gtgtggcttg  80880
ggaagatgtt actccaacgt cgcctctggt caacgacggt tctacattct ttgaatatga  80940
atacgacaag actgtggcga gcaataaccc gtttgttggc ctgaaagtcc gagcgcttgt  81000
acgggggaac cgcgttgctc ctccatcatt caaagacttc cgtcttattg ctctggcata  81060
aataatgttg aaaggtgggc gtaaagccca ccaaaccaat agaggataaa gatatgcgtg  81120
gaatgaaagt acaggggcac gcatccatgt tgagaagcag ttcttgtcca ggcgcgatca  81180
tttgtactga tcatgctgca ggtatggctg cattgcaagc ccgtcaacgc aacgaaaccc  81240
gtgaagccac cattgttgaa caatcaaacc agatatcgaa tctggaggcg acgatcaaaa  81300
tgatggccga aaagttgggg atagaaatcc ccgaaggagg tcagaatggc gacgcaagct  81360
gaaagatctg ggcttgatat ccgtggtatc ttgactgctg tcgtggcttc tgcattggtc  81420
```

```
tcggcggcgt cgttcctttg gtttatgggt gggatggaaa cacgcgtgaa tgtattggag  81480
cgagattcta ataaaatgga tcaggtcctt caaaaggtga atgacatgag tgagcgcatg  81540
gcgatcatga atacagacct cgcatatgtc aaacaaaata tggctgagtt aaaactcaat  81600
agcagcagcc tatcagacga tgtccgcaca ttgcggatta ctgtatctga tttgcagcaa  81660
cgagggaata acaatggccg tcaataaaat tcgcgacaag aaatctttta tgaactatgt  81720
cttgcgtaaa ttgggcgctc cggtcatcca aattaacctt gacagttcac aagtagaaga  81780
tgctgttgat gatgctctac agaagttttg ggaatatcat cgcgacggta gccaagatgc  81840
gttcttcctg taccaagtta agcaagaaga tatcgacaag ggttatattg aattcccaga  81900
agatattgac gatgtgattg aagttatccc tggacctcct attgagtcaa ttggaaactg  81960
ggcaactcct caatggcaaa tggcccaagc catgcttgta ccaaaagcgg cgcttgtgtc  82020
tattcgtctc attgattacg tttccatgca acagcgcctg tctgatatca caagcgtctt  82080
gaatgttcgt cgtaattttg tgtacaagaa gttccagcga cgcctttacc cgcaatttgc  82140
tgccaccatt gatgaaactc tggctttccg ttgttatcag aatatcgacc ccgaatcgga  82200
agaaaacgct gaagcatgga atgacatgtg gttgaaagcg tatgcgactg cattggttaa  82260
gcgccgttgg gctgaggtgc ttaagaaggc aagaggcatc cgtctcccag gtggtatcga  82320
actggatggt gatagtatgt tcagtgaggc cgagaccgag atagagcggt tggaggaaga  82380
attgcgtact ggtcagcaat accctatcga ttttatgatg ggataagaga aggcgggata  82440
acccgccttt ctttttataa cttgatgtcg cgttcggaag gatttgaatt tgctagaata  82500
taaccatcaa ccacgttctt ttcatcccac cattcaataa aatcattccc atctttgcct  82560
ttaataagac ccacaatgtt ataagaatta tttgcgactt tagcgtccac acagataatt  82620
ctcacacgcc ttccgtcacg agtttcttta atatcttcaa ccttcattta tcaattcctc  82680
aaaagaatta atgattgact aaataccttc aaaattgagg gtaaagtcat ggctacttca  82740
aaatatttca actatacagc acaccaaggt actcagaaat taattgacga cttggtggtc  82800
gagatgatac aactacgtgg gattgacgtc aagtatatcc cacgttccat cgttgaaaaa  82860
tacccaattt taaacgaggc tgaacataaa ttcgaccagg cgttcgatat cgaagtatac  82920
atgcaagatt accaaggctt taacacccaa atgtgggaga agtttggcgg tattcaatta  82980
caagatgaag tgacgttcac cattgctcgt cgccgttttt cggaagtgat tggtaatggg  83040
ccaggacttg agcagatgcc tcaagaaggt gatttgatat acctcccaat ggcgaacaag  83100
atattcaaag tgaataaccc gaataacgac gaagaattta tgcaattcgg taaatggtac  83160
acatattcct taccgtgcac gttgttccaa tatggtaatg aagattttga tactggtgta  83220
tctgaaattg acgacatcga taaacgttta caagatctag acggcgatgg tgtctataaa  83280
gatgccagtc tacagacaga taaccaattt gcggacgaaa tagagaaaga tctttcgccc  83340
aataaaatga agatagactt cggggaataa tcatggccag accatttgaa aaatatttct  83400
accatgaatc gttgttgaaa tacattcatg tcttcaacgc tatcatgtca gatttaaaag  83460
tcaaaaccga acgtggcttg atggaaatcc cgctgcatat ggctattggc cgtcgcaatg  83520
acctcaacag gaacgtgcca gccaatatgc tgccatttgc gactatgtcc ttcggtcaat  83580
tcgaaattaa taaacaagtg accaagtcgt atcataatca gatatcgact gcaactgcgc  83640
ggtccaaaca acgaattccg atcattatag attttgaata taacatcaga acgaagaaac  83700
tggtcgaaat gctacaggtg ttggaacaaa tttattctgt gttcactcct tctattgatt  83760
gtcagataaa agacaacgat acgttatctc aagatcaaaa cgtgaagatt atgttgacat  83820
cccataccat ttccgataac tgggaagggg atgccgctga atcaccccat atagattgca  83880
cctttaattt tcaattacat gggcacattt atggcgaaga ttattgggtc gatgacggct  83940
ctggcggtgg tgatccgaac gttatcaaag agataattat tgaaatgtct aatgatttga  84000
acacgccatg gtcggaactg cctgagtggt tccgagttga caaagatggc atacatcatc  84060
cggaggattg atcatgagca atatgtcaga aaggttactt gcgacgctag acgcggtgac  84120
tgccagagat gaagttggta aggaggcgat ggaagccgtc tctccacgtc caggtattga  84180
cttcgatgaa aaaacgggcg agtggtttgg tgaacgccca gaaggttatc agccgattcc  84240
agaacctcca tcattggaag atatcgcgtc caaagaatcc aaggttccgg agtttgcgga  84300
tactgatgcc acaacagatt acaagcggat acgcgataca acatacgcca tgcaggaagc  84360
cacgatgttc atgatggggc aagctgctaa attagctgca tctaccgaag ccccaagagc  84420
gttttccgtg tttcgtgaat tgggcgaact catgcgcggc ctgaacaaag acctgatgga  84480
aaaccaaaaa accatcaaag ctgtgacagg ggataaagaa ccgccgactg atgacacaac  84540
cgtggatgtt accacttcac ccgacgggac cacaacagta tctgttggga agaaagcgag  84600
atcttcgcgc gatttattga aaacgatcga agatgcacgc cgccgcgctg aagaacgcgc  84660
ccaggcaaaa gccacccaac aaaccgaaga tgaaattatc gacggtgaaa cggttgacgt  84720
gaaggaagaa gacgatggcg tatcagaagc gtgatataga atatgctccg ataaaaacgg  84780
ggtttaaaat cgacgacgtg aaattgcgta tggaccagac gttcatgcgc aagccttctg  84840
tgcgcgctcc acgagtcgag ttgatgctaa cagatgaaca agaagacgaa tttgttgaat  84900
gttcaatgga cgcgcattac ttcgctgcca attactacaa gataacgaca atcgataaag  84960
gcttcatcct tttcgatatg catgattatc agaaacaatt atttcacgat tttcaagatt  85020
atcgtttcaa tgccgttgtc caggcgcgtc agtccggtaa atgcgtccgt ggtgatactc  85080
ttgtttatgt ctatgataca gtcagtcaac aagagttgca tctcaccata gaagagcttc  85140
acaagcgctt cgaaggaccg aaccatgctg tgccactgaa taccattggc aaccacaata  85200
agtttgtaga cagccgtttc gggaaacgat attttgttga gtccgacact ggctgggttc  85260
cggttattgc cgctcataaa acgaaagaat acgctgaata cgtggtcagg actgaaaccg  85320
gacgcacaat tcatgtcgca gatgagcaca tgttcttcaa tgaatatggg cgcgaagtat  85380
ttgctaaaga catggaggcc ggagatgcca taatgaccca ggagggaata gaattcatct  85440
ctgagatctg ggagactggt gagtaccacc acatgtatga cttgcaagtc aagtccagcg  85500
atcaacgtta ttacacgaat gggttcctca gccataatac cacggtcgtg gctgcgtttc  85560
ttctttggta tgcgatgttc cactcagaca aagaaatcgc ggtactggca aacaaagaga  85620
aacaagcgat tgaaattctt gaccgtatca ggaaggcgta tcaggacctc ccattcttcc  85680
ttcagcaggg ttgtgagaag tttggttcta cactgataga gtttgagaac ggctctaaga  85740
tatatgctta tgcaacgtct tcggactcta ttcgtggtcg ttctgtatct ctcttgtacg  85800
tggacgaagt cgcattcatc gaaaatgact ttgaattttg ggaatcaaca ttcccagcga  85860
tcgcatctgc tgatacttca cgttgtattc tgaccagtac tccgaaaggc cagcgagggt  85920
tgttctatga tatcgtcacc aaagcagacc cgcgccatcc gcaatacaac gacttccatc  85980
ttaccgaagt cccttggtac aaggttccgg cgtacaccaa agaccctgat tgggaaacca  86040
aacaacgcgc tcgtctgggg gatgcccgtt ttgaccagga atttggaatc aagttccgtg  86100
gttctgtagg ttcattgata ccagccaaat gcttggataa aatgacatcc aagttatatc  86160
```

```
gagagcctaa tgagttcacc aaaatttaca aggaatatga cccgcaacgc atctacttcg  86220
ggatcgcaga tacggggaaa ggtgttgaag gagattattc ggttctgaca attctggata  86280
taacggaata cccgcatgtc atagcggcca agtacaggaa caatacaata cctccgatga  86340
tgtatgcata cacgatagct gatatgtgta ctgaatacgg ggaatgccct gtccttgtcg  86400
agacgaataa cgacgttggt ggacaggtta tcacgatctt gtatcaagaa attgagtatc  86460
cagagatcat attcacgtcg acggataaca aagggacagg gaaacggatt ggtggtcgta  86520
aaccagagcc aggcattaac accaacagga aagtgcgatc tattggttgt gctaacctga  86580
aagcgcttat tgagaaagaa atgttggtga ttgaagatca agacacgata gatgaactca  86640
gcacattcgt gttccgtggt gcgcgttatg aagcagatga tggatgtcac gacgactgcg  86700
ttatgccgtt ggtattatat tcttgggcag ttaaacaaga atggttcagt gatctgactt  86760
ctaccagtat ttctcaagac atgagaaata gaatgtcttc gactgagtca caacaagtat  86820
tcccatttgg tggtttagtc gtgggagaca ctccatctgg aactgagcat ctccctgggt  86880
tcggtggtgt tcaagtcttc gacgaacgtt cagggatgac aatggacgag tggtttaaga  86940
attgatcact aaatatcttt caaattgagc gaaactctac cgagaaggaa taacattatg  87000
gcaactcaaa gcttcagcgt tgcgccgtcc gtacagtgga ctgagcgtga tgccacgctt  87060
cagacttctc cgtccgtggt tgttcagggc gcgacagtcg gcaaatttca atggggtgaa  87120
gtcgaactcc cagtgctggt gactggtggt gagacgggtt tggtgaagaa attcttcaaa  87180
cctaatgaca gcactgcgac agatttcctt gtgattgcag actttttgtc ttacagctct  87240
atggcatggg tcactcgtgt tgttggtcct ctggccaaga actctgtcac caaaggccag  87300
acagccatca cgatcaaaaa caagctggat tttgaaacag caagtccgtc agcgtctatc  87360
acttgggctg gtcgttatcc aggatctctg gggaatgaca tcgccatcaa tgtttgtgac  87420
tccgctggat tcccgacatg ggaattccgt aacaactttg cgtacgcacc tcagtctggt  87480
gaattccatg ttgtggttgt agacaaagtt gggcgcatta ctgactctgc tggtgcggtt  87540
ggtcaggttg accgtatctc tgtttctggc acggcaaccg cagctggcac catcagtgtg  87600
gcgggtgaag atatcgcata tctggatact gatactccgg ccactttggc gaccaaaatt  87660
ggcgcggcgc tgacggcgct aacagatgtt tattcttctg tcgttgttaa gtctaacact  87720
gtcatcgtga cccataaagc cattggtccc cagacagtta ctgctattgt tccagatgat  87780
aaggggctga ctgcaaccgc cgtgattacc actgttggcg catctggttc tattatcgaa  87840
aaatacgaac tcatgcagaa cacacagggt tccaaaaagt ccgatggcgc gaatgcgtac  87900
ttcaaagatg tcatcaatga tacatcaaat tgggtgtaca ccttcgccac cgctctggcc  87960
gcaggtgttg ttgaattaga aggcggcgta gacgactaca atatcaaccg tgtcgcggct  88020
atccaagttc tgaacaacgc cgaagcatat gatgcgaagc cagtatttgc atactgtgaa  88080
gagttgattg aacaacaggc attaatcgac ttgtctaccg agcgaaaaga caccgtttcc  88140
ttcgtgtcgc ctttgcgtga tactgtggtc ggcaaccgtg gccgtgagat ggacgatgtg  88200
gtcgcttggc gtgaaagtct ggtgcgcgac tcctcctatt tcttcatgga cgacaactgg  88260
gcatacgtgt acgataaata caacgataag atgcgctgga tccctgcttg cggcggtaca  88320
gcgggtgttt gggcacgtag tattgaaatc gcgggtatct acaaatctcc tgcgttccac  88380
aaccgtggca aatacaacaa ctacaatcga atggcgtggt ctgcgtcttc cgatgaacgt  88440
gccgtgttgt accgcaacca gattaacagc atcgtgacct tctccaatga aggtatcgtg  88500
ttgtatggtg acaaaactgg tctgactcgt ccgtctgctt tcgatcgtat caatgttcgc  88560
ggtctgttta ttatggcaga acagaacatc gctgcaatcg ccaaatatta ccttggtgag  88620
aacaatgatg cgttcactcg cagtctgttc agcaacgctg ttcgtcctta tattcgccag  88680
ctggcaaata tgggtgcgat ctacgatggt aaagtcaagt gtgacgaaga taacaacact  88740
gctgacgtta ttgcggcaaa ccagatggtc gctggtatct ggctgaaacc ggaatacagc  88800
atcaattggg tgtatcttga ctttgctgca gttcgtccgg atatggagtt ctcggaaatt  88860
gaatccggcg gcggcatcgt tgctgcttct taaaagatca accccgcttc ggcggggttt  88920
tcctttatcc cacatatttg agttattgaa tgatatacgc atacaaaatt gaaatggttt  88980
gtaatggaaa ggtctacatc ggtgtgacca atgacccaca acgaagatat gatcagcatt  89040
ttgcgaatgc ctttcatcat ggcgtccaaa gtgaattgta tgacgccatg cgtaagtatg  89100
gaacatctgg atttactttc gttgtaattg ctcagaccga tgaagtccat aaatgggaat  89160
tagagaagca actcatcgct caatataatt cttatgagat gggttacaac atgaataaag  89220
gcggtaatga tggaagtcat atgctgggta aaactgcagc aaaattgaca tccacaggtg  89280
aacacattgg tcttgtttct ctcatagatc cccgttggga attgtgtgaa atcgaacctg  89340
tttcaagtaa tgttcatcat agtttcgatc tttcttctat gaagattaaa agattgacga  89400
ctaattagaa ttgtgtactc ttatttggag atataaaaat ggcgacagtc aatgagtttc  89460
gcgcagccat gtcacgaggg ggcggcgtac aacgccaaca ccgctggcgt gtgactgtaa  89520
actttccttc ttttgttgct ggttccgaca caattcgcga cgtgtccttg ctggctgtaa  89580
ctaccaacac cccgacaggt cagctgggtg aaattctggt gccctggggt ggtcgtgaac  89640
ttccattccc aggcgaccgt cgtttcgaag cactgcctgt aacattcatt aacgttgtga  89700
acaacgcgcc gtacaacgca tttgaagtgt ggcagcaatt catcaatggt agtgaaaaca  89760
accgtgccag cgcgaatcca gatgattatt tccgtgatat catcatggag cttctggatg  89820
cgaatgacaa tgtcaccaag acatggactt tgcagggtgg ctggcctcaa aacctcggcc  89880
aattggaact cgatatgtct gcgatggact cttatacaca gttcaccgtc gatctgcgtt  89940
atttccaagc cgtgtcagac aaatctttat aatgtcctcg gtgctggggg aatcatattc  90000
cccctcacta attacaagaa aatgttgagg acttagatca tggctggata cggcagaggg  90060
ttcttcggtt tgtttggcgg cggcggtttg gtgaacgcta aagtcgacac cgataagtta  90120
gcccaaaaac aagatgaacg gttgctaacc aaagcgacag ttgttgctct ggacgacgct  90180
caagacggtt ctataatcct tcagggtggt gcgaacacct acaactatgt tggcgttgaa  90240
agtgaacttc tcagcgttaa aacagttgtg gaagaatatc agtccatggc tcaacagcct  90300
gaaattcgca aagcggtgga cattattgtc aatgatgttg tcacctgtga ggaagatgaa  90360
actccagtga cagtaaacct tgacaaagtt gaagggatat ctgatactgt taaagaatct  90420
atcactgaat gcttcaaaga agttatgcac ttgatggact ttgacaatac ggcatatcag  90480
aagatccgga aatggtatgt tgacggtcga caagcatatc atgtcatcgt tgatcccacg  90540
aataaaaaag gcgggatcaa gaaattagtt atgcttgatt ctcgttgcat tcgtcctgtc  90600
tatatcgttg agaaggcgat gcgtgaaggc ggtattgaag caatagaatc cgtaacattg  90660
aagtattatt acaacccgaa ttataatcga aaccaattca ctggccaatc tggtacttcc  90720
cagaacttcc agccttcaca gcaagaactc gtattcgatg acgaaagcat tgtttacatc  90780
gatagtggtg aagagccatt ggccaatggt attgtcccag gcctttaaa tcctgctatc  90840
cgtccgttga acaacctggt tacgactgaa gatgcgactg taatttatgc catcactcgc  90900
```

```
gcccctgaga aacgcgcatt ctatcttgac gtcggtactc tcggtaagaa atctgctgaa  90960
gaatacatga ccatgatgat gggtaaattc aaaaaccgca acgcatatga ccgcaccact  91020
ggtaagataa caggtaatgc ccatcttatg ggtattgcag aggattattg gttgccgcgc  91080
cgcgaaggtc agaatgctac agagatcgcg actgttgggg gtgggaatca attgggtgaa  91140
atggatcacg tgaactattt ccgtgaaaaa ctctatgatg ctctaatgat ccctaagagc  91200
cgcctccaag aggaaggatc tattaacatt gggggttcta accttgcgga gattacacag  91260
gaagagctgc gtttcagcaa gttctgtgct gggttacgtc gtcgttactc ccatttcttt  91320
atggagtttt tacgtcgcca attaattttg aaaggcgtga ctgacgaaaa agattggaat  91380
gaaaaaatca agccgtttat taagtttgaa ttcacttctg atagctatat tcgtgagcaa  91440
caagaaaacg ccatattaaa tgatcgcctg gcttctctga acactgttga gccttttgtt  91500
ggttctatat tctccatcga ttatgtcatg cggaatgttc tgcgtatgtc agacgaagaa  91560
gttaaagaac aacaggctaa gatcgcggaa gagaagaaga aaggtctcta tccgaaggtt  91620
caagcagatg aaactggcaa ttatagtggt tcagatgtta gtccgttgaa gtttaaacct  91680
gagactctcc cattctccgg ttcaacagac gatagtattt aaagttcaac taaatataga  91740
aaattaattc ggagatcaaa atcatgagcg caattgatat cgttcgtgca gtaattgacg  91800
gtgacactga aactgctgtt gcagaatgca acatggaact tgatgcacgt agtcaagaac  91860
tattgaacca aggcacagca tatgttctgg attctatcgc agccgatatg aattcaaaca  91920
acaacggcca gtaaggagat gcatgatgga aatcacagag atcgccacgt tcgctgattt  91980
cctggcctct cgtatggacg agcagcgagt catcgataaa gtgaacgctc gtggtaaacg  92040
ccgccgccgc ttgaaatgtg cccctgggtt caaattgtcg gctgatggtt cacgttgtga  92100
agttatggac gccagcgaac gtcgtgttcg caagatcggc aaccgcaaag ccctccgctc  92160
taaaaagcgt atgggaatgg gctatcaacg taaaatcgag cgccgcaaga aaaaggctat  92220
gaagttccgc aaaatgatgg gactgagtaa gaacaagtaa ggagtttatg atgaaactgt  92280
tgcgtgagat cacagcgata gggaaggatc ttcaaatcgg tgaggccaca acctcaactg  92340
gtgggaaggc catgttcatc gaaggtccgt ttgtgatgtg taaccaagtc aaccgtaacg  92400
ggcgtaacta tgatctacag aaagtgggta ttcctgctgt cgaagcatac gacaaagagt  92460
atatccaaga tcgtcgcgca atcggtgaag tcacacatcc tgactatcct ttccctaatt  92520
tagtggaagc tgcgctcaaa accgaatccc ttcgatggga aggcactaat gccatcggtc  92580
gggcgagaat tttaaacaca ccaaaaggcc aaatcattcg tgcattggcc gaagcagact  92640
tcaatctggc cgtatctact cgtggcctgg gtgagactaa gtcggtaagc ggttatgatg  92700
atgttcagcc tggctttatg cttaccgccg ttgacgcagt tgaccgtcct tctggacaag  92760
tttgttatgt taaggctgtg agtgaatctg ttgaatggca gctggacgag gcttcgggta  92820
tttggatgcc tcgtgatgtt aaagggaaag ttgtagacca gttggtgaaa gccaatatcc  92880
aggttgaaga cgatttcctg cgccgccttg atgcagcatt gaatcatctg ggctgaattt  92940
cagctcacta aatactgaaa aatcgttcag aaggaaacta tcatgaaacc tgaattgcaa  93000
aatctgtttg aaggcgttaa cggcatcagc ccagatttcc tggataaagt atccaatttg  93060
ctggaatcga aagttgaagc ggctcgtctg aaagctatcc aagaaaccga agcagctggc  93120
aacgtcgagc gcctgaatct ggtagaatct caccagaaag aaatcgccga cctgaaagaa  93180
aatttcattc tgcaattggc tgggaaagtt gactcattcc tcaacgcggt ggttgaagaa  93240
tgggctaaca aaaatgcccc agctattgac gctcagatca aaactgaagc tgctgaacgc  93300
ttcctcactg gtttctccaa cgtgctgaaa gaagcaggtg tgagtttcgc tactgaccca  93360
gacggtcaga ttgccgccct caccagtcgc cttgctgaag cagaacaacg cgccaacatg  93420
gctaatacag agttgagcca actcaaagaa agcgagacta aacgccagcg caccgacgta  93480
attgatcgca tttgtgaagg tatggttgac accaagaaag acactgttgt caacctgctg  93540
gaaggtattg aattccagac cgagtctgaa ttcgaatcgc gtgttcgcac cttccgtaat  93600
ctggtagaag gtaaagatga cttctctgac aaagtcggta aagacaatga aaagggtaag  93660
ccagatggcg acaaggctga aaaagacatc aaagaaggta agaaacagaa aaaagaaggt  93720
gatgatgttg acgacgataa agacgacgac gacaaagacg aagttggcaa agaagtcaac  93780
gaagccgtcc gtcgccagat cagcgccatt ctgaacggct aattttagca gccacagccc  93840
tcgaaagggg gcttgatttt gaactactaa gtaatttcaa cttaactgaa tatcaatgta  93900
aggaacgagc atcatgacta agaaacttgt aaccgaagaa atgcgcaaac agtggctgcc  93960
agttctccaa aaagaatctg aagccatcca acctctgtct gccgaaaacg taaccatccg  94020
tctgatgcaa aaccaggccg agtggaacgc taaaaacctg ggcgaatccg acgctcctgg  94080
ttctgtaaac agcactgtcg gtaaatggca gccagtcctg atcgacatgg caaaacgtct  94140
agcgccgatc aacatcgcaa tggacttctt cggcgttcag ccgctgtctg gtcctgatgg  94200
tcagatcttc gcactgcgtg ctcgccaagg tgttggtgac ggttctacta ccgctcaggc  94260
gcgtaaagaa ctgttcatga acgaagccga ttccggctac tctggtgatg gcactgtaca  94320
ggctggtgac ccgtcaggct tcagtcaggc tgagatcgaa ggttccggct ctgtcgtgac  94380
cactatcggt aaaggtatgc cgtcaaccga cgcggaactg ctgggtacta ccaccaatcc  94440
gtgggcgcgt gttggtatta ccgttcagaa agcgaccgtt actgccaagt ctcgcggcct  94500
gtatgctgat tacagccatg aactgcgtca ggatatgatg gcaattcacg gcgaagacgt  94560
ggacaatatc ctgtctgacg tgatggtaac tgaaattcag gcggaaatga accgtgaatt  94620
catccgcacc atgaacttca gtgctgttcg tttcaaaaaa ttcggcacca acggtgttgt  94680
tgatatcgca caggacatct ccggtcgttg ggcgctggaa aaatggaaat tcctgacttt  94740
catgctggaa gtcgaagcga atggtatcgg cgttgacacc cgtcgtggta aaggcaaccg  94800
tgttctgtgt tctccgaacg tggcgtctgc tctggcgatg tccggcatgc tggactatgc  94860
tccggttctg caggaaaaca ccaaactggc tgttgacccg actggtcaga ccttcgcggg  94920
tgttctgtcc aacggcatgc gcgtctatgt tgacccatat gctgtagcag aatatatcac  94980
cctggcgtat aaaggcgcga ccgcgctgga tgctggtatc ttcttcgcac cgtatgtgcc  95040
gctggaaatg taccgtactc agggtgaaac caccttcgct ccgcgtatgg cgttcaaaac  95100
ccgttacggc atctgtgcta acccgttcgt tcagattccg gctaaccaag acccgcaggt  95160
ttacgtgact gctgacggta ttgctcaaga cagcaaccca tacttccgta aaggtctcat  95220
caaatctctg ttctaatcaa caggttttga taaacaaacc ccgccatgtg cggggttttt  95280
ctttataggg attcactata agaccgctaa tagttttcaa taagtgggca atgaacgatc  95340
attacctaac tttcacaact ggaacgctac tcatggctaa agaaactctg actaaagaaa  95400
actctaactt cgcagaatgg catgcagaat tagagcgtgt cgctcgttct caacatggct  95460
ctgccgccga tgctatggcg tggcatgaag attatgagtc tggcaaaacc ccgcgtcagg  95520
cttgggaaga tgaatggggg tggaatgatg cagactctaa ttcgtaagat atatctggat  95580
aagaactatt tggaatccaa aatcgaagtt ttctcggctc aaaaaataat tgaagacggt  95640
```

```
gaaacgagat attatctgaa acctgacctt tatcttccag gaagtagttt gaatcgcgat  95700
ataattcagt cggacggtat tactgttcgt tgggaaatgg cgtcacagga agacaactgt  95760
catagcataa cactttgaag agagatctat attatgtcaa aagaaaaata catattcatc  95820
agccccgcta cgaaggagtt cttcatctcc gacgtgaaag atcgtgttga gaagttccgc  95880
tacatgcgca gctatggtct ggcatccggt gatattgatt atcagtcact ggacaatgat  95940
cgccaagatc tgatcgacga cggttggcgt ttagttccgt cccctcagta cattcatatc  96000
acgttgtact atatgaagga cagcgggaag ttctattccg aaggtgaact cgtactcaat  96060
cgaggagaag cagaagccga acctgccaaa acctggatgt tggcgatgga tcagatccgt  96120
gaattgctgg actccggtaa tctgcctggc ctgatcaggg gttcaaaatt cgacgtgttc  96180
gttactggcc agggtcatcc tggtggatac ccacatctgt tccgtattaa ctgaggtcaa  96240
ttatgagcaa tttaccactg cttcaagtcg gtgacgtatt cattctcacg gcagaaatga  96300
ccgttgaaac tcaggtgcca aagcatttct tgtattctaa ttgcaagggt gattggcaaa  96360
tggactctgg ttatatcacc cctgagggat tcttcggtta catgcaagga cattacgtcg  96420
ttaccaaaac agccctacaa ggcggtagca ctggtcatga tccataccct gacggccatc  96480
atgtttgggc acagcatact gaaaatgaac gcatcagaat ctgtttctat cagacaggta  96540
gtttcaggaa tatgcaccgg aatgttccag tagtcggaaa ggctaaggcg caaacatgga  96600
cttgggagaa attatgaaaa tcaaaaagat aggcgcaagc ccattgacgg gaacaatctt  96660
ccagggtact ttgaacacca agaccagtat gtgggtcggt gagaagactg atgtgactaa  96720
cgactgtgta gcggctacgg ctgaacacat gcgtcacatc aagaaaagact actgcttccc  96780
tactaaagac ggcaagttcc tggtgctgag cgctgaggtt cacgacaccc ttcctgatcg  96840
cttcaaataa atttaaaatt tattcaataa acggggttta cttcttcaat aaaccccgta  96900
tacttcattc cataagcagc acaacactga ctctgaaatg aaggaactac accatgacca  96960
cagcaaaagt taccatctac gctttcgacg ctttctctaa atttgacgca ttcgtctcct  97020
ccgcatttgg tatcaaagaa gttgaagcag agaaaacttt ctgtggtgga ctcggcaagt  97080
ttgccaacct gagtttatcc ctgacagagt tcatgaaatc tcttgaaggt cactttgacg  97140
ccgaaaccat tcgcacttcc ttactcaaga aagacggcac ccctcgcaaa ctgtctggca  97200
agactagaat ttacgatgct gacggcttta ctgtgtctgt gcattttact gaagaacctg  97260
tgtacgaact tttcagcggg tctgaggacc tcactcacta tgtggtcagg aaaggcgatt  97320
cccgccctgt gttcgaatct ggcgacatcc tcgccgctat caaagaactt gcgcgtctga  97380
atagcctcta acagacgttt gttctaaacc tttgaacggg gtatggttaa tccataccct  97440
atcccataca aatagaggac tttatcatga ctacaagaat cccaccgcag tcgattgaaa  97500
tctcgaaggt cgtcaatatc gaacctcgtc gaggaacccg taaaccccgc gcggggcgtc  97560
atctgaccac caagctggat cttctgaaac agaagttcgg cgaccacagt gtgtttaccc  97620
gtatccgcaa cgcattaaag gaagggcgaa ccgagttgga gctatatcgt ccgaacggtt  97680
cgactcgagc gtatcagacc accgacggtt tgctggaact gatccgccta tcagggatga  97740
acatagaacc ccgttcatca ggaaccccgc tatgcagcct gtacgtcatc agcaatcttg  97800
gggcgctgtg agttctatga agaagtatat cgttcttata acgggttccc gttctataac  97860
tgagcgggac aaaatatttg ccaaattaga tgaactctta atccctcacg agatagagac  97920
gtttattgaa ggtgaagcag tgggtgtgga tctgatatcc cgtgattggt gtgaaatcaa  97980
ttatgtgcat atcacaccaa tgccgattcc tcaaaattac catacgttat atgggaaagg  98040
tgcgggcaat caacgtaaca aagatatgct ggacaaggct ctaacattgg cgaagcaaaa  98100
agatcttgag gtctttggaa ttgcattatg ggatggttcg tctactggga cgcaagacat  98160
gatcaagcgc atgaagaaag cggaataaa tgtcaatatc actctcatgg gcaaacccaa  98220
aaccaaacga ttgttataaa taaatttgcc acccatgagg agttatacca tgttacaaat  98280
actgttggtg ctttgtgtcg catttaccat gtacttcatg gcacgcatcg gttttattac  98340
tttagatgac atgaagggta tcccacgtga acccaaattc atctttctga agaagtttgc  98400
caaaaagttc tcagaaaact ttatttatca tctaccatga ttaaataccc ccaaaattgg  98460
gggtattttt atgaacgcac aaatctatga tgtcctttcc tctggcaatg catttagcaa  98520
tccgcttcca tccctctccg gtccttctca ggatttaata accagtggca tcaccaatat  98580
accattgata actgccaacg ctactccgga gatgcaggcg gctatggcag ctggtggact  98640
aacaccagaa aaactcacag cagccagcac catgtatagc accgccaaca cagggataac  98700
aactctgaac acatatggcg accaaagtat caatgacgcg tattctcgca tcggtacttc  98760
cgtgtcatac aaatcaggtc tgaagggtat atcacgagag ccaaacaatt gtgatttgat  98820
caacaaggct tttggtgttg ttcaggattt aggacgccaa tggctgaatg ctatggaagg  98880
cgctctacag accgtaacaa acaagatatc ggaattgtat gagatgatca tggaaggtgc  98940
ctcagaagga atggcaaagc tgcaggaatt ggctgcagaa gtaacgggac acatcaatac  99000
tgcgataacc gcagtcaacg gggttataag tgatattaca gatggtatag ccgcagaact  99060
tgcacacatt gaaagcatga tcaaagagtg cttgaatttc tcttttgcta acgtgctcgg  99120
ggaatgggct aaagatctgt gcgccggagg tgttattgac aaaataggga ctccagcatt  99180
aaaagaatcc ctgaaataaa tcaatgacga gcagggagga ctcccactgg ttcgatgcct  99240
tcgatcatca gggagtccac tccaacatcg ctcaggcgaa tccaaacctt acccccctggc  99300
cttatctcat agatgttcat ctcgtttcca acagcagacc cattcacaaa aacgccttga  99360
gtagcaatcc gaataggcgt tttggtgttg ttgattatct gaaaagatat cgtgatatcc  99420
cttgtcaatt ccacatttct tgcttttgta tatctcctca atttttcaaa gaaagatgga  99480
ttgaatgtgg ctatgatgct gttgttttgt gagtagtaaa tactggcaga cagataaggg  99540
atttttccct catcaccttt cctcaataga gggatcgtgg ttttccagta cggtctcaac  99600
gcctggttgt tatcatcaaa acaaccgacg gcttgtatgg tttggaaatt ctggaagtct  99660
gccacaactt gatccagtaa ctttttatta catttgtcga catcagcaga aatattgact  99720
ggtatagttc tgatttcagg atcccaaaga tcggtgacag aaatcacgga cgtgacaaag  99780
atacggcagc ttgtaagtac aagcaccatt atcatcgtca tgatccattt tctgaatccg  99840
cgtatcagga acactaaaaa attctccaca gcaaaggtgc taacatgaca ggtgtacaat  99900
tcaaaaacga aaatcctaat ttcgcggctt ccgataaatg gcgcttaacc atcggagacc  99960
tggtgctgct aacccgttcg atacacgact tcagtatccc tggcgtgtat tccgaaggta  100020
tcgaaggccc atcccctggc gatgtcctaa actctatacc ttcagaacgt ctcacgtatg  100080
accccatcgt atttacgttc gttatcgatg agagttggta caactgggaa cagatttaca  100140
attggatcgc ttcgaacgcg ggttcagatt tagccgtcag tagagatatt acgattgaac  100200
ttttagacaa catgaaccgt cctgttgggc ttcagttgct tctagaagaa gggcgaccaa  100260
cagcgctaga caacgtgttg gttgacgtgg atgcatcggt tcctcagttg gtcacaacgg  100320
tgacattcaa atatctgaaa ctgactccga cccgcgtaac ccgcgaaatt gataaacaat  100380
```

-continued

```
aagttataat acagagagtt gaaacagcag gaaataaatc atgagtgaaa caaaatttga  100440
aacaatgaag accgaagata taatcgcgga attagatcct cttatttcgg tgaatcctga  100500
agacatgaat ttagaccaaa tatcattgaa aattggtcgt tcatggatgg ctgtccagcg  100560
ccattacatt cgtgaagggc gttatctaga atttttgaca ggaaaattcc gtcaaatcga  100620
tctttattta cgtcggtatt atgcagggga attaccaccc aatatttatg tcgaacgtcc  100680
cctgaaagtt cgccccctga aatctgatat agacgtttgg gtaaaggctg atgacgatta  100740
cattgagtta tcgagcatgt tgcaagaaca aaaagccaaa gtaaaattaa tcgaaagtag  100800
tttagaacgt ttgaataaac tcggctatga agtgaaaaat gcgattgatt ggcgaaaata  100860
cttggacggc atgtgatggt ttccctgcag gctttgcgta aactcaatga ttttgagaac  100920
cgccattaca catttcagca gtatgccttg ccctttaagg aactgacttg tgtaacaacg  100980
gaaaacggac gccattatgt gtctccaaca ggcgtcaaac tcacatctgt aacaacgatg  101040
ttggggcgta ccggagatca tacatggtta gaagcctggc gggacaagtt aggacacgaa  101100
gccgccgata tcgaaacaga gcgttgcgca gaccgtgggg aaaaacttca tttggcctgt  101160
gaattatatc tcaaaaacag gccgatgaag gaagtgttag aagccgcagg ggaatacgtg  101220
tttatgttta aacaggtctt cccctacctg aacaaaatga gcaagatata cgcgcaggag  101280
attccgttat atagcgaagt ccttggtctt gctggtcgtg ttgatctcat cagcgtttac  101340
gagggaatcc ctagcattat cgatttcaaa acatccaaca ccctgaaaac tcggagcatg  101400
atagaagatt acagcattca actatgcctg tactcagtca tgtttcaaca gatgtttaat  101460
gttaagatcg aacgtttggt caatattata tctaacgaaa attctcttgt cccgactata  101520
atcgaattta atcgaaaaga cgttatttct aaaatgtttg atcgtgttcg cctgtatcat  101580
aaaatggata aagaacagaa cgggatctgg gcggatcgct aaatactcca taatattggg  101640
ggaattagtg atgtcagaaa ttcaaataat caaagttaac gaagtgcgca tgcgaatctt  101700
ggcggaagac tatatccgcg aagaactcaa tgattacttc aaatttgaag atcctaattt  101760
ccaaccgaat cccttcagta aatgggatgg cgtggtacgc ttgttcacaa agagttctgg  101820
ccttatagac atcggtctgt tgtttgaggt gtttaagttc tgtaagatga atggttacac  101880
catcaaatta gatcccgcct taaaatatat ccaagatata ccagacgaag agatacatac  101940
atttatcaat tccctgaacg ctgtttaccg tgatgaaaac aagcaatacc aaatcgcaac  102000
agtgcgcgac tatcaattcg actcagtggc cacagcaata cgccaatcca gatgcgtgct  102060
agaagcggct acgagcgcgg gtaaatcgtt tattttgtac atcatggcgc gttactacag  102120
gcaacgcaga gaggcactgg aaagcaatct caagacgttg atcgttgtac cttccattca  102180
cttggtgact cagttgtatg acaactttga ggaatacagc catggcacaa attggaatac  102240
catgatgaat gtccagatga tatgtgaagg tgcaacaaag gatatattca agcccatagt  102300
catttccact tggcagggta ttcagaatca gcccaaagaa tggttccatc aatttgggga  102360
tattgttgtc gacgaagtac acacatctaa atctgaaaag ctatcttata tcctgaacaa  102420
ctgcattaat gctgaccaaa gattgggagt aaccggaacc ctcgcgaata caaaggttgc  102480
agggttgcag gtcgttgccc attttggagc ataccataaa attattacag cacgtgattt  102540
aataaatctt ggttatgccg cagatatcca tgtcaacatg attgaagtca tacatcccat  102600
ggcggattgt atagaaatgc atggtgctga gtaccaaaag gaaatagaat tcctcatagc  102660
gaatgaacgt cgaaacgagt taatagccag aatggcattg tctttgaaag gtaacgtggc  102720
cgttatgttc gaacgcattg acgcccatat gatgattgtt tatgaaatgc tttcagccgt  102780
taagaaaaac gtatttgtca ttaacggcga agttaagaca gaagttcgta aacaaattca  102840
ggcagcgatg gaagagggcg aagatataac actgctggca tcttatggga ccatgcaaca  102900
gggagtgtcg atcaaaaaac ttcatcattt gatattggca cacccgagta aatcctatat  102960
tcgtgtcata cagactttag ggcgtctcat gcgccagcac tcttcaaagg atgttgccaa  103020
gatctgggat ttagtagaca acttgcgtta caaaggattt tcgtacaacc atgccctcag  103080
acattcgcat gagagatata aattttatct tatggagcga caccctgtac aaatgaagaa  103140
agtgtcgctc cagtaattca tttatcttga ttcacatagg cgggggttgc ctcgccgtct  103200
ttgttagaac cgaacaaaca acccatcgtg ttgatgcatt gttgtagaac ttccggctca  103260
agaatctgac tcatcagttc ttcattagat tccatcagcg ggatgacttt cacttcccgc  103320
gcctgtcctt gttggataat gccgatatac agacctttgg tgtctggcag taacgggatc  103380
accatcattg gtgtcacaac aaacttagaa gtgcgataga ggctgtgtaa gtaaacacct  103440
ttcaatgtcg gttgttcttc taccaacatt gaagacattg aaaggttgga ttcttgaact  103500
tcccccactg catataaacc cacgaattgt ttcatatatc actctcttgt tagtaaacat  103560
aactacataa taatctcatg ctgtgtttag accaaataaa ttattttgct agttgaataa  103620
aaatcgcttt cttgttgaac aatccgtgcg taatatacga gttgtgagct ttgcgagcaa  103680
cgagtattat cacgagcgaa gcgagtagac tgataaagaa aggtttttatt aaaacagaat  103740
attataaatg ccgtcaggca tttatttatc gcgcgtaggg cattttaaca cttgttctat  103800
aactgcaaac acgcgatact aatttgcgtc aaacatgact tgaaccccac tatattttga  103860
ggatataaac aatgcaagag atcactctct ctgaacgcac tttacaactg ctggccaact  103920
ttgaaaccat ttgcccttct atcgttctgg cacctggtaa aaagctgcgc actgttaacg  103980
actccagcac cgtcatcgct atcgctgaca tcgacgaaga cttcccgttt gaattcccta  104040
ttttggacct gaccaaactt ctggccattc agcgtctgcc tagtttcaaa ggcggtaaaa  104100
tcgaaatgtc ggaagatcat attttactga aaggtgaaaa ctcgcagctg caattctggc  104160
gctcagcaaa agaattgact gtcgttcctg ccgacagcat tgatctcccg tccgttgaat  104220
tcgaagcgac ggtcactcct gaaaaaatga aagagctgac ccgcgcctgt tctactctgg  104280
gacacaaaac tgttcgtctg gttgccagcg gcggtaaaac ccgtctggtc ggtacgacta  104340
cgactatcga taattccaac gattacaccg ttgaattggg tgaaactgct ctggctgatt  104400
tcgctatgcc tgtcgacgtt gttaacctga aaatgatcga gggcaactat gtgatccgcg  104460
cctgtgctga aatgcagctt gttaacttcc agtcggcaga tggtaccatc aactactacg  104520
ttggcatgca gctggattaa tcaatatcgc ttcggcgctt tattatcggt ggcggggtta  104580
ttatcccgcc ctttgaaatg ttttatctaa agaggctgca atgtccaaca ttactatcgt  104640
tacagaccaa tacgcgtggg aaaacaaata tcgtcctgat aatttagatg agatcgttct  104700
cccctcagac gtccgtgcca agatccatgg ttatgttacc tctggcaacg gaaacatccc  104760
ctctatgctg ttctactccc ctcagcctgg tacgggtaaa actacttctg ctctggccgt  104820
gtgcaatgaa atcggttgtg tgaaacctct gatgatcaac gcatcgcttg acaacagcat  104880
tgatgtgatt cgcgatcgtg tcattcaata tgctactggc gtcagcgttt tcggtggtcg  104940
gaaagtcgtc atcctcgacg aagttgagcg tctttctatg gcggctcagg aatcattgaa  105000
aggtatcgtg gaaaaggttt ccaagaactg ctcgtttatc ctgaccacca acgccaaaca  105060
gcgtgtcaat gagcctctgc gttctcgttg ccgtgaaatt gatttcatct ggtccgaaaa  105120
```

```
agaagccgac gaagttaaac ttcaatttat gcgtcgttgt gccactatcc tgacagaaga  105180
aggcattcca tacgaagctg gtgttattgc gtcgattgtc aagtcgtatt tccccgacaa  105240
ccgtaagatt atgggcaccc ttcaggataa tgccaccacg tttggtaaaa tcgatgaacg  105300
tgctttggct caggtgaaag cgggtgaatt ccaggcgttg gtcgatttct taaaggccaa  105360
tgattgggct ggtatgaagc aatgggtgac tgacaaccaa aactacatca cagaggactt  105420
ctactctcgt ttcttccatt tctgtgttcc gcagaacaaa gagaagaatc ctttgatcca  105480
aaacgaatct atcccagatt tggtctgtgt ttgtggtcag tcacagattg aacatcgttc  105540
agttggagac gtctggttac acggcgttta cttcctgacc aacgtcatgc tcaacatcaa  105600
gtggaagtga tattatggcc gctccgtcac tgttcgatta cctgggtgct ctgaacagca  105660
ccaaagagaa tctgttgttg accgaagacc ccgaaatcag aaaggctttt gatcctttca  105720
tgactcggcg cggccttgct cagagtaaag acacgttggt ggttgcagaa cgaatgaacc  105780
gcttccatgc cattactcct tggatgcaat ggaaccttgc gtttcatagt attccagcaa  105840
aacgccgtta tgacaaatgg tctaagaaag gagccatgga ccctgatgta aaattgattt  105900
ctgagtatta ctacatcagt cctgaaaagg cttctgagta tgttcgattc ctgccgaaag  105960
aagtcctggc tgaaatcaag gcgaaggtcg aacgttccaa cagcaacgaa aaagctaaac  106020
cgcgcaaggc taagtaattc aaattattgt taaaggggta cgagtcatgg cgcgtaatac  106080
gctggacatc ttgaaacttt cagctgttaa cgatgaggcc agcatcgttg attgtatggt  106140
tgaagttcaa ttgaaccaag ataaaccagg aatttttctg ggtatcaagg aaacgctgag  106200
ccgcatcggg gtgaacactc gtcaagagcc gaataccctg taccaaacat gtcatattct  106260
gcataaattt ggcagatatc acatcgtgca cttcaagcat cttttcatgc tggatgggca  106320
ttacaacggc tttacgcgtg aagatgtcct gcgtatgaat cggattattc ggcttttgga  106380
gcagtggaat atggttaaaa tactgcatcc ggaacagatt accgaagttg ctgatatgtc  106440
tcgaatcaaa gttgtaaaac atgaccaagt ttctgattgg aaactggttc caaaatatac  106500
catccgcccg actcgggcga aaagcgaata actggagtcg ctatattatg acaactacat  106560
ttaataaaaa cgtgagactg aatctggctt ttggtaatgc tgcaggggac gtgaccgacc  106620
ccgactttag caaaattcgc aatcaggcaa aactcgtgct ggaagagacc cgcgaacttc  106680
tggaagcggc ttattacgat catcaagtgg ttctaacatt agaattgaat cctcgagaaa  106740
gcgagacgcc gaccactacc gaagatctga tgaaagccat catggacgcg cagggtgata  106800
tcactactgt taacgacggt gtggcccata tcgcgggttt caatggtgat gagtgcttac  106860
agcgcgtgtt tgcttccaac atgagcaagt ttatccgctc tgaagatgaa gtcggtccgg  106920
ctctggacta ttactattct cgcggtttcc ctgatggaca attgcgtgtg gaaggcgaat  106980
tccctcaggc atgtattaaa gttaatgaaa ctgtcgtttg gaatggtaaa gaatatccta  107040
aagggaaatt ccttaaaaac atggctgttt tccaagagcc tgatttttct gacatgctga  107100
ccaaaactcc ttcccgtcag atcaacgata tcgttgccag catggcgatt gaagaaggtc  107160
aggtgtttat cgatgatctc aatggcgtgg cgttggtatc cccgaacaca ttgggtgtaa  107220
tcctttccat ggctgttgaa aaaacttctc aacctgtaga gatcgacggg caaatcgaaa  107280
gttatgtgcc agcgttcatc gtggatgaca ccaatatgcc taagctgtgt ggggtgtggg  107340
gttctaatgt tcgtgtttat gcgagcactc cagtgcagaa cacggtaaca cacctctccc  107400
gtatcgatta atataaaccg ttattcatta aacaacagag gctataatgg cctctgtttt  107460
tgtattctag agaggatacc atgaaagata aaccgtgtga cattccttat tgcggtgttc  107520
gggaaaccaa aattaaatct gcacacccca cgttaagtcc attccataaa caactcgcat  107580
acgaatggat gagcgagcgc tataagatcc acgtgagaaa ggacgtccaa cgtcttcctg  107640
ctccttggac ggataatccc atactacggc aggtcaagtt ctgtaacgtc cggagagagc  107700
acgacaggca gtctcttaac ctgatcaaca atatcgtcaa gaacgatgct ctgggcattg  107760
ccgacaagat gttcaactgt gttctgttcc gcatgttcaa cctctgggac ccgatcaagg  107820
ctatcggtga cgctcgtact atcaaagagt tcgcaaacat cgatcttgat gcaacccgca  107880
aaagtcttca ggaatttgag gccaacggtg gtaagatctt caccaatgcc ttcaacacag  107940
gcggtctaaa gcagtgtctg gcgttccccg aactcgttgt caaccacaag gagcagcgct  108000
ttggtggtat gatggttaag gtacaccgtg ttggccaggg tatcgttgat gaattggatt  108060
acaaggtcgc caagaagctg gttgaagaaa atcctgggga gtacacgatc gagggctggg  108120
agccgtacat gccgatgcgt gttatccgtt ccctgaaggc atttgtcaac aagtatcctg  108180
attatttcaa tgatctttta cgtcttgact ctccgctgaa agtttaccag cgcatgtatg  108240
acgacattga agggcttggg ccattcctgg catatcagat atgggtggac ttcacataca  108300
tccctgagta tccattcagt gagaatcact tcaccatcgc tggcccaggt tgccgtgcgg  108360
gtattgacct gatgttcctg gataaggacg gtatgactca tgaagagtgc atcttctggg  108420
ttcgagatca ccagtatcaa ttgtttgccc agtatggtta tgtccaagag cagttctggt  108480
cagccgaagc gccggaagat cagtgcatga atgtcatgca gctggagaac atgttctgtg  108540
aattgagcaa gtacacccgc tgtgttgagg ccattgagag aggggaaaag ccacgcggca  108600
aggtcggtta cgatggaggc ggagaataca aaaagcggtg cgatgaagtt gtcctcaaac  108660
gcggttccgt caatttgtta gatcgtttga agaaacctga ataaagaatc gctttacttc  108720
attcttcaat aaccccccttt caacgtatat tgacctcact ttaacgacgc gcccatttag  108780
ggcgctcaat ttgaactgaa acaggaagac tataccatgg cagaattcaa acctttcgca  108840
acggctgtta atgataacgt gctggcgatg tccgcaactg gtctgtttat gaccaacgtt  108900
gataaagatg ctctgtggga tttgtatttg gcatccttcc cagctggtac caacccgatg  108960
taccgcgaac gcactgaaca cgactgcacc tgctgtaaac aattcatccg taatatcggc  109020
ggcgtcgtga ctatcgatgc tgacctgaac gttatctcga tttgggacaa cattgagctg  109080
ggtaacgaat acgacgtggt ggctgcggcg ctgtcgacct tcgttaaaca acacgcaatc  109140
gtcgacgtgt atttcaacga ttctgctaaa gtcggcctgt ctcataacca cgaatctggt  109200
gaagacggca aaatccgcac gtataaccat ttccacaccg aactgctcgg cagctatgtc  109260
ctgcgttctg atgctattgc atctaaaaaa ggtgaaatcc gacaggctat cgaattattt  109320
gaacgcggtc tgcgtgaaat tactctggaa tcagcagaaa tcgttctgga attgattgat  109380
cagaattctt tgtatcgcgg cgctgaacat aaagctgcgg tgatgggctt cgtagtagcc  109440
aagacggcat atgaagaaat cccagaatct aaccgttctc tgtgggcatg gcgcactggt  109500
tatcgttcaa acaatcatgt tccacatggc attcgcaaca ccgttatcgg tactctgttg  109560
actgatatca gtgaaggcgt ggaactggaa aaggccgtta agtcgtttga aaccaaagtt  109620
gccccagcga actacaaacg cccgacggct ctggtctcca agtccatgat cgaaaacgct  109680
cagaaagaag tgattgctct cggtctggaa gattcgctgg cgcgtcgtta tgcagtttat  109740
gacgacctga cgatcaataa cgttctgttt gcagacctgg ctgctcaaaa agcgatggat  109800
ccattcgctc aactggccgc cgaagtgaaa acgccgacca agtcgctgga taaagttgaa  109860
```

```
gagattggca ttgacgactt cctgagcaat atcctgccga aagcgcattc aatggaagtg  109920
ctggttgaaa actcgcatac tggcaacctt atgtctctgg tcgctccggc tattgcaggt  109980
gctcctaacc ttttcaaatg gggcaacggt ttctcatggt catacaacgg cgaagtggcc  110040
gactccatca aagagcgtgt gaaagcggct ggcggtaaag tcgacgggtt cctccgtgta  110100
tccctggctt ggcacaacaa cgatgacctc gatctgcata tgttctttaa caatatggaa  110160
catgtgtact tccgcgatcg tcgttcaatg actggtgctc atctcgatat cgacatgaac  110220
ggtatggacg gcatcgaccc gaaccgctct ccggtagaaa acatcatctt cactgatgaa  110280
agaaagctgc gtgacggtga atatcgtttt gagattcaca actacaacca acgtgaaaag  110340
atcgacgaag ggtttgaaat tgaagttgaa tacaaaggcg ctacgcaacg ttttagccac  110400
aatgggttaa aagaccaggg gcgcatcact gccgtcgttc tgactgttaa agacaaacaa  110460
gtcgttagca tcaagtctga gctggcgaat gttgataaat ccaaagaaat ttggggcatt  110520
aagacagcga ccttccagaa ggtacagctg gtcctgaact caccaaacca ttgggatggt  110580
gaacaaactg gcaacaagca cgtcttcttc atcttggaag gttgtgcgaa tcctgaaggt  110640
actcgtggtt tctacaatga atatctgaag ccggaactgg ataaacatcg taaggttttt  110700
gaaatgttgg gtagtaaaat gaaagtacaa cccaacgaaa accaactgtc tggtttgggg  110760
ttctcgacaa cgcaacgcaa ccatgtgttc gtcaaagtgt ccggcgcgtt taaccgtact  110820
gtaaaagtca ttttctaatt gatttgacaa caacttcgta ataaggaaca aagaaatgtt  110880
tgatcaagca acccgtttaa aactgcgttt taactctaac aaaggtctgc tgtctgttga  110940
gcaggtttgg gatctgaatc tgaacgcact gaacgagctg gcgaaagatc tgagccgtca  111000
ggtgaaagaa gcagccagcg atgaagaaga cttcatcggt gtgaaaagcg cggtcgattc  111060
tcagttacaa ctgcggttcg atatcgtgaa agcgatcatc ggtgttaaac tgaaagaacg  111120
cgatgaaagc gcgaccgcag cagagcgtaa agcgaacaac caggcgatca tggaactgat  111180
ccagcgtaag aaacaacagg aactggaagg tctgtctgtt gaagaactgg aaaaactcct  111240
gaaataatct gacggctccg gcctgagaaa ccccgccgtg tgcggggttt cttttggaca  111300
aaaatcatga aatctattac gtgtgattac tgcggtcaac ctgcccaata cgtcgggtgt  111360
gatgttgtat acccccaccg ccccgacctc cgcaatctga agttctgggt atgctcgcca  111420
tgcgacgctc gtgtgggttg ccatacccat ggggatggta gacaacctct gggaaggatg  111480
gcgaatgccg ctctccgtgc tgctaagcag gaagctcata gatcgtttga ccctatctgg  111540
aaaggtgggc agaggagcag gagtgatgct tacagctggc tggctcataa tctggggatc  111600
aagaagcgcg attgccatat cggcttgttc gatatcgata tgtgccgtaa agtagtcgct  111660
gtgtgtaatc aactaaaggc acaagataat gtcaaaggaa atacaagaag catttgaaaa  111720
attatctcag gtaatgaccg actgcaaccg ccggaattat tgtgatgaag cgtataccaa  111780
attgaaaact gctgttgaaa ccgagctggc aggtctttcc gttttcaaag atattcagac  111840
cgaagtgcta tatctgtcgg atgaagattt aaggcgttgc cccgcaaga tttaccaatt  111900
actggatcgt ttggtgaaag tgggggtgaa taatgggtaa tcgtgaaggg attaaactca  111960
caccagaact tctgaagtca catattgctg aagtgattta tgaagaccgt gaagttggtg  112020
gtcaccgcgt cattacatgc catttcaaga tggacaatgg gttcgttgtg tggggtaaga  112080
atagttccac atcggtagac cctgccaact tcgatgaaga aataggcaag cagctggcct  112140
atgaaaagac cttttctcaa ctgtgggaac tggaagcata tcgcgcgatg gtagaaaagc  112200
agatcatcga tgtgtctgcc gaagatgcta agatcaacat tgatgaatat gtgtcagaaa  112260
gggaagcgat acatgagatg ggtggttctg aatttcttaa gggtaaagga caatccatcg  112320
tgtttcgtca tcccaaagat ccaagtcggg gatttcgcgt tgaatttgtt cgcaccgata  112380
atgaacgtta taacgaacga cgcaatggtg aggcacgatc tttggtggaa gcgtatcttc  112440
gctcgttcat gacttctgaa gaactaaatt ctgaacttgt cttgcgtttg gcgaaaacgt  112500
gtaatgctgc ttcaggggat tatccgtggt gtgacctgtc agaagacaaa cgccaagcag  112560
cctgtgatcg tgttaagaaa ttcttgttag atccgaaagc ccaacctggt gattccgtag  112620
gggcactgta tagagccatt gtggtgtcct acttgtaatt cttcaaaagt ctttcaaaat  112680
caataacgtc cggcaaaatg ctgggcgttt caattaataa gccaaggtat aatggcccaa  112740
ctgaaaacgc gggggaattt ctttgtccaa gccattcatt cgttccggag ttgattctct  112800
agactcccaa tttaagccga gcgaagtttt aatccaacaa attgaaacca atcgtgaatt  112860
catagaacac atgttggcaa agccggaagg cgaagccgct caaaccacca aagaaggtaa  112920
taacgatgat tgaatcatta acatttaaaa atgcggtagc aaccgtcgcg ccgtctaacc  112980
atgtaatcgt tgtggatatc tccggttcca tgtaccgttc acttcctgaa gttcgcaagc  113040
atctgaagga aaatctcccg tctctggtta aaccagaaga taccgtcagc attctttact  113100
tttcatcccg tggtgatttc ggtacggtat tcgctggccg tcagatcaat agcgcgaccg  113160
atctcagtga aatcaataaa ctgattgacc gcttcctgca accgtccggt tgtacgggat  113220
ttgtagaacc tctgaagttg gctgctgaaa ccgcgttgag cctgaacaaa cctggttatg  113280
tcaataacct ggcgttcatg accgacggct atgacaactg ctggcgctct aatgaaattc  113340
tggcagcagc tgaagtactg cccaaggcgt tcgataatat tacattcatc gaatatggct  113400
ggtattgtaa ccgcgaactt ctggctctga tgtccgagcg ttctggcgcg actcacgtgt  113460
ttgccgaagg tcagactgaa tatcagaccg aactggaaaa cgtactgaaa tcatctacgc  113520
cgaaagtggt tgttgatgtt cccctggttt acactcatgc catctacgtt gaaaacggcg  113580
tggcaactgt gctagccgta caacccgatg aagaacaccc gattggccac gtcagcatcc  113640
ctgaaagcgt ttctcagctg tgggttgtaa accctaacat gatcgaccag ctggataatc  113700
tggcagacac ccaggcggca tacgtgctgg cattctatgg cgtgtacacc atggacgccg  113760
atctggtctg ggccgcgctg aagaagacgg gtgacgtccg cttcatcaaa caatacagca  113820
actgtttcac caagcaggac tattccaaca tcaaagtcga tctgacccag gctatcgtgg  113880
atgaaactct acgcggcgta gatggcatcg attacaatat ggttccagct gaagatgcaa  113940
cgaccattgt tgatgtcttg acctacctgg ccgaagccga tgtctctgtt gtcactaagc  114000
atccattgtt ctcttacaac agcatcggtc gcggcactgt gcagaaagtt gatgacactg  114060
aagacaagct ggctgaacaa atcgccgaag ccaaaaccaa agcagagcgt aaagcgctgg  114120
ctctcaaact ggctgagcac gaagattgga caccggaatt tactccggtt gatgacaaag  114180
ggattgtccc aattagcaat ctggtctaca attcagagcg ccctaacatc agcattcaga  114240
ccgttcagca tgggacggtt gttgtgccgg agttcgtaca gaagaaatat gaactccctg  114300
aagaactggg aacctggcgt tatcgtaatt acaccatcgt caaagatgga atcatcaacc  114360
tgaagacgat gccgattact gccgaatctc cgattgtccg agctaaggtt gtccaagatt  114420
tgatcgccat gggcgttaat gtatttggtg gaccggaaat cttcatcgtt aatttagaaa  114480
gcgttccgat ggtcaaccgc gccatgacca agaacatcag tgctgccgaa ttcttcgctg  114540
acaacgttcg tcgcgaagcg ctgaaggcaa aacagaaagt tctgaaattc tatcgtgatg  114600
```

```
aactggttgg caaaggcaat gcaactggtc tggcttctaa atatggtaaa gaagccgccg  114660
atttcttgtc ggcaaatggc attcgcgact acgggttctc gccgaaaact acttctgtgg  114720
aatcaaccga tgtctacatg agccgtgagc tgaatgtgaa aatcaaaggt gcttcgtcgc  114780
tgccgagcat tgcgtcagtt atcaaaaagc aagcagatgg taaaaaactg aatgtcgctg  114840
atcagttgat tgccaatgct ttggccgaat acgacgcttt tgttaaatcg ccaatgatca  114900
ccagcgtacc tgaagagact cagaaaaagc tgattgaaag ctggatcgga gacgcagcaa  114960
aagcggccat taacgaagtc cgcgccctga acaaaactct gtctaaagta gtttacggca  115020
tcgtcgctgg tcatggttgg ttcactgatt tggatctgga agagtctacg atggatgtag  115080
aagttgatgg ggtgaaatac accgtcactg ccgaactggc cgaaaaagaa atcaaaatct  115140
aaatctaatt ggcggggaaa cccgccttta ctttcaggaa atgaatatga gcaacaaacc  115200
gacttatgtt gatgtcatgc gcgatttggc ccaatacgca tgtgacaacc tgaacatgga  115260
aacttggcgc gacggcgatc ataaagaaaa gttcgataat atcgacgaca acatcgatgc  115320
gttggctcct cttcgggcca agagcgatct cggcggtgat gatcttgaca tgattgaact  115380
catcatggaa gttgaagaac aatatgatgt tgaaatcagt gatgactggg taggcaaaca  115440
tggtgatgat cccacgctcg gcgaattagc tgaattggta gttgccctca gcaagtaaac  115500
caaaagaatc cccaatattt attggggatt tttactttta ggggtttact tcttctaaag  115560
aatatcctat tattcaataa ctggctaacg tggggttggc tagaaaagga gatacaaaat  115620
gaaactacca ggtcatattg aagtttatat gcggttatac aaagaaggta acgccgctgc  115680
taaagaacta cacgaactga ttttgtcata cggcgttaag tctgttacag aagtaaagaa  115740
caacaaaata gacggcgaat atgtgtcaat caatgggcgt ggtctgaaaa ccaacccaac  115800
atattttgtg ggtgtccatt tagacacagg gaaagaagtc gtggagatcg tggcataatg  115860
tctaataaga aagttgaaac gacggtagaa attgatcgta attggggatt actccgcgct  115920
aaaggttttc gtcgtgttta tatgaccaag gaagtttatg ttcagcgtcg cgacgttatt  115980
atcagcaaga aaggtaaaga gtgggttgct gaagaagttg acattgaaac aggtgtcgtg  116040
ggcaaagtaa aagcgaaggc ggctattttg ttttctcttc tgaagcatat caattaattc  116100
tataaactcc ggcggggtat gattaccccg cctatttgaa attgcaggaa cttatatcat  116160
gatctctgtc gagggtataa tatgacaaag gaacaagaac tcgctttgtt ctctatggtt  116220
cgcagtaatg ttaaattgag ttttagacaa gtggactcca ttattgatct tatgaaaatt  116280
aagaattcca tagataacga tcatttgcgc accgctcttt tgggattgtt ggaattcgtt  116340
ttgcgcggat ctgatcttgg accagtgaat gatattgacg acctgaccaa attgttaaac  116400
actggcggtg atggtttcga taccgctcgt attctgatta actgtggtcc taacaaagaa  116460
gaggtatgat gtggacaaag atttggtttg ggaaatcgtg aaaggtatcc tggtaataat  116520
tgctgtggtc tttatcctag gaggaaactt cttctattgg ttattgcggt atgaagagaa  116580
gcgtcgagag cggaaagaac agaagagaaa agatcgatgg atgaactaac taagggataa  116640
ccctatatcc cgaggtgtgt catgttcctt acatccttta ttgactggat gaatatcata  116700
aatggcctga ggatccctgt tgggaacctc gggctttctc gttcttctat gccgcaaatc  116760
gatgccgaca aacaagaaga ttttcacaaa tatcttgaag acaacggcgt gtctatagat  116820
gctgcgcaag tgcccatcaa aatgcttcgt cttacccaga acgaaatcaa caagatgaag  116880
gtctggaaga ttatgaagca aatccgaaat aagaaaccta tgggtcgagt ttgggtgtct  116940
tctgacaatt acgttgttga cggatctcac cgatttgtcg ctgcgttgaa catggacggc  117000
aaacagcgca tgaaggtcta caaagttgat ttgccagcga tggaatttgt taaactcgct  117060
aaacagtttc aaggggtgcg atacagaacg gtcagcgata cccgtttctg aatacgatag  117120
tttattgaaa ccctttactc aacatggtga cagccctatc attttatcca atgaaataag  117180
gagaatcacc atgaaacgtt taatcctcgg ggttgtgctg gcaggtctgg cattaccccgc  117240
cgccgccaag ctgaactcca caggtgacaa actgtggtct gatctttcct actgtgctgg  117300
gttctcccag gccgtggcta tagacaagtc cggttccata gagaatttcg ctgaactttg  117360
gaacacgggt aacgtctcca ctgctgttgt taatgctggg attgagttca accgttacaa  117420
acagggagcc tacaacttga aaggctacct gaatgacgat gaatttaacc gaggaggcat  117480
ggaggctggc gatctcatca tgactggccg tatgggcaca caaggccgta tgactgtaag  117540
gcaatgccgt tctctcccct ctccggcatt acagaagggt gtgcaaatcg ggcgtcgaca  117600
tttggatctg atcaatgatg gcaaccaatg catcaaggtg tttgaatata gtgccgacca  117660
agaatcagat cgacgtttga aaaaggaatg gcggacacgt gcccttggat tgagagcatg  117720
gctcgtagaa aacgattatt actacgagga tcgtgttcag aacggattga aagatctttc  117780
cactaatttg tctgtcaatc tagacgaccc aaggctttcg cgtgaactca agcaaacacg  117840
gattgactgc gacaatatga tgaaggagaa cgaaagatga gaaacataat attcttgtta  117900
ttcttttcta tgttggcatc attccaagtt atggcgactc cggccagcaa attgaatatt  117960
tgcgcggcct ggttgtctac ttatcaacaa tttcaccctg atgataaaga tacatctatc  118020
cttttatcgg attatgaagg tgagttgaaa cgccttgatc tctacagcgt ggatcaaata  118080
gagaatgctt tagatttgcc aatgatggag tccgctgccg acaatagcaa acagacgatc  118140
aaagatctga ctatgtgtcg ggaaatagcc actaatttcg ttggaaatca aagataattt  118200
tcaggttaaa atttaacttc cattgaactg aaaggaaata cttcgtgatg attattacta  118260
aaaagatcgc cgaatcgatc gttgaaaaga ataagatgtt cgcgcccaac aaagcaaagg  118320
tcattctgat tcacgaagac gggcgcgtca tcttcgctga gaagtttgag cagggttgtg  118380
ctttctggtt cgcagatact atgcgcgaaa gcaagctgca gggcatcatc tataaattga  118440
ccctggttgc caagcgcaat gatcagggtg attgggttac ggtctgcgat ttcagctcta  118500
aggttgaaac gaaagccaaa acccgccaag aaagaatttt agaggctcag gaaaaacttc  118560
gggtcgctcg cacatcatcc gcggagaagc cggaaataaa accagccgtt atgcctgtca  118620
ccaataatcc gctcccacct gtgggtcaaa aggctttcga acaatatgtt gaaaagagaa  118680
aagaagaatc tatgaagact ccggtagaaa ataatgatga gtctgaattc atttcaatac  118740
gacagttgtg cccgcaagaa caacgttatt cttctccaaa tgatttattt gtgtcattca  118800
gatgcaacgg gaagatcatc ctgtgtaaaa ctctgcgtga acaactacca tggcctaaca  118860
tcaatatgat ggtgagtcgc aattttaaac gatttgctat tagtgaaggg aacgattatc  118920
ccgtaaacaa gagcggaacg tatgccaaca aacatatgtg tggtaagttg tctttcccta  118980
acgattccgg aaccatccgc gttcgtttag aatgggatga aaccctgaac atgtatgttg  119040
gtgatataaa ataattcaat aacattaggg cggttattat taaaccgcct tttatttgag  119100
agatctatat tatgaataag aagagtcgta tcatcatcgg cgcggatcag ggaaatctgt  119160
attttgatac aactggtgct attgcccacg ccatccttcc aacaggtatt tctgtttatt  119220
gtgtcgaaca cccagatcca gcgatcaaac gactttgtta catccatcgt gaaaagggat  119280
tgattgtatt accggaaggc gcaattatgc gcgctcgttc ttggccgatc gattttaatt  119340
```

-continued

```
ccatgaccgc cagagagatt gacgcccgtt tcttcgcata caatatgaat cgaactttaa  119400
ggaacgaaac tcaaagagtt gcccatttcg ataatgaaac atataccgtg acattagaat  119460
ttcgcgttct tggtgaagct cttcaggtaa agaaaacgag ttgggcaacc gaagggacgt  119520
ttaccaatga ttatgctctt atcgatagat tgtgtaatcg gttccgaatt agcctgactg  119580
cgaatgaaga tttgggagaa tatgtatcat ggacagctcg ttctccacat atgaatggga  119640
tcatgatgga gagcgggact cgtaatcgtg ctgttcttca gctgctgttg ttagatgcgt  119700
attctcgcaa tcctctggaa tatttgtctc gagagcaaat cgacaacgct ctttcccatt  119760
gcaatcatct ggaggtgtga tatgtccggc gtatggtgtg atgtattatt agtgagattt  119820
tcaaacggga tggataacca gattatttca ttcttttatc ctgttccctt ttcttctatg  119880
ggtctgactg tcaagcgcgt tcttgacata gaagaaaaac tcaacgctat gccgtatatg  119940
gcgcgaccac acgtgctggg ttgtgaactg ttaaacgaaa tgatgatcga tgagaatctt  120000
gttgaaacaa ttatcacgcg tgaacagatg aaaactatac tggctcaggg agaaccccat  120060
gtcgaataaa ccgtttgaac ttaaatttcg cgtttggcat attccccagg ttcctgggat  120120
cgcttttcat gttgaggttc caacatttga agaagcgcag cgcctgaaga atgctctggg  120180
tgattatgat ttgttccagt tcaacaacaa tatcaagccg gattattgca atgcttcggg  120240
cattcagatt tatcaacatg atctgaccga tgatgatctt aatgatatgg gtctggatga  120300
tcgttgggtt gatatggaag atgttgacga actcaacgat tatttcgagc atctgcgcag  120360
tacagggtgg gaaatatgat ttcaaaatat attgtaaagc ctggggatac tctgtccagc  120420
atcgctctaa aattatatgg tgatgcccaa cagtatatca aattagccag attcaacaat  120480
atccaaaacc caggccatat cacggttggt caggttattt gtttacccac acctgtcgaa  120540
gacaaagaac acattatgat tccggttcaa ccgactcaga agtgtttgga tgcgatagct  120600
ggtttatttc ggccaggttt ttgtgatgga actattgaac gtcacattta tcaagcgatt  120660
gtggaaaacg caggtgtaaa atgatcggat taattcgtta cctgttcata ttcgtaattt  120720
caacattcat tttatttttc tttttcaaat acttgaaaga gactaaaatc taccgaagta  120780
aacgttggcg caaacgggtg agggtaactt tcctgctgct gatttcttcg gttacaataa  120840
ccgcactcac attgggtgca tatatctaca tttttgaagg ggtacattga tgttcaagaa  120900
attggtgttc ggtgcaatta tggttctggc tgcaagtcta ctttctggtt gtggtggcgt  120960
tatcgatgaa ggtaatgtcg gcgttcgcac ccaatggggt gaagtagaca tgaaccctgt  121020
aacagcgggg atctacacca gctttgtttc aagcgtggat gtttacacga ccaaagaagc  121080
cgttgtgagt ctgactaaaa tgacgccaaa ggccaaagac aacctgactc tggaagactt  121140
ggatgtggat gtttattaca cacccaatgt cgcaaaggtt ccgtggttcc ataccaaatt  121200
tgctggccag agcgctgaac tcgatgatgg cacgatagcg gtgggtttca atctagttaa  121260
aactgctgca gcatcttctt cgatggacgc cgtttcttct cttgattcta tgacaattca  121320
cacccaacgt gctgaattag agaagatgat taaagaccgc actcagcaac aattagagac  121380
tgctgcgcct ggcatgttca caatcacacg cgtgttggtc aaaaaggcgc tgacggatcc  121440
ttctattgag cagtctatcc gtgataatgt tatggcggac aaacgattgg atacggcaag  121500
aaagaacgtt gaaattcgcg agcaagaagc ccaagcgaac cagaaactga ccacttcgct  121560
gacgcctgaa tatcttcaac atgaatataa catggtatta caatcatgtg ccaatagtgg  121620
aaaatgtact ctgatcgttg acggatccgg ctcaggtaaa atgctgaacg tcggcaaata  121680
aacgctttat tcaataatat ttgttaggta agctgtagtc ctcttgtagt gaaacattgt  121740
aaacaactaa ctggagtaat ccgaatgaac cgtactgatt ttatcgctca catcgcccag  121800
actcagggta tgaccaaagg cgaagcagag aagatcgtgg catcctttat caatggcgta  121860
aaaactgcag tcgcagctgg ccaatctgtc caattcgtcg gcttcggcgc gtttgaagtt  121920
aaacatcagg aagcgcgcac tggtcgcaac ccgctgaacg ggcaagcgat tcagatcgaa  121980
gcgaaaaatg ttgttaaatt caaagtcggc gaaggtctga aagctgctgc caacggccag  122040
taatcacatc cagagcggtc gtgcctagca cagcgtgtta ggctaaaaga gaaagccgag  122100
gttaatgcct cggctttttc gttgttggaa ttcgggtaaa ctataacaga acccaaagga  122160
ggaacaacgt gacagcattt aatcaatacc gaaaggcgat tgacgccata ggccgtaagg  122220
ttcctataga agaaatacaa agccttgcca aaaacgaatt tccatatgac aaggcgaacc  122280
aaggccagat ggaatgtatc gtcgaagccg ttgatgcctt ggtcaacaaa aaggtcaaac  122340
acgtgatcat tgaagcccca actggcgtgg ggaaatcttt gattgggaca acaattcata  122400
aagtgattcg ccatttggtt ttacaggccg atccttatgg gcaattccgc acgtctatca  122460
gtacgcccac caaaggtcta caagatcagt atgctgctga aaaggcggtg gcgatagaca  122520
tcctgaaagg caagaagaac tatcgttgcc acgtacaccc agatgtgtat tacaacgccg  122580
tgcaatgccg tatagcatgc cgcgacgggc attgtagcaa acgccgttgt ccttatgtac  122640
aggcgcgcaa tttatggact gatatttcgt cattgcgttg cactaatgca gctatgatga  122700
ttgagatgtg caccaccatc tgtatgaagc ctgaaaaccg ttccgatatg ctgatcttag  122760
acgagtgcca taagatgccc tctacgctcc tagagcacac gataatggaa tacaatacaa  122820
aggctgtgga tgggctgcga actatccccg aagggaagga gatagtctct atcattgccg  122880
atatcgtaga acgcaccaag gactatgtct tgggcaagtt gtattccttg tccggtgaaa  122940
tgcattcgat gtttgaagac ctccatctta aagtggagtc tttgttggaa gttcttgaag  123000
aattggttga agatgaccgc ctgagtgaaa gccaggtgat gaaactcgcc gacattatcg  123060
atgtactaca caatctgagt gattattgtg gtattatgtc tcagacaaag gccagcacct  123120
ttatcgtaca ggaaaaggga gatgacttta ttcggtttaa acccgtcatg ccttctgatg  123180
taagtgaatt tggattgttc aggaaagccg attaccatgt tcatatgtcg gcaacaatct  123240
gcggaatcga ttcatatgcc cgttccttgg gtatccgcca gggggattat cattcaatac  123300
agattggaaa tccaatccca attgaaaatc ggaaagtcaa ctatatgccc atcgttaaga  123360
tgaccaacaa catgggcgat tatgaaatga aaaggctgac ggaatacatt gatgaaataa  123420
tcgcattcca tccagggcaa tctggcatca tacatacggt gagctatgat cgcgcattag  123480
caatacaaaa attcagcaaa taccagaact ttatccatgt gccacgcact cgaaaggcgt  123540
tgatggatat tatggaaaat gccttcagga caaaaacacc ttgtgttatt gccagtccgg  123600
ccatggaaga aggatatgac ttcaaaggtg attacagccg attccaaata ctgatcaaag  123660
ttccttacga ttatttgggt gatccattga tcgcacatat taattcagtg gatccgtctg  123720
cgtacttccg caacgcagta ttgcgcattg ttcagatgtg cggacgttcg gtcaggggtg  123780
tggatgactg ggctgcaaca tacataatcg attcttcctt tgaatctctt atgatgcgca  123840
acccagagtt cttcccaacc tggttcaccg atgcagtatt tgaagtttaa taacctgcaa  123900
taaacgataa atggcacttg atatttggtt caagtgtcgt tatcgtgatg atcatattat  123960
ccacatcttg actaaaagat atatttgcta ttggtttagt ctgaacgtgg ttgtacaggc  124020
tgtatatcaa atcttcacca cggtatccga ctttaccatc agtatcctgc caatggccta  124080
```

```
acgtggattc atgagcatgt actcggaatt ctatcatatg gaacaatgct tttgggattg  124140
ttttcagtat gctggttccg acaacaggga tatcaatagc agagtcgttg gaattgccct  124200
catatactga agcccaacca aatgttggat ctcctcccgc cacgggagtt ctcttccagt  124260
attggaattc tggattaccc gaagcgttct tttgcagaag gattacttca ccgccttcaa  124320
aattagaagt gtctatatca tcacgtgcta ataaatcagc tggagaacca ataaatttcc  124380
aggtttcgcg atctaaaata gacttataat aatcggtgaa tacgttgctg tcgttagctg  124440
cattgattgc gtctttaaga ccttcacctg tgaccatctc attgagtttt agccacatgt  124500
ttttgacagc tgacgcagct gcgacttgac cttcagtccc acccgccgtg tagtcataaa  124560
cgatgtccag cttttgtatg gaatcattta tagacaagag caaacgctca atttctgggg  124620
cggtcagact gaaacgatat gcgcgttctg acatgattcg ttcctcatcg ataaaaccag  124680
tttgggatac ttatacatga ttgaaatata cactgacggg gcatcttccc cgcagaagac  124740
acaagccgca ggttgggcat ttgctatcgg tccaatcact ggagagcaat ggaaagtgtt  124800
ttatgggtat ttaccccccac cgtcaacgaa taatatcgct gagttgcttg gggttataaa  124860
cgccttgaag attctatgga aattctctaa ttgtggggaa cgctgtattc cctcagccag  124920
tattatatcc gacagccaat atgttatcaa tagtgttttg gagtggcgta gaaaatggga  124980
atatgaagga atgccgccta agaacacaga acttctgctc gagttgttcg attattatga  125040
caaagtttgt tcaatttgtg aacttgaatt aaaatgggtg aaaggtcatg cggggaatat  125100
cggcaacgaa atcgcagatc agtggagcgt cagagccaaa gaaaatagct cgatggttct  125160
tgaaaataat cgtttcctgg tcagaaaggt tgttggttct ttcaatgaat tcattggtat  125220
ttgaggatta tcacgatggg tatgaatttt gtagacaggg gtgataacgt caccaaatat  125280
ttcactgacg aagataacga tcgagttgtg gggatattgc gtgattggat ccctgctcgt  125340
aaaaaggcat tagccgaagg aacaccccta ccaagaatcc ccaattatgt ggccatgaat  125400
gttcagatga taatcaagaa tatgagtatg cgttacaact accgtgatta tccatatcgt  125460
gaagacatgg tgagtgaagc ggttgtgaac atccttcgtt accttcacac ctttgatgtt  125520
agccatatcg gcaagaaagg aaagatcaac ttcttctctt gggtgactat gtgtgccgat  125580
cgctcattcg ccaagaaact cacgagtgaa gaagaacaca actacattaa attgcgttcc  125640
tttgaagaag caggtgggtt cgcagcttta tcggatgacc cagacttcca acaacaaacc  125700
ttcgttgata gcactgggat aacgatggac tttcgtgaac gcatcggtaa tttcgaaaat  125760
aagaaagaag cccagcgtga aaaggaacgc caaaagcaaa cggctatcaa agaagaggaa  125820
aagaataaga aaatccctcg cggtatactt cgatgtctta cgaagagtgt aaataccatt  125880
accgctgacg ccgaagacaa ttcagataat gacttcggct ctactcaatt tagtcttgaa  125940
gatataatgg acagccccac attgttagcc gaatcagttg gagaaaagaa taatggcgat  126000
tgctaaaatt ggcgatttac acatcgggag ccgcaatggt tcccgttacg ttcgtgaatt  126060
cataaagaat tatctcatca actattttat tcccgaattg gtagatgcag acattaaaga  126120
agtttggcaa ttcggcgaca catttgatgt tcgtaaattt atgtacgggc gcgacaaaga  126180
ttggttgaaa gatgaactga ctccagccct gagaaaggcg ggtatcaaat ggaatggcat  126240
cgttggaaac catgatatca ccttagaaga atctaaccgt atcaactggc catcctatct  126300
gaatgaatta gcgccagacg tctatcatta ttacagtgaa cccactgaag tttcgattga  126360
aggcgaaaag gtattgcttc tcccatggat caataaagag aattatgatg catctgttaa  126420
agcgatacaa gatacagacg ccaagtactg ttttgcgcat ctggagttgg cagggttcaa  126480
aatgtaccag tcctctgtat gtgataaagg tcagatcgac gtggcgctcc tttccaagtt  126540
cgaacgcgtg gataccggac atttccatac ccgttcgatg gaaggtaaca ttcagtatat  126600
tgggactcct tatcacctta cctgggaaga ccataaagac ggaacgaacc gaggattcta  126660
tgtagacgac atgaaaggcg gggaattgtt tattcccaac aacgagcaac aaacgttgtt  126720
ccgattcatc gaatacgact acacccaaat gtcttccgac accgaaggaa actggattga  126780
cccagattgg ctaaacaatg gtttgggtat tgaagggcaa atcgttaaag tgattgtaca  126840
gaaccgcgat aatgccaagc attatgaaaa gttctgcgac gcgctgaagc gctgtaaatg  126900
catcgattac aactttatag atcggactat cacagtctcg tctgagaagg tagaagtcac  126960
tgaagagatg gtggcgactg atgctgtgga agtcctaaag aaagatatcc gcgccgccaa  127020
taatatccag cgccctgaaa atgtttgcaa attagcagaa caattctata atgctgccca  127080
acaacgcctg aacacattgg atgcataata atgagcaacg tagatctatt atcaaaattt  127140
ggttcgctgt tgaaagaagc ggacgctcct gttattgttg aagcaccatt tgaaatccgt  127200
ggggaaatta ctcacaaact gactttccat cgtggtcgcg ctaagaactt tcgttctatc  127260
ggtaatgaat tcatggaaat tgattaccaa cgcaattcgg caaccttggt tacatccgat  127320
gacaatggcg ctggtaaatc caccatgctt gtctggctgc tgttcttcgt tctgtacaac  127380
gacacgtaca gcaagaaaga gaagaaagcc ggattggtta actctcaaaa caaaaaggaa  127440
tgcgtgggtg aagttgagtt ctcaactcgc ggtagtgaat ggaaagtccg tcggggtatc  127500
aaaccagatt ttgtagaagt ttatcagatg gtggaaggag agtggaagca agtcgtgaac  127560
gatgcggcca aagctgatat gaacaagtac atcgtgaatc tcatcggcgt ggaccagaag  127620
atgttcgaga actctttggt tctgggcaag gagaagttta ttcctttcac agagatgtat  127680
accgctgacc gccgcgccat ggttgaaaca atttgggact tgggtttctt cagcctgatg  127740
aatgaggatg ttaaagcatc tatcaaggcg gtaacgaacg aactcacgac ggtcaccaat  127800
gattacgcct ttcatgatgt gaatctaaaa ggccagcaag cgcagttgga acagatcaat  127860
aattccaatg cgatggttca gcaacaatct gcggatatcc ttgtccaaga gaaggaacgt  127920
ctgaatagcc tgaattcaga tatcggcgca gtgcaggaac aactgaccga gtcccgtgct  127980
caagactcta aattggaatc agaattatca gaagtccgta atcgcctgaa cgctgaaatg  128040
aaggtggata tcgatgccat caatgacgag tattttgcca aaattcaagc ggtacaggat  128100
gaggctgata ccaaggctga agactatgaa cgtatcgagg tgtctgatgg cgaacgttca  128160
ttacaagaaa ttcgtgagag aatggcggta gtcgcggaac gtaaaaatga tctggtcagc  128220
caacggaatg ctaacctgga tgaactgaac aaagcattag cgcggcgtca gcagggtgag  128280
aacttccgta tcaaattcgt aacagaaatg gaaggacatg aatctgccat caaacgtttt  128340
cacgatatgg gcacttgccc tacgtgtacg caattagtgt cggacgatac caaatcacgc  128400
attgaaagtc aatattatcc acaaatcatt gaactgactg acaagattct tcaggttgac  128460
acagccctag aagaagttaa ttccctgatt gagaattaca acgtcaaaga ttcagaatta  128520
tcttctcaga tttcggttgt tgacaaagaa ctggatgctt tgcgcaatga aatccgagaa  128580
gcggaatcag cgatcgctgc attaaaacgc gacatccaag gattctatga tgtggcagct  128640
gttgagaaaa catctttaca gcgggaacaa cagtccaaaa ttaacgatat cctcaaggcc  128700
gtagacaccc gttacgaaga tatcacgacg tcaatccgtc aagcgcgcga gcagctctct  128760
aagagtatca acgacacggc tgataaactc accagcctga aatcacgccg tgcccctctg  128820
```

```
gaggcatcca ttgccgattt agagcgtaaa ttggcggtta agccgacacc aactgacacc  128880
ctggaagaag agatcgctcg catcacggcg ttaatggaag atctgaatgc gcggcgcgta  128940
gagttggatg agaaattgca agacctgaac catcttctgt tcttcctaaa agatgatcag  129000
accaaggctc gaattatcag cctgtatttg cctttcctca atagtaaaat aaacgagtat  129060
cttgaagcac tcaatatgtt cttggatatt gctgttgatg atacatttga aatcaccatg  129120
agcgctgcag gtcgtaaagg gcaaagtatc ttctcgttat ctactggtca gcgtagtcgc  129180
ctgaacctgg ctgtgacatt agctttacgc gatgttgcaa acctcaaggc gtcggtgcaa  129240
tgtaacctgt ttgtgttaga tgaaatcctt gagaacatga gcgagcgcgg cgtacaagaa  129300
tcggttgaga tgctgaagca taaatttggc gggaacaatc tgttcgttat cagtcaacgc  129360
gagcaggaat tccaagagta tttccaacac aacatccgtt atggtctgcg taatggcatg  129420
actgaagtga ttaagaagga ttgatcatgg gaagtctgat tcgtgtttct aagatatcca  129480
agggcgctga aaagcgcctg tacaaagccg ttcgcctgat gatcctctac aagtacactg  129540
ctgagaatcg gtgctggcga aagaaaacac gtgcccgata tcagttagct cagtacaata  129600
tgaggcgtca tgtcgtccgg ttggcgttga agatcgcggg gaattacaag tattggactt  129660
gtgaggctgt tggtagccgc aaggctattg acctcataaa tgaccggaat ctatctttcc  129720
tgatcaatct atcggattat gaggacatgt cgtgaaagtc gtccacttca agaaggagcc  129780
atatgacgtc tacattgggc ggcctggcaa atggggtaat gacttcgaag tcaaagacca  129840
tgggcgcggc gtttgtatcg agttattcga agacgatttg tatgtgcgtc tgattgaagg  129900
ggaaatcact gaggatgaac tccttgaact ggacggaaag attctagggt gctggtgtaa  129960
accacgcccc tgccacgggg atgtttacgt caaagtgatc ggtcgtatta aactattccg  130020
taagttgggt aaatctttta ctgaatattt gagacaaaca tatgtcagaa gagaaagatg  130080
aaatacagat tgcttgtgat atcgctgtgg aattatggaa tcagcgaaat agacatcatc  130140
aggtagcatt gacaccaaaa cgttacctag agcaaggtgg gttgatcgtt gttgacgccg  130200
tcttgggttt caacaagtac acagatatgc aaatcctcca aggggatttc atagtggcat  130260
caaaatcagc atgggacgat cctatggagt ttgtctacgg ctggttagag tgtattgagg  130320
aatcatacca tctgatctac gaataaggtg aagggcacta aatatcaagt gccctttatc  130380
ttttaaccct gtcaggaggc tcaatcgagc tgcaagtcga caaacacata aggaacgcca  130440
tcatgacgat gacaacgttg aaggccatgg ccttgtccgt gacctttacc attgccagcg  130500
ggagtgtgca cgcttcccaa agtaccaccc aatgtgatta cgaattttct gatcagcaac  130560
tttcaactat ggccactgcc tatcacatag gcaaacagca agaccttggt ttcaccctag  130620
ccgcgatatc atggagggaa agccgcgccg gagaagatgt ggtatccatg cggaataacc  130680
tgaaatcggc taatatgggg gcattccaaa atcgcgtcca aaccgttggg aaacgggagg  130740
gatgcaaaac acagaagtgt tacgccaacg tggcgattaa attgctggtc aatcaagagt  130800
acgcagccaa tgcagccctt gatgaaatga atttctggct tggatatcat aaccaaaaca  130860
tccgcaaatc gctctcctct tacaatgccg gtttcagtcg taaccaaaaa tccaattcat  130920
acgctgctga tgtcgtgaag aaggctaaat atcttcaacg atgtgtgtct ttcaaaggca  130980
tggcaataaa cccgaaggtc gacccaggag tgatcgccat gaataagcgc acgattgaga  131040
aactcaagag gacccgataa tgaatatcac tccatcccag accggatacg agcacttaat  131100
ggtgtttatt gcgattcagg gggcaaaaga aggcatcatc agttctgaat attctggaac  131160
gatgcgcctg gctgattatg ttgctcccga agcgtttatc aagaaatgta tcgacgcatg  131220
gtgcctttat gctctcggca cgtatcctac tcctccggca ggtgagctac tgtttaccgt  131280
tccgacccca gccgctggcg acacagacgc gatctttgct gatatgttgg ccaaaggtta  131340
tttggcgtat gacagtgctc atgatgtcta cgatttctcg gcgttgaatc gtatcttcgg  131400
atacaccata acatccgaag ccaatattcc cgactatgga attctggcat ggggtattga  131460
cggtctcggc gcaacatatg cgtcttctga tgttggtcct gtattgattg acacaggtgt  131520
gacaatggag caatacatgt cacaattccc tcagcataat gttaccggaa gcgatatcat  131580
tatcgtctat cctggttcca atgcgttgtc ccgcctggtg gacggctgga aacctcagct  131640
gaaggacatc gttgctggaa tcagatttca catccctgtc gtcaatccca caccttaaaa  131700
taattcaata aaaggggcaa acgccccttt acttcttcaa taactaccgt ataattctaa  131760
acataagcag tacgacacca acttgaaaag caggaactat atcatgacca aaactgaatt  131820
gaacaacatt ctgaacgttg ctgggtacaa gaatattcgt cgtgggaata acaaaatcgc  131880
gcgtgaccgt agcaacaaaa tcatcaaggg gtttcccctg tgtaaaactg gtcctctcga  131940
tatcagcaac ccgtccaagc gcttgtttaa agacttattg cgtgaactcg gcactaaagg  132000
cctggtgcta gataaaaagg atgacctggt tgactttggc atcgcggtta tgaagattgc  132060
caaattcaaa ataactctgt gcgtacagac cattcagaca tatgactact ctgaaggccg  132120
tgacccgaat tacgaaacaa aatatgtcaa cgtaaggatt gaagggttat aatacgaata  132180
tgcgggggct tgatgcccct ttcttttcgc taattaagga aaaccgcacc gatttattat  132240
caggagaatt acaatggcca tccaatcttt cttaaatttc cttgacgagt ccaaacaatt  132300
ggacgaagcg tttaactccg ctccatacga attgactttc ggcaagaaaa atgctggtga  132360
cattttcttc acgttcgtag acgaagatga aaaagaattc cgcatccaat tttatacccc  132420
gcaggggctg ggcaagaacg ttcgtcaggt cttcataggc cagaaacgtg gttcaaccta  132480
tccagacgca atcggtcgtt tcaaaaaccc aatgcgtgtc atcgcatcca tgatcgaagc  132540
gactaaacaa ttcatggcga caccgctggg taaaaccatt gatgggtttg cgattaactt  132600
ctccaagaaa gctctagaac gcggaacgac gttactccca aaaattattc gtcaatctgg  132660
tctgaagcag aaactcaacg tcatggatct gacttatacc ccaatccctg accgtgcctt  132720
cgtatgggtt gtgcgtaaag gcaaggatcc tgctcaggta tttgatggtc cgaaaatgaa  132780
aggcgtgact tgggacgatc cagacaaagt cggtgacgtt cctgaccagg ctgctcgtga  132840
cgccgcacta caaggtgaca tggatgattt gagccaatcc ataaatgccg attctcgctg  132900
gattctgacc aaagctgatc atactcagcc tatgctggtc tggtctggta aagaacgtgg  132960
gcggactatt accgccaata tcgcacctca cgcgaatgaa cctggtgtgt atgctggtag  133020
tatcatgaac gagaaacgga tccgcgctca atccccagac gctattgtac gccaactggg  133080
attaccgcag atccctgtga atattctgaa tgatttcacc aagcagtcgt ccatcttctg  133140
gaaagagatg acgggggatt ctggaaaaat agacatgcag actttgccaa aaacaggatc  133200
tgtggatgac ttacgaaatc agggttatat tgctcgcctt ctggggattg tagacacata  133260
tgctccacaa caggtcggta tgtatgcagg tgagaaacta acacgaatcg gcgcgggcaa  133320
atatcgtact tcgggtggtc tggacattca ggtttatttc tggggaattg tcaacggaaa  133380
actttctgta gaagtggttt ctgatttatc tggcaatgaa cagctgatgc tggaaggcga  133440
cgtgaaaaac gctgcttttg aaatcgtcag tgcgatatcc cgtgctgctg attctcagtt  133500
caacggtgaa gtggaatgtc gtgttgttcc gatcaacggt gccccatacc cgattcaaaa  133560
```

```
ggtttcccgt tctcagggtt attcttatgt cgattgtatt tcgtttactt tgaagatcgc  133620
cgatgcattg ttaaatcgat ttactctggg taaggcagtc aaactcgatc tgataaaaga  133680
gttccctcga acgacgttta ttgttcgtta tgactggcgc agcaaagata ctctgatggt  133740
ccagtcttct gatgggaaga ctatcttcgg cgaaatcaac acaaattcca gtgataacgc  133800
tgtcatcact gcgaacctga aagccccaag caatgcgaag atatttggtg aaaccgttca  133860
tgggttctct gtggcttggg acttccagtt ccctgcgggt agccagctgc aagccgcaag  133920
attcgttacc aacgtgactt acgacttcga tcgtaataag gccaacatca cgaccatgct  133980
gacagaaaat ggccgaaatg tagtcaatag cagcggatat gacattcagt tatctgtcaa  134040
gtctgtgcaa gatgcattga atgagacttc acaacgcctg aaagacgctg cggctcaatt  134100
gagccatctt ggttcatcaa actataaccc gaacaagctg ttcctgaatg atatcaccgt  134160
cagtaagttt ggtgcaatta tgttccaaga caaagatctg gcacagtcca aaaaccgcac  134220
ggcagtcatt gatgctttgg ctcgggcgaa agatcaggtc gctggtggta agaatgcagg  134280
cgatctggcc acctatgccg gatccattcg tgatagcgct cctaatggac gagatctgga  134340
ttggcaggta tacacagcca gtaatggtac agttctgaat gttgcctggg atatcacttt  134400
ccgtcgcaat acgaccgaag gagcatatcg tgaattcaag gatcagatca accgtgccaa  134460
ccaatacctg caaacggtat acaacgacgc gaaatctaaa ggctataatc ctaccgagcc  134520
aaatctcatg actcttgaac gcgctcgcca atccgacgaa tgggctatga gtaatggtga  134580
tagtgcatac agtgaatatg aacaatcgct gggtggtaat cttcagatta gtctgaaata  134640
agtcatagcc ccttcggggg ctaaatacat caaaatcctt aggagatcca cgatgaaacc  134700
gtttatcgaa tattttaaag aacaagctca acaaccgcaa actcatggcg gcatacaagg  134760
caaaagtgta accatcacca aacaggccga cggaacccaa tggtgtactg gtgccaccgt  134820
gacccagatc actccagata atcaggccga catctataat ctggaattga ctaatggcaa  134880
caccatcaaa gtgaagctaa ctccagacca gacccacggc attacccaag gccaagaagt  134940
tgttgccgtc catgatggtt ttgaattttt cttcggcaag tcagctgaca aaggtcaggt  135000
tactgaagcg gaaggctggc gtttcgtcgg tgaccgtggc gctcatattc tgatgtatga  135060
cgcaaaagtt ggcggtgcct ccactatcct tcgcagtcca acagatcgaa ccaaatttgt  135120
tggtggtctc atcaacggta gaaaaatttt gggtaattcc ccagaagaac tggcggcaaa  135180
attaggtctt ccaaaaattc ctgataattt attaaaatcg ttttttggta aaaagtgatt  135240
ataaaataca atccccctaa atacaggggg attttctttt taggggtaaa tatcatggtc  135300
aatgcgagta tattcatcaa ccgtggactg cttgctatag cccactccca tgccctccac  135360
ttcgttacaa cgtcctatgc caagcacaag gcactcgggg agttctacgg ggaactggag  135420
gacttgctgg ataccttcac agaggcatat atcggcgcgg gtggtgtata tgtcccaggg  135480
tttgagaata ttaaactgta caacccagat cctatatcgt atgtcaacag tgttgttatc  135540
gacgtaaacg gaatttatgg tcaatgcgac agccatcttc aaaatacgct tgatgaaatc  135600
aaaactttgt gctatcaaac gatttacaaa ctgaagaaat tgtcctaact caataggatc  135660
atcgtcaggt tataattttg cccattcgtc atcaatagga tacagataac aatgggcaaa  135720
atctttatac cttctcactc agaaggttgt caaatcgctg caaaatttct acacaaacaa  135780
atgaattgtg gtgctgtgtt cgtagaacca aattcattcg ataatcgtga atcccctgac  135840
gccatcgggt tcagacctgg gggttgttct atattaatgg aagttaaagt ctcccgcgcc  135900
gacttcctga cagacaaaaa gaaacctcat cgcatgaatc cttccatagg catgggagca  135960
tatcgtttct atgtttgccc agcagatgtt attaaaattg aagacctccc tcccaaatgg  136020
ggtttgttgt acttcacccc tagaaaatct ttgaagcccg ttcacgttcc gaatatgcaa  136080
tattcctctt tgtcttcacc ggaacattat gcatcatatt tgtctaaatc tttgggcaaa  136140
agaagtccta cagatatccc tccttatcta ttagggtaca aacagatgct ggaagaattt  136200
gcccactttg atcgcaatca ggttgcggaa caaaatattc tgtatggggc ttggcgacag  136260
ctttgcatag ctcaaagtcg cggggtggat tataatgtga cagaagtgtt ccagaggcca  136320
aatatctaat gaaattcttg gacgaacaat acatcaattt tctcgccccc cgacttgata  136380
aattcagttg ggaacgtgtt ggcgctgtcg ccaaatttcg ttgcccatta tgtggggatt  136440
ctaagaagag tgccaacaag cgtcgtggtc acttctttta tgatcgtgat gacgatgtgt  136500
ttcgtttcaa gtgccacaac tgtaatgaaa tgagcggttg ggcgtttgaa ttctggttga  136560
agaagtttga cgagcgtctg tataatgaat acaaccttga aaaattcaga atcatggggg  136620
ataccagttc ccgcccgtta caaaaactca aaccactaca gcgcctgacc cagacagcac  136680
gtatcggttc tcaggtcgcc aaacgggatg aagagcacct tgggaatatg atacgccttg  136740
atcttcttga ccgtgatcat atcgcccgtc gttatgttga aggcagggga atgccggaga  136800
gtgcgttatc tcttttgtat tacagcaaaa acttccgcga agatcttttg aattttgaaa  136860
cagacgttga aaaacagaag aagatccctg aagatgaacg gttggttatc ccattctgga  136920
ctcaagacgg tcgcatgaag atcgttcagg ggcgcgcatt cggtgataac cttcctgata  136980
atgtgttgcg gtacgccact gtcaagccca aaaacgagga tactaaaatc tatggggaag  137040
agcgcatcat atggaataag accaaattgg tcgttgaagg tccaattgat agcctgttcc  137100
tcccgaattg tttagcaact gcggatgctg accttctgag cgccaagggg gatatctata  137160
tccctgacaa ccaatatcga aacaaacaag tttgtgacgg tatacagaag atgatagaca  137220
gcggagtcaa agtcgttctg tttccaccgg aaataccgtg gaaggatatc aatgatatgg  137280
ttcgccccga caagggaaat atcccgatac gtgatctgct tcagatcata gccaagaacg  137340
tatatcaggg gatgtcggcg tccttacgat tttctgactt gaggaagata tgatggattt  137400
gaaagaactg aatagtatgg acgatgaaga gattcttcgt gggtatctgc aagcccgtga  137460
aggatatgtc ctgtctggct tagaatctaa gagtttcatc catggttgga ggaacggaat  137520
ggtggacttc ggcggttgtc ctatcactga agaacaaatg aatttggctc gccagtattt  137580
gaaaaagaag ccgacctaaa actttttaac tcaaaaacct tctctctagg cctcattcta  137640
cgaggccttt taaaatactt caaaaataat ttaaaaattt attgaaaaag actttactct  137700
tcaataatca tgcactatta tagttcacat agggcggtac acaacacccc gccgaatgaa  137760
aagtgaaacg acccaactac attatgagga attacgtcat ggctactacc aaaactctga  137820
tcaccaacgg caccatctct tttgaactga acaccgaagt tgcaaaagtt gaaatgttcc  137880
gcatcgctca ggcagctggc ttcactggtg gcaaaacttc cttcatgaat ctgctgaacg  137940
gcaaagtgaa agcaaccaac ggtttcaccc tggtagagca ggttgtcgta gacaaagccg  138000
tggttgccaa aactgctgac aaggttggca tgctgaaaga cctgggccat gacatccacg  138060
ttgtcgaagc gaataccgaa acttacggca ccatcgtagt cggtaaaggt cgcattcagc  138120
tgaacccgct gaacaacgga accttctccg tgatggtatt cccgaaaaag ggttatgaca  138180
acagtgatat cgtgaaagcc gctggcggtg aagcgaaatc ccagtatgtc aaaatgggta  138240
aactgagcgc cgacgcagta gaaactctgg tgaacaaact ggcttaaccg caagggggaa  138300
```

```
acctcccccct ttcaaagttt tggtaggaga atgagacatg agtagagcaa ttatccaagc  138360
ctctcctggc gctctatggg ttgccgaccg aattcccaac gcgcactttc ctcagttcca  138420
agaggaactg gaacaagcaa tgttgaaaat atttgaaaaa tatgggtatg attccgaagt  138480
taggacttcc ttcaaagaaa tcatgcctgt cgtcgtggtc agataatcaa cactaaatcc  138540
tcaagttcga ctttcacttt aaataccttc gcatacattg cggaggtatt ttcttatggc  138600
cattctaaaa cttggcaacc gaggttctga agtcaaagcg cttcaacaaa gcctcaacaa  138660
aatcggtttc tcccttacag ccgatggcat atttggtaag gcaacagaga atgctgtcaa  138720
atccgttcag gcaggtgctg gattggtgat tgatggtatt gcaggtccaa aaaccttcta  138780
tgctatccgt aatgccggag acgctcatca ggaacatctt accgaagccg acttagttga  138840
cgcagcgcgt gaacttggtg tcgaactggc cagcatgaaa gctgttaacc aggtcgaatc  138900
tcggggaacg ggtttcacca aaacaggtaa gatcaaaact ctgttcgagc gccacatcat  138960
gtataagaaa gtggcggcta aattcggaca agcaagagcc aatgctctgt accaactcta  139020
cccaacattg gttaacccca attctggtgg ctatatcggc ggagacgcgg agttggaacg  139080
ccttcagggt gcaatcgccc ttgatgagga ctgcgcgtac gagagtgcgt cctacggctt  139140
attccagatc atggggttca attgccagat atgtggttat ccgaacgcca aagaaatgtt  139200
cacagatttt ctgactggtg aacgtgcaca tcttctggca tttgtgaaat tcatcaaagc  139260
tgacgccaat atgtggaaag cattgaagaa caaaaattgg gctgaattcg cccgtcggta  139320
caatggtcca gcatatgcca agaaccagta tgacaccaaa ctagcggcgg catacaagag  139380
tttctgttaa caaaaggccg gaaacggcct ttttctttat ctaacataca ggtatgctgg  139440
gcgcgtcgct taattaaagg tgtcgacaac ccctgtagat ataggaaggt tcaacatgca  139500
atctgcgtct aaagttgtat ccatgaagcc agcgaagaca aaatctgctc gtaagaaaga  139560
caccatccag aaggaagaag actggatgaa gttttccaaa ggcgatttca aaattgctcc  139620
gttcaatggc ctctcagaaa atcagaacct cgcatatcaa tccgcactca atgaacatct  139680
cactatcgct atcggtccgg caggtacagg caaatcctat tgtggtgcgt ccgctgctgc  139740
caagcatctg attgacaaaa ccatcaacaa gattatcatc acgcgttctc ctttaccgac  139800
tggaaccaca gcggggttcc ggcctggtga cacatatgaa aagctgatgc cttatttgat  139860
gccgctcata cagacattca aaaaggttct caaaacagat acgggttccg acggtttctt  139920
caactatctg tgggagaaac gcatcataga aattcaagac cttgaaactg taaagggaat  139980
gaccttcgat gattgtttcc tgattatcga agaggcgcag gaatgcgata tggagcaact  140040
gaaaaactta ttgactcgtg cttcagattc ttcgtacatc ttcgtgaatg gagatatcaa  140100
acagtctaac aagcgactgc gtgatagtgc gttacagacg tatgtagatt cctttaaaga  140160
cttcaacaac aagctggaaa caggttcttt gcaaattgac ggtgtagaaa tcggagatga  140220
atatcctgag tgggttcagc cattcagcat catcgaattc gataagtctg atcgtaatgg  140280
tcgcggtaac ttcacccgcc tgatgttaga aattaacgac ctgtacaaca tttaaatacc  140340
acacgaactt ccccgtcgcc ttcaatccat ggaggcgacg tataataaca gcctgcatta  140400
acacaaaccg aggatcgcta tgattaacat cataaagcgg gacggatctt ctgtcccctt  140460
tgacattgaa aaactccaca ctgttcttga acgtgcctgt gaaggattag aaggagtttc  140520
ggtgtctgag gtggaagcag catcgaagat tcagttcaca gacaatatga aaaccgaacg  140580
cattcaggat attatcatcc aagcggcggc tacattgatt tctgtagaaa aacccaacta  140640
ccaatatgtt gctgcccgtc tgaaatcgta tgacctgcgc aaagtcgtct atgggcgata  140700
caagccacct catttgcttg atatattcgc taaaaacatc aagcagggcg tttatgatcg  140760
tgaattcctc gaactctata cgaaagaaga atttgaagaa ctgaacacgg tcatcaatca  140820
caaacgcgac aagaatttta cttgggcggc tatgggccag ctcacgcaaa aatatctttt  140880
gcgcgatcgc tcagcagaca gcaaagtata ttacgaaacg cctcaagtca tgtatatggc  140940
gatcgcgatg gctctgttct ctgcatggga taaagaaacc cgcctgacga tggtgaagaa  141000
attttatgaa tacgccagta caggtaaatt cagtcttcca acacccatca tgtccggcgt  141060
tcgtacccca acccgccaat tcagttcttg tgttcttatc aaaactggtg acactttgga  141120
ctcaatcaat gctacagcca aaagtattgt tgattatgta tccaaacgcg ctgggatcgg  141180
atttgatgtc ggagcaattc gcggcatcgg tagccctatc cgaaaaggcg aaatggtgca  141240
cacaggcctg gttcctttca tcaaatatct gactggggca ttaaagtctt gctctcaagg  141300
cggtattcgt ggcggatcag caacttgcta tatccctatc tggcattatc aatttgatga  141360
tgttgtggtc ctgaagaata accgtggtct tgaagagaac cgtgaacgcc gtatcgacta  141420
cggtattcag atcaaccgtg tcatgttcga acgtctggtg aacaaacaac ccctgtattt  141480
gttcgatccg aaagacaacc gcgatatgta cgaagcgttt ttcgcagatg tcgataagtt  141540
ccgtaccctg tacgacaaca tggtcaaagc tgctgatgct ggtttggttc gtgccaagaa  141600
gatgaatgcg gaagaagtat tccagatgtt gttggatcag cgttcagata caggccgcat  141660
ctacatcgcg tttgtcgacc acatgaacca gtacagtcca ttcaatctag acacaatcta  141720
tagttctaat ctgtgtctgg agattgcgct tcctactcgt gaattccaac agtacgacga  141780
tgaagaaggt cggatcgctc tgtgtacttt ggcctctttt aacctgacgg cgtttgaaga  141840
cccgacagaa atggaagatg ttgctttcgt tctggtttca gctttggata tgttgttgga  141900
atatcaggac tacccagctc gccaagcccg tttggctgta gaagaatatc gtcctctggg  141960
tatcggtatc gtcaacgtcg cgcatttctt cgccaagaac ttcacggggt atggatctcc  142020
tgttgggtta gaactcctgg acaagtggat ggcgcacctg catttctatc tggtaaaggc  142080
ttcgaatcgt ctggccatga agtttggggc atgtaagaag gaaaccattc atcgttctgg  142140
taagataaca gccgaccttc aaccgttgcc gctggatatc ctccccaatg gtaaaaagcc  142200
ggaaggtatg gcatacggcc ttgactggga cggtttgaaa gactctctgc gttgccatgg  142260
tatccgcaat gctactctct tggcgatagc accaactgaa agctcctctc aggtgctgaa  142320
cgccacgaat ggtatagagc cacccaaagg cctcatcagt atcaaaggca gcaaggatgg  142380
cgtttacaag cagatcgttc cggacgttga aacccttggt cctctatatg acctgaaatg  142440
gaatctgtct tgtatcgact atttgaaaac agcggcggtc gcccagcgtt gggtagacca  142500
atccatcagc gttaatacac attatgatcc agagaaattc ccagacggga agatcccgcg  142560
ctctctcatg atgcaggata ttctgtcttt ctacatgtgg ggtggtaaaa ctctgtatta  142620
caacaccaac aaagactcta aggaagatga agagttgaaa caaattgaag atccgaatca  142680
ctgtgacacc tgtgttgtct gattaggtct ataccacaca atcgtttaat atcaggggtg  142740
attcgtcacc ccttattcat caggaaagaa acatgaacga acaaaagcaa ttctcagtat  142800
tcgatccatc ttcaaataat acaggactgc cattctttgg cgaccctgta agtatccagc  142860
gttatgacaa agtggcttgg ccttttgttc aaaaatggta tgaaaaaggc ctcagccaat  142920
tctggcgtcc ggaagaagtg gatgtcacca aagacaaagc ggactttgcc actctatccg  142980
ctgcggaaca acacatctac ttcagcaacc tgaaacgcca aaccatgctg gactctattc  143040
```

```
agggcgctgc tccgttcgaa gcgtttggcc cgtgggcatc aacaccagaa gcgcaatttg  143100
ctattctgga atggacgcgc caagaagcca tccactcact atcttacacg catatccttc  143160
gtaacacagt gaatgatcct ggtatcgttt ttgaccatgt tctggacgtt caggagatcg  143220
tagattgcgc cggacagatc agcgtatact acgacgacat ggtgcgttac agcggaatgc  143280
gtatggctgg acgcgcgttc acccgtgaag acatcatgaa cgccaagcgt gcattctggc  143340
gtgctctgtt tgctgctaac tccctcgaag gcgtccgttt ctatgtttca ttcgcatgct  143400
cttgggcatt catgcaattc ctcaacaaaa tggaaggcaa tgccaagatt attcgccaga  143460
tcgctcgtga cgagcaagat cacctcattc tgacacagac tttcctgaat cgtcttccgt  143520
tgttggaccc tgattttggt atcatccgtg aagaactgcg tggcgaaatg acccagatgt  143580
atgtggatgt ggtcaaccaa gagaaagagt gggcgaacta tctgttcaaa gacggatcca  143640
tgctgggtct gaacgcaaat atcttacacc aaatggttga ttggctagca acacatcgta  143700
tgggcgcgat tggccacccg taccctgggc aagcccgtaa agacaatccg gttccatgga  143760
taaatgagtg gctagataat aaaacaatgc aatacgcatt acaggaagcg gaagcccctg  143820
attatctgac tggtgtcctt actggatcag tctccgacgg tctgaaattt gtttaaaggt  143880
gagaaatgat tacgatctat tccaaacaag gttgtgcgca gtgtttacaa gccgaaaaca  143940
tctgccgcat tcgcggtatt gaacacaaga ttctgaaact tgataaagat tacaagctgg  144000
aagaattaca gaaaatcact ggtaaacagc gcatgtctat gcccgtgatt gtcctggccg  144060
atcaaaccgt gaccgatgtt actggactcg ccgcaagttt aaaacgttga tatttcaaag  144120
cccctgatcc aggggcttta cttttgaaac cttcccgcct atacttccca ataattcatt  144180
ggcaaacgcc acaaattgaa cagcaggaac tatatcatga ccaattctga aatatatcat  144240
gcttctatgc attatcatga cctacgcgcc cgtccaggac acgccaaaca aaaagcattc  144300
tgggtggcag aactcagatt acgccgtgcc gtcgttaacc accaaataat catgaatcgg  144360
aaaaacgaca aatcaccgtt gttggcagat tcttatcttg aactccgcac agcctatgaa  144420
caagccaaac agcacgtaat aggagcataa tatgtccaac aaattactca ccaacccccg  144480
ccacaacttt ggttatatcc aattaccaga agtgatagac acgttgtttg ctgaagacaa  144540
ggaagaagtt tgttgggcac cagcgactct tattgaacgc gaaattttca aatctgaagt  144600
agacgtgatg ttccgcatcg gttcatccgg agaccttcat tatttgggga aagtgaccga  144660
gttaaagacc tgccatgctc aaagattttt gcgcattgac accactcaat gtgacgactt  144720
ttcattcagc attctgcgtg aatatgttca ggtcaaccgt cctgtgtatc aacaccgccc  144780
ttatttgacg tcgatgcata tagacaatta tatttccgac attcatttac gtgcatcaac  144840
tatccatgaa gaagattctg gtatcgcggt tgatacagta ctcaatatga tcgtcattac  144900
tttggtgccg tgatatgtac aaattcccga tattagaaac agtgtactca gttcacaaaa  144960
aggaaggtcc attatttgaa aatttggata ttctgttaaa ggaaaatgtc cgtatccctc  145020
tggttctaaa gggaaagcaa ataggatata gccatgactg ccaaataatg cgttctgaag  145080
gcatcgacgt cttacgcatc cgtctaacat ttgtgttgac aggtaatctg gacggtatgg  145140
tggttaatct gaaaccaacc accatagtcc acagaacggg tgggaaaata ttatatcgtt  145200
tattaactca ttttgagttg gtgacaaaat gctctgccac ggacgttctt taatcaattt  145260
gtccgtttca accatatggt gtctgttatc ggctctgggt tgttgaccac ataaaacgtt  145320
atggttacac ccagagaatg ataatcttca gacaatgaca catcaactga ttgtatctcc  145380
gctctcggtt caaataaagc aatcgcgtct tcaactttgt ttttaacatc aacctgaatt  145440
gtgggattcg tattttcccc cagcatggta tacagcccag ccccgatact tgggtatgtc  145500
ggccaatccc caactgttgt catcacgata tttcgtacgg attgcaacac ggcatagaca  145560
cctgttttct ttgtgacatc tttggtgacc ggatgcatgc caaacttcag gtcaatgtcc  145620
ttgtactctt tcatgttaaa ccccttttgga tattgcctct ccggcacgag agggcattat  145680
ctaccctcgc cagtgtaatc atgcgtcttt accaccaaag ttgccgccat tatcctccag  145740
ttccggtttt atatcaattg gaccaggacc agaagtagat actggagttg ccccagcgcg  145800
tgatgcagca cgaccagcac cttcagcata tttgatgttg ccttcaatag tctgcgccac  145860
cgacaactta tcacaaacta tttcactagc cagtatttta ggcactttta aagtattgga  145920
aacttccaac atctcgcaga tgatacgcat cacgttttgc gcctgaattt cggccagctg  145980
tgaaaatttc atcaacgccg tgccagcaac cacattggag tagttcgatg aatgtagatg  146040
atagacctca cctgtcttgc gctgaacttc agtcccacca atggtcaggt tgtgatcacg  146100
accaacatag taacgtttgt caaacatcgt cagatcataa tgatctttga ctgatttatt  146160
gaccacgtcc ccgtcaggaa gcatctgctt ataagacccc gaggagtgca tccaatggag  146220
acgttccccg cctggtgtgt catcaacctc cataatatgc cccgaccgag atgccatgac  146280
attgttgtaa ggataacgag acccgccagc agaaggaacc gacacctctc ctgtgttatc  146340
aatatcttga acacgcccag aaggaggcgg agtttcctga acttttggtg tacgatcggg  146400
gattggctca gaccatttac cattttgttg cgcaggagcc gccgatgctg tcgtagcagg  146460
accaggccaa cgataaccca acacagatga gcggctgaag cgactcacct tcacagaatc  146520
tgattggttg cctccaatac accaaacata attggcatcg aatttctgta caaacgcaac  146580
gtgtccaaat gttgggttgt tgccacgacg gaatacaaca actgcgccgt aacggggttc  146640
tgacaaaggg gaaccccatt gcaaatatga acgagccaaa gccgagcgcg ttgaagtgta  146700
tcctgcttgg atcaacaccc atcccacaaa tgaagcgcac cagctgactt catcttccga  146760
agcgcccaaa gatgttgtct tgtgatattc caaaatcctt gggttattat tgaatttgcc  146820
agaatattct ttgacaccta attcaccacg agccactgtc atccatttct caggatcata  146880
accgtccaca ggcggttgag gttctggttg tgggtcgtct tcaatcttga caggaacatt  146940
ttcaacggcg ttatatttct gtctttctat agattgaaca acctggccca gcgccaacgg  147000
gtttgtgtct gaaccatccg ttggtgtcgc cgctggccaa acccaggcga tacgaatatt  147060
ttggtatgct tcatccaaag caaatcccat aacatccgac ccgactgtaa tacccgttgg  147120
agaccagcct aaacctgccg aggaggcgtt agatgctggc atgagcattt taccccaagg  147180
caataattcg gtaggtaaga gagtggtatc ttccgtgtgt acaccataga tgcgcacagc  147240
gacgcgcccg ttctggtcgg gatcattcac gtcttcaacg cgcccgtaaa accaacgcaa  147300
gttgtctaac atattgaaac ccattagtca attagaatca tgggttattt atggcgggga  147360
tttgaaatct gtcgaatagt aatattatag gaagctctgc ttccgttcaa ctttattctt  147420
ttcgtttcta ctcgctgaag ctcgtaacac cgccttgaca ggcagtccca ttccaatgcc  147480
atggaggcat aaaggcgagg aaaatactgt acacctcaga acatgcgtag aaaaggatta  147540
tttttgcttc aaaacaaatt caaaccccaa tttacacaac acttacttca gcaacaacgg  147600
tgttatagca atttaaggtt aaacgttcct gtcttaacct ataaaacagg taagcaaaga  147660
aaaccccaca ttacgtgggg ttggaagatt tcttggacaa acgtatcttt agtgtctctg  147720
ttagcaaatc aagatgccaa ggcatcgact cgcttatttc aaatatgcta tagccatgtg  147780
```

```
cctttaattc gtcacacatc acaaagtagg agagtaaatc aatttcaaaa attaaatgaa  147840
aatttcagtg acactgttaa atttgacttc atgttctttc ccacacgaag gacatttaat  147900
tttcgtcgcg taacggatac gaggaatctt tttaaagaaa tcgtcggata tatcttgaac  147960
aatctcagat tcaatatttt cccccaccca tttaacaaat tcatctttga cgcgttgacg  148020
ttctttagca acatcaggtg ctatgccagg ctctgccgga ttctctactt tccaaacctg  148080
accatcatcg tcatacaaac aatcaataaa tgtcgcgatc atttgctcca cagatgatgc  148140
ttcgttgagc actgaggcgt ccgagaagga cggttgacgc atcttgatgt gatagccacc  148200
agggaggtca aatgtttccc tgaagccttc tggggacacg catttcactt ggttgagggg  148260
gatcggtaaa acaagttctt gaccacattc tttaaggcca gaaactggtt cttcaccttc  148320
atttgtgtcg gatggaactt tgttgttaca tttgtatcgt atcttcatga cctcgccgat  148380
agatatacag cgcatcttta aaaatacttc ttcagtaaca ccgattggca gtttactaaa  148440
gggaacccca gcgtcaacac aactatcaaa cagttgctcc agcgtcgcca cacgttcact  148500
cataggagtg ttcggatcag caacctgaag taacatggtc tgttgccctg ctgtgaaagc  148560
gcggtattta atcaccgtcg gccagaaatc acttttgtgt gttctctcag ttttgggcaa  148620
tgatggtaaa ttcataatgt atctccacgg tatattgtaa ccatatttat aatgaggacc  148680
gaaaatgcac gcgttctgtt tcagtaaagt tggagaacaa cttaccatta attatccgga  148740
tacaaatacg gatttctttg tattgctaac ggatttcgca aataaattgg ggatcaagaa  148800
tatcgccatg actgtggacg atatgaaatt tggtcgtctg ggtgtaaaag atttattgaa  148860
ttacggattc aacgtaatca tcgtcgatca gacatacagc ccaattgacg aggaagatgt  148920
tattccagtt tgggttcaac gagacataaa cactctggat aagcattatc ccgattgtgt  148980
catcattggc gaattaatac catattttca taaacgtcgt cggcttgaat caattaaaag  149040
ttattttcaa gatagcgatg acggatataa aatggatgtc cttacgagcg gttgggttgt  149100
gaagaatacc acaggcaatg ccgaccgaat tacttcccgt ctttatgaat atgttaaaga  149160
acgggattat gaactggaga acaataatgc caaacgtaga acgcgctgat attcagcagg  149220
tacaagacgt catccttcaa cgcctccgcg ctgtgatcac aaatgaaaag ggagaaattg  149280
cgccagggtt tgaaggcgca ttcgacggtt tcgttgccga tgatcagggg aaccccgttg  149340
tacaaacgat cgctggcatg attatgctga atagcgaatt tatggctgat ggtaaaatcc  149400
attattctcc caatctcagt gttgacggag aatctttggc ttccgaagtg gttgatttaa  149460
cggttgccgt tggtgagttg ggttatgttt tgatggtttg caccgcgcat tatgtggacg  149520
ccaacggcca tgtgtcatat ggtgatgaag cgcggggaat caaacgtcat gtggatactg  149580
cggcagttct gcaacagatc cgccagatgc aagacaatat ggattccaaa ccccgcctga  149640
ttttgccaga tagtaaaatc gtgacaagat aatccggtct aaatacccat aacacaatga  149700
aacttcgtta tgggtatttt tatgaaattt tgcggaatcg actattctta tggctgtcct  149760
gccatgtgct tctgggatga taaagatcct ttggattttg accatcttca tttctatgcg  149820
catcatactg tagaaaaaca ttgtcgtcag gtacggcata acatcctcat tttacgccag  149880
ccgaaatatg aatccccaga agaacgcttc tacaatatct ccaaatgggc cgaagctgtt  149940
cttctaaccg agaagcctga tttcatcacc cttgaggggt acgcaatggg caactcgaag  150000
aattccaata acatatgcca gactgctgaa aatacatctt tattgaagca agcaatgcgc  150060
cggaataata tggaattcca gatcgttact ccttctttcg ttaaaaagca tttctgtggt  150120
aaaggaaacg ccgataaatt ggtaatgatc gatcatttcg agaagctgtt caacgttaag  150180
atgcgtggta taatggacat gttggacgtg aaggatccaa agcctatcga tgatcttgta  150240
gactcattcg caaacatggt gtctggacct tacttcatag aaaattatcc cgatttcaat  150300
agaggtgtaa gaaatgatta attactggct gttggcagat atactgcttt tcgccttgct  150360
gttgataacg gcatttattt gggttaaggg atttctgaca ttcctgcact cgttgagcgc  150420
catgatatct ttctatgctg tgtcccccca tagtgacgtc aatgtacgag cggcaaatca  150480
atctgacatg ttggctgaat acgtcatgat gcgtgataaa gcaaccagga tcgtcctgtt  150540
ttctacactg gcgggggcgg ttattatatt catacaacac gtcttggagg caactcatgc  150600
cgttttatga ttatgcctgt acaggttgtg gtaattcttt cagtaccaga aggtcttgtg  150660
ctgaacgcca tacgcctgaa ttagatccat gcgctgaatg tggcggtgaa atcaaaatgg  150720
tcattggagc accaaagatc gtatctggtg tccgtggccc acaatccgca cctgatggct  150780
tcaaagacgt attgcgtcat attaagaagc agtctgggaa ggggaataca atcgatgtct  150840
gaccaacaaa tagcacaagt ccttacacct gattcattct cagaattggt gttgatgcga  150900
gcgagccaac gcaaggagtc tattcttgaa acgatggcca gtgtttgtga agagtacgac  150960
atcgaagagg cgaaagttaa gaaactgatt acaccacctc tcctgtcaag gctaacagct  151020
gaatgttctg atgctcggtt gttgaagggt gaattgaaat ctaaaaaact catttaaggt  151080
tgtaacatga gcaaagagca aatttataaa ttgttgaagg cgcaagagta tctgccaggt  151140
tctattcgct ggcgtcatgg tagcctcaac gaacatgctg atgatatgga tcgcgttcgt  151200
ttcacaacgc cggaaggtaa atcctatgtc atcgagtacc atacattctt ggaaggtcat  151260
aaaaccttct cggatgtgta cgatattatt gagatagacc cagcaaaaca aatgattgcg  151320
ggttaactca atagcaaaag gcagtataat tacatcgtcg gaataataga caaatacatt  151380
tatagaatag cccgaagggg cggattatag aggaatataa aatgggtaac ttatttgatc  151440
gtcttaaaca atctcgtggc caacaagccg aagccatgca acagcgtctc gctcagcaag  151500
gtcagcgtgt tggtggcggt cgtgacccgc gcatctggaa gtggacttgg aatgaaaaag  151560
gcacttccga aaacattatt cgtttcctgc ctatcccttt agtggacatg aaggctcaag  151620
aagaaggcac catccctgaa gatgctgtgt taactccatg cgccatgatc atgaaacacg  151680
ctttccaggg tgctggcggc tggtatatcg aaaactcacc tcagactttc ggtaacgatg  151740
atccggttcg tgaccatgat cgtcctctgt gggcacaaca gaaagaaacg aacgatgaaa  151800
aactgaagac ggtcctgaaa aaacgtctgc cggacaccaa atactacgcc aacattctag  151860
tgatcaaaga tggcaataat ccggaaaata acggcaaggt cttcttgctg gaattcggta  151920
atgccgtcaa gaaaatcctg gattcggctc agaatcctaa gttctcaacc gacccgaaat  151980
tcgacccgtt cgatatgtgg gaaggtgcga atctgattct taacctgttc ggcgaagaga  152040
aagagttcgg aaactggaaa ggcctggttg ccaacttcac caacgtgaag tgggatagtc  152100
cggcaccgct gggaaccgac gaatacattg aagagatctg ggaaaaagag cacagcttgt  152160
ttgagttctt taatccggcc aacttcaaat cgtacgaaga tctggaaaaa cgtttgcgca  152220
aagttctggc catccctgat aatcagcctc tggttgaagg tggtgcttct actatggcac  152280
atgcgcctac ccagtctcag gaaccccagc gcccgacagc gcaggaaagc ctgaaccaac  152340
aacaatctca gccttctaat gcacagcaat ctgttccagc caataatggt ggtgcgggtg  152400
ccgatgcgaa acagacggct tccattgatg agttcgagca gttcctgaag caagactaat  152460
ttcactaaag ccccttcggg ggctttttag tttttaacga cgtcttgtaa caaaccgagt  152520
```

-continued

```
aaactactct tctcagacgc cgtcaggtta tcattgccta atatatccct ctggatgccg  152580
atagagatcc tttcgaagtc tgccaggctg atacccgcca aattatttac aagctgatcg  152640
agttgcttgt aggccagtag ggcttcacct gtaaagttcc cttccttaat ctttttatac  152700
agctgtccgg cttttgacgc tgcggtttcc caatctccgg aagcaagagc atcagcaatg  152760
cccaaaggaa gaaagtcgct ggcgaggctg cgcgtttcat attcagtctc cgataatact  152820
ttattgtaag agaacgatat attgtactgg ttaaattggt cggcggcact tttgtcgagg  152880
tcgatggaac tgaagttaat aggatgagcc tccgtcacat aaacacggtg caccacctgg  152940
tcttctgtat ccatttgctc tatacaaata tcagtcacga aatcttcgta ataacccatc  153000
ttggtcgtat atgggtcgaa tatcaaattc ttccatttat ccatgaccga cttttcataa  153060
tagtcgttgg caaggagaaa tgataactcc agatcaacgt ttgttttgtt gttcggcatc  153120
ttaatatggt tgccgttatt tgtcattggc gttgtatcaa tcccagtacc aggcaaagaa  153180
gcaaccatac acatcatttg taaggaacga gacgtctggt ttgtccctcc aaagaaagcg  153240
tttacaatac gggcgctttg tttgaacaga tccccaaatg atgaagatga aggatatgcg  153300
ttgccgtcat tggatagagt cgcattagaa tcgaaaatac caggcggcaa cgggattgta  153360
acacgaaatc tgttcttgcg ggaaatcccc cgctgaagca gttgcgttag aaaattgcga  153420
tagtcttcca cgatgaggac tccatttaaa taatatatct gctgatattt ataaggagtt  153480
gacaaatggc caagaacgct atgggtgaag aagacccgtt gttgcttcct gccgagatgg  153540
acgccccaga attggtcaag cgttacatcc gcaaatatcg tcaacatttt ggaccagaag  153600
cgaaacgtaa tatccgtcgg tctcacgtgt ggtttatgga acgcgtatcg aaagatgcca  153660
atttatcccc caaccacatg atgaaggcgt ttgctgaaaa taaacgtcct gttcagggtg  153720
tgcgctatat tgttggtcgc atgtactatt tcaaatatga tgcgctgacc aaagatgaac  153780
tcccgtattg ggatatgtat cctcttgtat tcttcttcaa ttttgtgaag ggtgacgggg  153840
taaaatttgg ggaacgtggt gtgacctatc tttatggtct caaccttcat tatttgccac  153900
caaagctcag attattagtg tttgaagatc ttatcaagtt gaggaacgaa agagcgtatc  153960
gttctaaaac tcgtttgaga cttacttggg atgccctgaa acggttcgcc aatcaccctc  154020
tgtacaacca ttgtgtgaaa ctgtaccgcg ctgatcaatt tcgttcacag ctttatgaga  154080
ttgagcctca atactgggaa gttgttttgt ttatgcgcac tgctcgattc cagaaacaga  154140
gccagatgtc tgtttggaaa gacgctcgtc gtaaacacaa aaatggttag ttctaaaagc  154200
cgttctatgg gataattcgc gaacggcttt ctataaacat gaggttccat atatgtcata  154260
tctacacaga atttttggta ttgaattcag ttccaacagc gttcgttatg accgcactca  154320
caaagactcc ggcggcaaga ctggttacga acttggatct cgtttggggt atactgaaga  154380
gcgccgcctg agtgaacaaa ctcttttcac agctatgggt attgaatttg aatccgaggc  154440
tgctttagat ctgggggatg aggttcgttt tggtaagcct gaagtcttag aatttgttga  154500
agacttcgtg acaggttata cccatgccgc taacaatcgt cgcgccgcca atgatgctgt  154560
tggtaaattt cattttgctg tgaaatacct tgccgacaag cgtattcaaa tggaagccga  154620
attcagtgaa gaaaacttga aagcagtttt cggagagact ggcgatttcc tattgacaga  154680
agaatccggt acttcttccg ctcgtcattt ctttagtcaa ccgtttatcg tgaagggatg  154740
taaaattctg attgatgaag aacatgtttt tggtattcat ccggatgttg tatacgatga  154800
agagacgtgt ctgatcattt ccagattgtt taacagcctg gcgtacactt catattcatt  154860
gatcgaacgc tgtatggaag aagagcatcg ccaagttgtt gtcaacaaaa ttcgcttaca  154920
tgttgagcag aattttaatg gattccattg cgcgtctggt gagattccaa acttctacat  154980
gtaaagatat caggggggct gtatgaagaa atatgttcgt ctgaacactg tacttgaatc  155040
agttatagaa tatttcataa tgcagcacct cagagcagaa aatgaacacg tgagcgacgc  155100
tctgacttat gatcaccgga tagtggttca ttccgtcgaa atagtggatg acgaattgtt  155160
gattgccaat gttgagcatg ctctctggga tgaagtgtta gatcagtacg ttcaaccgaa  155220
gttcacacag atcgagttat ctgccatgtg gccacctgaa acagttttca atattgatat  155280
acaaagttaa tattcacgtc agtccgcgct ataccagcgt tccgttgtct aacacagaag  155340
tgttaaccaa cttttcaata aaaagtggtt tacatcttct aaaaaggcag tatattaatg  155400
ttccagacgc acagttgaac attaaactgc caaagaaggt tactacacaa aagggttttt  155460
attatgtcct atattcttca tatcgagtcc ggcctgaaat ttgaaattga tggtaaaacc  155520
gctgctgatc ttcaagcaga aatcaaaggt gcagacctta tcatcggcaa cgtcacgtta  155580
cgccgtatga tggaaggcgt cctccagtca gccaacggct ttgaactcat tgaaggtctg  155640
agccaggaag agaaagaaga gactctcgaa gctcttgacc gcgctgaagc cgaaaaagtt  155700
aaaccgaccg aagatgcggg ggttaaacag ggcgacggtg aatcaaatcc ggtgattgac  155760
gccgaagaaa cggttgggca acctgtcggt gatcaaaatt cccagaccgt cgaagacggt  155820
tctcttgaag tcaacaaaga cggctccatt tccctggtag ttgaaggcga agaagttctt  155880
gacgaag                                                            155887
```